US012767984B2

(12) United States Patent
Hart et al.

(10) Patent No.: US 12,767,984 B2
(45) Date of Patent: Oct. 20, 2026

(54) METHODS AND SYSTEMS TO PERFORM GENETICALLY VARIANT PROTEIN ANALYSIS, AND RELATED MARKER GENETIC PROTEIN VARIATIONS AND DATABASES

(71) Applicant: LAWRENCE LIVERMORE NATIONAL SECURITY, LLC, Livermore, CA (US)

(72) Inventors: Bradley Ryan Hart, Livermore, CA (US); Deon Stafford Anex, Livermore, CA (US); Katelyn Elizabeth Mason, Mountain House, CA (US); Phillip Harris Paul, San Francisco, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 1181 days.

(21) Appl. No.: 16/644,661

(22) PCT Filed: Sep. 6, 2018

(86) PCT No.: PCT/US2018/049775
§ 371 (c)(1),
(2) Date: Mar. 5, 2020

(87) PCT Pub. No.: WO2019/051103
PCT Pub. Date: Mar. 14, 2019

(65) Prior Publication Data

US 2021/0095348 A1 Apr. 1, 2021

Related U.S. Application Data

(60) Provisional application No. 62/555,001, filed on Sep. 6, 2017.

(51) Int. Cl.
*C12Q 1/6883* (2018.01)
*G01N 30/72* (2006.01)
(Continued)

(52) U.S. Cl.
CPC .......... *C12Q 1/6883* (2013.01); *G01N 30/72* (2013.01); *G01N 33/6848* (2013.01);
(Continued)

(58) Field of Classification Search
None
See application file for complete search history.

(56) References Cited

U.S. PATENT DOCUMENTS

| | | | |
|---|---|---|---|
| 8,877,455 | B2 | 11/2014 | Parker |
| 2003/0027216 | A1 | 2/2003 | Kiernan et al. |

(Continued)

OTHER PUBLICATIONS

Pires, D.A.T et al. Some Mechanistic Aspects on Fmoc Solid Phase Peptide Synthesis, Int J Pept Res Ther (2014) 20:53-69 (Year: 2014).*

(Continued)

*Primary Examiner* — Xiaoyun R Xu
(74) *Attorney, Agent, or Firm* — Zilka-Kotab, P.C.

(57) ABSTRACT

Methods and systems to perform genetically variant protein analysis and related marker genetic protein variations and databases, which in several embodiments allow performing a reliable genetic variation protein analysis in biological samples of different types and conditions taking into account the features of the biological sample where the analysis is performed.

30 Claims, 43 Drawing Sheets

Specification includes a Sequence Listing.

(51) Int. Cl.
*G01N 33/68* (2006.01)
*C12Q 1/00* (2006.01)
*C12Q 1/37* (2006.01)
*G01N 1/44* (2006.01)
*G01N 30/88* (2006.01)

(52) U.S. Cl.
CPC .............. *C12Q 1/005* (2013.01); *C12Q 1/37* (2013.01); *C12Q 2523/301* (2013.01); *C12Q 2600/156* (2013.01); *G01N 1/44* (2013.01); *G01N 2030/8827* (2013.01); *G01N 2030/8831* (2013.01)

(56) References Cited

U.S. PATENT DOCUMENTS

| | | | |
|---|---|---|---|
| 2005/0112590 A1 | 5/2005 | Boom et al. |
| 2011/0236918 A1 | 9/2011 | Parker |
| 2012/0322093 A1 | 12/2012 | Koll et al. |

OTHER PUBLICATIONS

Bodzon-Kulakowska, A., et al., "Methods for samples preparation in proteomic research." Journal of Chromatography B, 2007. 849(1): p. 1-31.
Bunger, M.K., et al., "Detection and validation of non-synonymous coding SNPs from orthogonal analysis of shotgun proteomics data." J Proteome Res, 2007. 6(6): p. 2331-40.
Canas, B., et al., "Trends in sample preparation for classical and second generation proteomics." Journal of Chromatography A, 2007. 1153(1): p. 235-258.
Durbin, RM., et al., "A map of human genome variation from population-scale sequencing." Nature, 2010. 467(7319): p. 1061-73.
Gallien, S., et al., "Selectivity of LC-MS/MS analysis: implication for proteomics experiments." Journal of Proteomics, 2013. 81: p. 148-158.
Ghesquiere, B. et al., "Proteomics methods to study methionine oxidation." Mass Spectro Rev, 2014. 33(2): p. 147-56.
Gobom, J., et al., "Sample purification and preparation technique based on nano-scale reversed phase columns for the sensitive analysis of complex peptide mixtures by matrix assisted laser desorption/ionization mass spectrometry." Journal of Mass Spectrometry, 1999. 34(2): p. 105-116.
Han, Y. et al., "Spider: software for protein identification/ram sequence tags with de nova sequencing error." Journal of Bioinformatics and Computational Biology, 2005. 3(03): p. 697-716.
Harder, A, et al., "Comparison of yeast cell protein solubilization procedures for two-dimensional electrophoresis." Electrophoresis, 1999. 20(4-5): p. 826-829.
Hart et al., "Genetically variant Protein Analysis", LLNS Proprietary Information. 2017. 162 pages.
International Preliminary Report on Patentability (Chapter I) for International Application No. PCT/US2018/049775 filed on Sep. 6, 2018 on behalf of Lawrence Livermore National Security, LLC Mail Date: Mar. 10, 2020 7 pages.
Lubec, G., et al., "Structural stability of hair over three thousand years." Journal of Archaeological Science, 1987. 14(2): p. 113-120.
McNevin, D., et al., "Short tandem repeat (STR) genotyping of keratinised hair. Part I. Review of current status and knowledge gaps." Forensic Sci Int, 2005. 153(2-3): p. 237-46.
Melton, T., et al., "Forensic mitochondrial DNA analysis of 691 casework hairs." J Forensic Sci, 2005. 50(1): p. 73-80.
Metzker, M.L., "Sequencing technologies—the next generation." Nature Reviews. Genetics, 2010. 11(1): p. 31.
Nahnsen, S., et al., "Tools for label-free peptide quantification." Molecular & Cellular Proteomics, 2013. 12(3): p. 549-556.
Noble, J.E. et al., "Quantitation of protein." Methods in enzymology, 2009. 463: p. 73-95.
Ochoa-Rivas, A., et al., "Microwave and Ultrasound to Enhance Protein Extraction from Peanut Flour under Alkaline Conditions: Effects in Yield and Functional Properties of Protein Isolates". Food and Bioprocess Technology, 2017. 10(3): p. 543-555.
Phongthai, S. et al. "Optimization of microwave-assisted extraction of rice bran protein and its hydrolysates properties." Journal of Cereal Science, 2016. 70:p. 146-154.
Rice, R.H. et al., "Stabilization of bovine trypsin by reductive methylation." Biochimica et Biophysica Acta, 1977. 492(2): p. 316-321.
Rice, R.H., "Proteomic analysis of hair shaft and nail plate." J Cosmet Sci, 2011. 62(2): p. 229-36.
Robertson, J., "Managing the forensic examination of human hairs in contemporary forensic practice." Australian Journal of Forensic Sciences, 2017. 49(3): p. 239-260.
Sapan, C.V. et al., "Colorimetric protein assay techniques." Biotechnology and Applied Biochemistry, 1999. 29(2): p. 99-108.
Searle, B.C., "Scaffold: a bioinformatic tool for validating MS/MS-based proteomic studies." Proteomics, 2010. 10(6): p. 1265-1269.
Shao, S., et al., "Reproducible tissue homogenization and protein extraction for quantitative proteomics using MicroPestle-assisted pressure-cycling technology" Journal of Proteome Research, 2016. 15(6): p. 1821-1829.
Solazzo, C., et al., "Modeling deamidation in sheep alpha-keratin peptides and application to archeological wool textiles." Anal Chem, 2014. 86(1): p. 567-75.
Vihinen, M., "Bioinformatics in proteomics." Biomolecular Engineering, 2001. 18(5): p. 241-248.
Wu, A.H., et al., Role of liquid chromatography-high-resolution mass spectrometry (LCHRIMS) in clinical toxicology. Clinical Toxicology, 2012. 50(8): p. 733-742.
Ye, X. et al., "Microwave-assisted protein solubilization for mass spectrometry-based Shotgun proteome analysis." Analytical Chemistry, 2012. 84(14): p. 6181-6191.
Porto, Isabel M., et al. "Recovery and identification of mature enamel proteins in ancient teeth." European journal of oral sciences 119 (2011): 83-87.
Alfaro et al., "Detecting protein variants by mass spectrometry: a comprehensive study in cancer cell-lines", Genome Medicine, Epub. 18, Jul. 2017, vol. 9, article No. 62, pp. 1-12.
Bantscheff, M., et al., Quantitative mass spectrometry in proteomics: a critical review. Analytical and bioanalytical chemistry, 2007. 389(4): p. 1017-103.
Barker, W.C., et al., The protein information resource (FIR). Nucleic acids research, 2000. 28(1): p. 41-44.
Boeckmann, B., et al., The Swiss-Prot protein knowledgebase and its supplement TrEMBL in 2003. Nucleic acids research, 2003. 31(1): p. 365-370.
Brandon, M.C., et al., Mitomaster: a bioinformatics tool for the analysis of mitochondrial DNA sequences. Human mutation,2009. 30(1): p. 1-6.
Brun, V., et al., Isotope-labeled protein standards toward absolute quantitative proteomics. Molecular & Cellular Proteomics,2007. 6(12): p. 2139-2149.
Cann, H.M., et al., A human genome diversity cell line panel. Science, 2002. 296(5566): p. 261-2.
Cao, R., et al., dbSAP: single amino-acid polymorphism database for protein variationdetection., Nucleic acids research, 2016. 45(DI): p. D827-D832.
Consortium, U., UniProt: a hub for protein information. Nucleic acids research, 2014: p. gku989.
Cox, B. and A Emili, Tissue subcellular fractionation and protein extraction for use in mass-spectrometry-based proteomics. Nature protocols, 2006. 1 ( 4): p. 1872.
Domon, B. and R. Aebersold, Mass spectrometry and protein analysis. science, 2006. 312(5771): p. 212-217.
Feist, P. and AB. Hummon, Proteomic challenges: sample preparation techniques for microgram-quantity protein analysis from biological samples. International journal of molecular sciences, 2015. 16(2): p. 3537-3563.
Fenyo, D., J. Eriksson, and R. Beavis, Mass spectrometric protein identification using the global proteome machine. Methods Mol Biol, 2010. 673: p. 189-202.

(56) References Cited

OTHER PUBLICATIONS

Fic, E., et al., Comparison of protein precipitation methods for various rat brain structures prior to proteomic analysis. Electrophoresis, 2010. 31(21): p. 3573-3579.
Fusaro, V.A., et al., Prediction of high-responding peptides for targeted protein assays by mass spectrometry. Nature biotechnology, 2009. 27(2): p. 190-198.
Guillarme, D., et al., New trends in fast and high-resolution liquid chromatography: a critical comparison of existing approaches. Analytical and bioanalytical chemistry, 2010. 397(3): p. 1069-1082.
Gundry, R.L., et al., Preparation of proteins and peptides for mass spectrometry analysis in a bottom-up proteomics workjlow. Current protocols in molecular biology, 2009: p. 10.25. 1-10.25. 23.
Gupta, N., et al., Quantitative proteomic analysis of B cell lipid rafts reveals that ezrin regulates antigen receptor-mediated lipid raft dynamics. Nature immunology, 2006. 7(6): p. 625.
Hubbard, T., et al., The Ensembl genome database project. Nucleic acids research, 2002. 30(1): p. 38-41.
International Search Report for International Application No. PCT/US2018/049775 filed on Sep. 6, 2018 on behalf of Lawrence Livermore National Security, LLC. Mail date: Jan. 21, 2019. 5 pages.
Jaffe, J.D., et al., Accurate Inclusion Mass Screening A bridge from unbiased discovery to targeted assay development for biomarker verification. Molecular & Cellular Proteomics, 2008. 7(10): p. 1952-1962.
Jeffreys, H., An Invariant Form for the Prior Probability in Estimation Problems. Proceedings of the Royal Society of London. Series A, Mathematical and Physical Sciences, 1946. 186(1007): p. 453-461.
Jeong, J., et al., Novel oxidative modifications in redox-active cysteine residues. Mol Cell Proteomics,2011. 10(3): p. MI 10 000513.
Johnson, M., et al., NCBI Blast: a better web interface. Nucleic acids research, 2008. 36(suppl_2): p. W5-W9.
Kaye, D.H., Ultracrepidarianism in Forensic Science: The Hair Evidence Debacle. 2015.
Laatsch, C.N., et al. Human hair shaft proteomic profiling: individual differences, site specificity and cuticle analysis. PeerJ, 2014. 2, DOI: 10.7717/peerj.506.
Ng, S.B., et al., Targeted capture and massively parallel sequencing of twelve human exomes. Nature, 2009. 461 (7261): p. 272.
Parker, G.J., et al., "Demonstration of protein-based human identification using the hair shaft proteome." PloS one, 2016. 11(9): p. e0160653. .
Raymond, J.J., et al., Trace DNA success rates relating to volume crime offences. Forensic Science International: Genetics Supplement Series, 2009. 2(1): p. 136-137.
Robinson, N.E., Protein deamidation. Proc Natl Acad Sci U S A, 2002. 99(8): p. 5283-8.
Stulik, K., et al., Stationary phases for peptide analysis by high performance liquid chromatography: a review. Analytica chimica acta, 1997. 352(1-3): p. 1-19.
Sun, W., et al., Microwave-assisted protein preparation and enzymatic digestion in proteomics. Molecular & Cellular Proteomics, 2006. 5( 4): p. 769-776.
Thompson, J.D., D.G. Higgins, and T.J. Gibson, Clustal W. improving the sensitivity of progressive multiple sequence alignment through sequence weighting, position specific gap penalties and weight matrix choice. Nucleic acids research, 1994. 22(22): p. 4673-4680.
Written Opinion for International Application No. PCT/US2018/049775 filed on Sep. 6, 2018 on behalf of Lawrence Livermore National Security, LLC. Mail date: Jan. 21, 2019. 6 pages.
Wu, C.H., et al., The protein information resource. Nucleic acids research, 2003. 31(1): p. 345-347.
Wu, P.W., et al., Proteomic analysis of hair shafts from monozygotic twins: Expression profiles and genetically variant peptides. Proteomics, 2017.
Aebersold and Mann, "Mass spectrometry-based proteomics," Nature, vol. 422, Mar. 13, 2003 (10 pages).
Mann et al, "Analysis of Proteins and Proteomes by Mass Spectrometry," Annu. Rev. Biochem. 2001. 70:437-73 (39 pages).

* cited by examiner (To Fig. 1A)

| GN | Frequency EUR | AFR | nuc | rs# | Chr | SAP | peptide |
|---|---|---|---|---|---|---|---|
| BLMH | 0.562 | 0.378 | C | rs1050565 | 17 | I443V | HVPEEVLAVLEQEPIvLPAWDPMGALA- |
| | 0.884 | 0.927 | T | rs1050565 | 17 | I443V | HVPEEVLAVLEQWPIILPAWDPMGALA- |
| COL4A4 | 0.691 | 0.87 | G | rs3752895 | 2 | S1403P | GPpGPGCKGEPGLDGR |
| | 0.821 | 0.581 | A | rs3752895 | 2 | S1403P | GPSGPGCKGEPGLDGR |
| DSP | 0.269 | 0.642 | A | rs6929069 | 6 | R1738Q | GqSEADSDKNATILELR |
| | 0.984 | 0.858 | G | rs6929069 | 6 | R1738Q | GRSEADSDKNATILELR |
| ECHS1 | 0.995 | 0.752 | A | rs1049951 | 10 | T75I | IFEEDPAVGAIVLTGGDK |
| GSDMA | 0.491 | 0.642 | A | rs3894194 | 17 | R18Q | QLNPqGDLTPLDSLIDFK |
| | 0.813 | 0.915 | G | rs3894194 | 17 | R18Q | GDLTPLDSLIDFK |
| GSDMA | 0.699 | 0.476 | A | rs56030650 | 17 | T314N | GHEVnLEALPK |
| | 0.784 | 0.894 | C | rs56030650 | 17 | T314N | GHEVTLEALPK |
| GSDMA | 0.731 | 0.227 | G | rs7212938 | 17 | V128L | ALETVQER |
| | 0.781 | 0.979 | T | rs7212938 | 17 | V128L | ALETIQER |
| GSTP1 | 0.544 | 0.712 | G | rs1695 | 11 | I105V | YvSLIYTNYEAGKDDYVK |
| | 0.905 | 0.826 | A | rs1695 | 11 | I105V | YISLIYTNYEAGKDDYVK |
| HEX B | 0.264 | 0.028 | G | rs10805890 | 5 | I207V | GILvDTSR |
| | 0.971 | 1 | A | rs10805890 | 5 | I207V | GILIDTSR |
| HIST1H1T | 0.712 | 0.899 | C | rs198844 | 6 | V14L | MSETVPAASASAGVAAMDKLPTK |
| | 0.792 | 0.582 | G | rs198844 | 6 | V14L | MSETVPAASASAGIAAMDKLPTK |
| JUP | 0.121 | 0.02 | T | rs41283425 | 17 | R142H | SAIVHLINYQDDAELAThALPELTK |
| | 1 | 1 | C | rs41283425 | 17 | R142H | SAIVHLINYQDDAELATR |
| JUP | 0.013 | 0 | T | rs143043662 | 17 | V648I | NEGTATYAAARLFR |
| | 1 | 1 | C | rs143043662 | 17 | V648I | NEGTATYAAAVLFR |
| KRT1 | 0.042 | 0 | A | rs17678945 | 12 | A454S | NKLNDLEDALQQsKEDLAR |
| KRT31 | 0.169 | 0.065 | A | rs6503627 | 17 | A82V | DNvELENLIR |
| KRT31 | 0.05 | 0.004 | A | rs112544857 | 17 | A234V | SQYEvLVETNR |
| KRT31 | 0 | 0.004 | T | rs146247884 | 17 | V341M | QNQEYQmLLDVR |
| KRT32 | 0.748 | 0.493 | T | rs2071561 | 17 | S222Y | ADLEAQVEyLK |
| KRT32 | 0.459 | 0.098 | T | rs72830046 | 17 | R280H | CQYEAMVEANhR |
| | 0.939 | 1 | C | rs72830046 | 17 | R280H | CQYEAMVEANRR |
| KRT32 | 0.682 | 0.663 | A | rs2071563 | 17 | T395M | LEGEINmYR |
| | 0.832 | 0.796 | G | rs2071563 | 17 | T395M | LEGEINTYR |
| KRT32 | 0.493 | 0.476 | C | rs2604955 | 17 | N402S | LEGEINTYRSLLENEDCK |
| | 0.681 | 0.74 | T | rs2604955 | 17 | N402S | LEGEINTYRSLLEsEDCK |
| KRT33A | 0.446 | 0.597 | A | rs12937519 | 17 | A270V | QVVSSSEQLQSYQvEHELR |
| KRT33B | 0 | 0.02 | G | rs114488848 | 17 | V279L | TINALEIELQAQHNLR |
| KRT34 | 0.575 | 0.089 | T | rs2239710 | 17 | I238T | SQYEALVEINR |
| KRT35 | 0.702 | 0.451 | A | rs743686 | 17 | S36P | VSAMYSSSSCKLPSLSPVAR |
| | 0.778 | 0.927 | G | rs743686 | 17 | S36P | VSAMYSSSpCKLPSLSPVAR |
| KRT35 | 0 | 0.008 | A | rs138303862 | 17 | R163W | YETEVSLwQLVESDINGLR |
| | 1 | 1 | G | rs138303862 | 17 | R163W | YETEVSLRQLVESDINGLR |
| KRT35 | 0.306 | 0.134 | T | rs12451652 | 17 | C441Y | TNySPRPICVPCPGGRF |
| | 0.958 | 0.988 | C | rs12451652 | 17 | C441Y | TNCSPRPICVPCPGGRF |
| KRT35 | 0.708 | 0.623 | C | rs2071601 | 17 | P443A | TNCSaRPICVPCPGGRF |
| | 0.798 | 0.859 | G | rs2071601 | 17 | P443A | TNCSPRPICVPCPGGRF |

*FIG. 1B (part 1)*

| | | | | | | | |
|---|---|---|---|---|---|---|---|
| KRT37 | 0.475 | 0.297 | A | rs9910204 | 17 | G13C | TSFYSTSSCPLcCTMAPGAR |
| | 0.934 | 0.963 | C | rs9910204 | 17 | G13C | TSFYSTSSCPLGCTMAPGAR |
| KRT39 | 0 | 0.02 | T | rs142154718 | 17 | S86N | FSLDDCnWYGDGINSNEK |
| | 1 | 1 | C | rs142154718 | 17 | S86N | FSLDDCSWYGDGINSNEK |
| KRT40 | 0.647 | 0.925 | T | rs2010027 | 17 | R235H | NHEEEVNLLhEQLGDR |
| | 0.816 | 0.474 | C | rs2010027 | 17 | R235H | NHEEEVNLLREQLGDR |
| KRT40 | 0.433 | 0.11 | G | rs150812789 | 17 | C349R | TASALEIELQAQQSLTESLECTVAETEAQYSSQLAQIQr /LIDNLENQLAEIR |
| | 0.931 | 0.992 | A | rs150812789 | 17 | C349R | TASALEIELQAQQSLTESLECTVAETEAQYSSQLAQIQCLIDNLENQLAEIR |
| KRT81 | 0.282 | 0.045 | A | rs6580873 | 12 | R248L | LYEEEEILILQSHISDTSVVVK |
| | 0.56 | 0.122 | G | rs20715288 | 12 | G52R | GLTGGFGSHSVCr |
| KRT81 | 0.008 | 0.419 | G | rs79897879 | 12 | S13R | FrCISACGPRPGR |
| | 1 | 0.943 | T | rs79897879 | 12 | S13R | FSCISACGRPGR |
| KRT82 | 0.734 | 0.569 | A | rs2658658 | 12 | T458M | GAFLYEPCGVSmPVLSTGVLR |
| | 0.797 | 0.878 | G | rs2658658 | 12 | T458M | GAFLYEPCGVSTPVLSTGVL |
| KRT83 | 0.62 | 0.728 | C | rs2852464 | 12 | I279M | DLNMDCmVAEIK |
| | 0.863 | 0.768 | G | rs2852464 | 12 | I279M | DLNMDCIVAEIK |
| KRT83 | 0 | 0.077 | T | rs140835030 | 12 | G362S | LEAAVAQSEQQsEAALSDAR |
| KRT84 | 0.48 | 0.167 | A | rs951773 | 12 | C446R | CEYQELMNAKLGLDIEIATYR |
| | 0.942 | 0.996 | G | rs951773 | 12 | C446R | rEYQELMNAKLGLDIEIATYR |
| KRT85 | 0.092 | 0.041 | T | rs61630004 | 12 | R78H | IAVGGFRAGSChSFGYR |
| | 1 | 1 | C | rs61630004 | 12 | R78H | IAVGGFRAGSCGR |
| KRT86 | 0 | 0.065 | T | rs139895699 | 12 | R327C | TKEEINELNcMIQR |
| KRTAP10-8 | 0.095 | 0.089 | A | rs411254 | 21 | H26R | TYVIAASTMSVCSSDVGHVSR |
| | 0.997 | 1 | G | rs411254 | 21 | H26R | TYVIAASTMSVCSSDVGr |
| LRRC15 | 0.395 | 0.154 | A | rs13070515 | 3 | P286L | ELSIGIFGPMPNLR |
| | 0.944 | 0.984 | G | rs13070515 | 3 | P286L | ELSPGIFGPMPNLR |
| LRRC15 | 0.443 | 0.374 | T | rs13060627 | 3 | V270L | LYLSNNHISQLPPSIFMQLPQLNR |
| | 0.937 | 0.955 | C | rs13060627 | 3 | V270L | LYLSNNHISQLPPSVFMQLPQLNR |
| NEU2 | 0.755 | 0.9730 | C | rs2233391 | 2 | H168N | EWSTFAVGPGHCLQLHDR |
| | 0.788 | 0.285 | A | rs2233391 | 2 | H168N | EWSTFAVGPGHCLQLnDR |
| PKP1 | 0.021 | 0 | T | rs61818256 | 1 | R684W | AAEAAwLLLSDMWSSK |
| | 1 | 1 | C | rs61818256 | 1 | R684W | AAEAARLLLSDMWSKK |
| S100A3 | 0.085 | 0.589 | T | rs36022742 | 1 | R3K | AkPLEQAVAAIVCTFQEYAGR |
| | 0.998 | 0.858 | C | rs36022742 | 1 | R3K | ARPLEQAVAAIVCTFQEYAGR |
| SERPINB5 | 0.52 | 0.74 | A | rs1455555 | 18 | I319V | GVALSNVvHK |
| | 0.731 | 0.297 | G | rs1455555 | 18 | I319V | GVALSNVIHK |
| TGM3 | 0.317 | 0.696 | C | rs214803 | 20 | T13K | AALGVQSINWQTAFNR |
| | 0.982 | 0.838 | A | rs214803 | 20 | T13K | AALGVQSINWQkAFNR |

FIG. 1B (part 2)

Primers for PCR and Sequencing:

| Primer | Sequence (5'→3') | Usage |
|---|---|---|
| F15975 | CTC CAC CAT TAG CAC CCA AA | PCR and Sequencing |
| F16524 | AAG CCT AAA TAG CCC ACA CG | • |
| F015 | CAC CCT ATT AAC CAC TCA CG | • |
| F403 | TCT TTT GGC GGT ATG CAC TTT | • |
| R16410m | GAG GAT GGT GGT CAA GGG A | • |
| R042 | AGA GCT CCC GTG AGT GGT TA | • |
| R289 | CTG GTT AGG CTG GTG TTA GG | • |
| R635 | GAT GTG AGC CCG TCT AAA CA | • |

```
rCRS_HV1            -CTCCACCATTAGCACCCAAAGCTAAGATTCTAATTTAAACTATTCTCTGTTCTTTCATG
U1.003b-A_HV1       -------------------------------------------TTCTCTGTTCTTTCATG
L1.006a-A_HV1       TCTCCACCATTAGCACCCAAAGCTAAGATTCTAATTTAAACTATTCTCTGTTCTTTCATG
L1.046a+b-A_HV1     TCTCCACCATTAGCACCCAAAGCTAAGATTCTAATTTAAACTATTCTCTGTTCTTTCATG
                                                               *****************

rCRS_HV1            GGGAAGCAGATTTGGGTACCACCCAAGTATTGACTCACCCATCAACAACCGCTATGTATT
U1.003b-A_HV1       GGGAAGCAGATTTGGGTACCACCCAAGTATTGACTCACCCATCAACAACCGCTATGTATT
L1.006a-A_HV1       GGGAAGCAGATTTGGGTACCACCCAAGTATTGACTCACCCATCAACAACCGCTATGTATC
L1.046a+b-A_HV1     GGGAAGCAGATTTGGGTACCACCCAAGTATTGACTCACCCATCAACAACCGCTATGTATT
                    *********************************************************** 

rCRS_HV1            TCGTACATTACTGCCAGCCACCATGAATATTGTACGGTACCATAAATACTTGACCACCTG
U1.003b-A_HV1       TCGTACATTACTGCCAGCCACCATGAATATTGTACGGTACCATAAATACTTGACCACCTG
L1.006a-A_HV1       TCGTACATTACTGCCAGCCACCATGAATATTGTACGGTACCATAAATACTTGACCACCTG
L1.046a+b-A_HV1     TCGTACATTACTGCCAGCCACCATGAATATTGTACGGTACCATAAATACTTGACCACCTG
                    ************************************************************

rCRS_HV1            TAGTACATAAAAACCCAATCCACATCAAAACCCCCT-CCCCATGCTTACAAGCAAGTACA
U1.003b-A_HV1       TAGTACATGAAAACCCAATCCACATCAAAACCCCCCCCCCATGCTTACAAGCAAGTACA
L1.006a-A_HV1       TAGTACATAAAAACCCAATCCACATCAAAACCCCC-TCCCCATGCTTACAAGCAAGTACA
L1.046a+b-A_HV1     TAGTACATAAAAACCCAATCCACATCAAAACCCCC-TCCCCATGCTTACAAGCAAGTACA
                    ******** **************************  ***********************

rCRS_HV1            GCAATCAACCCTCAACTATCACACATCAACTGCAACTCCAAAGCCACCCTCACCCACTA
U1.003b-A_HV1       GCAATCAACCCTCAACTATCACACATCAACTGCAACTCCAAAGCCACCCTCACCCACTA
L1.006a-A_HV1       GCAAYCAACCCYCAACTATCACACATCAACTGCAACTCCAAAGCCACCCTCACCCACTA
L1.046a+b-A_HV1     GCAATCAACCCCCAACTATCACACATCAACTGTAACTCTAAAGCCACCCTCACCCACTA
                    **** ****** ******************** ** ** ********************

rCRS_HV1            GGATACCAACAAACCTACCCACCCTTAACAGTACATACTACATAAAGCCATTTACCGTAC
U1.003b-A_HV1       GGATACCAACAAACCTACCCACCCTTAACAGTTCATACTACATAAAGCCATTTACCGTAC
L1.006a-A_HV1       GGATACCAACAAACCTACCCACCCTTAACAGTACATACYACATAAAGYCATTTACCGTAC
L1.046a+b-A_HV1     GGATACCAACAAACCTACCCACCCTTAACAGTACATACCACATAAAGCCATTTACCGTAC
                    ******************************** ***** ******** ************

rCRS_HV1            ATAGCACATTACAGTCAAATCCCTTCTCGTCCCCATGGATGACCCCCCTCAGATAGGGGT
U1.003b-A_HV1       ATAGCACATTACAGTCAA------------------------------------------
L1.006a-A_HV1       ATAGCACATTACAGTCAAATCCCTTCTCGTCCCCATGGATGACCCCCCTCAGATAGGGGT
L1.046a+b-A_HV1     ATAGCACATTACAGTCAAATCCCTTCTCGTCCCCATGGATGACCCCCCTCAGATAGGGGT
                    ******************

rCRS_HV1            CCCTTGACCACCATCCTC-  SEQ ID NO:   436
U1.003b-A_HV1       -------------------  SEQ ID NO:   335
L1.006a-A_HV1       CCCTTGACCACCATCCTCA  SEQ ID NO:   438
L1.046a+b-A_HV1     CCCTTGACCACCATCCTCA  SEQ ID NO:   438
```

FIG. 6

| dbSNP | Protein | Allele Frequency | dbSNP | Protein | Allele Frequency |
|---|---|---|---|---|---|
| rs820878 | HEXB | 0.962 | rs202074479 | PABPC1 | 0.295 |
| r1769259 | FBP1 | 0.9441 | rs7766641 | HIST1H2BE | 0.2924 |
| rs389784 | KRTAP4-2 | 0.9269 | rs8064733 | KRT40 | 0.2744 |
| rs9891361 | KRT13 | 0.9003 | rs9908304 | KRT40 | 0.2732 |
| rs6580873 | KRT81 | 0.8302 | rs1510068 | KRT40 | 0.2731 |
| rs951773 | KRT84 | 0.7529 | rs13060627 | LRRC15 | 0.2702 |
| rs9897031 | KRTAP4-11 | 0.7273 | rs7134193 | TXNRD1 | 0.2407 |
| rs2289519 | SERPINB5 | 0.6819 | rs150812789 | KRT40 | 0.2329 |
| r2857671 | KRT83 | 0.6747 | rs11657323 | KRT36 | 0.2254 |
| rs2604955 | KRT32 | 0.6445 | rs71321355 | KRTAP11-1 | 0.2098 |
| rs4602 | KRT19 | 0.6426 | rs1613931 | KRT84 | 0.1957 |
| rs349771 | KRTAP4-11 | 0.622 | rs3829598 | KRTAP3-2 | 0.1746 |
| rs2301354 | KRT36 | 0.5561 | rs78158550 | KRT37 | 0.1692 |
| rs2071601 | KRT35 | 0.555 | rs62622847 | KRTAP1-3 | 0.1622 |
| rs1049205 | PPL | 0.5535 | rs34302939 | KRTAP10-12 | 0.1438 |
| rs2013335 | KRT78 | 0.5534 | rs11649834 | KRT40 | 0.1361 |
| rs743686 | KRT35 | 0.5531 | rs2857663 | KRT83 | 0.1135 |
| rs721957 | KRT40 | 0.5253 | rs2232387 | KRT75 | 0.1107 |
| rs2071561 | KRT32 | 0.4955 | rs425784 | KRTAP4-11 | 0.1104 |
| rs1455555 | SERPINB5 | 0.4915 | rs17843015 | KRT40 | 0.1062 |
| rs1497383 | KRTAP4-5 | 0.4881 | rs3750300 | PADI3 | 0.109 |
| rs2658658 | KRT82 | 0.4835 | rs41292543 | UQCRH | 0.086 |
| rs9916724 | KRT37 | 0.4803 | rs41285000 | SELENBP1 | 0.011 |
| rs877346 | KRTAP13-2 | 0.4787 | rs1131471 | TCHH | 0.509 |
| rs2071588 | KRT81 | 0.4092 | rs214803 | TGM3 | 0.821 |
| rs2071563 | KRT32 | 0.3829 | rs56030650 | GSDMA | 0.467 |
| rs2852464 | KRT83 | 0.3821 | rs9910204 | KRT37 | 0.311 |
| rs201076736 | PABPC1 | 0.377 | rs13070515 | LRRC15 | 0.248 |
| rs3744786 | KRT32 | 0.3276 | rs12451652 | KRT35 | 0.169 |
| rs1050565 | BLMH | 0.3248 | rs10805890 | HEXB | 0.159 |
| rs1695 | GSTP1 | 0.3191 | rs41283425 | JUP | 0.063 |
| rs72830046 | KRT32 | 0.3017 | rs17678945 | KRT1 | 0.023 |

*FIG. 12B*

Examples:

1. 20 GVPs
   *p* = 5.5e-7
   1.8M 2. 30 GVPs
   *p = 4.1e-10*
   *2.4B*

| Gene Name | rs#_nuc | Peptide | SAP | af | |
|---|---|---|---|---|---|
| | | | | EUR | AFR |
| AHSG | rs35457250_C | AHYDLRHTFMGVVSLGSPSGEVSHPR | R317C | 1.00 | 1.00 |
| | rs35457250_T | AHYDLcHTFMGVVSLGSPSGEVSHPR | | 0.02 | 0.00 |
| AZU1 | rs28626600_G | CQVAGWGSQRSGGR | R158H | 0.99 | 1.00 |
| | rs28626600_A | CQVAGWGSQhSGGR | | 0.24 | 0.01 |
| CILP | rs938952_C | QGGVVASLR | G1166S | 0.36 | 0.69 |
| | rs938952_T | QsGVVASLR | | 0.97 | 0.84 |
| COL1A2 | rs42524_C | GEQGPPGPPGFQGLPGPSGPAGEVGKPGER | P549A | 0.43 | 0.18 |
| | rs42524_G | GEQGPaGPPGFQGLPGPSGPAGEVGKPGER | | 0.95 | 0.99 |
| COL1A2 | rs139851311_G | GPQGHQGPAGPPGPPGPPGPPGVSGGGYDFGYDGDFYR | S1105A | 1.00 | 1.00 |
| | rs139851311_A | GPQGHQGPAGPPGPPGPPGPPGVaGGGYDFGYDGDFYR | | 0.00 | 0.00 |
| COL3A1 | rs1800255_G | GGAGPPGPEGGK | A698T | 0.94 | 0.99 |
| | rs1800255_A | GGtGPPGPEGGK | | 0.47 | 0.20 |
| COL4A4 | rs3752895_A | GPSGPGCK | S1403P | 0.82 | 0.58 |
| | rs3752895_G | GPpGPGCK | | 0.69 | 0.87 |
| COL9A3 | rs751557_C | GPGGAAGPK | A435E | 0.96 | 0.78 |
| | rs751557_A | GPGGAeGPK | | 0.39 | 0.68 |
| CTSG | rs45567233_T | NVNPVALPR | N125S | 0.99 | 1.00 |
| | rs45567233_C | NVsPVALPR | | 0.14 | 0.05 |
| ENO3 | rs238238_A | AVENINNTLGPALLQK | N71S | 0.54 | 0.71 |
| | rs238238_G | AVENINsTLGPALLQK | | 0.90 | 0.81 |
| MPO | rs2759_T | IICDNTGITTVSKNNIFMSNSYPR | I717V | 1.00 | 1.00 |
| | rs2759_C | IICDNTGITTVSKNNvFMSNSYPR | | 0.06 | 0.02 |
| MPO | rs56378716_A | SLMFMQWGQLLDHDLDFTPEPAAR | M215T | 1.00 | 1.00 |
| | rs56378716_G | SLtFMQWGQLLDHDLDFTPEPAAR | | 0.03 | 0.00 |
| SERPINA1 | rs1303_T | FNKPFVFLMIEQNTKSPLFMGK | E400D | 0.93 | 0.99 |
| | rs1303_G | FNKPFVFLMIdQNTKSPLFMGK | | 0.43 | 0.17 |
| SERPINF1 | rs1804145_C | ALYYDLISSPDIHGTYKELLDTVTAPQK | P132R | 1.00 | 1.00 |
| | rs1804145_G | ALYYDLISSPDIHGTYKELLDTVTAr | | 0.07 | 0.00 |
| SERPINF1 | rs1136287_C | SSTSPTTNVLLSPLSVATALSALSLGAEQR | T72M | 0.57 | 0.23 |
| | rs1136287_T | SSmSPTTNVLLSPLSVATALSALSLGAEQR | | 0.87 | 0.99 |
| STOM | rs41273438_A | NSTIVFPLPIDMLQGIIGAK | M275T | 1.00 | 1.00 |
| | rs41273438_G | NSTIVFPLPIDtLQGIIGAK | | 0.07 | 0.01 |
| TF | rs1049296_C | KPVEEYANCHLAR | P589S | 0.98 | 1.00 |
| | rs1049296_T | KsVEEYANCHLAR | | 0.26 | 0.12 |

FIG. 16

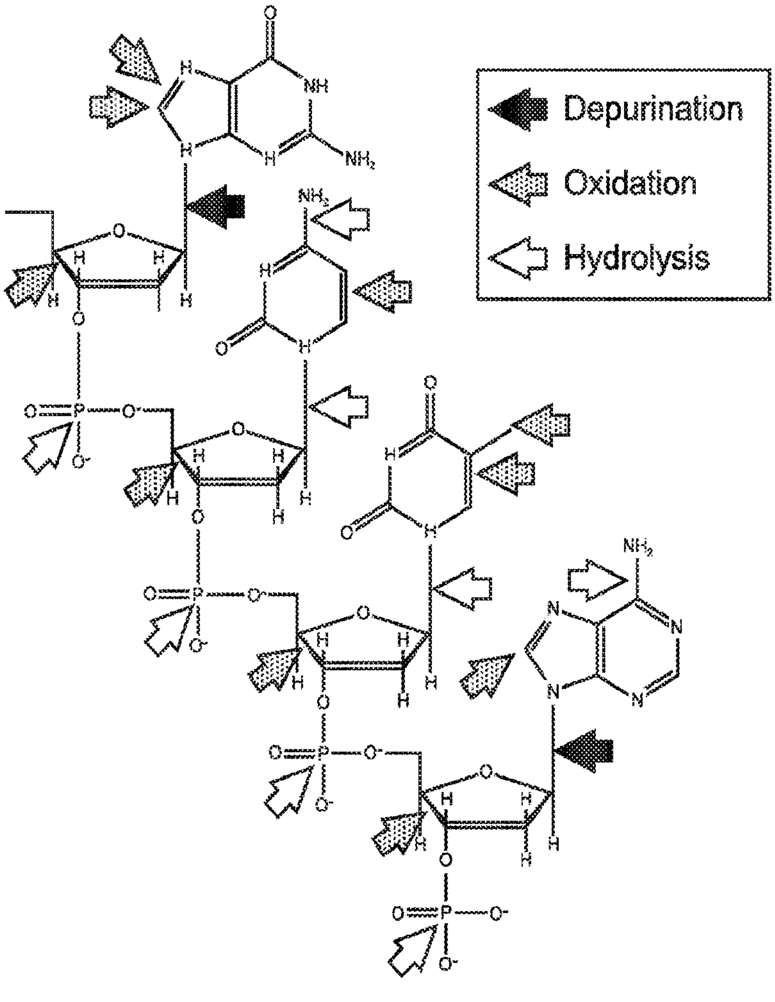
DNA
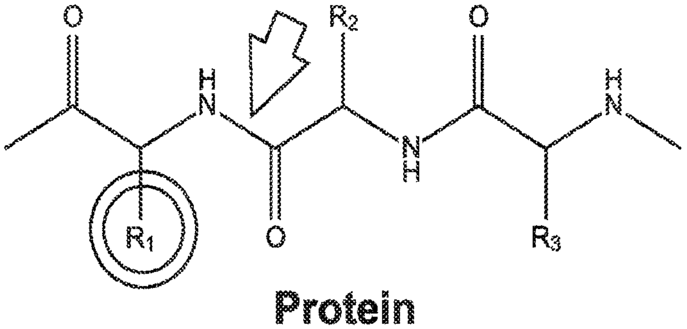
Protein
*FIG. 19*

| Category | Count |
|---|---|
| Variants processed | 863 |
| Variants filtered out | 0 |
| Novel / existing variants | 107 (12.4) / 756 (87.6) |
| Overlapped genes | 584 |
| Overlapped transcripts | 2952 |
| Overlapped regulatory features | 137 |
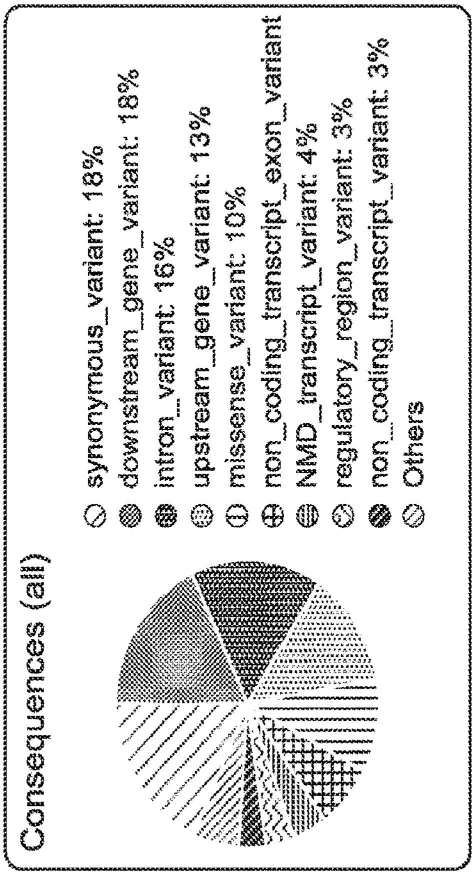
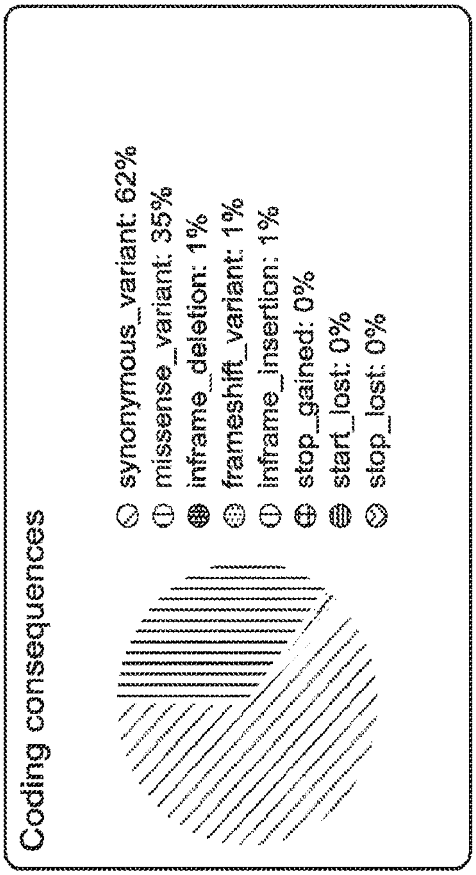
FIG. 32

<table>
<tr><th>Protein Group</th><th>Protein Accession</th><th>Peptide</th><th>Unique</th><th>RT</th><th>Area</th><th>Scan</th><th>Start</th><th>End</th></tr>
<tr><td>10</td><td>O76011-201|KRT34m</td><td>E.KETMQ(+.98)FLNDR.L</td><td>N</td><td>49.36</td><td>NA</td><td>20284</td><td>99</td><td>108</td></tr>
<tr><td>10</td><td>O76011-201|KRT34m</td><td>R.DSLENTLTESEAHYSSQ(+.98)LSQVQSLITNVESQLAEIR.C</td><td>N</td><td>96.1</td><td>37400</td><td>45296</td><td>336</td><td>371</td></tr>
<tr><td>10</td><td>O76011-201|KRT34m</td><td>R.TSC(+57.02)SSRPC(+57.02)V.P</td><td>N</td><td>21.92</td><td>1260000</td><td>7130</td><td>56</td><td>64</td></tr>
<tr><td>11</td><td>O76011|KRT34_HUMAN</td><td>R.TVNALEIELQAQHNLRDSLENTLTESEAHYSSQLSQVQSLITNVESQLAEIR.C</td><td>N</td><td>94.81</td><td>50500000</td><td>44602</td><td>320</td><td>371</td></tr>
<tr><td>11</td><td>O76011|KRT34_HUMAN</td><td>R.EVEQWFATQTEELNKQVVSSSEQLQSC(+57.02)QAEIIELR.R</td><td>N</td><td>91.42</td><td>NA</td><td>42673</td><td>284</td><td>318</td></tr>
<tr><td>11</td><td>O76011|KRT34_HUMAN</td><td>R.RTVNALEIELQAQHNLRDSLENTLTESEAHYSSQLSQVQSLITNVESQLAEIR.C</td><td>N</td><td>94.42</td><td>NA</td><td>44385</td><td>319</td><td>371</td></tr>
<tr><td>11</td><td>O76011-201|KRT34</td><td>R.TVNALEIELQAQHNLRDSLENTLTESEAHYSSQLSQVQSLITNVESQLAEIR.C</td><td>N</td><td>94.81</td><td>5.05E+07</td><td>44602</td><td>320</td><td>371</td></tr>
<tr><td>11</td><td>O76011-201|KRT34</td><td>R.EVEQWFATQTEELNKQVVSSSEQLQSC(+57.02)QAEIIELR.R</td><td>N</td><td>91.42</td><td>NA</td><td>42673</td><td>284</td><td>318</td></tr>
<tr><td>11</td><td>O76011-201|KRT34</td><td>R.RTVNALEIELQAQHNLRDSLENTLTESEAHYSSQLSQVQSLITNVESQLAEIR.C</td><td>N</td><td>94.42</td><td>NA</td><td>44385</td><td>319</td><td>371</td></tr>
</table>

FIG. 34

| symbol | dbSNP | MAT | mut | ExAF | ExAF.NFE | L4_00... |
|---|---|---|---|---|---|---|
| KRTAP10-4 | 21g.44637696_44637710del | | 275delCCVPV | 8.24E-06 | 0 | 43 |
| KRT10 | rs148510452 | X | 24delG | 8.24E-06 | 1.87E-05 | 56 |
| HIST1H1E | rs757147711 | | A68V | 1.65E-05 | 0 | 01, 03 |
| KRT82 | rs377470048 | | A243T | 5.77E-05 | 0 | 22, 24 |
| POTEF | rs762202335 | | G723S | 0.0001018 | 0.000235 | 45 |
| RIDA | rs146537203 | | A114V | 0.0001565 | 0.0002854 | 30 |
| HSPA2 | rs140108798 | | M62V | 0.0003706 | 0.0006301 | 34 |

FIG. 35

| | dbSNP | Location | allele | symbol | ENSG | ENST | effect | AA_pos | A.A |
|---|---|---|---|---|---|---|---|---|---|
| 230 | 1:g.161525687A>T | 1:161525687 | T | HSPA6 | ENSG00000173110 | ENST00000309758 | synonymous | 34 | T |
| 234 | rs404508 | 1:161526095 | C | HSPA6 | ENSG00000173110 | ENST00000309758 | synonymous | 479 | T |
| 238 | rs2268147 | 1:201283738 | T | PKP1 | ENSG00000081277 | ENST00000263946 | synonymous | 12 | Y |
| 239 | rs2268147 | 1:201283738 | T | PKP1 | ENSG00000081277 | ENST00000352845 | synonymous | 12 | Y |
| 240 | rs2268147 | 1:201283738 | T | PKP1 | ENSG00000081277 | ENST00000367324 | synonymous | 12 | Y |
| 242 | rs35507614 | 1:201313445 | G | PKP1 | ENSG00000081277 | ENST00000263946 | missense | 196 | I/V |
| 243 | rs35507614 | 1:201313445 | G | PKP1 | ENSG00000081277 | ENST00000352845 | missense | 196 | I/V |
| 244 | rs35507614 | 1:201313445 | G | PKP1 | ENSG00000081277 | ENST00000367324 | missense | 196 | I/V |
| 246 | rs1419114 | 1:203683316 | G | ATP2B4 | ENSG00000058668 | ENST00000341360 | synonymous | 37 | S |

| | codon | GMAF | EUR_MAF | ExAC_AF | ExAC_NFE_AF | appris | tranID | query | ref | alt | QUAL | filt | DP | GT | GATK | GQ | ID |
|---|---|---|---|---|---|---|---|---|---|---|---|---|---|---|---|---|---|
| 230 | acA/acT | - | - | - | - | P1 | 201 | P17066 | A | T | 180.80 | PASS | 7 | 1,1 | 1,1 | 21 | 52 |
| 234 | acT/acC | 0.8011 | 0.7883 | 0.770 | 0.7535 | P1 | 201 | P17066 | T | C | 1400.77 | PASS | 52 | 1,1 | 1,1 | 99 | 53 |
| 238 | taC/taT | 0.1803 | 0.0716 | 0.120 | 0.089 | N | 201 | Q13835 | C | T | 4106.77 | PASS | 146 | 1,1 | 1,1 | 99 | 54 |
| 239 | taC/taT | 0.1803 | 0.0716 | 0.120 | 0.089 | N | 202 | Q13835 | C | T | 4106.77 | PASS | 146 | 1,1 | 1,1 | 99 | 55 |
| 240 | taC/taT | 0.1803 | 0.0716 | 0.120 | 0.089 | P1 | 203 | Q13835 | C | T | 4106.77 | PASS | 146 | 1,1 | 1,1 | 99 | 56 |
| 242 | Ata/Gta | 0.1038 | 0.0616 | 0.063 | 0.08494 | N | 201 | Q13835 | A | G | 166.77 | PASS | 34 | 0,1 | 0,1 | 99 | 57 |
| 243 | Ata/Gta | 0.1038 | 0.0616 | 0.063 | 0.08494 | N | 202 | Q13835 | A | G | 166.77 | PASS | 34 | 0,1 | 0,1 | 99 | 58 |
| 244 | Ata/Gta | 0.1038 | 0.0616 | 0.063 | 0.08494 | P1 | 203 | Q13835 | A | G | 166.77 | PASS | 34 | 0,1 | 0,1 | 99 | 59 |
| 246 | tcA/tcG | 0.85 | 0.8976 | 0.876 | 0.8862 | N | 201 | P23634 | A | G | 2253.77 | PASS | 74 | 1,1 | 1,1 | 99 | 60 |

....

FIG. 36

| CHR | START | END | rsID | ref | alt | QUAL | filt | DP | GT | GATK | GQ | ZZ | | | |
|---|---|---|---|---|---|---|---|---|---|---|---|---|---|---|---|
| 17 | 51154159 | | 51154160 | | <NA> | CT | C | 67.73 | INDEL | 71 | 0,1 | 0,1 | 99 | 17:g.51154160del | |
| 17 | 75948558 | | 75948558 | | <NA> | C | CT | 50.73 | INDEL | 135 | 0,1 | 0,1 | 88 | 17:g.75948558_75948559insT | |
| 17 | 40701742 | | 40701743 | | <NA> | TA | T | 398.73 | PASS | 110 | 0,1 | 0,1 | 99 | 17:g.40701743del | |
| ... | | | | | | | | | | | | | | | |
| 8 | 143729168 | | 143729168 | | rs9969600 | | C | G | 1762.7 | PASS | 63 | 1,1 | 1,1 | 99 | 8:g.143729168C>G |
| 2 | 131218699 | | 131218699 | | rs9973941 | | G | C | 81.03 | PASS | 4 | 1,1 | 1,1 | 12 | 2:g.131218699G>C |
| 21 | 44628008 | | 44628008 | | rs9979457 | | G | T | 2470.7 | PASS | 93 | 1,1 | 1,1 | 99 | 21:g.44628008G>T |

FIG. 37

| chr | start | end | wid | names | symbol | ref | alt | QUAL | filt | DP | GT | GATK | GQ | | | | |
|---|---|---|---|---|---|---|---|---|---|---|---|---|---|---|---|---|---|
| 18 | 28572003 | | 28572003 | | 1 | 109492 | HIST1H2AC | | C | T | 196.77 | PASS | 11 | 0,1 | 0,1 | 50 | -- *note* |
| *poor DP* | | | | | | | | | | | | | | | | | |
| 18 | 28572141 | | 28572143 | | 3 | 109493 | HIST1H2AC | | AGG | A | 234.73 | PASS | 40 | 0,1 | 0,1 | 99 | -- *note* |
| *deletion* | | | | | | | | | | | | | | | | | |
| 18 | 28577109 | | 28577109 | | 1 | 109495 | HIST1H2AC | | T | TATTC | 789.73 | PASS | 48 | 0,1 | 0,1 | 99 | -- *note* |
| *insertion* | | | | | | | | | | | | | | | | | |
| 18 | 28611139 | | 28611139 | | 1 | 109496 | HIST1H2AC | | A | C | 7358.77 | | PASS | 227 | 1,1 | 1,1 | 99 |
| 18 | 28906461 | | 28906461 | | 1 | 109515 | FAM83H | | G | A | 11952.80 | | PASS | 269 | 1,1 | 1,1 | 99 |
| 12 | 55038408 | | 55038409 | | 2 | 81706 | GAPDHS | | AT | A | 159.73 | PASS | 18 | 1,1 | 1,1 | 1 | -- *note* |
| *poor GQ* | | | | | | | | | | | | | | | | | |

....

DP read depth

Qual measure of goodness of mutation call (per GATK specifications)

GQ measure of goodness of genotype call (per GATK specifications)

FIG. 38

| chr | start | end | wid | names | symbol | ref | alt | QUAL | filt | DP | GT | GATK | GQ | | |
|---|---|---|---|---|---|---|---|---|---|---|---|---|---|---|---|
| | 12 | 112638688 | | 112638692 | | 5 | 97906 | HECTD4CGTGT | | C,CGT | 627.73 | PASS | 27 | 1,2 | 1,2 |
| | 99 | | | | | | | | | | | | | | |
| | 10 | 73583573 | | 73583573 | | 1 | 78661 | PSAP | C | CA,CAA | 1017.73 | | PASS | 78 | 1,2 |
| | 1,2 | 99 | | | | | | | | | | | | | |
| | 10 | 120796572 | | 120796573 | | 2 | 81096 | EIF3A | TC | T,TCC | 571.73 | PASS | 42 | 1,2 | 1,2 |
| | 99 | | | | | | | | | | | | | | |
| | 18 | 61166280 | | 61166280 | | 1 | 130347 | SERPINB5 | | G | GTATATA,GTATATATA | | | 936.73 | |
| | PASS | 34 | 1,2 | 1,2 | 99 | | | | | | | | | | |

GATK = 0, 1, 2 means the state is given by REF, ALT1, ALT2 respectively many such cases are intron variants (but not all)

FIG. 39

METHODS AND SYSTEMS TO PERFORM GENETICALLY VARIANT PROTEIN ANALYSIS, AND RELATED MARKER GENETIC PROTEIN VARIATIONS AND DATABASES

The present application is the U.S. National Stage of International Patent Application No. PCT/US2018/049775 filed on Sep. 6, 2018 which claims priority to U.S. Provisional Application No. 62/555,001, entitled "Methods and Systems to Perform Genetically Variant Protein Analysis, and Related Marker Genetic Protein Variations and Databases" filed on Sep. 6, 2017, the content of each of which is incorporated herein by reference in its entirety.

STATEMENT OF INTEREST

The invention was made with Government support under Contract No. DE-AC52-07NA27344 between the U.S. Department of Energy and Lawrence Livermore National Security, LLC, for the operation of Lawrence Livermore National Security. The Government may have certain rights to the invention.

FIELD

The present disclosure relates to analysis of genetic variations in individuals, and in particular to the preparation and analysis of biological samples for identification and/or detection of markers genetic information in biological material.

BACKGROUND

Use of biological material to answer questions pertaining to legal situations, including criminal and civil cases, has rapidly integrated traditional techniques of forensic science that depend on qualitative expert opinion.

In particular, DNA and protein analysis provide techniques which constitute evidence with a sound scientific footing.

Despite the progress made in this field, challenges remain to develop methods of genetic variation analysis resulting in reliable results from a broad spectrum of biological samples, and in particular to develop methods of genetic variation analysis which minimize false positive and/or false negative results due to the specific features of the biological sample where the investigation is performed.

SUMMARY

Provided herein are methods and systems to perform genetically variant protein analysis and related marker genetic protein variations and databases, which in several embodiments allow performing a reliable genetic variation protein analysis in biological samples of different types and conditions taking into account the features of the biological sample where the analysis is performed.

In particular, in several embodiments, the methods and systems and related marker genetic protein variations and databases herein described comprise and/or use marker genetic protein variations validated to be detectable in the biological sample where the genetic protein variation analysis is performed. In several embodiments, the methods and systems and related marker genetic protein variations and databases herein described use preparation methods which maximize recovery of processable protein from such biological sample.

According to a first aspect, a method to prepare a biological sample for proteomic analysis, is described. The method comprises applying to the biological sample an energy field to obtain a processed biological sample comprising solubilized proteins to be used in the proteomic analysis. In some preferred embodiments, applying to the biological sample an energy field is performed by sonication with an energy field ranging from 150 to 1,200 Watts and frequency ranging from 20 to 80 kHz. In another embodiment microwave energy of up to 1,200 Watts can be used to obtain a processed biological sample comprising solubilized proteins.

According to a second aspect, a method and system are described to provide a marker genetic protein variation for a biological organism and a marker genetic protein variation obtainable thereby. In the method and system, the provided marker genetic protein variation is validated to be detectable in a biological sample of an individual of the biological organism.

The method comprises: providing a marker exome sequence of the biological organism, the marker exome sequence comprising a marker genetic variation for the biological organism.

The method further comprises detecting peptide sequences in the biological sample of the individual of the biological organism by performing proteomic analysis of said biological sample to provide proteomically detected peptide sequences.

The method also comprises providing the marker genetic protein variation for the biological organism detectable in the sample of the biological organism by comparing the provided marker exome sequence with the proteomically detected peptide sequences to provide the marker genetic protein variation validated to be detectable in the biological sample of an individual of the biological organism.

The system comprises exome sequences databases and/or reagents to detect exome sequences in an individual of the biological organism, in combination with reagents to perform proteomic analysis of the biological sample for simultaneous combined or sequential use in the method to provide a marker genetic protein variation validated for a biological sample herein described.

According to a third aspect, a method and system to detect a marker genetic protein variation in a biological sample are described. In the method and system, the marker genetic protein variation validated to be detectable in the biological sample.

The method comprises providing a marker mass spectrum of a marker peptide comprising a marker genetic protein variation corresponding to the genetic protein variation; and performing mass spectrometry of a fractionated digested peptide of the biological sample to obtain a mass spectrum of each of the fractionated digested peptide.

The method further comprises comparing the mass spectrum of the fractionated digested peptide with the marker mass spectrum of a marker peptide comprising the marker genetic protein variation to detect the genetic protein variation in the biological sample.

The system comprises protein databases, and/or reagents to perform proteomic analysis of the biological sample in combination with exome sequence databases for simultaneous combined or sequential use in the method to detect a marker genetic protein variation in a biological sample herein described.

According to a fourth aspect, a method and system to improve a marker genetic protein variation database system for a biological organism, and a database obtainable thereby, are described. In the method, system and database herein described, the marker genetic protein variation database system includes data for at least one biological organism and the improvement is the inclusion of one or more marker genetic protein validated to be detectable in a biological sample from an individual of the at least one biological organism.

The method comprises: producing a proteomic dataset from a biological sample from an individual of the at least one biological organism and comparing the proteomic dataset to a protein variant database to produce a set of proteomically detected proteins in the biological sample of the individual.

The method further comprises providing a set of represented genes proteomically detectable in the biological sample of the individual, the represented genes corresponding to the proteomically detected proteins in the biological sample of the individual.

The method also comprises: identifying a marker genetic protein variation validated for the biological sample of the individual, to be included in the marker genetic protein variation database system by providing a proteomically detectable genomic variation in the set of represented genes proteomically detectable in the biological sample of the individual, and providing the marker genetic protein variation validated for the biological sample by providing a proteomically detectable genetic protein variation corresponding to the detectable genomic variation in the biological sample of the individual.

The system comprises protein databases, and/or reagents to perform proteomic analysis of the biological sample in combination with exome sequence databases for simultaneous combined or sequential use in the method to improve a marker genetic protein variation database system for a biological organism herein described.

According to a fifth aspect, a method and system to improve a pooled marker genetic protein variation database system and a pooled marker genetic protein variation database obtainable thereby. In the method and system and related database, the pooled marker genetic protein variation database system comprising marker genetic protein variations common to a plurality of individuals.

The method comprises: providing a number of proteomic datasets of individuals of the plurality of individuals, the number statistically significant for the plurality of individuals, identifying a protein common to the provided number of proteomic datasets; and selecting from the identified protein common to the provided proteomic datasets, a protein detectable in a biological sample of an individual of the plurality of individuals.

The method further comprises providing a number of exome datasets of the individuals of the plurality of individuals, the number statistically significant for the plurality of individuals; and identifying a genetic variation in the provided number of exome datasets.

The method also comprises selecting from the identified genetic variation, a genetic variation detectable in the biological sample; and comparing the selected proteins detectable in the biological sample with the selected genetic variations detectable in the biological sample, to provide a marker genetic protein variation common to a plurality of individuals of a biological organism type and validated to be detectable in the biological sample.

The system comprises protein databases, and/or reagents to perform proteomic analysis of the biological sample in combination with exome sequence databases for simultaneous combined or sequential use in the method to improve a pooled marker genetic protein variation database system for a biological organism herein described.

According to a sixth aspect, a method and a system are described to detect a marker genetic variation for a biological organism validated to be detectable in a biological sample of an individual of the biological system.

The method comprises preparing the biological sample to obtain a processed biological sample comprising solubilized proteins to be used in a proteomic analysis; and fractionating the processed biological sample to obtain a solubilized protein fraction comprising the solubilized proteins from the sample and a solubilized DNA fraction comprising solubilized nuclear and/or mitochondrial genome from the sample.

The method further comprises detecting a genetic protein variation in the solubilized proteins from the sample by performing the proteomic analysis of the solubilized protein fraction; and detecting a genomic variation of the nuclear and/or mitochondrial genome by performing a genetic analysis of the solubilized DNA fraction.

The method also comprises comparing the detected genetic protein variation and/or the detected genomic variation with a marker genetic protein variation and/or of a marker genomic variation respectively from the marker genetic variation database system herein described.

The system comprises exome sequences databases and/or reagents to detect exome sequences in an individual of the biological organism, in combination with reagents to perform proteomic analysis of the biological sample for simultaneous combined or sequential use in the method to detect a marker genetic variation for a biological organism validated to be detectable in a biological sample of an individual of the biological system herein described.

According to a seventh aspect, a method to provide a marker genetic variation database system comprising marker genetic variation validated to be detectable in a biological sample, the method comprises preparing the biological sample to obtain a processed biological sample comprising solubilized proteins to be used in a proteomic analysis.

The method further comprises fractionating the processed biological sample to obtain a solubilized protein fraction comprising the solubilized proteins from the sample and a solubilized DNA fraction comprising solubilized nuclear and/or mitochondrial genome from the sample.

The method also comprises detecting a genetic protein variation in the solubilized proteins from the sample by performing the proteomic analysis of the solubilized protein fraction and detecting a genomic variation of the nuclear and/or mitochondrial genome by performing a genetic analysis of the solubilized DNA fraction.

The method additionally comprises combining the detected genetic protein variations and the detected genomic variation to provide the marker genetic variation database system comprising marker genetic variation validated to be detectable in a biological sample.

The system comprises protein databases, and/or reagents to perform proteomic analysis of the biological sample in combination with exome sequence databases for simultaneous combined or sequential use in the method to provide the marker genetic variation database system comprising marker genetic variation validated to be detectable in a biological sample herein described.

According to an eight aspect, a method and system are described to perform genetic analysis of a sample of a biological organism.

The method comprises preparing the biological sample to obtain a processed biological sample comprising solubilized proteins to be used in a proteomic analysis, and fractionating the processed biological sample to obtain a solubilized protein fraction comprising the solubilized proteins from the sample.

The method also comprises digesting the solubilized proteins from the sample with a site specific proteolytic enzyme to obtain digested solubilized proteins from the sample; fractionating the digested solubilized proteins to obtain fractionated digested peptides from the digested solubilized proteins from the biological sample and detecting a marker genetic variation of the fractionated digested peptides.

In the method, preparing the sample and/or detecting a genetic variation can be performed by any one of the methods according to any one of the first aspect to the seventh aspect of the instant disclosure. In particular, in methods according to the eighth aspect the preparing is performed by any one of the methods according to the first aspect herein described; and/or the detecting is performed by at least one of a first detecting method wherein the detecting is performed by any one of the methods according to the third aspect of the present disclosure; and a second detecting method wherein the detecting is performed by any one of the methods according to the sixth aspect of the present disclosure.

The system comprises exome sequences databases and/or reagents to detect exome sequences in an individual of the biological organism, in combination with reagents to perform proteomic analysis of the biological sample for simultaneous combined or sequential use in the method to perform genetic analysis of a sample of a biological organism herein described.

In preferred embodiments of the marker genetic protein variations, databases, methods and systems and related genetic protein variation analysis herein described, performing a proteomic analysis is carried out by performing mass spectrometry of a fractionated digested peptide of the biological sample to obtain a mass spectrum of each of the fractionated digested peptide.

In further preferred embodiments of the marker genetic protein variations, databases, methods and systems and related genetic protein variation analysis herein described, the sample is hair and/or skin.

The methods and systems and related marker genetic protein variations and databases herein described, allow in several embodiments performing a reliable genetic variation protein analysis in degraded samples, in samples from multiple contributors, in samples where genetic material is not present in detectable amounts, and/or in samples where the genetic material and/or protein material are present in low amounts, the reliable analysis performed.

In particular, the methods and systems and related marker genetic protein variations and databases herein described, allow in several embodiments to provide a sample for proteomic analysis with a reduced presence of fragments resulting from uncontrolled breaking of the protein, not due to the enzymatic digestion (e.g. through trypsin digestion).

Accordingly, the methods and systems and related marker genetic protein variations and databases herein described, allow in several embodiments performing proteolysis on samples including a small amount of processable material (e.g. single hair but also other kind of tissues possibly available in small amounts).

Additionally, the methods and systems and related marker genetic protein variations and databases herein described allow in several embodiments to provide a sample for proteomic analysis comprising a more representative/more complete detection of proteins present in the tissue sample per mass of tissue sample.

The methods and systems and related marker genetic protein variations and databases herein described, further allow, in several embodiments, to providing and/or using improved databases in view of inclusion of marker genetic protein variations validated for the biological sample where the genetic protein variation analysis is performed.

Accordingly, the methods and systems and related marker genetic protein variations and databases herein described, also allow, in several embodiments, to reduce false negatives present in databases built with a proteome-based discovery process.

Additionally, the methods and systems and related marker genetic protein variations and databases herein described which are based on marker genetic variation validated to be detectable in the biological sample of interest, also allow, in several embodiments, to provide and/or use a database customizable with validated markers genetically variant protein for an individual, a biological organisms or types of biological organism in accordance with the experimental design and particular query.

Furthermore, the methods and systems and related marker genetic protein variations and databases herein described, also allow, in several embodiments, to perform genetically variant protein analysis without the need of the “needle in a haystack” approach, in view of the ability to use proteomics to screen with validated marker genetic protein variation for an individual, alone or in combination with marker genomic variation (in nuclear and/or mitochondrial genomes), thus having a faster and reliable response to a specific query with respect to available methods to perform genetic variation analysis known to a skilled person.

Additionally, in view of the use of marker genetic protein variation validated for a biological sample analyzed, the methods and systems and related marker genetic protein variations and databases herein described, also allow, in several embodiments, to perform genetically variant protein analysis without the need to go through databases to obtain an output (even if such step could still be performed).

In view of the ability to perform combined analysis of genetic protein variation and nuclear and/or, preferably, mitochondrial genomic variation, the methods and systems and related marker genetic protein variations and databases herein described, also allow, in several embodiments, to provide a more accurate response to a query/increased ability to discriminate identity based on combined metrics from genetic protein variation and genomic variation following verification of proteomic as well as of genomic markers from a single biological sample (e.g. genomic mitochondrial markers herein also mtDNA markers).

In general, embodiments of the methods and systems and related marker genetic protein variations and databases herein described, which are based on at least one of the sample preparation methods herein described, the marker genetic protein variation validated for a specific sample herein described, and/or the combined analysis of genetic protein variation with nuclear and/or mitochondrial genomic variation herein described, provide a faster and/or more reliable genetic variation analysis for a specific biological sample with respect to methods, systems and databases available for a skilled person.

The methods and systems and related marker genetic protein variations and databases herein described, can be used in connection with various applications wherein an improved ability to perform genetic variation analysis of a biological sample is desired. For example, the methods and systems and related marker genetic protein variations and databases herein described can be used in several applications of forensic analysis, such as identification of individuals, biological organisms types and biological organism of interest from a biological sample, determining relatedness of individuals, paternity testing and additional forensic analysis applications identifiable by a skilled person. Additional exemplary applications include uses of the methods and systems in several fields wherein genetic variation analysis can be used including basic biology research, applied biology, bio-engineering, medical research, medical diagnostics, therapeutics, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIGS. 1A-1B show diagrams illustrating an exemplary individual identification using genetically variant protein analysis. FIG. 1A shows schematics illustrating the difference between a variant gasdermin (SEQ ID NOs: 1 and 2) with respect to a reference gasdermin wherein the gasdermin gene is GSDMA and the variant gasdermin is SNP=rs56030650. FIG. 1B (2 parts) illustrates an exemplary database including the SNP=rs56030650 and other variants in digested peptides (SEQ ID Nos: 3 to 85); together with the related frequency.

FIG. 3 shows a diagram illustrating a protein coverage heat maps (Panel A), protein coverage improvement in terms of number of amino acids detected (Panel B), number of protein identification (Panel C) and number of unique peptide identifications (Panel D) for sample preparations performed with conventional methods (indicated as "Bulk hair" or "Old Single Hair") and with sample preparation methods herein described (indicated as "Single Hair" or "New Single Hair").

FIG. 5A shows an exemplary mitochondrial genome (top) and exemplary primers for the related PCR/amplification (SEQ ID Nos. 136 to 143) (bottom). FIG. 5B shows photographs taken under ultraviolet light exposure of exemplary agarose gels stained with ethidium bromide showing DNA bands corresponding to amplicons of mtDNA haplogroup HV regions indicated in each lane of the gels, alongside a molecular size standard (indicated as "1 kb+Ladder"). In FIG. 5B, the mtDNA extract used for the amplification of the DNA bands shown was recovered from samples processed for both protein extraction and mtDNA extraction, as indicated in FIG. 4.

FIG. 6 shows DNA sequences of exemplary haplogroup HV mtDNA regions (SEQ ID NOS: 87 TO 90) using mtDNA extracts recovered from samples processed for both protein extraction and mtDNA extraction, as indicated in FIG. 4. In FIG. 6, the black boxes indicate exemplary SNPs identified in the sequences.

FIGS. 12A-12B show a schematic approach for the construction of a common GVP identity Panel comprising validated marker genetic protein variations common to individuals of an exemplary biological organism types according to the disclosure (FIG. 12A) and an exemplary panel obtainable thereby (FIG. 12B).

FIG. 16 shows an exemplary validated GVP identity panel (SEQ ID NOS: 91 to 124) for bone samples obtainable with the top-down approach herein described.

FIG. 19 shows exemplary diagrams of DNA and protein chemical structures, showing sites of depurination (solid-black arrow), oxidation (shaded arrow), or hydrolysis (hollow arrow).

FIGS. 31 to 39 illustrate exemplary steps of a method to perform genetic variation protein analysis for a sample tissues using databases (such as the panel of FIG. 34 SEQ ID NOS: 125 to 133), methods and systems herein described.

DETAILED DESCRIPTION

Provided herein are methods and systems to perform genetically variant protein analysis and related marker genetic protein variations and databases, which in several embodiments allow performing of a reliable genetic variation protein analysis in biological samples of different types and under different conditions, taking into account the features of the biological sample for which the analysis is performed.

The term "genetic variation" as used herein refers to diversity in gene frequencies and/or in gene sequences. In particular, genetic variation as used herein can refer to genes that are translated into corresponding proteins, which can result in diversity in corresponding protein frequency. Genetic variation in the sense of the disclosure can refer to differences between individuals or to differences between populations. Mutation is the ultimate source of genetic variation, but mechanisms such as sexual reproduction and genetic drift contribute to it as well.

Genetic variations in the sense of the disclosure comprise genomic variations (genetic variations in nuclear or mitochondrial DNA of individuals), and genetic protein variations (genetic variations within a genetically variant protein encoded by a non-synonymous variation in the protein coding region of the corresponding encoding gene).

Figure 1A:
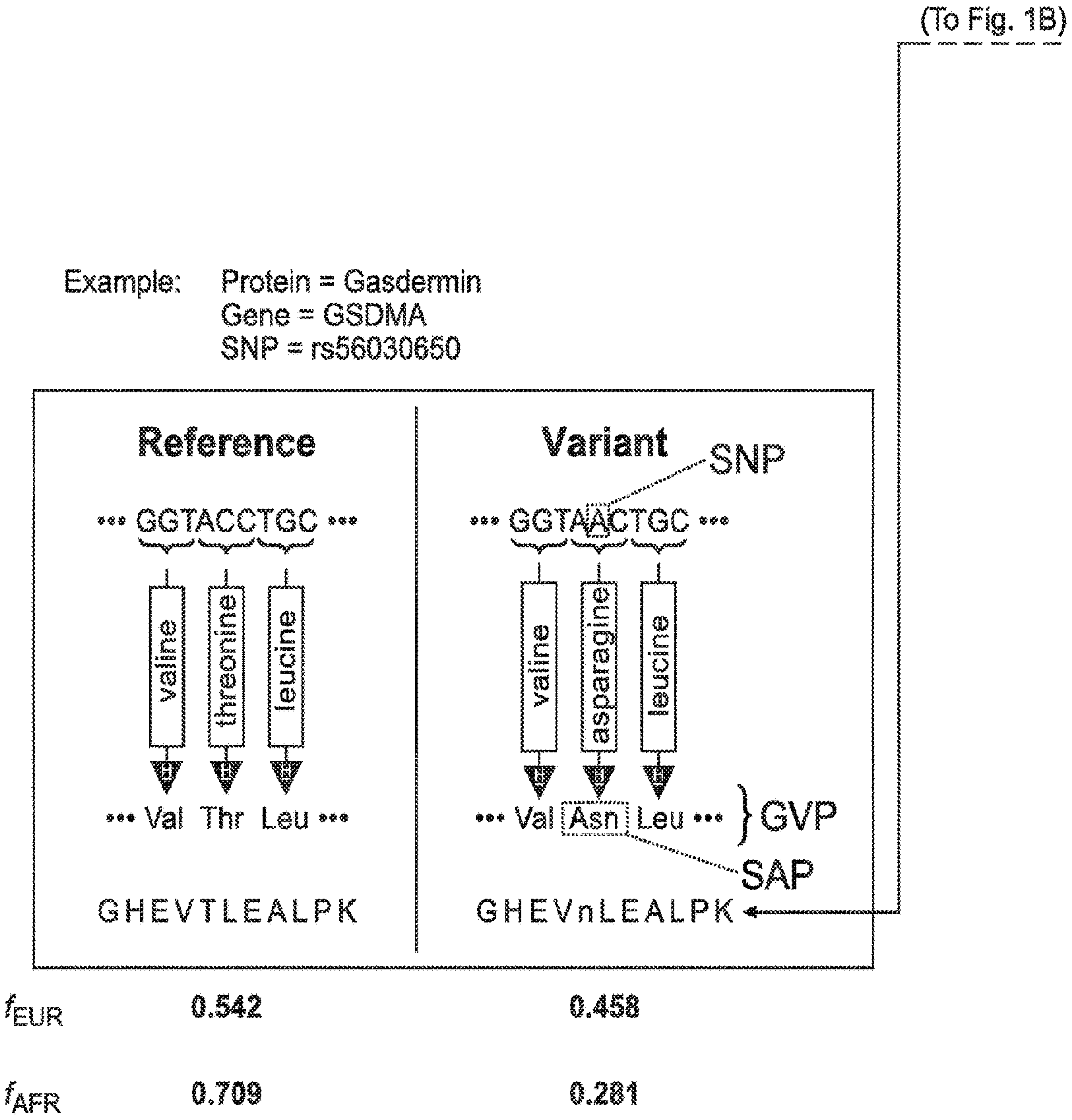

Accordingly, the term "genetically variant protein", or "GVP" as used herein refers to a protein encoded by a gene, wherein variants of the protein have a variation (e.g. a single amino acid polymorphisms (SAPs)) that is encoded by non-synonymous variation (e.g. a single nucleotide polymorphisms (nsSNPs)) in the protein-coding region of the gene (e.g., see FIGS. 1A-1B).

The term "single amino acid polymorphisms (SAPs))" refers to named amino acid variances derived from SNPs within coding regions. SAP can be quantitatively or qualitatively detected at the proteome level, with non-targeted or targeted proteomics as will be understood by a skilled person.

The term "single nucleotide polymorphism" or "SNP" refers to a variation in a single nucleotide that occurs at a specific position in the genome of an organism, where each variation occurs at a particular frequency within a population of the organism. For example, at a specific base position in the human genome, the base C appears in most individuals, but in a minority of individuals, the position is occupied by base A. There is a SNP at this specific base position, and the two possible nucleotide variations—C or A—are said to be alleles for this base position. SNPs can occur within protein-coding sequences of genes, non-coding regions of genes, or in the intergenic regions (regions between genes). The term "protein-coding" region, also referred to herein as the "coding region", "coding DNA sequence" or "CDS" as used herein refers to the portion of a gene's DNA or RNA, composed of exons, that codes for protein. The region is bounded at the 5' end by a start codon (typically ATG) and at the 3' end with a stop codon (typically TAA, TAG, or TGA). The coding region in mRNA is bounded by the five prime untranslated region (5'-UTR) and the three prime untranslated region (3'-UTR), which are also parts of the exons. The CDS is the portion of an mRNA transcript that is translated by a ribosome.

As understood by those skilled in the art, SNPs within a protein-coding sequence do not necessarily change the amino acid sequence of the protein that is produced, due to degeneracy of the genetic code. SNPs in the coding region are of two types, synonymous and nonsynonymous SNPs. Synonymous SNPs do not alter the amino acid sequence of a protein while nonsynonymous SNPs change the amino acid sequence of a protein. The nonsynonymous SNPs are of two types: missense and nonsense. A missense mutation is a point mutation in which a SNP results in a codon that codes for a different amino acid. In contrast, a nonsense mutation is a point mutation in a sequence of DNA that results in a premature stop codon, also referred to as a nonsense codon, in the transcribed mRNA, and in a truncated, incomplete, and usually nonfunctional protein product.

The term "protein" as used herein indicates a polypeptide with a particular secondary and tertiary structure that can interact with another molecule and in particular, with other biomolecules including other proteins, polynucleotides such as DNA and RNA, lipids, metabolites, hormones, chemokines, and/or small molecules. The term "polypeptide" as used herein indicates an organic linear polymer composed of two or more amino acid monomers and/or analogs thereof. The term "polypeptide" includes amino acid polymers of any length including full-length proteins and peptides, as well as analogs and fragments thereof. A polypeptide of three or more amino acids is also called a protein oligomer, peptide, or oligopeptide. In particular, the terms "peptide" and "oligopeptide" usually indicate a polypeptide with less than 100 amino acid monomers. In particular, in a protein, the polypeptide provides the primary structure of the protein, wherein the term "primary structure" of a protein refers to the sequence of amino acids in the polypeptide chain covalently linked to form the polypeptide polymer. A protein "sequence" indicates the order of the amino acids that form the primary structure. Covalent bonds between amino acids within the primary structure can include peptide bonds or disulfide bonds, and additional bonds identifiable by a skilled person. Polypeptides in the sense of the present disclosure are usually composed of a linear chain of alpha-amino acid residues covalently linked by peptide bond or a synthetic covalent linkage. The two ends of the linear polypeptide chain encompassing the terminal residues and the adjacent segment are referred to as the carboxyl terminus (C-terminus) and the amino terminus (N-terminus) based on the nature of the free group on each extremity. Unless otherwise indicated, counting of residues in a polypeptide is performed from the N-terminal end ($NH_2$-group), which is the end where the amino group is not involved in a peptide bond to the C-terminal end (—COOH group), which is the end where a COOH group is not involved in a peptide bond. Proteins and polypeptides can be identified by x-ray crystallography, direct sequencing, immunoprecipitation, and a variety of other methods as understood by a person skilled in the art. Proteins can be provided in vitro or in vivo by several methods identifiable by a skilled person. In some instances where the proteins are synthetic proteins, in at least a portion of the polymer two or more amino acid monomers and/or analogs thereof are joined through chemically-mediated condensation of an organic acid (—COOH) and an amine (—$NH_2$) to form an amide bond or a "peptide" bond.

As used herein the term "amino acid", "amino acid monomer", or "amino acid residue" refers to organic compounds composed of amine and carboxylic acid functional groups, along with a side-chain specific to each amino acid. In particular, alpha- or α-amino acid refers to organic compounds composed of amine (—$NH_2$) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D and L optical isomers.

Methods and systems herein described and related marker genetic protein variations and databases herein described allow performance of genetic protein variation analysis of a sample of a biological organism taking into account the features of the biological sample where the analysis is performed as will be understood by a skilled person upon reading of the present disclosure.

The wording "biological organism" as used herein indicates an entity that exhibits the properties of life and that comprises a genome which is expressed and translated in a proteome. Exemplary biological organisms comprise multicellular animals, plants, and fungi; or unicellular microorganisms such as protists, bacteria, and archaea. In preferred embodiments the biological organism comprises animals and in particular higher animals and in particular vertebrates such as mammals and in particular human beings (*Homo sapiens*).

Genetic protein variation analysis typically comprises preparing the biological sample to obtain a processed biological sample comprising solubilized proteins to be used in a proteomic analysis.

Existing methods of sample preparation for proteomics generally comprise performing techniques of cell and tissue disruption, protein solubilization, removal of contaminants, and protein enrichment methods [1].

In particular methods of cell and tissue disruption typically comprise homogenization of the sample. Homogenization methods used for the proteomics purposes can be divided into five major categories: mechanical, ultrasonic, pressure, freeze—thaw, and osmotic/detergent lysis. Mechanical homogenization can be performed using rotor—stator homogenizers, open blade mills, or glass-glass milling, among others known to those skilled in the art. Ultrasonic homogenizers, also called as disintegrators, sonicators, or sonificators, are based on the piezoelectric effect and on the principle of cavitation while generating the high energy or ultrasonic wave, interacting with the sample. More specifically, ultrasonic homogenizers generate sound energy electronically; this energy is converted to mechanical energy, and these changes result in the formation and implosion of small bubbles in the sample. Energy, resolved after explosion/implosion of gas microbubbles, effectively destroys solid particles such as cells, causing cell rupture and successful cell lysis. Ultrasonic devices are mainly used to homogenize small pieces of soft tissues (e.g., brain, blood, liver). Pressure homogenization typically uses a French press device, and is an effective method for homogenization of cells in suspension, but ineffective towards tissues or organs without previous preparation in another type of homogenizer. Freeze-thaw homogenization uses the effect of ice crystal formation in the tissue during freezing process. Osmotic and detergent lysis methods of disruption of cells utilize osmotic pressure or detergent interactions to destroy cells' walls and membranes. Osmotic lysis is often used to disrupt blood cells. Examples of commonly used detergents are Triton X-100, Tween 80, Nonidet P-40 (NP 40) and saponin.

In a genetic protein variation analysis, a homogenized sample is subjected to protein solubilization. Proteins in their native state are often insoluble. Breaking interactions involved in protein aggregation, e.g. disulfide/hydrogen bonds, van der Waals forces, ionic and hydrophobic interactions, allows disruption of proteins into a solution of individual polypeptides and thus promotes their solubilization. To avoid protein modifications, aggregation or precipitation resulting in the occurrence of artifacts and subsequent protein loss, sample solubilization process typically involves the use of chaotropes (e.g. urea and/or thiourea), detergents (e.g. 3-[(3-Cholamidopropyl)-dimethyl-ammonio]-1-propane sulfonate (CHAPS) or Triton X-100), reducing agents (dithiothreitol/dithioerythritol (DTT/DTE) or tributylphosphine (TBP)) and protease inhibitors in a sample buffer. Their proper use, together with the optimized cell disruption method, dissolution and concentration techniques determines effectiveness of solubilization. Chaotropes disrupt hydrogen bonds and hydrophilic interactions enabling proteins to unfold with all ionizable groups exposed to solution. Detergents and amphipathic molecules disrupt hydrophobic interactions, thus enabling protein extraction and solubilization. With respect to the ionic character of the hydrophilic group, they are classified into several groups: ionic (e.g. anionic sodium dodecyl sulfate (SDS)), non-ionic (uncharged, e.g. octyl glucoside, dodecyl maltoside and Triton X-100) or zwitterionic (having both positively and negatively charged groups with a net charge of zero, e.g. CHAPS, 3-[(3-Cholamidopropyl) dimethylammonio]-2-hydroxy-1-propanesulfonate (CHAPSO), tetradecanoylamidopropyl-dimethylammoniobutanesulfonate (ASB-14)). Reductants disrupt disulfide bonds between cysteine residues and thus promote unfolding of proteins. Typically, sulfhydryl reducing agents such as dithothreitol (DTT), dithioerythritol (DTE) are applied in the sample preparation protocol. To minimize uncontrolled enzymatic proteolysis by proteases present in samples, protein degradation can be minimized by quick and small scale tissue extraction, boiling the sample in SDS buffer with the high-pH Tris-base, or, on the contrary, lowering the pH and performing ice-cold precipitation in, e.g. 20% trichloroacetic acid. Alternatively, denaturation by boiling in water, focused microwave irradiation, and the use of organic solvents can be applied to inhibit proteases activity. Addition of protease inhibitors can be used to prevent uncontrolled enzymatic protein degradation in a sample. Addition of specific protease inhibitors (e.g. phenylmethylsulfonyl fluoride (PMSF), aminoethyl benzylsulfonyl fluoride (AEBSF), ethylene diamine tetraacetic acid (EDTA), pepstatin, benzamidine, leupeptin, aprotinin) or cocktails with a broader activity spectrum can be used.

In a genetic protein variation analysis, methods of homogenization and/or solubilization techniques for a particular sample type are identifiable by persons skilled in the art. Exemplary methods of homogenization comprise mechanical, ultrasonic, pressure, freeze-thaw, and osmotic/detergent lysis approaches as described herein. Exemplary method of solubilization comprise methods described herein that use reagents comprising one or more chaotropes, detergents, reducing agents and/or protease inhibitors in a sample buffer, as well as other materials and methods identifiable by skilled persons upon reading the present disclosure.

For example, exemplary methods to perform preparing a hair sample to obtain a processed hair sample comprising solubilized proteins to be used in a proteomic analysis comprise milling, denaturation, reduction, and alkylation. Some tissue types such as teeth and bones require additional steps to demineralize the sample material prior to homogenization and solubilization of proteins. There are several ways to extract peptide information from tissues such as teeth and bones, including using a hand-drill, crushing the sample material under liquid nitrogen and demineralization with EDTA or 1.2 M hydrochloric acid, and other methods identifiable by skilled persons.

Genetic protein variation analysis typically further comprises fractionating the processed biological sample to obtain a solubilized protein fraction comprising the solubilized proteins from the sample.

In a genetic protein variation analysis, fractionating the processed sample typically comprises removing buffers, salts, and detergent from the processed sample. The pH and ionic strength of sample solutions considerably influence protein solubility. Therefore, buffers, salts and detergents are included in sample solutions and often tend to interfere with further protein separation steps, inhibit the digestion process, interfere with the mass spectrometry analysis, or complicate data analysis significantly, and thus need to be removed. Salts removal can be accomplished using methods such as dialysis (e.g. using spin columns), ultrafiltration, gel filtration, precipitation with TCA or organic solvents, and solid-phase extraction, some of which are used in commercially available clean-up kits identifiable by those skilled in the art. Typical detergent removal methods include dialysis, gel filtration chromatography, hydrophobic adsorption chromatography and protein precipitation. Detergents such as SDS can be removed with nanoscale hydrophilic phase chromatography or acetone precipitation. Commercially available kits, e.g., detergent precipitation reagents or gels effective for binding and removal milligram quantities of various detergents from protein solutions can be used (e.g. Extracti-Gel D Detergent Removing Gel, ReadyPrep 2-D Cleanup Kit, and the SDS-Out SDS Precipitation Reagent and Kit, Pierce). Hydrophobic adsorption employing the use of insoluble resin (e.g. CALBIOSORB, Calbiochem) can also be used to remove excess detergent.

In a genetic protein variation analysis, fractionating the processed sample to obtain a solubilized protein fraction comprising the solubilized proteins from the sample can further comprise removing abundant proteins from the processed sample. Protein concentration in biological samples can vary more than 10 orders of magnitude and thus proteomic analyses and detection of less abundant proteins can be hampered by those molecules present at higher concentration. In some cases, removal of abundant proteins can be performed to increase detection of other molecules present at low concentrations. Various techniques can be used for the removal of high-abundant proteins, such as those based on affinity chromatography employing dye-ligands, their derivatives, mimetic ligands, proteins A and G, and antibodies (immunoaffinity depletion), and specific kits (e.g., Proteome Purify Immunodepletion Kit) can be utilized. Numerous proteins are complexed with lipids, and this interaction reduces their solubility. Moreover, by forming complexes with detergents, lipids reduce protein enrichment/separation efficacy. The use of centrifugal filter devices and a sample buffer including CHAPS allows for efficient lipid and salt removal. In order to exclude polysaccharides from the sample, precipitation in TCA, acetone, ammonium sulfate or phenol/ammonium acetate, followed by centrifugation can be performed. In order to remove DNA and RNA, methods such as digestion with protease-free DNase and RNase, or alternatively, protein precipitation from the solution are typically performed.

In a genetic protein variation analysis, fractionating the processed sample to obtain a solubilized protein fraction comprising the solubilized proteins from the sample can comprise protein enrichment processes. Various protein enrichment methods can be used to reduce the complexity of the sample by its pre-fractionation, or to enrich it with proteins of interest. Pre-fractionation is performed to isolate a sample into distinguishable fractions containing restricted numbers of molecules. The sample can be fractionated using a variety of approaches including precipitation, centrifugation, liquid chromatography and electrophoresis-based methods, filtration, and velocity or equilibrium sedimentation, among others identifiable by skilled persons.

Fractionating the processed sample to obtain a solubilized protein fraction comprising the solubilized proteins from the sample can also comprise removing contaminants. Samples injected onto chromatographic columns cannot contain insoluble particles or dispersed molecules that may cause column clogging and malfunction. Such contaminants are typically removed by centrifugation and/or sample filtration using spin-filters (e.g., 45 μm pores). In addition, samples should not contain buffers affecting LC separation, e.g. samples injected onto column should not be dissolved in buffer with higher eluting strength than of mobile phase. High concentration of detergents should be avoided when using reverse phase separation whereas samples injected on the ion-exchange column should not contain high contraction of background salts and other ionic contaminants that might disturb ionic equilibrium. Volatile buffers such as ammonium acetate or ammonium bicarbonate, are typically used in this case.

In a genetic protein variation analysis, fractionating the processed sample to obtain a solubilized protein fraction comprising the solubilized proteins from the sample can comprise any materials and methods or combination of materials and methods for removal of contaminants such as salts, buffers and detergents from the sample, and methods of sample concentration, enrichment, fractionation, filtration, and other methods identifiable by skilled persons upon reading the present disclosure, as described herein or otherwise known in the art can be used to perform fractionating the processed biological sample to obtain a solubilized protein fraction comprising the solubilized proteins from the sample.

Genetic protein variation analysis further comprises digesting the solubilized proteins from the sample to obtain digested solubilized proteins from the sample.

In a genetic protein variation analysis, digesting the solubilized proteins from the sample to obtain digested solubilized proteins from the sample can be performed non-enzymatically, e.g., with low pH or high temperatures, as well as enzymatically, e.g., by intra-molecular digestion or with a site specific proteolytic enzyme. In many methods, the digesting is performed with a site specific proteolytic enzyme.

In a genetic protein variation analysis, digesting the solubilized proteins from the sample with a site specific proteolytic enzyme to obtain digested solubilized proteins from the sample can be performed by any method identifiable to a skilled person. As understood by those skilled in the art, the terms "proteolytic enzyme", "protease", "peptidase", and "proteinase" refers to any enzyme that performs proteolysis, wherein the term "proteolysis" as used herein refers to protein catabolism by hydrolysis of peptide bonds.

As understood by those skilled in the art, proteases can be classified into seven broad groups, comprising serine proteases, cysteine proteases, threonine proteases, aspartic proteases, glutamic proteases, metalloproteases, and asparagine peptide lyases.

As understood by those skilled in the art, proteolytic catalysis is achieved by one of two mechanisms, wherein aspartic, glutamic and metallo-proteases activate a water molecule which performs a nucleophilic attack on the peptide bond to hydrolyze it. In contrast, serine, threonine and cysteine proteases use a nucleophilic residue (usually in a catalytic triad). That residue performs a nucleophilic attack to covalently link the protease to the substrate protein, releasing the first half of the product. This covalent acyl-enzyme intermediate is then hydrolyzed by activated water to complete catalysis by releasing the second half of the product and regenerating the free enzyme.

The terms "site specific proteolytic enzyme", "site specific protease", "site specific peptidase", and "site specific proteinase" refer to enzymes that perform proteolysis by cleavage of a protein substrate having a specific sequence. As understood by those skilled in the art, proteolysis can be highly promiscuous such that a wide range of protein substrates are hydrolyzed. This is the case for digestive enzymes such as trypsin which have to be able to cleave the array of proteins ingested into smaller peptide fragments. Promiscuous proteases typically bind to a single amino acid on the substrate and so only have specificity for that residue. For example, trypsin is specific for the sequences . . . K\ . . . or . . . R\ . . . ('\'=cleavage site). Conversely some proteases are highly specific and only cleave substrates with a certain sequence. Blood clotting (such as thrombin) and viral polyprotein processing (such as TEV protease) requires this level of specificity in order to achieve precise cleavage events. This is achieved by proteases having a long binding cleft or tunnel with several pockets along it which bind the specified residues. For example, TEV protease is specific for the sequence (SEQ ID No. 86) . . . ENLYFQ\S . . . ('\'=cleavage site).

Materials and methods for digestion of proteins using various proteases are identifiable by those skilled in the art and described herein.

Genetic protein variation analysis also comprises fractionating the digested solubilized proteins to obtain fractionated digested peptides from the digested solubilized proteins from the biological sample.

Methods to perform fractionating the digested solubilized proteins to obtain fractionated digested peptides from the digested solubilized proteins from the biological sample comprise chromatographic methods. The term "chromatography" as used herein refers to a technique for the separation of a mixture. More specifically, the term "chromatography" is a physical method of separation that distributes components to separate between two phases, one stationary (stationary phase), the other (the mobile phase) moving in a definite direction.

In chromatography, a mixture is dissolved in a fluid called the mobile phase, which carries it through a structure holding another material called the stationary phase. The various constituents of the mixture travel at different speeds, causing them to separate. The separation is based on differential partitioning between the mobile and stationary phases. Subtle differences in a compound's partition coefficient result in differential retention on the stationary phase and thus affect the separation. Chromatography can be preparative or analytical. The purpose of preparative chromatography is to separate the components of a mixture for later use, and is thus a form of purification. Analytical chromatography is done normally with smaller amounts of material and is for establishing the presence or measuring the relative proportions of analytes in a mixture. The two are not mutually exclusive.

As understood by those skilled in the art, chromatography is based on the concept of partition coefficient, wherein any solute partitions between two immiscible solvents. The term "partition coefficient" as defined herein refer to the ratio of concentrations of a compound in a mixture of two immiscible phases at equilibrium, and represents a measure of the difference in solubility of the compound in these two phases. It is also referred to as "distribution coefficient". When one solvent is made immobile (e.g., by adsorption on a solid support matrix) and another solvent is mobile it results in most common applications of chromatography. As understood by those skilled in the art, if the matrix support, or stationary phase, is polar (e.g. paper, silica etc.) it is referred to as "forward phase" or "normal phase" chromatography, and if it is non-polar (C-18) it is referred to as "reverse phase".

Chromatography techniques can be categorized according to chromatographic bed shape, wherein "column chromatography" refers to a separation technique in which the stationary bed is within a tube, and "planar chromatography", which refers to a separation technique in which the stationary phase is present as or on a plane, such as paper chromatography or thin layer chromatography. Accordingly, in some embodiments, any method using column chromatography or planar chromatography can be used to perform fractionating the digested solubilized proteins.

Chromatography techniques can also be categorized according to physical state of mobile phase. The term “gas chromatography” (GC), also sometimes known as “gas-liquid chromatography” (GLC), refers to a separation technique in which the mobile phase is a gas. The term “liquid chromatography” (LC) refers to a separation technique in which the mobile phase is a liquid. In particular, liquid chromatography that generally utilizes very small packing particles and a relatively high pressure is referred to as high performance liquid chromatography (HPLC). In HPLC the sample is forced by a liquid at high pressure (the mobile phase) through a column that is packed with a stationary phase composed of irregularly or spherically shaped particles, a porous monolithic layer, or a porous membrane. HPLC can be divided into two different sub-classes based on the polarity of the mobile and stationary phases. Methods in which the stationary phase is more polar than the mobile phase (e.g., toluene as the mobile phase, silica as the stationary phase) are termed “normal phase” or “forward phase” liquid chromatography, whereas the opposite (e.g., water-methanol mixture as the mobile phase and C18 (octadecylsilyl) as the stationary phase) is termed “reversed phase” liquid chromatography (RPLC).

Accordingly, gas chromatography or liquid chromatography can be used to perform fractionating the digested solubilized proteins in genetic protein variation analysis as will be understood by a skilled person.

Chromatography techniques can also be categorized according to separation mechanism. The term “ion exchange chromatography” refers to a technique that uses an ion exchange mechanism to separate analytes based on their respective charges. The term “size-exclusion chromatography” (SEC) also known as “gel permeation chromatography” (GPC) or “gel filtration chromatography” refers to a technique that separates molecules according to their size, or more accurately according to their hydrodynamic diameter or hydrodynamic volume. The term “expanded bed chromatographic adsorption” (EBA) refers to a biochemical separation process using a column that comprises a pressure equalization liquid distributor having a self-cleaning function below a porous blocking sieve plate at the bottom of the expanded bed, an upper part nozzle assembly having a backflush cleaning function at the top of the expanded bed, and a better distribution of the feedstock liquor added into the expanded bed ensuring that the fluid passed through the expanded bed layer displays a state of piston flow.

Accordingly, ion exchange chromatography, size-exclusion chromatography, or expanded bed chromatographic adsorption can be used to perform fractionating the digested solubilized proteins in genetic variation protein analysis of the instant disclosure. Other chromatography techniques can be used such as hydrophobic interaction chromatography, two-dimensional chromatography, simulated moving-bed chromatography, pyrolysis gas chromatography, fast protein liquid chromatography, countercurrent chromatography, periodic counter-current chromatography, aqueous normal-phase chromatography, or chiral chromatography, among others identifiable by persons skilled in the art can be used to perform fractionating the digested solubilized proteins.

In general, techniques identifiable by skilled persons that can be used to perform fractionating proteins or digested proteins of a biological sample comprise methods based on purification of peptides according to their isoelectric points (e.g., by running them through a pH graded gel or an ion exchange column), separation according to their size or molecular weight (e.g., via size exclusion chromatography or by SDS-PAGE (sodium dodecyl sulfate-polyacrylamide gel electrophoresis) analysis), or separation by polarity/hydrophobicity (e.g., via high performance liquid chromatography or reversed-phase chromatography).

Additional methods for fractionating proteins or digested proteins of a biological sample that can be used in some embodiments described herein comprise affinity chromatography. The term “affinity chromatography” refers to a separation technique based upon molecular conformation, which frequently utilizes application specific resins. These resins have ligands attached to their surfaces which are specific for the compounds to be separated. For example, immunoaffinity chromatography uses the specific binding of an antibody-antigen to selectively purify the target protein. The procedure involves immobilizing a protein to a solid substrate (e.g. a porous bead or a membrane), which then selectively binds the target, while everything else flows through. The target protein can be eluted by changing the pH or the salinity. The immobilized ligand can be an antibody (such as Immunoglobulin G) or it can be a protein (such as Protein A), among others identifiable by those skilled in the art.

Genetic protein variation analysis also comprises detecting a marker genetic variation of the fractionated digested peptides.

Various techniques can be used to perform detecting a marker genetic variation of the fractionated digested peptides in a genetic variation protein analysis, such as mass spectrometry. Mass Spectrometry (MS) is an analytical technique that ionizes chemical species and sorts the ions based on their mass-to-charge ratio. In simpler terms, a mass spectrum measures the masses within a sample. Mass spectrometry is used in many different fields and is applied to pure samples as well as complex mixtures. A mass spectrum is a plot of the ion signal as a function of the mass-to-charge ratio. These spectra are used to determine the elemental or isotopic signature of a sample, the masses of particles and of molecules, and to elucidate the chemical structures of molecules, such as peptides and other chemical compounds.

The terms “liquid chromatography mass-spectrometry” or “LC-MS” as used herein refer to an analytical chemistry technique that combines the physical separation capabilities of liquid chromatography (LC, or high-performance liquid chromatography, HPLC, or ultra-high-performance liquid chromatography, UHPLC) with the mass analysis capabilities of mass spectrometry (MS). The terms “tandem mass spectrometry”, or “MS/MS” as used herein refers to a mass-spectrometry technique that involves more than one stage of mass spectrometry analysis, with a step form of fragmentation occurring in between the stages. In a tandem mass spectrometer, ions are formed in the ion source and separated by mass-to-charge ratio in the first stage of mass spectrometry (MS1). Ions of a particular mass-to-charge ratio (precursor ions) are selected and fragment ions (product ions) are created by collision-induced dissociation, ion-molecule reaction, photodissociation, or other processes. The resulting ions are then separated and detected in a second stage of mass spectrometry (MS2). Thus, the terms “tandem liquid chromatography mass-spectrometry” and “LC-MS/MS” as used herein refer to a technique that couples liquid chromatography and tandem mass-spectrometry.

Typically, for LC-MS/MS proteomic analysis, the stationary LC phase is a C18 reverse-phase column. The reverse-phase column uses the hydrophobicity of peptides for separation, utilizing a gradient from low to high organic-phase solvent. Acidified methanol and acetonitrile are commonly used as organic-phase, also known as “B” or “strong”, solvents because of their miscibility with aqueous solutions.

Acidified water is most often the "weak" solvent, also known as "A". Both buffers are acidified with the same acid, generally with formic acid or trifluoroacetic acid (TFA) at 0.1% or 0.01%, respectively.

Examples of tandem mass-spectrometry instruments used for LC-MS/MS proteomics analysis comprise sector instruments, time-of-flight instruments, quadrupole mass analyzers, ion traps, and orbitraps, among others identifiable by those skilled in the art.

In proteomic analysis using LC-MS/MS, following purification of proteins from tissue samples, the purified proteins are enzymatically digested by a protease, typically, trypsin, which cleaves the protein into smaller detectable peptides, with molecular weights of about 400 to 4000. The peptides are then resolved using very low flow rate liquid chromatography, such as reversed phase liquid chromatography, and are then ionized and vaporized using methods such as fast atom bombardment (FAB), chemical ionization (CI), atmospheric-pressure chemical ionization (APCI), electrospray ionization (ESI), and matrix-assisted laser desorption/ionization (MALDI). The charged peptide is then funneled using electric fields into the mass spectrometer where its mass is measured (MS1). The instrument then fragments individual peptide backbones using either collision-induced or electron transfer dissociation and the resulting fragment masses are also measured (MS2). Both of these fragmentation methods break the peptide backbone at regular points. This allows the amino acid sequence to be determined. The information from tandem liquid chromatography mass-spectrometry, therefore, has three dimensions: time of retention on reversed phase, peptide mass (MS1) and individual peptide fragmentation masses (MS2). Mass spectrometry has matured to the point where over 10,000 peptide fragmentations can be obtained per run. The mass accuracy of peptide and fragmentation masses is now 1 ppm in both MS and MS2, removing ambiguity from the analysis.

The fragmentation data can be resolved using the data within the sample, based on the intrinsic properties of the data related to the peptide fragmentation, to provide de novo sequence information through a de novo peptide identification algorithm for LC-MS/MS which infers peptide sequences without knowledge of genomic data. Examples of de novo sequencing algorithms comprise Cyclobranch, DeNovoX, DeNos, Lutefisk, Novor, PEAKS, and Supernovo, among others identifiable by those skilled in the art.

The fragmentation data can also be resolved through comparison with predicted sequences derived from genomic and protein databases such as GenBank and UniProt. This method provides a statistical measure of probability that any fragmentation dataset is the predicted amino acid sequence through a database search peptide identification algorithm for LC-MS/MS which takes place against a database containing all amino acid sequences assumed to be present in the analyzed sample. Examples of database search algorithms comprise Andromeda, Byonic, Comet, Tide, Greylag, InsPecT, Mascot, MassMatrix, MassWiz, MS Amanda, MS-GF+, MyriMatch, OMSSA, PEAKS DB, pFind, Phenyx, ProblD, ProteinPilot Software, Protein Prospector, RAId, SEQUEST, SIMS, Sim Tandem, SQID, and X!Tandem, among others identifiable by those skilled in the art.

The allelic frequencies associated with each nucleotide and amino acid polymorphism within the fragmentation data are a product of the reference populations used in the single nucleotide polymorphism (SNP) data bases. The term "allelic frequency" as defined herein refers to the relative frequency of an allele (variant of a gene) at a particular locus in a population, expressed as a fraction or percentage. Examples of databases of human SNPs and SAPs comprise dbSNP, which is a SNP database from the National Center for Biotechnology Information (NCBI), as well as the 1000 Genomes Project, UniProt, Protein Mutation Database, HPMD, MSIPI, MS-CanProVar, Ensembl, COSMIC, and dbSAP [2], among others identifiable by those skilled in the art.

Accordingly, in a genetic protein variation analysis, any method of mass-spectrometry identifiable by skilled persons can be used to perform detecting a marker genetic variation of the fractionated digested peptides, such as techniques that use time-of-flight instruments, quadrupole mass analyzers, ion traps, and orbitraps, among others identifiable by those skilled in the art, that use any ionization and vaporization methods such as fast atom bombardment (FAB), chemical ionization (CI), atmospheric-pressure chemical ionization (APCI), electrospray ionization (ESI), and matrix-assisted laser desorption/ionization (MALDI), among others identifiable by skilled persons. Additionally, any method of peptide fragmentation known in the art, such as collision-induced or electron transfer dissociation can be used to detect a marker genetic variation of the fractionated digested peptides, and any method of peptide fragmentation data deconvolution, such as de novo sequencing, or comparison of peptide fragmentation data with predicted sequences derived from genomic and protein databases such as GenBank and UniProt can be used to perform detecting a marker genetic variation of the fractionated digested peptides.

Additionally, in a genetic variation protein analysis any peptide identification algorithms that can be used in database searches, such as Andromeda, Byonic, Comet, Tide, Greylag, InsPecT, Mascot, MassMatrix, MassWiz, MS Amanda, MS-GF+, MyriMatch, OMSSA, PEAKS DB, pFind, Phenyx, ProblD, ProteinPilot Software, Protein Prospector, RAId, SEQUEST, SIMS, Sim Tandem, SQID, and X!Tandem, among others identifiable by those skilled in the art, or in de novo searches, such as Cyclobranch, DeNovoX, DeNos, Lutefisk, Novor, PEAKS, and Supernovo, among others identifiable by those skilled in the art, can be used to perform detecting a marker genetic variation of the fractionated digested peptides. Additionally, in some embodiments, any databases of human SNPs and SAPs such as dbSNP, 1000 Genomes Project, UniProt, Protein Mutation Database, HPMD, MSIPI, MS-CanProVar, Ensembl, COSMIC, and dbSAP [2], among others identifiable by those skilled in the art can be used to perform detecting a marker genetic variation of the fractionated digested peptides.

An exemplary genetic protein variation analysis including specific protocols for performance of the related steps is shown in the paper Parker et al 2016 [3] incorporated herein by reference in its entirety and supplementary information of Parker et al. (2016) incorporated herein by reference in its entirety.

In a genetic protein variation analysis performed with methods and systems in accordance with the present disclosure, preparing the sample and/or detecting a genetic variation can be performed by any one of the methods and/or using anyone of the systems and databases according to any one of the first aspect to the seventh aspect of the present disclosure.

Accordingly, in some embodiments, preparing a biological sample to obtain a processed biological sample comprising solubilized proteins to be used in proteomic analysis can be performed by the method to prepare a biological sample for proteomic analysis according to the first aspect of the present disclosure. The method comprises applying to the biological sample an energy field to obtain a processed biological sample comprising solubilized proteins to be used in the proteomic analysis.

In particular, the energy field applied in methods for preparing a biological sample according to the first aspect of the disclosure comprises electromagnetic fields applied with parameters selected to result in protein solubilization while reducing breakage of the intramolecular peptidic bonds of the proteins in the sample.

In a method for preparing a biological sample according to the first aspect of the disclosure, typically, energy is applied at the initial solubilization stage of sample processing. Sample solubilization process typically involves the use of chaotropes (e.g. urea and/or thiourea), detergents (e.g. 3-[(3-Cholamidopropyl)-dimethyl-ammonio]-1-propane sulfonate (CHAPS) or Triton X-100), reducing agents (dithiothreitol/dithioerythritol (DTT/DTE) or tributylphosphine (TBP)) and protease inhibitors in a sample buffer.

In some embodiments the sample buffer can comprise reducing agents such as DTT, Dodecyltrimethylammonium bromide (DTBA), Betamercatptoethanol (BME), tris(2-carboxyethyl)phosphine (TCEP), and DTE. In particular, the applying can be performed with detergent in concentration ranging from 0.001 M to 10 M; 0.05 M to 0.2 M more preferably; and most preferably 0.1 M. In preferred embodiments the detergent comprises DTT.

In some embodiments the sample buffer can comprise detergents such as SDD, SDS, CHAPS, a Triton X-100, Lithium Dodecyl Sulfate (LDS)Tergitol-type NP-40 (NP-40) which is nonyl phenoxypolyethoxylethanol, commercially available with CAS 9016-45-9. The detergent concentrations depend on temperature and ultrasonic treatment time as will be understood by a skilled person. Specifically, decreasing SDD concentration by 1% drastically increases time for solubilization (60 minutes to 24 hours), whereas decreasing ultrasonic treatment incubation temperature also increases time (every 5 degrees C. decreased requires two hours or more ultrasonic treatment time). Increasing detergent concentration past 2% does not result in significant decreased ultrasonic incubation time. In preferred embodiments, the detergent comprises SDD.

A skilled person will understand that the composition of the sample buffer can vary depending on the time and condition of applying to the biological sample an energy field and can be adjusted by a skilled person to optimize protein solubilization upon reading of the present disclosure.

The term "solubilize", used herein with reference to solubilized proteins, refers to a transfer of proteins comprised within the biological sample to a solvent such as an aqueous solvent by disrupting the cells of the biological sample. Disruption of the cells of the biological sample can be performed by applying a force to the cell to alter the cell membrane continuity and integrity for a time and under condition to result in the lysis of the cell.

In some preferred embodiments, applying to the biological sample an energy field can be performed by sonication. The sonication process can be carried out using an ultrasonic processor operating at the ultrasound frequency of about 20-80 kHz and applying the sample the ultrasound for about 30-120 minutes. In some embodiments, the sonication process can be performed using an ultrasonic processor set to 1 to 100 kHz; preferably 5 to 50 kHz and more preferably 37 kHz.

In embodiments, wherein applying energy is performed by sonication, the power setting of the device can range from 1 to 100%; more preferably 50 to 100%; most preferably 100%.

In embodiments, wherein applying energy is performed by sonication, the applying can be performed by providing the energy with an ultrasonic mode selected from sweep, degas, and pulse. In preferred embodiments, applying energy can be performed by providing the energy with ultrasonic mode sweep.

In the preferred embodiments, wherein applying energy is performed by sonication, which includes any method for imparting acoustic energy to bring about cavitation of the sample including sonication baths, sonication probes/sonicators, or sonication flow-through systems are applicable. The biological sample can be subjected to sonication by placing a sample containing tube with a sonication bath or samples can be directly sonicated using a probe or by placing in a flow-through system directly.

As a person skilled in the art will understand, other mechanical cell disruption methods capable of creating high stress via pressure or abrasion with rapid agitation can also be used to mechanically disrupt the biological sample. Exemplary mechanical cell disruption methods include bead milling, cryomilling, microfluidizers, high pressure homogenizer, nitrogen cavitation, and others identifiable to a person skilled in the art.

In some other embodiments, applying to the biological sample an energy field through the application of microwaves can be performed by microwaving the biological sample using 500-1,200 Watt microwaves, wherein samples can be treated from 10 seconds to several minutes [4-7].

In some embodiments, applying energy can be performed with an incubation time ranging from 5 to 1,440 minutes; more preferably 20 to 90 minutes; most preferably 60 minutes.

In some embodiments, applying energy can be performed with temperature settings from 15 to 100° C.; more preferably 30 to 90° C.; most preferably 70° C.

The time and temperature of applying to the biological sample an energy field in accordance with the first aspect of the disclosure depend on the composition of the sample buffer as will be understood by a skilled person. For example, in embodiments where the applying is performed by sonication, presence and concentration of a detergent in the sample buffer depend on temperature and ultrasonic treatment time as will be understood by a skilled person. In particular, decreasing concentration of a detergent such as SDD, by 1% drastically increases time for solubilization (60 minutes to 24 hours). Whereas decreasing ultrasonic treatment incubation temperature also increases time (every 5 degrees C. decreased requires two hours or more ultrasonic treatment time). Increasing concentration of a detergent such as SDD in the sample buffer past 2% does not result in significant decreased ultrasonic incubation time. Additional adjustments and variations of the sample buffer compositions, time and temperature of applying to the biological sample an energy field in accordance with the first aspect of the disclosure are identifiable by a skilled person upon reading of the present disclosure.

In some embodiments the biological sample is a tissue sample. The term "tissue" as used herein refers to a cellular organizational level intermediate between cells and a complete organ or organism. A tissue is typically an ensemble of similar cells from the same origin that together carry out a specific function. Organs and organisms are then formed by the functional grouping together of multiple tissues. As used herein, the term tissue comprises ensembles of cells such as hair, skin, bone, teeth, blood and other body fluids, muscle, nerves, and other cellular material originating from one or more organisms, and also comprises artifacts originating from tissues such as fingerprints. In particular, as used herein, organisms from which tissues originate comprise mammals and in particular humans.

In some embodiments, the biological sample comprises hair. Hair is commonly found as trace evidence in crimes scene forensic investigations. Persistence of hair in the environment demonstrates the unique chemical stability that makes it an ideal biological material for analysis by forensic practices [8]. Largely, forensic analysis of hair evidence is performed by microscopic analysis of morphological characteristics and more recently mitochondrial DNA (mtDNA) sequencing. Both accepted techniques have intrinsic flaws (subjectivity and low discrimination, respectively) highlighting the essential need for development of new strategies to obtain information from hair evidence in the forensic communities [9, 10].

Specifically, proteomic analysis of hair has been shown to provide identification markers in the form of genetically variant peptides (GVPs) in human samples [3]. GVP detection targets mutations in protein amino acid sequences as a direct reflection of single-nucleotide polymorphisms (SNPs) found in DNA. The utility of this technique in forensic practice hinges on its ability to apply to practical sample sizes, for example a single hair.

In some embodiments, the biological sample can be a single hair. In some embodiments, the single-hair sample is about 0.1 to 20 cm in length, such as 2.5 cm, and 2-1630 μg in weight, such as 85 μg in some examples (see e.g. Example 2). Providing a single-hair sample can further comprise cutting the single-hair sample into pieces.

In some embodiments, the method of preparing the biological sample comprises providing a single-hair sample from an individual, dissolving the single-hair sample in a cell lysis solution, subjecting the cell lysis solution containing the single-hair sample to ultrasonication or thermolysis to provide a solubilized single-hair sample, and digesting the solubilized single-hair sample to obtain peptide samples. The obtained peptide samples are then subjected to proteomics analysis.

Exemplary methods to perform a proteomic tissue sample preparation using methods according to the first aspect and single hairs are described in Examples 2-4.

In some embodiments detecting a genetic variation can be performed with a method and system to provide a marker genetic protein variation for a biological organism and a marker genetic protein variation obtainable thereby according to the second aspect of the present disclosure. In these method and system, the provided marker genetic protein variation validated to be detectable and in particular proteomically detectable in a biological sample of an individual of the biological organism.

The method comprises: providing a marker exome sequence of the biological organism, the marker exome sequence comprising a marker genetic variation for the biological organism.

The method further comprises detecting peptide sequences in the biological sample of the individual of the biological organism by performing proteomic analysis of said biological sample to provide proteomically detected peptide sequences.

The method also comprises providing the marker genetic protein variation of the biological organism detectable in the sample of the biological organism by comparing the provided marker exome sequence with the proteomically detected peptide sequences to provide a marker genetic protein variation validated for the biological sample of an individual of the biological organism.

The system comprises exome sequence databases and/or reagents to detect exome sequences in an individual of the biological organism, in combination with reagents to perform proteomic analysis of the biological sample for simultaneous combined or sequential use in the method to provide a marker genetic protein variation validated for a biological sample herein described.

The term "exome" as used in the instant disclosure indicates the part of the genome of a biological organism composed of exons, the sequences which, when transcribed, remain within the mature RNA after introns are removed by RNA splicing and contribute to the final protein product encoded by that gene.

In some embodiments, providing at least one marker exome sequence from a genome each comprising a genetic variation of the genome comprises detecting exome sequences of the genome by sequencing exomes of the genome and detecting at least one marker exome sequence each comprising a genetic variation of the genome by comparing the detected exome sequences with a database of exome sequences of the biological organism.

The genome being sequenced for detecting exome sequences can be of the same individual of the biological organism where the biological sample is collected from for proteomic analysis, or a close relative of the individual who has a coefficient of relationship (r) of at least 0.5 with the individual. Herein, the coefficient of relationship is a measure of the degree of consanguinity or biological relationship between two individuals. For example, a parent and child pair have a value of r=0.5 and full siblings have a value of r=0.5.

Sequencing exomes of a genome can comprise collecting a sample from the individual and performing exome sequencing of the sample. In some instances, the sample is a blood sample or buccal sample. The type of sample collected from the individual for the exome sequencing can be the same or different from the type of sample collected for the proteomics analysis. For example, in some instances, the sample collected for the exome sequencing can be a blood sample while the biological sample collected for proteomic analysis can be a hair sample.

The exome sequencing can be performed by whole exome sequencing (WES or WXS). Whole exome sequencing typically comprises selecting the subset of DNA containing exons from the whole genome. Both array-based and in-solution capture techniques can be used to selectively capture the subset of DNA containing exons. The subset of DNA containing exons can then be sequenced using high-throughput DNA sequencing technology.

High-throughput DNA sequencing also referred to as next-generation sequencing (NGS) refers to a number of different modern nucleic acid sequencing technologies including Illumia™ sequencing, Roche 454™ sequencing, Ion torrent: Protein/PGM™ sequencing and SOLiD™ sequencing. Next-generation sequencing (NGS) generally refers to non-Sanger-based high-throughput DNA sequencing technologies. The NGS technologies can be based on immobilization of the nucleotide samples onto a solid support, cyclic sequencing reactions using automated fluidics devices and detection of molecular events by imaging. Cyclic array platforms achieve low costs by simultaneously decoding a two-dimensional array bearing millions or billions of distinct sequencing features, each containing one species of DNA physically immobilized on an array. In each cycle, an enzymatic process is applied to interrogate the identity of a single base position for all features in parallel. The enzymatic process is coupled to either the production of light or the incorporation of a fluorescent group. At the end of each cycle, data are acquired by imaging of the array. Subsequent cycles are typically performed interrogating different base position within the sequence. Detailed information about various next-generation sequencing approaches can be found in related literation and documents and will be understood by a person skilled in the art.

In some embodiments of the present disclosure exome sequencing can be performed by RNA exome sequencing e.g. with (e.g., with Illumina RNA Exome Capture Sequencing) as will be understood by a skilled person.

In particular, in certain tissue types (either coextracted in sample; e.g. skin or bone or from separate buccal swab) exome sequencing can be performed from RNA in the sample. In particular, in some embodiments the exome sequencing can be performed on the protein fraction of the sample wherein GVPs can be fractionated with their mRNA counterparts. In some embodiments exome sequencing can be performed following RNA extraction of samples (cell lysis, solubilization, purification) using a portion of a sample or a buccal swab and RNA-sequencing performed with technologies such as RNA-seq, RNA capture exome sequencing, and addition technologies identifiable by a skilled person RNA sequences can be translated into DNA subsequently and provide the presence/absence of missense SNPs that correspond to GVPs.

Detecting at least one marker exome sequence can be performed by comparing the detected exome sequences of the individual with a database of exome sequences of the biological organism. In general, the exome sequences generated from a sequencing procedure can be aligned to the sequence entries contained in the database of exome sequences of the biological organism using alignment/assembly tools identifiable by a person skilled in the art. Exemplary database of exome sequences of the biological organism includes the NHLBI Exome Sequencing Project (ESP) database.

In particular, the detected marker exome sequences are a set of exome sequences, each comprising one or more single nucleotide polymorphisms. Therefore, comparing the detected exome sequences of the individual with a database of exome sequences of the biological organism can identify one or more non-synonymous single nucleotide polymorphisms in the exome sequence of the individual.

The method further comprises detecting peptide sequences in the biological sample by performing proteomic analysis of the biological sample. The term "proteomic analysis" refers to the systematic identification and quantification of the complete set of proteins encoded in a biological system such as a cell, tissue, organ, biological fluid or organism. Proteomic analysis can be performed using mass spectrometry (MS) or liquid chromatography mass-spectrometry (LC-MS) as will be understood by a person skilled in the art. Performing proteomic analysis of the biological sample comprises fragmenting proteins in the biological sample into peptides, subjecting the fragmented sample to MS or LC-MS to obtain proteomic datasets, and analyzing the proteomic datasets to identify the peptide sequences of the biological sample. Analyzing the proteomic datasets can be performed using computational algorithm such as MASCOT, GPM or Petunia as will be understood by a person skilled in the art.

In certain embodiments, the proteomics analysis performed on the biological sample is shotgun proteomics analysis. Shotgun proteomic analysis refers to the use of bottom-up proteomics techniques in identifying proteins in complex mixtures using a combination of high performance liquid chromatography combined with mass spectrometry, and is an alternative to targeted proteomics and data-independent acquisition proteomics.

The method according to the second aspect of the instant disclosure, further comprises providing the marker genetic protein variation of the biological organism in the biological sample by comparing the detected marker exome sequence with the detected peptide sequences to provide a marker genetic protein variation validated for the biological organism.

The comparison can be performed by comparing each detected marker exome sequence comprising a generic variation of the genome such as SNPs with the detected peptide sequences stored in a database. The comparison can be carried out by any sequence comparison programs that compare a DNA sequence to a peptide sequence database, such as BLASTX. Such sequence comparison programs typically involve translating the DNA sequence in three frames and aligning the translated DNA sequence to each sequence in the peptide database, allowing gaps and frameshifts as will be understood by a person skilled in the art.

The detected marker exome sequence having a corresponding entry in the database containing the detected peptide sequences is then indicated as a marker genetic protein variation validated for the biological organism. The marker genetic protein variation validated for the biological organism can be further stored in a database which contains, for each data entry, a detected marker exome sequence comprising a genetic variation and a peptide sequence corresponding to the detected marker exome sequence. The data entry can further comprise an allele frequency for the genetic variation in the detected marker exome sequence.

In some embodiments, the biological organism is *Homo sapiens*. In some embodiments, the biological sample is a hair sample.

Exemplary validated marker exome sequences of *Homo Sapiens* are indicated in Examples 43 to 45 listing exemplary set of genes validated as being detectable in hair samples (Example 43, Table 8) bone samples (Example 44, Table 9) and skin samples (Example 45, Table 10) of a human being.

Exemplary validated marker genetic protein variations of *Homo Sapiens* are indicated in Examples 46 and Example 47 listing exemplary set of GVPs validated in hair samples (Example 46, Table 11) and skin samples (Example 47, Table 12) of a human being.

In some embodiments detecting a genetic variation can be performed with a method and system to detect a marker genetic protein variation in a biological sample according to a third aspect of the present disclosure. In the method and system, the marker genetic protein variation are validated to be detectable and in particular proteomically detectable in the biological sample.

The method comprises providing a marker mass spectrum of a marker peptide comprising a marker genetic protein variation corresponding to the genetic protein variation; and performing mass spectrometry of a fractionated digested peptide of the biological sample to obtain a mass spectrum of each of the fractionated digested peptide.

The method further comprises comparing the mass spectrum of the fractionated digested peptide with a marker mass spectrum of a marker peptide comprising the marker genetic protein variation to detect the genetic protein variation in the biological sample.

The system comprises protein databases, and/or reagents to perform proteomic analysis of the biological sample in combination with exome sequence databases for simultaneous combined or sequential use in the method to detect a marker genetic protein variation in a biological sample herein described. In preferred embodiments, the reagents comprise one or more marker peptides in accordance with the present disclosure.

In the method according to the third aspect, any method of performing mass spectrometry of a fractionated digested peptide of the biological sample as described herein or otherwise identifiable by persons skilled in the art can be used to obtain a mass spectrum of each of the fractionated digested peptides.

As understood by skilled persons, mass-spectrometry of fractionated digested peptides of a biological sample can produce a large number of mass spectra. In embodiments described herein, the term "mass spec dataset" is used to refer to a plurality of mass spectra obtained for a plurality of fractionated digested peptides of a biological sample (e.g., see FIG. 9).

As understood by persons skilled in the art, mass spectrometry (MS) is an analytical technique that ionizes chemical species and sorts the ions based on their mass-to-charge ratio. In simpler terms, mass spectrometry measures the masses within a sample. Mass spectrometry is used in many different fields and is applied to pure samples as well as complex mixtures. The term "mass spectrum" as used herein refers to a plot reporting a signal of one or more ions as a function of mass-to-charge ratio of the ions. Accordingly, mass spectra can be used to determine the elemental or isotopic signature of a sample, the masses of particles and of molecules, and to elucidate the chemical structures of molecules, such as peptides and other chemical compounds.

The terms "tandem mass spectrometry", or "MS/MS" as used herein refer to a mass-spectrometry technique that involves more than one stage of mass spectrometry analysis, with a step of fragmentation occurring in between the stages. In a tandem mass spectrometer, ions are formed in the ion source and separated by mass-to-charge ratio in the first stage of mass spectrometry (MS1). Ions of a particular mass-to-charge ratio (precursor ions) are selected and fragment ions (product ions) are created by collision-induced dissociation, ion-molecule reaction, photodissociation, or other processes. The resulting ions are then separated and detected in a second stage of mass spectrometry (MS2).

Accordingly, a mass spectrum of a peptide is a plot reporting a signal of one or more ions of a peptide as a function of mass-to-charge ratio of the ions. In particular, with reference to LC-MS/MS analysis of peptides (e.g. peptides produced by digesting proteins of a biological sample using a site-specific protease), a mass spectrum of a peptide can refer to a mass spectrum produced in the MS1 stage or the MS2 stage, wherein the mass spectrum produced in the MS1 stage refers to a mass spectrum of a peptide (e.g. a peptide produced by digesting a protein using a site specific protease) before fragmentation of the peptide occurs, and the mass spectrum produced in the MS2 stage refers to a mass spectrum produced after fragmentation of the peptide has occurred.

The term "marker peptide" as used herein refers to a peptide that comprises a genetic protein variation. In some embodiments, a marker peptide is a peptide produced by digesting a protein that comprises a genetic protein variation, wherein the marker peptide is the peptide produced by proteolytic digestion that comprises the genetic protein variation. In some embodiments, the genetic protein variation is encoded by a 'rare' non-synonymous single nucleotide polymorphism (nsSNP) having an allelic frequency lower than 0.5% or a 'private' nsSNP having an allelic frequency lower than 0.1% in a given population, wherein an allelic frequency is a product of the reference populations used in the single nucleotide polymorphism (SNP) data bases.

Accordingly, the terms "marker mass spectrum of a marker peptide" or "diagnostic LC-MS/MS spectrum" as used herein refer to a mass spectrum of a marker peptide. In some embodiments, the terms "marker mass spectrum of a marker peptide" or "diagnostic LC-MS/MS spectrum" as used herein refer to a mass spectrum of a marker peptide that is produced in the MS1 stage, or a mass spectrum of a marker peptide that is produced in the MS2 stage.

Figure 17:
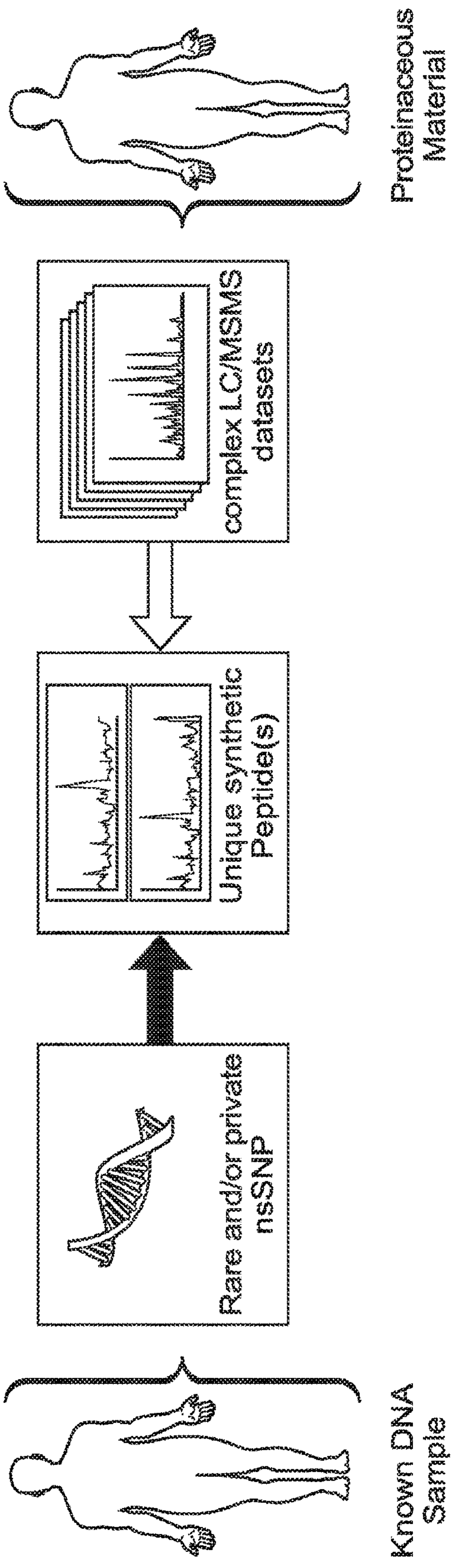
FIG. 17 shows a schematic of an exemplary method to create a custom GVP identification profile for an individual.

In some embodiments, the amino acid sequence of a marker peptide can be provided by first sequencing an exome of an individual, detecting a genetic variation comprised in a sequence of the exome of the individual, providing the corresponding encoded genetic protein variation by providing a translation of the exome sequence comprising the genetic variation, and providing the amino acid sequence of the peptide produced as a result of digesting the peptide using a site-specific protease (e.g. trypsin) (e.g., see FIG. 17). In other embodiments, an amino acid sequence of a marker peptide can be provided without reference to a specific individual exome sequence, but rather based on known marker peptide sequences, for example from a database such as dbSNP and others identifiable by skilled persons upon reading of the present disclosure.

In some embodiments, the amino acid sequence of a marker peptide for identification of an individual can be provided by sequencing the exomes of individuals related to the individual. In some embodiments, the individuals related to the individual can form a mother-father-child relationship.

Exemplary marker peptides comprising genetic protein variations are indicated in Examples 46 and Example 47 indicating exemplary set of GVPs and related mutated peptides validated in hair (Example 46, Table 11) and skin (Example 47, Table 12) samples. The marker peptides of Table 11 and Table 12 can be used in connection with method performed on biological samples from a human being.

In particular exemplary marker peptides that can be preferably used or comprise in the method and system according to the third aspect, comprise any combination of the peptides having sequence SEQ ID NO: 146 to SEQ ID NO: 748 (Example 46, Table 11) for detection in hair samples of human beings, and any combination of the peptides having sequence SEQ ID NO: 749 to SEQ ID NO: 829 (Example 47, Table 12) for detection in skin samples of human beings.

In some embodiments, a marker mass spectrum of a marker peptide can be provided by synthesizing a marker peptide and analyzing the marker peptide using LC-MS/MS. For example, peptides can be synthesized using biosynthetic methods, such as cell-based methods or cell-free methods known to those skilled in the art. Peptide biosynthesis can be performed by translation of DNA or RNA polynucleotides encoding the peptide. Thus, protein biosynthesis can be performed by providing cell-based or cell-free peptide translation systems with DNA or RNA polynucleotides encoding the peptide. Peptides can also be produced by liquid phase or solid-phase chemical peptide synthetic methods known to those skilled in the art. In other embodiments, a marker mass spectrum of a marker peptide can be provided by generating the mass spectrum in silico based on the predicted fragmentation products of the peptide as would be produced in the MS2 stage.

With regard to the method to detect a genetic protein variation in a biological sample according to the third aspect of the present disclosure, any method of performing mass spectrometry of a fractionated digested peptide of the biological sample as described herein or otherwise identifiable by persons skilled in the art can be used to obtain a mass spectrum of each of the fractionated digested peptides.

As understood by skilled persons, mass-spectrometry of fractionated digested peptides of a biological sample can produce a large number of mass spectra. In embodiments described herein, the term "mass spec dataset" is used to refer to a plurality of mass spectra obtained for a plurality of fractionated digested peptides of a biological sample (e.g., see FIG. 9).

In some embodiments, the step of comparing the mass spectrum of the fractionated digested peptides of the biological sample with a marker mass spectrum of a marker peptide as described herein can be performed without reference to a protein variant database.

In particular, in embodiments described herein, a mass spec data set produced from a set of fractionated digested peptides of a biological sample (e.g. an operational sample) can be spectrally searched directly with reference to a marker mass spectrum (e.g. see FIG. 17). The spectral searching with reference to the marker mass spectrum can be performed using commercially available or open source software such as MASCOT, PEAKS, and GPM, as well as others identifiable by those skilled in the art and described herein. Upon comparing the mass spec data set of the biological sample with a marker mass spectrum of a marker peptide, a detected identity between the marker mass spectrum of a marker peptide and a mass spectrum of a peptide of the biological sample indicates that the marker peptide is present in the biological sample (e.g., see FIG. 17).

In some embodiments, stable isotope labeled peptide standards can be used in the method to detect a genetic protein variation in a biological sample. For example, an internal standard of the marker peptide labeled with multiple stable isotopes (e.g., D replacing H residues in the peptide) can be added to the fractionated digested proteins of the biological sample analyzed by LC-MS/MS, so that the standard co-elutes with the native peptide to assist with identification, wherein the mass of the internal standard is shifted so that it doesn't interfere with the analysis. Stable isotopes of peptides can be obtained commercially (e.g., from Sigma Aldrich).

Figure 18:
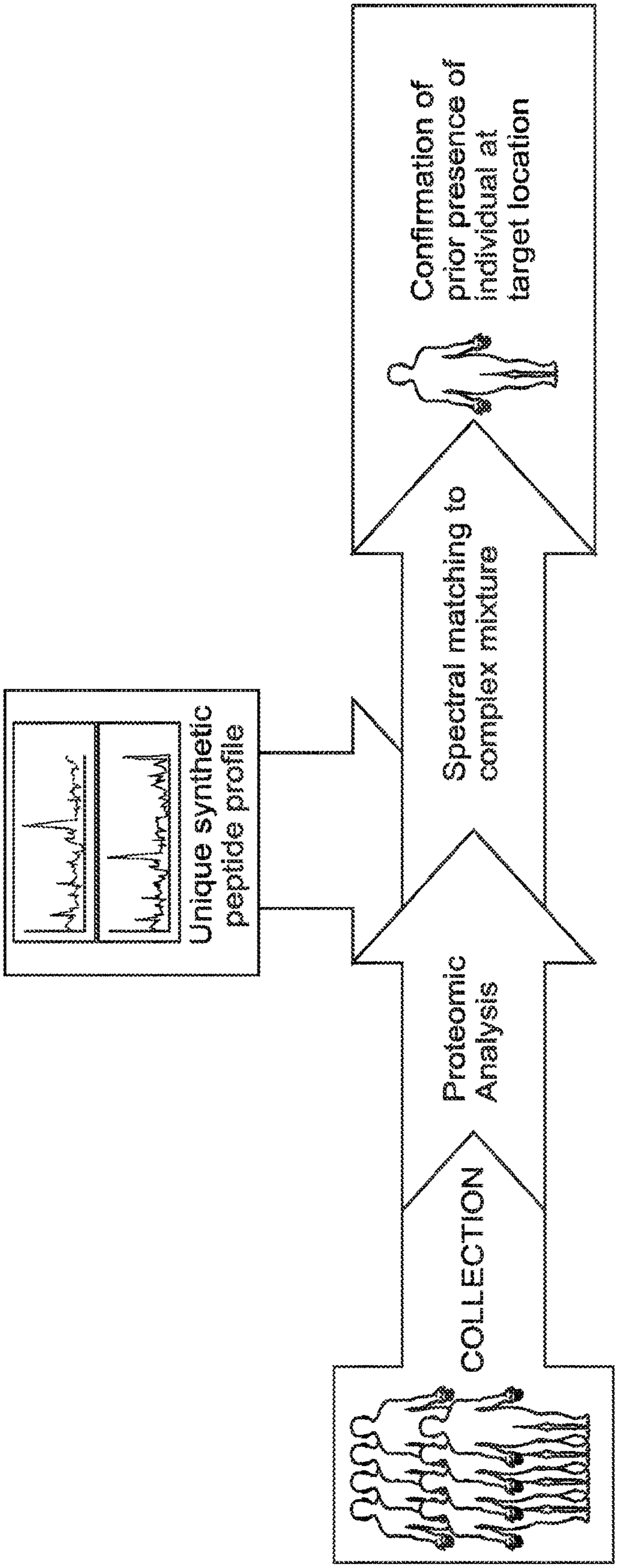
FIG. 18 shows a schematic of an exemplary method of applying an Individual GVP panel to an operational sample.

Accordingly, in some embodiments, a detected identity between the marker mass spectrum of a marker peptide and a mass spectrum of a peptide of the biological sample can be used to confirm the prior presence of an individual at a sample site (e.g., see FIG. 18).

In some embodiments, in the case of a detected identity between the marker mass spectrum of a marker peptide and a mass spectrum of a peptide of the biological sample, the spectral matching can be used to confirm the prior presence of an individual at a sample site when the biological sample comprises proteins from a plurality of individuals (e.g., see FIG. 18).

In some embodiments detecting a genetic variation can be performed with a database obtainable with methods and systems according to a fourth aspect of the present disclosure. According to the fourth aspect, a method and system to improve a marker genetic protein variation database system for a biological organism, and a database obtainable thereby, are described. In the method, system and database herein described, the marker genetic protein variation database system includes data for at least one biological organism and the improvement is inclusion of one or more marker genetic proteins validated to be detectable and in particular, proteomically detectable in the biological sample from an individual of the at least one biological organism.

In particular the methods and systems of the fourth aspect of the instant disclosure are based on a top-bottom exome-driven approach which begins with obtaining exome data, allowing identification of relevant SNPs, followed by proteomic validation of GVPs.

The method according to the fourth aspect comprises: producing a proteomic dataset from a biological sample from an individual of the at least one biological organism and comparing the proteomic dataset to a protein variant database to produce a set of proteomically detected proteins in the biological sample of the individual.

The method further comprises providing a set of represented genes proteomically detectable in the biological sample of the individual, the represented genes corresponding to the proteomically detected proteins in the biological sample of the individual.

The method also comprises: identifying a marker genetic protein variation validated for the biological sample of the individual, to be included in the marker genetic protein variation database system by providing a proteomically detectable genomic variation in the set of represented genes proteomically detectable in the biological sample of the individual, and providing the marker genetic protein variation validated genetic protein variation by providing a proteomically detectable genetic protein variation corresponding to the proteomically detectable genomic variation in the biological sample of the individual.

In some embodiments the proteomic data set is a mass spectrometry dataset.

The system comprises protein databases, and/or reagents to perform proteomic analysis of the biological sample in combination with exome sequence databases for simultaneous combined or sequential use in the method to improve a marker genetic protein variation database system for a biological organism herein described.

Herein, "database" refers to an organized collection of information. "Database system" refers to a system that includes at least one computer for the creation and storage of a database in computer memory. The database system can be stand-alone, distributed (networked), cloud-based (i.e. networked in a cloud computing system), or any standard database configuration. The database system can be shared among applications or dedicated to a single application. The database system can be local or remote. The database can be navigational, relational, object model, document model, flat file, associative, array, multidimensional, semantic, or any other logical structure. "Protein variant database" refers to a database of variant proteins or protein isoforms that are members of a set of highly similar proteins that originate from a single gene or gene family and are the result of genetic differences.

Detected proteins from the biological sample are determined by a proteomic analysis of the mass spectra obtained from individual biological samples. That proteomic analysis involves one or more databases which contain the protein sequences and their accession numbers. The proteins identified in the sample are then related though their unique protein accession numbers to the genes that code for them (the represented genes). This permits linking the observed protein with the responsible gene and therefore the associated statistics for that gene (SNPs, frequencies, etc.).

The mass spectrometry dataset can be obtained by taking the biological sample, for example one prepared by as described herein by dissolving, ultrasonication, and digestion, and running it through a mass spectrometer to determine a mass spectrum of the sample. Mass spectrometry can include hard ionization, soft ionization, inductively coupled plasma, photoionization, glow discharge, or other techniques, which can be selected based on the type of sample provided and the data required. For example, tandem liquid chromatography mass spectrometry can be used for prepared hair samples.

The mass spectrometry dataset can be compared, using existing spectrometry data analysis tools, to existing or created libraries of known spectra of known proteins (e.g. RefSeq, UniProt, Protein Mutation Database, HPMD, MSIPI, MS-CanProVar, dbSNP, Ensembl, COSMIC, or a custom database containing all of the single amino acid polymorphisms above some threshold allelic frequency) to determine the protein content of the biological sample, a.k.a. the proteomically detected proteins.

The data can be formatted in a number of different well-known proteomic datafile formats: as examples, mzML, Mascot Generic Format (MGF), or any proprietary format.

The identified variations in the detected proteins provide markers for genetic information (e.g., identifying genetic information) which can be verified against the genomic variations detectable in the original biological sample. This, the validated genetic protein variation, can be produced by comparing the provided mass spectrometry dataset of the original biological sample with the proteomically detectable genetic protein variation.

Providing a proteomically detectable genomic variation in the set of represented genes proteomically detectable in the biological sample of the individual can be performed by providing exome sequence data of the individual and comparing the exome sequence data of the individual with sequences from the represented genes proteomically detectable in the biological sample of the individual to determine the proteomically detectable genomic variation in the biological sample of the individual. Providing the exome sequence data of the individual can, for example, be performed by the methods explained herein, or by other known methods. The exome data can be procured from the original biological sample, or from some other biological sample, even one of a different type (blood, hair, saliva, etc.) than the original. Additionally, the exome data can be procured from any genetically relevant source, such as a close family member of the individual. Additionally, the exome data can be procured from a database of already determined genetic data.

Furthermore, providing a proteomically detectable genetic protein variation corresponding to the proteomically detectable genomic variation in the biological sample of the individual, can be performed through single nucleotide polymorphism (SNP) annotation on the proteomically detectable genomic variation in the biological sample of the individual to produce a corresponding mutant/reference protein sequence; and providing the proteomically detectable genetic protein variation from the annotated proteomically detectable genomic variation in the biological sample of the individual.

"SNP annotation" (or "annotation") as used herein refers to the process to predict the effect or function of an individual SNP by use of a tool (e.g., SNPeff, VEP, ANNOVAR, FATHMM, PhD-SNP, PolyPhen-2, SuSPect, F-SNP, AnnTools, SeattleSeq, SNPit, SCAN, Snap, SNPs&GO, LS-SNP, Snat, TREAT, TRAMS, Maviant, MutationTaster, SNPdat, Snpranker, NGS—SNP, SVA, VARIANT, SIFT, PhD-SNP and FAST-SNP). In annotation, biological information is extracted, collected, and displayed in a way that makes querying the data easier.

A genetic protein variation identity panel can be created by collecting the validated genetic protein variant proteomically detectable in the biological sample of the individual. This provides a genetic protein variation identity panel of the individual.

Exemplary represented genes and/or exome sequences of *Homo Sapiens* having a corresponding detected peptide sequence that can be used in the method and/or comprised in a database according to the fourth aspect are indicated in Examples 43 to 45 listing exemplary set of genes validated in hair samples (Example 43, Table 8) bone samples (Example 44, Table 9) and skin samples (Example 45, Table 10) of a human being.

Exemplary marker genetic protein variations validated in *Homo Sapiens* that can be used in the method and/or comprised in a database according to the fourth aspect if the instant disclosure, can comprise any one of the marker genetic protein variations indicated in Examples 46 and Example 47 listing exemplary set of GVPs validated in hair (Example 46, Table 11) and skin samples (Example 47, Table 12) of a human being.

In some embodiments, detecting a genetic variation can be performed with a pooled marker genetic variation database system obtainable with a method and system to improve a pooled marker genetic protein variation database system according to the fifth aspect of the present disclosure. In the method and system, the pooled marker genetic protein variation database system comprises marker genetic protein variations common to a plurality of individuals.

The method comprises: providing a number of proteomic datasets of individuals of the plurality of individuals, the number statistically significant for the plurality of individuals, identifying a protein common to the provided number of proteomic datasets; and selecting from the identified protein common to the provided proteomic datasets, a protein detectable in a biological sample of an individual of the plurality of individuals.

The method further comprises providing a number of exome datasets of the individuals of the plurality of individuals, the number statistically significant for the plurality of individuals; and identifying a genetic variation in the provided number of exome datasets.

The method also comprises selecting from the identified genetic variation, a genetic variation detectable in the biological sample; and comparing the selected proteins detectable in the biological sample with the selected genetic variations detectable in the biological sample, to provide a marker genetic protein variation common to a plurality of individuals of a biological organism type and validated to be detectable in the biological sample.

The system comprises protein databases, and/or reagents to perform proteomic analysis of the biological sample in combination with exome sequence databases for simultaneous combined or sequential use in the method to improve a pooled marker genetic protein variation database system for a biological organism herein described.

The process for creating a marker genetic protein variation database system can be repeated for a plurality of individuals, preferably ones sharing the same genetic variant or variants to be cataloged in the database, to provide a database comprising validated genetic protein variations proteomically detectable in the biological sample of the plurality of individuals of that biological organism type.

This database can be formed by collecting the represented genes common to the individuals into a proteomically detectable gene pool, providing validated genetic protein variations proteomically detectable in the biological sample of the plurality of individuals of the biological organism from the collected common represented, and collecting the validated genetic protein variants proteomically detectable in the biological sample of the individuals, in a genetic protein variation panel comprising a genetic protein variation panel common to the individuals.

The proteomically detectable gene pool can contain data corresponding to proteins that are common to some or all the validated genetic protein variants proteomically detectable in the biological sample of a given individual. This can be set against a threshold limit, for example only proteins that are common in at least (or over) 50% of all individuals in the pool.

Providing validated genetic protein variations proteomically detectable in the biological sample of the plurality of individuals can be performed to only include genomic variation with a frequency greater than some threshold limit, for example 1%, in the plurality of the individuals into a proteomically detectable gene pool.

One aspect of a method to improve a marker genetic protein variation database system comprising marker genetic protein variations common to a plurality of individuals includes: providing a number of proteomic datasets of individuals of the plurality of individuals, the number statistically significant for the plurality of individuals, identifying one or more proteins common to the provided number of proteomic datasets; selecting from the identified proteins common to the provided proteomic datasets, a protein detectable in a biological sample (e.g., hair) of an individual of the plurality of individuals; providing a number of exome datasets of the individuals of the plurality of individuals, the number statistically significant for the plurality of individuals; identifying a genetic variation in the provided number of exome datasets; selecting from the identified genetic variation, a genetic variation detectable in the biological sample; and comparing the selected proteins detectable in the biological sample with the selected genetic variations detectable in the biological sample, to provide a marker genetic protein variation common to a plurality of individuals of a biological organism type and detectable in the biological sample.

The database system is realizable in a computer system, either as a single computer (processor, memory, etc.) or as a network of computers, including, as examples, cloud, intranet, internet, or parallel processing systems. The database system can be centralized and accessible by web-based searches, or stand-alone.

Once created, the database can be searched to create identity metrics for a questioned biological sample of the same type (hair, blood, saliva, etc.) by GVP matching.

The term "exome" as used herein refers to the part of the genome formed by exons, the sequences which when transcribed remain within the mature RNA after introns are removed by RNA splicing. It consists of all DNA that is transcribed into mature RNA in cells of any type as distinct from the transcriptome, which is the RNA that has been transcribed only in a specific cell population. For example, humans have about 180,000 exons, constituting about 1% of the human genome, or approximately 30 million base pairs.

Exome sequencing, also known as whole exome sequencing (WES or WXS), typically consists of two steps: the first step is to select only the subset of DNA consisting of exons. The second step is to sequence the exonic DNA using any high-throughput DNA sequencing technology. In the first step, target-enrichment methods allow the selective capture of genomic regions of interest from a DNA sample prior to sequencing. Both array-based and in-solution capture techniques can be used. In array-based capture, microarrays containing single-stranded oligonucleotides with sequences from a genome (e.g. human exome) tile the region of interest fixed to the surface. Genomic DNA is sheared to form double-stranded fragments. The fragments undergo end-repair to produce blunt ends and adaptors with universal priming sequences are added. These fragments are hybridized to oligos on the microarray. Unhybridized fragments are washed away and the desired fragments are eluted. The fragments can then be amplified using PCR. Next-generation sequencing techniques can also be used with array-based capture. For example, the Sequence Capture Human Exome 2.1M Array can be used to capture ~180,000 coding exons. This method is both time-saving and cost-effective compared to PCR based methods. The Agilent Capture Array and the comparative genomic hybridization array are other methods that can be used for hybrid capture of target sequences. To capture genomic regions of interest using in-solution capture, a pool of custom oligonucleotides (probes) is synthesized and hybridized in solution to a fragmented genomic DNA sample. The probes (labeled with beads) selectively hybridize to the genomic regions of interest after which the beads (now including the DNA fragments of interest) can be pulled down and washed to clear excess material. The beads are then removed and the genomic fragments can be sequenced allowing for selective DNA sequencing of genomic regions (e.g., exons). In general, in the first step, any of a number of available exome enrichment platforms (e.g., Roche/NimbleGen's SeqCap EZ Human Exome Library, Illumina's Nextera Rapid Capture Exome, Agilent's SureSelect XT Human All Exon and Agilent's SureSelect QXT) can be used to allow the selective capture of genomic regions of interest from a DNA sample. In the second step, there are several sequencing platforms available in addition to classical Sanger sequencing. Other platforms include the Roche 454 sequencer, the Illumina Genome Analyzer II and the Life Technologies SOLiD & Ion Torrent, which can be used for exome sequencing. Any cellular material that contains genomic DNA can be used for exome sequencing, such as human blood samples, buccal sample and others identifiable by skilled persons.

Exome sequencing can also be performed by RNA exome sequencing (e.g., Illumina RNA Exome Capture Sequencing) according to approaches and techniques identifiable by a skilled person.

Figure 7:
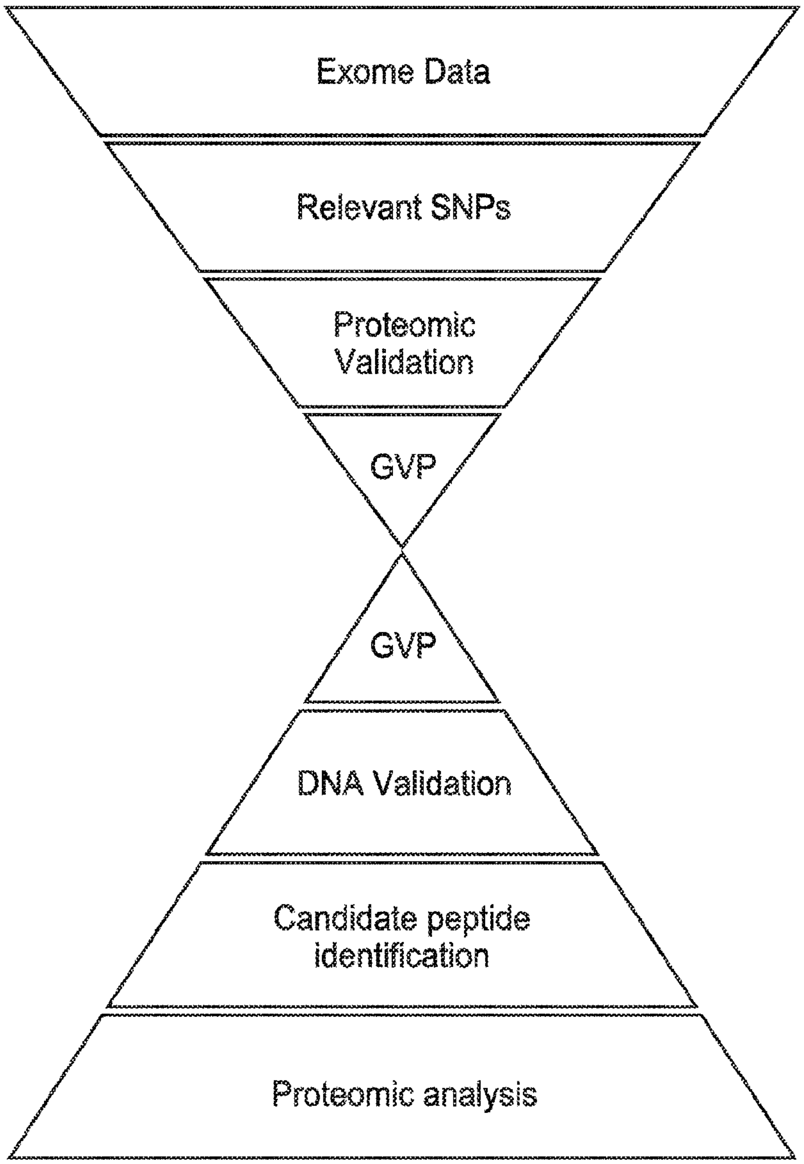
FIG. 7 shows a schematic illustration of the exome-driven (top-down) approaches according to the present disclosure in comparison with bottom-up approaches suitable to identify/detect genetic protein variations in a sample.

The term "exome-driven" as used herein refers to an approach of GVP discovery that begins with sequencing the exome of an individual, allowing identification of relevant SNPs, followed by proteomic validation of GVPs (see FIG. 7). Thus, the "exome-driven" approach features (1) obtaining exome sequence for each donor, (2) establishing a workflow to identify specific SNPs of interest, (3) targeted proteomic analysis allowing simplified identification of GVPs in raw MS data, and (4) allows a logic-driven GVP selection, identification, and validation process. In contrast, a "proteome-driven" discovery approach begins with proteomic analysis, followed by candidate peptide identification, and DNA validation of identified GVPs (see FIG. 7). Thus, the proteome-driven approach has limitations such as being a 'needle in a haystack' approach that is not compatible with targeted proteomic analysis and relies on manual MS interpretation to identify potential GVPs, wherein potential GVPs must then be validated by separate individual genotyping experiments.

Figure 8:
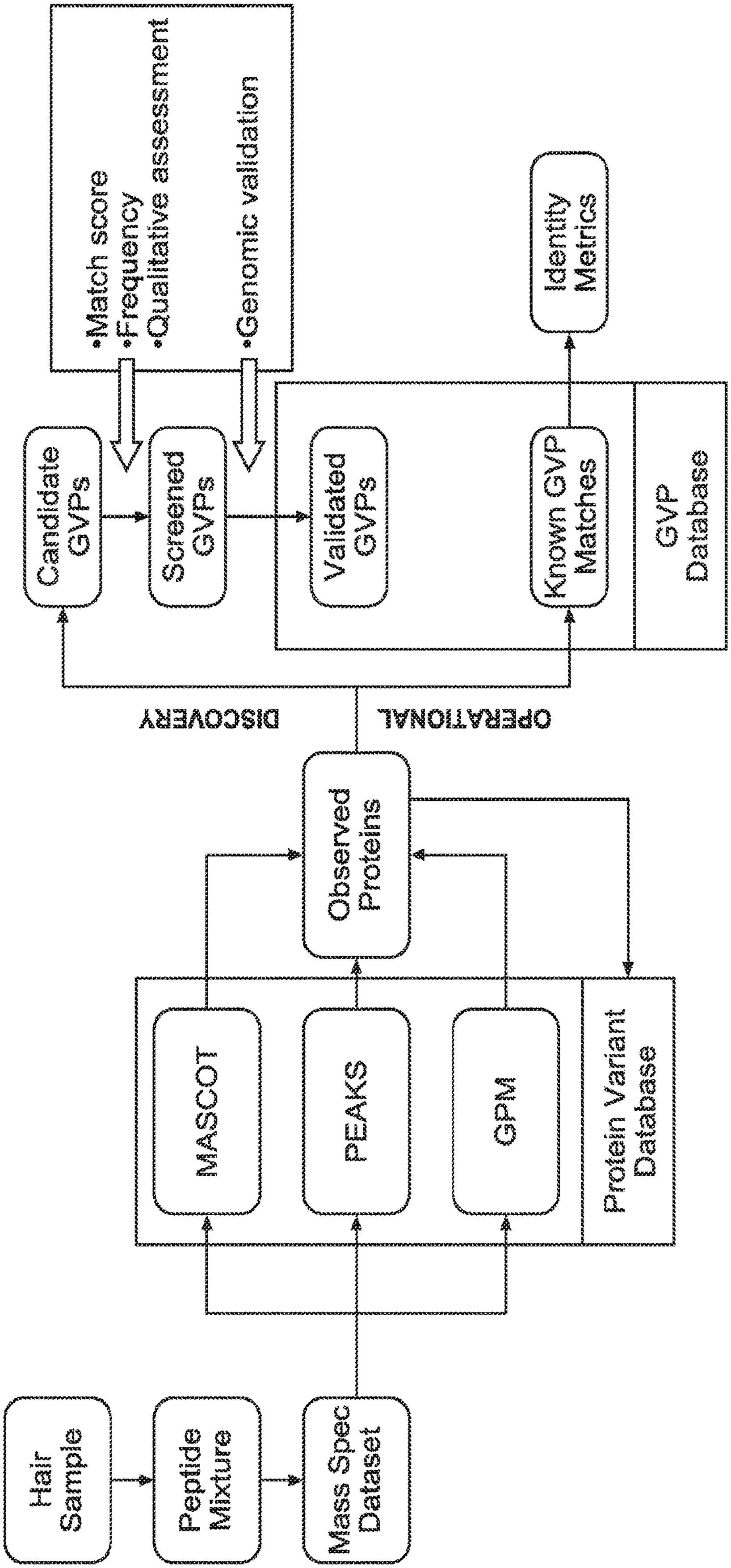
FIG. 8 shows a schematic representation of the steps of an exemplary "proteome-driven" GVP discovery and evaluation method.

In a typical "proteome-driven" GVP discovery approach that is used following existing methods and systems, a peptide mixture is obtained from a sample and is analyzed by LC-MS/MS. The resulting dataset is then analyzed with reference to a protein variant database using analysis software tools such as MASCOT, PEAKS, and GPM. Candidate GVPs in the observed proteins identified in the sample are screened using metrics such as match score, frequency, and qualitative assessment. The screened GVPs are then validated by confirming the GVPs comprise missense mutations genetically encoded by SNPs by genomic sequencing. The validated GVPs then are incorporated into a GVP database. FIG. 8 shows an exemplary schematic summarizing a typical proteome-driven GVP discovery approach (e.g. for hair samples).

The term "validated GVP" as used herein refers to a GVP that comprises a variation (e.g. a SAP) that has been confirmed to correspond to a variation (e.g., a nsSNP) in the exome of the same individual.

Figure 9:
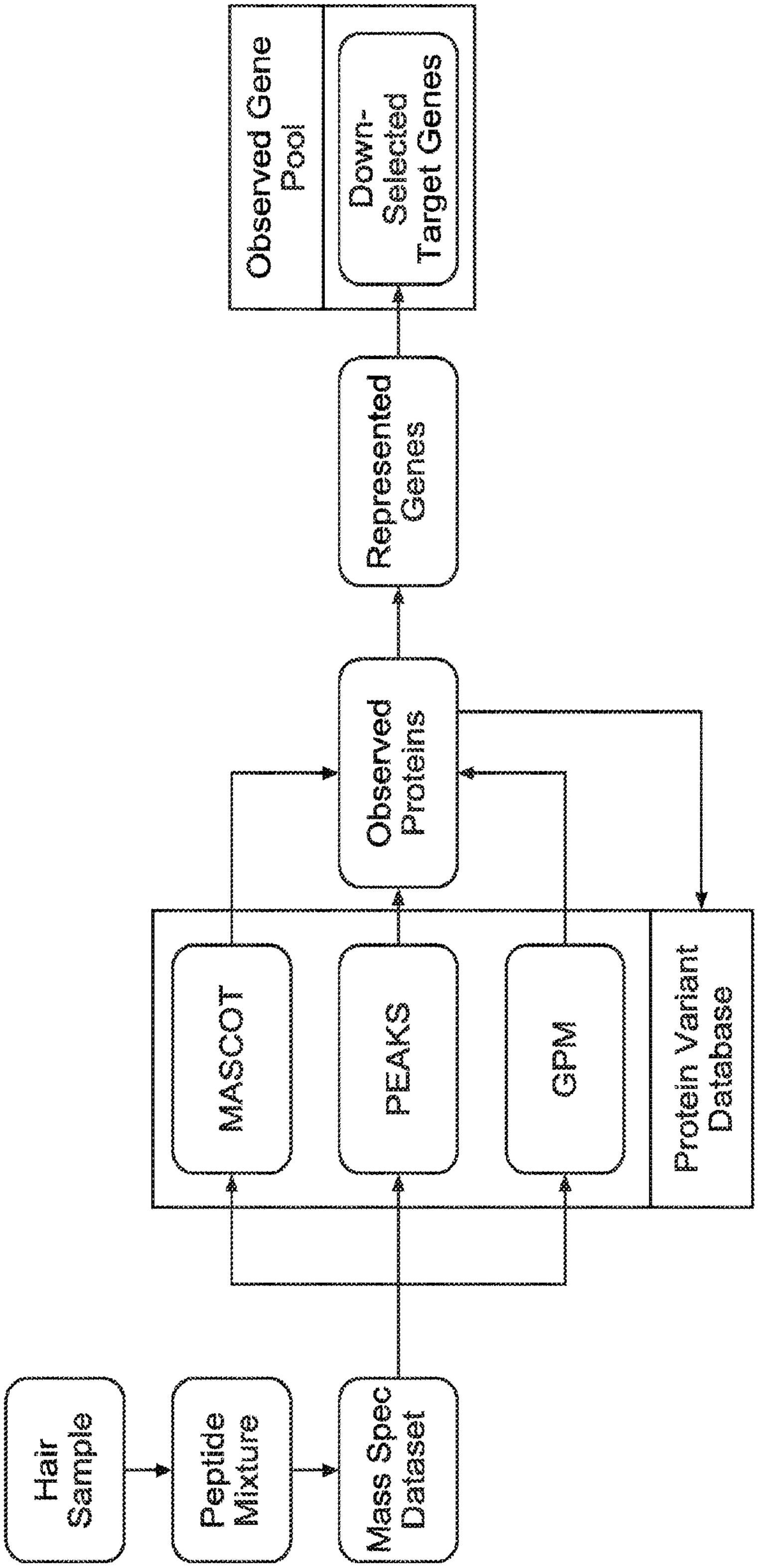
FIG. 9 shows a schematic of an exemplary method for determination of an 'Observed Gene Pool' according to a top-down approach herein described.
Figure 10:
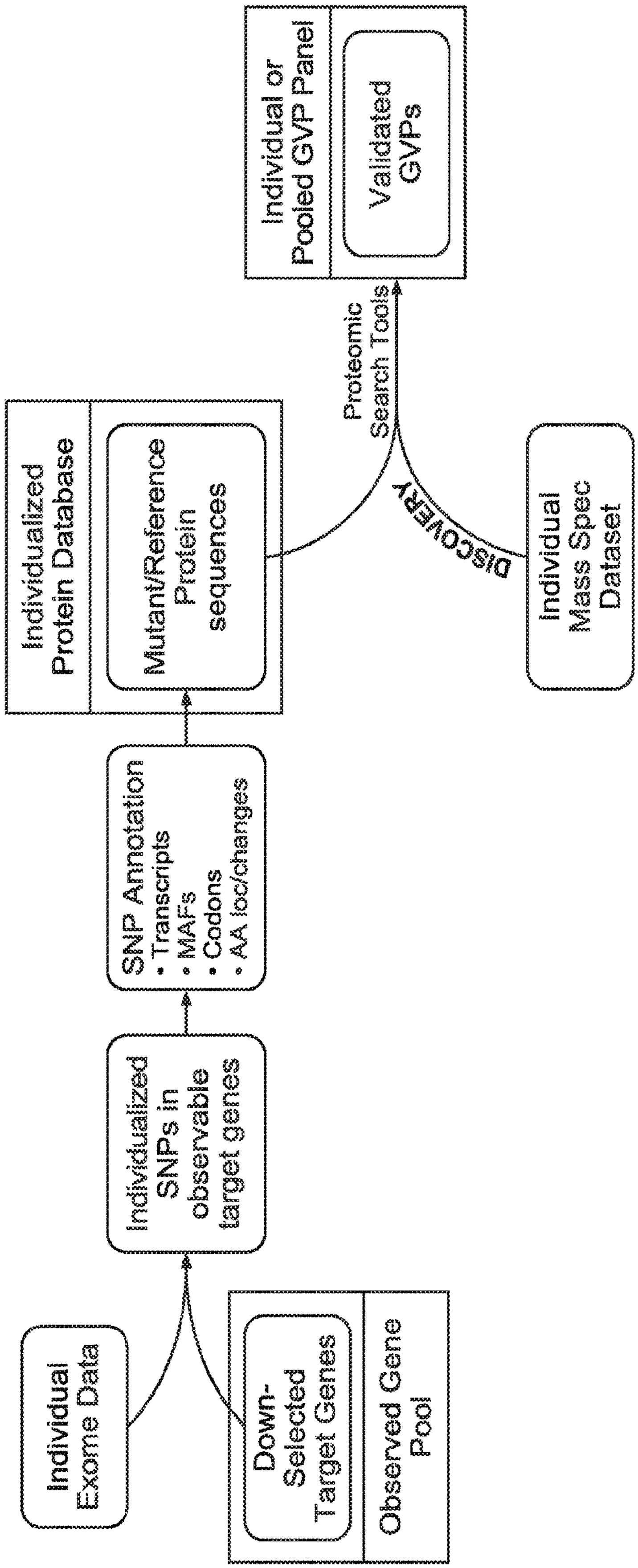
FIG. 10 shows a schematic of an exemplary "exome-driven" GVP discovery method, showing integration of genetic and proteomic data according to embodiments herein described.

A schematic summarizing the "exome-driven" GVP discovery approach is shown in FIGS. 9 and 10. As shown in FIG. 9, for a given tissue type (e.g. hair), the proteins detected by LC-MS/MS for a given individual are referred to herein as "observed proteins" that are encoded by "represented genes". Thus, the represented genes form the 'Down-selected Target Genes' of the 'Observed Gene Pool'.

In some embodiments, the exome-driven GVP discovery approach described herein can be used to assemble a panel of validated GVPs for a population of individuals, referred to herein as a "Common GVP Panel" or "Pooled GVP Panel". In particular, in the "Common GVP panel", GVPs are down selected for common nsSNPs, and a consensus panel is assembled from a large cohort. As described herein, the term "common nsSNPs" refers to nsSNPs having a frequency >1% and having a worldwide distribution.

In some embodiments, the exome-driven GVP discovery approach described herein can be used to assemble a panel of validated GVPs for an individual, referred to herein as an "Individual GVP Panel". In particular, for an 'Individual GVP Panel', GVPs can be down-selected based on low-frequency or 'rare' or 'private' nsSNPs and the GVP panel is unique to that individual (see FIG. 17). The term "down-select" as used herein refers to narrowing the field of choices based on specific conditions or characteristics. The term "rare SNPs" as used herein refers to nsSNPs having a frequency <0.05% in a given population.

An exemplary "exome-driven" GVP discovery method, showing integration of exomic and proteomic data for building a "Pooled GVP Panel" or an "Individual GVP Panel" is described in Example 14.

In some embodiments, exome-driven discovery of GVPs from a diverse cohort allows discovery of markers that are informative of biogeographic background.

The exome-driven GVP discovery methods and systems described herein can be used for discovery of validated GVPs for any tissue type. For example, an exemplary exome-driven method of building a panel of validated GVPs for hair samples is described in Example 15 and an exemplary panel of validated GVPs for bone is described in Example 21.

The exome-driven GVP discovery methods and systems described herein can be used in several embodiments in combination with samples from any tissue type prepared using any method.

In some embodiments, application of the product rule can be used to estimate the probability of a combination of individual nsSNPs (otherwise referred to herein as a "nsSNP profile") in a population. The term "product rule" as used herein refers to the multiplication of frequencies of individual nsSNPs in a profile in a population to calculate the overall frequency of the combination of nsSNPs in a nsSNP profile in the population.

Figure 13:
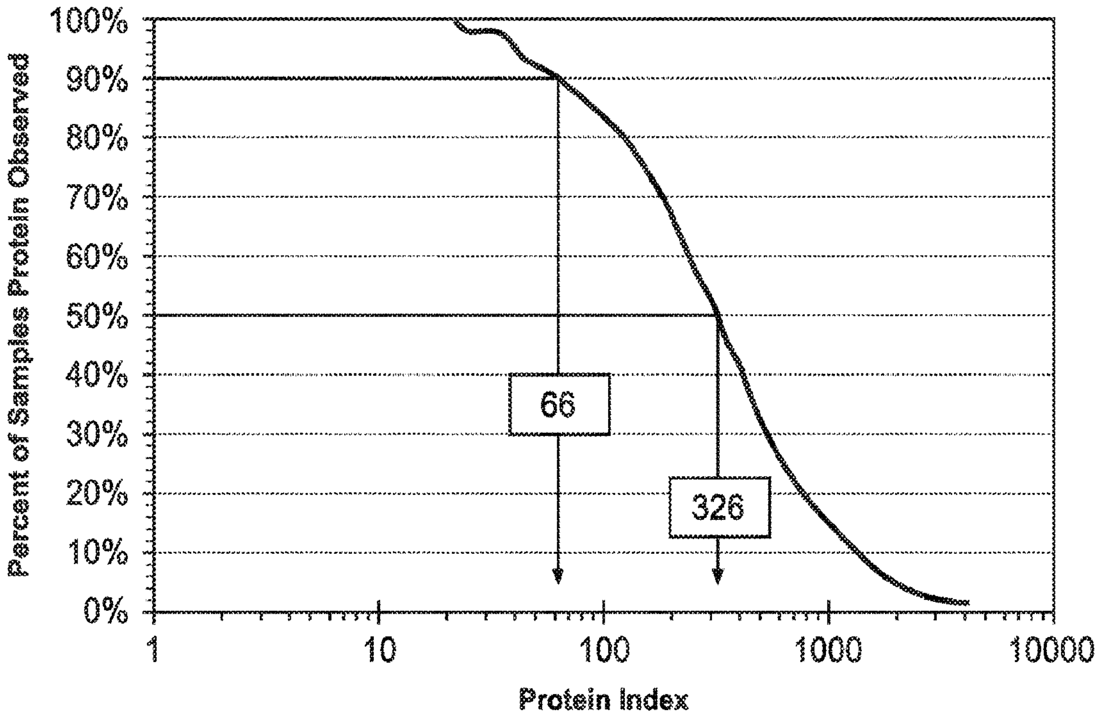
FIG. 13 shows an exemplary graph reporting results of an exemplary approach to provide identity metrics to be used in methods and systems to detect/provide a validated genetic marker variation herein described as well as to build related databases.

As understood by those skilled in the art, linkage disequilibrium (LD) can affect calculation of the overall frequency of the combination of nsSNPs in a nsSNP profile in the population, and thus can affect theoretical genotype match probabilities. The term "linkage disequilibrium" refers to non-random association of alleles at different loci in a given population. In general, DNA sequences that are close together on a chromosome have a tendency to be inherited together during the meiosis phase of sexual reproduction. Two loci that are physically near to each other are unlikely to be separated onto different chromatids during chromosomal crossover, and are therefore said to be more linked than markers that are far apart. Loci are said to be in linkage disequilibrium when the frequency of association of their different alleles is higher or lower than what would be expected if the loci were independent and associated randomly. Because nearby loci are often inherited together, in some embodiments the product rule doesn't directly apply. For example, many loci for exemplary validated GVPs shown in FIG. 13 are keratin genes, which are clustered on chromosomes 12 and 17. Thus, the loci encoding these GVPs may be linked though they are in different genes, and linked loci can be up to, for example, 220 kb apart. Therefore, in some embodiments, LD can be taken into account for calculation of the probability of an overall non-synonymous SNP profile in the population. LD can be factored into the calculation by computing LD between pairs of GVP loci located on the same chromosome, for example using data from the 1000 Genomes Project dataset. Next, clusters of linked loci can be grouped, by computation of joint genotype probabilities given LD for loci within each cluster and by multiplying cluster probabilities to get overall genotype likelihood.

In some embodiments, strategies for identification of candidate GVPs comprise studying a larger and more diverse cohort, increased proteomic detection through instrumentation, and bioinformatic data mining of previously collected datasets, among others identifiable by skilled persons upon reading of the present disclosure. In exemplary embodiments of the methods and systems described herein, sample sets comprise protein and DNA sample sets from cohorts comprising n=200-250 European Americans, n=30-50 African Americans, n=30-50 Hispanic, n=100 East Asian, and n=60 parent/offspring.

In some embodiments, the panel of validated GVPs is an Individual GVP panel.

In some embodiments, the panel of validated GVPs is a Pooled GVP panel.

Figure 11:
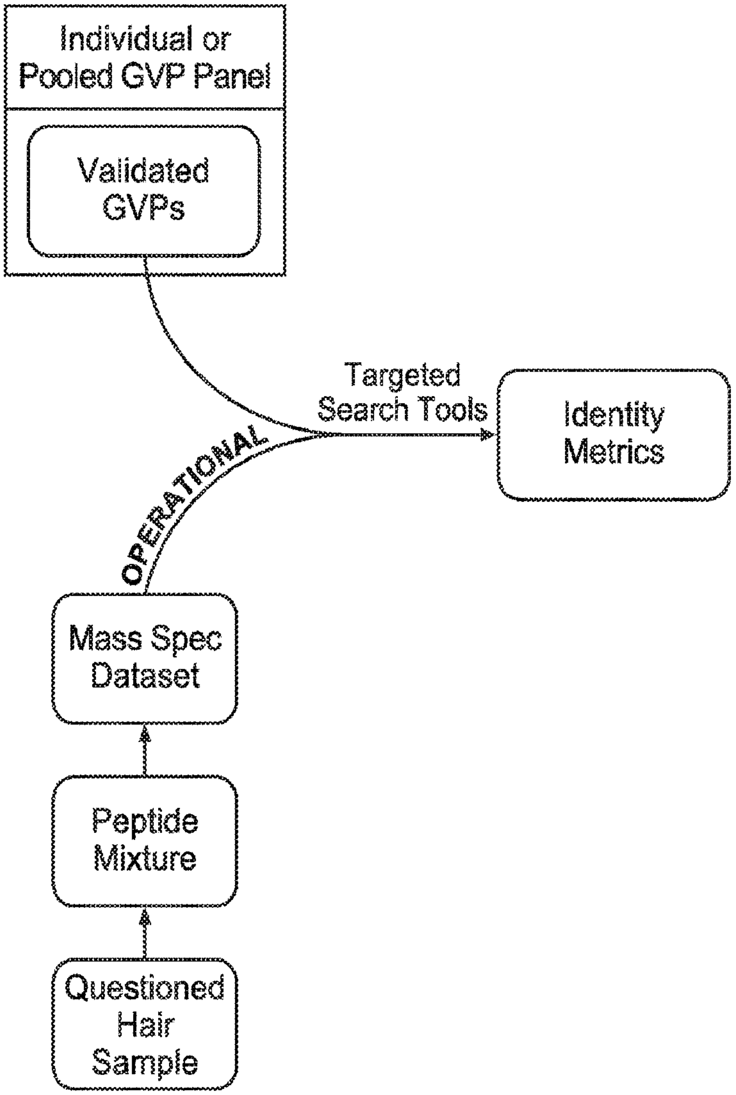
FIG. 11 shows a schematic of an exemplary application of an "exome-driven" validated GVP panel to operational samples.

A schematic of an exemplary method of how to apply an Individual or Pooled GVP panel to operational samples is shown in FIG. 11 and described in Example 16.

Exemplary represented validated genes and/or exome sequences of *Homo Sapiens* having a corresponding detected peptide sequence that can be used in the method and/or comprised in a database according to the fifth aspect of the instant disclosure are indicated in Examples 43 to 45 listing exemplary set of genes validated in hair samples (Example 43, Table 8) bone samples (Example 44, Table 8) and skin samples (Example 45, Table 10) of a human being.

Exemplary validated marker genetic protein variations that can be used in the method and/or comprised in a database according to the fifth aspect of the instant disclosure, can comprise any one of the marker genetic protein variations indicated in Examples 46 and Example 47 listing exemplary set of GVPs validated in hair (Example 46, Table 11) and skin (Example 47, Table 12) samples. The validated GVPs of Table 11, and Table 12 can preferably be used in connection with method performed on biological samples from a human being.

Further details concerning the methods and systems of the present disclosure will become more apparent hereinafter from the following detailed disclosure of examples by way of illustration only with reference to an experimental section.

In some embodiments detecting a genetic variation can be performed with a method and a system to detect a marker genetic variation for a biological organism validated to be detectable in a biological sample of an individual of the biological system, according to the sixth aspect of the present disclosure.

The method comprises preparing the biological sample to obtain a processed biological sample comprising solubilized proteins to be used in a proteomic analysis; and fractionating the processed biological sample to obtain a solubilized protein fraction comprising the solubilized proteins from the sample and a solubilized DNA fraction comprising solubilized nuclear and/or mitochondrial genome from the sample.

The method further comprises detecting a genetic protein variation in the solubilized proteins from the sample by performing the proteomic analysis of the solubilized protein fraction; and detecting a genomic variation of the nuclear and/or mitochondrial genome by performing a genetic analysis of the solubilized DNA fraction.

The method also comprises comparing the detected genetic protein variation and/or the detected genomic variation with a marker genetic protein variation and/or of a marker genomic variation respectively from the marker genetic variation database system herein described.

The system comprises exome sequences databases and/or reagents to detect exome sequences in an individual of the biological organism, in combination with reagents to perform proteomic analysis of the biological sample for simultaneous combined or sequential use in the method to detect a marker genetic variation for a biological organism validated to be detectable in a biological sample of an individual of the biological system herein described.

In embodiments of the method according to the sixth aspect, any method of preparing the biological sample identifiable by persons skilled in the art upon reading the present disclosure can be used in the method to detect a marker genetic variation in a biological sample of a biological organism.

In embodiments of the method according to the sixth aspect, any method to perform fractionating the processed biological sample to obtain a solubilized protein fraction comprising the solubilized proteins from the sample and a solubilized DNA fraction comprising solubilized nuclear and/or mitochondrial genome from the sample can be used in the method to detect a marker genetic variation in a biological sample of a biological organism.

In some embodiments, the fractionating can be performed for example by several methods of DNA purification from a solution containing protein and DNA. In general, successful nucleic acid purification requires effective disruption of cells or tissue or organ material, denaturation of nucleoprotein complexes, inactivation of nucleases such as DNase, and absence of contamination.

For example, commonly used procedures for DNA purification from detergents, proteins, salts and reagents used in sample preparation comprise alcohol precipitation, phenol-chloroform extraction, and mini-column purification, among other techniques known in the art. Alcohol precipitation can be performed using e.g., using ice-cold ethanol or isopropanol. Since DNA is insoluble in these alcohols, it will aggregate together, giving a pellet upon centrifugation. Precipitation of DNA can be improved by increasing of ionic strength, for example by adding sodium acetate. Phenol—chloroform extraction can be performed in which phenol denatures proteins in the sample. After centrifugation of the sample, denatured proteins remain in the organic phase while aqueous phase containing nucleic acid is mixed with the chloroform that removes phenol residues from solution. Mini-column purification can be performed, in which nucleic acids bind (adsorb) to a solid phase (e.g., silica or other) depending on the pH and the salt concentration of the buffer. For example, an exemplary method of performing fractionation of a biological sample into a DNA fraction and a protein fraction using mini-column purification is described in Example 7.

In embodiments of the method and system of combined mtDNA and proteomic analysis from a single sample, any method of sample preparation identifiable by those skilled in the art that can provide an extract of purified protein suitable for proteomic analysis and a mtDNA extract and/or nuclear DNA extract suitable for mtDNA and/or nuclear DNA analysis from a single biological sample can be used, and is not limited to exemplary methods described herein.

The exemplary procedures described herein reveal that protein identification markers (GVPs) can be detected from one-inch hair samples using LC-MS/MS of peptides. In exemplary embodiments described herein, protein extraction by ultrasonication and harsh detergents can fully dissolve the hair matrix, maximizing the ability of enzyme proteolysis and subsequently peptide concentration in samples. Additionally, the exemplary protein extraction procedure described herein is compatible with mtDNA extraction, copy number determination, and hyper-variable region sequencing (Example 7). Thus, in some embodiments, GVP discovery and mtDNA sequencing in combination provide a substantial measure of human identity because of the vast variation in allelic frequencies of SNPs. These exemplary embodiments illustrate the potential proteomic analysis of hair evidence has for becoming a widely implemented forensic tool.

As understood by skilled persons, the term “genome” refers to the total heritable genetic material of an organism, comprising DNA (or RNA in RNA viruses), wherein a genome comprises a plurality of genes.

In particular, in eukaryotes, and in particular in animals, the genome comprises both a “nuclear genome” and a “mitochondrial genome”. In plants, the genome also comprises a “chloroplast genome”. Thus, in embodiments herein described, the term “genome” can be applied specifically to mean the genes that are stored on a complete set of nuclear DNA (also referred to herein as the “nuclear genome”, typically arranged on chromosomes in a eukaryotic cell’s nucleus) and can also be applied to specifically refer to the genes that are within organelles that contain their own DNA, as with the “mitochondrial genome” or the “chloroplast genome”, as identifiable by persons skilled in the art upon reading of the present disclosure.

The mitochondrial genome is the entirety of hereditary information contained in mitochondria. Mitochondrial DNA (mtDNA) is not transmitted through nuclear DNA (nDNA).

While DNA is degraded as a function of biological processes, mitochondrial DNA has a higher template number than nuclear DNA and is more likely to survive apoptotic and subsequent environmental processes[11]. Accordingly, for some tissue sample types, recovery of both protein and mtDNA from tissue samples would allow incorporation of both proteomic and mtDNA haplotype analysis into a single measure of discrimination.

The terms "haplotype" or "haploid genotype" as used herein refers to a group of genes in an organism that are inherited together from a single parent and the term "haplogroup" refers to a group of similar haplotypes that share a common ancestor with a single-nucleotide polymorphism mutation. Accordingly, for example, a human mitochondrial DNA haplogroup is a haplogroup defined by differences in human mitochondrial DNA. The letter names of the haplogroups (not just mitochondrial DNA haplogroups) run from A to Z. The human mitochondrial genome is the entirety of hereditary information contained in human mitochondria. Mitochondrial DNA (mtDNA) is not transmitted through nuclear DNA (nDNA). In humans, as in most multicellular organisms, mitochondrial DNA is inherited only from the mother's ovum. In humans, mitochondrial DNA (mtDNA) forms closed circular molecules that contain 16,569 DNA base pairs, with each such molecule normally containing a full set of the mitochondrial genes. In humans, the 16,569 base pairs of mitochondrial DNA encode for 37 genes. Human mitochondrial DNA was the first significant part of the human genome to be sequenced.

For example, the current best practice to gain forensically informative genetic information from hair shafts is to obtain the mitochondrial DNA haplotype and determine the probability of occurrence in reference sample populations[12]. Incorporation of both proteomic and mtDNA haplotype analysis into a single measure of discrimination, would maximize the probative value of a biological sample such as hair shafts.

As understood by skilled persons, a genome (and in particular a nuclear genome) can comprise polynucleotides comprising repetitive DNA elements such as interspersed repeats, retrotransposons, long terminal repeats, non-long-terminal repeats, long-interspersed elements, short interspersed elements, DNA transposons, and tandem repeats, among others identifiable by skilled persons.

The term "interspersed repeat" refers to polynucleotide elements such as transposable elements (TEs), and in some embodiments can also refer to some protein coding gene families and pseudogenes. Transposable elements are able to integrate into the genome at another site within the cell. TEs can be classified into two categories, Class 1 (retrotransposons) and Class 2 (DNA transposons), as would be understood by skilled persons. Retrotransposons can be transcribed into RNA, which are then duplicated at another site into the genome. Retrotransposons can be divided into Long terminal repeats (LTRs) and Non-Long Terminal Repeats (Non-LTR). Long interspersed elements (LINEs) typically encode two Open Reading Frames (ORFs) to generate transcriptase and endonuclease, which are essential in retrotransposition. Short interspersed elements (SINEs) are typically less than 500 base pairs in length and require the LINEs machinery to function as nonautonomous retrotransposons. For example, the Alu element is the most common SINE found in primates, it has a length of about 350 base pairs and takes about 11% of the human genome with around 1,500,000 copies.

In particular, the term "tandem repeat" refers to a repeating pattern of one or more nucleotides in DNA wherein the repetitions are directly adjacent to each other. In particular, the term "minisatellite" refers to a tandem repeat having typically between 14 and 60 repeated nucleotides, whereas tandem repeats having fewer repeated nucleotides are typically referred to as "microsatellites" or "short tandem repeats" or "STR".

In particular, an STR is type of microsatellite consisting of a unit of 2-13 or more base pairs repeated hundreds of times in a row on the DNA strand. A microsatellite is a tract of repetitive DNA in which certain DNA motifs (ranging in length from 2-13 base pairs) are repeated, typically 5-50 times. Microsatellites occur at thousands of locations within an organism's genome; additionally, they have a higher mutation rate than other areas of DNA leading to high genetic diversity. Microsatellites are often grouped according to the length of the unit of repeated base pairs. For example, the sequence TATATATATA (SEQ ID NO: 134) is a dinucleotide microsatellite, and GTCGTCGTCGTCGTC (SEQ ID NO: 135) is a trinucleotide microsatellite (with A being Adenine, G Guanine, C Cytosine, and T Thymine). Repeat units of four and five nucleotides are referred to as tetra- and pentanucleotide motifs, respectively. Most eukaryotes have microsatellites, with the notable exception of some yeast species, and these microsatellites are distributed throughout the genome. The human genome for example contains 50,000-100,000 dinucleotide microsatellites, and lesser numbers of tri-, tetra- and pentanucleotide microsatellites. Many are located in non-coding parts of the human genome and therefore do not produce proteins, but they can also be located in regulatory regions and coding regions. Microsatellites and minisatellites together are classified as VNTR (variable number of tandem repeats) DNA.

STRs are often used in forensics because although the repeating sequence of base pairs of a specific microsatellite does not change from person to person, the number of times the sequence repeats does change. This allows the number of repeats of a sequence to identify a person through his/her DNA if the number of sequence repeats matches the initial DNA basis used for comparison. STRs can also be used to eliminate a person from suspicion or reduce the suspicion of a person if he/she does not have the same number of sequence repeats as the comparate DNA. STRs are widely used for DNA profiling in kinship analysis (such as paternity testing) and in forensic identification. They are also used in genetic linkage analysis/marker assisted selection to locate a gene or a mutation responsible for a given trait or disease. Microsatellites are also used in population genetics to measure levels of relatedness between subspecies, groups and individuals.

In particular, STR analysis is a tool in forensic analysis that evaluates specific STR regions found on nuclear DNA. STR analysis measures the exact number of repeating units. This method differs from restriction fragment length polymorphism analysis (RFLP) since STR analysis does not cut the DNA with restriction enzymes. Instead, probes are attached to desired regions on the DNA, and a polymerase chain reaction (PCR) is employed to discover the lengths of the short tandem repeats. This method uses highly polymorphic regions that have short repeated sequences of DNA (the most common is 4 bases repeated, but there are other lengths in use, including 3 and 5 bases). Because unrelated individuals typically have different numbers of repeat units, STRs can be used to discriminate between unrelated individuals. These STR loci (locations on a chromosome) are targeted with sequence-specific primers and amplified using PCR. The DNA amplicons that result are then separated and detected using electrophoresis methods, such as capillary electrophoresis and gel electrophoresis.

Several STR-based DNA-profiling systems are in use, identifiable by those skilled in the art. For example, in North America, systems that amplify the "CODIS 13 core loci" are almost universal, whereas in the United Kingdom the "DNA-17" 17 loci system is in use. Whichever system is used, many of the STR regions used are the same. These DNA-profiling systems typically use multiplex PCR, whereby many STR regions are tested at the same time. For example, the 13 loci that are currently used for discrimination in CODIS are independently assorted (having a certain number of repeats at one locus does not change the likelihood of having any number of repeats at any other locus), and therefore the product rule for probabilities can be applied.

Accordingly, in embodiments of the method according to the sixth aspect described herein, any method of genetic analysis identifiable by skilled persons can be used for detecting a genomic variation of the nuclear and/or mitochondrial genome.

In embodiments of the method according to the sixth aspect described herein, any method of combining the detected genetic protein variations and the detected genomic variation can be used to provide the marker genetic variation database system of the biological sample, the detected genetic protein variations and the detected genomic variation to provide the marker genetic variation database system of the biological sample.

In embodiments of the method according to the sixth aspect described herein, comparing the detected genetic protein variation and/or the detected genomic variation with a marker genetic protein variation and/or of a marker genomic variation respectively from the marker genetic variation database system can be performed with any methods identifiable by a skilled person In embodiments of the method and system of combined mtDNA and proteomic analysis from a single sample, any method of sample preparation identifiable by those skilled in the art that can provide an extract of purified protein suitable for proteomic analysis and a mtDNA extract suitable for mtDNA analysis from a single tissue sample can be used, and is not limited to exemplary methods described herein.

The system comprises equipment, reagents, and samples required to perform the method of the combined mtDNA and proteomic analysis from a single sample.

In some embodiments of a genetic variation analysis, detecting a genetic variation in a genetic variation analysis can be performed using a marker genetic variation database according to a seventh aspect herein described. The related method to provide the marker genetic variation database system comprising marker genetic variation validated to be detectable in a biological sample, comprises preparing the biological sample to obtain a processed biological sample comprising solubilized proteins to be used in a proteomic analysis.

The method further comprises fractionating the processed biological sample to obtain a solubilized protein fraction comprising the solubilized proteins from the sample and a solubilized DNA fraction comprising solubilized nuclear and/or mitochondrial genome from the sample.

The method also comprises detecting a genetic protein variation in the solubilized proteins from the sample by performing the proteomic analysis of the solubilized protein fraction and detecting a genomic variation of the nuclear and/or mitochondrial genome by performing a genetic analysis of the solubilized DNA fraction.

The method additionally comprises combining the detected genetic protein variations and the detected genomic variation to provide the marker genetic variation database system comprising marker genetic variation validated to be detectable in a biological sample.

The system comprises protein databases, and/or reagents to perform proteomic analysis of the biological sample in combination with exome sequence databases for simultaneous combined or sequential use in the method to provide the marker genetic variation database system comprising marker genetic variation validated to be detectable in a biological sample herein described.

In some embodiments wherein preparing the biological sample to obtain a processed biological sample comprising solubilized proteins to be used in a proteomic analysis, is performed by the method according to the first aspect.

In some embodiments detecting a genetic protein variation is performed by the method according to the sixth aspect.

Methods and systems and related marker genetic protein variations and databases herein described, can be used in several embodiments for proteomic information detection using liquid chromatography/mass spectrometry methods for forensic analysis of tissue samples to provide identity metrics of individuals. In several embodiments, the methods and systems described herein allow improved proteomic information recovery when genomic DNA is degraded or not available, and/or when there are multiple contributors to the sample.

In some embodiments of the instant disclosure a genetic analysis of a sample of a biological organism can be performed with methods and systems according to the eighth aspect of the disclosure. The method comprises

- preparing the biological sample to obtain a processed biological sample comprising solubilized proteins to be used in a proteomic analysis;
- fractionating the processed biological sample to obtain a solubilized protein fraction comprising the solubilized proteins from the sample;
- digesting the solubilized protein fraction from the sample to obtain digested peptides from the sample;
- fractionating the digested peptides to obtain fractionated digested peptides from the digested solubilized proteins from the biological sample.
- detecting a marker genetic variation of the fractionated digested peptides from the sample; in which
- preparing the sample is performed according to any one of the methods according to the first aspect of the disclosure, comprising any one of the related sets of embodiments; and/or
- detecting a genetic variation is performed by at least one of
- a first detecting method directed to detect a genetic protein variation by performing any one of the methods according to the third aspect, comprising any one of the related sets and subsets of claims; and
- a second detecting method directed to detect a genetic variation by performing any one of the methods according to the sixth aspect of the disclosure comprising any one of the related sets of embodiments.

In the method of the eighth aspect the genetic analysis is directed to detect one or more genetic variations in the sample, and preferably comprises detection of at least one genetically variant protein, which more preferably has been validated in the sample where detection is performed. Therefore in preferred embodiments of the method of the eighth aspect of the disclosure the genetic analysis is a genetic protein variation analysis directed to detect in the sample one or more genetic variations validated in the analyzed sample.

In some embodiments of the method according to the eight aspect, the preparing can be performed with existing methods of sample preparation for proteomics. Typically, these methods comprise performing cell and tissue disruption and performing protein solubilization according to approaches identifiable by a skilled person upon reading of the present disclosure. Typically these methods can also comprise performing removal of contaminants and/or performing protein enrichment following performing protein solubilization, according to approaches identifiable by a skilled person upon reading of the present disclosure.

In preferred embodiments of the method according to the eight aspect however, the preparing is performed by any one of the embodiments the method according to the first aspect of the present disclosure as will be understood by a skilled person.

In more preferred embodiments of the method of the eight aspect wherein the preparing is performed according to the method of the first aspect, the applying is performed by sonication, with a related processor preferably set at 5 to 50 kHz and more preferably at 37 kHz with a power setting preferably set at 50 to 100%; most preferably at 100%. In more preferred embodiments the applying is performed with an ultrasonic mode sweep.

In more preferred embodiments of the method of the eight aspect wherein the preparing is performed according to the method of the first aspect, the applying can be performed with an incubation time from 20 to 90 minutes; most preferably 60 minutes In more preferred embodiments of the method of the eight aspect wherein the preparing is performed according to the method of the first aspect, the applying can be performed with temperature settings from 30 to 90° C.; most preferably 70° C.

In any one of the embodiments of the method of the present disclosure according to the eighth aspect, the digesting can be performed with any methods identifiable by a skilled person upon reading of the present disclosure.

In preferred embodiments of method of the present disclosure according to the eighth aspect, the digesting is performed enzymatically with one or more proteolytic enzymes identifiable by a skilled person.

In more preferred embodiments of the method according to the eighth aspect, the digesting comprises digesting the solubilized proteins from the sample with a site specific proteolytic enzyme to obtain digested solubilized proteins from the sample.

In those more preferred embodiments the digesting can be performed in a sample buffer comprising an enzyme capable to perform site specific protease digestion such as trypsin, chymotrypsin, Lys-C, Arg-C, Asp-N, and Glu-C, non-specific; pepsin, and proteinase K.

In particular in those more preferred embodiments of the method according to the eighth aspect, the enzyme can be comprised in the sample buffer at concentrations for digest ranging from 0.0001 to 1 μg/μL; more preferably 0.01 to 0.001 μg/μL; most preferably 0.005 μg/μL.

In even more preferred embodiments of the method according to the eighth aspect, the proteolytic enzyme is trypsin.

In preferred embodiments of the method according to the eighth aspect of the present disclosure, the digesting is preceded by fractionating the processed biological sample to obtain a solubilized protein fraction comprising the solubilized proteins from the sample. In those embodiments, the solubilized proteins are fractionated in a solubilized protein fraction and digesting the solubilized proteins is performed by digesting the solubilized protein fraction. In those embodiments fractionating the solubilized proteins can be performed by any one of the methods identifiable by a skilled person upon reading of the present disclosure typically comprises removing buffers, salts, and detergent from the processed sample. In more preferred embodiments fractionating the solubilized proteins can further comprise removing abundant proteins from the processed sample, protein enrichment processes and/or removing contaminants which can be performed with any one of the methods identifiable by a skilled person upon reading of the present disclosure.

In any one of the embodiments of the method according to the eighth aspect of the present disclosure, the genetic analysis also comprises detecting a marker genetic variation of the digested peptides.

In preferred embodiments of the method according to the eighth aspect of the present disclosure, the detecting is performed by mass spectrometry according to methods identifiable by a skilled person upon reading of the present disclosure. In those embodiments, the concentration of proteolytic enzyme in the sample buffer used during the digesting is set taking into account that increased concentrations can cause suppression of sample detection, decrease LC column capacity; and decrease ability to observe sample peptides by overcrowding mass a spectrometry detector as will be understood by a skilled person.

In those preferred embodiments of the method of the eighth aspect, wherein the proteomic analysis is performed by Mass Spectrometry, the digesting can be performed in a buffer comprising mass spectrometry compatible surfactant, such as for example, Invitrosol, ProteaseMax, Rapigest SF, and PPS Silent Surfactant), in concentration (percent w/v) ranges broadly from 0.0001 to 1.0%; more preferably 0.001 to 0.2%; and most preferably 0.01%. Increasing concentrations can cause issues with electrospray efficiency during MS data acquisition. In preferred embodiments, the surfactant comprise ProteaseMax.

In preferred embodiments of the method according to the eighth aspect, the detecting is preceded by fractionating the digested solubilized proteins to obtain fractionated digested peptides from the digested solubilized proteins from the biological sample. In those embodiments, the digested peptides are fractionated digested peptides and detecting a marker genetic variation of the digested peptides is performed by detecting a marker genetic variation of the fractionated digested peptides.

In those preferred embodiments of the method according to the eighth aspect, fractionating the digested solubilized proteins can be performed by any suitable method of fractionating proteins identifiable by a skilled person upon reading of the present disclosure. Preferably, fractionating the digested solubilized proteins can be performed by any chromatographic techniques identifiable by a skilled person upon reading of the present disclosure.

In more preferred embodiments of the method according to the eighth aspect, the fractionating is performed by liquid chromatography and the detecting is performed by mass spectrometry in an approach that combines the physical separation capabilities of liquid chromatography with the mass analysis capabilities of any mass spectrometry as will be understood by a skilled person upon reading of the present disclosure.

In even more preferred embodiments of the method according to the eighth of the present disclosure, the detecting is performed according to any one of the methods according to the third aspect or the sixth aspect of the instant disclosure and/or using any of the related databases.

In particular in some of the even more preferred embodiments of the method according to the eighth aspect, the detecting is performed according to the third aspect of the instant disclosure by

- providing a marker mass spectrum of a marker peptide comprising a marker genetic protein variation corresponding to the genetic protein variation;
- performing mass spectrometry of a fractionated digested peptide of the biological sample to obtain a mass spectrum of each of the fractionated digested peptide; and
- comparing the mass spectrum of the fractionated digested peptide with a marker mass spectrum of a marker peptide comprising the marker genetic protein variation to detect the genetic protein variation in the biological sample.

In some embodiments of the even more preferred embodiments of the method according to the eighth aspect in which the detecting is performed by the method according to the third aspect of the present disclosure, the marker genetic protein variation is obtained by any one of the methods to provide a marker genetic protein variation for a biological organism according to the second aspect of the instant disclosure and/or is a marker genetic protein variation obtainable and/or obtained thereby.

In some embodiments of the even more preferred embodiments of the method according to the eighth aspect in which the detecting is performed by the method according to the third aspect of the present disclosure, the marker genetic protein variation comprises a marker genetic protein variation from the marker genetic protein variation database system according to the fourth aspect of the instant disclosure.

In some embodiments of the even more preferred embodiments of the method according to the eighth aspect in which the detecting is performed by the method according to the third aspect of the present disclosure, the marker genetic protein variation comprises a marker genetic protein variation from the marker genetic protein variation database system according to the fifth aspect of the instant disclosure.

In some embodiments of the even more preferred embodiments of the method according to the eighth aspect in which the detecting is performed by the method according to the third aspect of the present disclosure, the marker peptide comprises one or more of the marker peptides comprising a validate genetic protein variations indicated in Examples 46 and Example 47 indicating exemplary set of GVPs and related mutated peptides validated in hair samples (Example 46, Table 11) and skin samples (Example 47, Table 12) and in particular in hair and skin samples of human beings.

In particular exemplary marker peptides that can be preferably used or comprise in the method and system according to the eighth aspect, comprise any combination of the peptides having sequence SEQ ID NO: 150 to SEQ ID NO: 748 (Example 46, Table 11) for detection in hair samples, in particular for hair samples of human beings, and any combination of the peptides having sequence SEQ ID NO: 749 to SEQ ID NO: 829 (Example 47, Table 12) for detection in skin samples, in particular for skin samples of human beings.

In some of the even more preferred embodiments of the method according to the eighth aspect, the detecting is performed according to the sixth aspect of the instant disclosure by

- preparing the biological sample to obtain a processed biological sample comprising solubilized proteins to be used in a proteomic analysis;
- fractionating the processed biological sample to obtain a solubilized protein fraction comprising the solubilized proteins from the sample and a solubilized DNA fraction comprising solubilized nuclear and/or mitochondrial genome from the sample;
- detecting a genetic protein variation in the solubilized proteins from the sample by performing the proteomic analysis of the solubilized protein fraction;
- detecting a genomic variation of the nuclear and/or mitochondrial genome by performing a genetic analysis of the solubilized DNA fraction; and
- comparing the detected genetic protein variation and/or the detected genomic variation with a marker genetic protein variation and/or of a marker genomic variation respectively from the marker genetic variation database system herein described.

In some embodiments of the even more preferred embodiments of the method according to the eighth aspect in which the detecting is performed by the method according to the sixth aspect of the present disclosure, detecting a genetic protein variation is performed by detecting one or more marker genetic protein variations obtained by any one of the methods to provide a marker genetic protein variation for a biological organism according to the second aspect of the instant disclosure and/or is a marker genetic protein variation obtainable and/or obtained thereby.

In some embodiments of the even more preferred embodiments of the method according to the eighth aspect in which the detecting is performed by the method according to the sixth aspect of the present disclosure, detecting a genetic protein variation is performed by detect a genetic protein variation in a biological sample according to any one of the methods according to the third aspect of the instant disclosure.

In some more preferred embodiments of the even more preferred embodiments of the method according to the eighth aspect in which the detecting is performed by the method according to the sixth aspect of the present disclosure, in which detecting a genetic protein variation is performed by detect a genetic protein variation in a biological sample according to any one of the methods according to the third aspect of the instant disclosure, the marker genetic protein variation comprises a marker genetic protein variation from the marker genetic protein variation database system according to the fourth aspect or the fifth aspect of the instant disclosure.

In some embodiments of the even more preferred embodiments of the method according to the eighth aspect in which the detecting is performed by the method according to the third aspect of the present disclosure or the sixth aspect of the present disclosure, the marker genetic protein variation are peptide sequences corresponding to (translated from at least a portion of) a marker exome sequences indicated in Examples 43 to 45 listing exemplary set of genes validated in hair (Example 43, Table 8) bone (Example 44, Table 9) and skin samples (Example 45, Table 10) of a human being.

Preferred validated marker genetic protein variations of *Homo Sapiens* are indicated in Examples 46 and Example 47 listing exemplary set of GVPs validated in hair sample (Example 46, Table 11) and skin sample (Example 47, Table 12) of a human being.

Additional preferred embodiments of the method according to the eighth aspect are identifiable by a skilled person upon reading of the instant disclosure.

Any one of the embodiments of the method according to the eight aspect of the instant disclosure can be performed with components of the system according to the eighth aspect of the instant disclosure.

In any one of the systems according to the eight aspect, the system comprises exome sequences databases and/or reagents to detect exome sequences in an individual of the biological organism, alone or in combination with reagents to perform proteomic analysis of the biological sample for simultaneous combined or sequential use in the method to perform genetic analysis of a sample of a biological organism herein described.

In embodiments of the system according to the eighth aspects configured to perform a method according to the eighth aspect of the disclosure wherein the preparing is performed by the method according to the first aspect of the present disclosure, the system comprises a sample buffer typically comprising chaotropes (e.g. urea and/or thiourea), detergents (e.g. 3-[(3-Cholamidopropyl)-dimethyl-ammonio]-1-propane sulfonate (CHAPS) or Triton X-100), reducing agents (dithiothreitol/dithioerythritol (DTT/DTE) or tributylphosphine (TBP)) and protease inhibitors. Preferred embodiments of the sample buffer are identifiable by a skilled person upon reading of the present disclosure In embodiments of the system according to the eighth aspects configured to perform a method according to the eighth aspect of the disclosure wherein the detecting is performed according to any one of the methods according to the third aspect of the instant disclosure and/or using any of the related databases, the system comprises protein databases, and/or reagents to perform proteomic analysis of the biological sample in combination with exome sequence databases. In preferred embodiments, the reagents comprise a marker peptide in accordance with the present disclosure.

In embodiments of the system according to the eighth aspect, configured to perform a method according to the eighth aspect of the disclosure wherein the detecting is performed according to any one of the methods according to the sixth aspect of the instant disclosure and/or using any of the related databases, the system comprises exome sequences databases and/or reagents to detect exome sequences in an individual of the biological organism, in combination with reagents to perform proteomic analysis of the biological organism. In preferred embodiments, the reagents comprise a marker peptide in accordance with the present disclosure In even more preferred embodiments of the system according to the eighth aspect in which the reagents in the system comprises a marker peptide, the marker peptide comprises one or more of the marker peptides comprising a genetic protein variations validated in *Homo Sapiens* indicated in Examples 46 and Example 47 indicating exemplary set of GVPs and related mutated peptides validated in hair (Example 46, Table 11) and skin (Example 47, Table 12) samples of human beings. In particular exemplary marker peptides that can be preferably used or comprise in the method and system according to the third aspect, comprise any combination of the peptides having sequence SEQ ID NO: 150 to SEQ ID NO: 748 (Example 46, Table 11) for detection in hair samples of human beings, and any combination of the peptides having sequence SEQ ID NO: 749 to SEQ ID NO: 829 (Example 47, Table 12) for detection in skin samples of human beings.

In view of the above exemplary systems of the instant disclosure according to the eight aspect of the instant disclosure, comprise:

- one or more marker peptides which preferably can comprise
  - one or more of the peptides having sequence SEQ ID NO: 150 to SEQ ID NO: 748 for detection in hair samples of human beings; and/or
  - one or more of the peptides having sequence SEQ ID NO: 749 to SEQ ID NO: 829 for detection in skin samples of human beings;
- reagents for dissolving and/or digesting the sample and/or for detecting a marker genetic protein variation comprising for example
  - a reducing agent such as DTT, DTBA, BME, TCEP, and DTE), with detergent concentration ranges broadly from 0.001 M to 10 M; more preferably 0.05 M to 0.2 M; and most preferably 0.1 M; even more preferably the reducing agents comprise DTT;
  - a surfactant such as Invitrosol, ProteaseMax, Rapigest SF, and PPS Silent Surfactant, in particular in embodiments where the proteomic analysis is then performed by mass spectrometry; with surfactant concentration (percent w/v) ranging from 0.0001 to 1.0%; more preferably 0.001 to 0.2%; and even more preferably 0.01%; preferably the surfactant comprise ProteaseMax;
  - a detergent such as SDD, SDS, CHAPS, Triton, NP-40, and LDS) with detergent concentration (percent w/v) ranging from 0.001% to 10%; more preferably 1 to 3%; even more preferably 2%; preferably the detergent comprises SDD;
  - an enzyme for protein digestion, in particular to cut the proteins in the sample in a site specific fashion, such as trypsin, chymotrypsin, Lys-C, Arg-C, Asp-N, and Glu-C, non-specific; pepsin, and proteinase K; with concentrations for digest ranging from .0001 to 1 μg/μL; more preferably 0.01 to 0.001 μg/μL; even more preferably 0.005 μg/μL; preferably the enzyme comprises trypsin;
  - a buffer such as ammonium bicarbonate (preferred), ammonium hydrogen bicarbonate, acetates, and formates; and/or
  - ammonium bicarbonate (ABC) in concentrations ranging from 0.001 to 1M; more preferably 0.01 to 0.1 M; even more preferably 0.05 M
- to be combined in the system according to configurations identifiable by a skilled person upon reading of the present disclosure.

In some embodiments, the one or more marker peptide can be labeled.

The terms "label" and "labeled" as used herein refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemoluminescence, production of a compound in outcome of an enzymatic reaction and the like.

Accordingly, in embodiments of the disclosure a labeled peptide is a peptide attaching a label making the peptide capable of detection.

The terms "detect" or "detection" as used herein indicates the determination of the existence, presence or fact of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

In preferred embodiments of the disclosure, peptides comprised in one of any of the systems of the disclosure are isotopically labeled or chemically labeled.

In particular, in embodiments, wherein a peptide is isotopically labeled and the detecting is performed by MS, the peptide is preferably labeled at the C terminus amino acid if y-series fragments predominate the MSMS spectrum, and preferably labeled at the N terminus amino acid if b-series fragments predominate the MSMS spectrum.

In embodiments wherein the detecting is performed by mass spectrometry, the label can comprise tandem mass tags.

In embodiments of any systems of the disclosure, wherein one or more marker peptides are comprised in the system, reagents to similarly label the unknown sample can further be provided as component of the system as will be understood by a skilled person.

Additional components of the system according to any one of the systems herein described and in particular of the system according to the eight aspect of the disclosure can comprise:

- a column and/or a filter and related reagents for separating the mitocontrial DNA fraction from the protein/peptide fraction;
- reference material with known identity panel (e.g. a characterized hair sample);
- a template of an instrument method preloaded with the MSMS transitions corresponding to the identity panel; and/or
- a statistical tool to derive statistical measures (like random match probabilities and likelihood ratios) from the results of the detecting (e.g. LCMS results), for example statistical tools:
  - comprising population-specific frequencies for markers in an identity panel
  - accounting for linkage between markers if desired; and/or
  - providing algorithms for
    - individual identification;
    - paternity testing (or other familial relationship); and/or
    - ancestry determination, as well as possibly additional components in configurations selected to perform one or more methods herein described, the configurations identifiable by a skilled person upon reading of the present disclosure.

In preferred embodiments of the marker genetic protein variations, databases, methods and systems and related genetic protein variation analysis herein described, performing a proteomic analysis is carried out by performing mass spectrometry of a fractionated digested peptide of the biological sample to obtain a mass spectrum of each of the fractionated digested peptide.

In further preferred embodiments of the marker genetic protein variations, databases, methods and systems and related genetic protein variation analysis herein described, the sample is hair and/or skin.

Methods and systems and related marker genetic protein variations and databases herein described, also allow in several embodiments to provide more reliable results for a specific query (such as whether there is a match between a sample and a certain individual or groups of individuals linked together by common genetic features).

Methods and systems and related marker genetic protein variations and databases herein described, further allow in several embodiments to perform genetically variant protein analysis applicable to samples from all tissues and are therefore not limited to hair; also the targeted approaches can improve LC-MS/MS analysis of bulk sample as well as analysis of samples available in smaller amounts processable according to the first aspect with particular reference to forensics applications.

As used herein, the wordings "forensics", "forensic science" or "forensic analysis" refers to the application of science to criminal and civil laws, and in particular with regard to criminal investigation, as governed by the legal standards of admissible evidence and criminal procedure. Additionally, as used herein, the wordings "forensics", "forensic science" or "forensic analysis" also refer to the application of forensic techniques to other types of investigation, such as determination of relatedness of individuals, or bioarcheological research, among others identifiable by those skilled in the art upon reading of the present disclosure. Accordingly, forensics involves the collection, processing, and analysis of scientific evidence during the course of an investigation.

The systems herein disclosed can be provided in the form of kits of parts. In kit of parts for performing any one of the methods herein described, one or more marker peptide and/or other standards, and/or one or more databases can be included in the kit alone or in the presence of additional sequences, reagents such as labels, reducing agents, surfactants, detergents, enzymes, buffers, as well as additional components, such as columns, filters, templates, reference materials and/or statistical tools identifiable by a skilled person upon reading of the instant disclosure.

In a kit of parts, the one or more marker peptide, standards, and/or databases and additional reagents identifiable by a skilled person are comprised in the kit independently possibly included in a composition together with suitable vehicle carrier or auxiliary agents. For example, one or more marker peptides can be included in one or more compositions together with reagents for detection also in one or more suitable compositions.

Additional components of kits of parts according to the disclosure are identifiable by a skilled person upon reading of the present disclosure.

In embodiments herein described, the components of the kit can be provided, with suitable instructions and other necessary reagents, in order to perform the methods here disclosed. The kit will normally contain the compositions in separate containers. Instructions, for example written or audio instructions, on paper or electronic support such as tapes, CD-ROMs, flash drives, or by indication of a Uniform Resource Locator (URL), which contains a pdf copy of the instructions for carrying out the assay, will usually be included in the kit. The kit can also contain, depending on the particular method used, other packaged reagents and materials (i.e. wash buffers and the like).

Further details concerning the identification of the suitable carrier agent or auxiliary agent of the compositions, and generally manufacturing and packaging of the kit, can be identified by the person skilled in the art upon reading of the present disclosure

EXAMPLES

The methods and systems herein described and related marker genetic protein variations and databases are further illustrated in the following examples, which are provided by way of illustration and are not intended to be limiting.

In particular, the following examples illustrate exemplary methods, systems and related marker genetic protein variations and databases described herein. A person skilled in the art will appreciate the applicability and the necessary modifications to adapt the features described in detail in the present section, to additional methods and systems according to embodiments of the present disclosure.

Example 1: Individual Identification Using Genetically Variant Protein Analysis FIG. 1A shows a diagram of an exemplary genetically variant protein, gasdermin, encoded by the gene GSDMA, which is shown as a member of an exemplary panel of genetically variant proteins, shown as a list in FIG. 1B.

In particular FIG. 1A is a diagram showing partial sequences of an exemplary "Reference" gasdermin, showing a partial protein-coding DNA sequence GGTACCTGC (SEQ ID NO: 1) encoding the amino acid sequence Val Thr Leu, forming part of a peptide sequence GHEVTLEALPK (SEQ ID NO: 2). Shown below the "Reference" sequence diagram are exemplary frequencies of the "Reference" gasdermin peptide sequence in European ($f_{EUR}$) and African ($f_{AFR}$) populations.

Also in FIG. 1B is a diagram showing partial sequences of an exemplary "Variant" gasdermin, showing a partial protein-coding DNA sequence GGTAACTGC (SEQ ID NO: 2) (comprising a single nucleotide polymorphism (SNP) "A" indicated in a box labeled "SNP") encoding the amino acid sequence Val Asn Leu within a genetically variant peptide (GVP) comprising a single amino acid polymorphism (SAP) "Asn" indicated in a box labeled "SAP", forming part of a peptide sequence GHEVnLEALPK and GHEVTLEALPK (SEQ ID NO: 12 and 13). Shown below the "Variant" sequence diagram are exemplary frequencies of the "Reference" gasdermin peptide sequence in European ($f_{EUR}$) and African ($f_{AFR}$) populations. The exemplary SNP shown is identified as rs56030650, corresponding to an entry in the National Center for Biotechnology Information dbSNP database.

Example 2: Hair Sample Preparation for Proteomic Analysis

Single hair samples (1 inch; 25 mm) from three individuals were carefully measured and cut into four equal pieces. The cut hair was then placed into separate Protein LoBind Eppendorf tubes. 100 μL of extraction buffer containing 0.05 M ammonium bicarbonate (ABC), 0.1 M dithiothreitol (DTT), 2% sodium dodecanoate (SDD) was added to each tube. Samples were then incubated at 70° C. in an ultrasonic water bath (Elma) while being ultrasonicated at high energy and frequency settings for 60 minutes or until hair was completely dissolved into solution. SDD was removed by extraction with acidified ethyl acetate (pH 2-3, 0.75% trifluoroacetic acid). After addition of 100 uL acidified ethyl acetate to each tube, samples were quickly vortexed, incubated at room temperature for 5 min, and centrifuged for 5 min at max speed (20,000×g). The upper organic phase was removed, discarded to waste, and the extraction process was repeated once. The remaining lower aqueous phase was then readjusted to pH 8 with ABC [13]. Carbamidomethylation of free cysteines was performed by adding 6 μL of iodoacetamide (1.0 M) and incubation for 60 min in the dark at 25° C. To further solubilize proteins, 0.01% protease max (3 μL of 1.0% w/v) was added to each sample. Prior to proteolysis, the solubilized protein solution was concentrated to 50 uL using 10 kD molecular weight spin concentrators (Millipore). Trypsin (1 μL of 0.5 μg/μL) was then added to each protein sample. Protein digestion was performed at 25° C. for 20/22 hours while being continuously agitated by magnetic-bar stirring. Resulting peptide mixture is then filtered using 0.1 μm PTFE filter, and transferred into fresh vials for mass spectrometric analysis (stored at −4.0-20° C.). Additional step of speed vacuum (20 minutes at 60° C.) can be used to concentrate peptide fraction of samples.

Ultrasonic frequency of 37 kHz is used to maximize dissolving of hair as recommended for dissolving, mixing, dispersing in Elma Elmasonic P user manual. Lower frequency setting concentrates power throughout the water bath and results in better dissolving of hair than the higher option (80 kHz). Elevated temperature setting is used (70° C.) to achieve solubilization of hair matrix. Ultrasonic using sweep mode controls the sound pressure throughout the water bath. This setting applies a more homogeneous sounding of the cleaning bath by the continued displacement of the sound pressure maxima in the cleaning liquid, leading to a more uniform ultrasonic intensity throughout the ultrasonic tank and samples. Ultrasonic power setting of 100% is used for hair matrix solubilization to maximize the force applied. [Reference: www.imlab.be/imlab_nl/elma/Pdf/Elmasonic_P/Elmasonic_P_Operating_Instructions_ENG_Imlab.pdf)

Lower temperature settings ranging from 50-65° C. increase the time needed for complete solubilization substantially (from average of 60 minutes to 12 hours), but can be used to dissolve hair. Time of ultrasonic treatment at 70° C. depends on each given sample. Average of 30 to 60 minutes is efficient for hair solubilization. Brief sonication (30 seconds to 5 minutes) at lower temperature 37° C. is commonly a technique used for protein extractions for various tissues [14-17]. Protein extraction procedure is implemented at atmospheric pressure however, increasing pressure could decrease the amount of time needed for extraction [18].

Adaptation of method to perform sample preparation for proteomic analysis herein described exemplified herein for single hair to bone, teeth, fingerprint and other sample types would be achieved in several ways. For bone and tooth samples, single-hair extraction buffer could be applied to samples prior to mechanical milling procedures. Acid etching could be performed using 1 M HCl. This would be amenable to SDD liquid-liquid extraction step in the single-hair method due to the need to acidify ethyl acetate for SDD removal [19, 20]. In this case, non-acidified ethyl acetate would be used to extract SDD from samples. For finger-print and other samples, the single-hair method can be implemented by decreasing ultrasonic incubation time and decreasing sonication temperature. Exemplary adaptation of the protocol described in the current example to bone and teeth are reported in the following Examples 3 and 4.

Example 3: Bone Sample Preparation for Proteomic Analysis

Associated soft tissue was resected from each rib and a 20 mg block of cortical bone, roughly 1×3×4 mm, resected using a dental drill (NSK NE-213G) equipped with a diamond tip blade at room temperature (25° C.). Each sample was transferred into milling tubes that contained 2.8 mm ceramic bead media (Omni-International, Kennesaw, GA). Acid etching was performed by milling for 3 min @ 6.00 m/s in the presence of 1.2 M HCl (200 μL), reducing by addition of 3 μmol DTT (1.0 M) and incubation at 56° C. for 60 min. The supernatant was neutralized to pH 7.5-8.0 with a threefold molar excess of ammonium bicarbonate. Carbamidomethylation was then conducted by adding 6 μmol iodoacetamide and incubating at 22° C. and for 60 min in the dark. The reaction was quenched by the addition of 6 μmol DTT for 5 min. Solubilized proteins were then digested with the addition of 0.5 μg trypsin (TPCK-treated, sequencing grade, Worthington Inc., Lakewood, NJ), and 30 μg ProteaseMAX™ (Promega Inc., Madison, WI). The protein digest was performed at 37° C. for 20 to 22 hr. After digestion, peptide samples were centrifuged (30 min, 16,300 g, 22° C.), the supernatant filtered using a centrifugal 0.1 μm PTFE filter (Millipore Inc., Billerica, MA), and transferred into autosampler vials for mass spectrometric analysis (stored at −4.0 to −20° C.).

Example 4: Teeth Sample Preparation for Proteomic Analysis

The protocol for tooth sample processing was adapted from the Porto et al. manuscript published in 2011. Wisdom tooth enamel samples from individuals (5 female, 5 male, and 1 archaeological) were stored at ~20° C. until they were re-sectioned using a diamond tip blade at room temperature (25° C.). Enamel and enamel-dentine junction were carefully separated from the dentine, weighed, and ~20 mg was transferred into milling tubes that also contain milling beads.

Prior to milling, 200 μL of 1.2 M HCl was added to each sample. Samples were milled in acid for 3 min @ 6.00 m/s and then centrifuged at max speed (5 min, 16,300 g, 22° C.). The supernatant were neutralized by measuring pH using paper and adjusting it to 7.5-8.0 pH by adding 2 M ammonium bicarbonate 90 μL. Soluble proteins were reduced by adding of 3 μL DTT (1 M) and incubating at 56° C. for 60 min. Alkylation was performed by adding 6 μL of iodoacetamide (1 M) at 25° C. and incubating for 60 min in the dark. Carbamidomethylation reaction was quenched by the addition of 6 μL DTT (1 M) and incubating at room temperature for 5 min. To further solubilize proteins, 0.01% protease max (3 μL of 1.0% w/v) was added to each sample. Trypsin (1 μL of 0.5 μg/μL) was then added to each protein sample, and then incubated at 37° C. for 20/22 hr. After digestion, peptide samples were centrifuged (30 min, 16,300 g, 22° C.) to remove particulates, filtered using 0.45 μm PTFE filters into fresh vials for mass spectrometric analysis (stored at −4.0-20° C.).

Reference is made to [19, 20], each incorporated herein by reference in its entirety.

Example 5: Proteolytic Cleavage of Prepared Samples

Various applicable methods can be used to perform proteolytic cleavage (and in particular trypsinization) of proteins as will be understood by a skilled person.

In particular, during protein solubilization reduction of cysteine disulfide bonds is achieved using 100 mM of reducing agent dithiothreitol (DTT). DTT concentrations can vary from 50 mM to 180 mM. Carbamidomethylation of free cysteines is performed by adding 6 μL of iodoacetamide (1.0 M) and incubation for 60 min in the dark at 25° C. [21, 22]. Alkylation time can vary from 45-60 minutes, longer reaction times increase confidence in reaction completion.

To further solubilize proteins, 0.01% protease max (3 μL of 1.0% w/v) can be added to each sample. Prior to proteolysis, the solubilized protein solution was concentrated to 50 uL using 10 kD molecular weight spin concentrators (Millipore). Trypsin (1 μL of 0.5 μg/μL) is then added to each protein sample. Protein digestion is performed at 25° C. for 20/22 hours while being continuously agitated by magnetic-bar stirring.

Digestion time can range from 16-22 hours. Agitation can be achieved by other techniques including sample rotated, milling, and shaking [23].

Reference is also made to [1, 21-23], each of which is incorporated by reference in its entirety.

Example 6: Comparison of Methods for Sample Preparation for Proteomic Analysis

Figure 2:
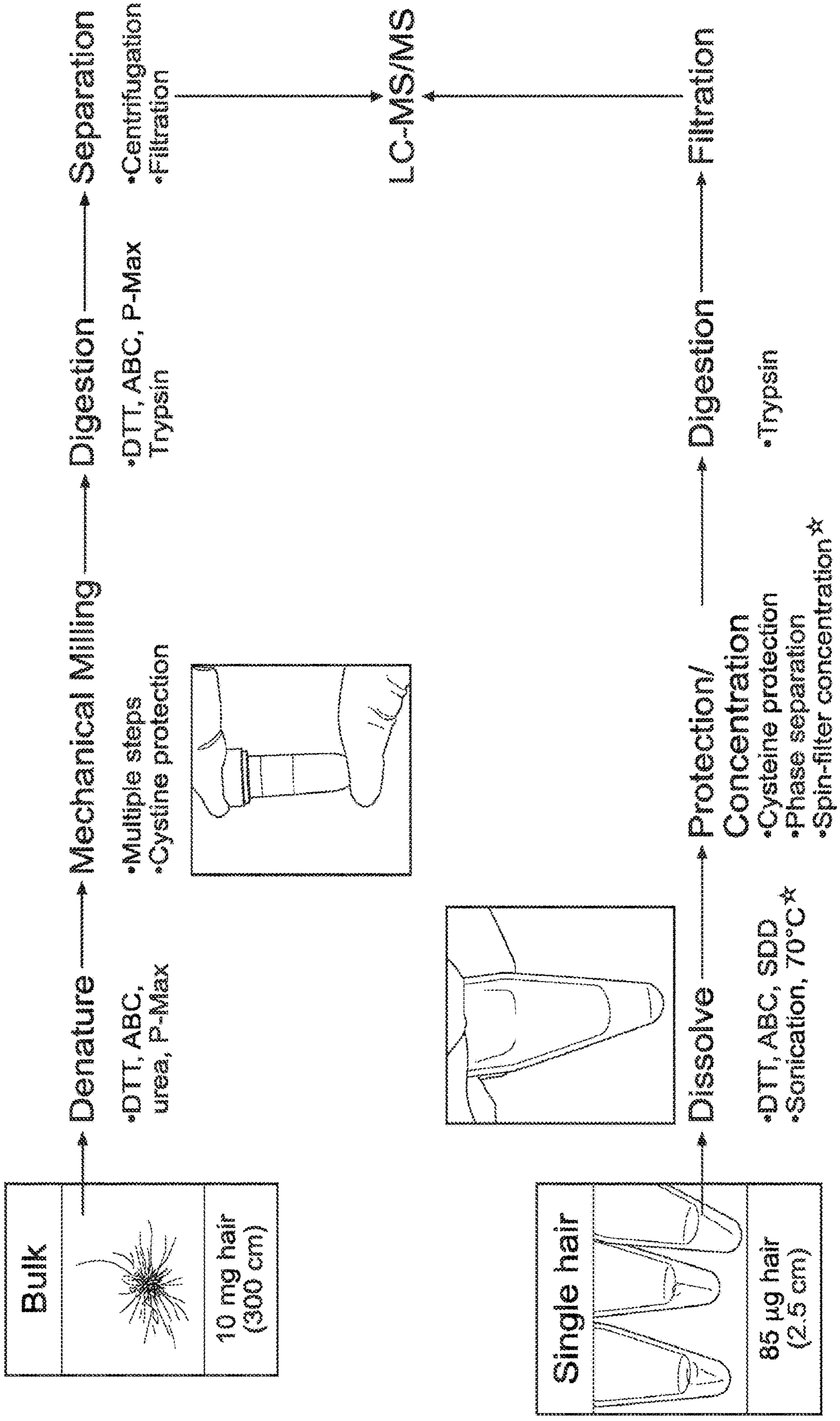
FIG. 2 shows a schematic overview of two exemplary methods for processing hair samples for proteomic analysis by tandem liquid chromatography mass-spectrometry (LC-MS/MS), for "Single hair" processing using an exemplary sample preparation method of the present disclosure or for "Bulk" hair processing performed with conventional preparation method, as will be understood by a skilled person. In the illustration of FIG. 2, method steps are separated by arrows.

An exemplary method of single hair sample processing performed according to method to perform sample preparation herein described and subsequent proteomic analysis of GVPs is shown in the lower portion of the schematic of FIG. 2, which also shows an exemplary "Bulk" hair processing method wherein sample preparation is performed with conventional methods for comparison.

In an exemplary single hair processing method according to the schematics of FIG. 2, single hair samples (25 mm) from three individuals were carefully measured and cut into four equal pieces. The cut hair was then placed into separate Protein LoBind Eppendorf tubes. 100 of extraction buffer containing 0.05 M ammonium bicarbonate (ABC), 0.1 M dithiothreitol (DTT), 2% sodium dodecanoate (SDD) was added to each tube. Samples were then incubated at 70° C. in an ultrasonic water bath (Elma) while being ultrasonicated at high energy and frequency settings, (here 330 W and 37 kHz respectively) for 60 minutes or until hair was completely dissolved into solution. SDD was removed by extraction with acidified ethyl acetate (pH 2-3, 0.75% trifluoroacetic acid). After addition of 100 μL acidified ethyl acetate to each tube, samples were quickly vortexed, incubated at room temperature for 5 min, and centrifuged for 5 min at max speed (20,000×g). The upper organic phase was removed, discarded to waste, and the extraction process was repeated once. The remaining lower aqueous phase was then readjusted to pH 8 with ABC [13]. Carbamidomethylation of free cysteines was performed by adding 6 μL of iodoacetamide (1.0 M) and incubation for 60 min in the dark at 25° C. To further solubilize proteins, 0.01% ProteaseMax reagent (Promega, 3 μL of 1.0% w/v) was added to each sample. Prior to proteolysis, the solubilized protein solution was concentrated to 50 μL using 10 kD molecular weight spin concentrators (Millipore). Trypsin (1 μL of 0.5 μg/μL) was then added to each protein sample. Protein digestion was performed at 25° C. for 20-22 hours while being continuously agitated by magnetic-bar stirring. After digestion, peptide samples were centrifuged (30 min, 16,300×g, 22° C.) to remove particulates, filtered using 0.1 μm PTFE filter, and transferred into fresh vials for mass spectrometric analysis (stored at −4.0-20° C.).

For comparison, in an exemplary "Bulk" hair method (e.g., using 10 mg hair sample), performed with conventional sample preparation methods, the sample is initially denatured using dithiothreitol (DTT), ammonium bicarbonate (ABC), urea, and ProteaseMax reagent (Promega, P-max), followed by mechanical milling of the sample comprising multiple steps as described herein and identifiable by those skilled in the art together with cysteine protection. Following mechanical milling, the proteins present in the sample are proteolytically digested with trypsin in a reaction mixture together with DTT, ABC and P-max, followed by centrifugation and filtration before analysis by LC-MS/MS. In contrast, in the exemplary "Single hair" method (e.g., using 85 μg hair, 2.5 cm in length) the sample is initially dissolved using a reaction mixture comprising DTT, ABC and sodium dodecanoate (SDD) and sonication at 70° C.

After dissolving, the sample is separated into organic phase, which is discarded, and aqueous phase, which is retained and further processed for protection of free cysteines, and spin-filter concentration of solubilized proteins, prior to proteolytic digestion by trypsin and filtration, followed by proteomic analysis by LC-MS/MS.

Figure 3:
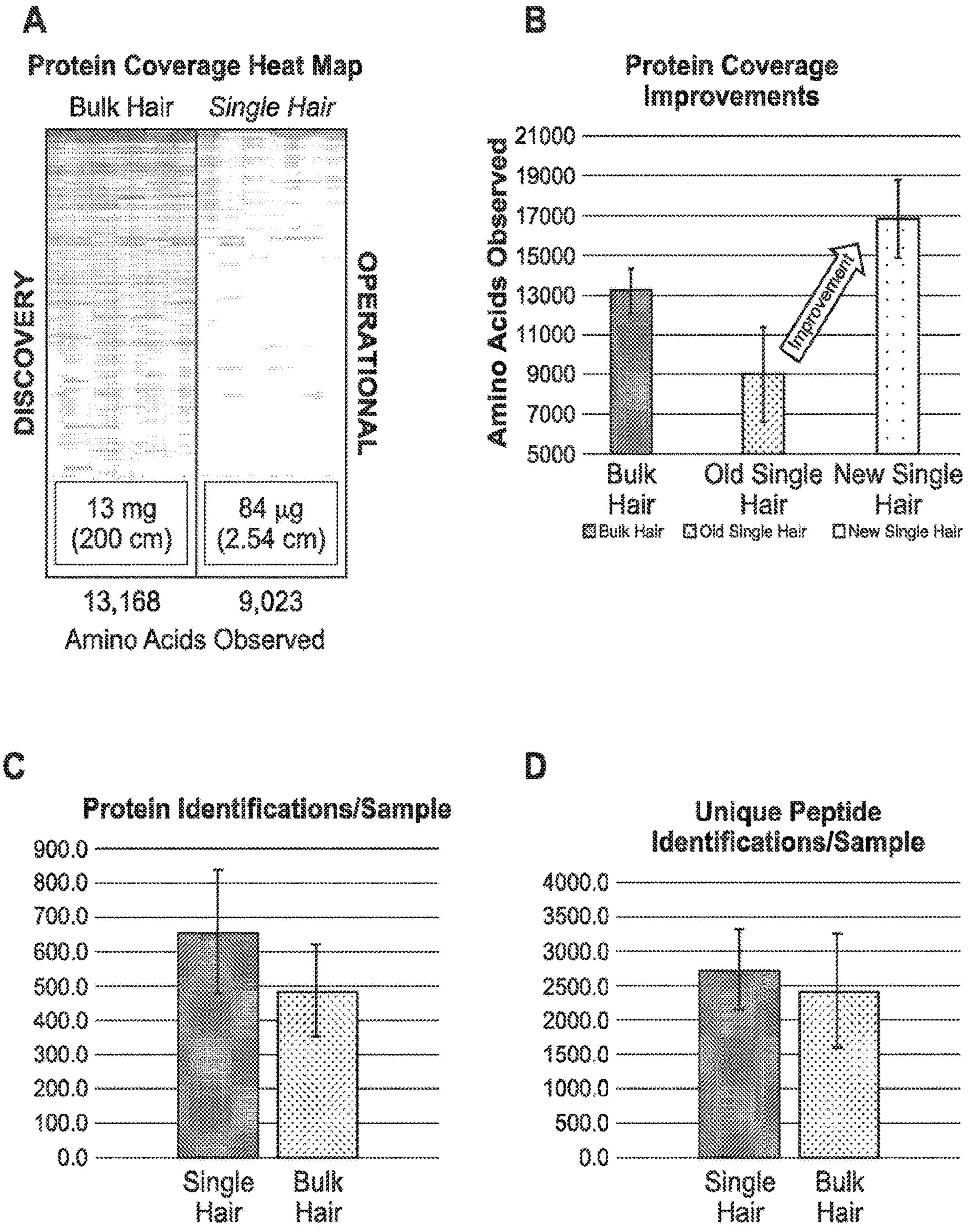
FIG. 3 shows graphs reporting exemplary results of proteomic analysis metrics using samples processed using the exemplary sample preparation methods illustrated in FIG. 2. In particular.

Exemplary results of proteomic metrics for samples processed using the exemplary method to perform a proteomic tissue sample preparation using single hairs, compared to an exemplary "Bulk" hair processing method are shown in FIG. 3.

In particular, FIG. 3 shows exemplary results illustrating improvements in proteomic sample preparation performed with using methods for sample preparation herein described in comparison with convention sample preparation methods.

In particular FIG. 3 Panel A shows a diagram showing exemplary protein coverage heat maps for an exemplary conventional sample preparation method (indicated as 'Bulk hair') and an exemplary sample preparation method of the present disclosure (indicated as 'Single hair'). In particular, the illustration of FIG. 3A show that the protein coverage from single hair provides detection of approx. 60% of amino acids relative to bulk method, wherein the 60% amino acids are observed with only ~1% of the bulk sample amount. The illustration of FIG. 3B also shows a detection of ~30% of known GVPs with the sample preparation method of the disclosure relative to convention methods (same subject).

FIG. 3 Panel B shows a graph reporting exemplary results of the number of amino acids observed (a measure of protein coverage) in samples processed using exemplary convention methods on bulk hair, and single hair' (indicated as "Bulk hair" and 'Old Single hair' respectively) or sample preparation according to the present disclosure (indicated as "New Single hair"). In particular, in the illustration of FIG. 3 Panel B, the graph shows an improvement in protein coverage (number of amino acids observed) using the sample preparation method of the disclosure which allow >80% increase in the number of amino acids observed and therefore allow proteomic results from 1" single hairs to be on par with proteomic results obtainable on bulk hair prepared with conventional methods.

FIG. 3 Panel C and D show graphs reporting exemplary results of the number of protein identifications in each sample (Panel C) and unique peptide identifications in each sample (Panel D) in samples processed with convention methods and the sample preparation methods of the disclosure (indicated as "Bulk hair" and "Single hair" respectively). In particular FIG. 3 Panel C and D show an improvement in these additional proteomic metrics which indicates reliability of detection in a specific sample, in samples prepared with sample preparation methods of the disclosure vs conventional preparation methods. Such an improvement is observed despite having the sample preparation methods performed in a biological sample (single hair) with a lower amount of biological material (and in particular protein material available). Such an improvement is associated with an improved detection the genetically variant peptides identified in each sample as would be understood by a skilled person.

In particular, an optimization of the data illustrated in FIG. 3 Panel C and Panel D for GVP detection can include preparation of inclusion lists, Multiple Reaction Monitoring (MRM), Explore additional MS data acquisition strategies, peptide standards/SI labeled and use alternative proteases, as would be understood by a skilled person.

As also indicated in other sections of the present disclosure although in the exemplary illustration of FIG. 3, the sample preparation of the present disclosure is illustrated with respect to single hairs, the sample preparation is also applicable to bulk hair or other samples wherein protein material is available in larger quantity.

The GVPs detected using the sample preparation method herein described can be comprised in databases of validated marker genetic variation herein described to the extent such GVPs are marker for biological organisms, type of biological organisms or individual thereof. Accordingly, an operational scenario is expected to also utilize inclusion/exclusion lists wherein the exclusion lists can refer to validated GVPs which are not marker for a specific query of interest.

Example 7: Combined mtDNA and Proteomic Analysis in a Single Hair Sample

Figure 4:
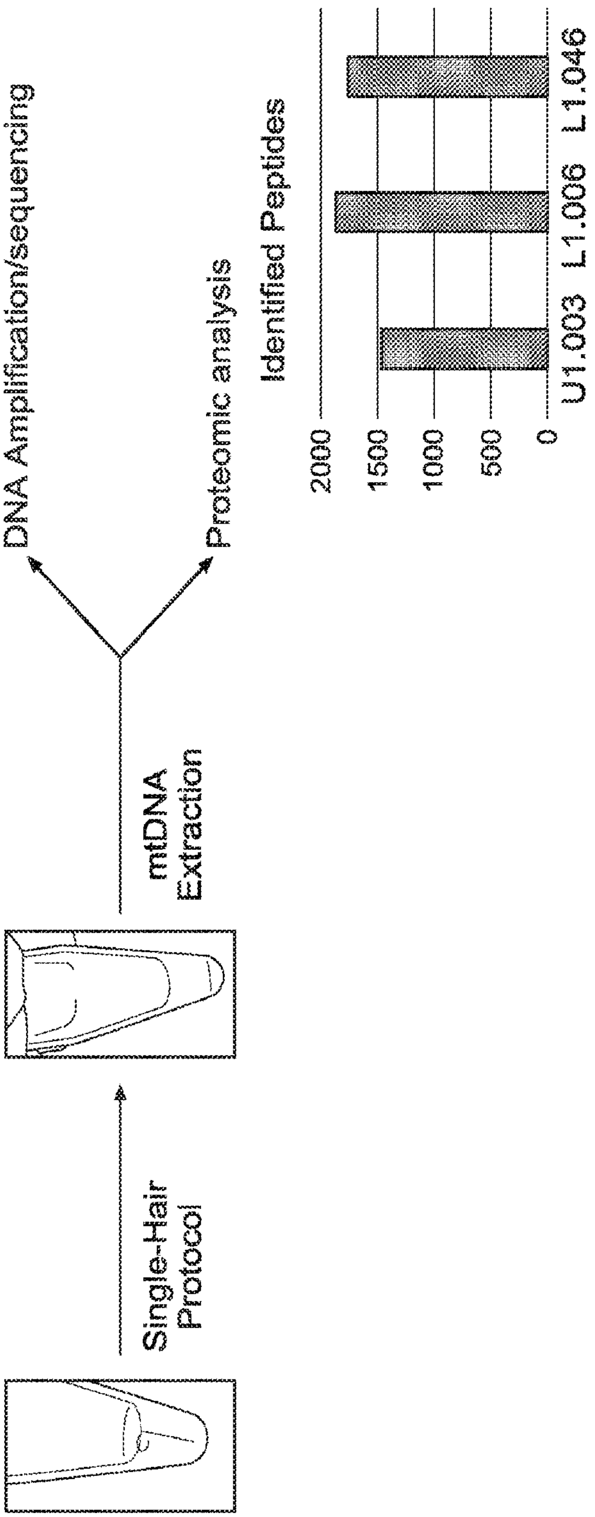
FIG. 4 shows a schematic overview of an exemplary method for concomitant protein and mitochondrial DNA (mtDNA) recovery and evaluation in a single sample. In the schematics the methods are shown by arrows.

An exemplary method sample processing for subsequent proteomic analysis of GVPs combined with analysis of mtDNA from a same sample is shown in the schematics of FIG. 4.

In particular, in the schematic of FIG. 4 the exemplary method of protein and mtDNA extraction is performed following a sample preparation performed with the sample preparation method herein described followed by proteomic analysis of the protein fraction and the genomic analysis of the mtDNA fraction, comprising DNA amplification and sequencing of the mtDNA.

In particular single hair samples (25 mm) from three individuals were carefully measured and cut into four equal pieces. The cut hair was then placed into separate Protein LoBind Eppendorf tubes. 100 μL of extraction buffer containing 0.05 M ammonium bicarbonate (ABC), 0.1 M dithiothreitol (DTT), 2% sodium dodecanoate (SDD) was added to each tube. Samples were then incubated at 70° C. in an ultrasonic water bath (Elma) while being ultrasonicated at high energy and frequency settings, (here 330 W and 37 kHz respectively) for 60 minutes or until hair was completely dissolved into solution. SDD was removed by extraction with acidified ethyl acetate (pH 2-3, 0.75% trifluoroacetic acid).

After addition of 100 uL acidified ethyl acetate to each tube, samples were quickly vortexed, incubated at room temperature for 5 min, and centrifuged for 5 min at max speed (20,000×g). The upper organic phase was removed, discarded to waste, and the extraction process was repeated once.

The remaining lower aqueous phase was then readjusted to pH 8 with ABC [13]. Carbamidomethylation of free cysteines was performed by adding 6 μL of iodoacetamide (1.0 M) and incubation for 60 min in the dark at 25° C. To further solubilize proteins, 0.01% ProteaseMax reagent (Promega, 3 μL of 1.0% w/v) was added to each sample. Prior to proteolysis, the solubilized protein solution was concentrated to 50 μL using 10 kD molecular weight spin concentrators (Millipore). Trypsin (1 μL of 0.5 μg/μL) was then added to each protein sample. Protein digestion was performed at 25° C. for 20-22 hours while being continuously agitated by magnetic-bar stirring.

A protocol for isolation of DNA from tissues was provided by the Qiagen QIAamp DNA Micro Kit. The steps of the Qiagen QIAamp DNA Micro Kit manual were followed with exception that the lysis procedural steps that include adding proteinase K, addition of Qiagen proprietary buffer 'ATL', pulse-vortexing, overnight incubation at 56° C., and addition of Qiagen proprietary buffer 'AL' were omitted and the aforementioned trypsin incubation was substituted for these steps. Accordingly, following trypsin proteolysis, 100 μL of 100% ethanol was added to each sample as recommended by Qiagen QIAamp DNA Micro Kit instructions. Samples were then vortexed for 15 seconds, incubated at 25° C. for 5 minutes, then added into separate QIAmp miniElute columns. Columns were closed and centrifuged at 6000×g for one minute. Flow-through was collected as the peptide fraction of the extraction, filtered using a 0.1 μm PTFE filter, and transferred into fresh vials for mass spectrometric analysis (stored at +4.0 to −20° C., or +4 to −12). The bound DNA fraction was then washed according to Qiagen QIAamp DNA Micro Kit instructions and eluted twice into the same collection tube with 20 μL of warm (37° C.) water by centrifugation for one minute (20,000×g).

In the illustration of FIG. 4, the graph reports results of exemplary peptides identified by performing proteomic analysis of the protein fraction.

The genetic material recovered with the process outlined in FIG. 4, allows efficient DNA amplification/sequencing in view of the high-quality mtDNA recovered from proteomic extracts.

Figure 5A:
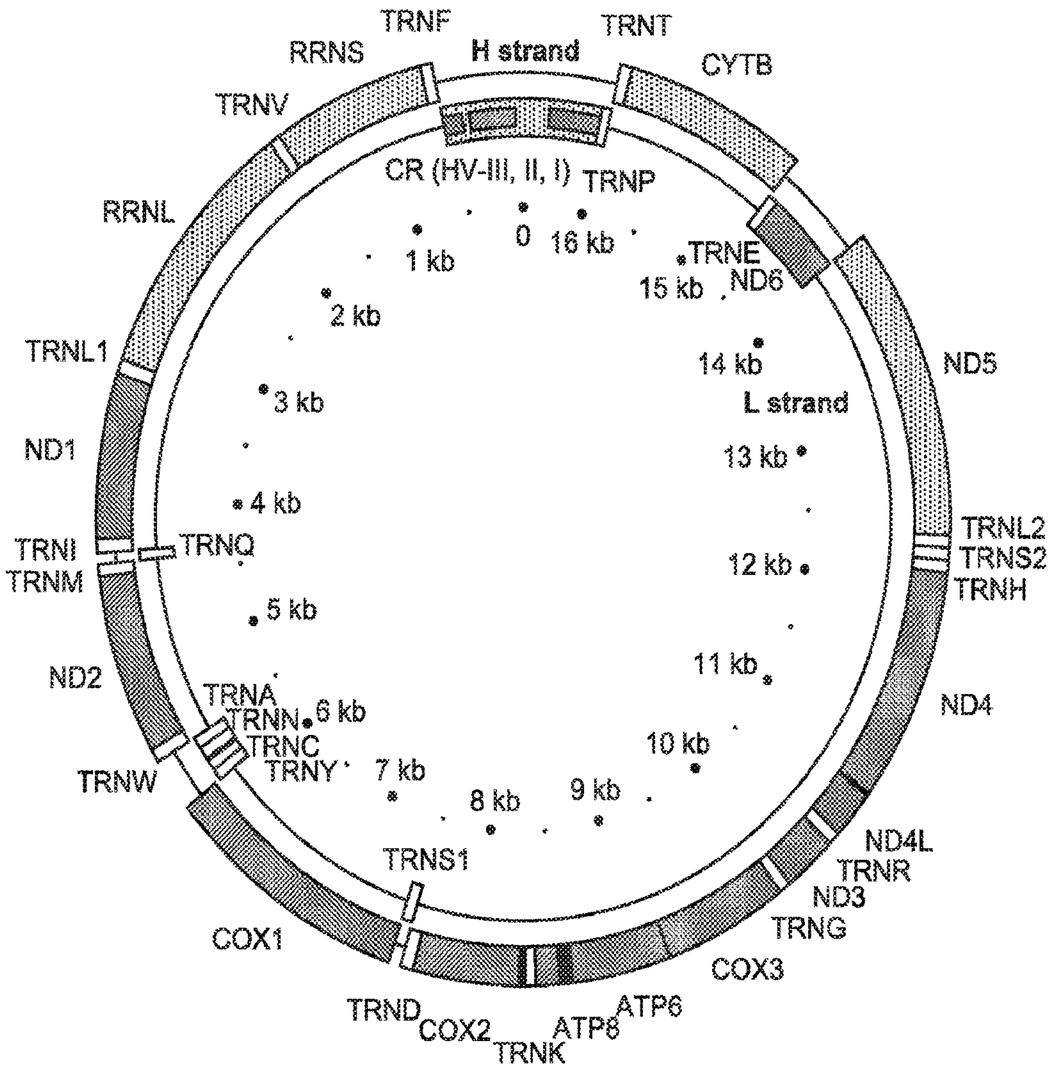
FIGS. 5A-5B show an exemplary mtDNA analysis performed according to embodiments herein described.

An exemplary illustration of DNA amplification/sequencing is illustrated in FIG. 5A wherein an exemplary mitochondrial genome and related primers are shown.

In particular the exemplary list of primers of FIG. 5A is for amplification and sequencing of amplicons of mtDNA haplogroup HV regions and is reported in Table 1 below.

TABLE 1 mtDNA gene primers for PCR and Sequencing:

| Primer | Sequence | Usage | SEQ ID NO: |
|---|---|---|---|
| F15975 | CTCCACCATTAGCACCCAAA | PCR and Sequencing | 136 |
| F16524 | AAGCCTAAATAGCCCACACG | PCR and Sequencing | 137 |

TABLE 1-continued mtDNA gene primers for PCR and Sequencing:

| Primer | Sequence | Usage | SEQ ID NO: |
|---|---|---|---|
| F015 | CACCCTATTAACCACTCACG | PCR and Sequencing | 138 |
| F403 | TCTTTTGGCGGTATGCACTTT | PCR and Sequencing | 139 |
| R16410m | GAGGATGGTGGTCAAGGGA | PCR and Sequencing | 140 |
| R042 | AGAGCTCCCGTGAGTGGTTA | PCR and Sequencing | 141 |
| R389 | CTGGTTAGGCTGGTGTTAGG | PCR and Sequencing | 142 |
| R635 | GATGTGAGCCCGTCTAAACA | PCR and Sequencing | 143 |

In a DNA amplification analysis of mtDNA, PCR was used for amplification of HV mtDNA regions. Amplicons were purified, quantified and sequenced using standard mtDNA protocols.

Figure 5B:
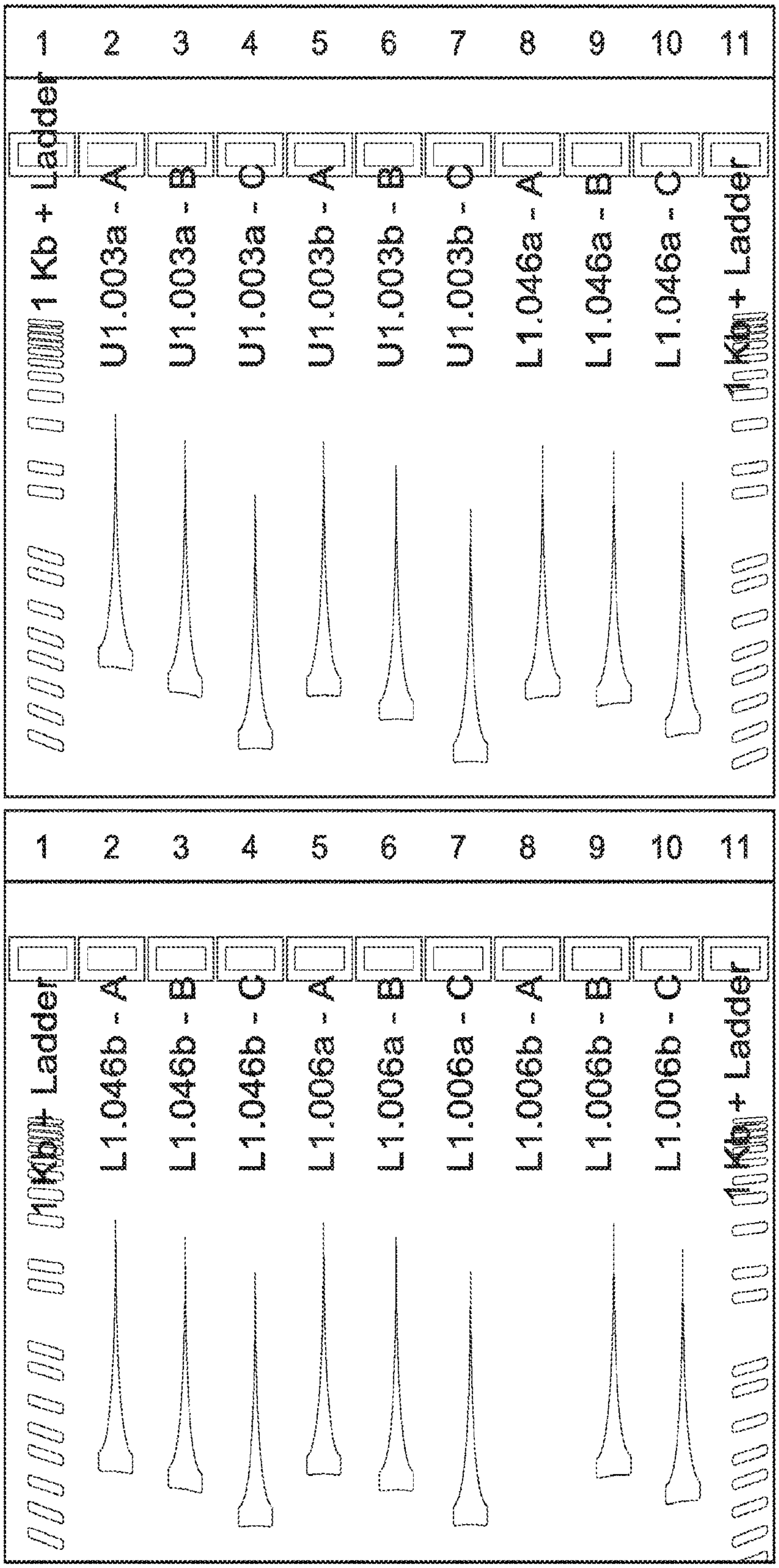

Exemplary results of PCR amplification of mtDNA recovered using the exemplary combined mtDNA and proteomic analysis sample processing protocol are shown in FIG. 5B.

The results of the above proteomic and genomic analysis can then be compared with databases to identify the validated marker GVPs to be detected and/or provided in databases herein described.

FIG. 6 shows an exemplary comparison of results of HV mtDNA region sequencing using mtDNA recovered using the exemplary combined mtDNA and proteomic analysis illustrated in the present example.

In particular in FIG. 6, an exemplary Clustal Omega alignment is shown of HV mtDNA regions of samples obtained from three independent subjects (indicated as U1.003b-A_HV1, SEQ ID NO: 88, L1.006a-A_HV1, SEQ ID NO: 89, and L1.046a+b-A_HV1, SEQ ID NO: 90) aligned with a reference mtDNA sequence (indicated as rCRS_HV1, SEQ ID NO: 87). The black boxes indicate exemplary SNPs identified in the sequences.

Example 8: Exome Sequence Analysis

Applicable methods to detect exome sequences of the sample of the biological organism are identifiable by a skilled person.

According to an exemplary protocol blood and buccal samples can be used to perform DNA collection from individuals. DNA is isolated from blood associated with each sample and was subsequently analyzed by Sanger sequencing (2016 Sorenson Genomics, LLC). Full exome sequencing of the extracted DNA was also obtained (10-0111_ACE Research Exome with Secondary Analysis; 8 Gb; Alignment, Variant Calling and Annotation; ©2016 Personalis Inc).

Comparison of detected exome sequences and a database of exome sequences of the biological organism can then be performed. Exemplary databases that can be used comprise protein and genome sequence databases such as Uniprot [24] (www.uniprot.org/), Exome Variant Server (evs.gs.washington.edu/EVS/) Swiss-Prot [25](www.ebi.ac.uk/swissprot/), Ensembl [26] (www.ensembl.org/index.html) can be used to identify genetically variant peptide sequences in proteins. Sequence alignment webservers including BLAST [27] (www.ncbi.nlm.nih.gov/BLAST/), Prowl [28]; (www.prowl.rockefeller.com), and Protein Information Resource [29, 30]; (pir.georgetown.edu/) can be used to determine if peptide sequences are unique to a single human gene.

References is also made to the following documents incorporated herein by reference in their entirety [25-30].

Example 9: Proteomic Analysis to Detect Peptide Sequences

Applicable methods to perform proteomic analysis to detect the peptide sequences are identifiable by a skilled person inclusive of any possible ways to perform a) LC separation of peptides orb) tandem MS analysis (to generate the 'raw MS data') c) analysis methods other than LC-MS/MS, e.g. protein quantification, antibody based assays, gel purification/isolation (2d and other), and additional methods.

In an exemplary approach, data acquisition was performed using Thermo Scientific Q Exactive Plus Hybrid Quadrupole-Orbitrap mass spectrometer fitted with Easy-nLC 1000 HPLC (Thermo Scientific, Asheville, NC, USA). Various combinations of liquid-chromatography systems coupled to mass spectrometers, peptide fragmentation techniques, and ionization methods can be used to generate peptide sequence identifications [31, 32]. Peptides were separated by reversed-phase liquid chromatography using a mobile phase A (0.01% TFA in water) and mobile phase B (0.01% TFA in acetonitrile) in a 97 minute gradient. 2 μL of each sample were injected onto a C18 trap cartridge and preceded by an Easy-Spray™ nanoflow (1 mm×150 mm) column (Thermo Scientific, Asheville, NC, USA) with a flow rate of 3 μL/min. Numerous reversed-phase columns are commercially produced and distributed that are applicable to perform proteomic analysis of peptide sequences [33-35]. Electrospray ionization was achieved in positive mode with a voltage of 2-4 kV. Dynamic exclusion data collection was implemented at a MS scan range of 180-1,800 m/z, top 10 precursor ions were chosen for subsequent MS/MS scans and excluded after 10 seconds.

Due to extremely small quantities of protein solubilized from extractions of a single hair, many conventional quantification assays have insufficient limits of detection for example Bradford assay and UV absorbance measurements at 280 nm [36, 37]. Peptide quantification via fluorometric assay (Pierce™) of small volumes using nano fluorospectrometer (NanoDrop™ 3300 Fluorospectrometer; Thermo Scientific™) is most applicable for the single-hair method [38].

References is also made to the following documents incorporated herein by reference in their entirety [31-38].

Example 10: Proteomic Analysis Performed by Liquid Chromatography and Mass Spectrometry Liquid Chromatography and Mass Spectrometry data acquisition was performed using Thermo Scientific Q Exactive Plus Hybrid Quadrupole-Orbitrap mass spectrometer fitted with Easy-nLC 1000 HPLC (Thermo Scientific, Asheville, NC, USA). Peptides were separated by reversed-phase liquid chromatography using a mobile phase A (0.01% TFA in water) and mobile phase B (0.01% TFA in acetonitrile) in a 97 minute gradient. 2 μL of each sample were injected onto a C18 trap cartridge and preceded by an Easy-Spray™ nanoflow (1 mm×150 mm) column (Thermo Scientific, Asheville, NC, USA) with a flow rate of 3 μL/min. Electrospray ionization was achieved in positive mode with a voltage of 2-4 kV. Dynamic exclusion data collection was implemented at a MS scan range of 180-1,800 m/z, top 10 precursor ions were chosen for subsequent MS/MS scans and excluded after 24 seconds.

Data Analysis was performed using PEAKS 7.5 (Bioinformatics Solutions Inc., Waterloo, Ontario, Canada) protein identification software was used to search each RAW data file to determine the specific proteins that were identified in each sample. Search settings included partial posttranslational modifications including oxidation of methionine, deamidation of asparagine and glutamine, and hydroxyproline. Precursor mass error of 15 ppm using monoisotopic mass was used for parent ion identifications and a 0.05 Da for fragment ions masses. A decoy database was generated within the software using a protein library of all human protein sequences exported from UniProtKB/Swiss-Prot knowledgebase (The UniProt Consortium; www.uniprot.org/). The decoy database is used to determine the false determination rate (FDR) of protein identifications. Protein identifications (IDs) were filtered by a 1% FDR. Filtered protein IDs found in each individual data file was outputted and aligned using Scaffold proteomics software [39]. IDs were then additionally filtered by having two or more unique peptides detected.

Characterization of genetically variant peptides (GVPs) was performed using the Global Proteome Machine webserver (GPM; www.thegpm.org). Raw data was exported and converted into mgf format using MSconvertGUI (Proteowizard 2.1.x; proteowizard.sourceforge.net) and submitted to the Global Proteome Machine webserver (GPM; www.thegpm.org). Default search settings were used with the exception of the human male NCBI reference protein database, a 20 ppm error for the primary scan, inclusion of complete cysteine carbamidomethylation (C+57), and partial modifications of oxidized methionine (M+16), and deamidation (N+1, Q+1). Results from this search were filtered by single nucleotide polymorphism (SNPs) accessions (rs numbers) to obtain a list of previously characterized potential GVPs.

Genetically Variant Peptide Confirmation from Genetic Sequencing was performed as follows: DNA was isolated from blood associated with each sample and was subsequently analyzed by Sanger sequencing (2016 Sorenson Genomics, LLC). Full exome sequencing of the extracted DNA was also obtained (10-0111_ACE Research Exome with Secondary Analysis; 8 Gb; Alignment, Variant Calling and Annotation; ©2016 Personalis Inc). Genotypes obtained by exome that corresponded to missense variants were used to validate the observation of GVPs in proteomic data. Potential GVP identifications were filtered to cases where proteomic detection of a GVP was correlated to the correct SNP genotype determined in exome sequence data.

Exome validated genetically variant peptides (GVPs) observed in each sample were directly correlated to corresponding genotypes of missense single nucleotide polymorphism (SNP) at each locus. Using the 1000 genomes project database (1000 Genomes Project Consortium, Phase 3) population, random match probabilities (RMP) were calculated for each possible genotype (p=probability allele 1, q=probability allele 2) where both alleles p and q are defined by equation 1.

$$p \text{ or } q = \frac{\text{number of times allele observed}}{\text{size of database}} \quad \text{Eq. (1)}$$

Genotype frequencies for each locus was calculated depending on heterozygosity of where heterozygous genotypes (2pq) and for minor allele homozygous ($p^2$). Individual profile frequencies (P) were then calculated by implementation of the product rule on each set of observed genotypes and their calculated RMP values ($a_1$ and for the first locus $a_2$ for the second . . . ; Equation 2)

$$P(a_1a_2) = P(p_1q_1 \mid p_1^2) \times P(p_2q_2 \mid p_2^2) \quad \text{Eq. (2)}$$

In cases where a heterozygous genotype was observed in the exome sequencing data and only one allele was detected in proteomic data, only the probability corresponding to the allele of the observed GVP was considered.

Example 11: Comparison of Detected Marker Exome Sequence with Detected Peptide Sequences to Provide a Validated Genetic Protein Variation Applicable methods to perform comparing the detected marker exome sequence with the detected peptide sequences to provide a marker genetic protein variation validated for the same of the biological organism, are identifiable by a skilled person.

There are several approaches to validate detected genetically variant peptides. Exemplary methods comprise implementing different protein identification software algorithms, DNA sequencing techniques, and mass spectrometry peptide confirmation. Single-hair method implements program PEAKS 7.5 (Bioinformatics Solutions Inc., Waterloo, Ontario, Canada) for variant peptide detection.

A reference database created by translating polymorphisms (missense SNPs, insertions, deletions, and stops/gains) that influence protein sequences observed in exome results into mutated protein sequences are used for peptide identification within software parameters. Experimental conditions and instrumental capabilities inform parameters chosen for search. Search settings include partial posttranslational modifications including oxidation of methionine, deamidation of asparagine and glutamine, and carbamidomethylation of cysteine. Precursor mass error of 30 ppm using monoisotopic mass was used for parent ion identifications and a 0.05 Da for fragment ions masses.

Other parameter settings can be chosen depending on instrument dependent metrics including parents and fragment mass errors. Additionally, software program PEAKS 7.5 (Bioinformatics Solutions Inc., Waterloo, Ontario, Canada) protein identification software can be used to identify putative peptide variants using a specific capability called Spider [40] without using mutated reference databases. Another approach, outlined in [3] uses the Global Proteome Machine webserver (GPM; www.thegpm.org) to detect possible peptide variants. Genetic confirmation of detected peptide variants can be performed by Sanger sequencing [41], whole-exome DNA sequencing, or other DNA sequencing methods [42].

Alternatively, observed genetically variant peptides can be confirmed using synthetic peptide internal standards that can be isotopically labeled [43].

References is also made to the following documents incorporated herein by reference in their entirety [40-43].

Example 12: Exemplary Genetic Protein Variations

Any detectable genetic protein variations can be used in methods and systems herein described as will be understood by a skilled person. Exemplary GVP comprise not only SAPS but also insertions, deletions, and stops variation as will be understood by a skilled person In particular, insertions, deletions, and stop mutations observed in exome sequencing results can be directly translated into reference mutated databases. Peptide masses reflecting these polymorphisms can also be predicted using in silico proteolysis analysis and targeted mass spectrometry techniques [44]. Targeted mass-spectrometry based techniques including parallel reaction monitoring, selected ion monitoring, or mass inclusion list methods during mass-spectrometry data acquisition can be used to confirm presence of variant peptides in samples [45-47].

References is also made to the following documents incorporated herein by reference in their entirety [44-47]

Example 13: Comparison of Top-Down Approaches and Bottom-Up Approaches for Identification/Detection of a Genetic Protein Variation A schematic comparison of the steps used to perform a top-down approach of the disclosure versus the conventional approaches to identify genetic protein variations is shown in FIG. 7.

In particular, FIG. 7 shows a diagram indicating two different approaches to GVP discovery, one approach being "exome-driven" otherwise referred to herein as "top-down discovery" as shown in the top triangle (dark grey), and the other being "proteome-driven" otherwise referred to herein as "bottom-up discovery", as shown in the bottom triangle (light grey).

As described herein, the proteome-based discovery approach begins with proteomic analysis, followed by candidate peptide identification, and DNA validation of identified GVPs.

Thus, the proteome-driven approach has limitations such as being a 'needle in a haystack' approach that is not compatible with targeted proteomic analysis and relies on manual MS interpretation to identify potential GVPs, wherein potential GVPs are then validated by separate individual genotyping experiments.

In contrast, the exome-driven approach begins with obtaining exome data, allowing identification of relevant SNPs, followed by proteomic validation of GVPs. Thus, the "exome-driven" approach features (1) obtaining exome sequence for each donor, (2) establishing a workflow to identify specific SNPs of interest, (3) targeted proteomic analysis allowing simplified identification of GVPs in raw MS data, and (4) allows a logic-driven GVP selection, identification, and validation process.

A more detailed exemplification of methods according to the bottom-up approach and the top-down approaches are illustrated in the following Examples 14 to 17.

Example 14: Identification of a Validated Common GVP Panel Following Bottom-Up Approach An exemplary method to identify a pooled marker genetic variation database in accordance with embodiments herein described is illustrated in FIG. 8.

In particular, FIG. 8 shows a schematic of an exemplary "proteome-driven" GVP discovery and evaluation method. In the exemplary proteome-driven GVP discovery approach, a peptide mixture is obtained from a sample (e.g. from hair) and is analyzed by LC-MS/MS to provide a 'Mass Spec Dataset', which is then analyzed with reference to a protein variant database using analysis software tools such as MASCOT, PEAKS, and GPM. In the GVP discovery workflow, candidate GVPs in the observed proteins identified in the sample are screened using metrics such as match score, frequency, and qualitative assessment.

The screened GVPs are then validated by confirming the GVPs comprise missense mutations genetically encoded by SNPs by genomic sequencing to provide validated GVPs. The validated GVPs then are incorporated into a GVP database, which is used for analysis of operational samples, wherein matches to known GVPs provide identity metrics.

Example 15: Exome-Driven Identification of a Validated Common GVP Panel in a Sample An exemplary top-down approach for identification of a panel of GVPs using an "exome-driven" discovery process are outlined in the schematic of FIG. 9 and FIG. 10, wherein the approach is exemplified for a hair sample.

In particular, FIG. 9 shows a schematic of an exemplary method wherein samples from a plurality of donors are used to build a database of the 'Observed Gene Pool' comprising the protein-coding genes that express proteins observed in a given sample type (e.g. hair). In the exemplary method, a peptide mixture is obtained from a sample (e.g. from hair) from a donor subject and is analyzed by LC-MS/MS to provide a 'Mass Spec Dataset', which is then analyzed with reference to a protein variant database using analysis software tools such as MASCOT, PEAKS, and GPM. The identified 'Observed Proteins' in the sample are thus encoded by 'Represented Genes' and form the 'Down-selected Target Genes' of the 'Observed Gene Pool'. Accordingly, samples from a plurality of donors are used to build a database of the 'Observed Gene Pool' comprising the protein-coding genes that express proteins observed in a given sample type (e.g. hair).

The 'Observed Gene Pool' built according to the method exemplified in FIG. 9, can then be used in the 'exome-driven' discovery of GVPs exemplified in the schematics shown in FIG. 10.

In the exemplary method illustrated by the schematic of FIG. 10, a donor subject's exome is sequenced to provide 'Individual Exome Data'. In particular, sequences of 'Down-selected target Genes' within the 'Observed Gene Pool' of a given tissue sample are analyzed to detect 'Individualized SNPs in observable target genes'. The SNPs are then annotated with information regarding the particular encoded transcripts in which they are comprised, the minor allele frequency (MAF), the genomic codon in which they are comprised, and the corresponding location and change in the amino acid encoded by the missense mutation. Using this information, an 'Individualized Protein Database' is built for the donor, comprising the sequences of mutant and reference proteins. In addition, a peptide mixture is obtained from a sample of a particular tissue type (e.g. from hair) from the same donor subject and is analyzed by LC-MS/MS to provide an 'Individual Mass Spec Dataset', which is then analyzed with reference to the donor subject's 'Individualized Protein Database' using Troteomic Search Tools' such as Andromeda, Byonic, Comet, Tide, Greylag, InsPecT, Mascot, MassMatrix, MassWiz, MS Amanda, MS-GF+, MyriMatch, OMSSA, PEAKS DB, pFind, Phenyx, ProblD, ProteinPilot Software, Protein Prospector, RAId, SEQUEST, SIMS, Sim Tandem, SQID, and X!Tandem, among others identifiable by those skilled in the art. or de novo search such as Cyclobranch, DeNovoX, DeNos, Lutefisk, Novor, PEAKS, and Supernovo, among others identifiable by those skilled in the art to provide 'Validated GVPs' that can be used in an 'Individual or Pooled GVP Panel'. Thus, validated GVPs comprising proteins having SAPs present in the sample from the donor are identified by targeted selection based on the observed gene pool encoded by the exome sequence of the same donor. For a 'Pooled GVP Panel', the process is repeated for a plurality of donors.

Example 16: Application of an "Exome-Driven" Validated Common GVP Panel to Operational Samples An exemplary application of a GVP panel of validated markers GVP identified and/or detected using methods and systems herein described is shown in FIG. 11.

According to the exemplified exome drive approach shown in FIG. 11, a peptide mixture is prepared and a 'Mass Spec Dataset' is obtained for an operational sample (e.g. a found sample from an unknown individual), such as a 'Questioned Hair Sample'. Using 'Targeted Search Tools, the 'Mass Spec Dataset' is analyzed with reference to a Pooled GVP Panel' (wherein the 'Pooled GVP panel' is also referred to herein as a 'Common GVP panel'), thus providing 'Identity Metrics' for the operational sample.

In the 'Common GVP panel', GVPs are down selected for common nsSNPs, and a consensus panel is assembled from a large cohort. As described herein, the term "common nsSNPs" refers to nsSNPs having a frequency >1% having a worldwide distribution. A Pooled GVP panel can be provided from a population of individuals, which can then be used for analysis of an operational sample (e.g. a questioned hair sample found at a crime scene), for example in cases where a DNA sample from an individual of interest is not available; thus, identity metrics (such as biogeographic information) can be obtained for the operational sample based on the 'Pooled GVP Panel'.

Example 17: Construction of a Common GVP Identity Panel

Figure 12A:
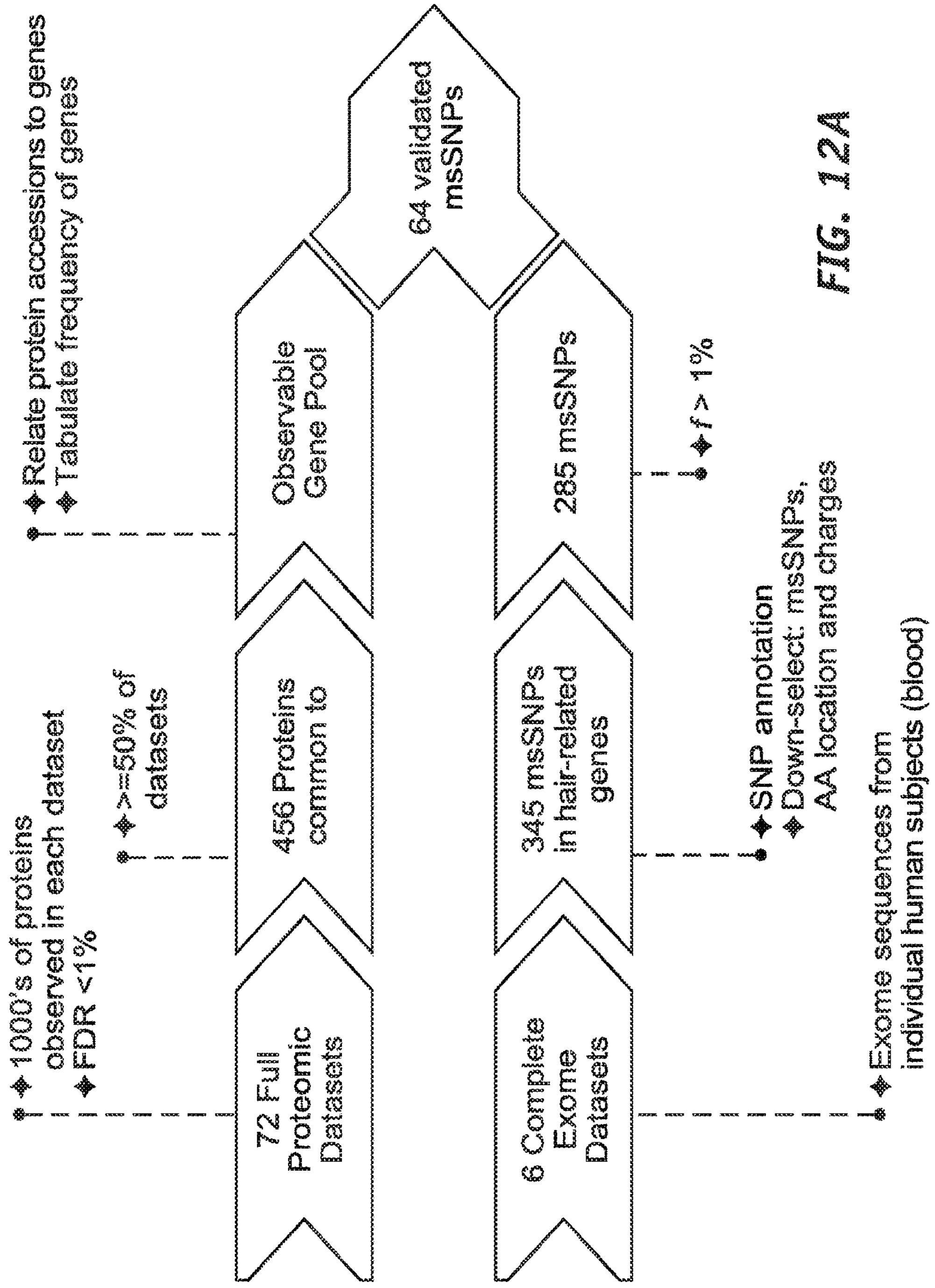

An exemplary method to provide a pooled marker genetic variation protein database is shown by FIGS. 12A-12B. In particular FIG. 12A shows a schematic showing exemplary construction of a validated pooled 'common' GVP identity panel and FIG. 12B shows an exemplary common GVP identity panel resulting from the approach of FIG. 12A.

In particular, the schematic of FIG. 12A shows an exemplary method for building a panel of validated common GVPs encoded by genes encoding proteins present in hair samples comprising 64 validated missense SNPs. In this exemplary "exome-driven" GVP discovery method, proteomic datasets and exome datasets are used together to validate a panel of common GVPs present in samples of a given tissue type (e.g. hair).

According to the illustration of FIG. 12A 72 proteomic datasets were provided, wherein 66 identified proteins were detected in at least 90% of individuals and 456 identified proteins were detected in at least 50% of individuals (FIG. 12 A top). Concurrently, exome sequences are obtained from donor individuals, in which 345 missense-encoding single nucleotide polymorphisms (msSNPs) were identified. Of these msSNPs, 285 had a frequency in the population of >1% (common msSNPs) (FIG. 12A bottom).

Of these common msSNPs, 64 encoded proteins that were also encoded by genes identified in the 'Observable Gene Pool'. A list of the exemplary 64 GVPs identified by the approach of FIG. 12A is shown in FIG. 12B. In particular, FIG. 12B shows a list of an exemplary validated GVP identity panel for hair samples that were identified following the method summarized in the schematic shown in FIG. 12A. The abbreviated name of each of the 64 proteins identified is shown in the middle column ("Protein"), the entry number for the National Center for Biotechnology Information Single Nucleotide Polymorphism Database ("dbNSP") missense mutation-encoding SNP is shown in the first column, and the allele frequency is shown in the third column ("Allele frequency").

Example 18: Determination of Amounts of Proteins/GVP Detectable in a Hair Sample Amount of proteins and number of GVP detectable in a hair sample can be provided with the approach exemplified in the schematics of FIG. 13.

According to the approach exemplified in FIG. 13, the amount/number can be provided by systematically looking at detectable proteins in individuals (e.g. up to 72 individuals) and then detecting the percentage of sample in which each protein is detected. In the Exemplary chart of FIG. 13, 4174 different proteins detected across cohort of 72 individuals 456 proteins detected in at least 50% of individuals and 66 proteins detected in at least 90% of individuals.

The related panel of proteins and GVPS is reported in Table 2 below

TABLE 2

| Protein | Missense SNPs |
|---|---|
| KRT86 | 245 |
| KRT33A | 141 |
| KRT34 | 134 |
| KRT36 | 216 |
| KRT38 | 246 |
| JUP | 368 |
| DSP | 1162 |
| LGALS3 | 114 |
| SFN | 83 |
| LGALS7 | 10 |
| KRT83 | 295 |
| KRT85 | 245 |
| SELENBP1 | 210 |
| TRIM29 | 267 |

Example 19: Identity Metrics

Identity metrics provide the theoretical probability that any two randomly selected profiles with a given number of loci will match (where each locus encodes a validated GVP and the median match probability for these loci is shown on the y-axis), assuming independence of each locus.

Figure 14:
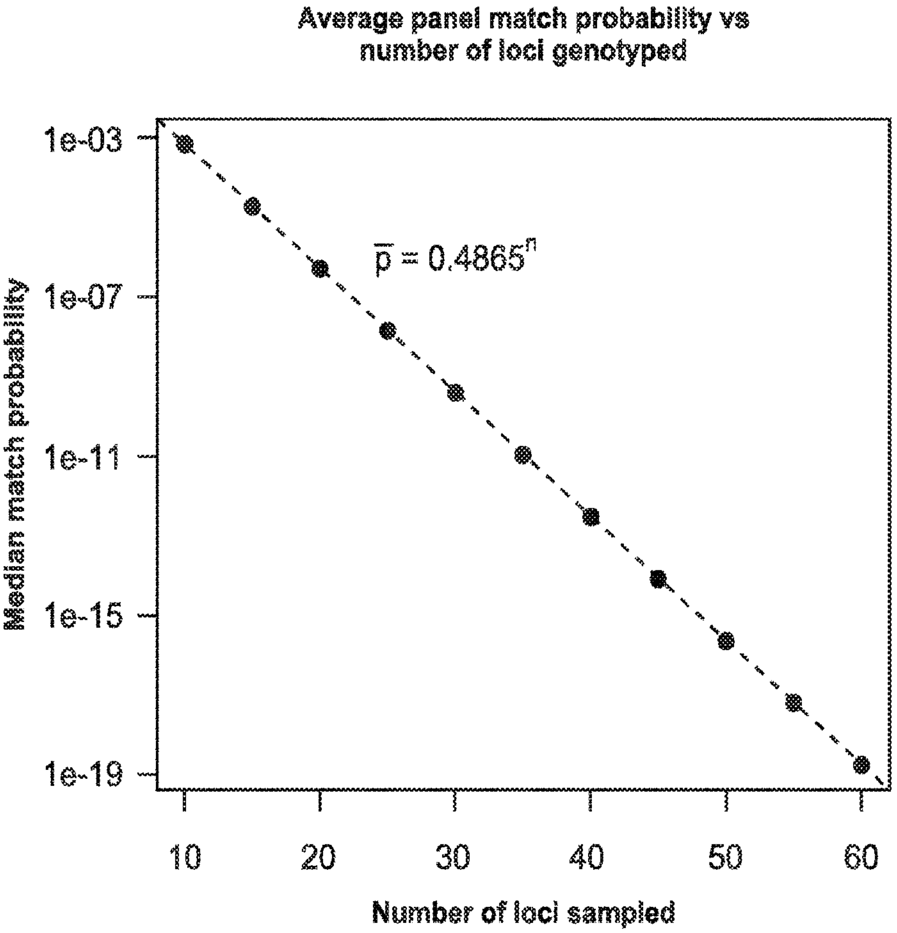
FIG. 14 shows an exemplary graph reporting an approach to provide identity metrics to be used in methods and systems to detect/provide a validated genetic marker variation herein described as well as to build related databases.

For example, in the illustration of FIG. 14, each locus encodes a validated GVP in the exemplary panel shown in FIG. 12B and the median match probability for these loci is shown on the y-axis. If the number of loci sampled (shown on the x-axis) is 20, the probability is $5.5\times10^{-7}$, or 1 in 1.8 million, and if the number of loci sampled is 30, the probability is $4.1\times10^{-10}$, or 1 in 2.4 billion.

Accordingly, for a common panel of 64 validated GVPs, FIG. 14 shows a graph indicating the theoretical probability that any two randomly selected profiles with a given number of loci will match, assuming independence of each locus. As understood by those skilled in the art, linkage disequilibrium (LD) can affect theoretical genotype match probabilities such as those exemplified in FIG. 14.

Example 20: Linkage Disequilibrium Affects Genotype Match Probabilities

Figure 15:
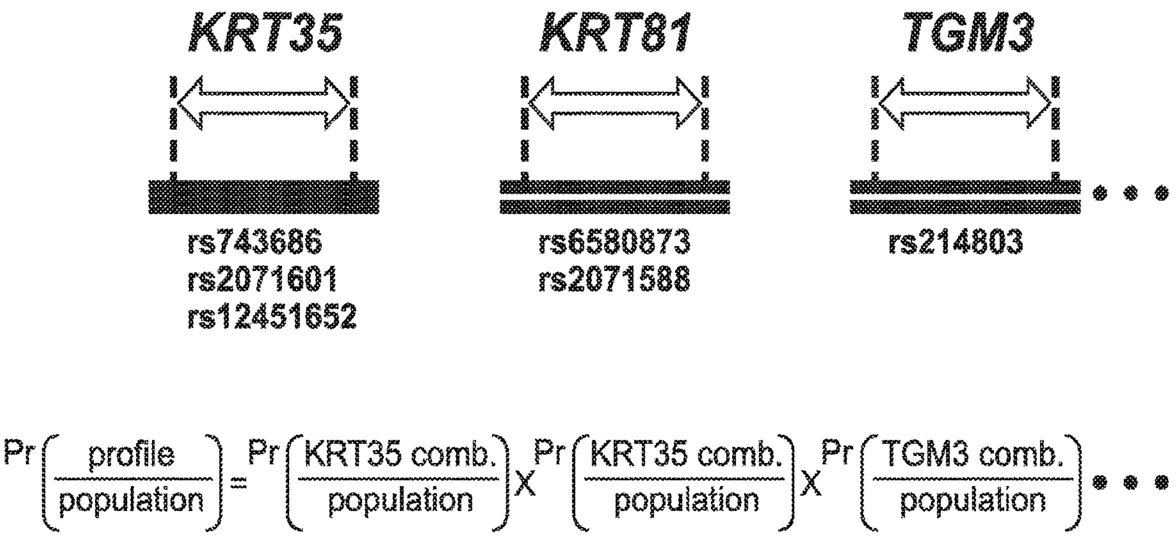
FIG. 15 shows a schematic showing an exemplary application of rule calculation showing how linkage disequilibrium affects genotype match probabilities in methods and systems herein described.

FIG. 15 shows an exemplary application of the product rule for calculation of the probability of an overall non-synonymous SNP profile in the population. However, nearby loci are often inherited together, therefore in some embodiments the product rule doesn't directly apply.

In the exemplary application of the product rule of FIG. 15, calculation of the probability of an overall non-synonymous SNP profile in the population (Pr(profile/population)) is estimated by determining the probability of detected nsSNP alleles, or allele combination in each gene, and then using the product rule to multiply these probabilities together (Pr(overall profile/population)). Shown are exemplary GVPs for three genes KRT35, KRT81, and TGM3, together with exemplary nsSNPs in these genes identified by their dbSNP entry IDs.

For example, many loci for exemplary validated GVPs shown in FIG. 12B are keratin genes, which are clustered on chromosomes 12 and 17. Thus, the loci encoding these GVPs may be linked though they are in different genes, and linked loci can be up to 220 kb apart]. Therefore, in some embodiments, LD can be taken into account for calculation of the probability of an overall non-synonymous SNP profile in the population. LD can be factored into the calculation by computing LD between pairs of GVP loci located on the same chromosome, for example using data from the 1000 Genomes Project dataset. Next, clusters of linked loci can be grouped, by computation of joint genotype probabilities given LD for loci within each cluster and by multiplying cluster probabilities to get overall genotype likelihood.

Example 21: Exome-Driven Identification of a Validated Common GVP Panel from Bone Samples It is expected that GVP based identification can be expanded to additional tissue types, and that protein-based identification can be conducted with multiple forensically relevant protein sources, such as hair, bone, teeth, and fingerprint protein.

FIG. 16 shows a list of an exemplary validated GVP identity panel for bone samples, that were identified following the method similar to that indicated for hair samples as summarized in the schematic shown in FIGS. 12A-12B. The abbreviated name of each of the 17 exemplary bone-related genes identified is shown in the left column ("Gene name"), the identifier for the National Center for Biotechnology Information Single Nucleotide Polymorphism Database (dbNSP) mis sense mutation-encoding SNP is shown in the second column, together with the allele ("rs#_nuc"), the amino acid sequence of the encoded peptide comprising the SNP for each allele is shown in the third column ("Peptide"), the corresponding single amino acid polymorphism ("SAP") is shown in the fourth column, and the allele frequency ("gf") for European ("EUR") and African ("AFR") populations is shown in the last two columns.

Example 22: Exome-Driven Identification of a Validated Individual GVP Panel

FIG. 17 shows a schematic of an exemplary method to create a custom GVP identification profile for an individual.

In an exemplary method illustrated by the schematic of FIG. 17, a DNA sample is obtained from an individual ("Known DNA sample") and the individual's exome is sequenced. One or more rare and/or private nsSNPs are then identified in the individual's exome, which can be used to create synthetic peptides encoded by the DNA sequences comprising the rare and/or private nsSNPs. Proteinaceous material (e.g. from a hair sample or other sample) is also collected from the same individual, which is processed and analyzed using LC-MS/MS. 'Diagnostic' LC-MS/MS spectra can then be generated for the synthetic peptides that can be used to identify a particular GVP from the individual in a complex LC-MS/MS dataset.

Accordingly. for an 'Individual GVP Panel', GVPs can be down-selected based on low-frequency or 'rare' or 'private' nsSNPs and the GVP panel is unique to that individual (see FIG. 17). The term "rare SNPs" as used herein refers to nsSNPs having a frequency <0.05% in a given population. For example, an 'Individual GVP Panel' can be provided when a DNA sample and optionally a protein sample is available from an individual of interest (e.g. a suspect of a crime in custody). The exome sequence of the individual is then obtained, rare nsSNPs identified, and 'diagnostic' LC-MS/MS spectra can then be generated for the synthetic peptides that can be used to identify a particular GVP particular to the individual.

Example 23: Application of an "Exome-Driven" Validated Individual GVP Panel to Operational Samples FIG. 18 shows a schematic of an exemplary method of applying an Individual GVP panel to an operational sample.

In the exemplary method, proteinaceous material (such as hair, house dust, fingerprint residue, urine/fecal matter, etc.) is collected ("Collection") from a target location (e.g. a crime scene), wherein in some embodiments the proteinaceous material can comprise proteins originating from multiple contributors. Proteomic analysis of the proteinaceous material then provides a large number of highly complex fragmentation patterns. Spectral matching to a custom identification profile ("Unique synthetic peptide profile", generated for a particular individual, e.g., following the exemplary method shown in FIG. 17) is performed, thus matching 'diagnostic' spectra for the individual to spectra present in the complex mixture in the LC-MS/MS data, thus confirming the prior presence of the individual at the target location. The exemplary method shown in the schematic is thus not dependent on identification of peptide sequences from databases, but instead uses a process of targeted spectral matching based on the individual GVP panel.

Accordingly, in the exemplary method illustrated by the schematics of FIG. 18, proteinaceous material (such as hair, house dust, fingerprint residue, urine/fecal matter, etc.) is collected from a target location (e.g. a crime scene), Spectral matching to a custom identification profile, is performed, thus matching 'diagnostic' spectra for the individual to spectra present in the complex mixture in the LC-MS/MS data, thus confirming the prior presence of the individual at the target location. The method is thus not dependent on identification of peptide sequences from databases, but instead uses targeted spectral matching based on the individual GVP profile. Thus, identity metrics can be obtained specific for the individual of interest and compared to the identity metrics of the operational sample. In particular, identification of rare nsSNPs in an individual allows in some embodiments the identification of a sample that originated from an individual in a complex sample that comprises samples from multiple contributors (see FIG. 18).

Example 24: Recovery of Trace DNA

Successful recovery of trace DNA was performed. In real-world data sets, there is 2% success rate at searchable profile from touch samples. 11% of rape kits result in successful prosecution. Table 3 shows examples of percentage of samples for which a profile is recovered [48].

TABLE 3

| Recovered profile from samples | % of samples |
|---|---|
| None | 44% |
| Unusable partial profile | 21% |
| Mixture (usable) | 22% (3%) |
| Usable partial profile | 6% |
| Full | 7% |

Example 25: Value and Challenges of Protein-Based Approach

Exemplary advantages and challenges of a protein-based approach comprise those in Table 4 below.

TABLE 4

| Advantages | Challenges |
|---|---|
| Genetic variation (nsSNPs) is retained in protein | Lack of an equivalent to PCR for amplification |
| Protein is considerably more stable than DNA | nsSNPs tend to be less discriminate than STR loci |
| Protein occurs at high levels in tissue | Each protein source/tissue expresses a subset of gene products |
| Extremely large pool of common variants available | Technology limited until recently-tools remain uncommon |
| New proteomic methodologies allow attomole-level analysis | |

A large reservoir of genetic variation exists in the proteome: Up to 60 k common variants (>0.5%), an estimated >1700 in the hair proteome alone.

FIG. 19 shows exemplary diagrams of DNA and protein chemical structures, showing sites of depurination, oxidation, or hydrolysis.

Example 26: Overview of GVP Identification and Validation Process

Figure 20:
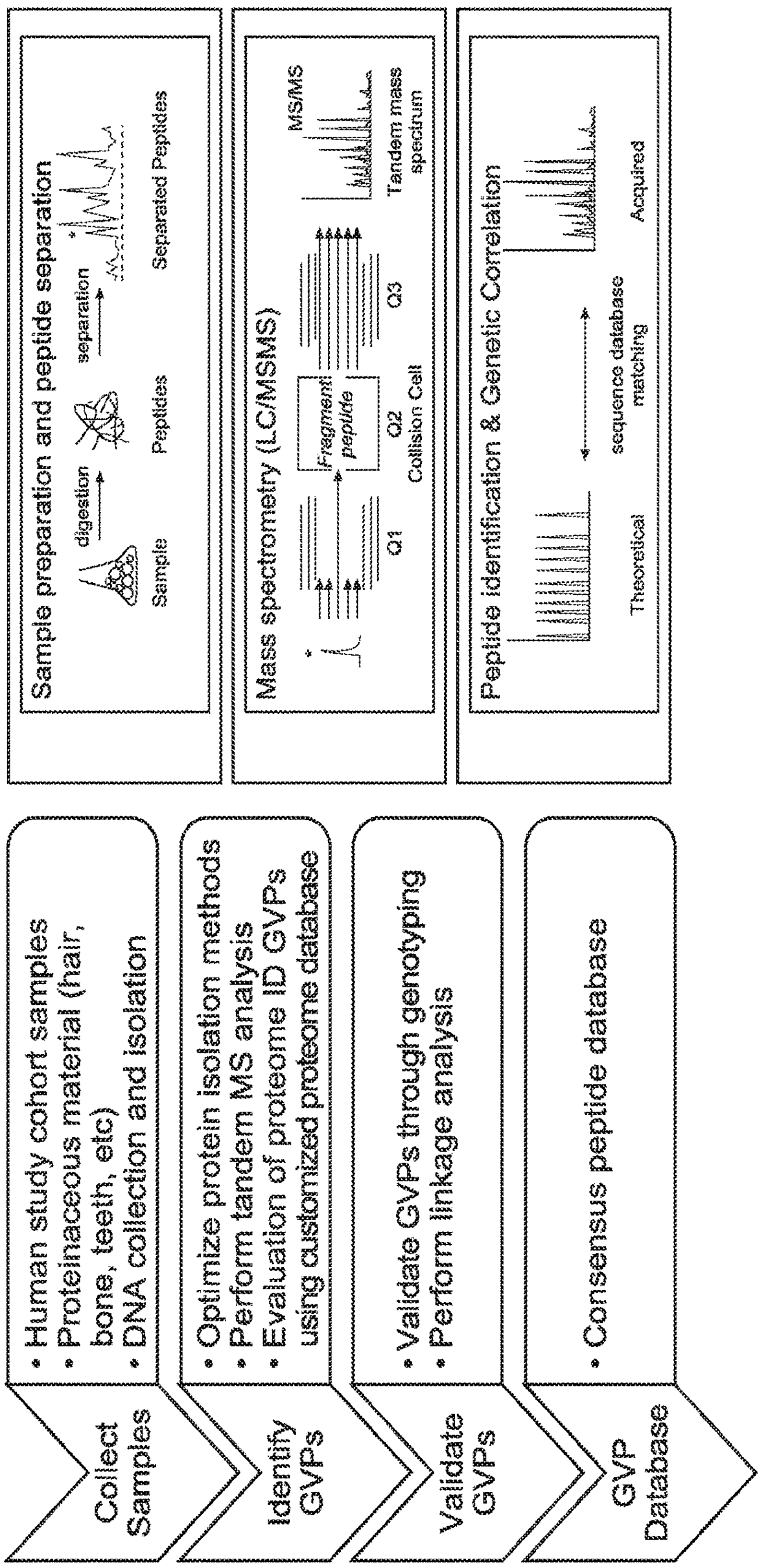
FIG. 20 shows a diagram of an exemplary overview of GVP identification and validation process.
Figure 21:
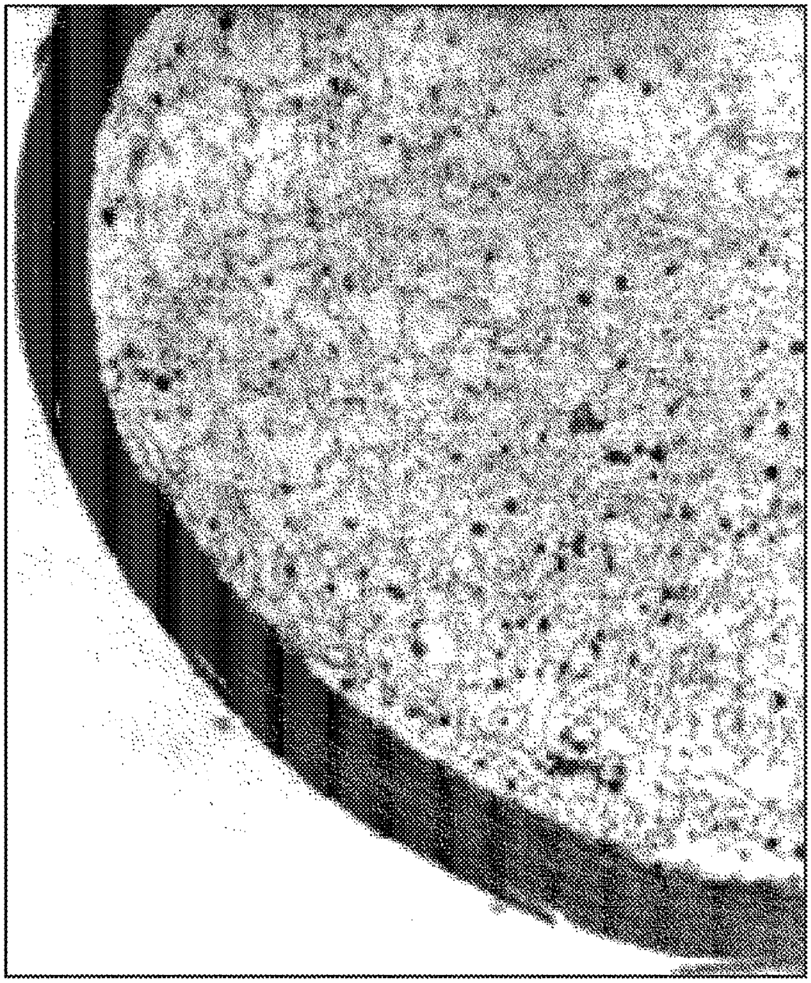
FIG. 21 shows an exemplary electron microscope image of a cross-section of a single hair.

FIG. 20 shows a diagram of an exemplary overview of GVP identification and validation process, showing a 'proteome-driven' GVP discovery approach.

Example 27: Automated In-Line Sample Processing

Figure 22:
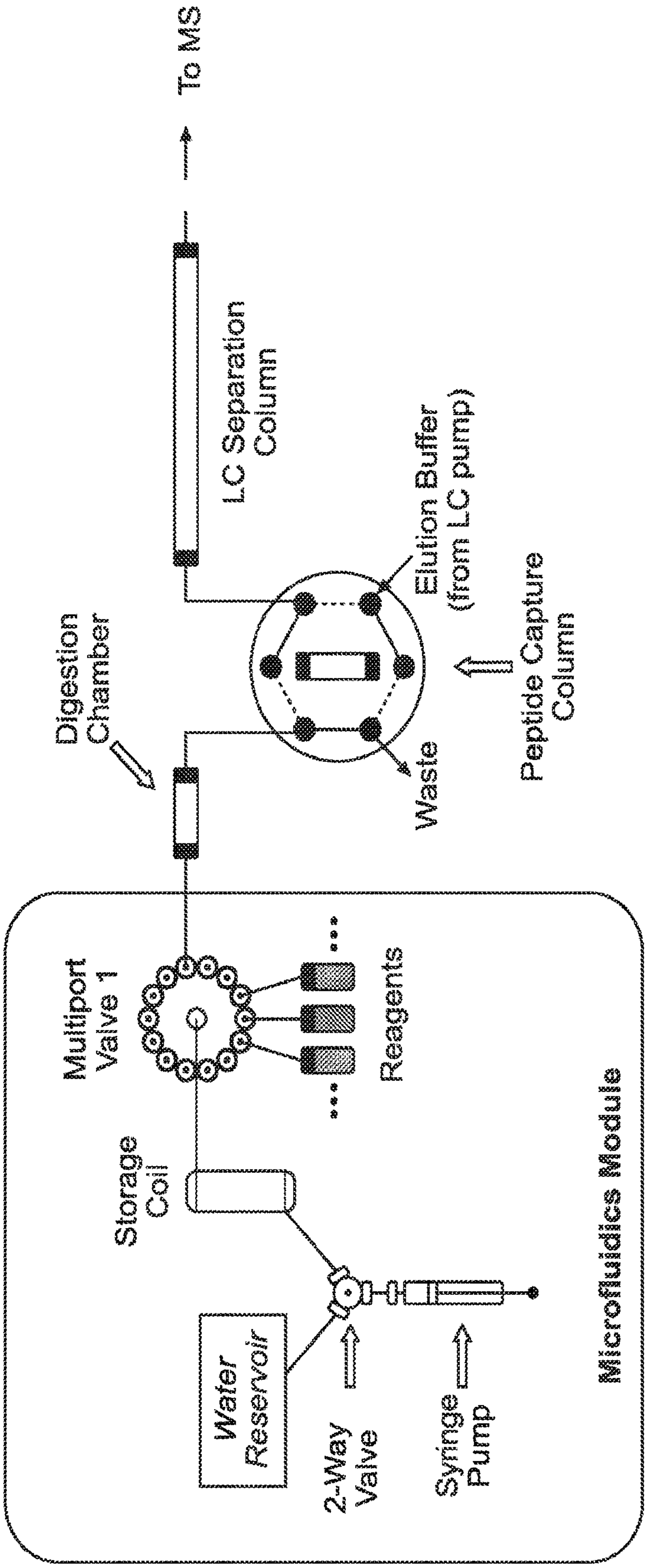
FIG. 22 shows a diagram of exemplary automated in-line sample processing.

FIG. 22 shows a diagram of exemplary automated in-line sample processing

In particular, FIG. 22 describes an arrangement of fluidic components that enable automated in-line sample processing of proteinaceous samples such as hair. The microfluidics module including syringe pump, storage cell, associated valves (2-way and multiport valve 1) and reagent reservoirs allow for a controlled introduction of reagents to and from a digestion container, which contains the sample of interest. Each component can be software controlled to enable automation, precision and reproducibility. Flows leaving the digestion chamber are introduced to an additional multiport valve which can be controlled via software to allow automation. This valve will direct effluent to either a waste stream or a peptide capture column depending on the stage of the process that is occurring. The purpose of the peptide capture column is to concentrate the peptides resulting from the digestion process as well as to assist in removing reagents that may interfere with the analysis process. Finally, the second multiport valve allows for the introduction of an elution buffer that elutes the peptides from the peptide capture column and into a liquid chromatography/mass spectrometry system for proteomic analysis.

Example 28: Improved Data Acquisition Approaches Maximize Discovery

This example describes exemplary improved data acquisition approaches to maximize GVP discovery.

Figure 23:
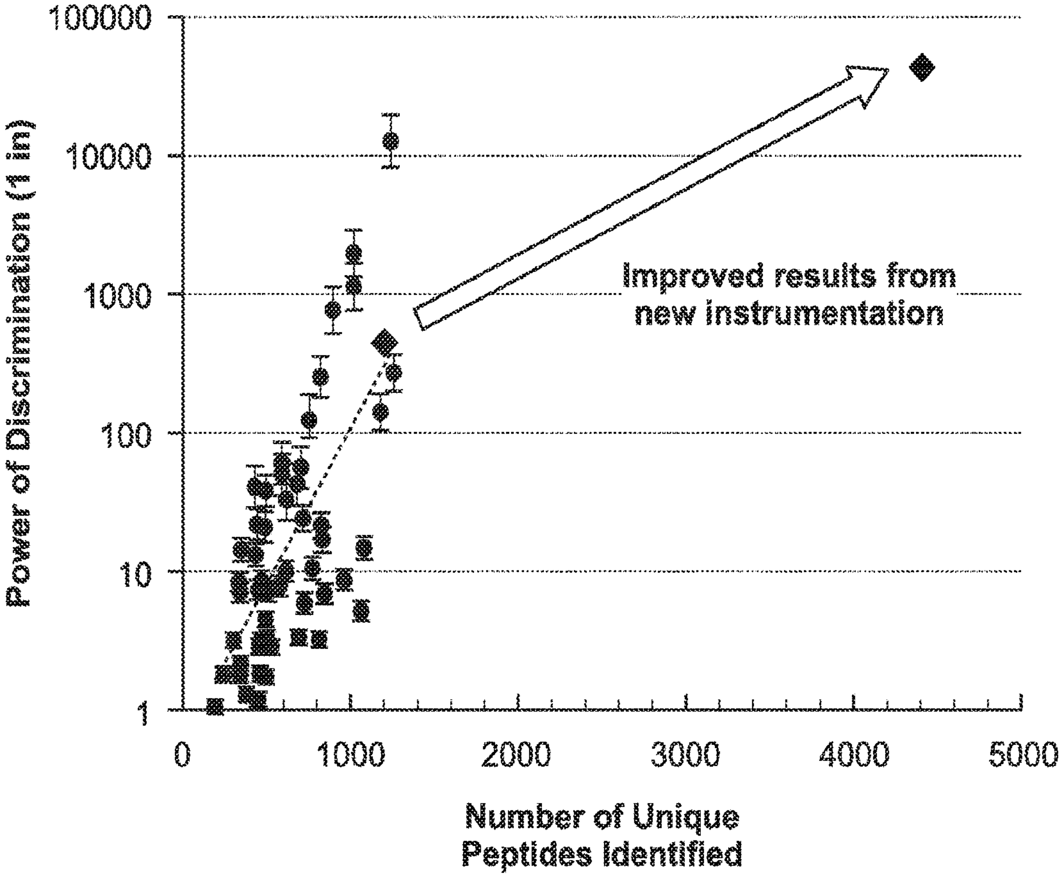
FIG. 23 shows a graph reporting exemplary results of power of discrimination as a function of number of unique peptides identified. In particular, the arrow indicates an exemplary improvement in results from new instrumentation.

Improvements in instrumentation can maximize GVP discovery, for example, use of an advanced hybrid mass spectrometer such as the Q-Exactive Plus, which features nano-LC and nanoelectrospray, and advanced hybrid mass-spectrometry (quadrupole-orbitrap). FIG. 23 shows a graph reporting exemplary results of power of discrimination as a function of number of unique peptides identified. In particular, the arrow indicates an exemplary improvement in results from new instrumentation.

Other improved data acquisition approaches comprise use of exclusion lists, wherein data for peaks already collected in previous runs are not collected, and focusing on weaker peaks. Also, use of inclusion lists, wherein data is only collected on a specific list of GVPs that have been previously discovered in other samples, and/or predicted from genomic or proteomic databases. Also, use of improved reference databases, such as those that include all SAPs, wherein more GVPs allow greater power of discrimination.

Example 29: Incorporation of GVP Profiles and DNA Based Measures of Identity

Figure 24:
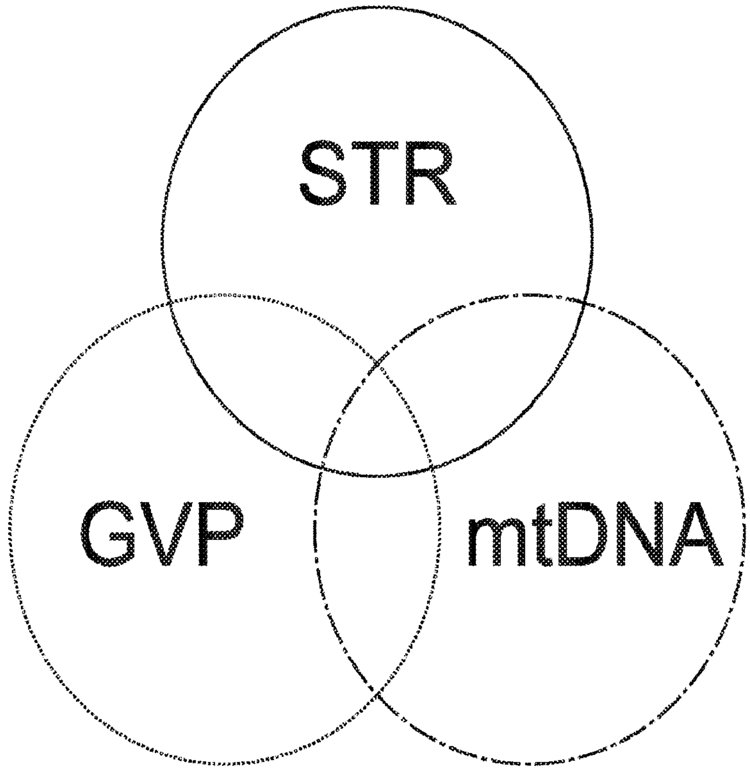
FIG. 24 shows a Venn diagram illustrating an exemplary incorporation of GVP profiles and DNA based measures of identity, wherein 'STR' refers to single tandem repeats, 'GVP' refers to genetically variant proteins and 'mtDNA' refers to mitochondrial DNA.

Incorporation of GVP profiles and DNA based measures of identity can be performed by integrating single tandem repeat (STR) and mitochondrial DNA (mtDNA) genetic information with GVPs, (see FIG. 24) allowing an increase in the power of discrimination to reach levels of individuality (>1 in 7 billion). In some instances, this requires the elucidation of statistical dependence patterns between each method, as understood by those skilled in the art. In particular, DNA STR typing and mtDNA analysis can result in partial or null profiles.

Example 30: Use of GVP Markers to Predict Biogeographic Background

It is expected that analysis of a diverse cohort will reveal markers that are informative of biogeographic background.

Figure 25:
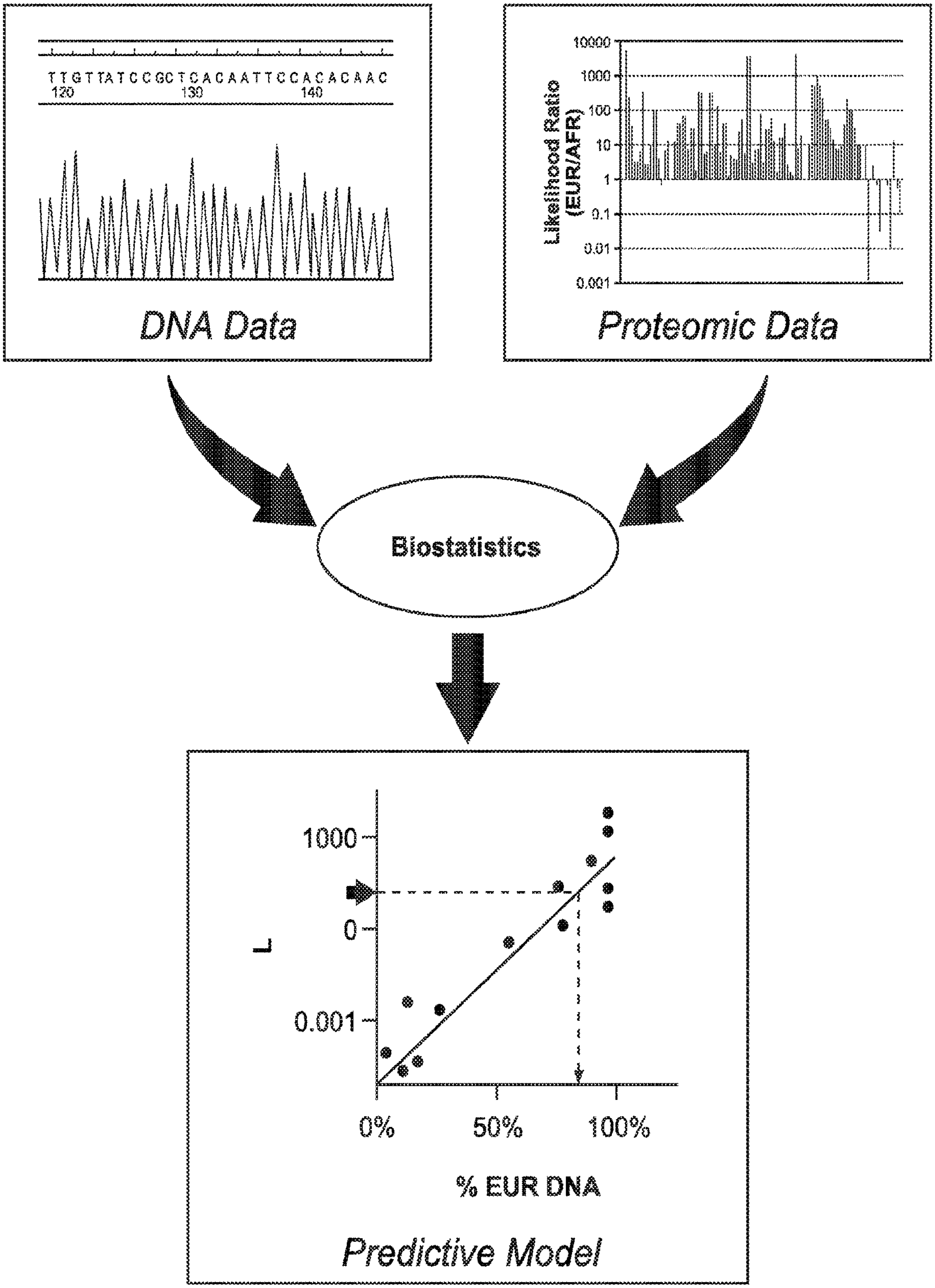
FIG. 25 shows a schematic showing exemplary use of GVP markers to predict biogeographic background.

An exemplary method is illustrated by the schematic of FIG. 25. In particular in the illustration of FIG. 25, the panel in top left shows an exemplary DNA data sequence, TTGTTATCCGCTCACAATTCCACACAAC (SEQ ID NO:144), and the panel in top right shows exemplary proteomic data showing a graph reporting exemplary likelihood ratio of European/African markers (EUR/AFR), which together can provide biostatistics useful for predicting biogeographic background. The graph on the bottom of FIG. 25 shows an exemplary predictive model reporting % European DNA in relation to likelihood ratio (L).

Inclusion of informative markers in likelihood ratio (L) and the biostatistical analytical model will enable prediction of biogeographic origin from proteomic data. The use of GVP markers will be validated to predict biogeographic background.

Example 31: Validation of GVP Application in Forensic Contexts

It is expected that comparison of MS data from two different protein samples from one individual will demonstrate the validity of the approaches described herein. For example, it is expected that GVP alleles will be consistent between physiological locations (e.g. hair from head versus body), and that GVP profiles will remain consistent with age, and/or chemical and/or environmental exposure.

Figure 26:
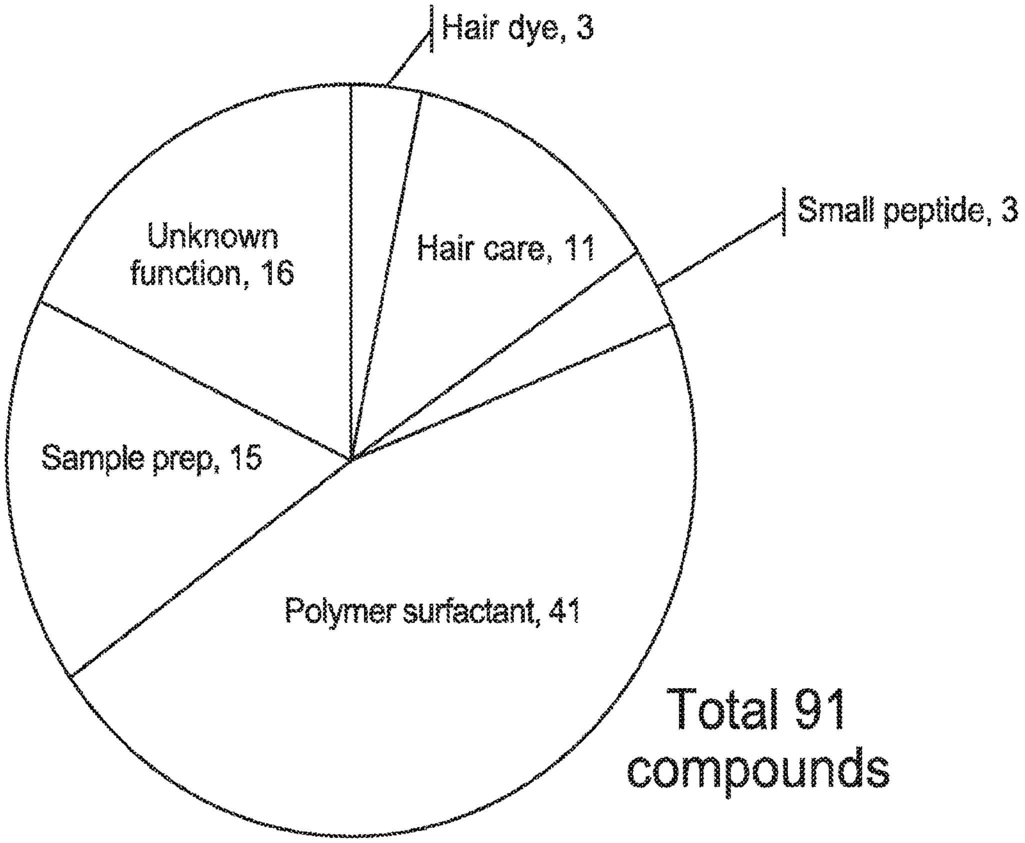
FIG. 26 shows a pie chart reporting exemplary results of chemical markers detected in in hair samples.

In particular, in a study to identify chemical markers in hair that are indicative of exposures to hair dye, exemplary results indicate surfactants comprise the majority of chemicals in hair care products (see FIG. 26). Other hair care compounds comprise emulsifiers, moisturizers, and detergents, whereas hair dye compounds are not very abundant in the samples.

Example 32: GVP Database Design

GVP databases can be designed based on the indications provided in the present disclosure comprising marker GVPs for biological organism, a biological organism type or an individual thereof as will be understood by a skilled person.

Figure 27:
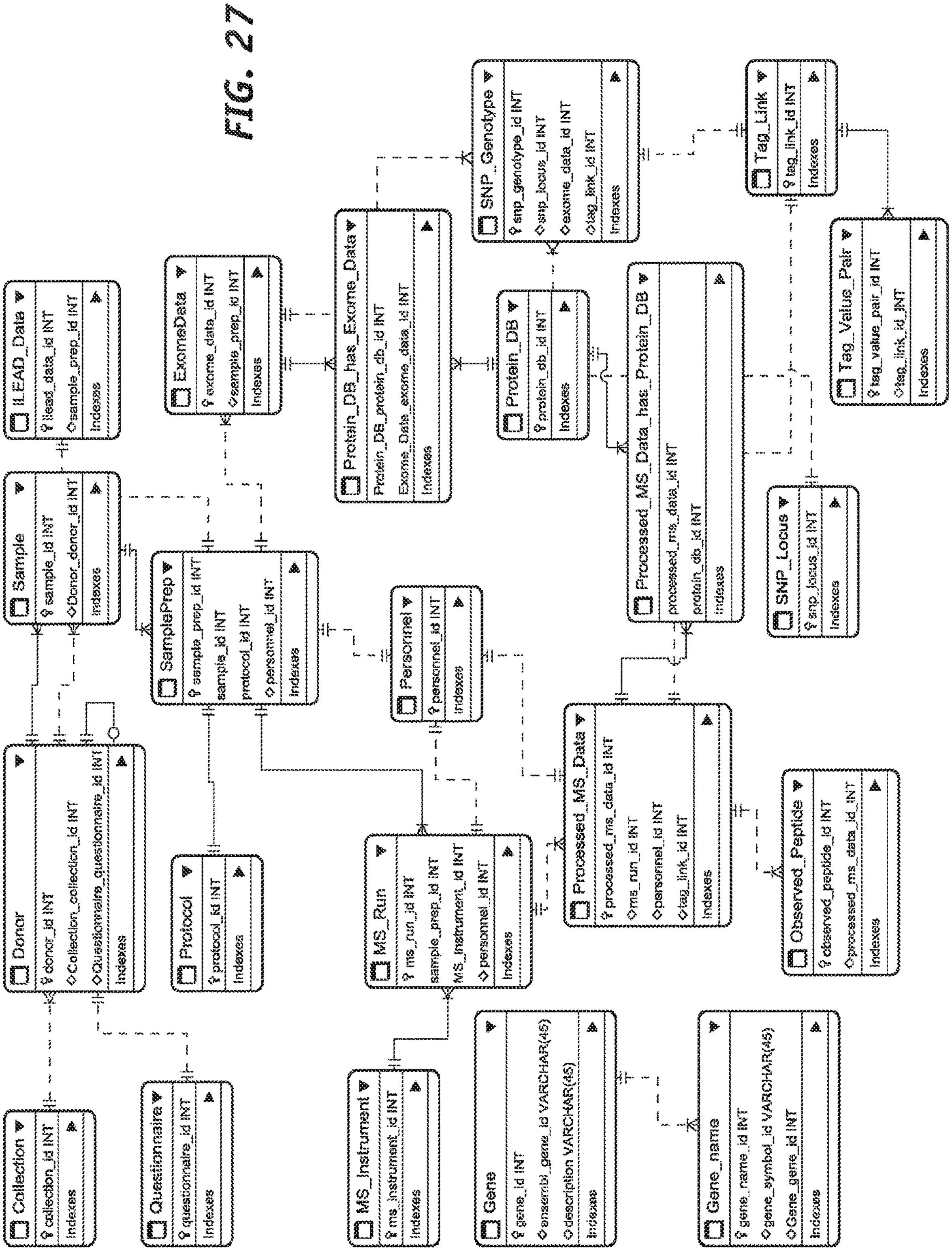
FIG. 27 shows a schematic showing an exemplary GVP database design, wherein an entity relationship diagram shows types of data entities and the relationships between them. The exemplary design allows flexibility by storing additional characteristics as tag-value pairs.

An exemplary GVP database design is shown in FIG. 27. The Entity relationship (ER) diagram shows types of data entities and the relationships between them. The Scheme allows flexibility by storing additional characteristics as tag-value pairs as will be understood by a skilled person The above schematics can be implemented by developing a central database resource for GVP and SNP genotyping, comprising web-based queries and data entry, bulk loading of sequencing and LC/MS data, streamlined data access for analysis tools, implemented using Django, a Python-based framework for web/database application development in accordance with the illustration of FIG. 27.

Example 33: GVP Analysis Workflow in Bones

Figure 28:
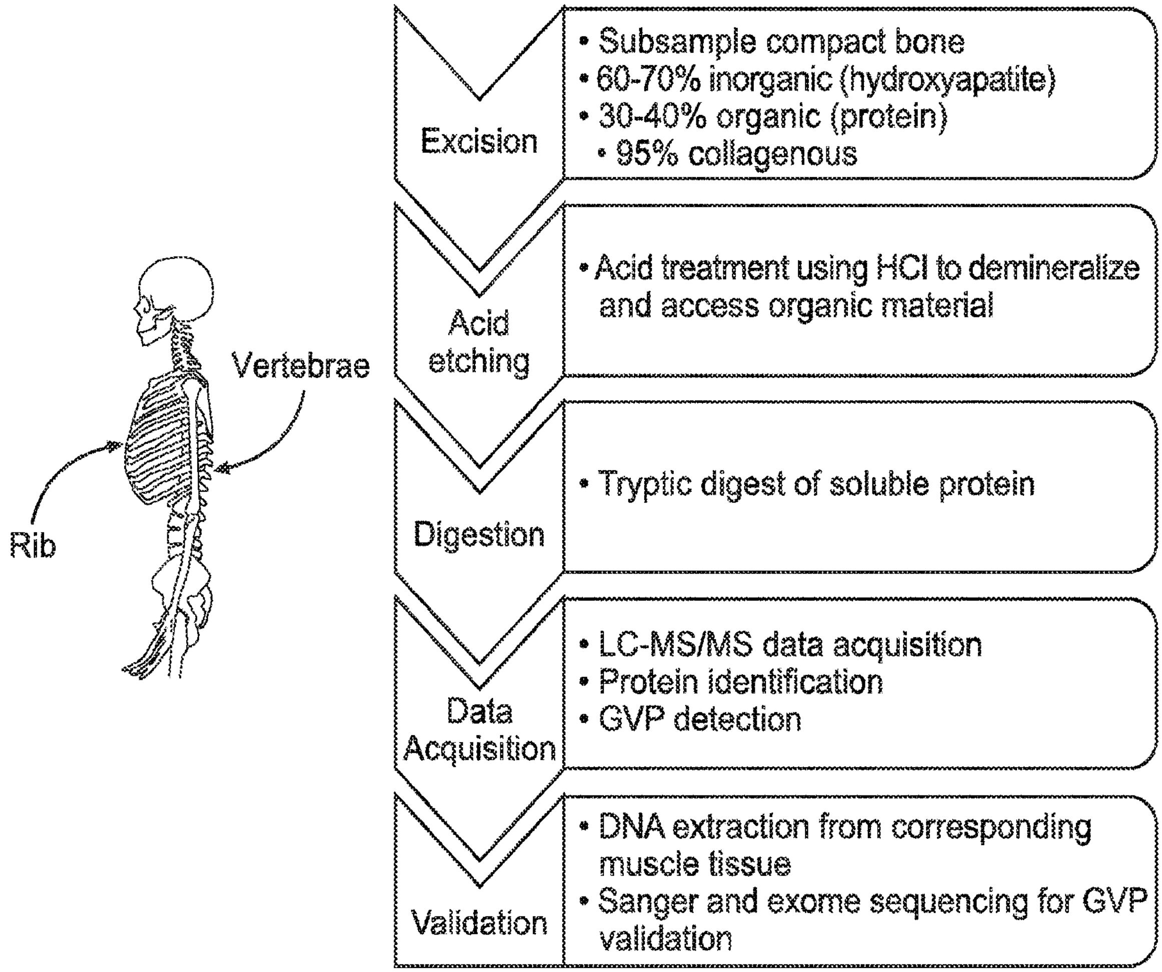
FIG. 28 shows a schematic of an exemplary bone GVP analysis workflow.

An exemplary GVP analysis workflow is shown in FIG. 28.

Example 34: Tooth Sex-Linked Protein Analysis Workflow

Figure 29:
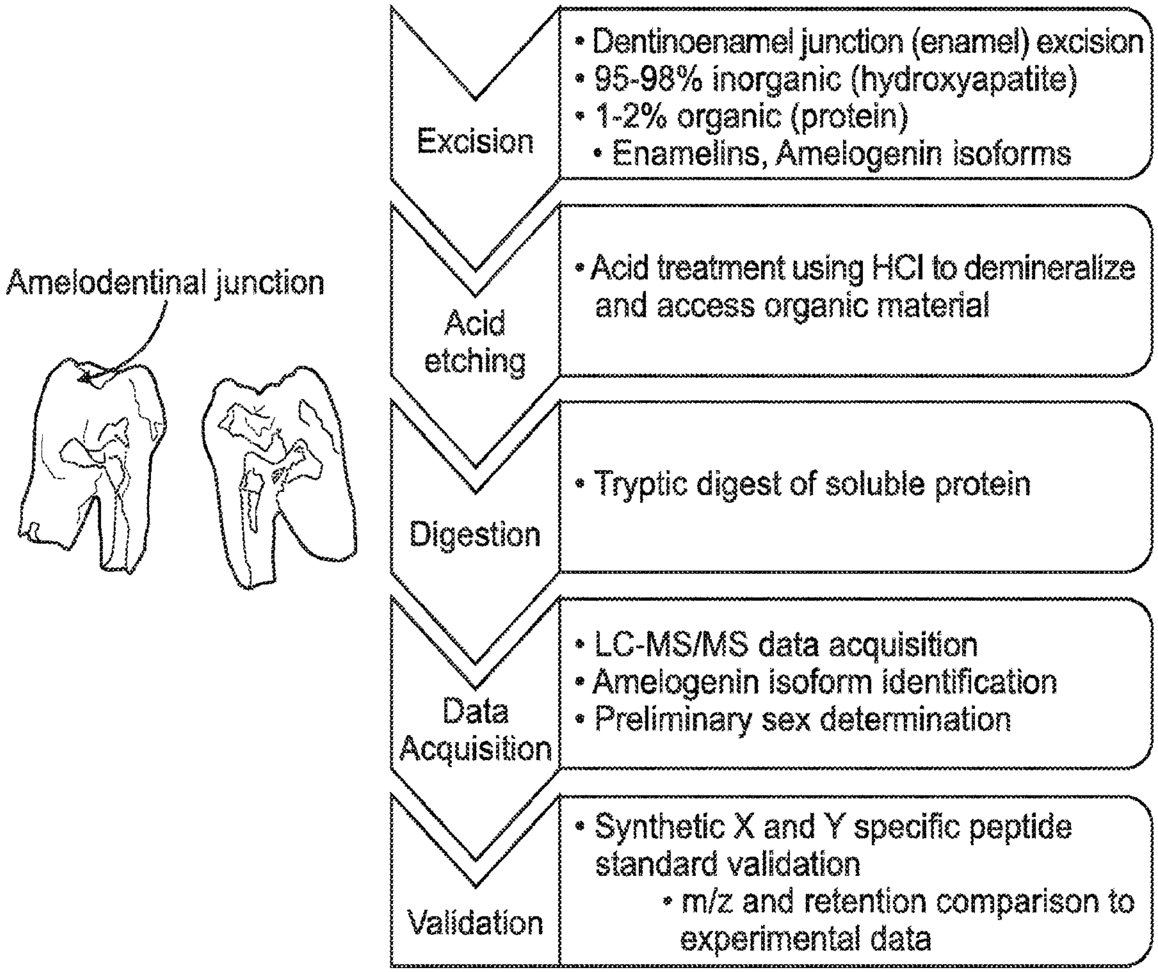
FIG. 29 shows a schematic of an exemplary tooth sex-linked protein analysis workflow.

An exemplary tooth sex-linked protein analysis workflow is shown in FIG. 29.

In this example, both amelogenin isoforms were identified from modern and archaeological teeth samples.

Example 35: Fingerprint/Touch Derived Samples

Figure 30:
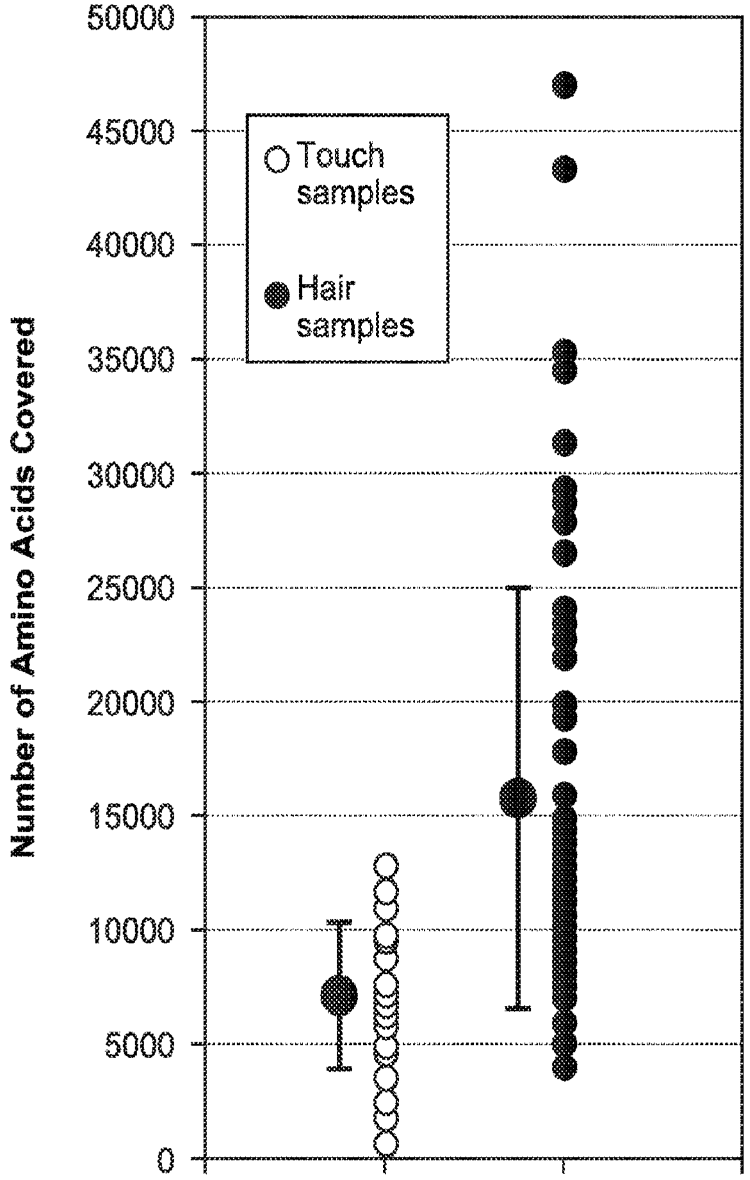
FIG. 30 shows a graph reporting exemplary results of protein coverage (number of amino acids covered) in 'touch samples' and 'hair samples'.

Touch samples were collected from multiple surfaces, such as those comprising DNA-incompatible materials. Samples were extracted with techniques identifiable by a skilled person. Samples were analyzed for protein coverage (see FIG. 30). As shown in FIG. 30, protein coverage from touch samples is similar to that achieved with hair samples Example 36: Tissue Procurement Cranial hair shafts and buffy coat DNA were collected from a cohort of 60 self-identifying unrelated European—

Americans (EA1, Sorenson Forensics LLC, Salt Lake City). Genomic DNA from each subject was screened using the Investigative LEAD™ Ancestry DNA Test (Sorenson Forensics LLC, Salt Lake City, UT) and genotype data was generated for 190 SNPs that are 'Ancestry Informative Markers', which span all 22 autosomal chromosomes[49]. Nine individuals had measurable non-European admixture and were excluded from the analysis. An additional collection was conducted using cranial hair shaft and nuclear DNA from another cohort of self-identified unrelated European—Americans (EA2, n=15). All material was collected using protocols, informed consents, and questionnaires that were approved by the Institutional Review Boards at Utah Valley University (IRB #00642) and Lawrence Livermore National Laboratory (IRB #11-007). Hair shaft material was also collected from a cohort of five African-American and five Kenyan subjects[50]. Cranial hair shafts were additionally collected from six individuals from two separate archaeological assemblages excavated in London and Kent: three individuals (S1-S3), dating from circa 1750-1850, and three individuals (S4-S6) from a cemetery in active use 1821-1853.

Example 37: Proteomic Data Acquisition and Identification of Single Amino Acid Polymorphism-Containing Peptides Hair from subjects was processed physically and biochemically and data was acquired as described. Briefly, hair was ground or milled; treated in a solution of urea, DTT, and detergent; alkylated; and then proteolyzed with trypsin. Resulting peptide mixtures were analyzed using tandem liquid chromatography mass spectrometry. The resulting proteomic datasets were converted to the Mascot generic format and analyzed using three different approaches: Mascot (software version 2.2.03, Matrix Science, Inc., Boston, MA), X!Tandem, using the GPM manager software (www.thegpm.org, release SLEDGEHAMMER (2013.09.01)), or X!Tandem using the Petunia Graphic User Interface (TANDEM CYCLONE TPP, download=2011.12.01.1—LabKey, Insilicos, ISB). A custom protein reference database was used (51 Methods; zenodo.org/record/58223: DOI: 10.5281/zenodo.58223) to ensure the identification of genetically variant peptides by both Mascot and the Petunia GUI peptide spectra matching algorithms [51]. Resulting peptide lists were screened for the presence of genetically variant peptides and identifications were collated for each subject. Inferences made through the use of GPM manager or the use of the customized reference database, in either X!Tandem or MASCOT, were compared for redundancy 0. The mass spectrometry proteomics data that has been submitted to the Global Proteome Machine (www.thegpm.org,) can be publicly accessed[52].

Example 38: Validation of Identified Genetically Variant Peptides

Identified candidate genetically variant peptides were filtered to reduce false-positive assignment using the following criteria for exclusion: low-quality expectation scores (X!Tandem, log(e)<−2; Mascot, expectation score >0.05), if the corresponding nsSNPs were distributed at less than 0.8% in the sample population (minor allelic frequency <0.4%), the presence of masses in a MS/MS fragmentation spectrum from a GVP consistent with the alternative allele, the incorporation of biological post-translational modifications in the assigned sequence (such as phosphorylation), and high variance between theoretical and observed primary masses (>0.2 Da). Amino acid polymorphisms assigned due to likely chemical modification or conversion were also excluded from the analysis (www.unimod.org)[53-55]. Rejected single amino acid polymorphisms include methionine to phenylalanine, asparagine to aspartate, glutamine to glutamate and cysteine to serine[53, 55, 56]. Peptides that were potentially derived from paralogous sequences, or that were potentially expressed in more than one gene product, were removed from the analysis. Inferred nsSNP loci were directly validated by Sanger sequencing of the subjects' nuclear DNA.

Example 39: Statistical Treatment of Individual Inferred nsSNP Profiles

An estimation of the probability of a given inferred nsSNP allele profile being detected in a sample population was calculated using a frequentist estimation of allele frequency, or frequency of an allele combination, within the reading frame of a gene (Pr(inferred nsSNP allele gene combinationipopulation)), and a Bayesian application of the product-rule[57, 58]. The occurrence of alleles, or allele combinations, was counted in European (n=379) and African (n=246) sample populations (www.1000genomes.org; Phase 1)[59]. The 1000 Genome Project sample populations were selected as sample populations because the African population did not have European admixture. The final probability of an individual SNP, or SNP combination, occurring within a gene reading frame, was estimated as $(x+\frac{1}{2})/(n+1)$, where x is the number of individuals with a given SNP, or combination of SNPs, in a sample population of size n[60]. The above expression represents the Bayesian posterior mean of a binomial probability using the Jeffreys Beta (½, ½) prior, which has the advantage of giving a non-zero estimate of the population probability even for x=0[60, 61]. Full independence between genes was assumed.

The effect of observed allele variation on the overall profile probability was estimated by parametric bootstrap resampling from a binomial $(n, (x+\frac{1}{2})/(n+1))$ distribution for each gene, multiplying the resulting probability estimates across genes, and taking the $5^{th}$ and $95^{th}$ percentiles of the resampling distribution (90% CI)[61]. A comparison of the inferred nsSNP profile probability in the sample European and African population was calculated as a likelihood (L) ratio (L=Pr(profile|EUR population)/Pr(profile|AFR population))[57].

Example 40: Same Sample Mitochondrial/Proteomics GV Detection and Database Building An exemplary method is described to perform a same sample mitochondrial/proteomics genetic variation detection and database building according to the following steps of the instant disclosure.

Preparing the Biological Sample

Applicable method to perform preparing the biological sample to obtain a processed biological sample comprising solubilized proteins to be used in a proteomic analysis, are identifiably by a skilled person upon reading of the instant disclosure In an exemplary approach using preparation methods of the instant disclosure, single hair samples (1 inch; 25 mm) from separate individuals were carefully measured and cut into four equal pieces. The cut hair was then placed into separate Protein LoBind Eppendorf tubes. 100 μL of extraction buffer containing 0.05 M ammonium bicarbonate (ABC), 0.1 M dithiothreitol (DTT), 2% sodium dodecanoate (SDD) was added to each tube. Samples were then incubated at 70° C. in an ultrasonic water bath (Elma) while being ultrasonicated at high energy and frequency settings for 60 minutes or until hair was completely dissolved into solution. SDD was removed by extraction with acidified ethyl acetate (pH 2-3, 0.75% trifluoroacetic acid). After addition of 100 uL acidified ethyl acetate to each tube, samples were quickly vortexed, incubated at room temperature for 5 min, and centrifuged for 5 min at max speed (20,000×g). The upper organic phase was removed, discarded to waste, and the extraction process was repeated once. The remaining lower aqueous phase was then readjusted to pH 8 with ABC [13]. Alternative step includes cold acetone precipitation overnight and resuspension of protein pellet into 0.05M ABC; 0.1M DTT; and 1% protease max. Carbamidomethylation of free cysteines was performed by adding 6 μL of iodoacetamide (1.0 M) and incubation for 60 min in the dark at 25° C. To further solubilize proteins, 0.01% protease max (3 μL of 1.0% w/v) was added to each sample. Prior to proteolysis, the solubilized protein solution was concentrated to 50 uL using 10 kD molecular weight spin concentrators (Millipore). Trypsin (2 μL of 0.5 μg/μL) was then added to each protein sample. Protein digestion was performed at 25° C. for 20/22 hours while being continuously agitated by magnetic-bar stirring. Protocol for isolation of DNA from tissues was provided by the Qiagen QIAamp® DNA Micro Kit. Manual suggestions were following with exception to the lysis procedural steps that include adding proteinase K, additional of proprietary buffer 'ATL', pulse-vortexing, overnight incubation at 56° C., and addition of proprietary buffer 'AL'. Previous trypsin incubation was substituted for these steps. Following trypsin proteolysis, 100 uL of 100% ethanol was added to each sample as recommended by Qiagen QIAamp® DNA Micro Kit instructions. Removing this set and not adding ethanol also yields amplifiable mtDNA from sample. Samples were then vortexed for 15 seconds, incubated at 25° C. for 5 minutes, then added into separate QIAmp miniElute columns. Columns were closed and centrifuged at 6000×g for one minute. Flow-through was collected as the peptide fraction of the extraction, filtered using 0.1 μm PTFE filter, and transferred into fresh vials for mass spectrometric analysis (stored at +4.0–-20° C.). Additional step of speed vacuum (20 minutes at 60° C.) can be used to concentrate peptide fraction of samples. The bound mtDNA fraction was then washed according to Qiagen QIAamp® DNA Micro Kit instructions and eluted twice into the same collection tube with 25 uL of warm (37° C.) water by centrifugation for one minute (20,000×g).

Fractionating the Processed Biological Sample

Applicable method to perform fractionating the processed biological sample to obtain solubilized protein fraction and a solubilized DNA fraction can also be identified by a skilled person.

In particular a solubilized protein fraction comprising the solubilized proteins from the sample can be obtained by the following exemplary SDD extraction and protein concentration procedure step which includes cold acetone precipitation (−4° C.) overnight and resuspension of protein pellet into 0.05M ABC; 0.1M DTT; and 1% protease max. Additional step of speed vacuum (20 minutes at 60° C.) can be used to concentrate peptide fraction of samples subsequent to proteolysis step.

A solubilized DNA fraction comprising solubilized nuclear and/or mitochondrial genome from the sample can be provided with the following exemplary method. Following trypsin proteolysis, 100 uL of 100% ethanol was added to each sample as recommended by Qiagen QIAamp® DNA Micro Kit instructions. Removing this set and not adding ethanol also yields amplifiable mtDNA from sample.

Detecting a Genetic Protein Variation in the Solubilized Protein Fraction

Applicable methods to perform detecting a genetic protein variation in the solubilized protein fraction from the sample by performing the proteomic analysis of the solubilized protein fraction are identifiable by a skilled person. in an exemplary method MS/MS data acquisition of peptide sequences was performed using Thermo Scientific Q Exactive Plus Hybrid Quadrupole-Orbitrap mass spectrometer fitted with Easy-nLC 1000 HPLC (Thermo Scientific, Asheville, NC, USA). Peptides were separated by reversed-phase liquid chromatography using a mobile phase A (0.01% TFA in water) and mobile phase B (0.01% TFA in acetonitrile) in a 97 minute gradient. 2 of each sample were injected onto a C18 trap cartridge and preceded by an Easy-Spray™ nanoflow (1 mm×150 mm) column (Thermo Scientific, Asheville, NC, USA) with a flow rate of 3 μL/min. Electrospray ionization was achieved in positive mode with a voltage of 2-4 kV. Dynamic exclusion data collection was implemented at a MS scan range of 180-1,800 m/z, top 10 precursor ions were chosen for subsequent MS/MS scans and excluded after 10 seconds.

Single-hair method implements program PEAKS 7.5 (Bioinformatics Solutions Inc., Waterloo, Ontario, Canada) for variant peptide detection. PEAKs software was used to search each RAW data file to determine the specific peptides that were identified in each sample. A reference database created by translating polymorphisms (missense SNPs, insertions, deletions, and stops/gains) that influence protein sequences observed in exome results into mutated protein sequences is used for peptide identification within software parameters. Experimental conditions and instrumental capabilities inform parameters chosen for search. Search settings include partial posttranslational modifications including oxidation of methionine, deamidation of asparagine and glutamine, and carbamidomethylation of cysteine. Precursor mass error of 30 ppm using monoisotopic mass was used for parent ion identifications and a 0.05 Da for fragment ions masses. A decoy database was generated within the software using a protein library of all human protein sequences exported from UniProtKB/Swiss-Prot knowledgebase (The UniProt Consortium; www.uniprot.org/). The decoy database is used to determine the false determination rate (FDR) of protein identifications. Protein identifications (IDs) were filtered by a 1% FDR. Data output from PEAKs searches including identified peptides, quality measures, and protein sequence position is then filtered for peptides containing predicted mutations using in-house text mining scripts.

Detecting a Genomic Variation in the DNA Fraction

Applicable method to perform detecting a genomic variation of the nuclear and/or mitochondrial genome by performing a genetic analysis of the solubilized DNA fraction; including methods to detect mitochondrial DNA variation or STR variation are identifiable by a skilled person, in an exemplary method to amplify mitochondrial control regions, PCR amplification was carried out with the following set of primers: F15975 and R16410m for HV1, F015 and R389 for HV2, F403 and R635 for HV3 in 50 ul reaction volumes with Q5 Hot Start High-Fidelity 2× Master Mix (New England Biolabs, Inc, Ipswich, MA, USA), containing 0.2 uM each forward and reverse primers and 5 ul genomic DNA. Amplification was carried out on a PTC-200 DNA Engine (MJ Research, Waltham, MA, USA) under the following conditions: 98° C. for 2 min; 15 cycles of 98° C. for 10 s, 56° C. for 30 s, 72° C. for 30 s; 25 cycles of 98° C. for 20 s, 56° C. for 30 s, 72° C. for 30 s+10 s/cycle; and a final extension at 72° C. for 2 min. PCR amplicons were gel purified on a 2.0% agarose gel using QIAquick Gel Extraction Kit (Qiagen Inc, Germantown, MD, USA) according to the manufacturer's instructions with the exception the DNA was eluted with 35 ul EB Buffer. Purified PCR amplicons were visualized via gel electrophoresis on 2.0% agarose and quantified using QuBit 2.0 Fluorometer (Thermo Fisher Scientific, Waltham, MA, USA). DNA sequencing was performed using a Big Dye Terminator v3.1 Cycle Sequencing Kit (Thermo Fisher Scientific, Waltham, MA, USA) with the following cycling conditions: 96° C. for 1 min; 30 cycles of 96° C. for 10 s, 50° C. for 5 s, 60° C. for 2 min. Sequencing reactions were analyzed on an ABI 3500 Genetic Analyzer (Applied Biosystems). Primers used for sequencing were the appropriate primers used during amplification. The results were analyzed and de novo assembled using Geneious R9.1.8 (Biomatters Ltd, Auckland, NZ). To ensure sequence data quality, each genomic DNA was amplified and sequenced in duplicate.

mtDNA variants were detected by alignment using Clustal multiple sequence alignment tool [62, 63]. mtDNA mutation database MitoMaster [63] was used in addition to confirm prior record of the observed mutations.

Combining the Detected Genetic Protein Variations and the Detected Genomic Variation to Provide the Marker Genetic Variation Applicable methods to perform combining the detected genetic protein variations and the detected genomic variation to provide the marker genetic variation database system of the biological sample, are identifiable by a skilled person. in an exemplary method Mutant genotypic frequencies available in mtDNA mutation database MitoMaster (Brandon 2009) and Ensembl [26] (www.ensembl.org/index.html) corresponding to the observed genetic variations in both peptides and mtDNA hyper-variable control regions were combined by calculating random match probabilities for each individual.

Comparing the Detected Genetic Protein Variation and/or the Detected Genomic Variation with a Marker Genetic Protein Variation and/or of a Marker Genomic Variation Applicable methods to perform comparing the detected genetic protein variation and/or the detected genomic variation with a marker genetic protein variation and/or of a marker genomic variation respectively from the marker genetic variation database system are identifiable by a skilled person.

Exemplary methods include a range of possibilities from simply taking the two comparisons as independent verification of identity match or exclusion between samples or it could include a combined statistical model that taken into account the appropriate statistical metrics (e.g. random match probability) of both the proteomic marker(s) and the genetic marker(s) to give an overall greater statistical measure.

Example 41: GVP Analysis for a Sample Tissue

Figure 31:
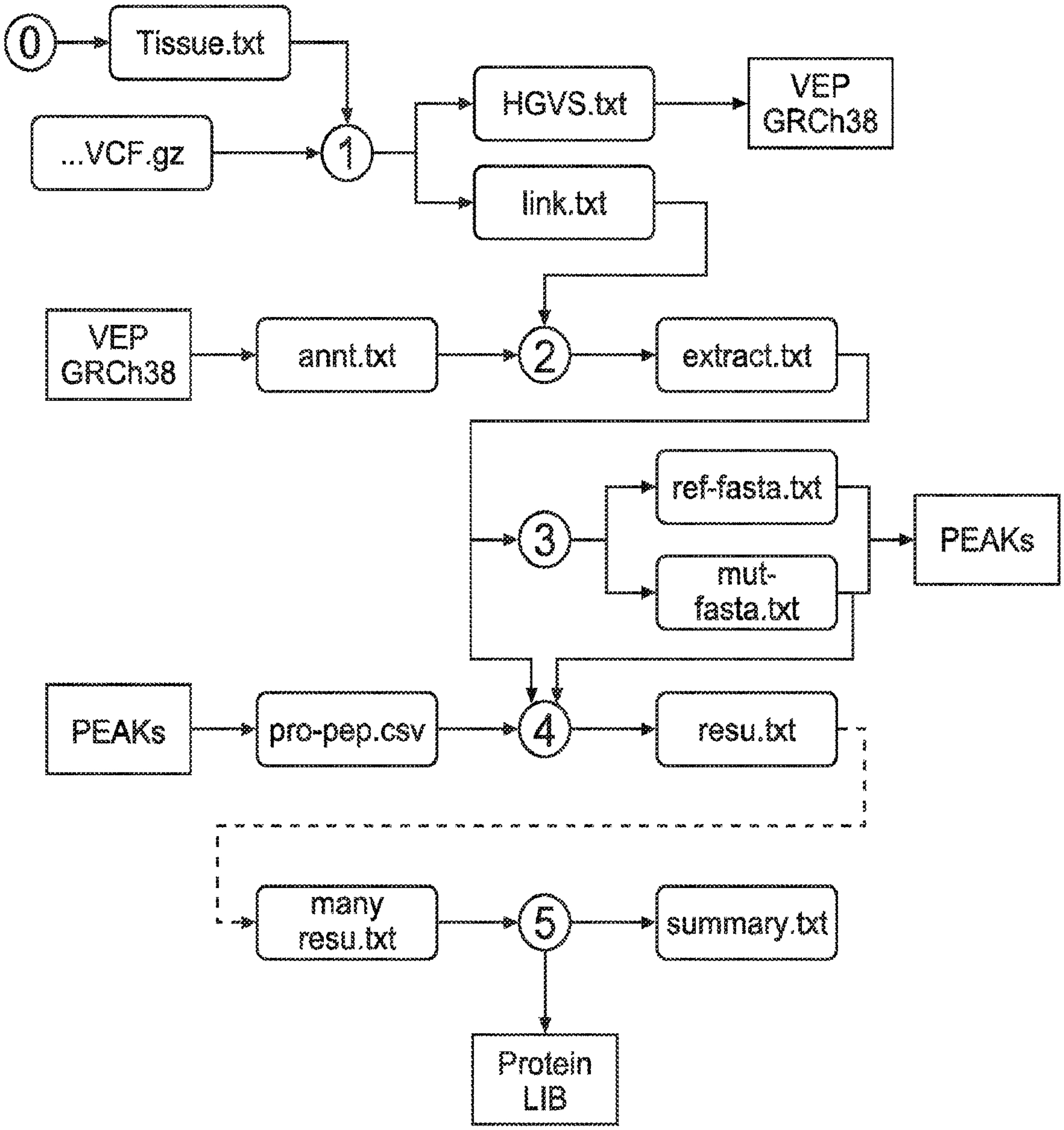

An example GVP analysis for a sample tissue can be broken down into the following parts, as shown in FIG. 31 and generally described as:

Part 0: Define a "tissue"—some set of genes to target

Part 1: Extract information of interest from Exome files and annotate under GRCh38

Part 2: Extract information of interest from annotated VCF, down select to preferred mutations, add supporting information Part 3: Mutate protein sequences and create FASTA files suitable for use with PEAKs Part 4: From PEAKs result, find "hits" peptides that carry programed-for mutations Part 5: Analyze "hits" Process steps 1-3 describe the data analysis process that is used to extract relevant genetic information from exome data and relating those to detectable proteins, thereby identifying genetic markers for potential detectable GVPs. Those process steps can be used to provide a proteomically detectable genomic variation in a set of represented genes proteomically detectable in the biological sample of the individual.

Applicable methods to perform providing a set of represented genes proteomically detectable in the biological sample of the individual, are identifiable by a skilled person upon reading of the instant disclosure, wherein the represented genes correspond to the proteomically detected proteins in the biological sample of the individual.

In an exemplary approach, for a single-hair approach herein described implements program PEAKS 7.5 (Bioinformatics Solutions Inc., Waterloo, Ontario, Canada) for variant peptide detection. A reference database created by translating polymorphisms (missense SNPs, insertions, deletions, and stops/gains) that influence protein sequences observed in exome results into mutated protein sequences are used for peptide identification within software parameters. Search settings include partial posttranslational modifications including oxidation of methionine, deamidation of asparagine and glutamine, and carbamidomethylation of cysteine. Precursor mass error of 30 ppm using monoisotopic mass was used for parent ion identifications and a 0.05 Da for fragment ions masses. Additionally, software program PEAKS 7.5 (Bioinformatics Solutions Inc., Waterloo, Ontario, Canada) protein identification software can be used to identify putative peptide variants using a specific capability called Spider [40] without using mutated reference databases. Another approach, outlined in [3] uses the Global Proteome Machine webserver (GPM; www.thegpm.org) to detect possible peptide variants.

In particular, process step 2 described the process to extract information of interest from exome results, down select to preferred mutations, add supporting information. This particular step filters the exome data to down select for proteins that we know we can see proteomically. This step can be used to perform selecting from the identified genetic variation, a genetic variation detectable in the sample of the biological organism.

Process step 4 describes the process for identifying peptides in proteomic data output from raw MS datafile analysis (e.g. using PEAKS, GPM or other commercial proteomic search tool) that contain mutations predicted by the exome data analysis performed in steps 1-2 (iiid above). This step can be used to perform providing the marker genetic protein variation validated by providing a proteomically detectable genetic protein variation corresponding to the proteomically detectable genomic variation in the biological sample of the individual.

Process step 5 describes combining results of hits identified in step 4 above, applying filters (e.g. peptide is only coded for by the identified gene). Results in a summary file that provides a pooled set of GVPs for a plurality of individuals. This step can be used to perform providing a number of proteomic datasets of individuals of the plurality of individuals, the number statistically significant for the plurality of individuals, including how to determine a statistically significant number of datasets.

Process step 5 also describes combining results of hits identified in step 4 above, applying filters (e.g. peptide is only coded for by the identified gene). Results in a summary file that provides a pooled set of GVPs for a plurality of individuals and includes information on commonality, allele frequency and any additional genetic or statistical information required. This step can be used to identify identifying a protein common to the provided number of proteomic datasets; including threshold and ranges of percentage of commonality of observed proteins.

Process step 5 further describes combining results of hits identified in 4 above, applying filters (e.g. peptide is only coded for by the identified gene). Results in a summary file that provides a pooled set of GVPs for a plurality of individuals and includes information on commonality, allele frequency and any additional genetic or statistical information required. This step can also be used to perform selecting from the identified protein common to the provided proteomic datasets, a protein detectable in the sample of the individuals of the plurality of individuals PART 0: Define a "Tissue"—Some Set of Genes to Target The tissue file (e.g. Tissue.txt) can be created by picking genes that appear frequently in a set of MS files as taken for a range of samples of a given tissue type (e.g. skin300g.txt, hair691g.txt, skhr838g.txt).

An example tissue file content is shown in Table 5. The required fields in this example are the standard gene symbol and CHR ("standard gene symbol" has an entrezID number, as in hg19 or hg38).

TABLE 5

Example tissue.txt

| PA | ENSG | Symbol | CHR | entrezID | Descr. | PA freq |
|---|---|---|---|---|---|---|
| Q9Y277 | ENSG00000078668 | VDAC3 | 8 | 7419 | Voltage-dependent anion channel 3 | 11 |
| P63167 | ENSG00000088986 | DYNLL1 | 12 | 8655 | Dynein light chain LC8-type 1 | 11 |
| Q9P0M6 | ENSG00000099284 | H2AFY2 | 10 | 55506 | H2A histone family member Y2 | 11 |

PART 1: Extract Information of Interest from Exome Files and Annotate Under GRCh38

Read-in list of target genes—tissue.txt.

Read-in VCF file—fname.svindeLvar.vcfgz (gzipped version).

Read meta data to confirm genomic coordinates (expecting 37d.5): e.g. VCF file L2_0051 reference is: hs37d5.fa.

Create TAB IX if none exist—fname.svindeLvar.vcfgz.tbi.

Subset VCF to target genes.

Extract all mutations in the subset VCF, clean-up formatting and data types. Carry through exome quality metrics for each entry.

Remove entries with filter of LowQual or "." (i.e. "to poor to call"). (See Table 6—note VQSR ranking).

TABLE 6

| Filter | Freq (L L2_51, hr691g) | Freq (L4_01BUC, skhr838g) |
|---|---|---|
| 99.90 to 100.00 | 44 | 102 |
| INDEL | 37 | 33 |
| INDEL, LowQual | 27 | 40 |
| LowQual | 266 | 263 |
| Pass | 3178 | 5398 |

Drop cases where ALT is a coma-delimited list. (See FIG. 39).

"Lift over" genomic coordinates from GRCh37 to GRCh38 (This example uses GRCh38.10).

Error check to confirm all SNPs collected conform to GRCh38, drop any deviants.

Summarize: L2_0051/hr691g—921 unique mutations processed.

Translate each surviving mutation into HGVS notation per varnomen.hgvs.org .

Write (no row names, no column names, one entry per row)—fname_tissue_hgvs.txt.

ZZ

18:g.46098362_46098363insACCCCC
18:g.63499047_63499048insTATATA
17:g.82081885_82081942del
. . .
8:g.143729168C>G
2:g.131218699G>C
21:g.44627940C>T Write companion file with linkage information for each mutation—fname_tissue_link.txt. The link file carries CHR, START, END, and rsID, which are not used beyond this point in the pipeline. (See FIG. 37).

Submit fname_tissue_hgvs.txt to ensembl Variant Effects Predictor (VEP) for GRCh38

PART 2: Extract Information of Interest from Annotated VCF, Down Select to Preferred Mutations, Add Supporting Information For the mutations submitted as L2_0051_hr691g_hgvs.txt , ensembl VEP replies are as shown in FIG. 32. (See www.ensembl.org/*Homo_sapiens*/Tools/VEP).

Recover the annotation results from VEP fname_tissue_annt.txt. The VEP annotation might contain all available G1000 and ExAC. AFs, SIFT, and Polyphen scores can be added. Note: as of Aug. 24, 2017 G1000 remains, but ExAC is replaced by gnomAD.

Figure 33:
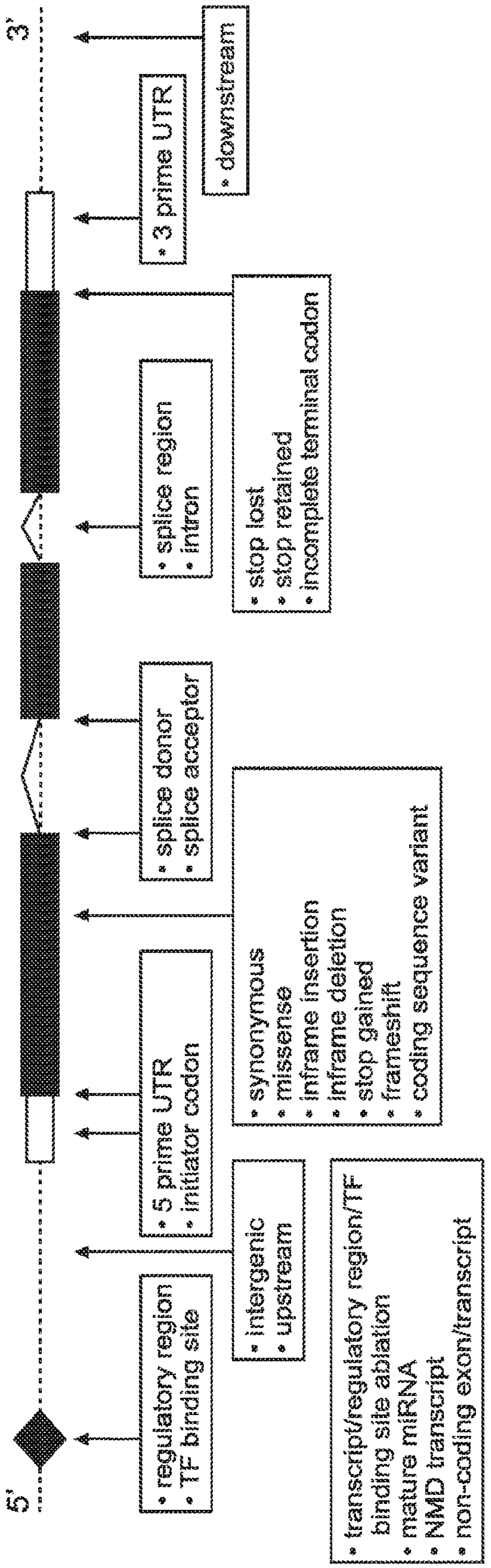

Read-in annotations. An example is shown in FIG. 33. (See www.ensembl.org/info/genome/variation/predicted_data.html).

Down-select to:

1) BIOTYPE=Protein_Coding
2) Consequence=frameshift, stop_gained_frameshift, inframe_deletion, inframe_insertion, missense, synonymous, missense_splice, splice_synonymous, stop_gained, stop_gained, splice, start_lost, protein_altering.

From bioMart add: Swissprot PA number (if not, then trEMBL PA number), APPRIS rank, ensembl external_transcript_name. Where an rsID is not returned, use a shortened version of HGVS call as the mutation "name" under dbSNP. Carry through G1000, G1000_EUR, ExAC, ExAC_NFE (as of Aug. 24, 2017, carry through gnomAD_AF and gnomAD_NFE_AF).

Read in link file fname_tissue_link.txt, add-on related REF, ALT, GATK and exome quality metrics. (see FIG. 36).

Summarize:

749 unique mutations by HGVS, 287 genes involved 2063 total mutations in all transcripts fraction 0.1177896 with GQ <max in L2_0051 (see Table 7)

TABLE 7

| Effect | Freq |
|---|---|
| Frameshift | 13 |
| inframe_deletion | 17 |
| inframe_insertion | 15 |
| Missense | 711 |
| missense, splice | 18 |
| splice, synonymous | 24 |
| start_lost | 2 |
| stop_gained | 3 |
| stop_gained, splice | 2 |
| synonymous | 1257 |

out of 749 unique mutations:

43 returned with no ExAC_NFE_MAF 42 returned with no ExAC_MAF 3 returned with ExAC_NFE_MAF=0

0 returned with ExAC_MAF=0

Write mutations to target—fname_tissue_extract.txt. Note:*extract.txt created to support workflows where *extract.txt from different exomes are combined into a *predicted*extract.txt. For example: Combine L4_0001 (P1) and L4_0002 (P2) to predict the child (L4_0003) as L4_0003_T1_p12xc_tissue_extract.txt for Triad1 parents predict child where child's exome is L4_0003.

PART 3: Mutate Protein Sequences and Create FASTA Files Suitable for Use with PEAKs Assumptions applied in GEN I mutations code:

Apply all mutations to one AA sequence (relaxed in GEN II code)

A frameshift is the end of useful information—treat the start of a frameshift as a stop-gained Treat two or three SNPs per codon as happening in the same strand and use the combination mutation Process all viable transcripts within a gene (use location and consequence per transcript), do not know which may be expressed.

"Base" protein sequence library in PEAKs is UniprotKB Swissprot (without isoforms)

PEAKs identifies a transcript by and passes-through the Accession|Entry_Name portion of the FASTA header:

Uniprot SwissProt header for KRT86

>sp|O43790|KRT86_HUMAN Keratin, type II cuticular Hb6 OS=*Homo sapiens* GN = KRT 86 PE = 1 SV = 1

(SEQ ID NO: 145)

MTCGSYCGGRAFSCISACGPRPGRCCITAAPYRGISCYRGLTGGFGSHSV

CGGFRAGSCGRSFGYRSGGVCGPSPPCITTV

The PA is 043790 (Uniprot is distinguished by: PA without appended -nnn and the Entry_Name carries "_species"). Uniprot Entry_Name may not be a standard gene name (e.g. for KRTAP1-1 Uniprot uses Entry_Name=KTP11).

From the GEN I mutations code

Entry_Name=standard gene name with "m" appended to indicate a mutated entry

Accession=PA-ensembl_transcript_name (to differentiate between different transcripts. PA alone is not enough: a given transcript can have multiple PA. A given PA can refer to transcripts in multiple genes.)

Within a gene, do not include duplicated mutated transcripts.

For mutated: Replace "description" with a list of mutations applied in transcript reference coordinates, append "h" for heterozygous ALL locations remain in transcripts reference coordinates, subsequent codes/analysis must unwind as needed GEN I header for a first transcript of KRT86—ENST00000293525

>sp|Q43790-201|KRT86m A321V 5del152 H560Kh OS=*Homo sapiens* GN=KRT86 PE=1 SV=1

>sp|Q43790-201|KRT86 dummy comment OS=*Homo sapiens* GN=KRT86 PE=1 SV=1

GEN I header for a second transcript of KRT86—ENST00000423955

>sp|Q43790-202|KRT86m A319V 5del152 H556Kh OS=*Homo sapiens* GN=KRT86 PE=1 SV=1

>sp|Q43790-2021KRT86 dummy comment OS=*Homo sapiens* GN=KRT86 PE=1 SV=1

Read in mutations to target—fname_tissue_extract.txt.

Convert all frameshifts to SNPs as X/*("*" indicates a stop and "X" indicates a wild-card in the AA sequence).

Detect multiple SNPs/codon events and compute change from combination, update mutations list.

Subset to genes that are mutated (i.e. drop genes that carry only synonymous mutations).

From bioMart upload AA sequences for all transcripts that may be called on. Within a gene: de-duplicate for transcripts that have identical AA sequences. Drop any transcript that carries an X (i.e. a wild-card AA).

Process the AA sequence for each transcript remaining. Apply stops (stop-gained and frameshifts) and trim AA sequence to length. Apply remaining SNPs that are in-range. Apply INDELs that are in range, process from tail-to-snout (as INDELs will accordion the sequence).

Generate FASTA headers for mutant and reference sequences.

Write: mutated AA sequences in FASTA format—fname_tissue_mutant_fasta.txt—and reference AA sequences in FASTA format—fname_tissue_ref_fasta.txt.

Submit for PEAKs analysis: use combination of "Base" protein list and mutant/ref FASTA.

PART 4: From PEAKs Result, Find Peptides that Carry Programed—For Mutations

Read-in PEAKs output (fname_tissueprotein-peptides.csv) and down-select to columns of interest (see FIG. 34).

Extract peptide sequence (remove PTMs and any lead/tail AA) e.g. R.TSC(+57.02)SSRPC(+57.02)V.P becomes TSCSSRPCV (SEQ ID NO. 127).

Separate PA and symbol, replace any UniprotKB Entry_Name with the standard gene name (e.g. replace KTP11 with KRTAP1-1).

Down select to those Protein Groups that carry a called-unique peptide assigned to a mutated transcript, and where the Peptide Group contains only the one mutated gene (may be a combination of mutated, reference and base transcripts from the one gene). Meaning of Unique in PEAKs output: The peptide (sans PTM) was detected uniquely within the present analysis. Such a called-unique peptide can be assigned to more than one transcript and/or gene. Each called-unique peptide is assigned to one Protein Group. There may be more than one called-unique peptide in a Protein Group. There may be more the one gene in a Protein Group. Filter by gene since Uniprot Entry_Name may not be a valid gene symbol for purposes of this example.

Read-in mutated FASTAfname_tissue_mutant_fasta.txt. Within each transcript (mutant FASTA entry) and for the selected Protein Groups:

- Unwind mutations into transcript coordinates (snout-to-tail to account for action of any INDELs) and
- Find those peptides that contain a programmed-for mutation.

Read-in fname_tissue_extract.txt . For "hits" (i.e. a programmed-for mutation found in a called-unique peptide) update entry with information about the mutation (e.g. dbSNP, AF' s, etc.).

Write out documented hits (group, peptide w/wo PTMs, MS meta data, mutation, AFs, GATK . . . )—fname_tissue_resu.txt.

PART 5: Hits Analysis

Read in hits results across a sample family—L4_0001_hair691g_resu.txt through L4_0063_hair691g_resu.txt (say)

Determine which peptides that carry the hits are unique within some test protein set:

- Write a list of peptides (sans PTM) L4_peptide_summary.txt,
- submit list of peptides to BLASTp or some other in-house- or web-tool to search for matches within the test protein set,
- test protein set—UniprotKB(Swissprot+isoforms and trEMBL)_HUMAN (about 172,164 protein sequences), and
- recover the results and indicate those peptides that are "no match" (i.e. the mutated peptide is not found in the test protein set).

Write—L4_resu_summary.txt (symbol, dbSNP, peptide sans PTM, no match, MS meta data, mutation meta data, AFs, GATK, file tag . . . )

Write—L4_resu_exec_summary.txt (symbol, dbSNP, no match in dnSNP, AFs, all file tags carrying this mutation) (see FIG. 35).

Supporting Tools

- Create a tissue set—
- read in a collection of PEAKs files
- convert Accession and Entry-Name to a proper symbol name
- tabulate frequency of occurrence of symbols through the file set
- Use bioMart to validate and add other information
- Output to tissue_number_genes.txt : symbol, entrezID, ENSG, gene description and frequency of observation
- Retention time analysis/prediction—
- read in a PEAKs file
- Apply Gilar's peptide retention model, treat PTMs as different AAs, to provide
- a multi-parameter linear regression model
- an optimized multi-parameter SVM model
- identify substantial outliers as possibly mis-identified in the MS/PEAKs analysis
- test for applicability against other PEAKs files
- Exclusion list—
- read in a collection of PEAKs files
- through the whole set collect the M/Z for all called-unique entries
- through the whole set collect the M/Z for all not-called-unique entries where the peak area is greater than some cut-off
- Round-off all carried M/Z (as given to 4 places) to 2 places
- Select those not-called-unique with M/Z that do not compete with the called-unique M/Z
- Output a table with two columns: a name (e.g. X100000#) and the selected M/Z to 2 places.

Example 42: GVP Analysis for a Sample Tissue

An example GVP analysis for a sample tissue can also be broken down into the following parts, generally described as:

- Part 0: Define a "tissue"—some set of genes to target
- Part 1: Extract information of interest from Exome files, possibly phase the exome using a computational tool (e.g. WhatsHAP) or method (e.g. pedigree phasing) or combination thereof as is known in the arts, and annotate under GRCh38
- Part 2: Extract information of interest from annotated VCF, down select to preferred mutations, add supporting information (e.g. allele and/or population frequencies from a data base such as gnomAD)
- Part 3: Mutate protein sequences and create FASTA files suitable for use with PEAKs
- Part 4: From PEAKs result, find "hits" peptides that carry programed-for mutations
- Part 5: Analyze "hits" to determine if reference hits are unique (i.e. related to one genomic location within a defined set of transcripts associated with a species e.g. ensembl human) and if mutated hits are novel (i.e. not found within a defined set of transcripts associated with a species e.g. ensembl human).

Parts 1 to 5 of the present example can be performed with methods similar to the ones indicated in Example 41 modified in view of the indications provided in the present example as will be understood by a skilled person upon reading of the present disclosure.

Example 43: Exemplary Genes Comprising Marker Exome Sequences Validated in Hair Type Samples An exemplary set of genes that can be used in methods and systems herein described as well as in related databases is reported herein. In particular, the exemplary set of genes comprises genes validated as proteomically detectable in hair samples of *Homo Sapiens* which can be used in methods and systems to detect a genetic variation and/or perform a genetic variation analysis where the biological organism is a human being, as well as in related databases, in accordance with the various aspects of the present disclosure.

Specifically, Table 8 shows a list of exemplary genes that appear in MS files taken for samples of a hair of a human being. The fields in this example indicate the preference (X=more preferred), the standard gene symbol (gene symbol), the chromosome where the gene is located (chr), a description of the gene (gene description) and the gene identifier in the database Ensembl at the date of filing of the instant disclosure (Ensembl Gene Identifier).

The exemplary genes of Table 8 can therefore be used in methods and systems of the disclosure wherein the sample comprises an hair sample from human beings,

TABLE 8

Exemplary genes identified in mass spectrometric analysis from hair type samples

| X = more preferable | gene symbol | chr | gene description | Ensembl gene identifier |
|---|---|---|---|---|
| | VDAC3 | 8 | voltage dependent anion channel 3 | ENSG00000078668 |
| | DYNLL1 | 12 | dynein light chain LC8-type 1 | ENSG00000088986 |
| | H2AFY2 | 10 | H2A histone family member Y2 | ENSG00000099284 |
| | SNU13 | 22 | SNU13 homolog, small nuclear ribonucleoprotein (U4/U6.U5) | ENSG00000100138 |
| | AHCY | 20 | adenosylhomocysteinase | ENSG00000101444 |
| | FBL | 19 | fibrillarin | ENSG00000105202 |
| | MYL12B | 18 | myosin light chain 12B | ENSG00000118680 |
| | EPHX2 | 8 | epoxide hydrolase 2 | ENSG00000120915 |
| | RPS10 | 6 | ribosomal protein S10 | ENSG00000124614 |
| | BMP2 | 20 | bone morphogenetic protein 2 | ENSG00000125845 |
| | SNRPN | 15 | small nuclear ribonucleoprotein polypeptide N | ENSG00000128739 |
| | AFDN | 6 | afadin, adherens junction formation factor | ENSG00000130396 |
| | PRPH | 12 | peripherin | ENSG00000135406 |
| | COX5B | 2 | cytochrome c oxidase subunit 5B | ENSG00000135940 |
| | ACTR2 | 2 | ARP2 actin related protein 2 homolog | ENSG00000138071 |
| | CSTB | 21 | cystatin B | ENSG00000160213 |
| | HIST1H2AA | 6 | histone cluster 1 H2A family member a | ENSG00000164508 |
| | KLK6 | 19 | kallikrein related peptidase 6 | ENSG00000167755 |
| | DYNLRB2 | 16 | dynein light chain roadblock-type 2 | ENSG00000168589 |
| | RAB1B | 11 | RAB1B, member RAS oncogene family | ENSG00000174903 |
| | GBA | 1 | glucosylceramidase beta | ENSG00000177628 |
| | RCC1 | 1 | regulator of chromosome condensation 1 | ENSG00000180198 |
| | RUVBL2 | 19 | RuvB like AAA ATPase 2 | ENSG00000183207 |
| | TMED9 | 5 | transmembrane p24 trafficking protein 9 | ENSG00000184840 |
| | KRT77 | 12 | keratin 77 | ENSG00000189182 |
| | ANXA4 | 2 | annexin A4 | ENSG00000196975 |
| | FAM49A | 2 | family with sequence similarity 49 member A | ENSG00000197872 |
| | KRTAP4-1 | 17 | keratin associated protein 4-1 | ENSG00000198443 |
| | PRR9 | 1 | proline rich 9 | ENSG00000203783 |
| | FIS1 | 7 | fission, mitochondrial 1 | ENSG00000214253 |
| | KRTAP10-9 | 21 | keratin associated protein 10-9 | ENSG00000221837 |
| | KRTAP10-10 | 21 | keratin associated protein 10-10 | ENSG00000221859 |
| | ARPC4 | 3 | actin related protein 2/3 complex subunit 4 | ENSG00000241553 |
| | EIF6 | 20 | eukaryotic translation initiation factor 6 | ENSG00000242372 |
| | EIF5AL1 | 10 | eukaryotic translation initiation factor 5A-like 1 | ENSG00000253626 |
| | RNASET2 | 6 | ribonuclease T2 | ENSG00000026297 |
| | ALDH3A2 | 17 | aldehyde dehydrogenase 3 family member A2 | ENSG00000072210 |
| | EIF3I | 1 | eukaryotic translation initiation factor 3 subunit I | ENSG00000084623 |
| | HNRNPC | 14 | heterogeneous nuclear ribonucleoprotein C (C1/C2) | ENSG00000092199 |
| | CRAT | 9 | carnitine O-acetyltransferase | ENSG00000095321 |
| | NUTF2 | 16 | nuclear transport factor 2 | ENSG00000102898 |
| | ECH1 | 19 | enoyl-CoA hydratase 1 | ENSG00000104823 |
| | ENDOU | 12 | endonuclease, poly(U) specific | ENSG00000111405 |
| | KHDRBS1 | 1 | KH RNA binding domain containing, signal transduction associated 1 | ENSG00000121774 |
| | DYNLRB1 | 20 | dynein light chain roadblock-type 1 | ENSG00000125971 |
| | NDUFA2 | 5 | NADH:ubiquinone oxidoreductase subunit A2 | ENSG00000131495 |
| | EDEM1 | 3 | ER degradation enhancing alpha-mannosidase like protein 1 | ENSG00000134109 |
| | NARS | 18 | asparaginyl-tRNA synthetase | ENSG00000134440 |
| | RPS6 | 9 | ribosomal protein S6 | ENSG00000137154 |
| | HNRNPA1L2 | 13 | heterogeneous nuclear ribonucleoprotein A1-like 2 | ENSG00000139675 |
| | PKLR | 1 | pyruvate kinase, liver and RBC | ENSG00000143627 |
| | ARL8A | 1 | ADP ribosylation factor like GTPase 8A | ENSG00000143862 |
| | ZNF462 | 9 | zinc finger protein 462 | ENSG00000148143 |
| | PRSS53 | 16 | protease, serine 53 | ENSG00000151006 |
| | CXADR | 21 | coxsackie virus and adenovirus receptor | ENSG00000154639 |
| | CBR1 | 21 | carbonyl reductase 1 | ENSG00000159228 |
| | PSMB4 | 1 | proteasome subunit beta 4 | ENSG00000159377 |
| | C21orf33 | 21 | chromosome 21 open reading frame 33 | ENSG00000160221 |
| | PGAM2 | 7 | phosphoglycerate mutase 2 | ENSG00000164708 |
| | LMAN2 | 5 | lectin, mannose binding 2 | ENSG00000169223 |
| | GNB2 | 7 | G protein subunit beta 2 | ENSG00000172354 |

TABLE 8-continued

| X = more preferable | gene symbol | chr | gene description | Ensembl gene identifier |
|---|---|---|---|---|
| Exemplary genes identified in mass spectrometric analysis from hair type samples | | | | |
| | MYL6B | 12 | myosin light chain 6B | ENSG00000196465 |
| | PSAP | 10 | prosaposin | ENSG00000197746 |
| | DDX39B | 6 | DExD-box helicase 39B | ENSG00000198563 |
| | RACK1 | 5 | receptor for activated C kinase 1 | ENSG00000204628 |
| | TUBB8 | 10 | tubulin beta 8 class VIII | ENSG00000261456 |
| | RPS10-NUDT3 | 6 | RPS10-NUDT3 readthrough | ENSG00000270800 |
| | PRSS3 | 9 | protease, serine 3 | ENSG00000010438 |
| | SARS | 1 | seryl-tRNA synthetase | ENSG00000031698 |
| | PSMC5 | 17 | proteasome 26S subunit, ATPase 5 | ENSG00000087191 |
| | HNRNPM | 19 | heterogeneous nuclear ribonucleoprotein M | ENSG00000099783 |
| | PABPC1L | 20 | poly(A) binding protein cytoplasmic 1 like | ENSG00000101104 |
| | PGRMC1 | X | progesterone receptor membrane component 1 | ENSG00000101856 |
| | NUP93 | 16 | nucleoporin 93 | ENSG00000102900 |
| | GPRC5D | 12 | G protein-coupled receptor class C group 5 member D | ENSG00000111291 |
| | PTK7 | 6 | protein tyrosine kinase 7 (inactive) | ENSG00000112655 |
| | GLO1 | 6 | glyoxalase I | ENSG00000124767 |
| | RPL23 | 17 | ribosomal protein L23 | ENSG00000125691 |
| | TUBB2B | 6 | tubulin beta 2B class IIb | ENSG00000137285 |
| | PPP2R1B | 11 | protein phosphatase 2 scaffold subunit Abeta | ENSG00000137713 |
| | SLC40A1 | 2 | solute carrier family 40 member 1 | ENSG00000138449 |
| | ARHGDIA | 17 | Rho GDP dissociation inhibitor alpha | ENSG00000141522 |
| | RPS11 | 19 | ribosomal protein S11 | ENSG00000142534 |
| | RPL7A | 9 | ribosomal protein L7a | ENSG00000148303 |
| | RPS3 | 11 | ribosomal protein S3 | ENSG00000149273 |
| | DBI | 2 | diazepam binding inhibitor, acyl-CoA binding protein | ENSG00000155368 |
| | PDCD6IP | 3 | programmed cell death 6 interacting protein | ENSG00000170248 |
| | YOD1 | 1 | YOD1 deubiquitinase | ENSG00000180667 |
| | SHMT2 | 12 | serine hydroxymethyltransferase 2 | ENSG00000182199 |
| | NDUFA13 | 19 | NADH:ubiquinone oxidoreductase subunit A13 | ENSG00000186010 |
| | HIST1H1T | 6 | histone cluster 1 H1 family member t | ENSG00000187475 |
| | PCBP2 | 12 | poly(rC) binding protein 2 | ENSG00000197111 |
| | SIRPA | 20 | signal regulatory protein alpha | ENSG00000198053 |
| | RNF39 | 6 | ring finger protein 39 | ENSG00000204618 |
| | CTC-260F20.3 | 19 | | ENSG00000258674 |
| | KRTAP10-7 | 21 | keratin associated protein 10-7 | ENSG00000272804 |
| | CH507-9B2.4 | 21 | | ENSG00000276612 |
| | CH507-9B2.3 | 21 | | ENSG00000280071 |
| | ARSF | X | arylsulfatase F | ENSG00000062096 |
| | GNB1 | 1 | G protein subunit beta 1 | ENSG00000078369 |
| | KHSRP | 19 | KH-type splicing regulatory protein | ENSG00000088247 |
| | RPLP0 | 12 | ribosomal protein lateral stalk subunit P0 | ENSG00000089157 |
| | PABPC4 | 1 | poly(A) binding protein cytoplasmic 4 | ENSG00000090621 |
| | EZR | 6 | ezrin | ENSG00000092820 |
| | AP1B1 | 22 | adaptor related protein complex 1 beta 1 subunit | ENSG00000100280 |
| | PSMC6 | 14 | proteasome 26S subunit, ATPase 6 | ENSG00000100519 |
| | PSMD7 | 16 | proteasome 26S subunit, non-ATPase 7 | ENSG00000103035 |
| | MYH14 | 19 | myosin heavy chain 14 | ENSG00000105357 |
| | PSMA1 | 11 | proteasome subunit alpha 1 | ENSG00000129084 |
| | FBP2 | 9 | fructose-bisphosphatase 2 | ENSG00000130957 |
| | TPT1 | 13 | tumor protein, translationally-controlled 1 | ENSG00000133112 |
| | ATIC | 2 | 5-aminoimidazole-4-carboxamide ribonucleotide formyltransferase/IMP cyclohydrolase | ENSG00000138363 |
| | RPS2 | 16 | ribosomal protein S2 | ENSG00000140988 |
| | CSNK1D | 17 | casein kinase 1 delta | ENSG00000141551 |
| | SH3BGRL3 | 1 | SH3 domain binding glutamate rich protein like 3 | ENSG00000142669 |
| | SPINT1 | 15 | serine peptidase inhibitor, Kunitz type 1 | ENSG00000166145 |
| | PGK2 | 6 | phosphoglycerate kinase 2 | ENSG00000170950 |
| | KRT27 | 17 | keratin 27 | ENSG00000171446 |
| | EIF2S3L | 12 | Putative eukaryotic translation initiation factor 2 subunit 3-like protein | ENSG00000180574 |
| | CAPN12 | 19 | calpain 12 | ENSG00000182472 |
| | KRT73 | 12 | keratin 73 | ENSG00000186049 |
| | PTRH1 | 9 | peptidyl-tRNA hydrolase 1 homolog | ENSG00000187024 |
| | KRTAP10-6 | 21 | keratin associated protein 10-6 | ENSG00000188155 |
| | XRCC6 | 22 | X-ray repair cross complementing 6 | ENSG00000196419 |
| | DYNC1H1 | 14 | dynein cytoplasmic 1 heavy chain 1 | ENSG00000197102 |
| | SERPINB13 | 18 | serpin family B member 13 | ENSG00000197641 |
| | RPL10A | 6 | ribosomal protein L10a | ENSG00000198755 |
| | ASPRV1 | 2 | aspartic peptidase, retroviral-like 1 | ENSG00000244617 |
| | RP1-5O6.7 | 22 | Casein kinase I isoform epsilon | ENSG00000283900 |

TABLE 8-continued

| Exemplary genes identified in mass spectrometric analysis from hair type samples | | | | |
|---|---|---|---|---|
| X = more preferable | gene symbol | chr | gene description | Ensembl gene identifier |
| | CAPG | 2 | capping actin protein, gelsolin like | ENSG00000042493 |
| | TUBA3D | 2 | tubulin alpha 3d | ENSG00000075886 |
| | BCORL1 | X | BCL6 corepressor-like 1 | ENSG00000085185 |
| | FH | 1 | fumarate hydratase | ENSG00000091483 |
| | ACOT7 | 1 | acyl-CoA thioesterase 7 | ENSG00000097021 |
| | SRSF3 | 6 | serine and arginine rich splicing factor 3 | ENSG00000112081 |
| | TRIM25 | 17 | tripartite motif containing 25 | ENSG00000121060 |
| | PSMF1 | 20 | proteasome inhibitor subunit 1 | ENSG00000125818 |
| | ASS1 | 9 | argininosuccinate synthase 1 | ENSG00000130707 |
| | EIF5A | 17 | eukaryotic translation initiation factor 5A | ENSG00000132507 |
| | EPRS | 1 | glutamyl-prolyl-tRNA synthetase | ENSG00000136628 |
| | GRHPR | 9 | glyoxylate and hydroxypyruvate reductase | ENSG00000137106 |
| | WARS | 14 | tryptophanyl-tRNA synthetase | ENSG00000140105 |
| | UQCRC2 | 16 | ubiquinol-cytochrome c reductase core protein II | ENSG00000140740 |
| | RPL11 | 1 | ribosomal protein L11 | ENSG00000142676 |
| | PSMA5 | 1 | proteasome subunit alpha 5 | ENSG00000143106 |
| | RPS3A | 4 | ribosomal protein S3A | ENSG00000145425 |
| | RPS14 | 5 | ribosomal protein S14 | ENSG00000164587 |
| | TPSAB1 | 16 | tryptase alpha/beta 1 | ENSG00000172236 |
| | DES | 2 | desmin | ENSG00000175084 |
| | IDH2 | 15 | isocitrate dehydrogenase (NADP(+)) 2, mitochondrial | ENSG00000182054 |
| | TPSB2 | 16 | tryptase beta 2 (gene/pseudogene) | ENSG00000197253 |
| | TUBA3C | 13 | tubulin alpha 3c | ENSG00000198033 |
| | UBA52 | 19 | ubiquitin A-52 residue ribosomal protein fusion product 1 | ENSG00000221983 |
| | TOLLIP | 11 | toll interacting protein | ENSG00000078902 |
| | ERMP1 | 9 | endoplasmic reticulum metallopeptidase 1 | ENSG00000099219 |
| | ABCD1 | X | ATP binding cassette subfamily D member 1 | ENSG00000101986 |
| | PPP2CB | 8 | protein phosphatase 2 catalytic subunit beta | ENSG00000104695 |
| | MTCH2 | 11 | mitochondrial carrier 2 | ENSG00000109919 |
| | PPP2CA | 5 | protein phosphatase 2 catalytic subunit alpha | ENSG00000113575 |
| | STX12 | 1 | syntaxin 12 | ENSG00000117758 |
| | LAMTOR5 | 1 | late endosomal/lysosomal adaptor, MAPK and MTOR activator 5 | ENSG00000134248 |
| | CKAP4 | 12 | cytoskeleton associated protein 4 | ENSG00000136026 |
| | RPS8 | 1 | ribosomal protein S8 | ENSG00000142937 |
| | COX6C | 8 | cytochrome c oxidase subunit 6C | ENSG00000164919 |
| | TPP1 | 11 | tripeptidyl peptidase 1 | ENSG00000166340 |
| | RPS21 | 20 | ribosomal protein S21 | ENSG00000171858 |
| | HECTD4 | 12 | HECT domain E3 ubiquitin protein ligase 4 | ENSG00000173064 |
| | PSMD2 | 3 | proteasome 26S subunit, non-ATPase 2 | ENSG00000175166 |
| | TALDO1 | 11 | transaldolase 1 | ENSG00000177156 |
| | PDE4DIP | 1 | phosphodiesterase 4D interacting protein | ENSG00000178104 |
| | TUBA8 | 22 | tubulin alpha 8 | ENSG00000183785 |
| | HIST2H2AB | 1 | histone cluster 2 H2A family member b | ENSG00000184270 |
| | TACSTD2 | 1 | tumor-associated calcium signal transducer 2 | ENSG00000184292 |
| | EIF3CL | 16 | eukaryotic translation initiation factor 3 subunit C-like | ENSG00000205609 |
| | RP11-295K3.1 | 11 | | ENSG00000250644 |
| | ATP6V0A1 | 17 | ATPase H+ transporting V0 subunit a1 | ENSG00000033627 |
| | RPL18 | 19 | ribosomal protein L18 | ENSG00000063177 |
| | WNT3 | 17 | Wnt family member 3 | ENSG00000108379 |
| | PRDX4 | X | peroxiredoxin 4 | ENSG00000123131 |
| | KIAA0368 | 9 | KIAA0368 | ENSG00000136813 |
| | ATP6V1G1 | 9 | ATPase H+ transporting V1 subunit G1 | ENSG00000136888 |
| | KRT71 | 12 | keratin 71 | ENSG00000139648 |
| | EIF4A3 | 17 | eukaryotic translation initiation factor 4A3 | ENSG00000141543 |
| | RBMX | X | RNA binding motif protein, X-linked | ENSG00000147274 |
| | H2AFZ | 4 | H2A histone family member Z | ENSG00000164032 |
| | CTSB | 8 | cathepsin B | ENSG00000164733 |
| | PDHB | 3 | pyruvate dehydrogenase (lipoamide) beta | ENSG00000168291 |
| | GLTPD2 | 17 | glycolipid transfer protein domain containing 2 | ENSG00000182327 |
| | KRTAP9-8 | 17 | keratin associated protein 9-8 | ENSG00000187272 |
| | APRT | 16 | adenine phosphoribosyltransferase | ENSG00000198931 |
| | RPS18 | 6 | ribosomal protein S18 | ENSG00000231500 |
| | HAGH | 16 | hydroxyacylglutathione hydrolase | ENSG00000063854 |
| | ME1 | 6 | malic enzyme 1 | ENSG00000065833 |
| | TUBB4A | 19 | tubulin beta 4A class IVa | ENSG00000104833 |
| | GAPDHS | 19 | glyceraldehyde-3-phosphate dehydrogenase, spermatogenic | ENSG00000105679 |
| | HIP1R | 12 | huntingtin interacting protein 1 related | ENSG00000130787 |
| | RPL8 | 8 | ribosomal protein L8 | ENSG00000161016 |
| | DCD | 12 | dermcidin | ENSG00000161634 |

TABLE 8-continued

Exemplary genes identified in mass spectrometric analysis from hair type samples

| X = more preferable | gene symbol | chr | gene description | Ensembl gene identifier |
|---|---|---|---|---|
| | HSP90B1 | 12 | heat shock protein 90 beta family member 1 | ENSG00000166598 |
| | PA2G4 | 12 | proliferation-associated 2G4 | ENSG00000170515 |
| | IMPDH2 | 3 | inosine monophosphate dehydrogenase 2 | ENSG00000178035 |
| | FAHD1 | 16 | fumarylacetoacetate hydrolase domain containing 1 | ENSG00000180185 |
| | EIF3C | 16 | eukaryotic translation initiation factor 3 subunit C | ENSG00000184110 |
| | H2AFX | 11 | H2A histone family member X | ENSG00000188486 |
| | AP2A1 | 19 | adaptor related protein complex 2 alpha 1 subunit | ENSG00000196961 |
| | KRT25 | 17 | keratin 25 | ENSG00000204897 |
| | NAV3 | 12 | neuron navigator 3 | ENSG00000067798 |
| | RTCB | 22 | RNA 2',3'-cyclic phosphate and 5'-OH ligase | ENSG00000100220 |
| | H2AFV | 7 | H2A histone family member V | ENSG00000105968 |
| | EIF3A | 10 | eukaryotic translation initiation factor 3 subunit A | ENSG00000107581 |
| | METAP2 | 12 | methionyl aminopeptidase 2 | ENSG00000111142 |
| | RTN4 | 2 | reticulon 4 | ENSG00000115310 |
| | EFHD1 | 2 | EF-hand domain family member D1 | ENSG00000115468 |
| | ATP6V1B1 | 2 | ATPase H+ transporting V1 subunit B1 | ENSG00000116039 |
| | YPEL5 | 2 | yippee like 5 | ENSG00000119801 |
| | PCMT1 | 6 | protein-L-isoaspartate (D-aspartate) O-methyltransferase | ENSG00000120265 |
| | ACLY | 17 | ATP citrate lyase | ENSG00000131473 |
| | RAN | 12 | RAN, member RAS oncogene family | ENSG00000132341 |
| | HNRNPD | 4 | heterogeneous nuclear ribonucleoprotein D | ENSG00000138668 |
| | PSMB6 | 17 | proteasome subunit beta 6 | ENSG00000142507 |
| | RPL7 | 8 | ribosomal protein L7 | ENSG00000147604 |
| | KRT24 | 17 | keratin 24 | ENSG00000167916 |
| | CHTF8 | 16 | chromosome transmission fidelity factor 8 | ENSG00000168802 |
| | CAPZA2 | 7 | capping actin protein of muscle Z-line alpha subunit 2 | ENSG00000198898 |
| | AK2 | 1 | adenylate kinase 2 | ENSG00000004455 |
| | RPS20 | 8 | ribosomal protein S20 | ENSG00000008988 |
| | PITHD1 | 1 | PITH domain containing 1 | ENSG00000057757 |
| | RPL6 | 12 | ribosomal protein L6 | ENSG00000089009 |
| | MLF2 | 12 | myeloid leukemia factor 2 | ENSG00000089693 |
| | DNAJB6 | 7 | DnaJ heat shock protein family (Hsp40) member B6 | ENSG00000105993 |
| | AJUBA | 14 | ajuba LIM protein | ENSG00000129474 |
| | ATP6V1E1 | 22 | ATPase H+ transporting V1 subunit E1 | ENSG00000131100 |
| | COX4I1 | 16 | cytochrome c oxidase subunit 4I1 | ENSG00000131143 |
| | TXN | 9 | thioredoxin | ENSG00000136810 |
| | NONO | X | non-POU domain containing, octamer-binding | ENSG00000147140 |
| | ATP5H | 17 | ATP synthase, H+ transporting, mitochondrial Fo complex subunit D | ENSG00000167863 |
| | HIST3H3 | 1 | histone cluster 3 H3 | ENSG00000168148 |
| | ATP5I | 4 | ATP synthase, H+ transporting, mitochondrial Fo complex subunit E | ENSG00000169020 |
| | KRT9 | 17 | keratin 9 | ENSG00000171403 |
| | NCCRP1 | 19 | non-specific cytotoxic cell receptor protein 1 homolog (zebrafish) | ENSG00000188505 |
| | POTEJ | 2 | POTE ankyrin domain family member J | ENSG00000222038 |
| | AP000304.12 | 21 | | ENSG00000249209 |
| | SRI | 7 | sorcin | ENSG00000075142 |
| | ETFB | 19 | electron transfer flavoprotein beta subunit | ENSG00000105379 |
| | ACTA2 | 10 | actin, alpha 2, smooth muscle, aorta | ENSG00000107796 |
| | DLST | 14 | dihydrolipoamide S-succinyltransferase | ENSG00000119689 |
| | RTN3 | 11 | reticulon 3 | ENSG00000133318 |
| | SPINK5 | 5 | serine peptidase inhibitor, Kazal type 5 | ENSG00000133710 |
| | RAC1 | 7 | ras-related C3 botulinum toxin substrate 1 (rho family, small GTP binding protein Rac1) | ENSG00000136238 |
| | ACTG2 | 2 | actin, gamma 2, smooth muscle, enteric | ENSG00000163017 |
| | RPN1 | 3 | ribophorin I | ENSG00000163902 |
| | CFL1 | 11 | cofilin 1 | ENSG00000172757 |
| | GDI1 | X | GDP dissociation inhibitor 1 | ENSG00000203879 |
| | KRTAP10-11 | 21 | keratin associated protein 10-11 | ENSG00000243489 |
| | HSP90AB1 | 6 | heat shock protein 90 alpha family class B member 1 | ENSG00000096384 |
| | ENO2 | 12 | enolase 2 | ENSG00000111674 |
| | LYPLA1 | 8 | lysophospholipase I | ENSG00000120992 |
| | ECHS1 | 10 | enoyl-CoA hydratase, short chain 1 | ENSG00000127884 |
| | CHAC1 | 15 | ChaC glutathione specific gamma-glutamylcyclotransferase 1 | ENSG00000128965 |
| | IL1F10 | 2 | interleukin 1 family member 10 (theta) | ENSG00000136697 |

TABLE 8-continued

| Exemplary genes identified in mass spectrometric analysis from hair type samples | | | | |
|---|---|---|---|---|
| X = more preferable | gene symbol | chr | gene description | Ensembl gene identifier |
| | PADI1 | 1 | peptidyl arginine deiminase 1 | ENSG00000142623 |
| | CALM2 | 2 | calmodulin 2 | ENSG00000143933 |
| | CALM3 | 19 | calmodulin 3 | ENSG00000160014 |
| | S100A9 | 1 | S100 calcium binding protein A9 | ENSG00000163220 |
| | TUBB6 | 18 | tubulin beta 6 class V | ENSG00000176014 |
| | CALM1 | 14 | calmodulin 1 | ENSG00000198668 |
| | RPS16 | 19 | ribosomal protein S16 | ENSG00000105193 |
| | TYRP1 | 9 | tyrosinase related protein 1 | ENSG00000107165 |
| | CAPZA1 | 1 | capping actin protein of muscle Z-line alpha subunit 1 | ENSG00000116489 |
| | RPL13 | 16 | ribosomal protein L13 | ENSG00000167526 |
| | HINT1 | 5 | histidine triad nucleotide binding protein 1 | ENSG00000169567 |
| | SDR16C5 | 8 | short chain dehydrogenase/reductase family 16C member 5 | ENSG00000170786 |
| | S100A16 | 1 | S100 calcium binding protein A16 | ENSG00000188643 |
| | PHB2 | 12 | prohibitin 2 | ENSG00000215021 |
| | ACTN1 | 14 | actinin alpha 1 | ENSG00000072110 |
| | FSCN1 | 7 | fascin actin-bundling protein 1 | ENSG00000075618 |
| | MYL6 | 12 | myosin light chain 6 | ENSG00000092841 |
| | PFN1 | 17 | profilin 1 | ENSG00000108518 |
| | CPEB4 | 5 | cytoplasmic poly adenylation element binding protein 4 | ENSG00000113742 |
| | ACTN4 | 19 | actinin alpha 4 | ENSG00000130402 |
| | EIF2S3 | X | eukaryotic translation initiation factor 2 subunit gamma | ENSG00000130741 |
| | NECTIN4 | 1 | nectin cell adhesion molecule 4 | ENSG00000143217 |
| | ACAA2 | 18 | acetyl-CoA acyltransferase 2 | ENSG00000167315 |
| | SEC24C | 10 | SEC24 homolog C, COPII coat complex component | ENSG00000176986 |
| | FCHSD1 | 5 | FCH and double SH3 domains 1 | ENSG00000197948 |
| | S100A6 | 1 | S100 calcium binding protein A6 | ENSG00000197956 |
| | CTNND1 | 11 | catenin delta 1 | ENSG00000198561 |
| | CTNNA2 | 2 | catenin alpha 2 | ENSG00000066032 |
| | ENO3 | 17 | enolase 3 | ENSG00000108515 |
| | IMMT | 2 | inner membrane mitochondrial protein | ENSG00000132305 |
| | EIF2S1 | 14 | eukaryotic translation initiation factor 2 subunit alpha | ENSG00000134001 |
| | PABPC3 | 13 | poly(A) binding protein cytoplasmic 3 | ENSG00000151846 |
| | G6PD | X | glucose-6-phosphate dehydrogenase | ENSG00000160211 |
| | KRT4 | 12 | keratin 4 | ENSG00000170477 |
| | RPL12 | 9 | ribosomal protein L12 | ENSG00000197958 |
| | PRSS1 | 7 | protease, serine 1 | ENSG00000204983 |
| | EPPK1 | 8 | epiplakin 1 | ENSG00000261150 |
| | ATP2B4 | 1 | ATPase plasma membrane Ca2+ transporting 4 | ENSG00000058668 |
| | CDC42 | 1 | cell division cycle 42 | ENSG00000070831 |
| | CAPZB | 1 | capping actin protein of muscle Z-line beta subunit | ENSG00000077549 |
| | CSNK1A1 | 5 | casein kinase 1 alpha 1 | ENSG00000113712 |
| | GOT1 | 10 | glutamic-oxaloacetic transaminase 1 | ENSG00000120053 |
| | PLB1 | 2 | phospholipase B1 | ENSG00000163803 |
| | METAP1 | 4 | methionyl aminopeptidase 1 | ENSG00000164024 |
| | SLC3A2 | 11 | solute carrier family 3 member 2 | ENSG00000168003 |
| | CSNK1E | 22 | casein kinase 1 epsilon | ENSG00000213923 |
| | PEBP1 | 12 | phosphatidylethanolamine binding protein 1 | ENSG00000089220 |
| | EEF1A2 | 20 | eukaryotic translation elongation factor 1 alpha 2 | ENSG00000101210 |
| | ILVBL | 19 | ilvB acetolactate synthase like | ENSG00000105135 |
| | KPNB1 | 17 | karyopherin subunit beta 1 | ENSG00000108424 |
| | PPIB | 15 | peptidylprolyl isomerase B | ENSG00000166794 |
| | KRT28 | 17 | keratin 28 | ENSG00000173908 |
| | KRTAP6-1 | 21 | keratin associated protein 6-1 | ENSG00000184724 |
| | RPS4X | X | ribosomal protein S4, X-linked | ENSG00000198034 |
| | MT-CO2 | MT | mitochondrially encoded cytochrome c oxidase II | ENSG00000198712 |
| | VCL | 10 | vinculin | ENSG00000035403 |
| | DLD | 7 | dihydrolipoamide dehydrogenase | ENSG00000091140 |
| | DDTL | 22 | D-dopachrome tautomerase-like | ENSG00000099974 |
| | TUBB1 | 20 | tubulin beta 1 class VI | ENSG00000101162 |
| | CPT1A | 11 | carnitine palmitoyltransferase 1A | ENSG00000110090 |
| | PGLS | 19 | 6-phosphogluconolactonase | ENSG00000130313 |
| | HADHB | 2 | hydroxyacyl-CoA dehydrogenase/3-ketoacyl-CoA thiolase/enoyl-CoA hydratase (trifunctional protein), beta subunit | ENSG00000138029 |
| | PPA2 | 4 | pyrophosphatase (inorganic) 2 | ENSG00000138777 |
| | TMED10 | 14 | transmembrane p24 trafficking protein 10 | ENSG00000170348 |

TABLE 8-continued

Exemplary genes identified in mass spectrometric analysis from hair type samples

| X = more preferable | gene symbol | chr | gene description | Ensembl gene identifier |
|---|---|---|---|---|
| | KRT72 | 12 | keratin 72 | ENSG00000170486 |
| | HIST1H2BL | 6 | histone cluster 1 H2B family member 1 | ENSG00000185130 |
| | KRTAP10-3 | 21 | keratin associated protein 10-3 | ENSG00000212935 |
| | PPP1CB | 2 | protein phosphatase 1 catalytic subunit beta | ENSG00000213639 |
| | ACPP | 3 | acid phosphatase, prostate | ENSG00000014257 |
| | RNH1 | 11 | ribonuclease/angiogenin inhibitor 1 | ENSG00000023191 |
| | SUN2 | 22 | Sad1 and UNC84 domain containing 2 | ENSG00000100242 |
| | CEP250 | 20 | centrosomal protein 250 | ENSG00000126001 |
| | DSG3 | 18 | desmoglein 3 | ENSG00000134757 |
| | HIST1H2BA | 6 | histone cluster 1 H2B family member a | ENSG00000146047 |
| | GJA1 | 6 | gap junction protein alpha 1 | ENSG00000152661 |
| | ATP5O | 21 | ATP synthase, H+ transporting, mitochondrial F1 complex, O subunit | ENSG00000241837 |
| | DDT | 22 | D-dopachrome tautomerase | ENSG00000099977 |
| | TARS | 5 | threonyl-tRNA synthetase | ENSG00000113407 |
| | CLTC | 17 | clathrin heavy chain | ENSG00000141367 |
| | ACOX1 | 17 | acyl-CoA oxidase 1 | ENSG00000161533 |
| | KRT6C | 12 | keratin 6C | ENSG00000170465 |
| | NIPSNAP1 | 22 | nipsnap homolog 1 | ENSG00000184117 |
| | POTEI | 2 | POTE ankyrin domain family member I | ENSG00000196834 |
| | RP4-777O23.3 | 7 | | ENSG00000281039 |
| | SLC25A5 | X | solute carrier family 25 member 5 | ENSG00000005022 |
| | PABPC1 | 8 | poly(A) binding protein cytoplasmic 1 | ENSG00000070756 |
| | CELSR1 | 22 | cadherin EGF LAG seven-pass G-type receptor 1 | ENSG00000075275 |
| | HNRNPH2 | X | heterogeneous nuclear ribonucleoprotein H2 | ENSG00000126945 |
| | CSRP1 | 1 | cysteine and glycine rich protein 1 | ENSG00000159176 |
| | FBP1 | 9 | fructose-bisphosphatase 1 | ENSG00000165140 |
| | UQCRFS1 | 19 | ubiquinol-cytochrome c reductase, Rieske iron-sulfur polypeptide 1 | ENSG00000169021 |
| | HIST2H2AC | 1 | histone cluster 2 H2A family member c | ENSG00000184260 |
| | P4HB | 17 | prolyl 4-hydroxylase subunit beta | ENSG00000185624 |
| | HIST1H2AD | 6 | histone cluster 1 H2A family member d | ENSG00000196866 |
| | VDAC1 | 5 | voltage dependent anion channel 1 | ENSG00000213585 |
| | NME1 | 17 | NME/NM23 nucleoside diphosphate kinase 1 | ENSG00000239672 |
| | HSPE1-MOB4 | 2 | HSPE1-MOB4 readthrough | ENSG00000270757 |
| | ACADVL | 17 | acyl-CoA dehydrogenase, very long chain | ENSG00000072778 |
| | PROCR | 20 | protein C receptor | ENSG00000101000 |
| | C1QBP | 17 | complement C1q binding protein | ENSG00000108561 |
| | CTSD | 11 | cathepsin D | ENSG00000117984 |
| | LDHA | 11 | lactate dehydrogenase A | ENSG00000134333 |
| | EIF4A2 | 3 | eukaryotic translation initiation factor 4A2 | ENSG00000156976 |
| | ENGASE | 17 | endo-beta-N-acetylglucosaminidase | ENSG00000167280 |
| | KRT19 | 17 | keratin 19 | ENSG00000171345 |
| | TUFM | 16 | Tu translation elongation factor, mitochondrial | ENSG00000178952 |
| | HIST3H2A | 1 | histone cluster 3 H2A | ENSG00000181218 |
| | KRTAP4-16 | 17 | keratin associated protein 4-16 | ENSG00000241241 |
| | TUBB3 | 16 | tubulin beta 3 class III | ENSG00000258947 |
| | COMT | 22 | catechol-O-methyltransferase | ENSG00000093010 |
| | ATP5D | 19 | ATP synthase, H+ transporting, mitochondrial F1 complex, delta subunit | ENSG00000099624 |
| | KRT17 | 17 | keratin 17 | ENSG00000128422 |
| | RPS27A | 2 | ribosomal protein S27a | ENSG00000143947 |
| | PDIA3 | 15 | protein disulfide isomerase family A member 3 | ENSG00000167004 |
| | HSPA6 | 1 | heat shock protein family A (Hsp70) member 6 | ENSG00000173110 |
| | ALYREF | 17 | Aly/REF export factor | ENSG00000183684 |
| | HIST1H2AE | 6 | histone cluster 1 H2A family member e | ENSG00000277075 |
| | HIST1H2AB | 6 | histone cluster 1 H2A family member b | ENSG00000278463 |
| | ATOX1 | 5 | antioxidant 1 copper chaperone | ENSG00000177556 |
| | GGCT | 7 | gamma-glutamylcyclotransferase | ENSG00000006625 |
| | RAB7A | 3 | RAB7A, member RAS oncogene family | ENSG00000075785 |
| | CUX2 | 12 | cut like homeobox 2 | ENSG00000111249 |
| | CAT | 11 | catalase | ENSG00000121691 |
| | LMNB2 | 19 | lamin B2 | ENSG00000176619 |
| | HIST3H2BB | 1 | histone cluster 3 H2B family member b | ENSG00000196890 |
| | KRTAP26-1 | 21 | keratin associated protein 26-1 | ENSG00000197683 |
| | NME2 | 17 | NME/NM23 nucleoside diphosphate kinase 2 | ENSG00000243678 |
| | GPI | 19 | glucose-6-phosphate isomerase | ENSG00000105220 |
| | GIPC1 | 19 | GIPC PDZ domain containing family member 1 | ENSG00000123159 |
| | MAP7 | 6 | microtubule associated protein 7 | ENSG00000135525 |
| | ACTA1 | 1 | actin, alpha 1, skeletal muscle | ENSG00000143632 |
| | HK1 | 10 | hexokinase 1 | ENSG00000156515 |
| | ACTC1 | 15 | actin, alpha, cardiac muscle 1 | ENSG00000159251 |
| | TUBA1C | 12 | tubulin alpha 1c | ENSG00000167553 |
| | HNRNPH1 | 5 | heterogeneous nuclear ribonucleoprotein H1 | ENSG00000169045 |

TABLE 8-continued

Exemplary genes identified in mass spectrometric analysis from hair type samples

| X = more preferable | gene symbol | chr | gene description | Ensembl gene identifier |
|---|---|---|---|---|
| | HSPA1L | 6 | heat shock protein family A (Hsp70) member 1 like | ENSG00000204390 |
| X | SLC25A3 | 12 | solute carrier family 25 member 3 | ENSG00000075415 |
| X | HSP90AA1 | 14 | heat shock protein 90 alpha family class A member 1 | ENSG00000080824 |
| X | GARS | 7 | glycyl-tRNA synthetase | ENSG00000106105 |
| X | KRT18 | 12 | keratin 18 | ENSG00000111057 |
| X | TAGLN2 | 1 | transgelin 2 | ENSG00000158710 |
| X | PCBP1 | 2 | poly(rC) binding protein 1 | ENSG00000169564 |
| X | CYCS | 7 | cytochrome c, somatic | ENSG00000172115 |
| X | KRTAP19-5 | 21 | keratin associated protein 19-5 | ENSG00000186977 |
| X | CDH1 | 16 | cadherin 1 | ENSG00000039068 |
| X | PARK7 | 1 | Parkinsonism associated deglycase | ENSG00000116288 |
| X | HNRNPA3 | 2 | heterogeneous nuclear ribonucleoprotein A3 | ENSG00000170144 |
| X | SERPINB5 | 18 | serpin family B member 5 | ENSG00000206075 |
| X | H2AFJ | 12 | H2A histone family member J | ENSG00000246705 |
| X | UQCRC1 | 3 | ubiquinol-cytochrome c reductase core protein I | ENSG00000010256 |
| X | PHGDH | 1 | phosphoglycerate dehydrogenase | ENSG00000092621 |
| X | ECHDC1 | 6 | ethylmalonyl-CoA decarboxylase 1 | ENSG00000093144 |
| X | PRDX1 | 1 | peroxiredoxin 1 | ENSG00000117450 |
| X | GOT2 | 16 | glutamic-oxaloacetic transaminase 2 | ENSG00000125166 |
| X | TKT | 3 | transketolase | ENSG00000163931 |
| X | TUBA1A | 12 | tubulin alpha 1a | ENSG00000167552 |
| X | KRT15 | 17 | keratin 15 | ENSG00000171346 |
| X | UQCRH | 1 | ubiquinol-cytochrome c reductase hinge protein | ENSG00000173660 |
| X | RPLP2 | 11 | ribosomal protein lateral stalk subunit P2 | ENSG00000177600 |
| X | KRT76 | 12 | keratin 76 | ENSG00000185069 |
| X | KRT3 | 12 | keratin 3 | ENSG00000186442 |
| X | NME1-NME2 | 17 | NME1-NME2 readthrough | ENSG00000011052 |
| X | GRN | 17 | granulin precursor | ENSG00000030582 |
| X | SSBP1 | 7 | single stranded DNA binding protein 1 | ENSG00000106028 |
| X | HNRNPA2B1 | 7 | heterogeneous nuclear ribonucleoprotein A2/B1 | ENSG00000122566 |
| X | ENDOD1 | 11 | endonuclease domain containing 1 | ENSG00000149218 |
| X | ALDOA | 16 | aldolase, fructose-bisphosphate A | ENSG00000149925 |
| X | GSDMA | 17 | gasdermin A | ENSG00000167914 |
| X | KRT2 | 12 | keratin 2 | ENSG00000172867 |
| X | HIST2H3PS2 | 1 | histone cluster 2 H3 pseudogene 2 | ENSG00000203818 |
| X | AHNAK | 11 | AHNAK nucleoprotein | ENSG00000124942 |
| X | ARL8B | 3 | ADP ribosylation factor like GTPase 8B | ENSG00000134108 |
| X | ATP6V1B2 | 8 | ATPase H+ transporting V1 subunit B2 | ENSG00000147416 |
| X | TCHH | 1 | trichohyalin | ENSG00000159450 |
| X | HIST1H2AJ | 6 | histone cluster 1 H2A family member j | ENSG00000276368 |
| X | GDI2 | 10 | GDP dissociation inhibitor 2 | ENSG00000057608 |
| X | HIST1H2BJ | 6 | histone cluster 1 H2B family member j | ENSG00000124635 |
| X | GFAP | 17 | glial fibrillary acidic protein | ENSG00000131095 |
| X | PMEL | 12 | premelanosome protein | ENSG00000185664 |
| X | KRTAP10-12 | 21 | keratin associated protein 10-12 | ENSG00000189169 |
| X | S100A14 | 1 | S100 calcium binding protein A14 | ENSG00000189334 |
| X | KRTAP4-3 | 17 | keratin associated protein 4-3 | ENSG00000196156 |
| X | YWHAH | 22 | tyrosine 3-monooxygenase/tryptophan 5-monooxygenase activation protein eta | ENSG00000128245 |
| X | PDIA6 | 2 | protein disulfide isomerase family A member 6 | ENSG00000143870 |
| X | FABP5 | 8 | fatty acid binding protein 5 | ENSG00000164687 |
| X | HEPHL1 | 11 | hephaestin like 1 | ENSG00000181333 |
| X | CRIP2 | 14 | cysteine rich protein 2 | ENSG00000182809 |
| X | KRT14 | 17 | keratin 14 | ENSG00000186847 |
| X | APOD | 3 | apolipoprotein D | ENSG00000189058 |
| X | H1F0 | 22 | H1 histone family member 0 | ENSG00000189060 |
| X | HSPA1B | 6 | heat shock protein family A (Hsp70) member 1B | ENSG00000204388 |
| X | HSPA1A | 6 | heat shock protein family A (Hsp70) member 1A | ENSG00000204389 |
| X | RBM14 | 11 | RNA binding motif protein 14 | ENSG00000239306 |
| X | KRTAP7-1 | 21 | keratin associated protein 7-1 (gene/pseudogene) | ENSG00000274749 |
| X | VIM | 10 | vimentin | ENSG00000026025 |
| X | CTNNA1 | 5 | catenin alpha 1 | ENSG00000044115 |
| X | SFPQ | 1 | splicing factor proline and glutamine rich | ENSG00000116560 |
| X | COX5A | 15 | cytochrome c oxidase subunit 5A | ENSG00000178741 |
| X | RP11-566K11.2 | 16 | | ENSG00000198211 |
| X | HSPA9 | 5 | heat shock protein family A (Hsp70) member 9 | ENSG00000113013 |
| X | HSPE1 | 2 | heat shock protein family E (Hsp10) member 1 | ENSG00000115541 |
| X | ANXA1 | 9 | annexin A1 | ENSG00000135046 |
| X | MEMO1 | 2 | mediator of cell motility 1 | ENSG00000162959 |
| X | KRT78 | 12 | keratin 78 | ENSG00000170423 |

TABLE 8-continued

| Exemplary genes identified in mass spectrometric analysis from hair type samples | | | | |
|---|---|---|---|---|
| X = more preferable | gene symbol | chr | gene description | Ensembl gene identifier |
| X | CALML5 | 10 | calmodulin like 5 | ENSG00000178372 |
| X | KRT6B | 12 | keratin 6B | ENSG00000185479 |
| X | BLMH | 17 | bleomycin hydrolase | ENSG00000108578 |
| X | HIST1H3J | 6 | histone cluster 1 H3 family member j | ENSG00000197153 |
| X | HIST1H3D | 6 | histone cluster 1 H3 family member d | ENSG00000197409 |
| X | HIST2H2BF | 1 | histone cluster 2 H2B family member f | ENSG00000203814 |
| X | HIST1H3G | 6 | histone cluster 1 H3 family member g | ENSG00000273983 |
| X | HIST1H3B | 6 | histone cluster 1 H3 family member b | ENSG00000274267 |
| X | HIST1H3E | 6 | histone cluster 1 H3 family member e | ENSG00000274750 |
| X | HIST1H3I | 6 | histone cluster 1 H3 family member i | ENSG00000275379 |
| X | HIST1H3A | 6 | histone cluster 1 H3 family member a | ENSG00000275714 |
| X | HIST1H3F | 6 | histone cluster 1 H3 family member f | ENSG00000277775 |
| X | HIST1H3C | 6 | histone cluster 1 H3 family member c | ENSG00000278272 |
| X | HIST1H3H | 6 | histone cluster 1 H3 family member h | ENSG00000278828 |
| X | HIST1H1D | 6 | histone cluster 1 H1 family member d | ENSG00000124575 |
| X | KRT16 | 17 | keratin 16 | ENSG00000186832 |
| X | TUBA4A | 2 | tubulin alpha 4a | ENSG00000127824 |
| X | RIDA | 8 | reactive intermediate imine deaminase A homolog | ENSG00000132541 |
| X | HSD17B4 | 5 | hydroxysteroid 17-beta dehydrogenase 4 | ENSG00000133835 |
| X | DSG1 | 18 | desmoglein 1 | ENSG00000134760 |
| X | CLIC3 | 9 | chloride intracellular channel 3 | ENSG00000169583 |
| X | FAM83H | 8 | family with sequence similarity 83 member H | ENSG00000180921 |
| X | HIST2H3D | 1 | histone cluster 2 H3 family member d | ENSG00000183598 |
| X | TUBB | 6 | tubulin beta class I | ENSG00000196230 |
| X | KRTAP4-6 | 17 | keratin associated protein 4-6 | ENSG00000198090 |
| X | TXNRD1 | 12 | thioredoxin reductase 1 | ENSG00000198431 |
| X | HIST2H3C | 1 | histone cluster 2 H3 family member c | ENSG00000203811 |
| X | HIST2H3A | 1 | histone cluster 2 H3 family member a | ENSG00000203852 |
| X | EEF1G | 11 | eukaryotic translation elongation factor 1 gamma | ENSG00000254772 |
| X | LGALS1 | 22 | galectin 1 | ENSG00000100097 |
| X | ACTBL2 | 5 | actin, beta like 2 | ENSG00000169067 |
| X | FABP4 | 8 | fatty acid binding protein 4 | ENSG00000170323 |
| X | PGAM1 | 10 | phosphoglycerate mutase 1 | ENSG00000171314 |
| X | POTEE | 2 | POTE ankyrin domain family member E | ENSG00000188219 |
| X | KRT6A | 12 | keratin 6A | ENSG00000205420 |
| X | KRTAP4-12 | 17 | keratin associated protein 4-12 | ENSG00000213416 |
| X | HIST1H2BB | 6 | histone cluster 1 H2B family member b | ENSG00000276410 |
| X | HEXB | 5 | hexosaminidase subunit beta | ENSG00000049860 |
| X | PLD3 | 19 | phospholipase D family member 3 | ENSG00000105223 |
| X | ALDH2 | 12 | aldehyde dehydrogenase 2 family (mitochondrial) | ENSG00000111275 |
| X | LMNB1 | 5 | lamin B1 | ENSG00000113368 |
| X | HNRNPA1 | 12 | heterogeneous nuclear ribonucleoprotein A1 | ENSG00000135486 |
| X | VCP | 9 | valosin containing protein | ENSG00000165280 |
| X | PRDX2 | 19 | peroxiredoxin 2 | ENSG00000167815 |
| X | FASN | 17 | fatty acid synthase | ENSG00000169710 |
| X | KRT10 | 17 | keratin 10 | ENSG00000186395 |
| X | HIST1H2BK | 6 | histone cluster 1 H2B family member k | ENSG00000197903 |
| X | KRTAP4-5 | 17 | keratin associated protein 4-5 | ENSG00000198271 |
| X | TGM1 | 14 | transglutaminase 1 | ENSG00000092295 |
| X | AIM1 | 6 | absent in melanoma 1 | ENSG00000112297 |
| X | H2AFY | 5 | H2A histone family member Y | ENSG00000113648 |
| X | HIST1H1C | 6 | histone cluster 1 H1 family member c | ENSG00000187837 |
| X | KRTAP2-2 | 17 | keratin associated protein 2-2 | ENSG00000214518 |
| X | PKP1 | 1 | plakophilin 1 | ENSG00000081277 |
| X | PGK1 | X | phosphoglycerate kinase 1 | ENSG00000102144 |
| X | KRT20 | 17 | keratin 20 | ENSG00000171431 |
| X | KRT79 | 12 | keratin 79 | ENSG00000185640 |
| X | HIST1H2BH | 6 | histone cluster 1 H2B family member h | ENSG00000275713 |
| X | TTBK2 | 15 | tau tubulin kinase 2 | ENSG00000128881 |
| X | SOD1 | 21 | superoxide dismutase 1 | ENSG00000142168 |
| X | HIST1H2BD | 6 | histone cluster 1 H2B family member d | ENSG00000158373 |
| X | YWHAG | 7 | tyrosine 3-monooxygenase/tryptophan 5-monooxygenase activation protein gamma | ENSG00000170027 |
| X | PLEC | 8 | plectin | ENSG00000178209 |
| X | ATG9B | 7 | autophagy related 9B | ENSG00000181652 |
| X | LAMP1 | 13 | lysosomal associated membrane protein 1 | ENSG00000185896 |
| X | HIST2H2AA3 | 1 | histone cluster 2 H2A family member a3 | ENSG00000203812 |
| X | KRTAP4-11 | 17 | keratin associated protein 4-11 | ENSG00000212721 |
| X | HIST2H2AA4 | 1 | histone cluster 2 H2A family member a4 | ENSG00000272196 |
| X | HADHA | 2 | hydroxyacyl-CoA dehydrogenase/3-ketoacyl-CoA thiolase/enoyl-CoA hydratase (trifunctional protein), alpha subunit | ENSG00000084754 |

TABLE 8-continued

Exemplary genes identified in mass spectrometric analysis from hair type samples

| X = more preferable | gene symbol | chr | gene description | Ensembl gene identifier |
|---|---|---|---|---|
| X | CRYAB | 11 | crystallin alpha B | ENSG00000109846 |
| X | KRT8 | 12 | keratin 8 | ENSG00000170421 |
| X | KRTAP16-1 | 17 | keratin associated protein 16-1 | ENSG00000212657 |
| X | HIST1H2BN | 6 | histone cluster 1 H2B family member n | ENSG00000233822 |
| X | HIST1H2BO | 6 | histone cluster 1 H2B family member o | ENSG00000274641 |
| X | CS | 12 | citrate synthase | ENSG00000062485 |
| X | ATP6V1A | 3 | ATPase H+ transporting V1 subunit A | ENSG00000114573 |
| X | TUBA1B | 12 | tubulin alpha 1b | ENSG00000123416 |
| X | YWHAQ | 2 | tyrosine 3-monooxygenase/tryptophan 5-monooxygenase activation protein theta | ENSG00000134308 |
| X | EIF4A1 | 17 | eukaryotic translation initiation factor 4A1 | ENSG00000161960 |
| X | PHB | 17 | prohibitin | ENSG00000167085 |
| X | HIST1H2BC | 6 | histone cluster 1 H2B family member c | ENSG00000180596 |
| X | KRTAP4-9 | 17 | keratin associated protein 4-9 | ENSG00000212722 |
| X | HIST1H2BM | 6 | histone cluster 1 H2B family member m | ENSG00000273703 |
| X | HIST1H2BG | 6 | histone cluster 1 H2B family member g | ENSG00000273802 |
| X | HIST1H2BE | 6 | histone cluster 1 H2B family member e | ENSG00000274290 |
| X | HIST1H2BF | 6 | histone cluster 1 H2B family member f | ENSG00000277224 |
| X | HIST1H2BI | 6 | histone cluster 1 H2B family member i | ENSG00000278588 |
| X | HSPA5 | 9 | heat shock protein family A (Hsp70) member 5 | ENSG00000044574 |
| X | ACAA1 | 3 | acetyl-CoA acyltransferase 1 | ENSG00000060971 |
| X | KRT23 | 17 | keratin 23 | ENSG00000108244 |
| X | PRDX6 | 1 | peroxiredoxin 6 | ENSG00000117592 |
| X | HSPD1 | 2 | heat shock protein family D (Hsp60) member 1 | ENSG00000144381 |
| X | RPSA | 3 | ribosomal protein SA | ENSG00000168028 |
| X | LYG2 | 2 | lysozyme g2 | ENSG00000185674 |
| X | PLCD1 | 3 | phospholipase C delta 1 | ENSG00000187091 |
| X | KRTAP9-9 | 17 | keratin associated protein 9-9 | ENSG00000198083 |
| X | KRTAP4-8 | 17 | keratin associated protein 4-8 | ENSG00000204880 |
| X | GSTP1 | 11 | glutathione S-transferase pi 1 | ENSG00000084207 |
| X | LDHB | 12 | lactate dehydrogenase B | ENSG00000111716 |
| X | GPNMB | 7 | glycoprotein nmb | ENSG00000136235 |
| X | YWHAB | 20 | tyrosine 3-monooxygenase/tryptophan 5-monooxygenase activation protein beta | ENSG00000166913 |
| X | TUBB4B | 9 | tubulin beta 4B class IVb | ENSG00000188229 |
| X | HSD17B10 | X | hydroxysteroid 17-beta dehydrogenase 10 | ENSG00000072506 |
| X | KRT1 | 12 | keratin 1 | ENSG00000167768 |
| X | KRTAP4-4 | 17 | keratin associated protein 4-4 | ENSG00000171396 |
| X | LRRC15 | 3 | leucine rich repeat containing 15 | ENSG00000172061 |
| X | HIST2H2BE | 1 | histone cluster 2 H2B family member e | ENSG00000184678 |
| X | KRT5 | 12 | keratin 5 | ENSG00000186081 |
| X | POTEF | 2 | POTE ankyrin domain family member F | ENSG00000196604 |
| X | KRTAP9-6 | 17 | keratin associated protein 9-6 | ENSG00000212659 |
| X | KRTAP2-1 | 17 | keratin associated protein 2-1 | ENSG00000212725 |
| X | KRTAP4-2 | 17 | keratin associated protein 4-2 | ENSG00000244537 |
| X | HIST1H2AH | 6 | histone cluster 1 H2A family member h | ENSG00000274997 |
| X | H3F3B | 17 | H3 histone family member 3B | ENSG00000132475 |
| X | H3F3A | 1 | H3 histone family member 3A | ENSG00000163041 |
| X | S100A3 | 1 | S100 calcium binding protein A3 | ENSG00000188015 |
| X | PPIA | 7 | peptidylprolyl isomerase A | ENSG00000196262 |
| X | HIST1H2AI | 6 | histone cluster 1 H2A family member i | ENSG00000196747 |
| X | HIST1H2AG | 6 | histone cluster 1 H2A family member g | ENSG00000196787 |
| X | KRTAP2-3 | 17 | keratin associated protein 2-3 | ENSG00000212724 |
| X | KRTAP2-4 | 17 | keratin associated protein 2-4 | ENSG00000213417 |
| X | KRTAP9-4 | 17 | keratin associated protein 9-4 | ENSG00000241595 |
| X | LY6G6D | 6 | lymphocyte antigen 6 family member G6D | ENSG00000244355 |
| X | HIST1H2AK | 6 | histone cluster 1 H2A family member k | ENSG00000275221 |
| X | HIST1H2AL | 6 | histone cluster 1 H2A family member l | ENSG00000276903 |
| X | HIST1H2AM | 6 | histone cluster 1 H2A family member m | ENSG00000278677 |
| X | YWHAE | 17 | tyrosine 3-monooxygenase/tryptophan 5-monooxygenase activation protein epsilon | ENSG00000108953 |
| X | PADI3 | 1 | peptidyl arginine deiminase 3 | ENSG00000142619 |
| X | HIST1H1E | 6 | histone cluster 1 H1 family member e | ENSG00000168298 |
| X | KRTAP9-1 | 17 | keratin associated protein 9-1 | ENSG00000240542 |
| X | DUSP14 | 17 | dual specificity phosphatase 14 | ENSG00000276023 |
| X | NEU2 | 2 | neuraminidase 2 | ENSG00000115488 |
| X | DSC3 | 18 | desmocollin 3 | ENSG00000134762 |
| X | LMNA | 1 | lamin A/C | ENSG00000160789 |
| X | YWHAZ | 8 | tyrosine 3-monooxygenase/tryptophan 5-monooxygenase activation protein zeta | ENSG00000164924 |
| X | KRTAP9-7 | 17 | keratin associated protein 9-7 | ENSG00000180386 |
| X | HIST1H2AC | 6 | histone cluster 1 H2A family member c | ENSG00000180573 |
| X | ANXA2 | 15 | annexin A2 | ENSG00000182718 |
| X | KRTAP9-2 | 17 | keratin associated protein 9-2 | ENSG00000239886 |
| X | ACTB | 7 | actin beta | ENSG00000075624 |

TABLE 8-continued

Exemplary genes identified in mass spectrometric analysis from hair type samples

| X = more preferable | gene symbol | chr | gene description | Ensembl gene identifier |
|---|---|---|---|---|
| X | KRT7 | 12 | keratin 7 | ENSG00000135480 |
| X | CTNNB1 | 3 | catenin beta 1 | ENSG00000168036 |
| X | HIST1H1B | 6 | histone cluster 1 H1 family member b | ENSG00000184357 |
| X | KRTAP13-1 | 21 | keratin associated protein 13-1 | ENSG00000198390 |
| X | ENO1 | 1 | enolase 1 | ENSG00000074800 |
| X | HSPA8 | 11 | heat shock protein family A (Hsp70) member 8 | ENSG00000109971 |
| X | TUBB2A | 6 | tubulin beta 2A class IIa | ENSG00000137267 |
| X | EEF1A1 | 6 | eukaryotic translation elongation factor 1 alpha 1 | ENSG00000156508 |
| X | KRT80 | 12 | keratin 80 | ENSG00000167767 |
| X | GDPD3 | 16 | glycerophosphodiester phosphodiesterase domain containing 3 | ENSG00000102886 |
| X | TPI1 | 12 | triosephosphate isomerase 1 | ENSG00000111669 |
| X | PPL | 16 | periplakin | ENSG00000118898 |
| X | FAM26D | 6 | family with sequence similarity 26 member D | ENSG00000164451 |
| X | VDAC2 | 10 | voltage dependent anion channel 2 | ENSG00000165637 |
| X | KRT75 | 12 | keratin 75 | ENSG00000170454 |
| X | PKM | 15 | pyruvate kinase, muscle | ENSG00000067225 |
| X | KRT37 | 17 | keratin 37 | ENSG00000108417 |
| X | KRTAP1-1 | 17 | keratin associated protein 1-1 | ENSG00000188581 |
| X | KRTAP9-3 | 17 | keratin associated protein 9-3 | ENSG00000204873 |
| X | CKMT1A | 15 | creatine kinase, mitochondrial 1A | ENSG00000223572 |
| X | CKMT1B | 15 | creatine kinase, mitochondrial 1B | ENSG00000237289 |
| X | UBC | 12 | ubiquitin C | ENSG00000150991 |
| X | UBB | 17 | ubiquitin B | ENSG00000170315 |
| X | KRT13 | 17 | keratin 13 | ENSG00000171401 |
| X | ATP5B | 12 | ATP synthase, H+ transporting, mitochondrial F1 complex, beta polypeptide | ENSG00000110955 |
| X | HSPA2 | 14 | heat shock protein family A (Hsp70) member 2 | ENSG00000126803 |
| X | EEF2 | 19 | eukaryotic translation elongation factor 2 | ENSG00000167658 |
| X | ACTG1 | 17 | actin gamma 1 | ENSG00000184009 |
| X | KRTAP1-3 | 17 | keratin associated protein 1-3 | ENSG00000221880 |
| X | KRTAP4-7 | 17 | keratin associated protein 4-7 | ENSG00000240871 |
| X | HIST1H4H | 6 | histone cluster 1 H4 family member h | ENSG00000158406 |
| X | C1orf204 | 1 | chromosome 1 open reading frame 204 | ENSG00000188004 |
| X | KRTAP24-1 | 21 | keratin associated protein 24-1 | ENSG00000188694 |
| X | HIST1H4C | 6 | histone cluster 1 H4 family member c | ENSG00000197061 |
| X | HIST1H4J | 6 | histone cluster 1 H4 family member j | ENSG00000197238 |
| X | HIST4H4 | 12 | histone cluster 4 H4 | ENSG00000197837 |
| X | VSIG8 | 1 | V-set and immunoglobulin domain containing 8 | ENSG00000243284 |
| X | HIST2H4B | 1 | histone cluster 2 H4 family member b | ENSG00000270276 |
| X | HIST2H4A | 1 | histone cluster 2 H4 family member a | ENSG00000270882 |
| X | HIST1H4K | 6 | histone cluster 1 H4 family member k | ENSG00000273542 |
| X | HIST1H4F | 6 | histone cluster 1 H4 family member f | ENSG00000274618 |
| X | HIST1H4L | 6 | histone cluster 1 H4 family member l | ENSG00000275126 |
| X | HIST1H4I | 6 | histone cluster 1 H4 family member i | ENSG00000276180 |
| X | HIST1H4E | 6 | histone cluster 1 H4 family member e | ENSG00000276966 |
| X | HIST1H4D | 6 | histone cluster 1 H4 family member d | ENSG00000277157 |
| X | HIST1H4A | 6 | histone cluster 1 H4 family member a | ENSG00000278637 |
| X | HIST1H4B | 6 | histone cluster 1 H4 family member b | ENSG00000278705 |
| X | MDH2 | 7 | malate dehydrogenase 2 | ENSG00000146701 |
| X | CALML3 | 10 | calmodulin like 3 | ENSG00000178363 |
| X | KRTAP13-2 | 21 | keratin associated protein 13-2 | ENSG00000182816 |
| X | MIF | 22 | macrophage migration inhibitory factor (glycosylation-inhibiting factor) | ENSG00000240972 |
| X | LAP3 | 4 | leucine aminopeptidase 3 | ENSG00000002549 |
| X | HSPB1 | 7 | heat shock protein family B (small) member 1 | ENSG00000106211 |
| X | KRT32 | 17 | keratin 32 | ENSG00000108759 |
| X | GAPDH | 12 | glyceraldehyde-3-phosphate dehydrogenase | ENSG00000111640 |
| X | TGM3 | 20 | transglutaminase 3 | ENSG00000125780 |
| X | ATP5A1 | 18 | ATP synthase, H+ transporting, mitochondrial F1 complex, alpha subunit 1, cardiac muscle | ENSG00000152234 |
| X | KRTAP11-1 | 21 | keratin associated protein 11-1 | ENSG00000182591 |
| X | PKP3 | 11 | plakophilin 3 | ENSG00000184363 |
| X | KRT40 | 17 | keratin 40 | ENSG00000204889 |
| X | KRT81 | 12 | keratin 81 | ENSG00000205426 |
| X | KRTAP3-3 | 17 | keratin associated protein 3-3 | ENSG00000212899 |
| X | KRTAP3-2 | 17 | keratin associated protein 3-2 | ENSG00000212900 |
| X | KRTAP3-1 | 17 | keratin associated protein 3-1 | ENSG00000212901 |
| X | KRT33A | 17 | keratin 33A | ENSG00000006059 |
| X | KRT31 | 17 | keratin 31 | ENSG00000094796 |
| X | DSP | 6 | desmoplakin | ENSG00000096696 |
| X | KRT36 | 17 | keratin 36 | ENSG00000126337 |
| X | KRT34 | 17 | keratin 34 | ENSG00000131737 |
| X | KRT33B | 17 | keratin 33B | ENSG00000131738 |

TABLE 8-continued

| Exemplary genes identified in mass spectrometric analysis from hair type samples | | | | |
|---|---|---|---|---|
| X = more preferable | gene symbol | chr | gene description | Ensembl gene identifier |
| X | LGALS3 | 14 | galectin 3 | ENSG00000131981 |
| X | KRT85 | 12 | keratin 85 | ENSG00000135443 |
| X | TRIM29 | 11 | tripartite motif containing 29 | ENSG00000137699 |
| X | SELENBP1 | 1 | selenium binding protein 1 | ENSG00000143416 |
| X | KRT84 | 12 | keratin 84 | ENSG00000161849 |
| X | KRT82 | 12 | keratin 82 | ENSG00000161850 |
| X | KRT86 | 12 | keratin 86 | ENSG00000170442 |
| X | KRT83 | 12 | keratin 83 | ENSG00000170523 |
| X | KRT38 | 17 | keratin 38 | ENSG00000171360 |
| X | JUP | 17 | junction plakoglobin | ENSG00000173801 |
| X | DSG4 | 18 | desmoglein 4 | ENSG00000175065 |
| X | SFN | 1 | stratifin | ENSG00000175793 |
| X | LGALS7B | 19 | galectin 7B | ENSG00000178934 |
| X | KRT39 | 17 | keratin 39 | ENSG00000196859 |
| X | KRT35 | 17 | keratin 35 | ENSG00000197079 |
| X | LGALS7 | 19 | galectin 7 | ENSG00000205076 |
| X | KRTAP1-5 | 17 | keratin associated protein 1-5 | ENSG00000221852 |

Example 44: Exemplary Genes Comprising Marker Exome Sequences Validated in Bone Type Samples An exemplary set of genes that can be used in methods and systems herein described as well as in related databases is reported herein. In particular, the exemplary set of genes comprises genes validated as proteomically detectable in bone samples of a *Homo Sapiens* which can be used in methods and systems to detect a genetic variation and/or perform a genetic variation analysis wherein the biological organism is a human being, as well as in related databases, in accordance with the various aspects of the present disclosure.

Specifically, Table 9 shows a list of exemplary genes that appear in MS files taken for samples of a bone of human beings. The fields in this example are the preference (X=more preferred), the standard gene symbol (gene symbol), the chromosome where the gene is located (chr), a description of the gene (gene description) and the gene identifier in the database Ensembl at the date of filing of the instant disclosure (Ensembl Gene Identifier).

The exemplary genes of Table 9 can be therefore used in particular in methods and systems of the disclosure wherein the sample comprises a bone sample from human beings.

TABLE 9

| Exemplary genes identified in mass spectrometric analysis of bone type samples | | | | |
|---|---|---|---|---|
| X = more preferred | gene symbol | chr | gene description | Ensembl gene identifier |
| | TUBB8 | 10 | tubulin beta 8 class VIII | ENSG00000261456 |
| | TTR | 18 | transthyretin | ENSG00000118271 |
| | FBN2 | 5 | fibrillin 2 | ENSG00000138829 |
| | COL4A6 | X | collagen type IV alpha 6 chain | ENSG00000197565 |
| | COL15A1 | 9 | collagen type XV alpha 1 chain | ENSG00000204291 |
| | ACAN | 15 | aggrecan | ENSG00000157766 |
| | CNN2 | 19 | calponin 2 | ENSG00000064666 |
| | CDK5RAP2 | 9 | CDK5 regulatory subunit associated protein 2 | ENSG00000136861 |
| | TPSAB1 | 16 | tryptase alpha/beta 1 | ENSG00000172236 |
| | MATR3 | 5 | matrin 3 | ENSG00000280987 |
| | RP1L1 | 8 | RP1 like 1 | ENSG00000183638 |
| | IGFBP3 | 7 | insulin like growth factor binding protein 3 | ENSG00000146674 |
| | FBLN1 | 22 | fibulin 1 | ENSG00000077942 |
| | CAPZB | 1 | capping actin protein of muscle Z-line beta subunit | ENSG00000077549 |
| | POSTN | 13 | periostin | ENSG00000133110 |
| | ELN | 7 | elastin | ENSG00000049540 |
| | MFAP5 | 12 | microfibrillar associated protein 5 | ENSG00000197614 |
| | UBB | 17 | ubiquitin B | ENSG00000170315 |
| | DDT | 22 | D-dopachrome tautomerase | ENSG00000099977 |
| | VIT | 2 | vitrin | ENSG00000205221 |
| | CYCS | 7 | cytochrome c, somatic | ENSG00000172115 |
| | CTSD | 11 | cathepsin D | ENSG00000117984 |
| | TRH | 3 | thyrotropin releasing hormone | ENSG00000170893 |
| | COL13A1 | 10 | collagen type XIII alpha 1 chain | ENSG00000197467 |
| | ATP11A | 13 | ATPase phospholipid transporting 11A | ENSG00000068650 |
| | RPL27A | 11 | ribosomal protein L27a | ENSG00000166441 |
| | UBC | 12 | ubiquitin C | ENSG00000150991 |
| | MFGE8 | 15 | milk fat globule-EGF factor 8 protein | ENSG00000140545 |
| | RPS10 | 6 | ribosomal protein S10 | ENSG00000124614 |
| | RPS20 | 8 | ribosomal protein S20 | ENSG00000008988 |

TABLE 9-continued

| X = more preferred | gene symbol | chr | gene description | Ensembl gene identifier |
|---|---|---|---|---|
| | TGFBI | 5 | transforming growth factor beta induced | ENSG00000120708 |
| | SRP14 | 15 | signal recognition particle 14 | ENSG00000140319 |
| | RPL19 | 17 | ribosomal protein L19 | ENSG00000108298 |
| | KMT2D | 12 | lysine methyltransferase 2D | ENSG00000167548 |
| | TPP1 | 11 | tripeptidyl peptidase 1 | ENSG00000166340 |
| | GRIN2D | 19 | glutamate ionotropic receptor NMDA type subunit 2D | ENSG00000105464 |
| | ANGPTL7 | 1 | angiopoietin like 7 | ENSG00000171819 |
| | CA2 | 8 | carbonic anhydrase 2 | ENSG00000104267 |
| | HBE1 | 11 | hemoglobin subunit epsilon 1 | ENSG00000213931 |
| | AMBP | 9 | alpha-1-microglobulin/bikunin precursor | ENSG00000106927 |
| | ORM1 | 9 | orosomucoid 1 | ENSG00000229314 |
| | PF4 | 4 | platelet factor 4 | ENSG00000163737 |
| | CYBB | X | cytochrome b-245 beta chain | ENSG00000165168 |
| | C2 | 6 | complement C2 | ENSG00000166278 |
| | C4A | 6 | complement C4A (Rodgers blood group) | ENSG00000244731 |
| | HSPA1B | 6 | heat shock protein family A (Hsp70) member 1B | ENSG00000204388 |
| | PF4V1 | 4 | platelet factor 4 variant 1 | ENSG00000109272 |
| | HSPA5 | 9 | heat shock protein family A (Hsp70) member 5 | ENSG00000044574 |
| | ACTN1 | 14 | actinin alpha 1 | ENSG00000072110 |
| | LCP1 | 13 | lymphocyte cytosolic protein 1 | ENSG00000136167 |
| | PLA2G2A | 1 | phospholipase A2 group IIA | ENSG00000188257 |
| | HIST1H1T | 6 | histone cluster 1 H1 family member t | ENSG00000187475 |
| | PPIB | 15 | peptidylprolyl isomerase B | ENSG00000166794 |
| | RPL12 | 9 | ribosomal protein L12 | ENSG00000197958 |
| | PEBP1 | 12 | phosphatidylethanolamine binding protein 1 | ENSG00000089220 |
| | RDX | 11 | radixin | ENSG00000137710 |
| | MYH9 | 22 | myosin heavy chain 9 | ENSG00000100345 |
| | NPTX2 | 7 | neuronal pentraxin 2 | ENSG00000106236 |
| | CXCL12 | 10 | C-X-C motif chemokine ligand 12 | ENSG00000107562 |
| | H2BFS | 21 | H2B histone family member S | ENSG00000234289 |
| | SNRPD3 | 22 | small nuclear ribonucleoprotein D3 polypeptide | ENSG00000100028 |
| | RPL7A | 9 | ribosomal protein L7a | ENSG00000148303 |
| | RPS4X | X | ribosomal protein S4, X-linked | ENSG00000198034 |
| | RPS26 | 12 | ribosomal protein S26 | ENSG00000197728 |
| | RPL39 | X | ribosomal protein L39 | ENSG00000198918 |
| | RPS21 | 20 | ribosomal protein S21 | ENSG00000171858 |
| | CAP1 | 1 | adenylate cyclase associated protein 1 | ENSG00000131236 |
| | DPT | 1 | dermatopontin | ENSG00000143196 |
| | KHDRBS1 | 1 | KH RNA binding domain containing, signal transduction associated 1 | ENSG00000121774 |
| | GAS6 | 13 | growth arrest specific 6 | ENSG00000183087 |
| | PDIA6 | 2 | protein disulfide isomerase family A member 6 | ENSG00000143870 |
| | HIST3H3 | 1 | histone cluster 3 H3 | ENSG00000168148 |
| | TMEM119 | 12 | transmembrane protein 119 | ENSG00000183160 |
| | TMPRSS6 | 22 | transmembrane protease, serine 6 | ENSG00000187045 |
| | AEBP1 | 7 | AE binding protein 1 | ENSG00000106624 |
| | COL27A1 | 9 | collagen type XXVII alpha 1 chain | ENSG00000196739 |
| | PGLYRP2 | 19 | peptidoglycan recognition protein 2 | ENSG00000161031 |
| | TUBB1 | 20 | tubulin beta 1 class VI | ENSG00000101162 |
| | COL17A1 | 10 | collagen type XVII alpha 1 chain | ENSG00000065618 |
| | PRSS56 | 2 | protease, serine 56 | ENSG00000237412 |
| | GLIPR2 | 9 | GLI pathogenesis related 2 | ENSG00000122694 |
| | APP | 21 | amyloid beta precursor protein | ENSG00000142192 |
| | CPNE1 | 20 | copine 1 | ENSG00000214078 |
| | RAN | 12 | RAN, member RAS oncogene family | ENSG00000132341 |
| | HSPE1 | 2 | heat shock protein family E (Hsp10) member 1 | ENSG00000115541 |
| | MATR3 | 5 | matrin 3 | ENSG00000015479 |
| | HINT1 | 5 | histidine triad nucleotide binding protein 1 | ENSG00000169567 |
| | RPS23 | 5 | ribosomal protein S23 | ENSG00000186468 |
| | CLU | 8 | clusterin | ENSG00000120885 |
| | EZR | 6 | ezrin | ENSG00000092820 |
| | HSPA8 | 11 | heat shock protein family A (Hsp70) member 8 | ENSG00000109971 |
| | RPL8 | 8 | ribosomal protein L8 | ENSG00000161016 |
| | ACAT1 | 11 | acetyl-CoA acetyltransferase 1 | ENSG00000075239 |
| | C4B | 6 | complement C4B (Chido blood group) | ENSG00000224389 |
| | HMBS | 11 | hydroxymethylbilane synthase | ENSG00000256269 |
| | APOA1 | 11 | apolipoprotein A1 | ENSG00000118137 |
| | FTH1 | 11 | ferritin heavy chain 1 | ENSG00000167996 |
| | COMP | 19 | cartilage oligomeric matrix protein | ENSG00000105664 |
| | RPS27A | 2 | ribosomal protein S27a | ENSG00000143947 |
| | CLEC11A | 19 | C-type lectin domain containing 11A | ENSG00000105472 |
| | APOA2 | 1 | apolipoprotein A2 | ENSG00000158874 |
| | APCS | 1 | amyloid P component, serum | ENSG00000132703 |

TABLE 9-continued

Exemplary genes identified in mass spectrometric analysis of bone type samples

| X = more preferred | gene symbol | chr | gene description | Ensembl gene identifier |
|---|---|---|---|---|
| | FN1 | 2 | fibronectin 1 | ENSG00000115414 |
| | C8A | 1 | complement C8 alpha chain | ENSG00000157131 |
| | TUBB | 6 | tubulin beta class I | ENSG00000196230 |
| | LPA | 6 | lipoprotein(a) | ENSG00000198670 |
| | CFH | 1 | complement factor H | ENSG00000000971 |
| | HIST1H2AG | 6 | histone cluster 1 H2A family member g | ENSG00000196787 |
| | HIST1H2AI | 6 | histone cluster 1 H2A family member i | ENSG00000196747 |
| | HIST1H2AK | 6 | histone cluster 1 H2A family member k | ENSG00000275221 |
| | HIST1H2AM | 6 | histone cluster 1 H2A family member m | ENSG00000278677 |
| | HIST1H2AL | 6 | histone cluster 1 H2A family member l | ENSG00000276903 |
| | POTEI | 2 | POTE ankyrin domain family member I | ENSG00000196834 |
| | HSPA1A | 6 | heat shock protein family A (Hsp70) member 1A | ENSG00000204389 |
| | HIST1H2AD | 6 | histone cluster 1 H2A family member d | ENSG00000196866 |
| | CMA1 | 14 | chymase 1 | ENSG00000092009 |
| | LOX | 5 | lysyl oxidase | ENSG00000113083 |
| | THBS2 | 6 | thrombospondin 2 | ENSG00000186340 |
| | CDC42 | 1 | cell division cycle 42 | ENSG00000070831 |
| | RPS25 | 11 | ribosomal protein S25 | ENSG00000118181 |
| | TUBB4B | 9 | tubulin beta 4B class IVb | ENSG00000188229 |
| | DMP1 | 4 | dentin matrix acidic phosphoprotein 1 | ENSG00000152592 |
| | TUBB2A | 6 | tubulin beta 2A class IIa | ENSG00000137267 |
| | PLEC | 8 | plectin | ENSG00000178209 |
| | PGAM4 | X | phosphoglycerate mutase family member 4 | ENSG00000226784 |
| | HIST3H2BB | 1 | histone cluster 3 H2B family member b | ENSG00000196890 |
| | LRRC59 | 17 | leucine rich repeat containing 59 | ENSG00000108829 |
| | HIST1H2AH | 6 | histone cluster 1 H2A family member h | ENSG00000274997 |
| | HIST1H2AJ | 6 | histone cluster 1 H2A family member j | ENSG00000276368 |
| | MYOC | 1 | myocilin | ENSG00000034971 |
| | H2AFJ | 12 | H2A histone family member J | ENSG00000246705 |
| | TUBB2B | 6 | tubulin beta 2B class IIb | ENSG00000137285 |
| | TNMD | X | tenomodulin | ENSG00000000005 |
| | RPS10-NUDT3 | 6 | RPS10-NUDT3 readthrough | ENSG00000270800 |
| | COL14A1 | 8 | collagen type XIV alpha 1 chain | ENSG00000187955 |
| | PCMT1 | 6 | protein-L-isoaspartate (D-aspartate) O-methyltransferase | ENSG00000120265 |
| | IGHG1 | 14 | immunoglobulin heavy constant gamma 1 (G1m marker) | ENSG00000211896 |
| | IGLL5 | 22 | immunoglobulin lambda like polypeptide 5 | ENSG00000254709 |
| | HIST1H3D | 6 | histone cluster 1 H3 family member d | ENSG00000282988 |
| | GSTP1 | 11 | glutathione S-transferase pi 1 | ENSG00000084207 |
| | HP1BP3 | 1 | heterochromatin protein 1 binding protein 3 | ENSG00000127483 |
| | YWHAE | 17 | tyrosine 3-monooxygenase/tryptophan 5-monooxygenase activation protein epsilon | ENSG00000108953 |
| | RPL3 | 22 | ribosomal protein L3 | ENSG00000100316 |
| | RPL31 | 2 | ribosomal protein L31 | ENSG00000071082 |
| | RARRES2 | 7 | retinoic acid receptor responder 2 | ENSG00000106538 |
| | CA1 | 8 | carbonic anhydrase 1 | ENSG00000133742 |
| | RPL26L1 | 5 | ribosomal protein L26 like 1 | ENSG00000037241 |
| | RPL15 | 3 | ribosomal protein L15 | ENSG00000174748 |
| | RPL6 | 12 | ribosomal protein L6 | ENSG00000089009 |
| | CRIP2 | 14 | cysteine rich protein 2 | ENSG00000182809 |
| | RPL26 | 17 | ribosomal protein L26 | ENSG00000161970 |
| | APOH | 17 | apolipoprotein H | ENSG00000091583 |
| | RPL27 | 17 | ribosomal protein L27 | ENSG00000131469 |
| | A2M | 12 | alpha-2-macroglobulin | ENSG00000175899 |
| | IGHG4 | 14 | immunoglobulin heavy constant gamma 4 (G4m marker) | ENSG00000211892 |
| | HPX | 11 | hemopexin | ENSG00000110169 |
| | FTL | 19 | ferritin light chain | ENSG00000087086 |
| | HIST1H2BJ | 6 | histone cluster 1 H2B family member j | ENSG00000124635 |
| | MIF | 22 | macrophage migration inhibitory factor (glycosylation-inhibiting factor) | ENSG00000240972 |
| | HIST1H1D | 6 | histone cluster 1 H1 family member d | ENSG00000124575 |
| | COL9A1 | 6 | collagen type IX alpha 1 chain | ENSG00000112280 |
| | PRDX6 | 1 | peroxiredoxin 6 | ENSG00000117592 |
| | SFN | 1 | stratifin | ENSG00000175793 |
| | MDH2 | 7 | malate dehydrogenase 2 | ENSG00000146701 |
| | CRIP1 | 14 | cysteine rich protein 1 | ENSG00000213145 |
| | COL4A4 | 2 | collagen type IV alpha 4 chain | ENSG00000081052 |
| | HNRNPK | 9 | heterogeneous nuclear ribonucleoprotein K | ENSG00000165119 |
| | COL24A1 | 1 | collagen type XXIV alpha 1 chain | ENSG00000171502 |
| | CAVIN1 | 17 | caveolae associated protein 1 | ENSG00000177469 |
| | HIST1H2BA | 6 | histone cluster 1 H2B family member a | ENSG00000146047 |

TABLE 9-continued

| Exemplary genes identified in mass spectrometric analysis of bone type samples | | | | |
|---|---|---|---|---|
| X = more preferred | gene symbol | chr | gene description | Ensembl gene identifier |
| X | ADH1C | 4 | alcohol dehydrogenase 1C (class I), gamma polypeptide | ENSG00000248144 |
| X | YWHAH | 22 | tyrosine 3-monooxygenase/tryptophan 5-monooxygenase activation protein eta | ENSG00000128245 |
| X | RPS7 | 2 | ribosomal protein S7 | ENSG00000171863 |
| X | MYL6 | 12 | myosin light chain 6 | ENSG00000092841 |
| X | FGG | 4 | fibrinogen gamma chain | ENSG00000171557 |
| X | RPL23 | 17 | ribosomal protein L23 | ENSG00000125691 |
| X | APOD | 3 | apolipoprotein D | ENSG00000189058 |
| X | CLEC3B | 3 | C-type lectin domain family 3 member B | ENSG00000163815 |
| X | ENO2 | 12 | enolase 2 | ENSG00000111674 |
| X | RPL18 | 19 | ribosomal protein L18 | ENSG00000063177 |
| X | HSPB1 | 7 | heat shock protein family B (small) member 1 | ENSG00000106211 |
| X | ANXA2 | 15 | annexin A2 | ENSG00000182718 |
| X | RPS19 | 19 | ribosomal protein S19 | ENSG00000105372 |
| X | A1BG | 19 | alpha-1-B glycoprotein | ENSG00000121410 |
| X | BLVRB | 19 | biliverdin reductase B | ENSG00000090013 |
| X | HMGN4 | 6 | high mobility group nucleosomal binding domain 4 | ENSG00000182952 |
| X | HIST1H2BK | 6 | histone cluster 1 H2B family member k | ENSG00000197903 |
| X | CILP | 15 | cartilage intermediate layer protein | ENSG00000138615 |
| X | PGK1 | X | phosphoglycerate kinase 1 | ENSG00000102144 |
| X | IGHA2 | 14 | immunoglobulin heavy constant alpha 2 (A2m marker) | ENSG00000211890 |
| X | C1QA | 1 | complement C1q A chain | ENSG00000173372 |
| X | C1QC | 1 | complement C1q C chain | ENSG00000159189 |
| X | C9 | 5 | complement C9 | ENSG00000113600 |
| X | ANXA1 | 9 | annexin A1 | ENSG00000135046 |
| X | SPARC | 5 | secreted protein acidic and cysteine rich | ENSG00000113140 |
| X | RNASE2 | 14 | ribonuclease A family member 2 | ENSG00000169385 |
| X | COL8A1 | 3 | collagen type VIII alpha 1 chain | ENSG00000144810 |
| X | COL4A5 | X | collagen type IV alpha 5 chain | ENSG00000188153 |
| X | ACTBL2 | 5 | actin, beta like 2 | ENSG00000169067 |
| X | EMILIN1 | 2 | elastin microfibril interfacer 1 | ENSG00000138080 |
| X | YWHAB | 20 | tyrosine 3-monooxygenase/tryptophan 5-monooxygenase activation protein beta | ENSG00000166913 |
| X | POTEF | 2 | POTE ankyrin domain family member F | ENSG00000196604 |
| X | GC | 4 | GC, vitamin D binding protein | ENSG00000145321 |
| X | H2AFY | 5 | H2A histone family member Y | ENSG00000113648 |
| X | VCAN | 5 | versican | ENSG00000038427 |
| X | YWHAZ | 8 | tyrosine 3-monooxygenase/tryptophan 5-monooxygenase activation protein zeta | ENSG00000164924 |
| X | NPM1 | 5 | nucleophosmin | ENSG00000181163 |
| X | PROC | 2 | protein C, inactivator of coagulation factors Va and VIIIa | ENSG00000115718 |
| X | TNC | 9 | tenascin C | ENSG00000041982 |
| X | YWHAQ | 2 | tyrosine 3-monooxygenase/tryptophan 5-monooxygenase activation protein theta | ENSG00000134308 |
| X | COL8A2 | 1 | collagen type VIII alpha 2 chain | ENSG00000171812 |
| X | SERPINA10 | 14 | serpin family A member 10 | ENSG00000140093 |
| X | CD44 | 11 | CD44 molecule (Indian blood group) | ENSG00000026508 |
| X | AK1 | 9 | adenylate kinase 1 | ENSG00000106992 |
| X | PARK7 | 1 | Parkinsonism associated deglycase | ENSG00000116288 |
| X | CP | 3 | ceruloplasmin | ENSG00000047457 |
| X | IGHA1 | 14 | immunoglobulin heavy constant alpha 1 | ENSG00000211895 |
| X | LMNA | 1 | lamin A/C | ENSG00000160789 |
| X | S100A8 | 1 | S100 calcium binding protein A8 | ENSG00000143546 |
| X | COL4A2 | 13 | collagen type IV alpha 2 chain | ENSG00000134871 |
| X | HMGB1 | 13 | high mobility group box 1 | ENSG00000189403 |
| X | PGAM1 | 10 | phosphoglycerate mutase 1 | ENSG00000171314 |
| X | PRDX5 | 11 | peroxiredoxin 5 | ENSG00000126432 |
| X | CORO1A | 16 | coronin 1A | ENSG00000102879 |
| X | PRDX2 | 19 | peroxiredoxin 2 | ENSG00000167815 |
| X | GGT5 | 22 | gamma-glutamyltransferase 5 | ENSG00000099998 |
| X | YWHAG | 7 | tyrosine 3-monooxygenase/tryptophan 5-monooxygenase activation protein gamma | ENSG00000170027 |
| X | COL28A1 | 7 | collagen type XXVIII alpha 1 chain | ENSG00000215018 |
| X | POTEE | 2 | POTE ankyrin domain family member E | ENSG00000188219 |
| X | COL26A1 | 7 | collagen type XXVI alpha 1 chain | ENSG00000160963 |
| X | SOST | 17 | sclerostin | ENSG00000167941 |
| X | EEF1D | 8 | eukaryotic translation elongation factor 1 delta | ENSG00000104529 |
| X | VCL | 10 | vinculin | ENSG00000035403 |
| X | GSN | 9 | gelsolin | ENSG00000148180 |
| X | TKT | 3 | transketolase | ENSG00000163931 |
| X | HP | 16 | haptoglobin | ENSG00000257017 |

TABLE 9-continued

Exemplary genes identified in mass spectrometric analysis of bone type samples

| X = more preferred | gene symbol | chr | gene description | Ensembl gene identifier |
|---|---|---|---|---|
| X | FHL1 | X | four and a half LIM domains 1 | ENSG00000022267 |
| X | ACTA1 | 1 | actin, alpha 1, skeletal muscle | ENSG00000143632 |
| X | SPP2 | 2 | secreted phosphoprotein 2 | ENSG00000072080 |
| X | SPP1 | 4 | secreted phosphoprotein 1 | ENSG00000118785 |
| X | FGB | 4 | fibrinogen beta chain | ENSG00000171564 |
| X | ENO3 | 17 | enolase 3 | ENSG00000108515 |
| X | CFL1 | 11 | cofilin 1 | ENSG00000172757 |
| X | COL21A1 | 6 | collagen type XXI alpha 1 chain | ENSG00000124749 |
| X | ALDOA | 16 | aldolase, fructose-bisphosphate A | ENSG00000149925 |
| X | PKM | 15 | pyruvate kinase, muscle | ENSG00000067225 |
| X | RPL13 | 16 | ribosomal protein L13 | ENSG00000167526 |
| X | CILP2 | 19 | cartilage intermediate layer protein 2 | ENSG00000160161 |
| X | PLG | 6 | plasminogen | ENSG00000122194 |
| X | HMGN2 | 1 | high mobility group nucleosomal binding domain 2 | ENSG00000198830 |
| X | PROS1 | 3 | protein S (alpha) | ENSG00000184500 |
| X | SOD3 | 4 | superoxide dismutase 3 | ENSG00000109610 |
| X | EPX | 17 | eosinophil peroxidase | ENSG00000121053 |
| X | RNASE3 | 14 | ribonuclease A family member 3 | ENSG00000169397 |
| X | HIST1H1C | 6 | histone cluster 1 H1 family member c | ENSG00000187837 |
| X | ITIH2 | 10 | inter-alpha-trypsin inhibitor heavy chain 2 | ENSG00000151655 |
| X | DEFA1 | 8 | defensin alpha 1 | ENSG00000206047 |
| X | DEFA1B | 8 | defensin alpha 1B | ENSG00000240247 |
| X | ACTC1 | 15 | actin, alpha, cardiac muscle 1 | ENSG00000159251 |
| X | FMOD | 1 | fibromodulin | ENSG00000122176 |
| X | HIST2H3D | 1 | histone cluster 2 H3 family member d | ENSG00000183598 |
| X | HIST2H3C | 1 | histone cluster 2 H3 family member c | ENSG00000203811 |
| X | HIST2H3A | 1 | histone cluster 2 H3 family member a | ENSG00000203852 |
| X | FLNA | X | filamin A | ENSG00000196924 |
| X | PRDX1 | 1 | peroxiredoxin 1 | ENSG00000117450 |
| X | GPI | 19 | glucose-6-phosphate isomerase | ENSG00000105220 |
| X | COL11A2 | 6 | collagen type XI alpha 2 chain | ENSG00000204248 |
| X | OLFML3 | 1 | olfactomedin like 3 | ENSG00000116774 |
| X | HSPD1 | 2 | heat shock protein family D (Hsp60) member 1 | ENSG00000144381 |
| X | AHSG | 3 | alpha 2-HS glycoprotein | ENSG00000145192 |
| X | COL6A3 | 2 | collagen type VI alpha 3 chain | ENSG00000163359 |
| X | LYZ | 12 | lysozyme | ENSG00000090382 |
| X | SOD1 | 21 | superoxide dismutase 1 | ENSG00000142168 |
| X | ACTG1 | 17 | actin gamma 1 | ENSG00000184009 |
| X | SERPINC1 | 1 | serpin family C member 1 | ENSG00000117601 |
| X | C3 | 19 | complement C3 | ENSG00000125730 |
| X | FGA | 4 | fibrinogen alpha chain | ENSG00000171560 |
| X | ANG | 14 | angiogenin | ENSG00000214274 |
| X | CAT | 11 | catalase | ENSG00000121691 |
| X | IGF1 | 12 | insulin like growth factor 1 | ENSG00000017427 |
| X | ENO1 | 1 | enolase 1 | ENSG00000074800 |
| X | H1F0 | 22 | H1 histone family member 0 | ENSG00000189060 |
| X | CA3 | 8 | carbonic anhydrase 3 | ENSG00000164879 |
| X | ELANE | 19 | elastase, neutrophil expressed | ENSG00000197561 |
| X | LGALS1 | 22 | galectin 1 | ENSG00000100097 |
| X | EEF2 | 19 | eukaryotic translation elongation factor 2 | ENSG00000167658 |
| X | PGAM2 | 7 | phosphoglycerate mutase 2 | ENSG00000164708 |
| X | HIST1H1B | 6 | histone cluster 1 H1 family member b | ENSG00000184357 |
| X | OGN | 9 | osteoglycin | ENSG00000106809 |
| X | PDIA3 | 15 | protein disulfide isomerase family A member 3 | ENSG00000167004 |
| X | COL10A1 | 6 | collagen type X alpha 1 chain | ENSG00000123500 |
| X | COL16A1 | 1 | collagen type XVI alpha 1 chain | ENSG00000084636 |
| X | PCOLCE | 7 | procollagen C-endopeptidase enhancer | ENSG00000106333 |
| X | OLFML1 | 11 | olfactomedin like 1 | ENSG00000183801 |
| X | HIST2H2AB | 1 | histone cluster 2 H2A family member b | ENSG00000184270 |
| X | COL22A1 | 8 | collagen type XXII alpha 1 chain | ENSG00000169436 |
| X | HTRA1 | 10 | HtrA serine peptidase 1 | ENSG00000166033 |
| X | OMD | 9 | osteomodulin | ENSG00000127083 |
| X | TLN1 | 9 | talin 1 | ENSG00000137076 |
| X | COL1A2 | 7 | collagen type I alpha 2 chain | ENSG00000164692 |
| X | EEF1A1 | 6 | eukaryotic translation elongation factor 1 alpha 1 | ENSG00000156508 |
| X | COL5A1 | 9 | collagen type V alpha 1 chain | ENSG00000130635 |
| X | COL6A1 | 21 | collagen type VI alpha 1 chain | ENSG00000142156 |
| X | C1QB | 1 | complement C1q B chain | ENSG00000173369 |
| X | LTF | 3 | lactotransferrin | ENSG00000012223 |
| X | MEPE | 4 | matrix extracellular phosphoglycoprotein | ENSG00000152595 |
| X | COL12A1 | 6 | collagen type XII alpha 1 chain | ENSG00000111799 |
| X | FBN1 | 15 | fibrillin 1 | ENSG00000166147 |
| X | PFN1 | 17 | profilin 1 | ENSG00000108518 |

TABLE 9-continued

Exemplary genes identified in mass spectrometric analysis of bone type samples

| X = more preferred | gene symbol | chr | gene description | Ensembl gene identifier |
|---|---|---|---|---|
| X | KNG1 | 3 | kininogen 1 | ENSG00000113889 |
| X | IGF2 | 11 | insulin like growth factor 2 | ENSG00000167244 |
| X | MPO | 17 | myeloperoxidase | ENSG00000005381 |
| X | THBS1 | 15 | thrombospondin 1 | ENSG00000137801 |
| X | MGP | 12 | matrix Gla protein | ENSG00000111341 |
| X | COL6A2 | 21 | collagen type VI alpha 2 chain | ENSG00000142173 |
| X | AZU1 | 19 | azurocidin 1 | ENSG00000172232 |
| X | HIST1H2BO | 6 | histone cluster 1 H2B family member o | ENSG00000274641 |
| X | HIST1H2BB | 6 | histone cluster 1 H2B family member b | ENSG00000276410 |
| X | DEFA3 | 8 | defensin alpha 3 | ENSG00000239839 |
| X | TPI1 | 12 | triosephosphate isomerase 1 | ENSG00000111669 |
| X | HIST1H3H | 6 | histone cluster 1 H3 family member h | ENSG00000278828 |
| X | HIST1H3I | 6 | histone cluster 1 H3 family member i | ENSG00000275379 |
| X | HIST1H3J | 6 | histone cluster 1 H3 family member j | ENSG00000197153 |
| X | HIST1H3A | 6 | histone cluster 1 H3 family member a | ENSG00000275714 |
| X | HIST1H3B | 6 | histone cluster 1 H3 family member b | ENSG00000274267 |
| X | HIST1H3C | 6 | histone cluster 1 H3 family member c | ENSG00000278272 |
| X | HIST1H3D | 6 | histone cluster 1 H3 family member d | ENSG00000197409 |
| X | HIST1H3E | 6 | histone cluster 1 H3 family member e | ENSG00000274750 |
| X | HIST1H3F | 6 | histone cluster 1 H3 family member f | ENSG00000277775 |
| X | HIST1H3G | 6 | histone cluster 1 H3 family member g | ENSG00000273983 |
| X | H3F3A | 1 | H3 histone family member 3A | ENSG00000163041 |
| X | HSPG2 | 1 | heparan sulfate proteoglycan 2 | ENSG00000142798 |
| X | COL7A1 | 3 | collagen type VII alpha 1 chain | ENSG00000114270 |
| X | AHNAK | 11 | AHNAK nucleoprotein | ENSG00000124942 |
| X | HIST2H2BE | 1 | histone cluster 2 H2B family member e | ENSG00000184678 |
| X | ASPN | 9 | asporin | ENSG00000106819 |
| X | HIST3H2A | 1 | histone cluster 3 H2A | ENSG00000181218 |
| X | HIST1H2AC | 6 | histone cluster 1 H2A family member c | ENSG00000180573 |
| X | COL5A2 | 2 | collagen type V alpha 2 chain | ENSG00000204262 |
| X | HBB | 11 | hemoglobin subunit beta | ENSG00000244734 |
| X | COL11A1 | 1 | collagen type XI alpha 1 chain | ENSG00000060718 |
| X | MB | 22 | myoglobin | ENSG00000198125 |
| X | VIM | 10 | vimentin | ENSG00000026025 |
| X | HIST1H2BC | 6 | histone cluster 1 H2B family member c | ENSG00000180596 |
| X | HIST1H2BF | 6 | histone cluster 1 H2B family member f | ENSG00000277224 |
| X | HIST1H2BE | 6 | histone cluster 1 H2B family member e | ENSG00000274290 |
| X | HIST1H2BG | 6 | histone cluster 1 H2B family member g | ENSG00000273802 |
| X | HIST1H2BI | 6 | histone cluster 1 H2B family member i | ENSG00000278588 |
| X | H2AFV | 7 | H2A histone family member V | ENSG00000105968 |
| X | PPIA | 7 | peptidylprolyl isomerase A | ENSG00000196262 |
| X | BGN | X | biglycan | ENSG00000182492 |
| X | ACTB | 7 | actin beta | ENSG00000075624 |
| X | IGFBP5 | 2 | insulin like growth factor binding protein 5 | ENSG00000115461 |
| X | GAPDH | 12 | glyceraldehyde-3-phosphate dehydrogenase | ENSG00000111640 |
| X | ALB | 4 | albumin | ENSG00000163631 |
| X | COL3A1 | 2 | collagen type III alpha 1 chain | ENSG00000168542 |
| X | SERPINF1 | 17 | serpin family F member 1 | ENSG00000132386 |
| X | H3F3B | 17 | H3 histone family member 3B | ENSG00000132475 |
| X | CHAD | 17 | chondroadherin | ENSG00000136457 |
| X | F2 | 11 | coagulation factor II, thrombin | ENSG00000180210 |
| X | F9 | X | coagulation factor IX | ENSG00000101981 |
| X | F10 | 13 | coagulation factor X | ENSG00000126218 |
| X | SERPINA1 | 14 | serpin family A member 1 | ENSG00000197249 |
| X | IGHG2 | 14 | immunoglobulin heavy constant gamma 2 (G2m marker) | ENSG00000211893 |
| X | HBD | 11 | hemoglobin subunit delta | ENSG00000223609 |
| X | COL1A1 | 17 | collagen type I alpha 1 chain | ENSG00000108821 |
| X | COL2A1 | 12 | collagen type II alpha 1 chain | ENSG00000139219 |
| X | TF | 3 | transferrin | ENSG00000091513 |
| X | BGLAP | 1 | bone gamma-carboxyglutamate protein | ENSG00000242252 |
| X | VTN | 17 | vitronectin | ENSG00000109072 |
| X | HIST1H2AB | 6 | histone cluster 1 H2A family member b | ENSG00000278463 |
| X | HIST1H2AE | 6 | histone cluster 1 H2A family member e | ENSG00000277075 |
| X | S100A9 | 1 | S100 calcium binding protein A9 | ENSG00000163220 |
| X | CKM | 19 | creatine kinase, M-type | ENSG00000104879 |
| X | DCN | 12 | decorin | ENSG00000011465 |
| X | CTSG | 14 | cathepsin G | ENSG00000100448 |
| X | H2AFZ | 4 | H2A histone family member Z | ENSG00000164032 |
| X | HIST1H1E | 6 | histone cluster 1 H1 family member e | ENSG00000168298 |
| X | H2AFX | 11 | H2A histone family member X | ENSG00000188486 |
| X | IBSP | 4 | integrin binding sialoprotein | ENSG00000029559 |
| X | PRTN3 | 19 | proteinase 3 | ENSG00000196415 |
| X | COL5A3 | 19 | collagen type V alpha 3 chain | ENSG00000080573 |
| X | LUM | 12 | lumican | ENSG00000139329 |

TABLE 9-continued

| X = more preferred | gene symbol | chr | gene description | Ensembl gene identifier |
|---|---|---|---|---|
| Exemplary genes identified in mass spectrometric analysis of bone type samples | | | | |
| X | PRELP | 1 | proline and arginine rich end leucine rich repeat protein | ENSG00000188783 |
| X | HIST1H2BD | 6 | histone cluster 1 H2B family member d | ENSG00000158373 |
| X | HIST1H4I | 6 | histone cluster 1 H4 family member i | ENSG00000276180 |
| X | HIST1H4K | 6 | histone cluster 1 H4 family member k | ENSG00000273542 |
| X | HIST1H4J | 6 | histone cluster 1 H4 family member j | ENSG00000197238 |
| X | HIST1H4L | 6 | histone cluster 1 H4 family member l | ENSG00000275126 |
| X | HIST2H4A | 1 | histone cluster 2 H4 family member a | ENSG00000270882 |
| X | HIST2H4B | 1 | histone cluster 2 H4 family member b | ENSG00000270276 |
| X | HIST1H4A | 6 | histone cluster 1 H4 family member a | ENSG00000278637 |
| X | HIST1H4B | 6 | histone cluster 1 H4 family member b | ENSG00000278705 |
| X | HIST1H4C | 6 | histone cluster 1 H4 family member c | ENSG00000197061 |
| X | HIST1H4D | 6 | histone cluster 1 H4 family member d | ENSG00000277157 |
| X | HIST1H4E | 6 | histone cluster 1 H4 family member e | ENSG00000276966 |
| X | HIST1H4F | 6 | histone cluster 1 H4 family member f | ENSG00000274618 |
| X | HIST1H4H | 6 | histone cluster 1 H4 family member h | ENSG00000158406 |
| X | HIST4H4 | 12 | histone cluster 4 H4 | ENSG00000197837 |
| X | HBA2 | 16 | hemoglobin subunit alpha 2 | ENSG00000188536 |
| X | HBA1 | 16 | hemoglobin subunit alpha 1 | ENSG00000206172 |
| X | HIST2H2AC | 1 | histone cluster 2 H2A family member c | ENSG00000184260 |
| X | HIST2H2BF | 1 | histone cluster 2 H2B family member f | ENSG00000203814 |
| X | HIST2H2AA3 | 1 | histone cluster 2 H2A family member a3 | ENSG00000203812 |
| X | HIST2H2AA4 | 1 | histone cluster 2 H2A family member a4 | ENSG00000272196 |
| X | HIST1H2BH | 6 | histone cluster 1 H2B family member h | ENSG00000275713 |
| X | HIST1H2BN | 6 | histone cluster 1 H2B family member n | ENSG00000233822 |
| X | HIST1H2BM | 6 | histone cluster 1 H2B family member m | ENSG00000273703 |
| X | HIST1H2BL | 6 | histone cluster 1 H2B family member l | ENSG00000185130 |

Example 45: Exemplary Genes Comprising Marker Exome Sequences Validated in Skin Samples An exemplary set of genes that can be used in methods and systems herein described as well as in related databases is reported herein. In particular, the exemplary set of genes comprises genes validated as proteomically detectable in skin samples of *Homo Sapiens* which can be used in methods and systems to detect a genetic variation and/or perform a genetic variation analysis, as well as in related databases, in accordance with the various aspects of the present disclosure.

Specifically, Table 10 shows a list of exemplary genes that appear in MS files taken for skin samples of human beings. The fields in this example are the preference (X=more preferable), the standard gene symbol (gene symbol), the chromosome wherein the gene is located (chr), a description of the gene (gene description) and an identifier in the database Ensembl at the date of filing of the instant disclosure (Ensembl Gene Identifier).

The exemplary genes of Table 10 can be used in particular in methods and system of the disclosure wherein the sample comprises a skin sample from human beings.

TABLE 10

| X = more preferable | gene symbol | chr | gene description | Ensembl gene identifier |
|---|---|---|---|---|
| Exemplary genes identified in mass spectrometric analysis of skin samples | | | | |
| | TULP1 | 6 | tubby like protein 1 | ENSG00000112041 |
| | ACTN4 | 19 | actinin alpha 4 | ENSG00000130402 |
| | PLXNC1 | 12 | plexin C1 | ENSG00000136040 |
| | KRT33A | 17 | keratin 33A | ENSG00000006059 |
| | LDHA | 11 | lactate dehydrogenase A | ENSG00000134333 |
| | PIGR | 1 | polymeric immunoglobulin receptor | ENSG00000162896 |
| | LTF | 3 | lactotransferrin | ENSG00000012223 |
| | SERPINB2 | 18 | serpin family B member 2 | ENSG00000197632 |
| | GSN | 9 | gelsolin | ENSG00000148180 |
| | TUBB | 6 | tubulin beta class I | ENSG00000196230 |
| | IVL | 1 | involucrin | ENSG00000163207 |
| | LCT | 2 | lactase | ENSG00000115850 |
| | NEFH | 22 | neurofilament heavy | ENSG00000100285 |
| | APEH | 3 | acylaminoacyl-peptide hydrolase | ENSG00000164062 |
| | IDE | 10 | insulin degrading enzyme | ENSG00000119912 |
| | ARF4 | 3 | ADP ribosylation factor 4 | ENSG00000168374 |
| | VCL | 10 | vinculin | ENSG00000035403 |
| | AMPD1 | 1 | adenosine monophosphate deaminase 1 | ENSG00000116748 |
| | PSMA2 | 7 | proteasome subunit alpha 2 | ENSG00000106588 |
| | PEBP1 | 12 | phosphatidylethanolamine binding protein 1 | ENSG00000089220 |
| | KIF5B | 10 | kinesin family member 5B | ENSG00000170759 |

TABLE 10-continued

Exemplary genes identified in mass spectrometric analysis of skin samples

| X = more preferable | gene symbol | chr | gene description | Ensembl gene identifier |
|---|---|---|---|---|
| | TALDO1 | 11 | transaldolase 1 | ENSG00000177156 |
| | ME1 | 6 | malic enzyme 1 | ENSG00000065833 |
| | CENPF | 1 | centromere protein F | ENSG00000117724 |
| | SSR4 | X | signal sequence receptor subunit 4 | ENSG00000180879 |
| | VAMP7 | X | vesicle associated membrane protein 7 | ENSG00000124333 |
| | S100A10 | 1 | S100 calcium binding protein A10 | ENSG00000197747 |
| | ARF3 | 12 | ADP ribosylation factor 3 | ENSG00000134287 |
| | TPM4 | 19 | tropomyosin 4 | ENSG00000167460 |
| | TUBA4A | 2 | tubulin alpha 4a | ENSG00000127824 |
| | TUBB4B | 9 | tubulin beta 4B class IVb | ENSG00000188229 |
| | ARF5 | 7 | ADP ribosylation factor 5 | ENSG00000004059 |
| | MAP3K10 | 19 | mitogen-activated protein kinase kinase kinase 10 | ENSG00000130758 |
| | AKAP13 | 15 | A-kinase anchoring protein 13 | ENSG00000170776 |
| | TUBB3 | 16 | tubulin beta 3 class III | ENSG00000258947 |
| | RAB39A | 11 | RAB39A, member RAS oncogene family | ENSG00000179331 |
| | FAM208B | 10 | family with sequence similarity 208 member B | ENSG00000108021 |
| | RAB12 | 18 | RAB12, member RAS oncogene family | ENSG00000206418 |
| | ANO7 | 2 | anoctamin 7 | ENSG00000146205 |
| | TUBA3E | 2 | tubulin alpha 3e | ENSG00000152086 |
| | S100A7A | 1 | S100 calcium binding protein A7A | ENSG00000184330 |
| | RAB43 | 3 | RAB43, member RAS oncogene family | ENSG00000172780 |
| | MAP7D3 | X | MAP7 domain containing 3 | ENSG00000129680 |
| | RASEF | 9 | RAS and EF-hand domain containing | ENSG00000165105 |
| | HIST3H2BB | 1 | histone cluster 3 H2B family member b | ENSG00000196890 |
| | SPATA5 | 4 | spermatogenesis associated 5 | ENSG00000145375 |
| | SYNE1 | 6 | spectrin repeat containing nuclear envelope protein 1 | ENSG00000131018 |
| | RB1CC1 | 8 | RB1 inducible coiled-coil 1 | ENSG00000023287 |
| | TTC28 | 22 | tetratricopeptide repeat domain 28 | ENSG00000100154 |
| | RAB39B | X | RAB39B, member RAS oncogene family | ENSG00000155961 |
| | IL12RB2 | 1 | interleukin 12 receptor subunit beta 2 | ENSG00000081985 |
| | TUBB2B | 6 | tubulin beta 2B class IIb | ENSG00000137285 |
| | RAB34 | 17 | RAB34, member RAS oncogene family | ENSG00000109113 |
| | LACRT | 12 | lacritin | ENSG00000135413 |
| | RAB33B | 4 | RAB33B, member RAS oncogene family | ENSG00000172007 |
| | RAB6B | 3 | RAB6B, member RAS oncogene family | ENSG00000154917 |
| | COG5 | 7 | component of oligomeric golgi complex 5 | ENSG00000164597 |
| | NOSIP | 19 | nitric oxide synthase interacting protein | ENSG00000142546 |
| | WNK2 | 9 | WNK lysine deficient protein kinase 2 | ENSG00000165238 |
| | RAB27B | 18 | RAB27B, member RAS oncogene family | ENSG00000041353 |
| | PPL | 16 | periplakin | ENSG00000118898 |
| | KRT34 | 17 | keratin 34 | ENSG00000131737 |
| | PNP | 14 | purine nucleoside phosphorylase | ENSG00000198805 |
| | CST4 | 20 | cystatin S | ENSG00000101441 |
| | CST1 | 20 | cystatin SN | ENSG00000170373 |
| | ANXA1 | 9 | annexin A1 | ENSG00000135046 |
| | SEMG1 | 20 | semenogelin I | ENSG00000124233 |
| | CAPN1 | 11 | calpain 1 | ENSG00000014216 |
| | PRSS1 | 7 | protease, serine 1 | ENSG00000204983 |
| | HSP90AA1 | 14 | heat shock protein 90 alpha family class A member 1 | ENSG00000080824 |
| | GSTP1 | 11 | glutathione S-transferase pi 1 | ENSG00000084207 |
| | HARS | 5 | histidyl-tRNA synthetase | ENSG00000170445 |
| | DES | 2 | desmin | ENSG00000175084 |
| | GM2A | 5 | GM2 ganglioside activator | ENSG00000196743 |
| | RAB3B | 1 | RAB3B, member RAS oncogene family | ENSG00000169213 |
| | RAB4A | 1 | RAB4A, member RAS oncogene family | ENSG00000168118 |
| | PSMA1 | 11 | proteasome subunit alpha 1 | ENSG00000129084 |
| | CAPZB | 1 | capping actin protein of muscle Z-line beta subunit | ENSG00000077549 |
| | ALDH9A1 | 1 | aldehyde dehydrogenase 9 family member A1 | ENSG00000143149 |
| | PSMB3 | 17 | proteasome subunit beta 3 | ENSG00000277791 |
| | SERPINB8 | 18 | serpin family B member 8 | ENSG00000166401 |
| | RAB13 | 1 | RAB13, member RAS oncogene family | ENSG00000143545 |
| | HIST1H4I | 6 | histone cluster 1 H4 family member i | ENSG00000276180 |
| | HIST1H4K | 6 | histone cluster 1 H4 family member k | ENSG00000273542 |
| | HIST1H4J | 6 | histone cluster 1 H4 family member j | ENSG00000197238 |

TABLE 10-continued

| Exemplary genes identified in mass spectrometric analysis of skin samples | | | | |
|---|---|---|---|---|
| X = more preferable | gene symbol | chr | gene description | Ensembl gene identifier |
| | HIST1H4L | 6 | histone cluster 1 H4 family member l | ENSG00000275126 |
| | HIST2H4A | 1 | histone cluster 2 H4 family member a | ENSG00000270882 |
| | HIST2H4B | 1 | histone cluster 2 H4 family member b | ENSG00000270276 |
| | HIST1H4A | 6 | histone cluster 1 H4 family member a | ENSG00000278637 |
| | HIST1H4B | 6 | histone cluster 1 H4 family member b | ENSG00000278705 |
| | HIST1H4C | 6 | histone cluster 1 H4 family member c | ENSG00000197061 |
| | HIST1H4D | 6 | histone cluster 1 H4 family member d | ENSG00000277157 |
| | HIST1H4E | 6 | histone cluster 1 H4 family member e | ENSG00000276966 |
| | HIST1H4F | 6 | histone cluster 1 H4 family member f | ENSG00000274618 |
| | HIST1H4H | 6 | histone cluster 1 H4 family member h | ENSG00000158406 |
| | HIST4H4 | 12 | histone cluster 4 H4 | ENSG00000197837 |
| | SEMG2 | 20 | semenogelin II | ENSG00000124157 |
| | MAP2K5 | 15 | mitogen-activated protein kinase kinase 5 | ENSG00000137764 |
| | TUBA3D | 2 | tubulin alpha 3d | ENSG00000075886 |
| | TUBA3C | 13 | tubulin alpha 3c | ENSG00000198033 |
| | CCDC40 | 17 | coiled-coil domain containing 40 | ENSG00000141519 |
| | KRT40 | 17 | keratin 40 | ENSG00000204889 |
| | SDR9C7 | 12 | short chain dehydrogenase/reductase family 9C member 7 | ENSG00000170426 |
| | SHROOM3 | 4 | shroom family member 3 | ENSG00000138771 |
| | RAB3C | 5 | RAB3C, member RAS oncogene family | ENSG00000152932 |
| | S100A16 | 1 | S100 calcium binding protein A16 | ENSG00000188643 |
| | SPEF2 | 5 | sperm flagellar 2 | ENSG00000152582 |
| | KIF13B | 8 | kinesin family member 13B | ENSG00000197892 |
| | TUBA8 | 22 | tubulin alpha 8 | ENSG00000183785 |
| | TGM5 | 15 | transglutaminase 5 | ENSG00000104055 |
| | CREG1 | 1 | cellular repressor of E1A stimulated genes 1 | ENSG00000143162 |
| | PGK1 | X | phosphoglycerate kinase 1 | ENSG00000102144 |
| | RAB3A | 19 | RAB3A, member RAS oncogene family | ENSG00000105649 |
| | RAB6A | 11 | RAB6A, member RAS oncogene family | ENSG00000175582 |
| | CALML3 | 10 | calmodulin like 3 | ENSG00000178363 |
| | PSMB6 | 17 | proteasome subunit beta 6 | ENSG00000142507 |
| | KDM5A | 12 | lysine demethylase 5A | ENSG00000073614 |
| | HSPA9 | 5 | heat shock protein family A (Hsp70) member 9 | ENSG00000113013 |
| | GDI2 | 10 | GDP dissociation inhibitor 2 | ENSG00000057608 |
| | SCAP | 3 | SREBF chaperone | ENSG00000114650 |
| | RAB11B | 19 | RAB11B, member RAS oncogene family | ENSG00000185236 |
| | UGP2 | 2 | UDP-glucose pyrophosphorylase 2 | ENSG00000169764 |
| | RAB41 | X | RAB41, member RAS oncogene family | ENSG00000147127 |
| | ZFYVE27 | 10 | zinc finger FYVE-type containing 27 | ENSG00000155256 |
| | REEP3 | 10 | receptor accessory protein 3 | ENSG00000165476 |
| | PLBD1 | 12 | phospholipase B domain containing 1 | ENSG00000121316 |
| | HIST2H2AB | 1 | histone cluster 2 H2A family member b | ENSG00000184270 |
| | H2AFZ | 4 | H2A histone family member Z | ENSG00000164032 |
| | POTEI | 2 | POTE ankyrin domain family member I | ENSG00000196834 |
| | EEF2 | 19 | eukaryotic translation elongation factor 2 | ENSG00000167658 |
| | PSMA3 | 14 | proteasome subunit alpha 3 | ENSG00000100567 |
| | S100A11 | 1 | S100 calcium binding protein A11 | ENSG00000163191 |
| | MYH9 | 22 | myosin heavy chain 9 | ENSG00000100345 |
| | RAB11A | 15 | RAB11A, member RAS oncogene family | ENSG00000103769 |
| | ACTA2 | 10 | actin, alpha 2, smooth muscle, aorta | ENSG00000107796 |
| | KRT33B | 17 | keratin 33B | ENSG00000131738 |
| | LGALSL | 2 | galectin like | ENSG00000119862 |
| | ACTBL2 | 5 | actin, beta like 2 | ENSG00000169067 |
| | H2AFV | 7 | H2A histone family member V | ENSG00000105968 |
| | DLG5 | 10 | discs large MAGUK scaffold protein 5 | ENSG00000151208 |
| | MUCL1 | 12 | mucin like 1 | ENSG00000172551 |
| | ALOXE3 | 17 | arachidonate lipoxygenase 3 | ENSG00000179148 |
| | RNASE7 | 14 | ribonuclease A family member 7 | ENSG00000165799 |
| | KRT37 | 17 | keratin 37 | ENSG00000108417 |
| | FMNL1 | 17 | formin like 1 | ENSG00000184922 |
| | RAB3D | 19 | RAB3D, member RAS oncogene family | ENSG00000105514 |
| | TPM3 | 1 | tropomyosin 3 | ENSG00000143549 |
| | HIST1H2AG | 6 | histone cluster 1 H2A family member g | ENSG00000196787 |
| | HIST1H2AI | 6 | histone cluster 1 H2A family member i | ENSG00000196747 |
| | HIST1H2AK | 6 | histone cluster 1 H2A family member k | ENSG00000275221 |
| | HIST1H2AM | 6 | histone cluster 1 H2A family member m | ENSG00000278677 |
| | HIST1H2AL | 6 | histone cluster 1 H2A family member l | ENSG00000276903 |
| | H2AFX | 11 | H2A histone family member X | ENSG00000188486 |
| | HIST1H2AD | 6 | histone cluster 1 H2A family member d | ENSG00000196866 |

TABLE 10-continued

Exemplary genes identified in mass spectrometric analysis of skin samples

| X = more preferable | gene symbol | chr | gene description | Ensembl gene identifier |
|---|---|---|---|---|
| | SERPINB4 | 18 | serpin family B member 4 | ENSG00000206073 |
| | EIF3E | 8 | eukaryotic translation initiation factor 3 subunit E | ENSG00000104408 |
| | RAN | 12 | RAN, member RAS oncogene family | ENSG00000132341 |
| | ACTG2 | 2 | actin, gamma 2, smooth muscle, enteric | ENSG00000163017 |
| | HIST2H2AC | 1 | histone cluster 2 H2A family member c | ENSG00000184260 |
| | HIST2H2AA3 | 1 | histone cluster 2 H2A family member a3 | ENSG00000203812 |
| | HIST2H2AA4 | 1 | histone cluster 2 H2A family member a4 | ENSG00000272196 |
| | RAB44 | 6 | RAB44, member RAS oncogene family | ENSG00000255587 |
| | HIST1H2BA | 6 | histone cluster 1 H2B family member a | ENSG00000146047 |
| | HIST1H2AH | 6 | histone cluster 1 H2A family member h | ENSG00000274997 |
| | HIST1H2AA | 6 | histone cluster 1 H2A family member a | ENSG00000164508 |
| | HIST1H2AJ | 6 | histone cluster 1 H2A family member j | ENSG00000276368 |
| | KRT82 | 12 | keratin 82 | ENSG00000161850 |
| | HIST1H2BK | 6 | histone cluster 1 H2B family member k | ENSG00000197903 |
| | CSTA | 3 | cystatin A | ENSG00000121552 |
| | HIST1H2AB | 6 | histone cluster 1 H2A family member b | ENSG00000278463 |
| | HIST1H2AE | 6 | histone cluster 1 H2A family member e | ENSG00000277075 |
| | HIST1H2BJ | 6 | histone cluster 1 H2B family member j | ENSG00000124635 |
| | HIST1H2BO | 6 | histone cluster 1 H2B family member o | ENSG00000274641 |
| | HIST1H2BB | 6 | histone cluster 1 H2B family member b | ENSG00000276410 |
| | VCP | 9 | valosin containing protein | ENSG00000165280 |
| | H2BFS | 21 | H2B histone family member S | ENSG00000234289 |
| | HIST1H2BD | 6 | histone cluster 1 H2B family member d | ENSG00000158373 |
| | PSMA6 | 14 | proteasome subunit alpha 6 | ENSG00000100902 |
| | YWHAG | 7 | tyrosine 3-monooxygenase/tryptophan 5-monooxygenase activation protein gamma | ENSG00000170027 |
| | HIST1H2BC | 6 | histone cluster 1 H2B family member c | ENSG00000180596 |
| | HIST1H2BF | 6 | histone cluster 1 H2B family member f | ENSG00000277224 |
| | HIST1H2BE | 6 | histone cluster 1 H2B family member e | ENSG00000274290 |
| | HIST1H2BG | 6 | histone cluster 1 H2B family member g | ENSG00000273802 |
| | HIST1H2BI | 6 | histone cluster 1 H2B family member i | ENSG00000278588 |
| | ACTC1 | 15 | actin, alpha, cardiac muscle 1 | ENSG00000159251 |
| | ACTA1 | 1 | actin, alpha 1, skeletal muscle | ENSG00000143632 |
| | TUBA1B | 12 | tubulin alpha 1b | ENSG00000123416 |
| | PLEC | 8 | plectin | ENSG00000178209 |
| | HIST2H2BE | 1 | histone cluster 2 H2B family member e | ENSG00000184678 |
| | HIST2H2BF | 1 | histone cluster 2 H2B family member f | ENSG00000203814 |
| | PPRC1 | 10 | peroxisome proliferator-activated receptor gamma, coactivator-related 1 | ENSG00000148840 |
| | SBSN | 19 | suprabasin | ENSG00000189001 |
| | TUBA1A | 12 | tubulin alpha 1a | ENSG00000167552 |
| | HIST3H2A | 1 | histone cluster 3 H2A | ENSG00000181218 |
| | HIST1H2AC | 6 | histone cluster 1 H2A family member c | ENSG00000180573 |
| | HIST1H2BH | 6 | histone cluster 1 H2B family member h | ENSG00000275713 |
| | HIST1H2BN | 6 | histone cluster 1 H2B family member n | ENSG00000233822 |
| | HIST1H2BM | 6 | histone cluster 1 H2B family member m | ENSG00000273703 |
| | HIST1H2BL | 6 | histone cluster 1 H2B family member l | ENSG00000185130 |
| | TUBA1C | 12 | tubulin alpha 1c | ENSG00000167553 |
| | THRA | 17 | thyroid hormone receptor, alpha | ENSG00000126351 |
| | GLRX | 5 | glutaredoxin | ENSG00000173221 |
| | AHNAK | 11 | AHNAK nucleoprotein | ENSG00000124942 |
| | SYPL1 | 7 | synaptophysin like 1 | ENSG00000008282 |
| | RRBP1 | 20 | ribosome binding protein 1 | ENSG00000125844 |
| | PSMD14 | 2 | proteasome 26S subunit, non-ATPase 14 | ENSG00000115233 |
| | ALDOA | 16 | aldolase, fructose-bisphosphate A | ENSG00000149925 |
| | THRB | 3 | thyroid hormone receptor beta | ENSG00000151090 |
| | KRT32 | 17 | keratin 32 | ENSG00000108759 |
| | TADA2B | 4 | transcriptional adaptor 2B | ENSG00000173011 |
| | HSPA1A | 6 | heat shock protein family A (Hsp70) member 1A | ENSG00000204389 |
| | HSPA1B | 6 | heat shock protein family A (Hsp70) member 1B | ENSG00000204388 |
| | YWHAQ | 2 | tyrosine 3-monooxygenase/tryptophan 5-monooxygenase activation protein theta | ENSG00000134308 |
| | PSMA5 | 1 | proteasome subunit alpha 5 | ENSG00000143106 |
| | LCN1 | 9 | lipocalin 1 | ENSG00000160349 |
| | KRT31 | 17 | keratin 31 | ENSG00000094796 |
| | C1orf68 | 1 | chromosome 1 open reading frame 68 | ENSG00000198854 |
| | DBF4B | 17 | DBF4 zinc finger B | ENSG00000161692 |
| | PSMA8 | 18 | proteasome subunit alpha 8 | ENSG00000154611 |
| | A2ML1 | 12 | alpha-2-macroglobulin like 1 | ENSG00000166535 |
| | PSMA7 | 20 | proteasome subunit alpha 7 | ENSG00000101182 |
| | KRT38 | 17 | keratin 38 | ENSG00000171360 |

TABLE 10-continued

Exemplary genes identified in mass spectrometric analysis of skin samples

| X = more preferable | gene symbol | chr | gene description | Ensembl gene identifier |
|---|---|---|---|---|
| | LMNA | 1 | lamin A/C | ENSG00000160789 |
| | TXN | 9 | thioredoxin | ENSG00000136810 |
| | CTSA | 20 | cathepsin A | ENSG00000064601 |
| | HSPA6 | 1 | heat shock protein family A (Hsp70) member 6 | ENSG00000173110 |
| | YWHAB | 20 | tyrosine 3-monooxygenase/tryptophan 5-monooxygenase activation protein beta | ENSG00000166913 |
| | RAB2A | 8 | RAB2A, member RAS oncogene family | ENSG00000104388 |
| | ECM1 | 1 | extracellular matrix protein 1 | ENSG00000143369 |
| | ASPRV1 | 2 | aspartic peptidase, retroviral-like 1 | ENSG00000244617 |
| | NCCRP1 | 19 | non-specific cytotoxic cell receptor protein 1 homolog (zebrafish) | ENSG00000188505 |
| | KRT222 | 17 | keratin 222 | ENSG00000213424 |
| | S100A14 | 1 | S100 calcium binding protein A14 | ENSG00000189334 |
| | ALOX12B | 17 | arachidonate 12-lipoxygenase, 12R type | ENSG00000179477 |
| | RAB2B | 14 | RAB2B, member RAS oncogene family | ENSG00000129472 |
| | CPA4 | 7 | carboxypeptidase A4 | ENSG00000128510 |
| | KRT83 | 12 | keratin 83 | ENSG00000170523 |
| | YWHAH | 22 | tyrosine 3-monooxygenase/tryptophan 5-monooxygenase activation protein eta | ENSG00000128245 |
| | RAB35 | 12 | RAB35, member RAS oncogene family | ENSG00000111737 |
| | LOR | 1 | loricrin | ENSG00000203782 |
| | RAB8A | 19 | RAB8A, member RAS oncogene family | ENSG00000167461 |
| | RAB10 | 2 | RAB10, member RAS oncogene family | ENSG00000084733 |
| | KRT81 | 12 | keratin 81 | ENSG00000205426 |
| | KRT35 | 17 | keratin 35 | ENSG00000197079 |
| | KRT86 | 12 | keratin 86 | ENSG00000170442 |
| | ALB | 4 | albumin | ENSG00000163631 |
| | AZGP1 | 7 | alpha-2-glycoprotein 1, zinc-binding | ENSG00000160862 |
| | SFN | 1 | stratifin | ENSG00000175793 |
| | YWHAZ | 8 | tyrosine 3-monooxygenase/tryptophan 5-monooxygenase activation protein zeta | ENSG00000164924 |
| | KRT85 | 12 | keratin 85 | ENSG00000135443 |
| | POTEE | 2 | POTE ankyrin domain family member E | ENSG00000188219 |
| | KRT26 | 17 | keratin 26 | ENSG00000186393 |
| | RAB8B | 15 | RAB8B, member RAS oncogene family | ENSG00000166128 |
| | ENO2 | 12 | enolase 2 | ENSG00000111674 |
| | UBC | 12 | ubiquitin C | ENSG00000150991 |
| | FLG | 1 | filaggrin | ENSG00000143631 |
| | CTNNB1 | 3 | catenin beta 1 | ENSG00000168036 |
| | KRT20 | 17 | keratin 20 | ENSG00000171431 |
| | PRPH | 12 | peripherin | ENSG00000135406 |
| | YWHAE | 17 | tyrosine 3-monooxygenase/tryptophan 5-monooxygenase activation protein epsilon | ENSG00000108953 |
| | POTEF | 2 | POTE ankyrin domain family member F | ENSG00000196604 |
| | ENO3 | 17 | enolase 3 | ENSG00000108515 |
| | HSP90B1 | 12 | heat shock protein 90 beta family member 1 | ENSG00000166598 |
| | RAB15 | 14 | RAB15, member RAS oncogene family | ENSG00000139998 |
| | RPS27A | 2 | ribosomal protein S27a | ENSG00000143947 |
| | FABP5 | 8 | fatty acid binding protein 5 | ENSG00000164687 |
| | PKP1 | 1 | plakophilin 1 | ENSG00000081277 |
| | KRT74 | 12 | keratin 74 | ENSG00000170484 |
| | GSDMA | 17 | gasdermin A | ENSG00000167914 |
| | S100A8 | 1 | S100 calcium binding protein A8 | ENSG00000143546 |
| | HSP90AB1 | 6 | heat shock protein 90 alpha family class B member 1 | ENSG00000096384 |
| | UBB | 17 | ubiquitin B | ENSG00000170315 |
| | BLMH | 17 | bleomycin hydrolase | ENSG00000108578 |
| | GGCT | 7 | gamma-glutamylcyclotransferase | ENSG00000006625 |
| | HSPA2 | 14 | heat shock protein family A (Hsp70) member 2 | ENSG00000126803 |
| | RAB1B | 11 | RAB1B, member RAS oncogene family | ENSG00000174903 |
| | CAT | 11 | catalase | ENSG00000121691 |
| | CTSD | 11 | cathepsin D | ENSG00000117984 |
| | SERPINB3 | 18 | serpin family B member 3 | ENSG00000057149 |
| | UBA52 | 19 | ubiquitin A-52 residue ribosomal protein fusion product 1 | ENSG00000221983 |
| | EEF1A2 | 20 | eukaryotic translation elongation factor 1 alpha 2 | ENSG00000101210 |
| | DSC1 | 18 | desmocollin 1 | ENSG00000134765 |
| | KRT25 | 17 | keratin 25 | ENSG00000204897 |
| | POF1B | X | premature ovarian failure, 1B | ENSG00000124429 |
| | KRT12 | 17 | keratin 12 | ENSG00000187242 |

TABLE 10-continued

Exemplary genes identified in mass spectrometric analysis of skin samples

| X = more preferable | gene symbol | chr | gene description | Ensembl gene identifier |
|---|---|---|---|---|
| | KRT36 | 17 | keratin 36 | ENSG00000126337 |
| | S100A9 | 1 | S100 calcium binding protein A9 | ENSG00000163220 |
| | PKM | 15 | pyruvate kinase, muscle | ENSG00000067225 |
| | S100A7 | 1 | S100 calcium binding protein A7 | ENSG00000143556 |
| | HAL | 12 | histidine ammonia-lyase | ENSG00000084110 |
| | CALML5 | 10 | calmodulin like 5 | ENSG00000178372 |
| | PIP | 7 | prolactin induced protein | ENSG00000159763 |
| | LGALS7 | 19 | galectin 7 | ENSG00000205076 |
| | LGALS7B | 19 | galectin 7B | ENSG00000178934 |
| | HSPB1 | 7 | heat shock protein family B (small) member 1 | ENSG00000106211 |
| | RAB1A | 2 | RAB1A, member RAS oncogene family | ENSG00000138069 |
| | GAPDHS | 19 | glyceraldehyde-3-phosphate dehydrogenase, spermatogenic | ENSG00000105679 |
| X | ANXA2 | 15 | annexin A2 | ENSG00000182718 |
| X | VIM | 10 | vimentin | ENSG00000026025 |
| X | KPRP | 1 | keratinocyte proline rich protein | ENSG00000203786 |
| X | KRT84 | 12 | keratin 84 | ENSG00000161849 |
| X | GFAP | 17 | glial fibrillary acidic protein | ENSG00000131095 |
| X | EIF4A2 | 3 | eukaryotic translation initiation factor 4A2 | ENSG00000156976 |
| X | SERPINB12 | 18 | serpin family B member 12 | ENSG00000166634 |
| X | HSPA5 | 9 | heat shock protein family A (Hsp70) member 5 | ENSG00000044574 |
| X | KRT28 | 17 | keratin 28 | ENSG00000173908 |
| X | KRT73 | 12 | keratin 73 | ENSG00000186049 |
| X | KRT19 | 17 | keratin 19 | ENSG00000171345 |
| X | CASP14 | 19 | caspase 14 | ENSG00000105141 |
| X | EIF4A1 | 17 | eukaryotic translation initiation factor 4A1 | ENSG00000161960 |
| X | DSC3 | 18 | desmocollin 3 | ENSG00000134762 |
| X | KRT72 | 12 | keratin 72 | ENSG00000170486 |
| X | KRT24 | 17 | keratin 24 | ENSG00000167916 |
| X | KRT23 | 17 | keratin 23 | ENSG00000108244 |
| X | ARG1 | 6 | arginase 1 | ENSG00000118520 |
| X | TGM3 | 20 | transglutaminase 3 | ENSG00000125780 |
| X | KRT71 | 12 | keratin 71 | ENSG00000139648 |
| X | ENO1 | 1 | enolase 1 | ENSG00000074800 |
| X | KRT18 | 12 | keratin 18 | ENSG00000111057 |
| X | LYZ | 12 | lysozyme | ENSG00000090382 |
| X | TGM1 | 14 | transglutaminase 1 | ENSG00000092295 |
| X | DCD | 12 | dermcidin | ENSG00000161634 |
| X | PRDX1 | 1 | peroxiredoxin 1 | ENSG00000117450 |
| X | EEF1A1 | 6 | eukaryotic translation elongation factor 1 alpha 1 | ENSG00000156508 |
| X | GAPDH | 12 | glyceraldehyde-3-phosphate dehydrogenase | ENSG00000111640 |
| X | JUP | 17 | junction plakoglobin | ENSG00000173801 |
| X | PRDX2 | 19 | peroxiredoxin 2 | ENSG00000167815 |
| X | KRT27 | 17 | keratin 27 | ENSG00000171446 |
| X | KRT7 | 12 | keratin 7 | ENSG00000135480 |
| X | KRT15 | 17 | keratin 15 | ENSG00000171346 |
| X | FLG2 | 1 | filaggrin family member 2 | ENSG00000143520 |
| X | KRT80 | 12 | keratin 80 | ENSG00000167767 |
| X | KRT75 | 12 | keratin 75 | ENSG00000170454 |
| X | HSPA1L | 6 | heat shock protein family A (Hsp70) member 1 like | ENSG00000204390 |
| X | KRT6A | 12 | keratin 6A | ENSG00000205420 |
| X | HRNR | 1 | hornerin | ENSG00000197915 |
| X | HSPA8 | 11 | heat shock protein family A (Hsp70) member 8 | ENSG00000109971 |
| X | DSP | 6 | desmoplakin | ENSG00000096696 |
| X | KRT76 | 12 | keratin 76 | ENSG00000185069 |
| X | KRT13 | 17 | keratin 13 | ENSG00000171401 |
| X | DSG1 | 18 | desmoglein 1 | ENSG00000134760 |
| X | KRT79 | 12 | keratin 79 | ENSG00000185640 |
| X | ACTB | 7 | actin beta | ENSG00000075624 |
| X | ACTG1 | 17 | actin gamma 1 | ENSG00000184009 |
| X | KRT17 | 17 | keratin 17 | ENSG00000128422 |
| X | KRT78 | 12 | keratin 78 | ENSG00000170423 |
| X | KRT8 | 12 | keratin 8 | ENSG00000170421 |
| X | KRT3 | 12 | keratin 3 | ENSG00000186442 |
| X | KRT4 | 12 | keratin 4 | ENSG00000170477 |
| X | KRT6C | 12 | keratin 6C | ENSG00000170465 |
| X | KRT16 | 17 | keratin 16 | ENSG00000186832 |

TABLE 10-continued

| Exemplary genes identified in mass spectrometric analysis of skin samples | | | | |
|---|---|---|---|---|
| X = more preferable | gene symbol | chr | gene description | Ensembl gene identifier |
| X | KRT77 | 12 | keratin 77 | ENSG00000189182 |
| X | KRT5 | 12 | keratin 5 | ENSG00000186081 |
| X | KRT14 | 17 | keratin 14 | ENSG00000186847 |
| X | KRT6B | 12 | keratin 6B | ENSG00000185479 |
| X | KRT9 | 17 | keratin 9 | ENSG00000171403 |
| X | KRT2 | 12 | keratin 2 | ENSG00000172867 |
| X | KRT1 | 12 | keratin 1 | ENSG00000167768 |
| X | KRT10 | 17 | keratin 10 | ENSG00000186395 |

Example 46: Exemplary GVP Detectable in Hair Samples

An exemplary set of GVPs that can be used in methods and systems herein described as well as in related databases is reported herein. In particular, the exemplary set of GVP comprises genes validated as proteomically detectable in hair samples of a *Homo Sapiens* which can be used in methods and systems to detect a genetic variation and/or perform a genetic variation analysis, as well as in related databases, in accordance with the various aspects of the present disclosure.

Specifically, Table 11 shows a list of exemplary GVP detectable in hair samples of human beings. The fields in Table 11 are the chromosome where the gene is located (CHR), the gene name (gene name), mutation identifier (mutation ID), the sequence of the corresponding mutated peptide (mutated peptide (GVP)), the related sequence identifier in the sequence listing of the instant disclosure (SEQ ID NO), and the subpopulations including all populations (ALL), Non-Finnish European subpopulation (NFE), African subpopulation (AFR), East Asian subpopulation (EAS), South Asian subpopulation (SAS), and Latino subpopulation (AMR).

The exemplary GVPs of Table 11 can be therefore be used in methods and systems of the disclosure wherein the sample comprises hair samples from human beings.

TABLE 11

| Exemplary GVP detectable in hair samples | | | | | | | | | | |
|---|---|---|---|---|---|---|---|---|---|---|
| CHR | gene name | mutation ID | mutated peptide (GVP) | SEQ ID NO | ALL | NFE | AFR | EAS | SAS | AMR |
| 17 | KRT33B | rs61741663 | AAPAVDLNR | 146 | | | X | | | |
| 8 | RIDA | rs146537203 | AAYQVAVLPK | 147 | | | | | | |
| 17 | KRTAP1-1 | rs149188249 | ACCQTSFCGFR | 148 | | | | X | | X |
| 21 | KRTAP11-1 | rs71321355 | ACQPTCYQR | 149 | X | X | X | | X | X |
| 21 | KRTAP11-1 | rs71321355 | ACQPTCYQRTSCVSNPCQ VTCSR | 150 | X | X | X | | X | X |
| 17 | KRT32 | rs2071561 | ADLEAQVEYLKEELMCLK | 151 | | | X | | | |
| 17 | KRT32 | rs2071561 | ADLEAQVEYLKEELMCL KK | 152 | | | X | | | |
| 12 | KRT82 | rs377470048 | ADLETNTEALVQEIDFLK | 153 | | | | | | |
| 17 | KRT32 | rs2604956 | AELERQNQEYQVLLDVR | 154 | X | X | | | | |
| 17 | KRT32 | rs2604956 | AELERQNQEYQVLLDVR AR | 155 | X | X | | | | |
| 12 | KRT81 | rs79897879 | AFRCISACGPRPGR | 156 | | | X | X | | |
| 12 | KRT81 | rs202205489 | AFSCISACGPQPGR | 157 | | | | | | |
| 12 | KRT81 | rs202205489 | AFSCISACGPQPGRC | 158 | | | | | | |
| 2 | POTEF | rs762202335 | AGFASDDAPR | 159 | | | | | | |
| 12 | KRT6B | rs144860693 | AGGSYGFGGAR | 160 | X | X | X | X | X | X |
| 12 | KRT85 | rs61630004 | AGSCGHSF | 161 | | | | | X | |
| 12 | KRT85 | rs61630004 | AGSCGHSFGYR | 162 | | | | | X | |
| 12 | KRT6A | rs11540301 | AIGGGLSSVGGGSSTIKY STTSSSSR | 163 | | | X | | | X |

TABLE 11-continued

| Exemplary GVP detectable in hair samples | | | | | | | | | | |
|---|---|---|---|---|---|---|---|---|---|---|
| CHR | gene name | mutation ID | mutated peptide (GVP) | SEQ ID NO | ALL | NFE | AFR | EAS | SAS | AMR |
| 1 | S100A3 | rs36022742 | AKPLEQAVAAIVCTFQEY AGR | 164 | X | X | X | | X | X |
| 6 | HIST1H1E | rs757147711 | ALAVAGYDVEKNNSR | 165 | | | | | | |
| 17 | GSDMA | rs7212938 | ALETLQER | 166 | | | | | | X |
| 19 | MYH14 | rs680446 | ALRAELEALLSSKDDIGK SVHELER | 167 | | | | | | |
| 12 | KRT81 | rs2071588 | APYRGISCYRGLTGGFGS HSVCR | 168 | X | X | X | X | X | X |
| 17 | KRT32 | rs11078993 | AQMQCMITNVEAQLAEI QADLERQNQEYQVLLDVR | 169 | X | | X | X | X | X |
| 17 | KRT32 | rs2604956 | AQMQCMITNVEAQLAEI RAELERQNQEYQVLLDVR | 170 | X | X | | | | |
| 17 | KRT40 | rs8064733 | ARLEGEINMYR | 171 | X | X | | X | X | X |
| 17 | KRT40 | rs11649834 | ARLEGEINMYR | 172 | X | X | | X | X | X |
| 17 | KRT32 | rs2071563 | ARLEGEINMYR | 173 | X | X | X | X | X | X |
| 17 | KRT32 | rs2604956 | ARYSSQLAQMQCMITNV EAQLAEIRAELERQNQEY QVLLDVR | 174 | X | X | | | | |
| 17 | KRT34 | rs61740668 | ARYSSQLSQVQSLITNVE SQLAEIRCDLEWQNQEY QVLLDVR | 175 | | | | | | |
| 17 | KRT34 | rs2071599 | ARYSSQLSQVQSLITNVE SQLAEIRCDLEWQNQEY QVLLDVR | 176 | X | X | X | X | X | X |
| 17 | KRT37 | rs9916724 | ASAASMCLLANVAHANR | 177 | X | | X | X | | X |
| 17 | KRT33A | rs12937519 | ATQTEELNKQVVSSSEQL QSYQVEIIELRR | 178 | X | X | X | X | X | X |
| 12 | KRT81 | rs4761786 | ATVIRHGETLCR | 179 | | | | | | |
| 13 | TUBA3C | rs36215077 | AVFVDLEPTVLDEVR | 180 | | | | | | |
| 13 | TUBA3C | rs36215077 | AVFVDLEPTVLDEVRTGT YR | 181 | | | | | | |
| 21 | KRTAP11-1 | rs71321355 | CCEPTACQPTCYQRTSCV SNPCQVTCSR | 182 | X | X | X | | X | X |
| 12 | KRT82 | rs61730590 | CCQINIEPIFEGYISALRR | 183 | | | | | | |
| 17 | KRTAP9-6 | rs12938692 | CCQNTCCRTTCCQPTCVT SCCQPSCCSTPCCQPICCG SSCCGQTSCGSSCGQSSS CAPVYCRR | 184 | X | X | X | X | X | |
| 17 | KRTAP9-1 | rs238824 | CCQPCCHPTCYQTTCFRT TCCQPTCCQPTCCR | 185 | | | | | | |
| 17 | KRTAP4-2 | rs389784 | CCQPTCCRPSCGQTTCCR | 186 | | | | | | |
| 17 | KRTAP4-9 | rs7207685 | CCQPTCYRPSCCVSSCCR PQCCQPVCCQPTCCR | 187 | | | | X | | |
| 17 | KRTAP4-6 | rs73983172 | CCRSSCCPSCCQTTCCR | 188 | | | X | | | |
| 17 | KRT34 | rs199674249 | CDLERQNQEYQVLLDVC AR | 189 | | | | | | |
| 17 | KRT34 | rs61740668 | CDLEWQNQEYQVLLDVR | 190 | | | | | | |

TABLE 11-continued

Exemplary GVP detectable in hair samples

| CHR | gene name | mutation ID | mutated peptide (GVP) | SEQ ID NO | ALL | NFE | AFR | EAS | SAS | AMR |
|---|---|---|---|---|---|---|---|---|---|---|
| 12 | KRT83 | rs2857663 | CECCQSNLEPLFAGYIET LRR | 191 | X | X | X | X | X | X |
| 17 | KRT40 | rs17843015 | CEDGVSTSNEKETMQFL NDR | 192 | X | X | X | X | X | X |
| 17 | KRT39 | rs112557906 | CEPSPWTFCK | 193 | | | X | | | |
| 21 | KRTAP11-1 | rs71321355 | CEPTACQPTCYQR | 194 | X | X | X | | X | X |
| 17 | KRTAP1-5 | rs62623375 | CETSCYQPR | 195 | | | X | X | | X |
| 17 | KRTAP4-2 | rs389784 | CFRPQCCQSVCCQPTCCR PSCGQTTCCR | 196 | | | | | | |
| 17 | KRTAP4-7 | rs11655310 | CGQVLCQETCCRPSCCQT TCCR | 197 | | | | X | | |
| 17 | KRTAP4-7 | rs383835 | CGSVCSDQGCSQVLCQE TCCRPSCCQTTCCR | 198 | | | | X | | |
| 17 | KRT35 | rs189378138 | CHYETLVENNRR | 199 | | | | | | |
| 12 | KRT83 | rs2857671 | CKPCGQLNTTCGGGSCG QGRY | 200 | | | | | | |
| 17 | KRT33A | rs754250148 | CQLGDHLNVEVDAAPTV DLNQVLNETR | 201 | | | | | | |
| 17 | KRT33B | rs61741663 | CQLGDRLNVEVDAAPAV DLNR | 202 | | | X | | | |
| 17 | KRT33B | rs61741663 | CQLGDRLNVEVDAAPAV DLNRVLNETR | 203 | | | X | | | |
| 17 | KRT34 | rs139103580 | CQLGDRLNVEVDTAPTV DLNQVLNETR | 204 | | | | | | |
| 12 | KRT83 | rs140635030 | CQNSKLEAAVAQSEQQS EAALSDAR | 205 | | | | | | |
| 17 | KRTAP9-6 | rs12938692 | CQNTCCRTTCCQPTCVTS CCQPSCCSTPCCQPICCGS SCCGQTSCGSSCGQSSSC APVYCR | 206 | X | X | X | X | X | |
| 17 | KRTAP1-5 | rs12943824 | CQPSCCETSCCQPSCCET SCCQPSCWQISSCGTGCG IGGGISYGQEGSSGAVSTR | 207 | | | | | | |
| 17 | KRTAP1-5 | rs62623375 | CQPSCCETSCYQPR | 208 | | | X | X | | X |
| 17 | KRTAP4-2 | rs389784 | CQSVCCQPTCCRPSCGQT TCCR | 209 | | | | | | |
| 17 | KRTAP1-1 | rs149188249 | CQTSFCGFR | 210 | | | | X | | X |
| 17 | KRTAP4-2 | rs62067292 | CQTTCCRTTCCRPSCCVS SCCRPQCCQSVCCQPSCC SPSCCQTTCCR | 211 | | X | | | | |
| 17 | KRTAP4-7 | rs11650484 | CQTTCCRTTCYRPSCCVS SCCRPQCCQSVCCQPTCC RPSCCETTCCHPR | 212 | | | | X | | |
| 17 | KRT32 | rs728300 | CQYEAMVEANHR | 213 | X | X | X | X | X | X |
| 17 | KRT40 | rs721957 | CQYETVLANNRR | 214 | | | | | | |
| 17 | KRTAP4-4 | rs74572864 | CRPQCCQTICCR | 215 | | | | X | | |
| 17 | KRTAP1-3 | rs62622849 | CRTGCGIGGGIGYGQEGS SGAVSTR | 216 | X | | X | X | | X |

TABLE 11-continued

Exemplary GVP detectable in hair samples

| CHR | gene name | mutation ID | mutated peptide (GVP) | SEQ ID NO | ALL | NFE | AFR | EAS | SAS | AMR |
|---|---|---|---|---|---|---|---|---|---|---|
| 17 | KRTAP4-7 | rs11655310 | CSDQGCGQVLCQETCCR PSCCQTTCCR | 217 | | | | X | | |
| 17 | KRT38 | rs138667284 | CTVNALEVK | 218 | | | | | | |
| 17 | KRT38 | rs138667284 | CTVNALEVKR | 219 | | | | | | |
| 17 | KRT40 | rs17843015 | DGVSTSNEKETMQFLND RLASYLEKVR | 220 | X | X | X | X | X | X |
| 12 | KRT81 | rs141587304 | DLNMDCIIDEIK | 221 | | | | | | |
| 12 | KRT81 | rs141587304 | DLNMDCIIDEIKAQYDDI | 222 | | | | | | |
| 12 | KRT83 | rs2852464 | DLNMDCMVAEIK | 223 | X | X | X | X | X | X |
| 12 | KRT83 | rs2852464 | DLNMDCMVAEIKAQYD DIATR | 224 | X | X | X | X | X | X |
| 2 | NEU2 | rs2233391 | DLTDAAIGPAYREWSTFA VGPGHCLQLNDR | 225 | X | | X | | X | X |
| 2 | NEU2 | rs2233390 | DLTDTAIGPAYR | 226 | | | | | | |
| 12 | KRT84 | rs951773 | DMARQLREYQELMNAK LGLDIEIATYR | 227 | | | | | | |
| 1 | SFN | rs149812347 | DMPPTNPIR | 228 | | | | | | |
| 17 | KRT33B | rs12450621 | DNAELKNLIR | 229 | | X | | | X | |
| 17 | KRT33B | rs12450621 | DNAELKNLIRER | 230 | | X | | | X | |
| 17 | KRT31 | rs6503627 | DNVELENLIR | 231 | X | X | | | | |
| 17 | KRT31 | rs6503627 | DNVELENLIRER | 232 | X | X | | | | |
| 17 | KRT32 | rs16966929 | DSLENMLTESEAR | 233 | | | | | | |
| 17 | KRT34 | rs148645199 | DSLENTLTESEAHYSSQL SQMQSLITNVESQLAEIR CDLER | 234 | | | | | | |
| 17 | KRT34 | rs148645199 | DSLENTLTESEAHYSSQL SQMQSLITNVESQLAEIR CDLERQNQEYQVLLDVR | 235 | | | | | | |
| 17 | KRT34 | rs61740668 | DSLENTLTESEAHYSSQL SQVQSLITNVESQLAEIRC DLEW | 236 | | | | | | |
| 17 | KRT32 | rs11078993 | DSLENTLTESEARYSSQL AQMQCMITNVEAQLAEI QADLER | 237 | X | | X | X | X | X |
| 17 | KRT32 | rs11078993 | DSLENTLTESEARYSSQL AQMQCMITNVEAQLAEI QADLERQNQEYQVLLDVR | 238 | X | | X | X | X | X |
| 17 | KRT32 | rs2604956 | DSLENTLTESEARYSSQL AQMQCMITNVEAQLAEI RAELERQNQEYQVLLDVR | 239 | X | X | | | | |
| 17 | KRT39 | rs17843021 | DSQECILMETEAR | 240 | X | X | X | X | X | X |
| 12 | KRT82 | rs377470048 | DVDTAFLMKADLETNTE ALVQEIDFLK | 241 | | | | | | |
| 12 | KRT85 | rs112554450 | EAECVEANSGR | 242 | | | | | | |
| 12 | KRT85 | rs112554450 | EAECVEANSGRLAS | 248243 | | | | | | |
| 12 | KRT85 | rs112554450 | EAECVEANSGRLASELN HVQEVLEGYKK | 244 | | | | | | |

TABLE 11-continued

| Exemplary GVP detectable in hair samples | | | | | | | | | | |
|---|---|---|---|---|---|---|---|---|---|---|
| CHR | gene name | mutation ID | mutated peptide (GVP) | SEQ ID NO | ALL | NFE | AFR | EAS | SAS | AMR |
| 12 | KRT85 | rs112554450 | EAECVEANSGRLASELN HVQEVLEGYKKK | 245 | | | | | | |
| 17 | KRT32 | rs11078993 | EAQLAEIQADLERQNQE YQVLLDVR | 246 | X | | X | X | X | X |
| 12 | KRT86 | rs139895699 | EEINELNCMIQR | 247 | | | | | | |
| 20 | TGM3 | rs6048066 | EEYVQEDAGILFVGSTNR | 248 | | | X | | | |
| 17 | KRT39 | rs7213256 | EHCSACGPLSQILVK | 249 | X | X | | | X | X |
| 17 | KRT32 | rs117304287 | EIMQFLNDR | 250 | | | | | | |
| 17 | KRT32 | rs117304287 | EIMQFLNDRLASYLTR | 251 | | | | | | |
| 17 | KRT32 | rs2604956 | EIRAELERQNQEYQVLLD VR | 252 | X | X | | | | |
| 12 | KRT82 | rs143454001 | ELDVDGIIAEIKAQYDDIT SR | 253 | | | | | | |
| 12 | KRT82 | rs61730589 | ELDVDSIIAEIK | 254 | | | | | | |
| 12 | KRT82 | rs61730589 | ELDVDSIIAEIKAQYDDIA SR | 255 | | | | | | |
| 1 | SFN | rs77755255 | EMPPSNPIR | 256 | | | | | | |
| 16 | PPL | rs2037912 | ENLQLETR | 257 | | | X | | X | |
| 21 | KRTAP11-1 | rs71321355 | EPTACQPTCYQR | 258 | X | X | X | | X | X |
| 17 | KRT31 | rs6503627 | ERDNVELENLIR | 259 | X | X | | | | |
| 17 | KRT31 | rs6503627 | ERDNVELENLIRER | 260 | X | X | | | | |
| 17 | KRT33B | rs34771886 | ESQLAEIHSDLERQNQEY QVLLDVR | 261 | | | | | | |
| 21 | KRTAP11-1 | rs71321355 | ETCCEPTACQPTCYQR | 262 | X | X | X | | X | X |
| 17 | KRTAP4-9 | rs149483591 | ETCCHPSCCETTCCR | 263 | | | X | | | |
| 17 | KRTAP4-11 | rs113376601 | ETCCHPSCCETTCCR | 264 | X | | X | X | | X |
| 17 | KRT33A | rs140696036 | ETMQFLNDCLASYLEK | 265 | | | | | | |
| 17 | KRT33A | rs140696036 | ETMQFLNDCLASYLEKVR | 266 | | | | | | |
| 17 | KRT33A | rs140696036 | ETMQFLNDCLASYLEKV RQLERDNAELENLIR | 267 | | | | | | |
| 17 | KRT34 | rs112570296 | EVEQWFATQTEELNKQV VSSSEQLQSCQVEIIELR | 268 | | | | | | |
| 17 | KRT34 | rs112570296 | EVEQWFATQTEELNKQV VSSSEQLQSCQVEIIELRR | 269 | | | | | | |
| 17 | KRT33A | rs12937519 | EVEQWFATQTEELNKQV VSSSEQLQSYQVEIIE | 270 | X | X | X | X | X | X |
| 17 | KRT33A | rs12937519 | EVEQWFATQTEELNKQV VSSSEQLQSYQVEIIELR | 271 | X | X | X | X | X | X |
| 17 | KRT33A | rs12937519 | EVEQWFATQTEELNKQV VSSSEQLQSYQVEIIELRR | 272 | X | X | X | X | X | X |
| 17 | KRT34 | rs77779192 | EVEQWFATQTEK | 273 | | | | | | |
| 17 | KRT34 | rs77779192 | EVEQWFATQTEKLNK | 274 | | | | | | |
| 17 | KRT34 | rs77779192 | EVEQWFATQTEKLNKQV VSSSEQLQSCQAEIIELRR | 275 | | | | | | |

TABLE 11-continued

| Exemplary GVP detectable in hair samples | | | | | | | | | | |
|---|---|---|---|---|---|---|---|---|---|---|
| CHR | gene name | mutation ID | mutated peptide (GVP) | SEQ ID NO | ALL | NFE | AFR | EAS | SAS | AMR |
| 20 | TGM3 | rs149720612 | FDILPSQSGTK | 276 | | | | | | |
| 12 | KRT86 | rs58717266 | FLEQQNKLLETKLPFYQNR | 277 | X | X | | X | X | X |
| 12 | KRT83 | rs2857663 | FLEQQNKLLETKLQFYQ NCECCQSNLEPLFAGYIE TLRR | 278 | X | X | X | X | X | X |
| 12 | KRT82 | rs377470048 | FLMKADLETNTEALVQEI DFLKSLYEEEICLLQSQIS ETSVIVK | 279 | | | | | | |
| 17 | KRTAP1-3 | rs62622849 | FPSFSTSGTCSSSCCQPSC CETSCCQPSCCQTSSCRT GCGIGGGIGYGQEGSSGA VSTR | 280 | X | | X | X | | X |
| 12 | KRT81 | rs79897879 | FRCISACGPRPGR | 281 | | | X | X | | |
| 12 | KRT81 | rs79897879 | FRCISACGPRPGRCCITAA PYR | 282 | | | X | X | | |
| 17 | KRT39 | rs142154718 | FSLDDCNWYGEGINSNE KETMQILNER | 283 | | | | | | |
| 17 | KRT39 | rs778437878 | FSLDDCSR | 284 | | | | | | |
| 17 | KRTAP1-1 | rs35024033 | FSTGGTCDSSCCQPSCCE TSCCQPSCYQTSSYGTGC GIGGGIGYGQEGSSGAVS TR | 285 | | | X | | | |
| 12 | KRT82 | rs1732263 | GAFLYDPCGVSTPVLSTG VLR | 286 | | | X | | X | |
| 12 | KRT82 | rs2658658 | GAFLYEPCGVSMPVLSTG VLR | 287 | X | | X | X | X | X |
| 17 | KRTAP1-3 | rs142863014 | GCGTGGGIGYGQEGSSG AVSTR | 288 | | | | | | |
| 11 | TRIM29 | rs11604169 | GCPSLMR | 289 | | | | X | | X |
| 21 | KRTAP13-2 | rs3804010 | GCQEICWEPTSCQTSYVE SRPCQTSCYRPR | 290 | X | X | X | X | X | X |
| 21 | KRTAP13-2 | rs3804010 | GCQEICWEPTSCQTSYVE SRPCQTSCYRPRT | 291 | X | X | X | X | X | X |
| 21 | KRTAP19-5 | rs117415039 | GCRPSCYGGYGFSGFY | 292 | | | | | | |
| 12 | KRT81 | rs2071588 | GFGSHSVCR | 293 | X | X | X | X | X | X |
| 17 | KRTAP1-3 | rs62622849 | GFPSFSTSGTCSSSCCQPS CCETSCCQPSCCQTSSCR TGCGIGGGIGYGQEGSSG AVSTR | 294 | X | | X | X | | X |
| 21 | KRTAP13-2 | rs61748317 | GFSYPSNLVYSTDLCSPSI CQLGSSLYR | 295 | | | | | | |
| 12 | KRT81 | rs2071588 | GGFGSHSVCR | 296 | X | X | X | X | X | X |
| 12 | KRT2 | rs2634041 | GGGFGGGSGFGGGSGFS GGGFGGGGFGGGR | 297 | X | X | X | X | | X |
| 12 | KRT2 | rs76412202 | GGGFGGGSSFGGGSGFSG GGFSGGGFGGGR | 298 | | | | | | |
| 12 | KRT84 | rs79539700 | GGPDFGYR | 299 | | | | | | |
| 1 | SELENBP1 | rs72710112 | GGPVQVLEDK | 300 | | | | | | |
| 1 | SELENBP1 | rs72710112 | GGPVQVLEDKELK | 301 | | | | | | |

TABLE 11-continued

| Exemplary GVP detectable in hair samples | | | | | | | | | | |
|---|---|---|---|---|---|---|---|---|---|---|
| CHR | gene name | mutation ID | mutated peptide (GVP) | SEQ ID NO | ALL | NFE | AFR | EAS | SAS | AMR |
| 17 | KRTAP4-11 | rs349771 | GGVSCHTTCYRPTCVISS CPRPLC | 302 | | | X | X | | X |
| 17 | KRTAP4-11 | rs349771 | GGVSCHTTCYRPTCVISS CPRPLCCASSC | 303 | | | X | X | | X |
| 17 | KRTAP4-11 | rs349771 | GGVSCHTTCYRPTCVISS CPRPLCCASSCC | 304 | | | X | X | | X |
| 5 | HEXB | rs10805890 | GILVDTSR | 305 | X | X | | X | X | X |
| 12 | KRT83 | rs2857671 | GLCKPCGQLNTTCGGGS CGQGRY | 306 | | | | | | |
| 1 | PKP1 | rs142096411 | GLPQIAHLLQSGNSDVVR | 307 | | | | | | |
| 12 | KRT82 | rs201747652 | GLQALGCLGSR | 308 | | | | | | |
| 12 | KRT81 | rs2071588 | GLTGGFGSHSVCR | 309 | X | X | X | X | X | X |
| 12 | KRT81 | rs2071588 | GLTGGFGSHSVCRG | 310 | X | X | X | X | X | X |
| 12 | KRT81 | rs2071588 | GLTGGFGSHSVCRGFR | 311 | X | X | X | X | X | X |
| 12 | KRT81 | rs2071588 | GLTGGFGSHSVCRGFRA | 312 | X | X | X | X | X | X |
| 12 | KRT6B | rs28538343 | GPGFPVCPPGGIQEVTVN QNLLTPLNLQIDPAIQR | 313 | X | X | X | X | X | X |
| 17 | KRTAP1-5 | rs145881217 | GQEGSSGAVSTCIR | 314 | | | | | | |
| 12 | KRT83 | rs2857671 | GQLNTTCGGGSCGQGRY | 315 | | | | | | |
| 6 | DSP | rs6929069 | GQSEADSDKNATILELR | 316 | X | X | X | X | X | X |
| 17 | KRTAP4-7 | rs11655310 | GQVLCQETCCRPSCCQTT CCR | 317 | | | | X | | |
| 17 | KRTAP4-11 | rs140898464 | GRVSCHTTCYRPTCVISS CPRPVCCASSCC | 318 | | | X | X | | X |
| 12 | KRT86 | rs57242951 | GSCGRSFGYHSGGVCGPS PPCITTVSVNESLLTPLNL EIDPNAQCVKQEEK | 319 | | | | | | |
| 12 | KRT81 | rs2071588 | GSHSVCR | 320 | X | X | X | X | X | X |
| 17 | KRTAP4-7 | rs11655310 | GSVCSDQGCGQDLCQET CCRPSCCQTTCCR | 321 | | | | X | | |
| 17 | KRTAP4-7 | rs11655310 | GSVCSDQGCGQVLCQET CCRPSCCQTTCCR | 322 | | | | X | | |
| 18 | SERPINB5 | rs1455555 | GVALSNVVHK | 323 | X | | X | X | X | X |
| 18 | SERPINB5 | rs1455555 | GVALSNVVHKVCLEITED GGDSIEVPGAR | 324 | X | | X | X | X | X |
| 12 | KRT86 | rs56677856 | GVDCAYLR | 325 | | | | | | |
| 11 | PKP3 | rs200371913 | GVGGAVPGAVLEPVAPA PSVR | 326 | | X | | | | |
| 17 | KRTAP4-11 | rs349771 | GVSCHTTCYRPTCVISSC | 327 | | | X | X | | X |
| 17 | KRTAP4-11 | rs349771 | GVSCHTTCYRPTCVISSC PR | 328 | | | X | X | | X |
| 17 | KRTAP4-11 | rs349771 | GVSCHTTCYRPTCVISSC PRPL | 329 | | | X | X | | X |
| 17 | KRTAP4-11 | rs349771 | GVSCHTTCYRPTCVISSC PRPLCC | 330 | | | X | X | | X |

TABLE 11-continued

Exemplary GVP detectable in hair samples

| CHR | gene name | mutation ID | mutated peptide (GVP) | SEQ ID NO | ALL | NFE | AFR | EAS | SAS | AMR |
|---|---|---|---|---|---|---|---|---|---|---|
| 17 | KRTAP4-11 | rs349771 | GVSCHTTCYRPTCVISSC PRPLCCA | 331 | | | X | X | | X |
| 17 | KRTAP4-11 | rs349771 | GVSCHTTCYRPTCVISSC PRPLCCASS | 332 | | | X | X | | X |
| 17 | KRTAP4-11 | rs349771 | GVSCHTTCYRPTCVISSC PRPLCCASSCC | 333 | | | X | X | | X |
| 12 | KRT82 | rs2658658 | GVSMPVLSTGVLR | 334 | X | | X | X | X | X |
| 11 | HEPHL1 | rs1945783 | HFCTDPDSVDKK | 335 | | | | | | |
| 11 | HEPHL1 | rs1945783 | HFCTDPDSVDKKDAVFQR | 336 | | | | | | |
| 7 | ATG9B | rs7804893 | HFSELPHELR | 337 | X | X | X | X | | X |
| 12 | KRT81 | rs4761786 | HGETLCR | 338 | | | | | | |
| 12 | KRT83 | rs200128355 | HGETLCR | 339 | | | | | | |
| 12 | KRT83 | rs2852464 | HISDTSVVVKLDNSRDLN MDCMVAEIKAQYDDIATR | 340 | X | X | X | X | X | X |
| 17 | KRT33A | rs148752041 | HNAELENLIR | 341 | | | | | | |
| 17 | KRT33A | rs148752041 | HNAELENLIRER | 342 | | | | | | |
| 6 | DSP | rs140965835 | HQNQNTIQELLQNCSDYL MR | 343 | | | | | | |
| 12 | KRT85 | rs61630004 | HSFGYR | 344 | | | | | X | |
| 12 | KRT86 | rs57242951 | HSGGVCGPSPPCITTVSV NESLLTPLNLEIDPNAQC VK | 345 | | | | | | |
| 12 | KRT86 | rs57242951 | HSGGVCGPSPPCITTVSV NESLLTPLNLEIDPNAQC VKQEEKEQIK | 346 | | | | | | |
| 17 | KRT32 | rs144111267 | HTVNTLEIELQAQHSLR | 347 | | | | | | |
| 17 | KRT32 | rs144111267 | HTVNTLEIELQAQHSLRD SLENTLTESEAR | 348 | | | | | | |
| 17 | BLMH | rs1050565 | HVPEEVLAVLEQEPIVLP AWDPMGALA | 349 | X | X | X | X | X | X |
| 12 | KRT85 | rs61630004 | IAVGGFRAGSCGHSFGYR | 350 | | | | | X | |
| 12 | KRT85 | rs139493548 | IAVGGSRAGSCGR | 351 | | | | | | |
| 2 | IL1F10 | rs6761276 | ICTLPNR | 352 | | | | X | | |
| 20 | TGM3 | rs114998364 | IDVPTLEPK | 353 | | | | | | |
| 20 | TGM3 | rs214830 | IDVPTLGPKER | 354 | | | | | | |
| 14 | LGALS3 | rs11125 | IHVLVEPDHFK | 355 | X | X | | | X | |
| 17 | KRT40 | rs9908304 | ILCMKAENSR | 356 | X | X | | X | X | X |
| 17 | KRT32 | rs2071561 | ILDDLTLCKADLEAQVEY | 357 | | | X | | | |
| 17 | KRT32 | rs2071561 | ILDDLTLCKADLEAQVEY LKEELMCLKK | 358 | | | X | | | |
| 17 | KRT34 | rs566233643 | ILNELTLCK | 359 | | | | | | |
| 17 | KRT34 | rs566233643 | ILNELTLCKSDLESQVESL REELICLK | 360 | | | | | | |
| 17 | KRT34 | rs566233643 | ILNELTLCKSDLESQVESL REELICLKK | 361 | | | | | | |

TABLE 11-continued

Exemplary GVP detectable in hair samples

| CHR | gene name | mutation ID | mutated peptide (GVP) | SEQ ID NO | ALL | NFE | AFR | EAS | SAS | AMR |
|---|---|---|---|---|---|---|---|---|---|---|
| 12 | KRT81 | rs202205489 | ISACGPQPGR | 362 | | | | | | |
| 12 | KRT83 | rs2852464 | ISDTSVVVKLDNSRDLN MDCMVAEIKAQYDDIATR | 363 | X | X | X | X | X | X |
| 21 | KRTAP11-1 | rs9636845 | ISNPCSTTYSRPLTFVSSG SQPLGGISSVCQPVGGIST VCQPVGGVSTVCQPACG VSR | 364 | X | X | | X | X | X |
| 6 | DSP | rs749679496 | ITNLTQQLEQAPIVK | 365 | | | | | | |
| 6 | DSP | rs749679496 | ITNLTQQLEQAPIVKK | 366 | | | | | | |
| 6 | HIST1H1E | rs757147711 | KALAVAGYDVEKNNSR | 367 | | | | | | |
| 6 | HIST1H1E | rs200744473 | KATGAAIPK | 368 | | | | | | |
| 12 | KRT83 | rs766508559 | KKYEEEVALQATAENEF VALKK | 369 | | | | | | |
| 12 | KRT83 | rs2852464 | KLDNSRDLNMDCMVAEI KAQYDDIATR | 370 | X | X | X | X | X | X |
| 17 | KRT35 | rs761727354 | KNHEEEVNSLHCQLGDR | 371 | | | | | | |
| 12 | KRT83 | rs2857671 | KPCGQLNTTCGGGSCGQ GRY | 372 | | | | | | |
| 12 | KRT81 | rs751670289 | KSDLEANVDALIQEIDFLR | 373 | | | | | | |
| 12 | KRT81 | rs751670289 | KSDLEANVDALIQEIDFL RR | 374 | | | | | | |
| 12 | KRT86 | rs111429470 | KSDLEANVEALIQEIDFL RWLYEEEIRVLQSHISDT SVVVK | 375 | | | | | | |
| 12 | KRT84 | rs1613931 | KVQFLEQQNKLLETK | 376 | X | X | | X | X | X |
| 12 | KRT82 | rs1791634 | KYEEELSLRPCVQNEFVA LKK | 377 | | | | | | |
| 12 | KRT83 | rs766508559 | KYEEEVALQATAENEFV ALKK | 378 | | | | | | |
| 5 | HEXB | rs77499935 | LAPGTVVEVWKDSAYPE ELSR | 379 | | | | | | |
| 21 | KRTAP10-12 | rs61745911 | LASCGSLLYRPTCSR | 380 | X | | X | | X | |
| 17 | KRT34 | rs201477948 | LASDDFRSKYQMEQSLR | 381 | | | | | | |
| 17 | KRT34 | rs372070920 | LASDNFR | 382 | | | | | | |
| 17 | KRT34 | rs372070920 | LASDNFRSKYQTEQSLR | 383 | | | | | | |
| 17 | KRT40 | rs140634473 | LASYLEKVH | 384 | | | | | | |
| 17 | KRT13 | rs9891361 | LAVDDFR | 385 | | | X | | | |
| 1 | SFN | rs78707984 | LAYQEAMDISK | 386 | | | | | | |
| 1 | SFN | rs78707984 | LAYQEAMDISKK | 387 | | | | | | |
| 12 | KRT83 | rs2857671 | LCKPCGQLNTTCGGGSC GQGRY | 388 | | | | | | |
| 12 | TXNRD1 | rs7134193 | LCLSPPASDSR | 389 | X | X | X | | X | X |
| 12 | KRT3 | rs3887954 | LDLDSIIAEVGA | 390 | | | X | X | X | X |
| 14 | LGALS3 | rs10148371 | LDNNWGKEER | 391 | | | X | | | |

TABLE 11-continued

| Exemplary GVP detectable in hair samples | | | | | | | | | | |
|---|---|---|---|---|---|---|---|---|---|---|
| CHR | gene name | mutation ID | mutated peptide (GVP) | SEQ ID NO | ALL | NFE | AFR | EAS | SAS | AMR |
| 12 | KRT81 | rs141587304 | LDNSRDLNMDCIIDEIKA QYDDIVTR | 392 | | | | | | |
| 12 | KRT83 | rs2852464 | LDNSRDLNMDCMVAEIK | 393 | X | X | X | X | X | X |
| 12 | KRT83 | rs2852464 | LDNSRDLNMDCMVAEIK AQYDDIATR | 394 | X | X | X | X | X | X |
| 12 | KRT83 | rs140635030 | LEAAVAQSEQQSEAALS DAR | 395 | | | | | | |
| 12 | KRT83 | rs140635030 | LEAAVAQSEQQSEAALS DARCK | 396 | | | | | | |
| 17 | KRT32 | rs2071563 | LEGEINMYR | 397 | X | X | X | X | X | X |
| 17 | KRT31 | rs6503627 | LERDNVELENLIR | 398 | X | X | | | | |
| 17 | KRT39 | rs112120285 | LESEITTYR | 399 | | | | | | |
| 1 | VSIG8 | rs62624468 | LGCPYILDPEDYGPNGLD IEWMQVNSDPAHHR | 400 | | | X | | | |
| 17 | KRT33B | rs34771886 | LITNVESQLAEIHSDLER | 401 | | | | | | |
| 17 | KRT37 | rs16966811 | LLDDVTLAK | 402 | X | X | X | X | X | X |
| 17 | KRT37 | rs16966811 | LLDDVTLAKADLEAQQE SLKEEQLSLKSNHEQEVK | 403 | X | X | X | X | X | X |
| 12 | KRT86 | rs58717266 | LLETKLPFYQNR | 404 | X | X | | X | X | X |
| 12 | KRT86 | rs58717266 | LLETKLPFYQNRECCQSN LEPLFEGYIETLRR | 405 | X | X | | X | X | X |
| 17 | KRT32 | rs146792525 | LNIEVDTAPPVDLTR | 406 | | | | | | |
| 12 | KRT81 | rs141587304 | LNMDCIIDEIKAQYDDIV TR | 407 | | | | | | |
| 12 | KRT83 | rs2857671 | LNTTCGGGSCGQGRY | 408 | | | | | | |
| 17 | KRT33B | rs61741663 | LNVEVDAAPAVDLNR | 409 | | | X | | | |
| 17 | KRT31 | rs112544857 | LNVEVDAAPTVDLNRVL NETRSQYEVLVETNRR | 410 | | | | | | |
| 17 | KRT36 | rs75790652 | LNVEVDGAPPVDLNKILE DMR | 411 | | | | X | | X |
| 12 | KRT86 | rs58717266 | LPFYQNR | 412 | X | X | | X | X | X |
| 12 | KRT86 | rs58717266 | LPFYQNRECCQSNLEPLF EGYIETLRR | 413 | X | X | | X | X | X |
| 17 | KRT32 | rs3744786 | LPTTFRPASCLSKTYLSSS CRAASGISGSMGPGSWY SEGAFNGNEKETMQFLN DR | 414 | X | X | X | X | X | X |
| 12 | KRT83 | rs2857663 | LQFYQNCECCQSNLEPLF AGYIETLR | 415 | X | X | X | X | X | X |
| 12 | KRT83 | rs2857663 | LQFYQNCECCQSNLEPLF AGYIETLRR | 416 | X | X | X | X | X | X |
| 16 | PPL | rs2037912 | LQLERENLQLETR | 417 | | | X | | X | |
| 6 | DSP | rs2076299 | LQRVQCDLQK | 418 | X | | X | X | X | X |
| 17 | KRT33A | rs12937519 | LQSYQVEIIELRRTVNAL EIELQAQHNLR | 419 | X | X | X | X | X | X |
| 17 | KRTAP4-11 | rs349771 | LRPVCGGVSCHTT | 420 | | | X | X | | X |

TABLE 11-continued

Exemplary GVP detectable in hair samples

| CHR | gene name | mutation ID | mutated peptide (GVP) | SEQ ID NO | ALL | NFE | AFR | EAS | SAS | AMR |
|---|---|---|---|---|---|---|---|---|---|---|
| 12 | TXNRD1 | rs7134193 | LSPPASDSR | 421 | X | X | X | | X | X |
| 12 | KRT85 | rs77184300 | LSSRSSLSHTQDVDCAYLRKSDLEANVEALVEESSFLR | 422 | | | | | | |
| 12 | KRT83 | rs140635030 | LTAEVENAKCQNSKLEAAVAQSEQQSEAALSDAR | 423 | | | | | | |
| 12 | KRT81 | rs2071588 | LTGGFGSHSVCR | 424 | X | X | X | X | X | X |
| 12 | KRT81 | rs2071588 | LTGGFGSHSVCRGFR | 425 | X | X | X | X | X | X |
| 1 | SELENBP1 | rs72710112 | LTGQLFLGGSIVKGGPVQVLEDKELK | 426 | | | | | | |
| 6 | DSP | rs41302885 | LTVNSAIAR | 427 | | | | | | |
| 19 | PGLS | rs183992141 | LVPFNHAESTYGLYR | 428 | | | | | | |
| 17 | KRT34 | rs201477948 | LVVNIDNAKLASDDFRSKYQMEQSLR | 429 | | | | | | |
| 17 | KRT34 | rs372070920 | LVVNIDNAKLASDNFR | 430 | | | | | | |
| 17 | KRT34 | rs372070920 | LVVNIDNAKLASDNFRSK | 431 | | | | | | |
| 17 | KRT34 | rs372070920 | LVVNIDNAKLASDNFRSKYQTEQSLR | 432 | | | | | | |
| 17 | KRT33A | rs145389769 | LVVRIDNAK | 433 | | | | | | |
| 17 | KRT33A | rs145389769 | LVVRIDNAKLASDDFR | 434 | | | | | | |
| 17 | KRT33A | rs145389769 | LVVRIDNAKLASDDFRTK | 435 | | | | | | |
| 12 | KRT83 | rs2857671 | LVVSTGLCKPCGQLNTTCGGGSCGQGRY | 436 | | | | | | |
| 1 | S100A3 | rs36022742 | MAKPLEQAVAAIVCTFQEYAGR | 437 | X | X | X | | X | X |
| 12 | KRT83 | rs2852464 | MDCMVAEIK | 438 | X | X | X | X | X | X |
| 12 | KRT83 | rs2852464 | MDCMVAEIKAQYDDIATR | 439 | X | X | X | X | X | X |
| 17 | KRT39 | rs17843021 | MRDSQECILMETEAR | 440 | X | X | X | X | X | X |
| 12 | KRT83 | rs2852464 | MVAEIKAQYDDIATR | 441 | X | X | X | X | X | X |
| 22 | COMT | rs4680 | MVDFAGMKDKVTLVVGASQDIIPQLK | 442 | X | | X | X | X | X |
| 17 | KRT36 | rs2301354 | MVNALEIELQAQHSMR | 443 | | | X | X | | |
| 17 | KRTAP4-9 | rs149483591 | MVSSCCGSVCSDQGCGQDLCQETCCHPSCCETTCCR | 444 | | | X | | | |
| 17 | KRTAP4-7 | rs11655310 | MVSSCCGSVCSDQGCGQDLCQETCCRPSCCQTTCCR | 445 | | | | X | | |
| 17 | KRTAP4-7 | rs383835 | MVSSCCGSVCSDQGCSQVLCQETCCRPSCCQTTCCRTTCYRPSCCVSS | 446 | | | | X | | |
| 17 | KRTAP4-5 | rs749779892 | MVSSCCGSVSSEQSCGLENCCCPSCCQTTCCR | 447 | | | X | X | | |
| 17 | KRT32 | rs2071560 | MVVNTDNAK | 448 | | | | X | | X |
| 17 | KRT32 | rs2071560 | MVVNTDNAKLAADDFR | 449 | | | | X | | X |
| 17 | KRTAP4-5 | rs749779892 | NCCCPSCCQTTCCR | 450 | | | X | X | | |

TABLE 11-continued

| Exemplary GVP detectable in hair samples | | | | | | | | | | |
|---|---|---|---|---|---|---|---|---|---|---|
| CHR | gene name | mutation ID | mutated peptide (GVP) | SEQ ID NO | ALL | NFE | AFR | EAS | SAS | AMR |
| 17 | KRT40 | rs1510068 | NEKETMQFLNDRLANYL EKVR | 451 | X | X | | X | X | X |
| 17 | KRT40 | rs2010027 | NHEEEVNLLHEQLGDR | 452 | X | X | | X | X | X |
| 17 | KRT35 | rs761727354 | NHEEEVNSLHCQLGDR | 453 | | | | | | |
| 17 | KRT35 | rs761727354 | NHEEEVNSLHCQLGDRL NVEVDAAPPVDLNRVLE EMR | 454 | | | | | | |
| 12 | KRT7 | rs6580870 | NKYEDEINR | 455 | | | | | | |
| 1 | PKP1 | rs569372122 | NLSSADAGHQTMR | 456 | | | | | | |
| 12 | KRT83 | rs2857671 | NLVVSTGLCKPCGQLNT TCGGGSCGQGRY | 457 | | | | | | |
| 11 | TRIM29 | rs11604169 | NNPGCPSLMR | 458 | | | | X | | X |
| 14 | HSPA2 | rs140108798 | NQVAVNPTNTIFDAKR | 459 | | | | | | |
| 17 | KRT31 | rs6503627 | NVELENLIR | 460 | X | X | | | | |
| 17 | KRT37 | rs9916724 | NVFVSPIDVGCQPVAEAS AASMCLLANVAHANR | 461 | X | | X | X | | X |
| 20 | TGM3 | rs214814 | NWNGSVEILK | 462 | X | X | X | X | X | X |
| 20 | TGM3 | rs214814 | NWNGSVEILKNWKK | 463 | X | X | X | X | X | X |
| 17 | KRTAP9-9 | rs9894258 | PACYETTCCR | 464 | | | X | | | |
| 12 | KRT83 | rs2857671 | PCGQLNTTCGGGSCGQG RY | 465 | | | | | | |
| 21 | KRTAP11-1 | rs9636845 | PCSTTYSRPLTFVSSGSQP LGGISSVCQPVGGISTVC QPVGGVSTVCQPACGVSR | 466 | X | X | | X | X | X |
| 17 | KRTAP9-1 | rs238824 | PICGSSCCQPCCHPTCYQ TTCFRTTCCQPTCCQPTC CRNTSCQPT | 467 | | | | | | |
| 17 | KRTAP4-1 | rs35382039 | PLCCQTTCRPR | 468 | | | X | | | |
| 21 | KRTAP11-1 | rs9636845 | PLTFVSSGSQPLGGISSVC QPVGGISTVCQPVGGVST VCQPACGVSR | 469 | X | X | | X | X | X |
| 17 | KRTAP4-9 | rs7207685 | PQCCQPVCCQPTCCRPR | 470 | | | | X | | |
| 17 | KRTAP4-5 | rs238830 | PQCCQSVCYQPTCCHPSC CISSCCHPYCCESSCCRPC CCRPSCCQTTCCR | 471 | | X | | X | | |
| 17 | KRTAP4-4 | rs74572864 | PQCCQTICCR | 472 | | | | X | | |
| 1 | PKP1 | rs142096411 | PQIAHLLQSGNSDVVR | 473 | | | | | | |
| 17 | KRTAP1-3 | rs62622849 | PSCCQTSSCR | 474 | X | | X | X | | X |
| 17 | KRTAP4-2 | rs62067292 | PSCCSPSCCQTTCCR | 475 | | X | | | | |
| 17 | KRTAP4-7 | rs11650484 | PSCCVSSCCRPQCCQSVC CQPTCCRPSCCETTCCHP RCCI | 476 | | | | X | | |
| 17 | KRTAP4-6 | rs73983172 | PSCCVSSCCRPQCCQSVC CQPTCCRSSCCPSCCQTT CCR | 477 | | | X | | | |

TABLE 11-continued

| Exemplary GVP detectable in hair samples | | | | | | | | | | |
|---|---|---|---|---|---|---|---|---|---|---|
| CHR | gene name | mutation ID | mutated peptide (GVP) | SEQ ID NO | ALL | NFE | AFR | EAS | SAS | AMR |
| 21 | KRTAP10-10 | rs4818949 | PSSCQPTCCTSSPCQQAC CVPVCSKSVCYMPVCSG ASTSCCQQSSCQPACCTA SCCR | 478 | X | X | X | X | X | X |
| 21 | KRTAP10-10 | rs4818950 | PSSCQPTCCTSSPCQQAC CVPVCSKSVCYMPVCSG ASTSCCQQSSCQPACCTA SCCR | 479 | | | X | | | |
| 17 | KRTAP3-2 | rs3829598 | PTGPATTICSSDKSCCCG | 480 | X | X | | X | X | X |
| 17 | KRTAP4-11 | rs349771 | PVCGGVSCHTTCYRPTC VISSCPRPLCCASSCC | 481 | | | X | X | | X |
| 1 | VSIG8 | rs41264827 | PVVPMCWTEGHMTYGN DVVLK | 482 | | | | | | |
| 17 | KRT32 | rs11078993 | QCMITNVEAQLAEIQADL ERQNQEYQVLLDVR | 483 | X | | X | X | X | X |
| 12 | KRT84 | rs1613931 | QFLEQQNKLLETK | 484 | X | X | | X | X | X |
| 17 | KRT33B | rs12450621 | QLERDNAELK | 485 | | X | | | X | |
| 17 | KRT33B | rs12450621 | QLERDNAELKNLIR | 486 | | X | | | X | |
| 17 | KRT33B | rs12450621 | QLERDNAELKNLIRER | 487 | | X | | | X | |
| 17 | KRT31 | rs6503627 | QLERDNVELENLIR | 488 | X | X | | | | |
| 17 | KRT31 | rs6503627 | QLERDNVELENLIRER | 489 | X | X | | | | |
| 17 | KRT36 | rs8082683 | QLERENVELESR | 490 | | | X | | | |
| 17 | KRT33A | rs148752041 | QLERHNAELENLIR | 491 | | | | | | |
| 17 | KRT33A | rs148752041 | QLERHNAELENLIRER | 492 | | | | | | |
| 16 | PPL | rs8063727 | QLLAGLDKVASDLDQQEK | 493 | | | | | | |
| 20 | TGM3 | rs146717993 | QLLVDFSCNKFPAIK | 494 | | | | | | |
| 12 | KRT75 | rs199744850 | QLQTQVGDTSVVLSMDN NCNLDLDSIIAEVK | 495 | | | | | | |
| 12 | KRT84 | rs951773 | QLREYQELMNAKLGLDI EIATYRR | 496 | | | | | | |
| 17 | KRT39 | rs17843023 | QNQEYEILMDVK | 497 | | | X | X | | |
| 17 | KRT34 | rs199674249 | QNQEYQVLLDVCAR | 498 | | | | | | |
| 17 | KRT34 | rs199674249 | QNQEYQVLLDVCARLEC EINTYR | 499 | | | | | | |
| 17 | KRT40 | rs8064733 | QNQEYQVLLDVKARLEG EINTYR | 500 | X | X | | X | X | X |
| 17 | KRTAP9-6 | rs12938692 | QNTCCRTTCCQPTCVTSC CQPSCCSTPCCQPICCGSS CCGQTSCGSSCGQSSSCA PVYCR | 501 | X | X | X | X | X | |
| 17 | KRTAP9-3 | rs374150255 | QPCCHPTCCQNTCCRTTC CQPICVTSCCQPSCCSTPC CQPTRCGSSCGQSSSCAP VYCR | 502 | | | | | | |
| 17 | KRTAP1-3 | rs62622849 | QPSCCQTSSCR | 503 | X | | X | X | | X |

TABLE 11-continued

| Exemplary GVP detectable in hair samples | | | | | | | | | | |
|---|---|---|---|---|---|---|---|---|---|---|
| CHR | gene name | mutation ID | mutated peptide (GVP) | SEQ ID NO | ALL | NFE | AFR | EAS | SAS | AMR |
| 17 | KRTAP9-6 | rs181901202 | QPVCCGSSCCGQTSCGSS CGQSSSCAPVYCR | 504 | | | | | | |
| 17 | KRTAP4-9 | rs7207685 | QPVCCQPTCCRPRCCISS CCRPSCCVSSCCKPQCCQ SVCCQPNCCRPS | 505 | | | | X | | |
| 12 | KRT83 | rs2852464 | QSHISDTSVVVKLDNSRD LNMDCMVAEIKAQYDDI ATR | 506 | X | X | X | X | X | X |
| 17 | KRT27 | rs116593021 | QSVEADLNGLR | 507 | | | | | | |
| 17 | KRT27 | rs116593021 | QSVEADLNGLRR | 508 | | | | | | |
| 14 | LGALS3 | rs11125 | QSVFPFESGKPFKIHVLVE PDHFK | 509 | X | X | | | X | |
| 17 | KRTAP1-1 | rs149188249 | QTSFCGFR | 510 | | | | X | | X |
| 21 | KRTAP13-2 | rs3804010 | QTSYVESRPCQTSCYRPR | 511 | X | X | X | X | X | X |
| 21 | KRTAP11-1 | rs9636845 | QTTCISNPCSTTYSRPLTF VSSGSQPLGGISSVCQPV GGISTVCQPVGGVSTVCQ PACGVSR | 512 | X | X | | X | X | X |
| 17 | KRT33A | rs12937519 | QVEIIELR | 513 | X | X | X | X | X | X |
| 17 | KRT33A | rs12937519 | QVEIIELRR | 514 | X | X | X | X | X | X |
| 17 | KRT34 | rs112570296 | QVVSSSEQLQSCQVEIIELR | 515 | | | | | | |
| 17 | KRT34 | rs112570296 | QVVSSSEQLQSCQVEIIEL RR | 516 | | | | | | |
| 17 | KRT33A | rs12937519 | QVVSSSEQLQSYQVEIIELR | 517 | X | X | X | X | X | X |
| 17 | KRT33A | rs12937519 | QVVSSSEQLQSYQVEIIEL RR | 518 | X | X | X | X | X | X |
| 17 | KRT33A | rs12937519 | QVVSSSEQLQSYQVEIIEL RRTVNALEIELQAQHNLR | 519 | X | X | X | X | X | X |
| 17 | KRTAP9-3 | rs374150255 | RCGSSCGQSSSCAPVYCR | 520 | | | | | | |
| 12 | KRT83 | rs2852464 | RDLNMDCMVAEIKAQY DDIATR | 521 | X | X | X | X | X | X |
| 12 | KRT85 | rs112554450 | REAECVEANSGR | 522 | | | | | | |
| 12 | KRT85 | rs112554450 | REAECVEANSGRLASELN HVQEVLEGYK | 523 | | | | | | |
| 12 | KRT85 | rs112554450 | REAECVEANSGRLASELN HVQEVLEGYKK | 524 | | | | | | |
| 17 | KRT33A | rs12937519 | REVEQWFATQTEELNKQ VVSSSEQLQSYQVEIIELRR | 525 | X | X | X | X | X | X |
| 17 | KRT34 | rs77779192 | REVEQWFATQTEK | 526 | | | | | | |
| 17 | KRT34 | rs77779192 | REVEQWFATQTEKLNK | 527 | | | | | | |
| 12 | KRT84 | rs951773 | REYQELMNAKLGLDIEIA TYR | 528 | | | | | | |
| 12 | KRT81 | rs2071588 | RGLTGGFGSHSVCR | 529 | X | X | X | X | X | X |
| 6 | DSP | rs6929069 | RGQSEADSDKNATILELR | 530 | X | X | X | X | X | X |
| 17 | KRT32 | rs2071561 | RILDDLTLCKADLEAQVE YLKEELMCLK | 531 | | | X | | | |
| 17 | KRT34 | rs566233643 | RILNELTLCK | 532 | | | | | | |

TABLE 11-continued

Exemplary GVP detectable in hair samples

| CHR | gene name | mutation ID | mutated peptide (GVP) | SEQ ID NO | ALL | NFE | AFR | EAS | SAS | AMR |
|---|---|---|---|---|---|---|---|---|---|---|
| 17 | KRT36 | rs2301354 | RMVNALEIELQAQHSMR | 533 | | | X | X | | |
| 17 | KRTAP4-5 | rs137947981 | RPCCCRPSCCQTTCCR | 534 | | | X | | | |
| 17 | KRTAP4-7 | rs777211664 | RPSCCIPCCCRPTCVISTC PRPLCC | 535 | X | X | | | X | |
| 17 | KRT31 | rs6503627 | RQLERDNVELENLIR | 536 | X | X | | | | |
| 12 | KRT84 | rs951773 | RQLREYQELMNAKLGLD IEIATYR | 537 | | | | | | |
| 21 | KRTAP11-1 | rs9636845 | RQTTCISNPCSTTYSRPLT FVSSGSQPLGGISSVCQPV GGISTVCQPVGGVSTVCQ PACGVSR | 538 | X | X | | X | X | X |
| 12 | KRT86 | rs57242951 | RSFGYHSGGVCGPSPPCI TTVSVNESLLTPLNLEIDP NAQCVK | 539 | | | | | | |
| 12 | KRT86 | rs57242951 | RSFGYHSGGVCGPSPPCI TTVSVNESLLTPLNLEIDP NAQCVKQEEKEQIK | 540 | | | | | | |
| 17 | KRTAP4-6 | rs73983172 | RSSCCPSCCQTTCCR | 541 | | | X | | | |
| 17 | KRT40 | rs8064910 | RTASALEIELQAQQSLTE SLECTVAETEAQYSSQLA QIQRLIDNLENQLAEIR | 542 | | | | | | |
| 17 | KRTAP9-4 | rs199605390 | RTCYHPTTVCLPGCLNQS CGSSCCQPCCR | 543 | | | | | | |
| 17 | KRTAP9-4 | rs199605390 | RTCYHPTTVCLPGCLNQS CGSSCCQPCCRPACCETT CFQPTCVY | 544 | | | | | | |
| 17 | KRTAP9-4 | rs2191379 | RTCYHPTTVCLPGCLNQS CGSSCCQPCCRPACCETT CFQPTCVY | 545 | | | | | | |
| 17 | KRTAP9-4 | rs199605390 | RTCYHPTTVCLPGCLNQS CGSSCCQPCCRPACCETT CFQPTCVYS | 546 | | | | | | |
| 17 | KRTAP9-4 | rs2191379 | RTCYHPTTVCLPGCLNQS CGSSCCQPCCRPACCETT CFQPTCVYS | 547 | | | | | | |
| 17 | KRTAP9-4 | rs2191379 | RTCYYPTTVCLPGCLNQS CGSNCCQPCCRPACCETT CFQPTCVYS | 548 | | | | | | |
| 17 | KRTAP9-4 | rs2191379 | RTCYYPTTVCLPGCLNQS CGSNCCQPCCRPACCETT CFQPTCVYSCCQPFCC | 549 | | | | | | |
| 17 | KRTAP1-3 | rs62622849 | RTGCGIGGGIGYGQEGSS GAVSTR | 550 | X | | X | X | | X |
| 17 | KRTAP1-3 | rs142863014 | RTGCGTGGGIGYGQEGSS GAVSTR | 551 | | | | | | |
| 17 | KRTAP1-3 | rs62622849 | RTGCGTGGGIGYGQEGSS GAVSTR | 552 | X | | X | X | | X |
| 12 | KRT86 | rs139895699 | RTKEEINELNCMIQR | 553 | | | | | | |
| 17 | KRT31 | rs151023228 | RTVNSLEIELQAQHNLR | 554 | | | | | | |
| 17 | KRT31 | rs151023228 | RTVNSLEIELQAQHNLRD SLENTLTESEAR | 555 | | | | | | |

TABLE 11-continued

Exemplary GVP detectable in hair samples

| CHR | gene name | mutation ID | mutated peptide (GVP) | SEQ ID NO | ALL | NFE | AFR | EAS | SAS | AMR |
|---|---|---|---|---|---|---|---|---|---|---|
| 17 | KRT32 | rs16966929 | RTVNTLEIELQAQHSLRD SLENMLTESEAR | 556 | | | | | | |
| 14 | LGALS3 | rs10148371 | RVIVCNTKLDNNWGKEER | 557 | | | X | | | |
| 21 | KRTAP10-12 | rs34302939 | RVPVPSCCVPTSSCQPSCSR | 558 | X | X | | X | X | X |
| 21 | KRTAP10-12 | rs34302939 | RVPVPSCCVPTSSCQPSCS RL | 559 | X | X | | X | X | X |
| 17 | KRT35 | rs743686 | RVSAMYSSSPCKLPSLSP VARSFSACSVGLGR | 560 | | | | X | | |
| 12 | KRT86 | rs749337520 | RVSSDPSNSNVVVGTTN ACAPSAR | 561 | | | | | | |
| 17 | KRT32 | rs11078993 | RYSSQLAQMQCMITNVE AQLAEIQADLERQNQEY QVLLDVR | 562 | X | | X | X | X | X |
| 19 | GIPC1 | rs45458894 | SAGGRPGSGPQLGSGR | 563 | X | X | X | | X | X |
| 17 | JUP | rs41283425 | SAIVHLINYQDDAELATH ALPELTK | 564 | | X | | | | |
| 17 | JUP | rs41283425 | SAIVHLINYQDDAELATH ALPELTKLLNDEDPVVVTK | 565 | | X | | | | |
| 17 | JUP | rs150245906 | SAIVHLINYQDDAK | 566 | | | | | | |
| 17 | JUP | rs150245906 | SAIVHLINYQDDAKLATR | 567 | | | | | | |
| 17 | KRT35 | rs2071601 | SARPICVPCPGGRF | 568 | | | | X | | |
| 1 | SFN | rs149812347 | SAYQEAMDISKKDMPPT NPIR | 569 | | | | | | |
| 17 | KRTAP4-7 | rs11655310 | SCCGSVCSDQGCGQVLC QETCCRPSCCQTTCCR | 570 | | | | | X | |
| 17 | KRTAP4-7 | rs777211664 | SCCISSCCRRPTCVISTCPR | 571 | X | X | | | X | |
| 17 | KRTAP4-7 | rs777211664 | SCCISSCCRRPTCVISTCP RPL | 572 | X | X | | | X | |
| 17 | KRTAP1-3 | rs142863014 | SCCQPSCCQTSSCGTGCG TGGGIGYGQEGSSGAVSTR | 573 | | | | | | |
| 17 | KRTAP1-1 | rs149188249 | SCCQTSFCGFR | 574 | | | | X | | X |
| 17 | KRTAP1-3 | rs62622849 | SCCQTSSCRTGCGIGGGI GYGQEGSSGAVSTR | 575 | X | | X | X | | X |
| 17 | KRTAP4-2 | rs389784 | SCCQTTCCRTTCCRPSCC VSSCFRPQCCQSVCCQPT CCRPSCGQTTCCR | 576 | | | | | | |
| 17 | KRTAP4-2 | rs389784 | SCCVSSCFRPQCCQSVCC QPTCCRPSCGQTTCCRT | 577 | | | | | | |
| 12 | KRT85 | rs61630004 | SCGHSFGYR | 578 | | | | | X | |
| 12 | KRT86 | rs57242951 | SCGRSFGYHSGGVCGPSP PCITTVSVNESLLTPLNLE IDPNAQCVKQEEKEQIK | 579 | | | | | | |
| 17 | KRTAP1-3 | rs62622849 | SCRTGCGIGGGIGYGQEG SSGAVSTR | 580 | X | | X | X | | X |
| 17 | KRTAP1-5 | rs62623375 | SCYQPR | 581 | | | X | X | | X |
| 12 | KRT81 | rs751670289 | SDLEANVDALIQEIDFLRR | 582 | | | | | | |
| 17 | KRTAP4-7 | rs11655310 | SDQGCGQDLCQETCCRP SCCQTTCCR | 583 | | | | X | | |

TABLE 11-continued

Exemplary GVP detectable in hair samples

| CHR | gene name | mutation ID | mutated peptide (GVP) | SEQ ID NO | ALL | NFE | AFR | EAS | SAS | AMR |
|---|---|---|---|---|---|---|---|---|---|---|
| 1 | PKP1 | rs34704938 | SEPDLYYDPR | 584 | | | X | | | |
| 12 | KRT86 | rs57242951 | SFGYHSGGVCGPSPPCITT VSVNESLLTPLNLEIDPN AQCVK | 585 | | | | | | |
| 12 | KRT86 | rs57242951 | SFGYHSGGVCGPSPPCITT VSVNESLLTPLNLEIDPN AQCVKQEEK | 586 | | | | | | |
| 12 | KRT86 | rs57242951 | SFGYHSGGVCGPSPPCITT VSVNESLLTPLNLEIDPN AQCVKQEEKEQIK | 587 | | | | | | |
| 12 | KRT86 | rs57242951 | SFGYHSGGVCGPSPPCITT VSVNESLLTPLNLEIDPN AQCVKQEEKEQIKSLNSR | 588 | | | | | | |
| 17 | KRTAP1-3 | rs62622849 | SFSTSGTCSSSCCQPSCCE TSCCQPSCCQTSSCRTGC GIGGGIGYGQEGSSGAVS TR | 589 | X | | X | X | | X |
| 17 | KRT39 | rs7213256 | SGAIESTAPACTSSSPCSL KEHCSACGPLSQILVK | 590 | X | X | | | X | X |
| 17 | KRT39 | rs7213256 | SGAIESTAPACTSSSPCSL KEHCSACGPLSQILVKI | 591 | X | X | | | X | X |
| 12 | KRT81 | rs4761786 | SKCEEMKATVIRHGETLCR | 592 | | | | | | |
| 17 | KRT37 | rs200713258 | SKCHESTVCPNYQSYFR | 593 | | | | | | |
| 17 | KRT34 | rs201477948 | SKYQMEQSLR | 594 | | | | | | |
| 12 | KRT85 | rs139493548 | SLCNLGSCGPRIAVGGSRA | 595 | | | | | | |
| 17 | KRT40 | rs200400895 | SLGETNAELESR | 596 | | | | | | |
| 21 | KRTAP13-1 | rs151147550 | SLGYGGCGFPSLGYGVG FCHPTYLASR | 597 | | | | | | |
| 17 | KRT37 | rs16966811 | SLHQLVEADKCGTQKLL DDVTLAK | 598 | X | X | X | X | X | X |
| 17 | KRT37 | rs149061216 | SLHQLVEVDKCGTQK | 599 | | | | | | |
| 17 | KRT39 | rs7213256 | SLKEHCSACGPLSQILVK | 600 | X | X | | | X | X |
| 17 | KRT33A | rs140430944 | SLLESEDCKLPSNPCATT NACDKSTGPCISKPCGLR AR | 601 | | | | | | |
| 17 | KRT24 | rs114431517 | SLNDRLANYLDKVR | 602 | | | | | | |
| 11 | PKP3 | rs77752215 | SLSLSLADSGHLPDLHGF NSYGSHR | 603 | | | | | | |
| 11 | PKP3 | rs148364325 | SLTSLIR | 604 | | | | | | |
| 12 | KRT82 | rs2658658 | SMPVLSTGVLR | 605 | X | | X | X | X | X |
| 17 | KRT35 | rs743686 | SPCKLPSLSPVAR | 606 | | | | X | | |
| 21 | KRTAP13-2 | rs113360916 | SPCQTSCYHPR | 607 | | | | | | |
| 9 | CRAT | rs3118635 | SPMVPLPMPK | 608 | | | | | | |
| 17 | KRT32 | rs11078993 | SQLAQMQCMITNVEAQL AEIQADLERQNQEYQVL LDVR | 609 | X | | X | X | X | X |

TABLE 11-continued

| Exemplary GVP detectable in hair samples | | | | | | | | | | |
|---|---|---|---|---|---|---|---|---|---|---|
| CHR | gene name | mutation ID | mutated peptide (GVP) | SEQ ID NO | ALL | NFE | AFR | EAS | SAS | AMR |
| 17 | KRT32 | rs2604956 | SQLAQMQCMITNVEAQL AEIRAELERQNQEYQVLL DVR | 610 | X | X | | | | |
| 17 | KRT34 | rs150738879 | SQLGDCLNVEVDTAPTV DLNQVLNETR | 611 | | | | | | |
| 17 | KRT34 | rs2239710 | SQLGDCLNVEVDTAPTV DLNQVLNETRSQYEALV ETNRR | 612 | | | | | | |
| 17 | KRT34 | rs150738879 | SQLGDCLNVEVDTAPTV DLNQVLNETRSQYEALV ETNRR | 613 | | | | | | |
| 17 | KRT34 | rs140296098 | SQLGDRLNLEVDTAPTV DLNQVLNETR | 614 | | | | | | |
| 17 | KRT31 | rs112544857 | SQYEVLVETNR | 615 | | | | | | |
| 17 | KRT31 | rs112544857 | SQYEVLVETNRR | 616 | | | | | | |
| 17 | KRT31 | rs112544857 | SQYEVLVETNRREVEQW FTTQTEELNKQVVSSSEQ LQSYQAEIIELR | 617 | | | | | | |
| 11 | PKP3 | rs200371913 | SRGVGGAVPGAVLEPVA PAPSVR | 618 | | X | | | | |
| 21 | KRTAP11-1 | rs9636845 | SRPLTFVSSGSQPLGGISS VCQPVGGISTVCQPVGG VSTVCQPACGVSR | 619 | X | X | | X | X | X |
| 21 | KRTAP11-1 | rs9636845 | SRQTTCISNPCSTTYSRPL TFVSSGSQPLGGISSVCQP VGGISTVCQPVGGVSTVC QPACGVSR | 620 | X | X | | X | X | X |
| 17 | KRTAP4-6 | rs73983172 | SSCCPSCCQTTCCRTTCCR | 621 | | | X | | | |
| 17 | KRTAP4-5 | rs749779892 | SSEQSCGLENCCCPSCCQ TTCCR | 622 | | | X | X | | |
| 17 | KRTAP1-5 | rs145881217 | SSGAVSTCIR | 623 | | | | | | |
| 12 | KRT1 | rs14024 | SSGGSSSVR | 624 | X | X | X | | X | X |
| 21 | KRTAP13-2 | rs113360916 | SSPCQTSCYHPR | 625 | | | | | | |
| 17 | KRT33A | rs12937519 | SSSEQLQSYQVEIIELRRT VNALEIELQAQHNLRDSL ENTLTESEAR | 626 | X | X | X | X | X | X |
| 17 | KRT35 | rs743686 | SSSPCKLPSLSPVAR | 627 | | | | X | | |
| 18 | DSG4 | rs61734847 | SSTMGALRDYADADINM AFLDSYFSEK | 628 | | | X | | | |
| 17 | KRTAP9-1 | rs145585952 | STCCQPSCVIR | 629 | | | | | | |
| 17 | KRT33A | rs140430944 | STGPCISKPCG | 630 | | | | | | |
| 17 | KRT33A | rs140430944 | STGPCISKPCGL | 631 | | | | | | |
| 17 | KRT33A | rs140430944 | STGPCISKPCGLR | 632 | | | | | | |
| 17 | KRTAP9-6 | rs12938692 | STPCCQPICCGSSCCGQTS CGSSCGQSSSCAPVYCR | 633 | X | X | X | X | X | |
| 21 | KRTAP24-1 | rs372198438 | STSCRPLSYLSR | 634 | | | | | | |
| 17 | KRTAP1-3 | rs62622849 | STSGTCSSSCCQPSCCETS CCQPSCCQTSSCRTGCGI GGGIGYGQEGSSGAVSTR | 635 | X | | X | X | | X |

TABLE 11-continued

Exemplary GVP detectable in hair samples

| CHR | gene name | mutation ID | mutated peptide (GVP) | SEQ ID NO | ALL | NFE | AFR | EAS | SAS | AMR |
|---|---|---|---|---|---|---|---|---|---|---|
| 17 | KRTAP1-3 | rs142863014 | STSGTCSSSCCQPSCCETS CCQPSCCQTSSCRTGCGT GGGIGYGQEGSSGAVSTR | 636 | | | | | | |
| 17 | KRTAP1-3 | rs62622849 | STSGTCSSSCCQPSCCETS CCQPSCCQTSSCRTGCGT GGGIGYGQEGSSGAVSTR | 637 | X | | X | X | | X |
| 21 | KRTAP11-1 | rs9636845 | STTYSRPLTFVSSGSQPLG GISSVCQPVGGISTVCQP VGGVSTVCQPACGVSR | 638 | X | X | | X | X | X |
| 17 | KRT37 | rs144652431 | STVNALEVER | 639 | | | | | | |
| 17 | KRTAP1-1 | rs35024033 | SYGTGCGIGGGIGYGQEG SSGAVSTR | 640 | | | X | | | |
| 6 | DSP | 6:g.7568542A > T | SYKPIILR | 641 | | | | | | |
| 21 | KRTAP10-6 | rs201732843 | SYVSSPCCR | 642 | | | X | X | | |
| 21 | KRTAP11-1 | rs71321355 | TACQPTCYQR | 643 | X | X | X | | X | X |
| 17 | KRT40 | rs8064910 | TASALEIELQAQQSLTESL ECTVAETEAQYSSQLAQI QR | 644 | | | | | | |
| 12 | KRT76 | rs11170271 | TATENEFVGLKK | 645 | X | X | X | X | X | X |
| 17 | KRTAP9-4 | rs199605390 | TCYHPTTVCLPGCLNQSC GSSCCQPCCRPACCETTC FQPTCVY | 646 | | | | | | |
| 17 | KRTAP9-4 | rs2191379 | TCYHPTTVCLPGCLNQSC GSSCCQPCCRPACCETTC FQPTCVY | 647 | | | | | | |
| 17 | KRTAP1-3 | rs142863014 | TGCGTGGGIGYGQEGSS GAVSTR | 648 | | | | | | |
| 17 | KRTAP1-3 | rs62622849 | TGCGTGGGIGYGQEGSS GAVSTR | 649 | X | | X | X | | X |
| 12 | KRT81 | rs2071588 | TGGFGSHSVCR | 650 | X | X | X | X | X | X |
| 12 | KRT81 | rs2071588 | TGGFGSHSVCRGFRA | 651 | X | X | X | X | X | X |
| 17 | KRT40 | rs17843015 | TGSCNSPCLVGNCAWCE DGVSTSNEKETMQFLND RLASYLEKVR | 652 | X | X | X | X | X | X |
| 18 | DSG4 | rs7229252 | TICIDSPSVLISVNEHSYG SPFTFCVVDEPPGTADM WDVR | 653 | | | X | | | |
| 12 | KRT86 | rs139895699 | TKEEINELNCMIQR | 654 | | | | | | |
| 17 | KRT35 | rs2071601 | TNCSARPICVPCPGGR | 655 | | | | X | | |
| 17 | KRT35 | rs2071601 | TNCSARPICVPCPGGRF | 656 | | | | X | | |
| 17 | KRT35 | rs12451652 | TNYSPRPICVPCPGGR | 657 | X | X | X | X | X | X |
| 17 | KRT35 | rs12451652 | TNYSPRPICVPCPGGRF | 658 | X | X | X | X | X | X |
| 17 | KRTAP1-5 | rs62623375 | TSCYQPR | 659 | | | X | X | | X |
| 17 | KRTAP1-1 | rs149188249 | TSFCGFR | 660 | | | | X | | X |
| 18 | ATP5A1 | rs77958705 | TSIAVDTIINQKR | 661 | | | | | | |
| 12 | KRT83 | rs2852464 | TSVVVKLDNSRDLNMDC MVAEIKAQYDDIATR | 662 | X | X | X | X | X | X |

TABLE 11-continued

Exemplary GVP detectable in hair samples

| CHR | gene name | mutation ID | mutated peptide (GVP) | SEQ ID NO | ALL | NFE | AFR | EAS | SAS | AMR |
|---|---|---|---|---|---|---|---|---|---|---|
| 17 | KRTAP9-6 | rs12938692 | TTCCQPTCVTSCCQPSCC STPCCQPICCGSSCCGQTS CGSSCGQSSSCAPVYCR | 663 | X | X | X | X | X | |
| 17 | KRTAP4-1 | rs752970851 | TTCCRPSCCG | 664 | | | | | | |
| 17 | KRTAP4-1 | rs752970851 | TTCCRPSCCGS | 665 | | | | | | |
| 17 | KRTAP4-1 | rs752970851 | TTCCRPSCCGSS | 666 | | | | | | |
| 17 | KRTAP4-1 | rs752970851 | TTCCRPSCCGSSC | 667 | | | | | | |
| 17 | KRTAP4-4 | rs75030409 | TTCCRPSCCRPR | 668 | | | | | | |
| 17 | KRTAP4-2 | rs389784 | TTCCRPSCCVSSCFRPQC CQSVCCQPTCC | 669 | | | | | | |
| 17 | KRTAP4-2 | rs389784 | TTCCRTTCCRPSCCVSSC FRPQCCQSVCCQPTCCR | 670 | | | | | | |
| 17 | KRTAP4-2 | rs389784 | TTCCRTTCCRPSCCVSSC FRPQCCQSVCCQPTCCRP SCGQTTCCR | 671 | | | | | | |
| 17 | KRTAP9-9 | rs144403228 | TTCFQPTCVSSSCQPSCC | 672 | | | | | | |
| 17 | KRTAP9-4 | rs2191379 | TTCFQPTCVYSCCQPFCC | 673 | | | | | | |
| 12 | KRT83 | rs2857671 | TTCGGGSCGQGRY | 674 | | | | | | |
| 17 | KRTAP9-3 | rs112082369 | TTCWKPTTVTTCSSTPCC QPSCCVSSCCQPCCHPTC CQNTCCRTTCCQPI | 675 | X | X | X | X | X | X |
| 17 | KRTAP9-7 | rs57771667 | TTCWKPTTVTTCSSTS | 676 | | | X | | | |
| 17 | KRTAP9-7 | rs57771667 | TTCWKPTTVTTCSSTSC | 677 | | | X | | | |
| 17 | KRTAP9-7 | rs57771667 | TTCWKPTTVTTCSSTSCC QPSCCVSSCCQPCCHPTC CQNTCCRTTCCQPTC | 678 | | | X | | | |
| 17 | KRTAP4-4 | rs444509 | TTSCRPSCCVS | 679 | | | X | | | |
| 17 | KRTAP4-4 | rs444509 | TTSCRPSCCVSS | 680 | | | X | | | |
| 1 | TCHH | rs2515663 | TVDLILELLDR | 681 | | | | | | |
| 17 | KRT32 | rs147160974 | TVGTPCSPCPQGRY | 682 | | | | | | |
| 17 | KRT31 | rs151023228 | TVNSLEIELQAQHNLR | 683 | | | | | | |
| 17 | KRT31 | rs151023228 | TVNSLEIELQAQHNLRDS LENTLTESEAR | 684 | | | | | | |
| 17 | KRT31 | rs151023228 | TVNSLEIELQAQHNLRDS LENTLTESEARYSSQLSQ VQSLITNVESQLAEIR | 685 | | | | | | |
| 17 | KRT32 | rs16966929 | TVNTLEIELQAQHSLRDS LENMLTESEAR | 686 | | | | | | |
| 17 | KRT32 | rs3744786 | TYLSSSCR | 687 | X | X | X | X | X | X |
| 17 | KRTAP4-2 | rs389784 | VCCQPTCCRPSCGQTTCCR | 688 | | | | | | |
| 17 | KRTAP4-7 | rs11655310 | VCSDQGCGQVLCQETCC RPSCCQTTCCR | 689 | | | | X | | |
| 17 | KRT31 | rs6503627 | VELENLIR | 690 | X | X | | | | |
| 17 | KRT40 | rs140634473 | VHSLEETNAELESR | 691 | | | | | | |
| 14 | LGALS3 | rs10148371 | VIVCNTKLDNNWGKEER | 692 | | | X | | | |

TABLE 11-continued

| Exemplary GVP detectable in hair samples | | | | | | | | | | |
|---|---|---|---|---|---|---|---|---|---|---|
| CHR | gene name | mutation ID | mutated peptide (GVP) | SEQ ID NO | ALL | NFE | AFR | EAS | SAS | AMR |
| 12 | KRT83 | rs2852464 | VKLDNSRDLNMDCMVA EIKAQYDDIATR | 693 | X | X | X | X | X | X |
| 17 | KRT32 | rs72830046 | VLEEMRCQYEAMVEAN HR | 694 | X | X | X | X | X | X |
| 18 | DSC3 | rs276937 | VLNDGTVYTAR | 695 | X | X | X | | | X |
| 17 | KRT31 | rs112544857 | VLNETRSQYEVLVETNR | 696 | | | | | | |
| 17 | KRT31 | rs112544857 | VLNETRSQYEVLVETNRR | 697 | | | | | | |
| 8 | FAM83H | rs9969600 | VNLHHVDFLR | 698 | | | | | | |
| 6 | DSP | rs2076299 | VQCDLQKANSSATETINK LKVQEQELTR | 699 | X | | X | X | X | X |
| 6 | DSP | rs28763967 | VQEQELTCLR | 700 | | | | | | |
| 20 | TGM3 | rs149720612 | VRFDILPSQSGTK | 701 | | | | | | |
| 12 | KRT86 | rs58717266 | VRFLEQQNKLLETKLPFY QNR | 702 | X | X | | X | X | X |
| 17 | KRT33B | rs12450621 | VRQLERDNAELK | 703 | | X | | | X | |
| 17 | KRT33B | rs12450621 | VRQLERDNAELKNLIR | 704 | | X | | | X | |
| 17 | KRT31 | rs6503627 | VRQLERDNVELENLIR | 705 | X | X | | | | |
| 17 | KRT31 | rs6503627 | VRQLERDNVELENLIRER | 706 | X | X | | | | |
| 17 | KRT33A | rs148752041 | VRQLERHNAELENLIR | 707 | | | | | | |
| 17 | KRT33A | rs148752041 | VRQLERHNAELENLIRER | 708 | | | | | | |
| 17 | KRTAP1-3 | rs62622847 | VRWCRPDCR | 709 | X | X | X | X | X | X |
| 17 | KRT35 | rs743686 | VSAMYSSSPCK | 710 | | | | X | | |
| 17 | KRT35 | rs743686 | VSAMYSSSPCKLPSLSPV AR | 711 | | | | X | | |
| 17 | KRTAP4-11 | rs140898464 | VSCHTTCYRPTCVISSCPR PVC | 712 | | | X | X | | X |
| 17 | KRTAP4-11 | rs140898464 | VSCHTTCYRPTCVISSCPR PVCCA | 713 | | | X | X | | X |
| 17 | KRT34 | rs116116504 | VSGNSCGPCGTSQK | 714 | | | | | | |
| 12 | KRT86 | rs749337520 | VSSDPSNSNVVVGTTNA | 715 | | | | | | |
| 12 | KRT86 | rs749337520 | VSSDPSNSNVVVGTTNA CAPSAR | 716 | | | | | | |
| 21 | KRTAP11-1 | rs9636845 | VSSGSQPLGGISSVCQPV GGISTVCQPVGGVSTVCQ PACGVSR | 717 | X | X | | X | X | X |
| 17 | KRT33A | rs12937519 | VSSSEQLQSYQVEIIELR | 718 | X | X | X | X | X | X |
| 17 | JUP | rs1126821 | VSVELTNSLFKHDPAAW EAAQSMIPINEPYGDDLD ATYRPMYSSDVPLDPLEM | 719 | | | | X | | X |
| 12 | KRT83 | rs2852464 | VVKLDNSRDLNMDCMV AEIKAQYDDIATR | 720 | X | X | X | X | X | X |
| 12 | KRT83 | rs2852464 | VVVKLDNSRDLNMDCM VAEIKAQYDDIATR | 721 | X | X | X | X | X | X |
| 12 | KRT2 | rs638043 | WELLQQMNVDTRPINLE PIFQGYIDSLKR | 722 | X | X | | | X | X |

TABLE 11-continued

Exemplary GVP detectable in hair samples

| CHR | gene name | mutation ID | mutated peptide (GVP) | SEQ ID NO | ALL | NFE | AFR | EAS | SAS | AMR |
|---|---|---|---|---|---|---|---|---|---|---|
| 12 | KRT86 | rs111429470 | WLYEEEIR | 723 | | | | | | |
| 12 | KRT86 | rs111429470 | WLYEEEIRVLQSHISDTSVVVK | 724 | | | | | | |
| 17 | KRTAP4-4 | rs444509 | YCQTTCCRTTSCRPSCCVSSCCRPQCCQTTCCR | 725 | | | X | | | |
| 12 | KRT83 | rs766508559 | YEEEVALQATAENEFVALKK | 726 | | | | | | |
| 17 | KRT31 | rs112544857 | YEVLVETNRR | 727 | | | | | | |
| 17 | KRT34 | rs201477948 | YQMEQSLR | 728 | | | | | | |
| 17 | KRT33B | rs34771886 | YSLENTLTESEARYSSQLSQVQSLITNVESQLAEIHSDLERQNQEYQVLLDVR | 729 | | | | | | |
| 17 | KRT40 | rs8064910 | YSSQLAQIQRLIDNLENQLAEIR | 730 | | | | | | |
| 17 | KRT36 | rs11657323 | YSSQLAQMQCLISTVEAQLSEIR | 731 | X | X | X | | X | X |
| 17 | KRT36 | rs11657323 | YSSQLAQMQCLISTVEAQLSEIRCDLER | 732 | X | X | X | | X | X |
| 17 | KRT36 | rs11657323 | YSSQLAQMQCLISTVEAQLSEIRCDLERQNQEYQVLLDVK | 733 | X | X | X | | X | X |
| 17 | KRT32 | rs11078993 | YSSQLAQMQCMITNVEAQLAEIQADLER | 734 | X | | X | X | X | X |
| 17 | KRT32 | rs11078993 | YSSQLAQMQCMITNVEAQLAEIQADLERQNQEYQVLLDVR | 735 | X | | X | X | X | X |
| 17 | KRT32 | rs2604956 | YSSQLAQMQCMITNVEAQLAEIQAELERQNQEYQVLLDVR | 736 | X | X | | | | |
| 17 | KRT32 | rs11078993 | YSSQLAQMQCMITNVEAQLAEIQAELERQNQEYQVLLDVR | 737 | X | | X | X | X | X |
| 17 | KRT32 | rs2604956 | YSSQLAQMQCMITNVEAQLAEIRAELER | 738 | X | X | | | | |
| 17 | KRT32 | rs2604956 | YSSQLAQMQCMITNVEAQLAEIRAELERQNQEYQVLLDVR | 739 | X | X | | | | |
| 17 | KRT34 | rs148645199 | YSSQLSQMQSLITNVESQLAEIR | 740 | | | | | | |
| 17 | KRT33B | rs34771886 | YSSQLSQVQSLITNVESQLAEIHSDLER | 741 | | | | | | |
| 17 | KRT33B | rs34771886 | YSSQLSQVQSLITNVESQLAEIHSDLERQNQEYQVLLDVR | 742 | | | | | | |
| 17 | KRT34 | rs199674249 | YSSQLSQVQSLITNVESQLAEIRCDLERQNQEYQVLLDVC | 743 | | | | | | |
| 17 | KRT34 | rs61740668 | YSSQLSQVQSLITNVESQLAEIRCDLEWQNQEYQVLLDVR | 744 | | | | | | |
| 17 | KRT35 | rs743686 | YSSSPCKLPSLSPVAR | 745 | | | | X | | |
| 11 | GSTP1 | rs1695 | YVSLIYTNYEAGKDDYVK | 746 | X | X | X | X | X | |

TABLE 11-continued

| Exemplary GVP detectable in hair samples | | | | | | | | | | |
|---|---|---|---|---|---|---|---|---|---|---|
| CHR | gene name | mutation ID | mutated peptide (GVP) | SEQ ID NO | ALL | NFE | AFR | EAS | SAS | AMR |
| 11 | GSTP1 | rs1695 | YVSLIYTNYEVGKDDYVK | 747 | X | X | X | X | X | |
| 11 | GSTP1 | rs1138272 | YVSLIYTNYEVGKDDYVK | 748 | X | X | | | X | |

X = more preferable for sub-population

Example 47: Exemplary GVP Detectable in Skin Samples

An exemplary set of GVPs that can be used in methods and systems herein described as well as in related databases is reported herein. In particular, the exemplary set of GVPs comprises genes validated as proteomically detectable in skin samples of a *Homo Sapiens* which can be used in methods and systems to detect a genetic variation and/or perform a genetic variation analysis, as well as in related databases, in accordance with the various aspects of the present disclosure.

Specifically, Table 12 shows a list of exemplary GVP detectable in skin samples. The fields in Table 12 are the name of the gene (gene name), mutation identifier (mutation ID), sequence of the mutated peptide (mutated peptide (GVP)), sequence identifier in the sequence listing of the instant disclosure (SEQ ID NO), and the subpopulations including all populations (ALL), Non-Finnish European subpopulation (NFE), African subpopulation (AFR), East Asian subpopulation (EAS), South Asian subpopulation (SAS), and Latino subpopulation (AMR).

The exemplary GVPs of Table 12 can be used in method and systems of the instant disclosure wherein the sample comprises a skin sample from human beings.

TABLE 12

| Exemplary GVP detectable in skin samples | | | | | | | | | |
|---|---|---|---|---|---|---|---|---|---|
| gene name | mutation ID | mutated peptide (GVP) | SEQ ID NO | All | NFE | AFR | EAS | SAS | AMR |
| DSC1 | rs17800159 | AASSQTPTMCTTTVTIK | 749 | X | X | | | X | X |
| KRT78 | rs61764062 | AEAEALYQIK | 750 | X | | | X | X | X |
| KRT6B | rs144860693 | AGGSYGFGGAR | 751 | X | X | X | X | X | X |
| ECM1 | rs13294 | APYPNYDRDILTIDISR | 752 | X | X | X | X | X | X |
| ECM1 | rs13294 | DILTIDISR | 753 | X | X | X | X | X | X |
| POF1B | rs363774 | EELGHLQNDLTSLENDK | 754 | | | | | | |
| POF1B | rs363774 | EELGHLQNDLTSLENDKMR | 755 | | | | | | |
| FLG2 | rs3818831 | EFHPVLK | 756 | X | X | X | | X | X |
| FLG2 | rs3818831 | EFHPVLKNPDDPDTVDVIMH | 757 | X | X | X | | X | X |
| FLG2 | rs3818831 | EFHPVLKNPDDPDTVDVIMHMLDR | 758 | X | X | X | | X | X |
| ECM1 | rs3737240 | EGMPAPFGDQSHPEPESWNAAQHCQQDR | 759 | X | X | X | X | X | X |
| FLG2 | rs3818831 | ELLEKEFHPVLK | 760 | X | X | X | | X | X |
| KRT6A | rs144401677 | EQGTKTVRQNMEPLFEQYINNLR | 761 | | | | | | |
| KRT78 | rs2013335 | FGEWSGGPGLSLCPPGGIQEVTINQNPL TPLK | 762 | | | X | | | |
| KRT2 | rs638043 | FLEQQNQVLQTKWELLQQMNVDTRPINL EPIFQGYIDSLKR | 763 | X | X | | | X | X |
| KRT14 | rs11551758 | FSSGGAYGLGGGYGGGF | 764 | | | X | | | |
| KRT14 | rs6503640 | FSSGGAYGLGGGYGGGF | 765 | | | | | | |
| KRT14 | rs3826550 | FSSGGAYGLGGGYGGGFSSSSSSFGSGF GGGYGGGLGTGLGGGFGGGFAGGDGLLV GSEK | 766 | X | X | X | X | X | X |
| FLG2 | rs3818831 | GELKELLEKEFHPVLK | 767 | X | X | X | | X | X |
| HAL | rs7297245 | GETISGGNFHGEYPAK | 768 | | | | | | |

TABLE 12-continued

Exemplary GVP detectable in skin samples

| gene name | mutation ID | mutated peptide (GVP) | SEQ ID NO | All | NFE | AFR | EAS | SAS | AMR |
|---|---|---|---|---|---|---|---|---|---|
| KRT2 | rs2634041 | GGGFGGGSGFGGGSGF | 769 | X | X | X | X | | X |
| KRT2 | rs2634041 | GGGFGGGSGFGGGSGFSGGGF | 770 | X | X | X | X | | X |
| KRT2 | rs2634041 | GGGFGGGSGFGGGSGFSGGGFGGGGFGGGR | 771 | X | X | X | X | | X |
| KRT10 | rs747151268 | GGGSFGGGFGGGFGGDGGLLSGNEK | 772 | X | X | X | X | X | X |
| KRT10 | rs17855579 | GGGSFGGGYGGGSSGGGSSGGGY | 773 | | | | | | |
| KRT10 | rs17855579 | GGGSFGGGYGGGSSGGGSSGGGYGGGH | 774 | | | | | | |
| KRT10 | rs17855579 | GGGSFGGGYGGGSSGGGSSGGGYGGGHGG | 775 | | | | | | |
| KRT10 | rs17855579 | GGGSFGGGYGGGSSGGGSSGGGYGGGHGGSSGGGY | 776 | | | | | | |
| KRT10 | rs17855579 | GGGSFGGGYGGGSSGGGSSGGGYGGGHGGSSGGGYGGGSSGGGY | 777 | | | | | | |
| KRT77 | rs636127 | GGSGGGYGSGCGGGGGSYGGSGR | 778 | | | | | | |
| KPRP | rs16834461 | GHPAVCQPQGR | 779 | X | X | X | X | X | X |
| C1orf68 | rs1332500 | GSGLGAGQGTNGASVK | 780 | X | X | | X | X | X |
| KRT1 | rs14024 | GSSSGGVKSSGGSSSVR | 781 | X | X | X | | X | X |
| KRT10 | rs4261597 | GSYGSSSFGGSYGGSFGGGSFGGGSFGGGSFGGGGFGGGGFGGGFGGGFGGDGGLLSGNEK | 782 | | | | | | |
| FLG | rs7512857 | HAGIGHGQASSAVR | 783 | X | X | X | | X | X |
| JUP | rs1126821 | HDPAAWEAAQSMIPINEPYGDDLDATYRPM | 784 | | | | X | | X |
| JUP | rs1126821 | HDPAAWEAAQSMIPINEPYGDDLDATYRPMYSSDV | 785 | | | | X | | X |
| JUP | rs1126821 | HDPAAWEAAQSMIPINEPYGDDLDATYRPMYSSDVPLDPLEMH | 786 | | | | X | | X |
| DSC1 | rs28620831 | HGLVATHTLTVR | 787 | | X | | | | |
| S100A7 | rs3014837 | IDKPSLLTMMK | 788 | | | | | | |
| JUP | rs41283425 | INYQDDAELATHALPELTK | 789 | | X | | | | |
| KRT14 | rs59780231 | LEQEITTYR | 790 | | | | X | | X |
| JUP | rs41283425 | LINYQDDAELATHALPELTK | 791 | | X | | | | |
| KPRP | rs17612167 | LPLHQC | 792 | X | X | | X | X | X |
| KPRP | rs4329520 | LRPEPSISLEPR | 793 | | | | X | X | |
| KRT5 | rs11549950 | LSGEGVGPVNISVVTSSVSSGYGSGSGYGGGLGGGLGGGLGGGLAGGGSGS | 794 | X | X | X | | X | X |
| POF1B | rs363774 | LVLSTFSNIREELGHLQNDLTSLENDK | 795 | | | | | | |
| KRT2 | rs638043 | MNVDTRPINLEPIFQGYIDSLKR | 796 | X | X | | | X | X |
| JUP | rs199826380 | NLSDVATKQEGLENVLK | 797 | | | | | | |
| DSP | rs17604693 | NTNFAQK | 798 | | | | | | |
| KRT2 | rs638043 | NVDTRPINLEPIFQGYIDSLK | 799 | X | X | | | X | X |
| KRT2 | rs638043 | NVDTRPINLEPIFQGYIDSLKR | 800 | X | X | | | X | X |

TABLE 12-continued

Exemplary GVP detectable in skin samples

| gene name | mutation ID | mutated peptide (GVP) | SEQ ID NO | All | NFE | AFR | EAS | SAS | AMR |
|---|---|---|---|---|---|---|---|---|---|
| TGM3 | rs214814 | NWNGSVEILK | 801 | X | X | X | X | X | X |
| DSG1 | rs3752095 | PILDPLGYGNVTVTESFTTSDTLKPSVH VHDNRPASNVVVTER | 802 | X | X | X | X | X | X |
| JUP | rs199826380 | QEGLENVLK | 803 | | | | | | |
| KRT6B | rs11170126 | QNLELLFEQYINNLR | 804 | | | | | | |
| KRT6A | rs144401677 | QNMEPLFEQYINNLR | 805 | | | | | | |
| ECM1 | rs13294 | RAPYPNYDRDILTIDISR | 806 | X | X | X | X | X | X |
| S100A7 | rs3014837 | RDDKIDKPSLLTMMK | 807 | | | | | | |
| JUP | rs41283425 | SAIVHLINYQDDAELATHALPELTK | 808 | | X | | | | |
| ANXA2 | rs17845226 | SALSGHLETLILGLLK | 809 | X | X | | | | X |
| KRT5 | rs11549949 | SGGLSVGGSGFSASSGR | 810 | X | X | X | | X | X |
| FLG2 | rs16842865 | SGHSSYGQHGFGSSQSSGYGQHGSSSGQ TSGFGQHK | 811 | | | | | | |
| KRT78 | rs2253798 | SLNSFGR | 812 | X | X | X | X | X | X |
| KRT1 | rs14024 | SSGGSSSVR | 813 | X | X | X | | X | X |
| KRT14 | rs3826550 | SSSSSSFGSGFGGGYGGGLGTGLGGGFG GGFAGGDGLLVGSEK | 814 | X | X | X | X | X | X |
| C1orf68 | rs41268474 | STSYCYLAPR | 815 | X | X | X | X | X | X |
| KRT14 | rs59780231 | TRLEQEITTY | 816 | | | | X | | X |
| KRT14 | rs59780231 | TRLEQEITTYR | 817 | | | | X | | X |
| LOR | rs6661601 | TSGGGGGGGGGGGGCGFFGGGGSGGGS SGSGCGY | 818 | X | X | X | X | X | X |
| DSC1 | rs17800159 | TTTVTIK | 819 | X | X | | | X | X |
| KRT2 | rs638043 | VDTRPINLEPIFQGYIDSLK | 820 | X | X | | | X | X |
| KRT2 | rs638043 | VDTRPINLEPIFQGYIDSLKR | 821 | X | X | | | X | X |
| DSC3 | rs35630063 | VEDENDSHPVFTEAIYNFEVLESSR | 822 | | | | | | |
| DSG1 | rs139922779 | VVSPISGADLHGMLEMPDLR | 823 | | | | | | |
| DSG1 | rs139922779 | VVSPISGADLHGMLEMPDLRDGSNVIVT ER | 824 | | | | | | |
| KRT2 | rs638043 | WELLQQMNVDTR | 825 | X | X | | | X | X |
| KRT2 | rs638043 | WELLQQMNVDPRPINLEPIFQGY | 826 | X | X | | | X | X |
| KRT2 | rs638043 | WELLQQMNVDTRPINLEPIFQGYIDSLK | 827 | X | X | | | X | X |
| KRT2 | rs638043 | WELLQQMNVDTRPINLEPIFQGYIDSLK R | 828 | X | X | | | X | X |
| KRT36 | rs11657323 | YSSQLAQMQCLISTVEAQLSEIR | 829 | X | X | X | | X | X |

X = more preferable for sub-population

In summary according to the first aspect, a method is described to prepare a biological sample for proteomic analysis, the method comprising applying to the biological sample an energy field resulting in an increased thermodynamic or total energy of the sample to obtain a processed biological sample comprising solubilized proteins to be used in the proteomic analysis.

In a first set of embodiments of the method of the first aspect, applying to the biological sample an energy field is performed by sonication and in particular by sonication baths, sonication probes, or flow-through sonication systems. In a second set of embodiments of the method of the first aspect which can comprise the method of the first aspect performed according to the first set of embodiments, the biological sample is hair and/or skin. In a third set of embodiments of the method of the first aspect which can comprise the method of the first aspect performed according to the first set of embodiments of the method of the first aspect, the biological sample can be bone or teeth.

In summary according to the second aspect, a method is described to provide a marker genetic protein variation of a biological organism in a biological sample of the biological organism.

The method comprises:

- detecting exome sequences of the sample of the biological organism by sequencing exomes of a genome from the sample of the biological organism;
- detecting a marker exome sequence comprising a genetic variation of the genome of the biological organism by comparing the detected exome sequences with a database of exome sequences of the biological organism;
- detecting peptide sequences of the sample of the biological organism by performing proteomic analysis of the sample of the biological organism; and providing the marker genetic protein variation of the biological organism in the sample of the biological organism by comparing the detected marker exome sequence with the detected peptide sequences to provide a marker genetic protein variation validated for the same of the biological organism.

In a first set of embodiments of the method of the second aspect, the biological organism is *Homo sapiens*. In a second set of embodiments of the method of the second aspect which can comprise the method of the second aspect performed according to the first set of embodiments, the biological sample is hair.

According to the second aspect of the disclosure, a marker genetic protein variation of a biological organism is also described. The marker genetic protein variation of the second aspect is validated for a sample of the biological organism, and is obtainable and obtained by any one of the method according to the second aspect.

In summary according to the third aspect, a method is described to improve a marker genetic protein variation database system including data for at least one biological organism. The method comprises

- producing a mass spectrometry dataset from a biological sample from an individual of the at least one biological organism;
- comparing the mass spectrometry dataset to a protein variant database to produce a set of proteomically detected proteins in the biological sample of the individual;
- providing a set of represented genes proteomically detectable in the biological sample of the individual, the represented genes corresponding to the proteomically detected proteins in the biological sample of the individual; and
- identifying a marker genetic protein variation validated for the biological sample of the individual, to be included in the marker genetic protein variation database system by
- providing a proteomically detectable genomic variation in the set of represented genes proteomically detectable in the biological sample of the individual, and
- providing the marker genetic protein variation validated genetic protein variation by providing a proteomically detectable genetic protein variation corresponding to the proteomically detectable genomic variation in the biological sample of the individual.

In a first set of embodiments of the method of the third aspect, providing the marker validated genetic protein variation, further comprises: providing a mass spectrometry dataset from the biological sample of the individual; and comparing the provided mass spectrometry dataset with the proteomically detectable genetic protein variation to provide the validated genetic protein variation.

In a second set of embodiments of the method of the third aspect which can comprise the method of the third aspect performed according to the first set of embodiments, providing a proteomically detectable genomic variation in the set of represented genes proteomically detectable in the biological sample of the individual is performed by providing exome sequence data of the individual; and comparing the exome sequence data of the individual with sequences from the represented genes proteomically detectable in the biological sample of the individual to determine the proteomically detectable genomic variation in the biological sample of the individual.

In a third set of embodiments of the method of the third aspect which can comprise the method of the third aspect performed according to the first set of embodiments or the second set of embodiments, providing a proteomically detectable genetic protein variation corresponding to the proteomically detectable genomic variation in the biological sample of the individual, is performed by: performing annotation on the proteomically detectable genomic variation in the biological sample of the individual to produce a corresponding mutant/reference protein sequence; and providing the proteomically detectable genetic protein variation from the annotated proteomically detectable genomic variation in the biological sample of the individual.

In a fourth set of embodiments of the method of the third aspect, which can comprise the method of the third aspect performed according to the first set of embodiments, the second set of embodiments or the third set of embodiments, the method further comprises creating a genetic protein variation identity panel by collecting the validated genetic protein variant proteomically detectable in the biological sample of the individual to provide a genetic protein variation identity panel of the individual.

In a fifth set of embodiments of the method of the third aspect, which can comprise the method of the third aspect performed according to the first set of embodiments, the second set of embodiments, the third set of embodiments or the fourth set of embodiments, the steps are repeated for a plurality of individuals of the at least one biological organism, to provide a database comprising validated genetic protein variations proteomically detectable in the biological sample of the plurality of individuals of the biological organism type.

In a first subset of embodiments of the fifth set of embodiments of the method according to the third aspect, the method further comprises: collecting the represented genes common to the plurality of the individuals into a proteomically detectable gene pool; providing validated genetic protein variations proteomically detectable in the biological sample of the plurality of individuals of the at least one biological organism from the collected common represented; and collecting the validated genetic protein variant proteomically detectable in the biological sample of the plurality of individuals, in the genetic protein variation panel is a genetic protein variation panel common to the plurality of individuals.

In a second subset of embodiments of the fifth set of embodiments of the method according the third aspect, the proteomically detectable gene pool contains data corresponding to proteins that are common to over 50% of all the validated genetic protein variant proteomically detectable in the biological sample of the individual.

In some embodiments of the first subset of embodiments or the second subset of embodiments of the fifth set of embodiments of the method according to the third aspect, the providing validated genetic protein variations proteomically detectable in the biological sample of the plurality of individuals is performed to only include genomic variation with a frequency greater than 1% in the plurality of the individuals into a proteomically detectable gene pool.

In a sixth set of embodiments of the method of the third aspect, which can comprise the method of the third aspect performed according to the first set of embodiments, the second set of embodiments, the third set of embodiments, the fourth set of embodiments or the fifth set of embodiments comprising any related subsets of embodiments, the at least one biological organism is *Homo sapiens.*

In a seventh set of embodiments of the method of the third aspect, which can comprise the method of the third aspect performed according to the first set of embodiments, the second set of embodiments, the third set of embodiments, the fourth set of embodiments, the fifth set of embodiments comprising any related subsets of embodiments, or the sixth set of embodiments, the biological sample is hair or skin.

According to the third aspect, a marker genetic protein variation database system is also described obtainable and/or obtained by the methods according to third aspect, which comprises the method of the third aspect performed according to any one of the related sets or subsets of embodiments.

In summary according to the fourth aspect, a method is described to improve a marker genetic protein variation database system comprising marker genetic protein variations common to a plurality of individuals. The method comprises

- providing a number of proteomic datasets of individuals of the plurality of individuals, the number statistically significant for the plurality of individuals;
- identifying a protein common to the provided number of proteomic datasets;
- selecting from the identified protein common to the provided proteomic datasets, a protein detectable in a biological sample of an individual of the plurality of individuals;
- providing a number of exome datasets of the individuals of the plurality of individuals, the number statistically significant for the plurality of individuals;
- identifying a genetic variation in the provided number of exome datasets;
- selecting from the identified genetic variation, a genetic variation detectable in the biological sample; and
- comparing the selected proteins detectable in the biological sample with the selected genetic variations detectable in the biological sample, to provide a marker genetic protein variation common to a plurality of individuals of a biological organism type and detectable in the biological sample.

In a first set of embodiments of the method of the fourth aspect, the individual is a *Homo sapiens.*

In a second set of embodiments of the method of the fourth aspect which can comprise the method of the fourth aspect performed according to the first set of embodiments, the biological sample is hair.

According to the fourth aspect, a marker genetic protein variation database system is also described, comprising genetic protein variations common to a plurality of individuals. The genetic protein variation database system is obtainable by the method according to sixth aspect, which comprises the method of the fourth aspect performed according to any one of the related sets of embodiments.

In summary, according to the fifth aspect a method is described to detect a genetic protein variation in a biological sample. The method comprises

- providing a marker mass spectrum of a marker peptide comprising a marker genetic protein variation corresponding to the genetic protein variation;
- performing mass spectrometry of a fractionated digested peptide of the biological sample to obtain a mass spectrum of each of the fractionated digested peptide; and
- comparing the mass spectrum of the fractionated digested peptide with a marker mass spectrum of a marker peptide comprising the marker genetic protein variation to detect the genetic protein variation in the biological sample.

In a first set of embodiments of the method according to the fifth aspect, the fractionated digested peptides are obtained by preparing the biological sample to obtain a processed biological sample comprising solubilized proteins to be used in the protein analysis, fractionating the processed biological sample to obtain a solubilized protein fraction comprising the solubilized proteins from the sample, digesting the solubilized proteins from the sample with a site specific proteolytic enzyme to obtain digested solubilized proteins from the sample, and fractionating the digested solubilized proteins to obtain fractionated digested peptides from the digested solubilized proteins from the biological sample.

In a first subset of embodiments of the first set of embodiments of the method of the fifth aspect preparing the biological sample is performed according to the method of the first aspect of the disclosure comprising any one of the related sets of embodiments.

In a second set of embodiments of the method of the fifth aspect which can comprise the method of the fifth aspect performed according to the first set of embodiments, the marker peptide comprises a plurality of marker peptides each comprising a marker genetic protein variation.

In a third set of embodiments of the method of the fifth aspect which can comprise the method of the fifth aspect performed according to the first set of embodiments or the second set of embodiments, the marker genetic protein variation comprises a marker genetic protein variation according to the second aspect of the disclosure.

In a fourth set of embodiments of the method of the fifth aspect which can comprise the method of the fifth aspect performed according to the first set of embodiments, the second set of embodiments or the third set of embodiments, the marker genetic protein variation comprises a marker genetic protein variation from a marker genetic protein variation database system according to the third aspect of the disclosure comprising any one of the related sets of embodiments.

In a fifth set of embodiments of the method of the fifth aspect which can comprise the method of the fifth aspect performed according to the first set of embodiments, the second set of embodiments, the third set of embodiments or the fourth set of embodiments, the marker genetic protein variation comprises a marker genetic protein variation from a marker genetic protein variation database system according to the fourth aspect of the disclosure comprising any one of the related sets of embodiments.

In summary according to the sixth aspect, a method is described to provide a marker genetic variation database system for a biological sample. The method comprises:

preparing the biological sample to obtain a processed biological sample comprising solubilized proteins to be used in a proteomic analysis.

fractionating the processed biological sample to obtain a solubilized protein fraction comprising the solubilized proteins from the sample and a solubilized DNA fraction comprising solubilized nuclear and/or mitochondrial genome from the sample;

detecting a genetic protein variation in the solubilized proteins from the sample by performing the proteomic analysis of the solubilized protein fraction;

detecting a genomic variation of the nuclear and/or mitochondrial genome by performing a genetic analysis of the solubilized DNA fraction; and combining the detected genetic protein variations and the detected genomic variation to provide the marker genetic variation database system of the biological sample.

In a first set of embodiments of the method according to the sixth aspect, preparing the biological sample to obtain a processed biological sample comprising solubilized proteins to be used in a proteomic analysis, is performed by the method of the first aspect, comprising any one of the related sets of embodiments.

In a second set of embodiments of the method of the sixth aspect which can comprise the method of the sixth aspect performed according to the first set of embodiments, detecting a genetic protein variation is performed by the method according to the fifth aspect comprising any one of the related sets and subsets of embodiments.

In a third set of embodiments of the method of the sixth aspect which can comprise the method of the sixth aspect performed according to the first set of embodiments or second sets of embodiments, the genetic protein variation is a single amino acid polymorphism (SAP), an amino acid deletion and/or an amino acid insertion.

In a fourth set of embodiments of the method of the sixth aspect which can comprise the method of the sixth aspect performed according to the first set of embodiments, second sets of embodiments or third sets of embodiments, the genomic variation is a single nucleotide polymorphism (SNP), a nucleotide deletion or a nucleotide insertion.

In a fifth set of embodiments of the method of the sixth aspect which can comprise the method of the sixth aspect performed according to the first set of embodiments, the second set of embodiments, the third set of embodiments or the fourth set of embodiments, the genomic variation is within the short tandem repeat (STR) regions of the genome.

In a sixth set of embodiments of the method of the sixth aspect which can comprise the method of the sixth aspect performed according to the first set of embodiments, the second set of embodiments, the third set of embodiments the fourth set of embodiments or the fifth set of embodiments, the genomic variation is within the mitochondrial DNA.

According to the sixth aspect, a marker genetic variation database system is also described obtainable by the method according to the sixth aspect of the disclosure, comprising any one of the related sets of embodiments.

In summary according to the seventh aspect, a method is described to detect a marker genetic variation in a biological sample of a biological organism. The method comprises preparing the biological sample to obtain a processed biological sample comprising solubilized proteins to be used in a proteomic analysis;

fractionating the processed biological sample to obtain a solubilized protein fraction comprising the solubilized proteins from the sample and a solubilized DNA fraction comprising solubilized nuclear and/or mitochondrial genome from the sample;

detecting a genetic protein variation in the solubilized proteins from the sample by performing the proteomic analysis of the solubilized protein fraction;

detecting a genomic variation of the nuclear and/or mitochondrial genome by performing a genetic analysis of the solubilized DNA fraction; and comparing the detected genetic protein variation and/or the detected genomic variation with a marker genetic protein variation and/or of a marker genomic variation respectively from the marker genetic variation database system of the sixth aspect of the disclosure.

In a first set of embodiments of the method according to the seventh aspect, preparing the biological sample to obtain a processed biological sample comprising solubilized proteins to be used in a proteomic analysis, is performed by the method according to the first aspect of the disclosure comprising any one of the related sets of embodiments.

In a second set of embodiments of the method of the seventh aspect which can comprise the method of the seventh aspect performed according to the first set of embodiments, detecting a genetic protein variation is performed by the method according to the fifth aspect of the disclosure comprising any one of the related sets and subsets of embodiments.

In a third set of embodiments of the method of the seventh aspect which can comprise the method of the seventh aspect performed according to the first set of embodiments or second sets of embodiments, the genetic protein variation is a single amino acid polymorphism (SAP), an amino acid deletion and/or an amino acid insertion.

In a fourth set of embodiments of the method of the seventh aspect which can comprise the method of the seventh aspect performed according to the first set of embodiments, second sets of embodiments or third sets of embodiments, the genomic variation is a single nucleotide polymorphism (SNP), a nucleotide deletion or a nucleotide insertion.

In a fifth set of embodiments of the method of the seventh aspect which can comprise the method of the seventh aspect performed according to the first set of embodiments, the second set of embodiments, the third set of embodiments or the fourth set of embodiments, the genomic variation is within the short tandem repeat (STR) regions of the genome.

In a sixth set of embodiments of the method of the seventh aspect which can comprise the method of the seventh aspect performed according to the first set of embodiments, the second set of embodiments, the third set of embodiments or the fourth set of embodiments, the genomic variation is within the mitochondrial DNA.

In summary according to the eight aspect of the disclosure, a method is described to perform genetic analysis of a sample of a biological organism. The method comprises preparing the biological sample to obtain a processed biological sample comprising solubilized proteins to be used in a proteomic analysis;

fractionating the processed biological sample to obtain a solubilized protein fraction comprising the solubilized proteins from the sample;

digesting the solubilized protein fraction from the sample to obtain digested peptides from the sample;

fractionating the digested peptides to obtain fractionated digested peptides from the digested solubilized proteins from the biological sample.

detecting a marker genetic variation of the fractionated digested peptides from the sample; in which preparing the sample is performed according to any one of the methods according to the first aspect of the disclosure, comprising any one of the related sets of embodiments; and/or detecting a genetic variation is performed by at least one of the method to detect a genetic protein variation of any one of the methods according to the fifth aspect, comprising any one of the related sets and subsets of claims; and the method to detect a genetic variation of any one of the methods according to the seventh aspect of the disclosure comprising any one of the related sets of embodiments.

Preferably in any one of the embodiments of the method to perform genetic analysis of a sample of a biological organism of the eight aspect the preparing is performed according to any one of the methods according to the first aspect of the disclosure, comprising any one of the related sets of embodiments and the detecting is performed at least one of the method to detect a genetic protein variation of any one of the methods according to the fifth aspect, comprising any one of the related sets and subsets of claims; and the method to detect a genetic variation of any one of the methods according to the seventh aspect of the disclosure comprising any one of the related sets of embodiments.

In view of the above, in summary described herein are methods and systems to perform genetically variant protein analysis and related marker genetic protein variations and databases, which in several embodiments allow performing a reliable genetic variation protein analysis in biological samples of different types and conditions taking into account the features of the biological sample where the analysis is performed. The examples set forth above are provided to give those of ordinary skill in the art a complete disclosure and description of how to perform the embodiments of the methods and systems of the disclosure, and are not intended to limit the scope of what the inventors regard as their disclosure. Those skilled in the art will recognize how to adapt the features of the exemplified methods and systems herein disclosed to additional methods and systems according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file IL-13212-Sequence-Listing_ST25 is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible sub-combinations of the group are intended to be individually included in the disclosure. Every combination of components or materials described or exemplified herein can be used to practice the disclosure, unless otherwise stated. One of ordinary skill in the art will appreciate that methods, system elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the genetic circuits, genetic molecular components, and methods steps set forth in the present description. As will be obvious to one of skill in the art, methods and systems useful for the present methods and systems may include a large number of optional composition and processing elements and steps.

In particular, it will be understood that various modifications may be made without departing from the spirit and scope of the present disclosure. Accordingly, other embodiments are within the scope of the following claims.

REFERENCES

1. Bodzon-Kulakowska, A., et al., *Methods for samples preparation in proteomic research*. Journal of Chromatography B, 2007. 849(1): p. 1-31.
2. Cao, R., et al., *dbSAP: single amino-acid polymorphism database for protein variation detection*. Nucleic acids research, 2016. 45(D1): p. D827-D832.
3. Parker, G. J., et al., *Demonstration of protein-based human identification using the hair shaft proteome*. PloS one, 2016. 11(9): p. e0160653.
4. Ochoa-Rivas, A., et al., *Microwave and Ultrasound to Enhance Protein Extraction from Peanut Flour under Alkaline Conditions: Effects in Yield and Functional Properties of Protein Isolates*. Food and Bioprocess Technology, 2017. 10(3): p. 543-555.
5. Phongthai, S., S.-T. Lim, and S. Rawdkuen, *Optimization of microwave-assisted extraction of rice bran protein and its hydrolysates properties*. Journal of Cereal Science, 2016. 70: p. 146-154.
6. Sun, W., et al., *Microwave-assisted protein preparation and enzymatic digestion in proteomics*. Molecular & Cellular Proteomics, 2006. 5(4): p. 769-776.
7. Ye, X. and L. Li, *Microwave-assisted protein solubilization for mass spectrometry-based shotgun proteome analysis*. Analytical chemistry, 2012. 84(14): p. 6181-6191.
8. Lubec, G., et al., *Structural stability of hair over three thousand years*. Journal of archaeological science, 1987. 14(2): p. 113-120.
9. Kaye, D. H., *Ultracrepidarianism in Forensic Science: The Hair Evidence Debacle*. 2015.
10. Robertson, J., *Managing the forensic examination of human hairs in contemporary forensic practice*. Australian Journal of Forensic Sciences, 2017. 49(3): p. 239-260.
11. McNevin, D., et al., *Short tandem repeat (STR) genotyping of keratinised hair. Part* 1. *Review of current status and knowledge gaps*. Forensic Sci Int, 2005. 153(2-3): p. 237-46.
12. Melton, T., et al., *Forensic mitochondrial DNA analysis of* 691 *casework* hairs. J Forensic Sci, 2005. 50(1): p. 73-80.
13. Rice, R. H., G. E. Means, and W. D. Brown, *Stabilization of bovine trypsin by reductive methylation*. Biochimica et Biophysica Acta (BBA)-Protein Structure, 1977. 492(2): p. 316-321.
14. Cox, B. and A. Emili, *Tissue subcellular fractionation and protein extraction for use in mass-spectrometry-based proteomics*. Nature protocols, 2006. 1(4): p. 1872.
15. Fic, E., et al., *Comparison of protein precipitation methods for various rat brain structures prior to proteomic analysis*. Electrophoresis, 2010. 31(21): p. 3573-3579.
16. Gupta, N., et al., *Quantitative proteomic analysis of B cell lipid rafts reveals that ezrin regulates antigen receptor-mediated lipid raft dynamics*. Nature immunology, 2006. 7(6): p. 625.
17. Harder, A., et al., *Comparison of yeast cell protein solubilization procedures for two-dimensional electrophoresis*. Electrophoresis, 1999. 20(4-5): p. 826-829.
18. Shao, S., et al., *Reproducible tissue homogenization and protein extraction for quantitative proteomics using MicroPestle-assisted pressure-cycling technology*. Journal of proteome research, 2016. 15(6): p. 1821-1829.
19. Rice, R. H., *Proteomic analysis of hair shaft and nail plate*. J Cosmet Sci, 2011. 62(2): p. 229-36.
20. Wu, P. W., et al., *Proteomic analysis of hair shafts from monozygotic twins: Expression profiles and genetically variant peptides*. Proteomics, 2017.
21. Canas, B., et al., *Trends in sample preparation for classical and second generation proteomics*. Journal of Chromatography A, 2007. 1153(1): p. 235-258.
22. Gundry, R. L., et al., *Preparation of proteins and peptides for mass spectrometry analysis in a bottom-up proteomics workflow*. Current protocols in molecular biology, 2009: p. 10.25. 1-10.25. 23.
23. Feist, P. and A. B. Hummon, *Proteomic challenges: sample preparation techniques for microgram-quantity protein analysis from biological samples*. International journal of molecular sciences, 2015. 16(2): p. 3537-3563.
24. Consortium, U., *UniProt: a hub for protein information*. Nucleic acids research, 2014: p. gku989.
25. Boeckmann, B., et al., *The SWISS-PROT protein knowledgebase and its supplement TrEMBL in* 2003. Nucleic acids research, 2003. 31(1): p. 365-370.
26. Hubbard, T., et al., *The Ensembl genome database project*. Nucleic acids research, 2002. 30(1): p. 38-41.
27. Johnson, M., et al., *NCBI BLAST: a better web interface*. Nucleic acids research, 2008. 36(suppl_2): p. W5-W9.
28. Vihinen, M., *Bioinformatics in proteomics*. Biomolecular engineering, 2001. 18(5): p. 241-248.
29. Barker, W. C., et al., *The protein information resource (PIR)*. Nucleic acids research, 2000. 28(1): p. 41-44.
30. Wu, C. H., et al., *The protein information resource*. Nucleic acids research, 2003. 31(1): p. 345-347.
31. Bantscheff, M., et al., *Quantitative mass spectrometry in proteomics: a critical review.* Analytical and bioanalytical chemistry, 2007. 389(4): p. 1017-1031.
32. Domon, B. and R. Aebersold, *Mass spectrometry and protein analysis*. science, 2006. 312(5771): p. 212-217.
33. Gobom, J., et al., *Sample purification and preparation technique based on nano-scale reversed-phase columns for the sensitive analysis of complex peptide mixtures by matrix-assisted laser desorption/ionization mass spectrometry*. Journal of Mass Spectrometry, 1999. 34(2): p. 105-116.
34. Guillarme, D., et al., *New trends in fast and high-resolution liquid chromatography: a critical comparison of existing approaches*. Analytical and bioanalytical chemistry, 2010. 397(3): p. 1069-1082.
35. Ŝtulík, K., et al., *Stationary phases for peptide analysis by high performance liquid chromatography: a review*. Analytica chimica acta, 1997. 352(1-3): p. 1-19.
36. Noble, J. E. and M. J. Bailey, *Quantitation of protein*. Methods in enzymology, 2009. 463: p. 73-95.
37. Sapan, C. V., R. L. Lundblad, and N. C. Price, *Colorimetric protein assay techniques*. Biotechnology and applied Biochemistry, 1999. 29(2): p. 99-108.
38. Nahnsen, S., et al., *Tools for label-free peptide quantification*. Molecular & Cellular Proteomics, 2013. 12(3): p. 549-556.
39. Searle, B. C., *Scaffold: a bioinformatic tool for validating MS/MS-based proteomic studies*. Proteomics, 2010. 10(6): p. 1265-1269.
40. Han, Y., B. Ma, and K. Zhang, *SPIDER: software for protein identification from sequence tags with de novo*

*sequencing error*. Journal of bioinformatics and computational biology, 2005. 3(03): p. 697-716.
41. Metzker, M. L., *Sequencing technologies—the next generation*. Nature reviews. Genetics, 2010. 11(1): p. 31.
42. Ng, S. B., et al., *Targeted capture and massively parallel sequencing of twelve human exomes*. Nature, 2009. 461 (7261): p. 272.
43. Brun, V., et al., *Isotope-labeled protein standards toward absolute quantitative proteomics*. Molecular & Cellular Proteomics, 2007. 6(12): p. 2139-2149.
44. Fusaro, V. A., et al., *Prediction of high-responding peptides for targeted protein assays by mass spectrometry*. Nature biotechnology, 2009. 27(2): p. 190-198.
45. Gallien, S., et al., *Selectivity of LC-MS/MS analysis: implication for proteomics experiments*. Journal of proteomics, 2013. 81: p. 148-158.
46. Jaffe, J. D., et al., *Accurate Inclusion Mass Screening A bridge from unbiased discovery to targeted assay development for biomarker verification*. Molecular & Cellular Proteomics, 2008. 7(10): p. 1952-1962.
47. Wu, A. H., et al., *Role of liquid chromatography-high-resolution mass spectrometry (LC-HR/MS) in clinical toxicology*. Clinical Toxicology, 2012. 50(8): p. 733-742.
48. Raymond, J. J., et al., *Trace DNA success rates relating to volume crime offences*. Forensic Science International: Genetics Supplement Series, 2009. 2(1): p. 136-137.
49. Cann, H. M., et al., *A human genome diversity cell line panel*. Science, 2002. 296(5566): p. 261-2.
50. Laatsch, C. N., et al. *Human hair shaft proteomic profiling: individual differences, site specificity and cuticle analysis*. PeerJ, 2014. 2, DOI: 10.7717/peerj.506.
51. Bunger, M. K., et al., *Detection and validation of non-synonymous coding SNPs from orthogonal analysis of shotgun proteomics data*. J Proteome Res, 2007. 6(6): p. 2331-40.
52. Fenyo, D., J. Eriksson, and R. Beavis, *Mass spectrometric protein identification using the global proteome machine*. Methods Mol Biol, 2010. 673: p. 189-202.
53. Jeong, J., et al., *Novel oxidative modifications in redox-active cysteine residues*. Mol Cell Proteomics, 2011. 10(3): p. M110 000513.
54. Solazzo, C., et al., *Modeling deamidation in sheep alpha-keratin peptides and application to archeological wool textiles*. Anal Chem, 2014. 86(1): p. 567-75.
55. Ghesquiere, B. and K. Gevaert, *Proteomics methods to study methionine oxidation*. Mass Spectrom Rev, 2014. 33(2): p. 147-56.
56. Robinson, N. E., *Protein deamidation*. Proc Natl Acad Sci USA, 2002. 99(8): p. 5283-8.
57. Evert, I. W. and B. S. Weir, *Interpreting DNA Evidence: Statistical Genetics for Forensic Scientists*. 1st ed. 1998: Sinauer Associates.
58. Butler, J. M., *Fundamentals of Forensic DNA Typing*. 2010: Academic Press.
59. Durbin, R. M., et al., *A map of human genome variation from population-scale sequencing*. Nature, 2010. 467 (7319): p. 1061-73.
60. Jeffreys, H., *An Invariant Form for the Prior Probability in Estimation Problems*. Proceedings of the Royal Society of London. Series A, Mathematical and Physical Sciences, 1946. 186(1007): p. 453-461.
61. Gelman, A., et al., *Bayesian Data Analysis*. Second Edition ed. CRC Texts in Statistical Science. Vol. Book 106. 2003: Chapman & Hall.
62. Thompson, J. D., D. G. Higgins, and T. J. Gibson, *CLUSTAL W: improving the sensitivity of progressive multiple sequence alignment through sequence weighting, position-specific gap penalties and weight matrix choice*. Nucleic acids research, 1994. 22(22): p. 4673-4680.
63. Brandon, M. C., et al., *MITOMASTER: a bioinformatics tool for the analysis of mitochondrial DNA sequences*. Human mutation, 2009. 30(1): p. 1-6.

The invention claimed is:

1. A method to perform genetic analysis of a sample of a biological organism, the method comprising preparing the sample to obtain a processed sample comprising solubilized proteins by applying to the sample an energy field resulting in an increased thermodynamic and/or total energy of the sample to obtain a processed sample comprising the solubilized proteins;

fractionating the processed sample to obtain a solubilized protein fraction comprising the solubilized proteins from the sample;

digesting the solubilized protein fraction from the sample to obtain digested peptides from the sample;

fractionating the digested peptides to obtain fractionated digested peptides from the digested solubilized protein fraction from the sample; and detecting a marker genetic variation of the fractionated digested peptides from the sample through proteomic analysis, wherein the detecting the marker genetic variation is performed by a first detecting method comprising:

providing a marker mass spectrum of a marker peptide comprising a marker genetic protein variation corresponding to the marker genetic protein variation, performing mass spectrometry of a digested peptide of the sample to obtain a detected mass spectrum of each of the digested peptides, and comparing the detected mass spectrum with the marker mass spectrum to detect a genetic protein variation in the sample.

2. The method of claim 1, wherein the preparing the sample comprises performing cell and tissue disruption and performing protein solubilization.

3. The method of claim 2, wherein preparing the sample comprises:

performing removal of contaminants and/or performing protein enrichment following performing protein solubilization.

4. The method of claim 1, wherein the applying is performed by sonication.

5. The method of claim 1, wherein the fractionating the processed sample and/or the fractionating the digested peptides is performed by a chromatography technique.

6. The method of claim 1, wherein the digesting is performed enzymatically with one or more site specific proteolytic enzymes.

7. The method of claim 6, wherein the one or more site specific proteolytic enzymes is selected from the group consisting of: trypsin, chymotrypsin, Lys-C, Arg-C, Asp-N, and Glu-C, non-specific-pepsin, and proteinase K.

8. The method of claim 1, wherein the detecting a marker genetic variation of the digested peptides from the sample is performed by mass spectrometry.

9. The method of claim 1, wherein providing the marker mass spectrum of a marker peptide comprising a marker genetic protein variation corresponding to the marker genetic protein variation, is performed by synthesizing a marker peptide and analyzing the marker peptide by performing mass spectrometry.

10. The method of claim 1, wherein performing mass spectrometry of a digested peptide of the sample to obtain a detected mass spectrum of each of the digested peptides is performed by tandem mass spectrometry.

11. The method of claim 1, wherein the marker peptide comprises a plurality of marker peptides each comprising a marker genetic protein variation.

12. The method of claim 1, wherein the genetic protein variation is a single amino acid polymorphism (SAP), an amino acid deletion and/or an amino acid insertion.

13. The method of claim 1, wherein the marker genetic protein variation comprises a marker genetic protein variation validated to be detectable in the sample.

14. The method of claim 1, wherein the sample is a sample of a single hair.

15. The method of claim 1, wherein the sample is hair, and wherein the marker peptide comprises a validated genetic protein variation of a gene listed in Table 8 of the specification.

16. The method of claim 1, wherein the sample is hair, and wherein the marker genetic protein variation comprises one or more genetic protein variations listed in Table 11 of the specification.

17. A system to perform genetic analysis of a sample of a biological organism, the system comprising:

a reagent configured for preparing the sample upon application of an energy field to the sample to obtain a processed sample comprising solubilized proteins, and/or a marker peptide comprising a genetic protein variation validated to be detectable in the sample, alone or in combination with other reagents effective to enable performance of the preparing, the digesting, and/or the detecting recited in the method of claim 1.

18. The system of claim 17, further comprising information to access a database comprising information about genetic protein variations.

19. The system of claim 17, wherein the sample is a single-hair sample.

20. The system of claim 17, wherein the sample is hair, and wherein the marker peptide comprises a validated genetic protein variation of a gene listed in Table 8 of the specification.

21. The system of claim 17, wherein the sample is hair, and wherein the marker genetic protein variation comprises one or more genetic protein variations listed in Table 11 of the specification.

22. The system of claim 17, wherein the sample is hair, and wherein the marker peptide comprises one or more peptides having sequence SEQ ID NO: 151 to SEQ ID NO: 721.

23. The method of claim 1, wherein the applying is performed by applying electromagnetic energy.

24. The method of claim 1, wherein the applying is performed by applying acoustic energy.

25. A method to perform genetic analysis of a sample of a biological organism, the method comprising:

preparing the sample to obtain a processed sample comprising solubilized proteins;

fractionating the processed sample to obtain a solubilized protein fraction comprising the solubilized proteins from the sample;

digesting the solubilized protein fraction from the sample to obtain digested peptides from the sample;

fractionating the digested peptides to obtain fractionated digested peptides from the digested solubilized protein fraction from the sample;

detecting a marker genetic variation of the fractionated digested peptides from the sample through proteomic analysis, the detecting the marker genetic variation comprising:

providing a marker mass spectrum of a marker peptide comprising a marker genetic protein variation corresponding to the marker genetic protein variation;

performing mass spectrometry of a digested peptide of the sample to obtain a detected mass spectrum of each of the digested peptides; and comparing the detected mass spectrum with the marker mass spectrum to detect a genetic protein variation in the sample, wherein comparing the detected mass spectrum of the digested peptides of the sample with a marker mass spectrum is performed by comparing the detected mass spectrum of the digested peptides with a mass spectrum of a protein variant database.

26. The method of claim 25, wherein the protein variant database comprises a marker genetic protein variation validated to be detectable in the sample.

27. A method to perform genetic analysis of a sample of a biological organism, the method comprising applying to the sample an energy field resulting in an increased thermodynamic and/or total energy of the sample to obtain a processed sample comprising solubilized proteins;

fractionating the processed sample to obtain a solubilized protein fraction comprising the solubilized proteins from the sample and a solubilized DNA fraction comprising nuclear and/or mitochondrial genome;

digesting the solubilized protein fraction from the sample to obtain digested peptides from the sample;

fractionating the digested peptides to obtain fractionated digested peptides from the digested solubilized protein fraction from the sample; and detecting a marker genetic variation of the fractionated digested peptides from the sample through a comparison of proteomic analysis of the solubilized protein fraction and genetic analysis of the solubilized DNA fraction of the sample, wherein a genetic protein variation is detected by performing the proteomic analysis of the solubilized protein fraction, wherein the genetic protein variation is a marker genetic protein variation, detecting the genetic protein variation comprises:

providing a marker mass spectrum of a marker peptide comprising a marker genetic protein variation corresponding to the marker genetic protein variation, performing mass spectrometry of a digested peptide of the sample to obtain a detected mass spectrum of each of the digested peptides, and comparing the detected mass spectrum with the marker mass spectrum, to detect the genetic protein variation in the sample.

28. The method of claim 27, wherein a genomic variation of the nuclear and/or mitochondrial genome is detected by performing the genetic analysis of the solubilized DNA fraction, wherein the genomic variation is a single nucleotide polymorphism (SNP), a nucleotide deletion and/or a nucleotide insertion.

29. The method of claim 27, wherein a genomic variation of the nuclear and/or mitochondrial genome is detected by performing the genetic analysis of the solubilized DNA fraction, wherein the genomic variation is within short tandem repeat (STR) regions of the nuclear genome or within the mitochondrial genome.

30. The method of claim 27, wherein a genetic protein variation is detected by performing the proteomic analysis of the solubilized protein fraction, wherein the genetic protein variation is a marker genetic protein variation, detecting the genetic protein variation comprises:

providing a marker mass spectrum of a marker peptide comprising a marker genetic protein variation corresponding to the marker genetic protein variation, performing mass spectrometry of a digested peptide of the sample to obtain a detected mass spectrum of each of the digested peptide, and comparing the detected mass spectrum with the marker mass spectrum, to detect the genetic protein variation in the sample.

* * * * *

SEQUENCE LISTING

```
<160> NUMBER OF SEQ ID NOS: 829

<210> SEQ ID NO 1
<211> LENGTH: 9
<212> TYPE: DNA
<213> ORGANISM: Homo sapiens

<400> SEQUENCE: 1

ggtacctgc                                                               9


<210> SEQ ID NO 2
<211> LENGTH: 9
<212> TYPE: DNA
<213> ORGANISM: Homo sapiens

<400> SEQUENCE: 2

ggtaactgc                                                               9


<210> SEQ ID NO 3
<211> LENGTH: 27
<212> TYPE: PRT
<213> ORGANISM: Homo sapiens

<400> SEQUENCE: 3

His Val Pro Glu Glu Val Leu Ala Val Leu Glu Gln Glu Pro Ile Val
1               5                   10                  15
```

```
Leu Pro Ala Trp Asp Pro Met Gly Ala Leu Ala
            20                  25


<210> SEQ ID NO 4
<211> LENGTH: 27
<212> TYPE: PRT
<213> ORGANISM: Homo sapiens

<400> SEQUENCE: 4

His Val Pro Glu Glu Val Leu Ala Val Leu Glu Gln Glu Pro Ile Ile
1               5                   10                  15

Leu Pro Ala Trp Asp Pro Met Gly Ala Leu Ala
            20                  25


<210> SEQ ID NO 5
<211> LENGTH: 16
<212> TYPE: PRT
<213> ORGANISM: Homo sapiens

<400> SEQUENCE: 5

Gly Pro Pro Gly Pro Gly Cys Lys Gly Glu Pro Gly Leu Asp Gly Arg
1               5                   10                  15


<210> SEQ ID NO 6
<211> LENGTH: 16
<212> TYPE: PRT
<213> ORGANISM: Homo sapiens

<400> SEQUENCE: 6

Gly Pro Ser Gly Pro Gly Cys Lys Gly Glu Pro Gly Leu Asp Gly Arg
1               5                   10                  15


<210> SEQ ID NO 7
<211> LENGTH: 17
<212> TYPE: PRT
<213> ORGANISM: Homo sapiens

<400> SEQUENCE: 7

Gly Gln Ser Glu Ala Asp Ser Asp Lys Asn Ala Thr Ile Leu Glu Leu
1               5                   10                  15

Arg


<210> SEQ ID NO 8
<211> LENGTH: 17
<212> TYPE: PRT
<213> ORGANISM: Homo sapiens

<400> SEQUENCE: 8

Gly Arg Ser Glu Ala Asp Ser Asp Lys Asn Ala Thr Ile Leu Glu Leu
1               5                   10                  15

Arg


<210> SEQ ID NO 9
<211> LENGTH: 18
<212> TYPE: PRT
<213> ORGANISM: Homo sapiens

<400> SEQUENCE: 9

Ile Phe Glu Glu Asp Pro Ala Val Gly Ala Ile Val Leu Thr Gly Gly
1               5                   10                  15

Asp Lys
```

<210> SEQ ID NO 10
<211> LENGTH: 18
<212> TYPE: PRT
<213> ORGANISM: Homo sapiens

<400> SEQUENCE: 10

Gln Leu Asn Pro Gln Gly Asp Leu Thr Pro Leu Asp Ser Leu Ile Asp
1 5 10 15

Phe Lys

<210> SEQ ID NO 11
<211> LENGTH: 13
<212> TYPE: PRT
<213> ORGANISM: Homo sapiens

<400> SEQUENCE: 11

Gly Asp Leu Thr Pro Leu Asp Ser Leu Ile Asp Phe Lys
1 5 10

<210> SEQ ID NO 12
<211> LENGTH: 11
<212> TYPE: PRT
<213> ORGANISM: Homo sapiens

<400> SEQUENCE: 12

Gly His Glu Val Asn Leu Glu Ala Leu Pro Lys
1 5 10

<210> SEQ ID NO 13
<211> LENGTH: 11
<212> TYPE: PRT
<213> ORGANISM: Homo sapiens

<400> SEQUENCE: 13

Gly His Glu Val Thr Leu Glu Ala Leu Pro Lys
1 5 10

<210> SEQ ID NO 14
<211> LENGTH: 8
<212> TYPE: PRT
<213> ORGANISM: Homo sapiens

<400> SEQUENCE: 14

Ala Leu Glu Thr Val Gln Glu Arg
1 5

<210> SEQ ID NO 15
<211> LENGTH: 8
<212> TYPE: PRT
<213> ORGANISM: Homo sapiens

<400> SEQUENCE: 15

Ala Leu Glu Thr Ile Gln Glu Arg
1 5

<210> SEQ ID NO 16
<211> LENGTH: 18
<212> TYPE: PRT
<213> ORGANISM: Homo sapiens

<400> SEQUENCE: 16

Tyr Val Ser Leu Ile Tyr Thr Asn Tyr Glu Ala Gly Lys Asp Asp Tyr
1 5 10 15

Val Lys

<210> SEQ ID NO 17
<211> LENGTH: 18
<212> TYPE: PRT
<213> ORGANISM: Homo sapiens

<400> SEQUENCE: 17

```
Tyr Ile Ser Leu Ile Tyr Thr Asn Tyr Glu Ala Gly Lys Asp Asp Tyr
1               5                   10                  15

Val Lys
```

<210> SEQ ID NO 18
<211> LENGTH: 8
<212> TYPE: PRT
<213> ORGANISM: Homo sapiens

<400> SEQUENCE: 18

```
Gly Ile Leu Val Asp Thr Ser Arg
1               5
```

<210> SEQ ID NO 19
<211> LENGTH: 8
<212> TYPE: PRT
<213> ORGANISM: Homo sapiens

<400> SEQUENCE: 19

```
Gly Ile Leu Ile Asp Thr Ser Arg
1               5
```

<210> SEQ ID NO 20
<211> LENGTH: 23
<212> TYPE: PRT
<213> ORGANISM: Homo sapiens

<400> SEQUENCE: 20

```
Met Ser Glu Thr Val Pro Ala Ala Ser Ala Ser Ala Gly Val Ala Ala
1               5                   10                  15

Met Asp Lys Leu Pro Thr Lys
            20
```

<210> SEQ ID NO 21
<211> LENGTH: 23
<212> TYPE: PRT
<213> ORGANISM: Homo sapiens

<400> SEQUENCE: 21

```
Met Ser Glu Thr Val Pro Ala Ala Ser Ala Ser Ala Gly Ile Ala Ala
1               5                   10                  15

Met Asp Lys Leu Pro Thr Lys
            20
```

<210> SEQ ID NO 22
<211> LENGTH: 25
<212> TYPE: PRT
<213> ORGANISM: Homo sapiens

<400> SEQUENCE: 22

```
Ser Ala Ile Val His Leu Ile Asn Tyr Gln Asp Asp Ala Glu Leu Ala
1               5                   10                  15

Thr His Ala Leu Pro Glu Leu Thr Lys
            20                  25
```

```
<210> SEQ ID NO 23
<211> LENGTH: 18
<212> TYPE: PRT
<213> ORGANISM: Homo sapiens

<400> SEQUENCE: 23

Ser Ala Ile Val His Leu Ile Asn Tyr Gln Asp Asp Ala Glu Leu Ala
1               5                   10                  15

Thr Arg


<210> SEQ ID NO 24
<211> LENGTH: 14
<212> TYPE: PRT
<213> ORGANISM: Homo sapiens

<400> SEQUENCE: 24

Asn Glu Gly Thr Ala Thr Tyr Ala Ala Ala Arg Leu Phe Arg
1               5                   10


<210> SEQ ID NO 25
<211> LENGTH: 14
<212> TYPE: PRT
<213> ORGANISM: Homo sapiens

<400> SEQUENCE: 25

Asn Glu Gly Thr Ala Thr Tyr Ala Ala Ala Val Leu Phe Arg
1               5                   10


<210> SEQ ID NO 26
<211> LENGTH: 19
<212> TYPE: PRT
<213> ORGANISM: Homo sapiens

<400> SEQUENCE: 26

Asn Lys Leu Asn Asp Leu Glu Asp Ala Leu Gln Gln Ser Lys Glu Asp
1               5                   10                  15

Leu Ala Arg


<210> SEQ ID NO 27
<211> LENGTH: 10
<212> TYPE: PRT
<213> ORGANISM: Homo sapiens

<400> SEQUENCE: 27

Asp Asn Val Glu Leu Glu Asn Leu Ile Arg
1               5                   10


<210> SEQ ID NO 28
<211> LENGTH: 11
<212> TYPE: PRT
<213> ORGANISM: Homo sapiens

<400> SEQUENCE: 28

Ser Gln Tyr Glu Val Leu Val Glu Thr Asn Arg
1               5                   10


<210> SEQ ID NO 29
<211> LENGTH: 12
<212> TYPE: PRT
<213> ORGANISM: Homo sapiens

<400> SEQUENCE: 29

Gln Asn Gln Glu Tyr Gln Met Leu Leu Asp Val Arg
1               5                   10
```

<210> SEQ ID NO 30
<211> LENGTH: 11
<212> TYPE: PRT
<213> ORGANISM: Homo sapiens

<400> SEQUENCE: 30

Ala Asp Leu Glu Ala Gln Val Glu Tyr Leu Lys
1 5 10

<210> SEQ ID NO 31
<211> LENGTH: 12
<212> TYPE: PRT
<213> ORGANISM: Homo sapiens

<400> SEQUENCE: 31

Cys Gln Tyr Glu Ala Met Val Glu Ala Asn His Arg
1 5 10

<210> SEQ ID NO 32
<211> LENGTH: 12
<212> TYPE: PRT
<213> ORGANISM: Homo sapiens

<400> SEQUENCE: 32

Cys Gln Tyr Glu Ala Met Val Glu Ala Asn Arg Arg
1 5 10

<210> SEQ ID NO 33
<211> LENGTH: 9
<212> TYPE: PRT
<213> ORGANISM: Homo sapiens

<400> SEQUENCE: 33

Leu Glu Gly Glu Ile Asn Met Tyr Arg
1 5

<210> SEQ ID NO 34
<211> LENGTH: 9
<212> TYPE: PRT
<213> ORGANISM: Homo sapiens

<400> SEQUENCE: 34

Leu Glu Gly Glu Ile Asn Thr Tyr Arg
1 5

<210> SEQ ID NO 35
<211> LENGTH: 18
<212> TYPE: PRT
<213> ORGANISM: Homo sapiens

<400> SEQUENCE: 35

Leu Glu Gly Glu Ile Asn Thr Tyr Arg Ser Leu Leu Glu Asn Glu Asp
1 5 10 15

Cys Lys

<210> SEQ ID NO 36
<211> LENGTH: 18
<212> TYPE: PRT
<213> ORGANISM: Homo sapiens

<400> SEQUENCE: 36

Leu Glu Gly Glu Ile Asn Thr Tyr Arg Ser Leu Leu Glu Ser Glu Asp
1 5 10 15

Cys Lys

<210> SEQ ID NO 37
<211> LENGTH: 19
<212> TYPE: PRT
<213> ORGANISM: Homo sapiens

<400> SEQUENCE: 37

Gln Val Val Ser Ser Ser Glu Gln Leu Gln Ser Tyr Gln Val Glu His
1 5 10 15

Glu Leu Arg

<210> SEQ ID NO 38
<211> LENGTH: 16
<212> TYPE: PRT
<213> ORGANISM: Homo sapiens

<400> SEQUENCE: 38

Thr Ile Asn Ala Leu Glu Ile Glu Leu Gln Ala Gln His Asn Leu Arg
1 5 10 15

<210> SEQ ID NO 39
<211> LENGTH: 11
<212> TYPE: PRT
<213> ORGANISM: Homo sapiens

<400> SEQUENCE: 39

Ser Gln Tyr Glu Ala Leu Val Glu Ile Asn Arg
1 5 10

<210> SEQ ID NO 40
<211> LENGTH: 20
<212> TYPE: PRT
<213> ORGANISM: Homo sapiens

<400> SEQUENCE: 40

Val Ser Ala Met Tyr Ser Ser Ser Ser Cys Lys Leu Pro Ser Leu Ser
1 5 10 15

Pro Val Ala Arg
20

<210> SEQ ID NO 41
<211> LENGTH: 20
<212> TYPE: PRT
<213> ORGANISM: Homo sapiens

<400> SEQUENCE: 41

Val Ser Ala Met Tyr Ser Ser Ser Pro Cys Lys Leu Pro Ser Leu Ser
1 5 10 15

Pro Val Ala Arg
20

<210> SEQ ID NO 42
<211> LENGTH: 19
<212> TYPE: PRT
<213> ORGANISM: Homo sapiens

<400> SEQUENCE: 42

Tyr Glu Thr Glu Val Ser Leu Trp Gln Leu Val Glu Ser Asp Ile Asn
1 5 10 15

Gly Leu Arg

<210> SEQ ID NO 43
<211> LENGTH: 19
<212> TYPE: PRT
<213> ORGANISM: Homo sapiens

<400> SEQUENCE: 43

Tyr Glu Thr Glu Val Ser Leu Arg Gln Leu Val Glu Ser Asp Ile Asn
1 5 10 15

Gly Leu Arg

<210> SEQ ID NO 44
<211> LENGTH: 17
<212> TYPE: PRT
<213> ORGANISM: Homo sapiens

<400> SEQUENCE: 44

Thr Asn Tyr Ser Pro Arg Pro Ile Cys Val Pro Cys Pro Gly Gly Arg
1 5 10 15

Phe

<210> SEQ ID NO 45
<211> LENGTH: 17
<212> TYPE: PRT
<213> ORGANISM: Homo sapiens

<400> SEQUENCE: 45

Thr Asn Cys Ser Pro Arg Pro Ile Cys Val Pro Cys Pro Gly Gly Arg
1 5 10 15

Phe

<210> SEQ ID NO 46
<211> LENGTH: 17
<212> TYPE: PRT
<213> ORGANISM: Homo sapiens

<400> SEQUENCE: 46

Thr Asn Cys Ser Ala Arg Pro Ile Cys Val Pro Cys Pro Gly Gly Arg
1 5 10 15

Phe

<210> SEQ ID NO 47
<211> LENGTH: 17
<212> TYPE: PRT
<213> ORGANISM: Homo sapiens

<400> SEQUENCE: 47

Thr Asn Cys Ser Pro Arg Pro Ile Cys Val Pro Cys Pro Gly Gly Arg
1 5 10 15

Phe

<210> SEQ ID NO 48
<211> LENGTH: 20
<212> TYPE: PRT
<213> ORGANISM: Homo sapiens

<400> SEQUENCE: 48

Thr Ser Phe Tyr Ser Thr Ser Ser Cys Pro Leu Cys Cys Thr Met Ala
1 5 10 15

Pro Gly Ala Arg
20

<210> SEQ ID NO 49
<211> LENGTH: 20
<212> TYPE: PRT
<213> ORGANISM: Homo sapiens

<400> SEQUENCE: 49

Thr Ser Phe Tyr Ser Thr Ser Ser Cys Pro Leu Gly Cys Thr Met Ala
1 5 10 15

Pro Gly Ala Arg
20

<210> SEQ ID NO 50
<211> LENGTH: 18
<212> TYPE: PRT
<213> ORGANISM: Homo sapiens

<400> SEQUENCE: 50

Phe Ser Leu Asp Asp Cys Asn Trp Tyr Gly Asp Gly Ile Asn Ser Asn
1 5 10 15

Glu Lys

<210> SEQ ID NO 51
<211> LENGTH: 18
<212> TYPE: PRT
<213> ORGANISM: Homo sapiens

<400> SEQUENCE: 51

Phe Ser Leu Asp Asp Cys Ser Trp Tyr Gly Asp Gly Ile Asn Ser Asn
1 5 10 15

Glu Lys

<210> SEQ ID NO 52
<211> LENGTH: 16
<212> TYPE: PRT
<213> ORGANISM: Homo sapiens

<400> SEQUENCE: 52

Asn His Glu Glu Glu Val Asn Leu Leu His Glu Gln Leu Gly Asp Arg
1 5 10 15

<210> SEQ ID NO 53
<211> LENGTH: 16
<212> TYPE: PRT
<213> ORGANISM: Homo sapiens

<400> SEQUENCE: 53

Asn His Glu Glu Glu Val Asn Leu Leu Arg Glu Gln Leu Gly Asp Arg
1 5 10 15

<210> SEQ ID NO 54
<211> LENGTH: 52
<212> TYPE: PRT
<213> ORGANISM: Homo sapiens

<400> SEQUENCE: 54

Thr Ala Ser Ala Leu Glu Ile Glu Leu Gln Ala Gln Gln Ser Leu Thr
1 5 10 15

Glu Ser Leu Glu Cys Thr Val Ala Glu Thr Glu Ala Gln Tyr Ser Ser
20 25 30

Gln Leu Ala Gln Ile Gln Arg Leu Ile Asp Asn Leu Glu Asn Gln Leu
35 40 45

Ala Glu Ile Arg
    50

<210> SEQ ID NO 55
<211> LENGTH: 52
<212> TYPE: PRT
<213> ORGANISM: Homo sapiens

<400> SEQUENCE: 55

Thr Ala Ser Ala Leu Glu Ile Glu Leu Gln Ala Gln Gln Ser Leu Thr
1               5                   10                  15

Glu Ser Leu Glu Cys Thr Val Ala Glu Thr Glu Ala Gln Tyr Ser Ser
            20                  25                  30

Gln Leu Ala Gln Ile Gln Cys Leu Ile Asp Asn Leu Glu Asn Gln Leu
        35                  40                  45

Ala Glu Ile Arg
    50

<210> SEQ ID NO 56
<211> LENGTH: 22
<212> TYPE: PRT
<213> ORGANISM: Homo sapiens

<400> SEQUENCE: 56

Leu Tyr Glu Glu Glu Glu Ile Leu Ile Leu Gln Ser His Ile Ser Asp
1               5                   10                  15

Thr Ser Val Val Val Lys
            20

<210> SEQ ID NO 57
<211> LENGTH: 13
<212> TYPE: PRT
<213> ORGANISM: Homo sapiens

<400> SEQUENCE: 57

Gly Leu Thr Gly Gly Phe Gly Ser His Ser Val Cys Arg
1               5                   10

<210> SEQ ID NO 58
<211> LENGTH: 13
<212> TYPE: PRT
<213> ORGANISM: Homo sapiens

<400> SEQUENCE: 58

Phe Arg Cys Ile Ser Ala Cys Gly Pro Arg Pro Gly Arg
1               5                   10

<210> SEQ ID NO 59
<211> LENGTH: 13
<212> TYPE: PRT
<213> ORGANISM: Homo sapiens

<400> SEQUENCE: 59

Phe Ser Cys Ile Ser Ala Cys Gly Pro Arg Pro Gly Arg
1               5                   10

<210> SEQ ID NO 60
<211> LENGTH: 21
<212> TYPE: PRT
<213> ORGANISM: Homo sapiens

<400> SEQUENCE: 60

Gly Ala Phe Leu Tyr Glu Pro Cys Gly Val Ser Met Pro Val Leu Ser

```
1               5                   10                  15

Thr Gly Val Leu Arg
            20


<210> SEQ ID NO 61
<211> LENGTH: 20
<212> TYPE: PRT
<213> ORGANISM: Homo sapiens

<400> SEQUENCE: 61

Gly Ala Phe Leu Tyr Glu Pro Cys Gly Val Ser Thr Pro Val Leu Ser
1               5                   10                  15

Thr Gly Val Leu
            20


<210> SEQ ID NO 62
<211> LENGTH: 12
<212> TYPE: PRT
<213> ORGANISM: Homo sapiens

<400> SEQUENCE: 62

Asp Leu Asn Met Asp Cys Met Val Ala Glu Ile Lys
1               5                   10


<210> SEQ ID NO 63
<211> LENGTH: 12
<212> TYPE: PRT
<213> ORGANISM: Homo sapiens

<400> SEQUENCE: 63

Asp Leu Asn Met Asp Cys Ile Val Ala Glu Ile Lys
1               5                   10


<210> SEQ ID NO 64
<211> LENGTH: 20
<212> TYPE: PRT
<213> ORGANISM: Homo sapiens

<400> SEQUENCE: 64

Leu Glu Ala Ala Val Ala Gln Ser Glu Gln Gln Ser Glu Ala Ala Leu
1               5                   10                  15

Ser Asp Ala Arg
            20


<210> SEQ ID NO 65
<211> LENGTH: 21
<212> TYPE: PRT
<213> ORGANISM: Homo sapiens

<400> SEQUENCE: 65

Cys Glu Tyr Gln Glu Leu Met Asn Ala Lys Leu Gly Leu Asp Ile Glu
1               5                   10                  15

Ile Ala Thr Tyr Arg
            20


<210> SEQ ID NO 66
<211> LENGTH: 21
<212> TYPE: PRT
<213> ORGANISM: Homo sapiens

<400> SEQUENCE: 66

Arg Glu Tyr Gln Glu Leu Met Asn Ala Lys Leu Gly Leu Asp Ile Glu
1               5                   10                  15
```

```
Ile Ala Thr Tyr Arg
            20


<210> SEQ ID NO 67
<211> LENGTH: 17
<212> TYPE: PRT
<213> ORGANISM: Homo sapiens

<400> SEQUENCE: 67

Ile Ala Val Gly Gly Phe Arg Ala Gly Ser Cys His Ser Phe Gly Tyr
1               5                   10                  15

Arg


<210> SEQ ID NO 68
<211> LENGTH: 13
<212> TYPE: PRT
<213> ORGANISM: Homo sapiens

<400> SEQUENCE: 68

Ile Ala Val Gly Gly Phe Arg Ala Gly Ser Cys Gly Arg
1               5                   10


<210> SEQ ID NO 69
<211> LENGTH: 14
<212> TYPE: PRT
<213> ORGANISM: Homo sapiens

<400> SEQUENCE: 69

Thr Lys Glu Glu Ile Asn Glu Leu Asn Cys Met Ile Gln Arg
1               5                   10


<210> SEQ ID NO 70
<211> LENGTH: 21
<212> TYPE: PRT
<213> ORGANISM: Homo sapiens

<400> SEQUENCE: 70

Thr Tyr Val Ile Ala Ala Ser Thr Met Ser Val Cys Ser Ser Asp Val
1               5                   10                  15

Gly His Val Ser Arg
            20


<210> SEQ ID NO 71
<211> LENGTH: 18
<212> TYPE: PRT
<213> ORGANISM: Homo sapiens

<400> SEQUENCE: 71

Thr Tyr Val Ile Ala Ala Ser Thr Met Ser Val Cys Ser Ser Asp Val
1               5                   10                  15

Gly Arg


<210> SEQ ID NO 72
<211> LENGTH: 14
<212> TYPE: PRT
<213> ORGANISM: Homo sapiens

<400> SEQUENCE: 72

Glu Leu Ser Ile Gly Ile Phe Gly Pro Met Pro Asn Leu Arg
1               5                   10


<210> SEQ ID NO 73
```

<211> LENGTH: 14
<212> TYPE: PRT
<213> ORGANISM: Homo sapiens

<400> SEQUENCE: 73

Glu Leu Ser Pro Gly Ile Phe Gly Pro Met Pro Asn Leu Arg
1 5 10

<210> SEQ ID NO 74
<211> LENGTH: 24
<212> TYPE: PRT
<213> ORGANISM: Homo sapiens

<400> SEQUENCE: 74

Leu Tyr Leu Ser Asn Asn His Ile Ser Gln Leu Pro Pro Ser Ile Phe
1 5 10 15

Met Gln Leu Pro Gln Leu Asn Arg
20

<210> SEQ ID NO 75
<211> LENGTH: 24
<212> TYPE: PRT
<213> ORGANISM: Homo sapiens

<400> SEQUENCE: 75

Leu Tyr Leu Ser Asn Asn His Ile Ser Gln Leu Pro Pro Ser Val Phe
1 5 10 15

Met Gln Leu Pro Gln Leu Asn Arg
20

<210> SEQ ID NO 76
<211> LENGTH: 18
<212> TYPE: PRT
<213> ORGANISM: Homo sapiens

<400> SEQUENCE: 76

Glu Trp Ser Thr Phe Ala Val Gly Pro Gly His Cys Leu Gln Leu His
1 5 10 15

Asp Arg

<210> SEQ ID NO 77
<211> LENGTH: 18
<212> TYPE: PRT
<213> ORGANISM: Homo sapiens

<400> SEQUENCE: 77

Glu Trp Ser Thr Phe Ala Val Gly Pro Gly His Cys Leu Gln Leu Asn
1 5 10 15

Asp Arg

<210> SEQ ID NO 78
<211> LENGTH: 16
<212> TYPE: PRT
<213> ORGANISM: Homo sapiens

<400> SEQUENCE: 78

Ala Ala Glu Ala Ala Trp Leu Leu Leu Ser Asp Met Trp Ser Ser Lys
1 5 10 15

<210> SEQ ID NO 79
<211> LENGTH: 16
<212> TYPE: PRT
<213> ORGANISM: Homo sapiens

<400> SEQUENCE: 79

Ala Ala Glu Ala Ala Arg Leu Leu Leu Ser Asp Met Trp Ser Ser Lys
1 5 10 15

<210> SEQ ID NO 80
<211> LENGTH: 21
<212> TYPE: PRT
<213> ORGANISM: Homo sapiens

<400> SEQUENCE: 80

Ala Lys Pro Leu Glu Gln Ala Val Ala Ala Ile Val Cys Thr Phe Gln
1 5 10 15

Glu Tyr Ala Gly Arg
20

<210> SEQ ID NO 81
<211> LENGTH: 21
<212> TYPE: PRT
<213> ORGANISM: Homo sapiens

<400> SEQUENCE: 81

Ala Arg Pro Leu Glu Gln Ala Val Ala Ala Ile Val Cys Thr Phe Gln
1 5 10 15

Glu Tyr Ala Gly Arg
20

<210> SEQ ID NO 82
<211> LENGTH: 10
<212> TYPE: PRT
<213> ORGANISM: Homo sapiens

<400> SEQUENCE: 82

Gly Val Ala Leu Ser Asn Val Val His Lys
1 5 10

<210> SEQ ID NO 83
<211> LENGTH: 10
<212> TYPE: PRT
<213> ORGANISM: Homo sapiens

<400> SEQUENCE: 83

Gly Val Ala Leu Ser Asn Val Ile His Lys
1 5 10

<210> SEQ ID NO 84
<211> LENGTH: 16
<212> TYPE: PRT
<213> ORGANISM: Homo sapiens

<400> SEQUENCE: 84

Ala Ala Leu Gly Val Gln Ser Ile Asn Trp Gln Thr Ala Phe Asn Arg
1 5 10 15

<210> SEQ ID NO 85
<211> LENGTH: 16
<212> TYPE: PRT
<213> ORGANISM: Homo sapiens

<400> SEQUENCE: 85

Ala Ala Leu Gly Val Gln Ser Ile Asn Trp Gln Lys Ala Phe Asn Arg
1 5 10 15

<210> SEQ ID NO 86
<211> LENGTH: 7
<212> TYPE: PRT
<213> ORGANISM: Artificial sequence
<220> FEATURE:
<223> OTHER INFORMATION: synthetic polypeptide

<400> SEQUENCE: 86

Glu Asn Leu Tyr Phe Gln Ser
1               5

<210> SEQ ID NO 87
<211> LENGTH: 434
<212> TYPE: DNA
<213> ORGANISM: Homo sapiens

<400> SEQUENCE: 87
ctccaccatt agcacccaaa gctaagattc taatttaaac tattctctgt tctttcatgg 60
ggaagcagat ttgggtacca cccaagtatt gactcaccca tcaacaaccg ctatgtattt 120
cgtacattac tgccagccac catgaatatt gtacggtacc ataaatactt gaccacctgt 180
agtacataaa aacccaatcc acatcaaaac cccctcccca tgcttacaag caagtacagc 240
aatcaaccct caactatcac acatcaactc caactccaaa gccaccctca cccactagga 300
taccaacaaa cctacccacc cttaacagta catactacat aaacccattt accgtacata 360
gcacattaca gtcaaatccc ttctcgtccc catggatgac ccccctcaga tagggtccct 420
tgaccaccat cctc 434

<210> SEQ ID NO 88
<211> LENGTH: 333
<212> TYPE: DNA
<213> ORGANISM: Homo sapiens

<400> SEQUENCE: 88
ttctctgttc tttcatgggg aagcagattt gggtaccacc caagtattga ctcacccatc 60
aacaaccgct atgtatttcg tacattactg ccagccacca tgaatattgt acggtaccat 120
aaatacttga ccacctgtag tacatgaaaa cccaatccac atcaaaaccc cccccccatg 180
cttacaagca agtacagcaa tcaaccctca actatcacac atcaactcca actccaaagc 240
caccctcacc cactaggata ccaacaaacc tacccaccct taacagttca tactacataa 300
acccatttac cgtacatagc acattacagt caa 333

<210> SEQ ID NO 89
<211> LENGTH: 436
<212> TYPE: DNA
<213> ORGANISM: Homo sapiens

<400> SEQUENCE: 89
tctccaccat tagcacccaa agctaagatt ctaatttaaa ctattctctg ttctttcatg 60
gggaagcaga tttgggtacc acccaagtat tgactcaccc atcaacaacc gctatgtatc 120
tcgtacatta ctgccagcca ccatgaatat tgtacggtac cataaatact tgaccacctg 180
tagtacataa aaacccaatc cacatcaaaa ccccctcccc atgcttacaa gcaagtacag 240
caaycaaccc ycaactatca cacatcaact ccaactccaa agccaccctc acccactagg 300
ataccaacaa acctacccac ccttaacagt acatacyaca taaacycatt taccgtacat 360
agcacattac agtcaaatcc cttctcgtcc ccatggatga ccccccctcag atagggtccc 420 ttgaccacca tcctca 436

<210> SEQ ID NO 90
<211> LENGTH: 436
<212> TYPE: DNA
<213> ORGANISM: Homo sapiens

<400> SEQUENCE: 90
tctccaccat tagcacccaa agctaagatt ctaatttaaa ctattctctg ttctttcatg 60
gggaagcaga tttgggtacc acccaagtat tgactcaccc atcaacaacc gctatgtatt 120
tcgtacatta ctgccagcca ccatgaatat tgtacggtac cataaatact tgaccacctg 180
tagtacataa aaacccaatc cacatcaaaa ccccctcccc atgcttacaa gcaagtacag 240
caatcaaccc ccaactatca cacatcaact ctaactctaa agccaccctc acccactagg 300
ataccaacaa acctacccac ccttaacagt acataccaca taaacccatt taccgtacat 360
agcacattac agtcaaatcc cttctcgtcc ccatggatga cccccctcag atagggtccc 420
ttgaccacca tcctca 436

<210> SEQ ID NO 91
<211> LENGTH: 26
<212> TYPE: PRT
<213> ORGANISM: Homo sapiens

<400> SEQUENCE: 91

Ala His Tyr Asp Leu Arg His Thr Phe Met Gly Val Val Ser Leu Gly
1 5 10 15

Ser Pro Ser Gly Glu Val Ser His Pro Arg
20 25

<210> SEQ ID NO 92
<211> LENGTH: 26
<212> TYPE: PRT
<213> ORGANISM: Homo sapiens

<400> SEQUENCE: 92

Ala His Tyr Asp Leu Cys His Thr Phe Met Gly Val Val Ser Leu Gly
1 5 10 15

Ser Pro Ser Gly Glu Val Ser His Pro Arg
20 25

<210> SEQ ID NO 93
<211> LENGTH: 14
<212> TYPE: PRT
<213> ORGANISM: Homo sapiens

<400> SEQUENCE: 93

Cys Gln Val Ala Gly Trp Gly Ser Gln Arg Ser Gly Gly Arg
1 5 10

<210> SEQ ID NO 94
<211> LENGTH: 14
<212> TYPE: PRT
<213> ORGANISM: Homo sapiens

<400> SEQUENCE: 94

Cys Gln Val Ala Gly Trp Gly Ser Gln His Ser Gly Gly Arg
1 5 10

<210> SEQ ID NO 95
<211> LENGTH: 9
<212> TYPE: PRT

<213> ORGANISM: Homo sapiens

<400> SEQUENCE: 95

Gln Gly Gly Val Val Ala Ser Leu Arg
1 5

<210> SEQ ID NO 96
<211> LENGTH: 9
<212> TYPE: PRT
<213> ORGANISM: Homo sapiens

<400> SEQUENCE: 96

Gln Ser Gly Val Val Ala Ser Leu Arg
1 5

<210> SEQ ID NO 97
<211> LENGTH: 30
<212> TYPE: PRT
<213> ORGANISM: Homo sapiens

<400> SEQUENCE: 97

Gly Glu Gln Gly Pro Pro Gly Pro Pro Gly Phe Gln Gly Leu Pro Gly
1 5 10 15

Pro Ser Gly Pro Ala Gly Glu Val Gly Lys Pro Gly Glu Arg
20 25 30

<210> SEQ ID NO 98
<211> LENGTH: 30
<212> TYPE: PRT
<213> ORGANISM: Homo sapiens

<400> SEQUENCE: 98

Gly Glu Gln Gly Pro Ala Gly Pro Pro Gly Phe Gln Gly Leu Pro Gly
1 5 10 15

Pro Ser Gly Pro Ala Gly Glu Val Gly Lys Pro Gly Glu Arg
20 25 30

<210> SEQ ID NO 99
<211> LENGTH: 38
<212> TYPE: PRT
<213> ORGANISM: Homo sapiens

<400> SEQUENCE: 99

Gly Pro Gln Gly His Gln Gly Pro Ala Gly Pro Pro Gly Pro Pro Gly
1 5 10 15

Pro Pro Gly Pro Pro Gly Val Ser Gly Gly Gly Tyr Asp Phe Gly Tyr
20 25 30

Asp Gly Asp Phe Tyr Arg
35

<210> SEQ ID NO 100
<211> LENGTH: 38
<212> TYPE: PRT
<213> ORGANISM: Homo sapiens

<400> SEQUENCE: 100

Gly Pro Gln Gly His Gln Gly Pro Ala Gly Pro Pro Gly Pro Pro Gly
1 5 10 15

Pro Pro Gly Pro Pro Gly Val Ala Gly Gly Gly Tyr Asp Phe Gly Tyr
20 25 30

Asp Gly Asp Phe Tyr Arg
35

<210> SEQ ID NO 101
<211> LENGTH: 12
<212> TYPE: PRT
<213> ORGANISM: Homo sapiens

<400> SEQUENCE: 101

Gly Gly Ala Gly Pro Pro Gly Pro Glu Gly Gly Lys
1 5 10

<210> SEQ ID NO 102
<211> LENGTH: 12
<212> TYPE: PRT
<213> ORGANISM: Homo sapiens

<400> SEQUENCE: 102

Gly Gly Thr Gly Pro Pro Gly Pro Glu Gly Gly Lys
1 5 10

<210> SEQ ID NO 103
<211> LENGTH: 8
<212> TYPE: PRT
<213> ORGANISM: Homo sapiens

<400> SEQUENCE: 103

Gly Pro Ser Gly Pro Gly Cys Lys
1 5

<210> SEQ ID NO 104
<211> LENGTH: 8
<212> TYPE: PRT
<213> ORGANISM: Homo sapiens

<400> SEQUENCE: 104

Gly Pro Pro Gly Pro Gly Cys Lys
1 5

<210> SEQ ID NO 105
<211> LENGTH: 9
<212> TYPE: PRT
<213> ORGANISM: Homo sapiens

<400> SEQUENCE: 105

Gly Pro Gly Gly Ala Ala Gly Pro Lys
1 5

<210> SEQ ID NO 106
<211> LENGTH: 9
<212> TYPE: PRT
<213> ORGANISM: Homo sapiens

<400> SEQUENCE: 106

Gly Pro Gly Gly Ala Glu Gly Pro Lys
1 5

<210> SEQ ID NO 107
<211> LENGTH: 9
<212> TYPE: PRT
<213> ORGANISM: Homo sapiens

<400> SEQUENCE: 107

Asn Val Asn Pro Val Ala Leu Pro Arg
1 5

<210> SEQ ID NO 108
<211> LENGTH: 9
<212> TYPE: PRT
<213> ORGANISM: Homo sapiens

<400> SEQUENCE: 108

Asn Val Ser Pro Val Ala Leu Pro Arg
1               5

<210> SEQ ID NO 109
<211> LENGTH: 16
<212> TYPE: PRT
<213> ORGANISM: Homo sapiens

<400> SEQUENCE: 109

Ala Val Glu Asn Ile Asn Asn Thr Leu Gly Pro Ala Leu Leu Gln Lys
1               5                   10                  15

<210> SEQ ID NO 110
<211> LENGTH: 16
<212> TYPE: PRT
<213> ORGANISM: Homo sapiens

<400> SEQUENCE: 110

Ala Val Glu Asn Ile Asn Ser Thr Leu Gly Pro Ala Leu Leu Gln Lys
1               5                   10                  15

<210> SEQ ID NO 111
<211> LENGTH: 24
<212> TYPE: PRT
<213> ORGANISM: Homo sapiens

<400> SEQUENCE: 111

Ile Ile Cys Asp Asn Thr Gly Ile Thr Thr Val Ser Lys Asn Asn Ile
1               5                   10                  15

Phe Met Ser Asn Ser Tyr Pro Arg
            20

<210> SEQ ID NO 112
<211> LENGTH: 24
<212> TYPE: PRT
<213> ORGANISM: Homo sapiens

<400> SEQUENCE: 112

Ile Ile Cys Asp Asn Thr Gly Ile Thr Thr Val Ser Lys Asn Asn Val
1               5                   10                  15

Phe Met Ser Asn Ser Tyr Pro Arg
            20

<210> SEQ ID NO 113
<211> LENGTH: 24
<212> TYPE: PRT
<213> ORGANISM: Homo sapiens

<400> SEQUENCE: 113

Ser Leu Met Phe Met Gln Trp Gly Gln Leu Leu Asp His Asp Leu Asp
1               5                   10                  15

Phe Thr Pro Glu Pro Ala Ala Arg
            20

<210> SEQ ID NO 114
<211> LENGTH: 24
<212> TYPE: PRT
<213> ORGANISM: Homo sapiens

<400> SEQUENCE: 114

Ser Leu Thr Phe Met Gln Trp Gly Gln Leu Leu Asp His Asp Leu Asp
1               5                   10                  15

Phe Thr Pro Glu Pro Ala Ala Arg
            20

<210> SEQ ID NO 115
<211> LENGTH: 22
<212> TYPE: PRT
<213> ORGANISM: Homo sapiens

<400> SEQUENCE: 115

Phe Asn Lys Pro Phe Val Phe Leu Met Ile Glu Gln Asn Thr Lys Ser
1               5                   10                  15

Pro Leu Phe Met Gly Lys
            20

<210> SEQ ID NO 116
<211> LENGTH: 22
<212> TYPE: PRT
<213> ORGANISM: Homo sapiens

<400> SEQUENCE: 116

Phe Asn Lys Pro Phe Val Phe Leu Met Ile Asp Gln Asn Thr Lys Ser
1               5                   10                  15

Pro Leu Phe Met Gly Lys
            20

<210> SEQ ID NO 117
<211> LENGTH: 28
<212> TYPE: PRT
<213> ORGANISM: Homo sapiens

<400> SEQUENCE: 117

Ala Leu Tyr Tyr Asp Leu Ile Ser Ser Pro Asp Ile His Gly Thr Tyr
1               5                   10                  15

Lys Glu Leu Leu Asp Thr Val Thr Ala Pro Gln Lys
            20                  25

<210> SEQ ID NO 118
<211> LENGTH: 26
<212> TYPE: PRT
<213> ORGANISM: Homo sapiens

<400> SEQUENCE: 118

Ala Leu Tyr Tyr Asp Leu Ile Ser Ser Pro Asp Ile His Gly Thr Tyr
1               5                   10                  15

Lys Glu Leu Leu Asp Thr Val Thr Ala Arg
            20                  25

<210> SEQ ID NO 119
<211> LENGTH: 30
<212> TYPE: PRT
<213> ORGANISM: Homo sapiens

<400> SEQUENCE: 119

Ser Ser Thr Ser Pro Thr Thr Asn Val Leu Leu Ser Pro Leu Ser Val
1               5                   10                  15

Ala Thr Ala Leu Ser Ala Leu Ser Leu Gly Ala Glu Gln Arg
            20                  25                  30

<210> SEQ ID NO 120
<211> LENGTH: 30
<212> TYPE: PRT
<213> ORGANISM: Homo sapiens

<400> SEQUENCE: 120

Ser Ser Met Ser Pro Thr Thr Asn Val Leu Leu Ser Pro Leu Ser Val
1 5 10 15

Ala Thr Ala Leu Ser Ala Leu Ser Leu Gly Ala Glu Gln Arg
20 25 30

<210> SEQ ID NO 121
<211> LENGTH: 20
<212> TYPE: PRT
<213> ORGANISM: Homo sapiens

<400> SEQUENCE: 121

Asn Ser Thr Ile Val Phe Pro Leu Pro Ile Asp Met Leu Gln Gly Ile
1 5 10 15

Ile Gly Ala Lys
20

<210> SEQ ID NO 122
<211> LENGTH: 20
<212> TYPE: PRT
<213> ORGANISM: Homo sapiens

<400> SEQUENCE: 122

Asn Ser Thr Ile Val Phe Pro Leu Pro Ile Asp Thr Leu Gln Gly Ile
1 5 10 15

Ile Gly Ala Lys
20

<210> SEQ ID NO 123
<211> LENGTH: 13
<212> TYPE: PRT
<213> ORGANISM: Homo sapiens

<400> SEQUENCE: 123

Lys Pro Val Glu Glu Tyr Ala Asn Cys His Leu Ala Arg
1 5 10

<210> SEQ ID NO 124
<211> LENGTH: 13
<212> TYPE: PRT
<213> ORGANISM: Homo sapiens

<400> SEQUENCE: 124

Lys Ser Val Glu Glu Tyr Ala Asn Cys His Leu Ala Arg
1 5 10

<210> SEQ ID NO 125
<211> LENGTH: 10
<212> TYPE: PRT
<213> ORGANISM: Homo sapiens

<400> SEQUENCE: 125

Lys Glu Thr Met Gln Phe Leu Asn Asp Arg
1 5 10

<210> SEQ ID NO 126
<211> LENGTH: 36
<212> TYPE: PRT

<213> ORGANISM: Homo sapiens

<400> SEQUENCE: 126

Asp Ser Leu Glu Asn Thr Leu Thr Glu Ser Glu Ala His Tyr Ser Ser
1 5 10 15

Gln Leu Ser Gln Val Gln Ser Leu Ile Thr Asn Val Glu Ser Gln Leu
20 25 30

Ala Glu Ile Arg
35

<210> SEQ ID NO 127
<211> LENGTH: 9
<212> TYPE: PRT
<213> ORGANISM: Homo sapiens

<400> SEQUENCE: 127

Thr Ser Cys Ser Ser Arg Pro Cys Val
1 5

<210> SEQ ID NO 128
<211> LENGTH: 52
<212> TYPE: PRT
<213> ORGANISM: Homo sapiens

<400> SEQUENCE: 128

Thr Val Asn Ala Leu Glu Ile Glu Leu Gln Ala Gln His Asn Leu Arg
1 5 10 15

Asp Ser Leu Glu Asn Thr Leu Thr Glu Ser Glu Ala His Tyr Ser Ser
20 25 30

Gln Leu Ser Gln Val Gln Ser Leu Ile Thr Asn Val Glu Ser Gln Leu
35 40 45

Ala Glu Ile Arg
50

<210> SEQ ID NO 129
<211> LENGTH: 35
<212> TYPE: PRT
<213> ORGANISM: Homo sapiens

<400> SEQUENCE: 129

Glu Val Glu Gln Trp Phe Ala Thr Gln Thr Glu Glu Leu Asn Lys Gln
1 5 10 15

Val Val Ser Ser Ser Glu Gln Leu Gln Ser Cys Gln Ala Glu Ile Ile
20 25 30

Glu Leu Arg
35

<210> SEQ ID NO 130
<211> LENGTH: 53
<212> TYPE: PRT
<213> ORGANISM: Homo sapiens

<400> SEQUENCE: 130

Arg Thr Val Asn Ala Leu Glu Ile Glu Leu Gln Ala Gln His Asn Leu
1 5 10 15

Arg Asp Ser Leu Glu Asn Thr Leu Thr Glu Ser Glu Ala His Tyr Ser
20 25 30

Ser Gln Leu Ser Gln Val Gln Ser Leu Ile Thr Asn Val Glu Ser Gln
35 40 45

Leu Ala Glu Ile Arg

50

<210> SEQ ID NO 131
<211> LENGTH: 52
<212> TYPE: PRT
<213> ORGANISM: Homo sapiens

<400> SEQUENCE: 131

Thr Val Asn Ala Leu Glu Ile Glu Leu Gln Ala Gln His Asn Leu Arg
1               5                   10                  15

Asp Ser Leu Glu Asn Thr Leu Thr Glu Ser Glu Ala His Tyr Ser Ser
            20                  25                  30

Gln Leu Ser Gln Val Gln Ser Leu Ile Thr Asn Val Glu Ser Gln Leu
        35                  40                  45

Ala Glu Ile Arg
    50

<210> SEQ ID NO 132
<211> LENGTH: 35
<212> TYPE: PRT
<213> ORGANISM: Homo sapiens

<400> SEQUENCE: 132

Glu Val Glu Gln Trp Phe Ala Thr Gln Thr Glu Glu Leu Asn Lys Gln
1               5                   10                  15

Val Val Ser Ser Ser Glu Gln Leu Gln Ser Cys Gln Ala Glu Ile Ile
            20                  25                  30

Glu Leu Arg
        35

<210> SEQ ID NO 133
<211> LENGTH: 53
<212> TYPE: PRT
<213> ORGANISM: Homo sapiens

<400> SEQUENCE: 133

Arg Thr Val Asn Ala Leu Glu Ile Glu Leu Gln Ala Gln His Asn Leu
1               5                   10                  15

Arg Asp Ser Leu Glu Asn Thr Leu Thr Glu Ser Glu Ala His Tyr Ser
            20                  25                  30

Ser Gln Leu Ser Gln Val Gln Ser Leu Ile Thr Asn Val Glu Ser Gln
        35                  40                  45

Leu Ala Glu Ile Arg
    50

<210> SEQ ID NO 134
<211> LENGTH: 10
<212> TYPE: DNA
<213> ORGANISM: Artificial sequence
<220> FEATURE:
<223> OTHER INFORMATION: synthetic polynucleotide

<400> SEQUENCE: 134
tatatatata                                                            10

<210> SEQ ID NO 135
<211> LENGTH: 15
<212> TYPE: DNA
<213> ORGANISM: Artificial sequence
<220> FEATURE:
<223> OTHER INFORMATION: synthetic polynucleotide

<400> SEQUENCE: 135
gtcgtcgtcg tcgtc 15

<210> SEQ ID NO 136
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 136
ctccaccatt agcacccaaa 20

<210> SEQ ID NO 137
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 137
aagcctaaat agcccacacg 20

<210> SEQ ID NO 138
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 138
caccctatta accactcacg 20

<210> SEQ ID NO 139
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 139
tcttttggcg gtatgcactt t 21

<210> SEQ ID NO 140
<211> LENGTH: 19
<212> TYPE: DNA
<213> ORGANISM: Artificial sequence
<220> FEATURE:
<223> OTHER INFORMATION: synthetic polynucleotide

<400> SEQUENCE: 140
gaggatggtg gtcaaggga 19

<210> SEQ ID NO 141
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 141
agagctcccg tgagtggtta 20

<210> SEQ ID NO 142
<211> LENGTH: 20

<212> TYPE: DNA
<213> ORGANISM: Artificial sequence
<220> FEATURE:
<223> OTHER INFORMATION: synthetic polynucleotide

<400> SEQUENCE: 142
ctggttaggc tggtgttagg 20

<210> SEQ ID NO 143
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 143
gatgtgagcc cgtctaaaca 20

<210> SEQ ID NO 144
<211> LENGTH: 28
<212> TYPE: DNA
<213> ORGANISM: Homo sapiens

<400> SEQUENCE: 144
ttgttatccg ctcacaattc cacacaac 28

<210> SEQ ID NO 145
<211> LENGTH: 81
<212> TYPE: PRT
<213> ORGANISM: Homo sapiens

<400> SEQUENCE: 145

Met Thr Cys Gly Ser Tyr Cys Gly Gly Arg Ala Phe Ser Cys Ile Ser
1 5 10 15

Ala Cys Gly Pro Arg Pro Gly Arg Cys Cys Ile Thr Ala Ala Pro Tyr
20 25 30

Arg Gly Ile Ser Cys Tyr Arg Gly Leu Thr Gly Gly Phe Gly Ser His
35 40 45

Ser Val Cys Gly Gly Phe Arg Ala Gly Ser Cys Gly Arg Ser Phe Gly
50 55 60

Tyr Arg Ser Gly Gly Val Cys Gly Pro Ser Pro Pro Cys Ile Thr Thr
65 70 75 80

Val

<210> SEQ ID NO 146
<211> LENGTH: 9
<212> TYPE: PRT
<213> ORGANISM: Homo sapiens

<400> SEQUENCE: 146

Ala Ala Pro Ala Val Asp Leu Asn Arg
1 5

<210> SEQ ID NO 147
<211> LENGTH: 10
<212> TYPE: PRT
<213> ORGANISM: Homo sapiens

<400> SEQUENCE: 147

Ala Ala Tyr Gln Val Ala Val Leu Pro Lys
1 5 10

<210> SEQ ID NO 148
<211> LENGTH: 11
<212> TYPE: PRT
<213> ORGANISM: Homo sapiens

<400> SEQUENCE: 148

Ala Cys Cys Gln Thr Ser Phe Cys Gly Phe Arg
1 5 10

<210> SEQ ID NO 149
<211> LENGTH: 9
<212> TYPE: PRT
<213> ORGANISM: Homo sapiens

<400> SEQUENCE: 149

Ala Cys Gln Pro Thr Cys Tyr Gln Arg
1 5

<210> SEQ ID NO 150
<211> LENGTH: 23
<212> TYPE: PRT
<213> ORGANISM: Homo sapiens

<400> SEQUENCE: 150

Ala Cys Gln Pro Thr Cys Tyr Gln Arg Thr Ser Cys Val Ser Asn Pro
1 5 10 15

Cys Gln Val Thr Cys Ser Arg
20

<210> SEQ ID NO 151
<211> LENGTH: 18
<212> TYPE: PRT
<213> ORGANISM: Homo sapiens

<400> SEQUENCE: 151

Ala Asp Leu Glu Ala Gln Val Glu Tyr Leu Lys Glu Glu Leu Met Cys
1 5 10 15

Leu Lys

<210> SEQ ID NO 152
<211> LENGTH: 19
<212> TYPE: PRT
<213> ORGANISM: Homo sapiens

<400> SEQUENCE: 152

Ala Asp Leu Glu Ala Gln Val Glu Tyr Leu Lys Glu Glu Leu Met Cys
1 5 10 15

Leu Lys Lys

<210> SEQ ID NO 153
<211> LENGTH: 18
<212> TYPE: PRT
<213> ORGANISM: Homo sapiens

<400> SEQUENCE: 153

Ala Asp Leu Glu Thr Asn Thr Glu Ala Leu Val Gln Glu Ile Asp Phe
1 5 10 15

Leu Lys

<210> SEQ ID NO 154
<211> LENGTH: 17
<212> TYPE: PRT
<213> ORGANISM: Homo sapiens

<400> SEQUENCE: 154

Ala Glu Leu Glu Arg Gln Asn Gln Glu Tyr Gln Val Leu Leu Asp Val
1               5                   10                  15

Arg

<210> SEQ ID NO 155
<211> LENGTH: 19
<212> TYPE: PRT
<213> ORGANISM: Homo sapiens

<400> SEQUENCE: 155

Ala Glu Leu Glu Arg Gln Asn Gln Glu Tyr Gln Val Leu Leu Asp Val
1               5                   10                  15

Arg Ala Arg

<210> SEQ ID NO 156
<211> LENGTH: 14
<212> TYPE: PRT
<213> ORGANISM: Homo sapiens

<400> SEQUENCE: 156

Ala Phe Arg Cys Ile Ser Ala Cys Gly Pro Arg Pro Gly Arg
1               5                   10

<210> SEQ ID NO 157
<211> LENGTH: 14
<212> TYPE: PRT
<213> ORGANISM: Homo sapiens

<400> SEQUENCE: 157

Ala Phe Ser Cys Ile Ser Ala Cys Gly Pro Gln Pro Gly Arg
1               5                   10

<210> SEQ ID NO 158
<211> LENGTH: 15
<212> TYPE: PRT
<213> ORGANISM: Homo sapiens

<400> SEQUENCE: 158

Ala Phe Ser Cys Ile Ser Ala Cys Gly Pro Gln Pro Gly Arg Cys
1               5                   10                  15

<210> SEQ ID NO 159
<211> LENGTH: 10
<212> TYPE: PRT
<213> ORGANISM: Homo sapiens

<400> SEQUENCE: 159

Ala Gly Phe Ala Ser Asp Asp Ala Pro Arg
1               5                   10

<210> SEQ ID NO 160
<211> LENGTH: 11
<212> TYPE: PRT
<213> ORGANISM: Homo sapiens

<400> SEQUENCE: 160

Ala Gly Gly Ser Tyr Gly Phe Gly Gly Ala Arg
1               5                   10

<210> SEQ ID NO 161
<211> LENGTH: 8

<212> TYPE: PRT
<213> ORGANISM: Homo sapiens

<400> SEQUENCE: 161

Ala Gly Ser Cys Gly His Ser Phe
1 5

<210> SEQ ID NO 162
<211> LENGTH: 11
<212> TYPE: PRT
<213> ORGANISM: Homo sapiens

<400> SEQUENCE: 162

Ala Gly Ser Cys Gly His Ser Phe Gly Tyr Arg
1 5 10

<210> SEQ ID NO 163
<211> LENGTH: 26
<212> TYPE: PRT
<213> ORGANISM: Homo sapiens

<400> SEQUENCE: 163

Ala Ile Gly Gly Gly Leu Ser Ser Val Gly Gly Gly Ser Ser Thr Ile
1 5 10 15

Lys Tyr Ser Thr Thr Ser Ser Ser Ser Arg
20 25

<210> SEQ ID NO 164
<211> LENGTH: 21
<212> TYPE: PRT
<213> ORGANISM: Homo sapiens

<400> SEQUENCE: 164

Ala Lys Pro Leu Glu Gln Ala Val Ala Ala Ile Val Cys Thr Phe Gln
1 5 10 15

Glu Tyr Ala Gly Arg
20

<210> SEQ ID NO 165
<211> LENGTH: 15
<212> TYPE: PRT
<213> ORGANISM: Homo sapiens

<400> SEQUENCE: 165

Ala Leu Ala Val Ala Gly Tyr Asp Val Glu Lys Asn Asn Ser Arg
1 5 10 15

<210> SEQ ID NO 166
<211> LENGTH: 8
<212> TYPE: PRT
<213> ORGANISM: Homo sapiens

<400> SEQUENCE: 166

Ala Leu Glu Thr Leu Gln Glu Arg
1 5

<210> SEQ ID NO 167
<211> LENGTH: 25
<212> TYPE: PRT
<213> ORGANISM: Homo sapiens

<400> SEQUENCE: 167

Ala Leu Arg Ala Glu Leu Glu Ala Leu Leu Ser Ser Lys Asp Asp Ile
1 5 10 15

Gly Lys Ser Val His Glu Leu Glu Arg
20 25

<210> SEQ ID NO 168
<211> LENGTH: 23
<212> TYPE: PRT
<213> ORGANISM: Homo sapiens

<400> SEQUENCE: 168

Ala Pro Tyr Arg Gly Ile Ser Cys Tyr Arg Gly Leu Thr Gly Gly Phe
1 5 10 15

Gly Ser His Ser Val Cys Arg
20

<210> SEQ ID NO 169
<211> LENGTH: 35
<212> TYPE: PRT
<213> ORGANISM: Homo sapiens

<400> SEQUENCE: 169

Ala Gln Met Gln Cys Met Ile Thr Asn Val Glu Ala Gln Leu Ala Glu
1 5 10 15

Ile Gln Ala Asp Leu Glu Arg Gln Asn Gln Glu Tyr Gln Val Leu Leu
20 25 30

Asp Val Arg
35

<210> SEQ ID NO 170
<211> LENGTH: 35
<212> TYPE: PRT
<213> ORGANISM: Homo sapiens

<400> SEQUENCE: 170

Ala Gln Met Gln Cys Met Ile Thr Asn Val Glu Ala Gln Leu Ala Glu
1 5 10 15

Ile Arg Ala Glu Leu Glu Arg Gln Asn Gln Glu Tyr Gln Val Leu Leu
20 25 30

Asp Val Arg
35

<210> SEQ ID NO 171
<211> LENGTH: 11
<212> TYPE: PRT
<213> ORGANISM: Homo sapiens

<400> SEQUENCE: 171

Ala Arg Leu Glu Gly Glu Ile Asn Met Tyr Arg
1 5 10

<210> SEQ ID NO 172
<211> LENGTH: 11
<212> TYPE: PRT
<213> ORGANISM: Homo sapiens

<400> SEQUENCE: 172

Ala Arg Leu Glu Gly Glu Ile Asn Met Tyr Arg
1 5 10

<210> SEQ ID NO 173
<211> LENGTH: 11
<212> TYPE: PRT
<213> ORGANISM: Homo sapiens

<400> SEQUENCE: 173

```
Ala Arg Leu Glu Gly Glu Ile Asn Met Tyr Arg
1               5                   10
```

<210> SEQ ID NO 174
<211> LENGTH: 42
<212> TYPE: PRT
<213> ORGANISM: Homo sapiens

<400> SEQUENCE: 174

```
Ala Arg Tyr Ser Ser Gln Leu Ala Gln Met Gln Cys Met Ile Thr Asn
1               5                   10                  15

Val Glu Ala Gln Leu Ala Glu Ile Arg Ala Glu Leu Glu Arg Gln Asn
            20                  25                  30

Gln Glu Tyr Gln Val Leu Leu Asp Val Arg
        35                  40
```

<210> SEQ ID NO 175
<211> LENGTH: 42
<212> TYPE: PRT
<213> ORGANISM: Homo sapiens

<400> SEQUENCE: 175

```
Ala Arg Tyr Ser Ser Gln Leu Ser Gln Val Gln Ser Leu Ile Thr Asn
1               5                   10                  15

Val Glu Ser Gln Leu Ala Glu Ile Arg Cys Asp Leu Glu Trp Gln Asn
            20                  25                  30

Gln Glu Tyr Gln Val Leu Leu Asp Val Arg
        35                  40
```

<210> SEQ ID NO 176
<211> LENGTH: 42
<212> TYPE: PRT
<213> ORGANISM: Homo sapiens

<400> SEQUENCE: 176

```
Ala Arg Tyr Ser Ser Gln Leu Ser Gln Val Gln Ser Leu Ile Thr Asn
1               5                   10                  15

Val Glu Ser Gln Leu Ala Glu Ile Arg Cys Asp Leu Glu Trp Gln Asn
            20                  25                  30

Gln Glu Tyr Gln Val Leu Leu Asp Val Arg
        35                  40
```

<210> SEQ ID NO 177
<211> LENGTH: 17
<212> TYPE: PRT
<213> ORGANISM: Homo sapiens

<400> SEQUENCE: 177

```
Ala Ser Ala Ala Ser Met Cys Leu Leu Ala Asn Val Ala His Ala Asn
1               5                   10                  15

Arg
```

<210> SEQ ID NO 178
<211> LENGTH: 30
<212> TYPE: PRT
<213> ORGANISM: Homo sapiens

<400> SEQUENCE: 178

```
Ala Thr Gln Thr Glu Glu Leu Asn Lys Gln Val Val Ser Ser Ser Glu
```

```
1               5                   10                  15

Gln Leu Gln Ser Tyr Gln Val Glu Ile Ile Glu Leu Arg Arg
            20                  25                  30


<210> SEQ ID NO 179
<211> LENGTH: 12
<212> TYPE: PRT
<213> ORGANISM: Homo sapiens

<400> SEQUENCE: 179

Ala Thr Val Ile Arg His Gly Glu Thr Leu Cys Arg
1               5                   10


<210> SEQ ID NO 180
<211> LENGTH: 15
<212> TYPE: PRT
<213> ORGANISM: Homo sapiens

<400> SEQUENCE: 180

Ala Val Phe Val Asp Leu Glu Pro Thr Val Leu Asp Glu Val Arg
1               5                   10                  15


<210> SEQ ID NO 181
<211> LENGTH: 20
<212> TYPE: PRT
<213> ORGANISM: Homo sapiens

<400> SEQUENCE: 181

Ala Val Phe Val Asp Leu Glu Pro Thr Val Leu Asp Glu Val Arg Thr
1               5                   10                  15

Gly Thr Tyr Arg
            20


<210> SEQ ID NO 182
<211> LENGTH: 28
<212> TYPE: PRT
<213> ORGANISM: Homo sapiens

<400> SEQUENCE: 182

Cys Cys Glu Pro Thr Ala Cys Gln Pro Thr Cys Tyr Gln Arg Thr Ser
1               5                   10                  15

Cys Val Ser Asn Pro Cys Gln Val Thr Cys Ser Arg
            20                  25


<210> SEQ ID NO 183
<211> LENGTH: 19
<212> TYPE: PRT
<213> ORGANISM: Homo sapiens

<400> SEQUENCE: 183

Cys Cys Gln Ile Asn Ile Glu Pro Ile Phe Glu Gly Tyr Ile Ser Ala
1               5                   10                  15

Leu Arg Arg


<210> SEQ ID NO 184
<211> LENGTH: 63
<212> TYPE: PRT
<213> ORGANISM: Homo sapiens

<400> SEQUENCE: 184

Cys Cys Gln Asn Thr Cys Cys Arg Thr Thr Cys Cys Gln Pro Thr Cys
1               5                   10                  15
```

Val Thr Ser Cys Cys Gln Pro Ser Cys Cys Ser Thr Pro Cys Cys Gln
20 25 30

Pro Ile Cys Cys Gly Ser Ser Cys Cys Gly Gln Thr Ser Cys Gly Ser
35 40 45

Ser Cys Gly Gln Ser Ser Ser Cys Ala Pro Val Tyr Cys Arg Arg
50 55 60

<210> SEQ ID NO 185
<211> LENGTH: 32
<212> TYPE: PRT
<213> ORGANISM: Homo sapiens

<400> SEQUENCE: 185

Cys Cys Gln Pro Cys Cys His Pro Thr Cys Tyr Gln Thr Thr Cys Phe
1 5 10 15

Arg Thr Thr Cys Cys Gln Pro Thr Cys Cys Gln Pro Thr Cys Cys Arg
20 25 30

<210> SEQ ID NO 186
<211> LENGTH: 18
<212> TYPE: PRT
<213> ORGANISM: Homo sapiens

<400> SEQUENCE: 186

Cys Cys Gln Pro Thr Cys Cys Arg Pro Ser Cys Gly Gln Thr Thr Cys
1 5 10 15

Cys Arg

<210> SEQ ID NO 187
<211> LENGTH: 33
<212> TYPE: PRT
<213> ORGANISM: Homo sapiens

<400> SEQUENCE: 187

Cys Cys Gln Pro Thr Cys Tyr Arg Pro Ser Cys Cys Val Ser Ser Cys
1 5 10 15

Cys Arg Pro Gln Cys Cys Gln Pro Val Cys Cys Gln Pro Thr Cys Cys
20 25 30

Arg

<210> SEQ ID NO 188
<211> LENGTH: 17
<212> TYPE: PRT
<213> ORGANISM: Homo sapiens

<400> SEQUENCE: 188

Cys Cys Arg Ser Ser Cys Cys Pro Ser Cys Cys Gln Thr Thr Cys Cys
1 5 10 15

Arg

<210> SEQ ID NO 189
<211> LENGTH: 19
<212> TYPE: PRT
<213> ORGANISM: Homo sapiens

<400> SEQUENCE: 189

Cys Asp Leu Glu Arg Gln Asn Gln Glu Tyr Gln Val Leu Leu Asp Val
1 5 10 15

Cys Ala Arg

<210> SEQ ID NO 190
<211> LENGTH: 17
<212> TYPE: PRT
<213> ORGANISM: Homo sapiens

<400> SEQUENCE: 190

Cys Asp Leu Glu Trp Gln Asn Gln Glu Tyr Gln Val Leu Leu Asp Val
1 5 10 15

Arg

<210> SEQ ID NO 191
<211> LENGTH: 21
<212> TYPE: PRT
<213> ORGANISM: Homo sapiens

<400> SEQUENCE: 191

Cys Glu Cys Cys Gln Ser Asn Leu Glu Pro Leu Phe Ala Gly Tyr Ile
1 5 10 15

Glu Thr Leu Arg Arg
20

<210> SEQ ID NO 192
<211> LENGTH: 20
<212> TYPE: PRT
<213> ORGANISM: Homo sapiens

<400> SEQUENCE: 192

Cys Glu Asp Gly Val Ser Thr Ser Asn Glu Lys Glu Thr Met Gln Phe
1 5 10 15

Leu Asn Asp Arg
20

<210> SEQ ID NO 193
<211> LENGTH: 10
<212> TYPE: PRT
<213> ORGANISM: Homo sapiens

<400> SEQUENCE: 193

Cys Glu Pro Ser Pro Trp Thr Phe Cys Lys
1 5 10

<210> SEQ ID NO 194
<211> LENGTH: 13
<212> TYPE: PRT
<213> ORGANISM: Homo sapiens

<400> SEQUENCE: 194

Cys Glu Pro Thr Ala Cys Gln Pro Thr Cys Tyr Gln Arg
1 5 10

<210> SEQ ID NO 195
<211> LENGTH: 9
<212> TYPE: PRT
<213> ORGANISM: Homo sapiens

<400> SEQUENCE: 195

Cys Glu Thr Ser Cys Tyr Gln Pro Arg
1 5

<210> SEQ ID NO 196
<211> LENGTH: 28
<212> TYPE: PRT
<213> ORGANISM: Homo sapiens

<400> SEQUENCE: 196

Cys Phe Arg Pro Gln Cys Cys Gln Ser Val Cys Cys Gln Pro Thr Cys
1 5 10 15

Cys Arg Pro Ser Cys Gly Gln Thr Thr Cys Cys Arg
20 25

<210> SEQ ID NO 197
<211> LENGTH: 22
<212> TYPE: PRT
<213> ORGANISM: Homo sapiens

<400> SEQUENCE: 197

Cys Gly Gln Val Leu Cys Gln Glu Thr Cys Cys Arg Pro Ser Cys Cys
1 5 10 15

Gln Thr Thr Cys Cys Arg
20

<210> SEQ ID NO 198
<211> LENGTH: 31
<212> TYPE: PRT
<213> ORGANISM: Homo sapiens

<400> SEQUENCE: 198

Cys Gly Ser Val Cys Ser Asp Gln Gly Cys Ser Gln Val Leu Cys Gln
1 5 10 15

Glu Thr Cys Cys Arg Pro Ser Cys Cys Gln Thr Thr Cys Cys Arg
20 25 30

<210> SEQ ID NO 199
<211> LENGTH: 12
<212> TYPE: PRT
<213> ORGANISM: Homo sapiens

<400> SEQUENCE: 199

Cys His Tyr Glu Thr Leu Val Glu Asn Asn Arg Arg
1 5 10

<210> SEQ ID NO 200
<211> LENGTH: 21
<212> TYPE: PRT
<213> ORGANISM: Homo sapiens

<400> SEQUENCE: 200

Cys Lys Pro Cys Gly Gln Leu Asn Thr Thr Cys Gly Gly Gly Ser Cys
1 5 10 15

Gly Gln Gly Arg Tyr
20

<210> SEQ ID NO 201
<211> LENGTH: 27
<212> TYPE: PRT
<213> ORGANISM: Homo sapiens

<400> SEQUENCE: 201

Cys Gln Leu Gly Asp His Leu Asn Val Glu Val Asp Ala Ala Pro Thr
1 5 10 15

Val Asp Leu Asn Gln Val Leu Asn Glu Thr Arg
20 25

<210> SEQ ID NO 202
<211> LENGTH: 21
<212> TYPE: PRT

<213> ORGANISM: Homo sapiens

<400> SEQUENCE: 202

Cys Gln Leu Gly Asp Arg Leu Asn Val Glu Val Asp Ala Ala Pro Ala
1 5 10 15

Val Asp Leu Asn Arg
20

<210> SEQ ID NO 203
<211> LENGTH: 27
<212> TYPE: PRT
<213> ORGANISM: Homo sapiens

<400> SEQUENCE: 203

Cys Gln Leu Gly Asp Arg Leu Asn Val Glu Val Asp Ala Ala Pro Ala
1 5 10 15

Val Asp Leu Asn Arg Val Leu Asn Glu Thr Arg
20 25

<210> SEQ ID NO 204
<211> LENGTH: 27
<212> TYPE: PRT
<213> ORGANISM: Homo sapiens

<400> SEQUENCE: 204

Cys Gln Leu Gly Asp Arg Leu Asn Val Glu Val Asp Thr Ala Pro Thr
1 5 10 15

Val Asp Leu Asn Gln Val Leu Asn Glu Thr Arg
20 25

<210> SEQ ID NO 205
<211> LENGTH: 25
<212> TYPE: PRT
<213> ORGANISM: Homo sapiens

<400> SEQUENCE: 205

Cys Gln Asn Ser Lys Leu Glu Ala Ala Val Ala Gln Ser Glu Gln Gln
1 5 10 15

Ser Glu Ala Ala Leu Ser Asp Ala Arg
20 25

<210> SEQ ID NO 206
<211> LENGTH: 61
<212> TYPE: PRT
<213> ORGANISM: Homo sapiens

<400> SEQUENCE: 206

Cys Gln Asn Thr Cys Cys Arg Thr Thr Cys Cys Gln Pro Thr Cys Val
1 5 10 15

Thr Ser Cys Cys Gln Pro Ser Cys Cys Ser Thr Pro Cys Cys Gln Pro
20 25 30

Ile Cys Cys Gly Ser Ser Cys Cys Gly Gln Thr Ser Cys Gly Ser Ser
35 40 45

Cys Gly Gln Ser Ser Ser Cys Ala Pro Val Tyr Cys Arg
50 55 60

<210> SEQ ID NO 207
<211> LENGTH: 55
<212> TYPE: PRT
<213> ORGANISM: Homo sapiens

<400> SEQUENCE: 207

```
Cys Gln Pro Ser Cys Cys Glu Thr Ser Cys Cys Gln Pro Ser Cys Cys
1               5                   10                  15

Glu Thr Ser Cys Cys Gln Pro Ser Cys Trp Gln Ile Ser Ser Cys Gly
            20                  25                  30

Thr Gly Cys Gly Ile Gly Gly Gly Ile Ser Tyr Gly Gln Glu Gly Ser
        35                  40                  45

Ser Gly Ala Val Ser Thr Arg
    50                  55


<210> SEQ ID NO 208
<211> LENGTH: 14
<212> TYPE: PRT
<213> ORGANISM: Homo sapiens

<400> SEQUENCE: 208

Cys Gln Pro Ser Cys Cys Glu Thr Ser Cys Tyr Gln Pro Arg
1               5                   10


<210> SEQ ID NO 209
<211> LENGTH: 22
<212> TYPE: PRT
<213> ORGANISM: Homo sapiens

<400> SEQUENCE: 209

Cys Gln Ser Val Cys Cys Gln Pro Thr Cys Cys Arg Pro Ser Cys Gly
1               5                   10                  15

Gln Thr Thr Cys Cys Arg
            20


<210> SEQ ID NO 210
<211> LENGTH: 9
<212> TYPE: PRT
<213> ORGANISM: Homo sapiens

<400> SEQUENCE: 210

Cys Gln Thr Ser Phe Cys Gly Phe Arg
1               5


<210> SEQ ID NO 211
<211> LENGTH: 47
<212> TYPE: PRT
<213> ORGANISM: Homo sapiens

<400> SEQUENCE: 211

Cys Gln Thr Thr Cys Cys Arg Thr Thr Cys Cys Arg Pro Ser Cys Cys
1               5                   10                  15

Val Ser Ser Cys Cys Arg Pro Gln Cys Cys Gln Ser Val Cys Cys Gln
            20                  25                  30

Pro Ser Cys Cys Ser Pro Ser Cys Cys Gln Thr Thr Cys Cys Arg
        35                  40                  45


<210> SEQ ID NO 212
<211> LENGTH: 49
<212> TYPE: PRT
<213> ORGANISM: Homo sapiens

<400> SEQUENCE: 212

Cys Gln Thr Thr Cys Cys Arg Thr Thr Cys Tyr Arg Pro Ser Cys Cys
1               5                   10                  15

Val Ser Ser Cys Cys Arg Pro Gln Cys Cys Gln Ser Val Cys Cys Gln
            20                  25                  30
```

```
Pro Thr Cys Cys Arg Pro Ser Cys Cys Glu Thr Thr Cys Cys His Pro
        35                  40                  45

Arg


<210> SEQ ID NO 213
<211> LENGTH: 12
<212> TYPE: PRT
<213> ORGANISM: Homo sapiens

<400> SEQUENCE: 213

Cys Gln Tyr Glu Ala Met Val Glu Ala Asn His Arg
1               5                   10


<210> SEQ ID NO 214
<211> LENGTH: 12
<212> TYPE: PRT
<213> ORGANISM: Homo sapiens

<400> SEQUENCE: 214

Cys Gln Tyr Glu Thr Val Leu Ala Asn Asn Arg Arg
1               5                   10


<210> SEQ ID NO 215
<211> LENGTH: 12
<212> TYPE: PRT
<213> ORGANISM: Homo sapiens

<400> SEQUENCE: 215

Cys Arg Pro Gln Cys Cys Gln Thr Ile Cys Cys Arg
1               5                   10


<210> SEQ ID NO 216
<211> LENGTH: 25
<212> TYPE: PRT
<213> ORGANISM: Homo sapiens

<400> SEQUENCE: 216

Cys Arg Thr Gly Cys Gly Ile Gly Gly Gly Ile Gly Tyr Gly Gln Glu
1               5                   10                  15

Gly Ser Ser Gly Ala Val Ser Thr Arg
            20                  25


<210> SEQ ID NO 217
<211> LENGTH: 27
<212> TYPE: PRT
<213> ORGANISM: Homo sapiens

<400> SEQUENCE: 217

Cys Ser Asp Gln Gly Cys Gly Gln Val Leu Cys Gln Glu Thr Cys Cys
1               5                   10                  15

Arg Pro Ser Cys Cys Gln Thr Thr Cys Cys Arg
            20                  25


<210> SEQ ID NO 218
<211> LENGTH: 9
<212> TYPE: PRT
<213> ORGANISM: Homo sapiens

<400> SEQUENCE: 218

Cys Thr Val Asn Ala Leu Glu Val Lys
1               5
```

<210> SEQ ID NO 219
<211> LENGTH: 10
<212> TYPE: PRT
<213> ORGANISM: Homo sapiens

<400> SEQUENCE: 219

Cys Thr Val Asn Ala Leu Glu Val Lys Arg
1 5 10

<210> SEQ ID NO 220
<211> LENGTH: 27
<212> TYPE: PRT
<213> ORGANISM: Homo sapiens

<400> SEQUENCE: 220

Asp Gly Val Ser Thr Ser Asn Glu Lys Glu Thr Met Gln Phe Leu Asn
1 5 10 15

Asp Arg Leu Ala Ser Tyr Leu Glu Lys Val Arg
20 25

<210> SEQ ID NO 221
<211> LENGTH: 12
<212> TYPE: PRT
<213> ORGANISM: Homo sapiens

<400> SEQUENCE: 221

Asp Leu Asn Met Asp Cys Ile Ile Asp Glu Ile Lys
1 5 10

<210> SEQ ID NO 222
<211> LENGTH: 21
<212> TYPE: PRT
<213> ORGANISM: Homo sapiens

<400> SEQUENCE: 222

Asp Leu Asn Met Asp Cys Ile Ile Asp Glu Ile Lys Ala Gln Tyr Asp
1 5 10 15

Asp Ile Val Thr Arg
20

<210> SEQ ID NO 223
<211> LENGTH: 12
<212> TYPE: PRT
<213> ORGANISM: Homo sapiens

<400> SEQUENCE: 223

Asp Leu Asn Met Asp Cys Met Val Ala Glu Ile Lys
1 5 10

<210> SEQ ID NO 224
<211> LENGTH: 21
<212> TYPE: PRT
<213> ORGANISM: Homo sapiens

<400> SEQUENCE: 224

Asp Leu Asn Met Asp Cys Met Val Ala Glu Ile Lys Ala Gln Tyr Asp
1 5 10 15

Asp Ile Ala Thr Arg
20

<210> SEQ ID NO 225
<211> LENGTH: 30
<212> TYPE: PRT
<213> ORGANISM: Homo sapiens

<400> SEQUENCE: 225

Asp Leu Thr Asp Ala Ala Ile Gly Pro Ala Tyr Arg Glu Trp Ser Thr
1 5 10 15

Phe Ala Val Gly Pro Gly His Cys Leu Gln Leu Asn Asp Arg
20 25 30

<210> SEQ ID NO 226
<211> LENGTH: 12
<212> TYPE: PRT
<213> ORGANISM: Homo sapiens

<400> SEQUENCE: 226

Asp Leu Thr Asp Thr Ala Ile Gly Pro Ala Tyr Arg
1 5 10

<210> SEQ ID NO 227
<211> LENGTH: 27
<212> TYPE: PRT
<213> ORGANISM: Homo sapiens

<400> SEQUENCE: 227

Asp Met Ala Arg Gln Leu Arg Glu Tyr Gln Glu Leu Met Asn Ala Lys
1 5 10 15

Leu Gly Leu Asp Ile Glu Ile Ala Thr Tyr Arg
20 25

<210> SEQ ID NO 228
<211> LENGTH: 9
<212> TYPE: PRT
<213> ORGANISM: Homo sapiens

<400> SEQUENCE: 228

Asp Met Pro Pro Thr Asn Pro Ile Arg
1 5

<210> SEQ ID NO 229
<211> LENGTH: 10
<212> TYPE: PRT
<213> ORGANISM: Homo sapiens

<400> SEQUENCE: 229

Asp Asn Ala Glu Leu Lys Asn Leu Ile Arg
1 5 10

<210> SEQ ID NO 230
<211> LENGTH: 12
<212> TYPE: PRT
<213> ORGANISM: Homo sapiens

<400> SEQUENCE: 230

Asp Asn Ala Glu Leu Lys Asn Leu Ile Arg Glu Arg
1 5 10

<210> SEQ ID NO 231
<211> LENGTH: 10
<212> TYPE: PRT
<213> ORGANISM: Homo sapiens

<400> SEQUENCE: 231

Asp Asn Val Glu Leu Glu Asn Leu Ile Arg
1 5 10

<210> SEQ ID NO 232
<211> LENGTH: 12
<212> TYPE: PRT
<213> ORGANISM: Homo sapiens

<400> SEQUENCE: 232

Asp Asn Val Glu Leu Glu Asn Leu Ile Arg Glu Arg
1               5                   10

<210> SEQ ID NO 233
<211> LENGTH: 13
<212> TYPE: PRT
<213> ORGANISM: Homo sapiens

<400> SEQUENCE: 233

Asp Ser Leu Glu Asn Met Leu Thr Glu Ser Glu Ala Arg
1               5                   10

<210> SEQ ID NO 234
<211> LENGTH: 41
<212> TYPE: PRT
<213> ORGANISM: Homo sapiens

<400> SEQUENCE: 234

Asp Ser Leu Glu Asn Thr Leu Thr Glu Ser Glu Ala His Tyr Ser Ser
1               5                   10                  15

Gln Leu Ser Gln Met Gln Ser Leu Ile Thr Asn Val Glu Ser Gln Leu
            20                  25                  30

Ala Glu Ile Arg Cys Asp Leu Glu Arg
        35                  40

<210> SEQ ID NO 235
<211> LENGTH: 53
<212> TYPE: PRT
<213> ORGANISM: Homo sapiens

<400> SEQUENCE: 235

Asp Ser Leu Glu Asn Thr Leu Thr Glu Ser Glu Ala His Tyr Ser Ser
1               5                   10                  15

Gln Leu Ser Gln Met Gln Ser Leu Ile Thr Asn Val Glu Ser Gln Leu
            20                  25                  30

Ala Glu Ile Arg Cys Asp Leu Glu Arg Gln Asn Gln Glu Tyr Gln Val
        35                  40                  45

Leu Leu Asp Val Arg
    50

<210> SEQ ID NO 236
<211> LENGTH: 41
<212> TYPE: PRT
<213> ORGANISM: Homo sapiens

<400> SEQUENCE: 236

Asp Ser Leu Glu Asn Thr Leu Thr Glu Ser Glu Ala His Tyr Ser Ser
1               5                   10                  15

Gln Leu Ser Gln Val Gln Ser Leu Ile Thr Asn Val Glu Ser Gln Leu
            20                  25                  30

Ala Glu Ile Arg Cys Asp Leu Glu Trp
        35                  40

<210> SEQ ID NO 237
<211> LENGTH: 41
<212> TYPE: PRT

<213> ORGANISM: Homo sapiens

<400> SEQUENCE: 237

Asp Ser Leu Glu Asn Thr Leu Thr Glu Ser Glu Ala Arg Tyr Ser Ser
1 5 10 15

Gln Leu Ala Gln Met Gln Cys Met Ile Thr Asn Val Glu Ala Gln Leu
20 25 30

Ala Glu Ile Gln Ala Asp Leu Glu Arg
35 40

<210> SEQ ID NO 238
<211> LENGTH: 53
<212> TYPE: PRT
<213> ORGANISM: Homo sapiens

<400> SEQUENCE: 238

Asp Ser Leu Glu Asn Thr Leu Thr Glu Ser Glu Ala Arg Tyr Ser Ser
1 5 10 15

Gln Leu Ala Gln Met Gln Cys Met Ile Thr Asn Val Glu Ala Gln Leu
20 25 30

Ala Glu Ile Gln Ala Asp Leu Glu Arg Gln Asn Gln Glu Tyr Gln Val
35 40 45

Leu Leu Asp Val Arg
50

<210> SEQ ID NO 239
<211> LENGTH: 53
<212> TYPE: PRT
<213> ORGANISM: Homo sapiens

<400> SEQUENCE: 239

Asp Ser Leu Glu Asn Thr Leu Thr Glu Ser Glu Ala Arg Tyr Ser Ser
1 5 10 15

Gln Leu Ala Gln Met Gln Cys Met Ile Thr Asn Val Glu Ala Gln Leu
20 25 30

Ala Glu Ile Arg Ala Glu Leu Glu Arg Gln Asn Gln Glu Tyr Gln Val
35 40 45

Leu Leu Asp Val Arg
50

<210> SEQ ID NO 240
<211> LENGTH: 13
<212> TYPE: PRT
<213> ORGANISM: Homo sapiens

<400> SEQUENCE: 240

Asp Ser Gln Glu Cys Ile Leu Met Glu Thr Glu Ala Arg
1 5 10

<210> SEQ ID NO 241
<211> LENGTH: 27
<212> TYPE: PRT
<213> ORGANISM: Homo sapiens

<400> SEQUENCE: 241

Asp Val Asp Thr Ala Phe Leu Met Lys Ala Asp Leu Glu Thr Asn Thr
1 5 10 15

Glu Ala Leu Val Gln Glu Ile Asp Phe Leu Lys
20 25

<210> SEQ ID NO 242
<211> LENGTH: 11
<212> TYPE: PRT
<213> ORGANISM: Homo sapiens

<400> SEQUENCE: 242

Glu Ala Glu Cys Val Glu Ala Asn Ser Gly Arg
1               5                   10

<210> SEQ ID NO 243
<211> LENGTH: 14
<212> TYPE: PRT
<213> ORGANISM: Homo sapiens

<400> SEQUENCE: 243

Glu Ala Glu Cys Val Glu Ala Asn Ser Gly Arg Leu Ala Ser
1               5                   10

<210> SEQ ID NO 244
<211> LENGTH: 28
<212> TYPE: PRT
<213> ORGANISM: Homo sapiens

<400> SEQUENCE: 244

Glu Ala Glu Cys Val Glu Ala Asn Ser Gly Arg Leu Ala Ser Glu Leu
1               5                   10                  15

Asn His Val Gln Glu Val Leu Glu Gly Tyr Lys Lys
            20                  25

<210> SEQ ID NO 245
<211> LENGTH: 29
<212> TYPE: PRT
<213> ORGANISM: Homo sapiens

<400> SEQUENCE: 245

Glu Ala Glu Cys Val Glu Ala Asn Ser Gly Arg Leu Ala Ser Glu Leu
1               5                   10                  15

Asn His Val Gln Glu Val Leu Glu Gly Tyr Lys Lys Lys
            20                  25

<210> SEQ ID NO 246
<211> LENGTH: 25
<212> TYPE: PRT
<213> ORGANISM: Homo sapiens

<400> SEQUENCE: 246

Glu Ala Gln Leu Ala Glu Ile Gln Ala Asp Leu Glu Arg Gln Asn Gln
1               5                   10                  15

Glu Tyr Gln Val Leu Leu Asp Val Arg
            20                  25

<210> SEQ ID NO 247
<211> LENGTH: 12
<212> TYPE: PRT
<213> ORGANISM: Homo sapiens

<400> SEQUENCE: 247

Glu Glu Ile Asn Glu Leu Asn Cys Met Ile Gln Arg
1               5                   10

<210> SEQ ID NO 248
<211> LENGTH: 18
<212> TYPE: PRT
<213> ORGANISM: Homo sapiens

<400> SEQUENCE: 248

Glu Glu Tyr Val Gln Glu Asp Ala Gly Ile Leu Phe Val Gly Ser Thr
1 5 10 15

Asn Arg

<210> SEQ ID NO 249
<211> LENGTH: 15
<212> TYPE: PRT
<213> ORGANISM: Homo sapiens

<400> SEQUENCE: 249

Glu His Cys Ser Ala Cys Gly Pro Leu Ser Gln Ile Leu Val Lys
1 5 10 15

<210> SEQ ID NO 250
<211> LENGTH: 9
<212> TYPE: PRT
<213> ORGANISM: Homo sapiens

<400> SEQUENCE: 250

Glu Ile Met Gln Phe Leu Asn Asp Arg
1 5

<210> SEQ ID NO 251
<211> LENGTH: 16
<212> TYPE: PRT
<213> ORGANISM: Homo sapiens

<400> SEQUENCE: 251

Glu Ile Met Gln Phe Leu Asn Asp Arg Leu Ala Ser Tyr Leu Thr Arg
1 5 10 15

<210> SEQ ID NO 252
<211> LENGTH: 20
<212> TYPE: PRT
<213> ORGANISM: Homo sapiens

<400> SEQUENCE: 252

Glu Ile Arg Ala Glu Leu Glu Arg Gln Asn Gln Glu Tyr Gln Val Leu
1 5 10 15

Leu Asp Val Arg
20

<210> SEQ ID NO 253
<211> LENGTH: 21
<212> TYPE: PRT
<213> ORGANISM: Homo sapiens

<400> SEQUENCE: 253

Glu Leu Asp Val Asp Gly Ile Ile Ala Glu Ile Lys Ala Gln Tyr Asp
1 5 10 15

Asp Ile Thr Ser Arg
20

<210> SEQ ID NO 254
<211> LENGTH: 12
<212> TYPE: PRT
<213> ORGANISM: Homo sapiens

<400> SEQUENCE: 254

Glu Leu Asp Val Asp Ser Ile Ile Ala Glu Ile Lys
1 5 10

<210> SEQ ID NO 255
<211> LENGTH: 21
<212> TYPE: PRT
<213> ORGANISM: Homo sapiens

<400> SEQUENCE: 255

Glu Leu Asp Val Asp Ser Ile Ile Ala Glu Ile Lys Ala Gln Tyr Asp
1               5                   10                  15

Asp Ile Ala Ser Arg
            20

<210> SEQ ID NO 256
<211> LENGTH: 9
<212> TYPE: PRT
<213> ORGANISM: Homo sapiens

<400> SEQUENCE: 256

Glu Met Pro Pro Ser Asn Pro Ile Arg
1               5

<210> SEQ ID NO 257
<211> LENGTH: 8
<212> TYPE: PRT
<213> ORGANISM: Homo sapiens

<400> SEQUENCE: 257

Glu Asn Leu Gln Leu Glu Thr Arg
1               5

<210> SEQ ID NO 258
<211> LENGTH: 12
<212> TYPE: PRT
<213> ORGANISM: Homo sapiens

<400> SEQUENCE: 258

Glu Pro Thr Ala Cys Gln Pro Thr Cys Tyr Gln Arg
1               5                   10

<210> SEQ ID NO 259
<211> LENGTH: 12
<212> TYPE: PRT
<213> ORGANISM: Homo sapiens

<400> SEQUENCE: 259

Glu Arg Asp Asn Val Glu Leu Glu Asn Leu Ile Arg
1               5                   10

<210> SEQ ID NO 260
<211> LENGTH: 14
<212> TYPE: PRT
<213> ORGANISM: Homo sapiens

<400> SEQUENCE: 260

Glu Arg Asp Asn Val Glu Leu Glu Asn Leu Ile Arg Glu Arg
1               5                   10

<210> SEQ ID NO 261
<211> LENGTH: 25
<212> TYPE: PRT
<213> ORGANISM: Homo sapiens

<400> SEQUENCE: 261

Glu Ser Gln Leu Ala Glu Ile His Ser Asp Leu Glu Arg Gln Asn Gln

```
1               5                   10                  15

Glu Tyr Gln Val Leu Leu Asp Val Arg
            20                  25


<210> SEQ ID NO 262
<211> LENGTH: 16
<212> TYPE: PRT
<213> ORGANISM: Homo sapiens

<400> SEQUENCE: 262

Glu Thr Cys Cys Glu Pro Thr Ala Cys Gln Pro Thr Cys Tyr Gln Arg
1               5                   10                  15


<210> SEQ ID NO 263
<211> LENGTH: 15
<212> TYPE: PRT
<213> ORGANISM: Homo sapiens

<400> SEQUENCE: 263

Glu Thr Cys Cys His Pro Ser Cys Cys Glu Thr Thr Cys Cys Arg
1               5                   10                  15


<210> SEQ ID NO 264
<211> LENGTH: 15
<212> TYPE: PRT
<213> ORGANISM: Homo sapiens

<400> SEQUENCE: 264

Glu Thr Cys Cys His Pro Ser Cys Cys Glu Thr Thr Cys Cys Arg
1               5                   10                  15


<210> SEQ ID NO 265
<211> LENGTH: 16
<212> TYPE: PRT
<213> ORGANISM: Homo sapiens

<400> SEQUENCE: 265

Glu Thr Met Gln Phe Leu Asn Asp Cys Leu Ala Ser Tyr Leu Glu Lys
1               5                   10                  15


<210> SEQ ID NO 266
<211> LENGTH: 18
<212> TYPE: PRT
<213> ORGANISM: Homo sapiens

<400> SEQUENCE: 266

Glu Thr Met Gln Phe Leu Asn Asp Cys Leu Ala Ser Tyr Leu Glu Lys
1               5                   10                  15

Val Arg


<210> SEQ ID NO 267
<211> LENGTH: 32
<212> TYPE: PRT
<213> ORGANISM: Homo sapiens

<400> SEQUENCE: 267

Glu Thr Met Gln Phe Leu Asn Asp Cys Leu Ala Ser Tyr Leu Glu Lys
1               5                   10                  15

Val Arg Gln Leu Glu Arg Asp Asn Ala Glu Leu Glu Asn Leu Ile Arg
            20                  25                  30


<210> SEQ ID NO 268
<211> LENGTH: 35
```

<212> TYPE: PRT
<213> ORGANISM: Homo sapiens

<400> SEQUENCE: 268

Glu Val Glu Gln Trp Phe Ala Thr Gln Thr Glu Glu Leu Asn Lys Gln
1 5 10 15

Val Val Ser Ser Ser Glu Gln Leu Gln Ser Cys Gln Val Glu Ile Ile
20 25 30

Glu Leu Arg
35

<210> SEQ ID NO 269
<211> LENGTH: 36
<212> TYPE: PRT
<213> ORGANISM: Homo sapiens

<400> SEQUENCE: 269

Glu Val Glu Gln Trp Phe Ala Thr Gln Thr Glu Glu Leu Asn Lys Gln
1 5 10 15

Val Val Ser Ser Ser Glu Gln Leu Gln Ser Cys Gln Val Glu Ile Ile
20 25 30

Glu Leu Arg Arg
35

<210> SEQ ID NO 270
<211> LENGTH: 33
<212> TYPE: PRT
<213> ORGANISM: Homo sapiens

<400> SEQUENCE: 270

Glu Val Glu Gln Trp Phe Ala Thr Gln Thr Glu Glu Leu Asn Lys Gln
1 5 10 15

Val Val Ser Ser Ser Glu Gln Leu Gln Ser Tyr Gln Val Glu Ile Ile
20 25 30

Glu

<210> SEQ ID NO 271
<211> LENGTH: 35
<212> TYPE: PRT
<213> ORGANISM: Homo sapiens

<400> SEQUENCE: 271

Glu Val Glu Gln Trp Phe Ala Thr Gln Thr Glu Glu Leu Asn Lys Gln
1 5 10 15

Val Val Ser Ser Ser Glu Gln Leu Gln Ser Tyr Gln Val Glu Ile Ile
20 25 30

Glu Leu Arg
35

<210> SEQ ID NO 272
<211> LENGTH: 36
<212> TYPE: PRT
<213> ORGANISM: Homo sapiens

<400> SEQUENCE: 272

Glu Val Glu Gln Trp Phe Ala Thr Gln Thr Glu Glu Leu Asn Lys Gln
1 5 10 15

Val Val Ser Ser Ser Glu Gln Leu Gln Ser Tyr Gln Val Glu Ile Ile
20 25 30

Glu Leu Arg Arg

35

<210> SEQ ID NO 273
<211> LENGTH: 12
<212> TYPE: PRT
<213> ORGANISM: Homo sapiens

<400> SEQUENCE: 273

Glu Val Glu Gln Trp Phe Ala Thr Gln Thr Glu Lys
1 5 10

<210> SEQ ID NO 274
<211> LENGTH: 15
<212> TYPE: PRT
<213> ORGANISM: Homo sapiens

<400> SEQUENCE: 274

Glu Val Glu Gln Trp Phe Ala Thr Gln Thr Glu Lys Leu Asn Lys
1 5 10 15

<210> SEQ ID NO 275
<211> LENGTH: 36
<212> TYPE: PRT
<213> ORGANISM: Homo sapiens

<400> SEQUENCE: 275

Glu Val Glu Gln Trp Phe Ala Thr Gln Thr Glu Lys Leu Asn Lys Gln
1 5 10 15

Val Val Ser Ser Ser Glu Gln Leu Gln Ser Cys Gln Ala Glu Ile Ile
20 25 30

Glu Leu Arg Arg
35

<210> SEQ ID NO 276
<211> LENGTH: 11
<212> TYPE: PRT
<213> ORGANISM: Homo sapiens

<400> SEQUENCE: 276

Phe Asp Ile Leu Pro Ser Gln Ser Gly Thr Lys
1 5 10

<210> SEQ ID NO 277
<211> LENGTH: 19
<212> TYPE: PRT
<213> ORGANISM: Homo sapiens

<400> SEQUENCE: 277

Phe Leu Glu Gln Gln Asn Lys Leu Leu Glu Thr Lys Leu Pro Phe Tyr
1 5 10 15

Gln Asn Arg

<210> SEQ ID NO 278
<211> LENGTH: 39
<212> TYPE: PRT
<213> ORGANISM: Homo sapiens

<400> SEQUENCE: 278

Phe Leu Glu Gln Gln Asn Lys Leu Leu Glu Thr Lys Leu Gln Phe Tyr
1 5 10 15

Gln Asn Cys Glu Cys Cys Gln Ser Asn Leu Glu Pro Leu Phe Ala Gly
20 25 30

Tyr Ile Glu Thr Leu Arg Arg
        35

<210> SEQ ID NO 279
<211> LENGTH: 44
<212> TYPE: PRT
<213> ORGANISM: Homo sapiens

<400> SEQUENCE: 279

Phe Leu Met Lys Ala Asp Leu Glu Thr Asn Thr Glu Ala Leu Val Gln
1               5                   10                  15

Glu Ile Asp Phe Leu Lys Ser Leu Tyr Glu Glu Glu Ile Cys Leu Leu
            20                  25                  30

Gln Ser Gln Ile Ser Glu Thr Ser Val Ile Val Lys
        35                  40

<210> SEQ ID NO 280
<211> LENGTH: 59
<212> TYPE: PRT
<213> ORGANISM: Homo sapiens

<400> SEQUENCE: 280

Phe Pro Ser Phe Ser Thr Ser Gly Thr Cys Ser Ser Ser Cys Cys Gln
1               5                   10                  15

Pro Ser Cys Cys Glu Thr Ser Cys Cys Gln Pro Ser Cys Cys Gln Thr
            20                  25                  30

Ser Ser Cys Arg Thr Gly Cys Gly Ile Gly Gly Gly Ile Gly Tyr Gly
        35                  40                  45

Gln Glu Gly Ser Ser Gly Ala Val Ser Thr Arg
    50                  55

<210> SEQ ID NO 281
<211> LENGTH: 13
<212> TYPE: PRT
<213> ORGANISM: Homo sapiens

<400> SEQUENCE: 281

Phe Arg Cys Ile Ser Ala Cys Gly Pro Arg Pro Gly Arg
1               5                   10

<210> SEQ ID NO 282
<211> LENGTH: 22
<212> TYPE: PRT
<213> ORGANISM: Homo sapiens

<400> SEQUENCE: 282

Phe Arg Cys Ile Ser Ala Cys Gly Pro Arg Pro Gly Arg Cys Cys Ile
1               5                   10                  15

Thr Ala Ala Pro Tyr Arg
            20

<210> SEQ ID NO 283
<211> LENGTH: 27
<212> TYPE: PRT
<213> ORGANISM: Homo sapiens

<400> SEQUENCE: 283

Phe Ser Leu Asp Asp Cys Asn Trp Tyr Gly Glu Gly Ile Asn Ser Asn
1               5                   10                  15

Glu Lys Glu Thr Met Gln Ile Leu Asn Glu Arg
            20                  25

<210> SEQ ID NO 284
<211> LENGTH: 8
<212> TYPE: PRT
<213> ORGANISM: Homo sapiens

<400> SEQUENCE: 284

Phe Ser Leu Asp Asp Cys Ser Arg
1               5

<210> SEQ ID NO 285
<211> LENGTH: 56
<212> TYPE: PRT
<213> ORGANISM: Homo sapiens

<400> SEQUENCE: 285

Phe Ser Thr Gly Gly Thr Cys Asp Ser Ser Cys Cys Gln Pro Ser Cys
1               5                   10                  15

Cys Glu Thr Ser Cys Cys Gln Pro Ser Cys Tyr Gln Thr Ser Ser Tyr
            20                  25                  30

Gly Thr Gly Cys Gly Ile Gly Gly Gly Ile Gly Tyr Gly Gln Glu Gly
        35                  40                  45

Ser Ser Gly Ala Val Ser Thr Arg
    50                  55

<210> SEQ ID NO 286
<211> LENGTH: 21
<212> TYPE: PRT
<213> ORGANISM: Homo sapiens

<400> SEQUENCE: 286

Gly Ala Phe Leu Tyr Asp Pro Cys Gly Val Ser Thr Pro Val Leu Ser
1               5                   10                  15

Thr Gly Val Leu Arg
            20

<210> SEQ ID NO 287
<211> LENGTH: 21
<212> TYPE: PRT
<213> ORGANISM: Homo sapiens

<400> SEQUENCE: 287

Gly Ala Phe Leu Tyr Glu Pro Cys Gly Val Ser Met Pro Val Leu Ser
1               5                   10                  15

Thr Gly Val Leu Arg
            20

<210> SEQ ID NO 288
<211> LENGTH: 22
<212> TYPE: PRT
<213> ORGANISM: Homo sapiens

<400> SEQUENCE: 288

Gly Cys Gly Thr Gly Gly Gly Ile Gly Tyr Gly Gln Glu Gly Ser Ser
1               5                   10                  15

Gly Ala Val Ser Thr Arg
            20

<210> SEQ ID NO 289
<211> LENGTH: 7
<212> TYPE: PRT
<213> ORGANISM: Homo sapiens

<400> SEQUENCE: 289

Gly Cys Pro Ser Leu Met Arg
1               5

<210> SEQ ID NO 290
<211> LENGTH: 30
<212> TYPE: PRT
<213> ORGANISM: Homo sapiens

<400> SEQUENCE: 290

Gly Cys Gln Glu Ile Cys Trp Glu Pro Thr Ser Cys Gln Thr Ser Tyr
1               5                   10                  15

Val Glu Ser Arg Pro Cys Gln Thr Ser Cys Tyr Arg Pro Arg
            20                  25                  30

<210> SEQ ID NO 291
<211> LENGTH: 31
<212> TYPE: PRT
<213> ORGANISM: Homo sapiens

<400> SEQUENCE: 291

Gly Cys Gln Glu Ile Cys Trp Glu Pro Thr Ser Cys Gln Thr Ser Tyr
1               5                   10                  15

Val Glu Ser Arg Pro Cys Gln Thr Ser Cys Tyr Arg Pro Arg Thr
            20                  25                  30

<210> SEQ ID NO 292
<211> LENGTH: 16
<212> TYPE: PRT
<213> ORGANISM: Homo sapiens

<400> SEQUENCE: 292

Gly Cys Arg Pro Ser Cys Tyr Gly Gly Tyr Gly Phe Ser Gly Phe Tyr
1               5                   10                  15

<210> SEQ ID NO 293
<211> LENGTH: 9
<212> TYPE: PRT
<213> ORGANISM: Homo sapiens

<400> SEQUENCE: 293

Gly Phe Gly Ser His Ser Val Cys Arg
1               5

<210> SEQ ID NO 294
<211> LENGTH: 60
<212> TYPE: PRT
<213> ORGANISM: Homo sapiens

<400> SEQUENCE: 294

Gly Phe Pro Ser Phe Ser Thr Ser Gly Thr Cys Ser Ser Ser Cys Cys
1               5                   10                  15

Gln Pro Ser Cys Cys Glu Thr Ser Cys Cys Gln Pro Ser Cys Cys Gln
            20                  25                  30

Thr Ser Ser Cys Arg Thr Gly Cys Gly Ile Gly Gly Gly Ile Gly Tyr
        35                  40                  45

Gly Gln Glu Gly Ser Ser Gly Ala Val Ser Thr Arg
    50                  55                  60

<210> SEQ ID NO 295
<211> LENGTH: 28
<212> TYPE: PRT

<213> ORGANISM: Homo sapiens

<400> SEQUENCE: 295

Gly Phe Ser Tyr Pro Ser Asn Leu Val Tyr Ser Thr Asp Leu Cys Ser
1               5                   10                  15

Pro Ser Ile Cys Gln Leu Gly Ser Ser Leu Tyr Arg
            20                  25

<210> SEQ ID NO 296
<211> LENGTH: 10
<212> TYPE: PRT
<213> ORGANISM: Homo sapiens

<400> SEQUENCE: 296

Gly Gly Phe Gly Ser His Ser Val Cys Arg
1               5                   10

<210> SEQ ID NO 297
<211> LENGTH: 30
<212> TYPE: PRT
<213> ORGANISM: Homo sapiens

<400> SEQUENCE: 297

Gly Gly Gly Phe Gly Gly Gly Ser Gly Phe Gly Gly Gly Ser Gly Phe
1               5                   10                  15

Ser Gly Gly Gly Phe Gly Gly Gly Gly Phe Gly Gly Gly Arg
            20                  25                  30

<210> SEQ ID NO 298
<211> LENGTH: 30
<212> TYPE: PRT
<213> ORGANISM: Homo sapiens

<400> SEQUENCE: 298

Gly Gly Gly Phe Gly Gly Gly Ser Ser Phe Gly Gly Gly Ser Gly Phe
1               5                   10                  15

Ser Gly Gly Gly Phe Ser Gly Gly Gly Phe Gly Gly Gly Arg
            20                  25                  30

<210> SEQ ID NO 299
<211> LENGTH: 8
<212> TYPE: PRT
<213> ORGANISM: Homo sapiens

<400> SEQUENCE: 299

Gly Gly Pro Asp Phe Gly Tyr Arg
1               5

<210> SEQ ID NO 300
<211> LENGTH: 10
<212> TYPE: PRT
<213> ORGANISM: Homo sapiens

<400> SEQUENCE: 300

Gly Gly Pro Val Gln Val Leu Glu Asp Lys
1               5                   10

<210> SEQ ID NO 301
<211> LENGTH: 13
<212> TYPE: PRT
<213> ORGANISM: Homo sapiens

<400> SEQUENCE: 301

Gly Gly Pro Val Gln Val Leu Glu Asp Lys Glu Leu Lys
1 5 10

<210> SEQ ID NO 302
<211> LENGTH: 24
<212> TYPE: PRT
<213> ORGANISM: Homo sapiens

<400> SEQUENCE: 302

Gly Gly Val Ser Cys His Thr Thr Cys Tyr Arg Pro Thr Cys Val Ile
1 5 10 15

Ser Ser Cys Pro Arg Pro Leu Cys
20

<210> SEQ ID NO 303
<211> LENGTH: 29
<212> TYPE: PRT
<213> ORGANISM: Homo sapiens

<400> SEQUENCE: 303

Gly Gly Val Ser Cys His Thr Thr Cys Tyr Arg Pro Thr Cys Val Ile
1 5 10 15

Ser Ser Cys Pro Arg Pro Leu Cys Cys Ala Ser Ser Cys
20 25

<210> SEQ ID NO 304
<211> LENGTH: 30
<212> TYPE: PRT
<213> ORGANISM: Homo sapiens

<400> SEQUENCE: 304

Gly Gly Val Ser Cys His Thr Thr Cys Tyr Arg Pro Thr Cys Val Ile
1 5 10 15

Ser Ser Cys Pro Arg Pro Leu Cys Cys Ala Ser Ser Cys Cys
20 25 30

<210> SEQ ID NO 305
<211> LENGTH: 8
<212> TYPE: PRT
<213> ORGANISM: Homo sapiens

<400> SEQUENCE: 305

Gly Ile Leu Val Asp Thr Ser Arg
1 5

<210> SEQ ID NO 306
<211> LENGTH: 23
<212> TYPE: PRT
<213> ORGANISM: Homo sapiens

<400> SEQUENCE: 306

Gly Leu Cys Lys Pro Cys Gly Gln Leu Asn Thr Thr Cys Gly Gly Gly
1 5 10 15

Ser Cys Gly Gln Gly Arg Tyr
20

<210> SEQ ID NO 307
<211> LENGTH: 18
<212> TYPE: PRT
<213> ORGANISM: Homo sapiens

<400> SEQUENCE: 307

Gly Leu Pro Gln Ile Ala His Leu Leu Gln Ser Gly Asn Ser Asp Val 1 5 10 15

Val Arg

<210> SEQ ID NO 308
<211> LENGTH: 11
<212> TYPE: PRT
<213> ORGANISM: Homo sapiens

<400> SEQUENCE: 308

Gly Leu Gln Ala Leu Gly Cys Leu Gly Ser Arg
1 5 10

<210> SEQ ID NO 309
<211> LENGTH: 13
<212> TYPE: PRT
<213> ORGANISM: Homo sapiens

<400> SEQUENCE: 309

Gly Leu Thr Gly Gly Phe Gly Ser His Ser Val Cys Arg
1 5 10

<210> SEQ ID NO 310
<211> LENGTH: 14
<212> TYPE: PRT
<213> ORGANISM: Homo sapiens

<400> SEQUENCE: 310

Gly Leu Thr Gly Gly Phe Gly Ser His Ser Val Cys Arg Gly
1 5 10

<210> SEQ ID NO 311
<211> LENGTH: 16
<212> TYPE: PRT
<213> ORGANISM: Homo sapiens

<400> SEQUENCE: 311

Gly Leu Thr Gly Gly Phe Gly Ser His Ser Val Cys Arg Gly Phe Arg
1 5 10 15

<210> SEQ ID NO 312
<211> LENGTH: 17
<212> TYPE: PRT
<213> ORGANISM: Homo sapiens

<400> SEQUENCE: 312

Gly Leu Thr Gly Gly Phe Gly Ser His Ser Val Cys Arg Gly Phe Arg
1 5 10 15

Ala

<210> SEQ ID NO 313
<211> LENGTH: 35
<212> TYPE: PRT
<213> ORGANISM: Homo sapiens

<400> SEQUENCE: 313

Gly Pro Gly Phe Pro Val Cys Pro Pro Gly Gly Ile Gln Glu Val Thr
1 5 10 15

Val Asn Gln Asn Leu Leu Thr Pro Leu Asn Leu Gln Ile Asp Pro Ala
20 25 30

Ile Gln Arg
35

<210> SEQ ID NO 314
<211> LENGTH: 14
<212> TYPE: PRT
<213> ORGANISM: Homo sapiens

<400> SEQUENCE: 314

Gly Gln Glu Gly Ser Ser Gly Ala Val Ser Thr Cys Ile Arg
1               5                   10

<210> SEQ ID NO 315
<211> LENGTH: 17
<212> TYPE: PRT
<213> ORGANISM: Homo sapiens

<400> SEQUENCE: 315

Gly Gln Leu Asn Thr Thr Cys Gly Gly Gly Ser Cys Gly Gln Gly Arg
1               5                   10                  15

Tyr

<210> SEQ ID NO 316
<211> LENGTH: 17
<212> TYPE: PRT
<213> ORGANISM: Homo sapiens

<400> SEQUENCE: 316

Gly Gln Ser Glu Ala Asp Ser Asp Lys Asn Ala Thr Ile Leu Glu Leu
1               5                   10                  15

Arg

<210> SEQ ID NO 317
<211> LENGTH: 21
<212> TYPE: PRT
<213> ORGANISM: Homo sapiens

<400> SEQUENCE: 317

Gly Gln Val Leu Cys Gln Glu Thr Cys Cys Arg Pro Ser Cys Cys Gln
1               5                   10                  15

Thr Thr Cys Cys Arg
            20

<210> SEQ ID NO 318
<211> LENGTH: 30
<212> TYPE: PRT
<213> ORGANISM: Homo sapiens

<400> SEQUENCE: 318

Gly Arg Val Ser Cys His Thr Thr Cys Tyr Arg Pro Thr Cys Val Ile
1               5                   10                  15

Ser Ser Cys Pro Arg Pro Val Cys Cys Ala Ser Ser Cys Cys
            20                  25                  30

<210> SEQ ID NO 319
<211> LENGTH: 51
<212> TYPE: PRT
<213> ORGANISM: Homo sapiens

<400> SEQUENCE: 319

Gly Ser Cys Gly Arg Ser Phe Gly Tyr His Ser Gly Gly Val Cys Gly
1               5                   10                  15

Pro Ser Pro Pro Cys Ile Thr Thr Val Ser Val Asn Glu Ser Leu Leu
            20                  25                  30

Thr Pro Leu Asn Leu Glu Ile Asp Pro Asn Ala Gln Cys Val Lys Gln

```
        35                  40                  45

Glu Glu Lys
    50


<210> SEQ ID NO 320
<211> LENGTH: 7
<212> TYPE: PRT
<213> ORGANISM: Homo sapiens

<400> SEQUENCE: 320

Gly Ser His Ser Val Cys Arg
1               5


<210> SEQ ID NO 321
<211> LENGTH: 30
<212> TYPE: PRT
<213> ORGANISM: Homo sapiens

<400> SEQUENCE: 321

Gly Ser Val Cys Ser Asp Gln Gly Cys Gly Gln Asp Leu Cys Gln Glu
1               5                   10                  15

Thr Cys Cys Arg Pro Ser Cys Cys Gln Thr Thr Cys Cys Arg
            20                  25                  30


<210> SEQ ID NO 322
<211> LENGTH: 30
<212> TYPE: PRT
<213> ORGANISM: Homo sapiens

<400> SEQUENCE: 322

Gly Ser Val Cys Ser Asp Gln Gly Cys Gly Gln Val Leu Cys Gln Glu
1               5                   10                  15

Thr Cys Cys Arg Pro Ser Cys Cys Gln Thr Thr Cys Cys Arg
            20                  25                  30


<210> SEQ ID NO 323
<211> LENGTH: 10
<212> TYPE: PRT
<213> ORGANISM: Homo sapiens

<400> SEQUENCE: 323

Gly Val Ala Leu Ser Asn Val Val His Lys
1               5                   10


<210> SEQ ID NO 324
<211> LENGTH: 29
<212> TYPE: PRT
<213> ORGANISM: Homo sapiens

<400> SEQUENCE: 324

Gly Val Ala Leu Ser Asn Val Val His Lys Val Cys Leu Glu Ile Thr
1               5                   10                  15

Glu Asp Gly Gly Asp Ser Ile Glu Val Pro Gly Ala Arg
            20                  25


<210> SEQ ID NO 325
<211> LENGTH: 8
<212> TYPE: PRT
<213> ORGANISM: Homo sapiens

<400> SEQUENCE: 325

Gly Val Asp Cys Ala Tyr Leu Arg
1               5
```

<210> SEQ ID NO 326
<211> LENGTH: 21
<212> TYPE: PRT
<213> ORGANISM: Homo sapiens

<400> SEQUENCE: 326

Gly Val Gly Gly Ala Val Pro Gly Ala Val Leu Glu Pro Val Ala Pro
1 5 10 15

Ala Pro Ser Val Arg
20

<210> SEQ ID NO 327
<211> LENGTH: 18
<212> TYPE: PRT
<213> ORGANISM: Homo sapiens

<400> SEQUENCE: 327

Gly Val Ser Cys His Thr Thr Cys Tyr Arg Pro Thr Cys Val Ile Ser
1 5 10 15

Ser Cys

<210> SEQ ID NO 328
<211> LENGTH: 20
<212> TYPE: PRT
<213> ORGANISM: Homo sapiens

<400> SEQUENCE: 328

Gly Val Ser Cys His Thr Thr Cys Tyr Arg Pro Thr Cys Val Ile Ser
1 5 10 15

Ser Cys Pro Arg
20

<210> SEQ ID NO 329
<211> LENGTH: 22
<212> TYPE: PRT
<213> ORGANISM: Homo sapiens

<400> SEQUENCE: 329

Gly Val Ser Cys His Thr Thr Cys Tyr Arg Pro Thr Cys Val Ile Ser
1 5 10 15

Ser Cys Pro Arg Pro Leu
20

<210> SEQ ID NO 330
<211> LENGTH: 24
<212> TYPE: PRT
<213> ORGANISM: Homo sapiens

<400> SEQUENCE: 330

Gly Val Ser Cys His Thr Thr Cys Tyr Arg Pro Thr Cys Val Ile Ser
1 5 10 15

Ser Cys Pro Arg Pro Leu Cys Cys
20

<210> SEQ ID NO 331
<211> LENGTH: 25
<212> TYPE: PRT
<213> ORGANISM: Homo sapiens

<400> SEQUENCE: 331

Gly Val Ser Cys His Thr Thr Cys Tyr Arg Pro Thr Cys Val Ile Ser

```
1               5                   10                  15

Ser Cys Pro Arg Pro Leu Cys Cys Ala
            20                  25


<210> SEQ ID NO 332
<211> LENGTH: 27
<212> TYPE: PRT
<213> ORGANISM: Homo sapiens

<400> SEQUENCE: 332

Gly Val Ser Cys His Thr Thr Cys Tyr Arg Pro Thr Cys Val Ile Ser
1               5                   10                  15

Ser Cys Pro Arg Pro Leu Cys Cys Ala Ser Ser
            20                  25


<210> SEQ ID NO 333
<211> LENGTH: 29
<212> TYPE: PRT
<213> ORGANISM: Homo sapiens

<400> SEQUENCE: 333

Gly Val Ser Cys His Thr Thr Cys Tyr Arg Pro Thr Cys Val Ile Ser
1               5                   10                  15

Ser Cys Pro Arg Pro Leu Cys Cys Ala Ser Ser Cys Cys
            20                  25


<210> SEQ ID NO 334
<211> LENGTH: 13
<212> TYPE: PRT
<213> ORGANISM: Homo sapiens

<400> SEQUENCE: 334

Gly Val Ser Met Pro Val Leu Ser Thr Gly Val Leu Arg
1               5                   10


<210> SEQ ID NO 335
<211> LENGTH: 12
<212> TYPE: PRT
<213> ORGANISM: Homo sapiens

<400> SEQUENCE: 335

His Phe Cys Thr Asp Pro Asp Ser Val Asp Lys Lys
1               5                   10


<210> SEQ ID NO 336
<211> LENGTH: 18
<212> TYPE: PRT
<213> ORGANISM: Homo sapiens

<400> SEQUENCE: 336

His Phe Cys Thr Asp Pro Asp Ser Val Asp Lys Lys Asp Ala Val Phe
1               5                   10                  15

Gln Arg


<210> SEQ ID NO 337
<211> LENGTH: 10
<212> TYPE: PRT
<213> ORGANISM: Homo sapiens

<400> SEQUENCE: 337

His Phe Ser Glu Leu Pro His Glu Leu Arg
1               5                   10
```

<210> SEQ ID NO 338
<211> LENGTH: 7
<212> TYPE: PRT
<213> ORGANISM: Homo sapiens

<400> SEQUENCE: 338

His Gly Glu Thr Leu Cys Arg
1               5

<210> SEQ ID NO 339
<211> LENGTH: 7
<212> TYPE: PRT
<213> ORGANISM: Homo sapiens

<400> SEQUENCE: 339

His Gly Glu Thr Leu Cys Arg
1               5

<210> SEQ ID NO 340
<211> LENGTH: 36
<212> TYPE: PRT
<213> ORGANISM: Homo sapiens

<400> SEQUENCE: 340

His Ile Ser Asp Thr Ser Val Val Val Lys Leu Asp Asn Ser Arg Asp
1               5                   10                  15

Leu Asn Met Asp Cys Met Val Ala Glu Ile Lys Ala Gln Tyr Asp Asp
            20                  25                  30

Ile Ala Thr Arg
        35

<210> SEQ ID NO 341
<211> LENGTH: 10
<212> TYPE: PRT
<213> ORGANISM: Homo sapiens

<400> SEQUENCE: 341

His Asn Ala Glu Leu Glu Asn Leu Ile Arg
1               5                   10

<210> SEQ ID NO 342
<211> LENGTH: 12
<212> TYPE: PRT
<213> ORGANISM: Homo sapiens

<400> SEQUENCE: 342

His Asn Ala Glu Leu Glu Asn Leu Ile Arg Glu Arg
1               5                   10

<210> SEQ ID NO 343
<211> LENGTH: 20
<212> TYPE: PRT
<213> ORGANISM: Homo sapiens

<400> SEQUENCE: 343

His Gln Asn Gln Asn Thr Ile Gln Glu Leu Leu Gln Asn Cys Ser Asp
1               5                   10                  15

Tyr Leu Met Arg
            20

<210> SEQ ID NO 344
<211> LENGTH: 6
<212> TYPE: PRT

<213> ORGANISM: Homo sapiens

<400> SEQUENCE: 344

His Ser Phe Gly Tyr Arg
1               5

<210> SEQ ID NO 345
<211> LENGTH: 38
<212> TYPE: PRT
<213> ORGANISM: Homo sapiens

<400> SEQUENCE: 345

His Ser Gly Gly Val Cys Gly Pro Ser Pro Pro Cys Ile Thr Thr Val
1               5                   10                  15

Ser Val Asn Glu Ser Leu Leu Thr Pro Leu Asn Leu Glu Ile Asp Pro
            20                  25                  30

Asn Ala Gln Cys Val Lys
        35

<210> SEQ ID NO 346
<211> LENGTH: 46
<212> TYPE: PRT
<213> ORGANISM: Homo sapiens

<400> SEQUENCE: 346

His Ser Gly Gly Val Cys Gly Pro Ser Pro Pro Cys Ile Thr Thr Val
1               5                   10                  15

Ser Val Asn Glu Ser Leu Leu Thr Pro Leu Asn Leu Glu Ile Asp Pro
            20                  25                  30

Asn Ala Gln Cys Val Lys Gln Glu Glu Lys Glu Gln Ile Lys
        35                  40                  45

<210> SEQ ID NO 347
<211> LENGTH: 17
<212> TYPE: PRT
<213> ORGANISM: Homo sapiens

<400> SEQUENCE: 347

His Thr Val Asn Thr Leu Glu Ile Glu Leu Gln Ala Gln His Ser Leu
1               5                   10                  15

Arg

<210> SEQ ID NO 348
<211> LENGTH: 30
<212> TYPE: PRT
<213> ORGANISM: Homo sapiens

<400> SEQUENCE: 348

His Thr Val Asn Thr Leu Glu Ile Glu Leu Gln Ala Gln His Ser Leu
1               5                   10                  15

Arg Asp Ser Leu Glu Asn Thr Leu Thr Glu Ser Glu Ala Arg
            20                  25                  30

<210> SEQ ID NO 349
<211> LENGTH: 27
<212> TYPE: PRT
<213> ORGANISM: Homo sapiens

<400> SEQUENCE: 349

His Val Pro Glu Glu Val Leu Ala Val Leu Glu Gln Glu Pro Ile Val
1               5                   10                  15

Leu Pro Ala Trp Asp Pro Met Gly Ala Leu Ala
20 25

<210> SEQ ID NO 350
<211> LENGTH: 18
<212> TYPE: PRT
<213> ORGANISM: Homo sapiens

<400> SEQUENCE: 350

Ile Ala Val Gly Gly Phe Arg Ala Gly Ser Cys Gly His Ser Phe Gly
1 5 10 15

Tyr Arg

<210> SEQ ID NO 351
<211> LENGTH: 13
<212> TYPE: PRT
<213> ORGANISM: Homo sapiens

<400> SEQUENCE: 351

Ile Ala Val Gly Gly Ser Arg Ala Gly Ser Cys Gly Arg
1 5 10

<210> SEQ ID NO 352
<211> LENGTH: 7
<212> TYPE: PRT
<213> ORGANISM: Homo sapiens

<400> SEQUENCE: 352

Ile Cys Thr Leu Pro Asn Arg
1 5

<210> SEQ ID NO 353
<211> LENGTH: 9
<212> TYPE: PRT
<213> ORGANISM: Homo sapiens

<400> SEQUENCE: 353

Ile Asp Val Pro Thr Leu Glu Pro Lys
1 5

<210> SEQ ID NO 354
<211> LENGTH: 11
<212> TYPE: PRT
<213> ORGANISM: Homo sapiens

<400> SEQUENCE: 354

Ile Asp Val Pro Thr Leu Gly Pro Lys Glu Arg
1 5 10

<210> SEQ ID NO 355
<211> LENGTH: 11
<212> TYPE: PRT
<213> ORGANISM: Homo sapiens

<400> SEQUENCE: 355

Ile His Val Leu Val Glu Pro Asp His Phe Lys
1 5 10

<210> SEQ ID NO 356
<211> LENGTH: 10
<212> TYPE: PRT
<213> ORGANISM: Homo sapiens

<400> SEQUENCE: 356

Ile Leu Cys Met Lys Ala Glu Asn Ser Arg
1               5                   10

<210> SEQ ID NO 357
<211> LENGTH: 27
<212> TYPE: PRT
<213> ORGANISM: Homo sapiens

<400> SEQUENCE: 357

Ile Leu Asp Asp Leu Thr Leu Cys Lys Ala Asp Leu Glu Ala Gln Val
1               5                   10                  15

Glu Tyr Leu Lys Glu Glu Leu Met Cys Leu Lys
            20                  25

<210> SEQ ID NO 358
<211> LENGTH: 28
<212> TYPE: PRT
<213> ORGANISM: Homo sapiens

<400> SEQUENCE: 358

Ile Leu Asp Asp Leu Thr Leu Cys Lys Ala Asp Leu Glu Ala Gln Val
1               5                   10                  15

Glu Tyr Leu Lys Glu Glu Leu Met Cys Leu Lys Lys
            20                  25

<210> SEQ ID NO 359
<211> LENGTH: 9
<212> TYPE: PRT
<213> ORGANISM: Homo sapiens

<400> SEQUENCE: 359

Ile Leu Asn Glu Leu Thr Leu Cys Lys
1               5

<210> SEQ ID NO 360
<211> LENGTH: 27
<212> TYPE: PRT
<213> ORGANISM: Homo sapiens

<400> SEQUENCE: 360

Ile Leu Asn Glu Leu Thr Leu Cys Lys Ser Asp Leu Glu Ser Gln Val
1               5                   10                  15

Glu Ser Leu Arg Glu Glu Leu Ile Cys Leu Lys
            20                  25

<210> SEQ ID NO 361
<211> LENGTH: 28
<212> TYPE: PRT
<213> ORGANISM: Homo sapiens

<400> SEQUENCE: 361

Ile Leu Asn Glu Leu Thr Leu Cys Lys Ser Asp Leu Glu Ser Gln Val
1               5                   10                  15

Glu Ser Leu Arg Glu Glu Leu Ile Cys Leu Lys Lys
            20                  25

<210> SEQ ID NO 362
<211> LENGTH: 10
<212> TYPE: PRT
<213> ORGANISM: Homo sapiens

<400> SEQUENCE: 362

Ile Ser Ala Cys Gly Pro Gln Pro Gly Arg 1 5 10

<210> SEQ ID NO 363
<211> LENGTH: 35
<212> TYPE: PRT
<213> ORGANISM: Homo sapiens

<400> SEQUENCE: 363

Ile Ser Asp Thr Ser Val Val Val Lys Leu Asp Asn Ser Arg Asp Leu
1 5 10 15

Asn Met Asp Cys Met Val Ala Glu Ile Lys Ala Gln Tyr Asp Asp Ile
20 25 30

Ala Thr Arg
35

<210> SEQ ID NO 364
<211> LENGTH: 58
<212> TYPE: PRT
<213> ORGANISM: Homo sapiens

<400> SEQUENCE: 364

Ile Ser Asn Pro Cys Ser Thr Thr Tyr Ser Arg Pro Leu Thr Phe Val
1 5 10 15

Ser Ser Gly Ser Gln Pro Leu Gly Gly Ile Ser Ser Val Cys Gln Pro
20 25 30

Val Gly Gly Ile Ser Thr Val Cys Gln Pro Val Gly Gly Val Ser Thr
35 40 45

Val Cys Gln Pro Ala Cys Gly Val Ser Arg
50 55

<210> SEQ ID NO 365
<211> LENGTH: 15
<212> TYPE: PRT
<213> ORGANISM: Homo sapiens

<400> SEQUENCE: 365

Ile Thr Asn Leu Thr Gln Gln Leu Glu Gln Ala Pro Ile Val Lys
1 5 10 15

<210> SEQ ID NO 366
<211> LENGTH: 16
<212> TYPE: PRT
<213> ORGANISM: Homo sapiens

<400> SEQUENCE: 366

Ile Thr Asn Leu Thr Gln Gln Leu Glu Gln Ala Pro Ile Val Lys Lys
1 5 10 15

<210> SEQ ID NO 367
<211> LENGTH: 16
<212> TYPE: PRT
<213> ORGANISM: Homo sapiens

<400> SEQUENCE: 367

Lys Ala Leu Ala Val Ala Gly Tyr Asp Val Glu Lys Asn Asn Ser Arg
1 5 10 15

<210> SEQ ID NO 368
<211> LENGTH: 9
<212> TYPE: PRT
<213> ORGANISM: Homo sapiens

<400> SEQUENCE: 368

Lys Ala Thr Gly Ala Ala Ile Pro Lys
1 5

<210> SEQ ID NO 369
<211> LENGTH: 22
<212> TYPE: PRT
<213> ORGANISM: Homo sapiens

<400> SEQUENCE: 369

Lys Lys Tyr Glu Glu Glu Val Ala Leu Gln Ala Thr Ala Glu Asn Glu
1 5 10 15

Phe Val Ala Leu Lys Lys
20

<210> SEQ ID NO 370
<211> LENGTH: 27
<212> TYPE: PRT
<213> ORGANISM: Homo sapiens

<400> SEQUENCE: 370

Lys Leu Asp Asn Ser Arg Asp Leu Asn Met Asp Cys Met Val Ala Glu
1 5 10 15

Ile Lys Ala Gln Tyr Asp Asp Ile Ala Thr Arg
20 25

<210> SEQ ID NO 371
<211> LENGTH: 17
<212> TYPE: PRT
<213> ORGANISM: Homo sapiens

<400> SEQUENCE: 371

Lys Asn His Glu Glu Glu Val Asn Ser Leu His Cys Gln Leu Gly Asp
1 5 10 15

Arg

<210> SEQ ID NO 372
<211> LENGTH: 20
<212> TYPE: PRT
<213> ORGANISM: Homo sapiens

<400> SEQUENCE: 372

Lys Pro Cys Gly Gln Leu Asn Thr Thr Cys Gly Gly Gly Ser Cys Gly
1 5 10 15

Gln Gly Arg Tyr
20

<210> SEQ ID NO 373
<211> LENGTH: 19
<212> TYPE: PRT
<213> ORGANISM: Homo sapiens

<400> SEQUENCE: 373

Lys Ser Asp Leu Glu Ala Asn Val Asp Ala Leu Ile Gln Glu Ile Asp
1 5 10 15

Phe Leu Arg

<210> SEQ ID NO 374
<211> LENGTH: 20
<212> TYPE: PRT
<213> ORGANISM: Homo sapiens

<400> SEQUENCE: 374

Lys Ser Asp Leu Glu Ala Asn Val Asp Ala Leu Ile Gln Glu Ile Asp
1 5 10 15

Phe Leu Arg Arg
20

<210> SEQ ID NO 375
<211> LENGTH: 41
<212> TYPE: PRT
<213> ORGANISM: Homo sapiens

<400> SEQUENCE: 375

Lys Ser Asp Leu Glu Ala Asn Val Glu Ala Leu Ile Gln Glu Ile Asp
1 5 10 15

Phe Leu Arg Trp Leu Tyr Glu Glu Glu Ile Arg Val Leu Gln Ser His
20 25 30

Ile Ser Asp Thr Ser Val Val Val Lys
35 40

<210> SEQ ID NO 376
<211> LENGTH: 15
<212> TYPE: PRT
<213> ORGANISM: Homo sapiens

<400> SEQUENCE: 376

Lys Val Gln Phe Leu Glu Gln Gln Asn Lys Leu Leu Glu Thr Lys
1 5 10 15

<210> SEQ ID NO 377
<211> LENGTH: 21
<212> TYPE: PRT
<213> ORGANISM: Homo sapiens

<400> SEQUENCE: 377

Lys Tyr Glu Glu Glu Leu Ser Leu Arg Pro Cys Val Gln Asn Glu Phe
1 5 10 15

Val Ala Leu Lys Lys
20

<210> SEQ ID NO 378
<211> LENGTH: 21
<212> TYPE: PRT
<213> ORGANISM: Homo sapiens

<400> SEQUENCE: 378

Lys Tyr Glu Glu Glu Val Ala Leu Gln Ala Thr Ala Glu Asn Glu Phe
1 5 10 15

Val Ala Leu Lys Lys
20

<210> SEQ ID NO 379
<211> LENGTH: 21
<212> TYPE: PRT
<213> ORGANISM: Homo sapiens

<400> SEQUENCE: 379

Leu Ala Pro Gly Thr Val Val Glu Val Trp Lys Asp Ser Ala Tyr Pro
1 5 10 15

Glu Glu Leu Ser Arg
20

<210> SEQ ID NO 380

<211> LENGTH: 15
<212> TYPE: PRT
<213> ORGANISM: Homo sapiens

<400> SEQUENCE: 380

Leu Ala Ser Cys Gly Ser Leu Leu Tyr Arg Pro Thr Cys Ser Arg
1 5 10 15

<210> SEQ ID NO 381
<211> LENGTH: 17
<212> TYPE: PRT
<213> ORGANISM: Homo sapiens

<400> SEQUENCE: 381

Leu Ala Ser Asp Asp Phe Arg Ser Lys Tyr Gln Met Glu Gln Ser Leu
1 5 10 15

Arg

<210> SEQ ID NO 382
<211> LENGTH: 7
<212> TYPE: PRT
<213> ORGANISM: Homo sapiens

<400> SEQUENCE: 382

Leu Ala Ser Asp Asn Phe Arg
1 5

<210> SEQ ID NO 383
<211> LENGTH: 17
<212> TYPE: PRT
<213> ORGANISM: Homo sapiens

<400> SEQUENCE: 383

Leu Ala Ser Asp Asn Phe Arg Ser Lys Tyr Gln Thr Glu Gln Ser Leu
1 5 10 15

Arg

<210> SEQ ID NO 384
<211> LENGTH: 9
<212> TYPE: PRT
<213> ORGANISM: Homo sapiens

<400> SEQUENCE: 384

Leu Ala Ser Tyr Leu Glu Lys Val His
1 5

<210> SEQ ID NO 385
<211> LENGTH: 7
<212> TYPE: PRT
<213> ORGANISM: Homo sapiens

<400> SEQUENCE: 385

Leu Ala Val Asp Asp Phe Arg
1 5

<210> SEQ ID NO 386
<211> LENGTH: 11
<212> TYPE: PRT
<213> ORGANISM: Homo sapiens

<400> SEQUENCE: 386

Leu Ala Tyr Gln Glu Ala Met Asp Ile Ser Lys
1 5 10

<210> SEQ ID NO 387
<211> LENGTH: 12
<212> TYPE: PRT
<213> ORGANISM: Homo sapiens

<400> SEQUENCE: 387

Leu Ala Tyr Gln Glu Ala Met Asp Ile Ser Lys Lys
1 5 10

<210> SEQ ID NO 388
<211> LENGTH: 22
<212> TYPE: PRT
<213> ORGANISM: Homo sapiens

<400> SEQUENCE: 388

Leu Cys Lys Pro Cys Gly Gln Leu Asn Thr Thr Cys Gly Gly Gly Ser
1 5 10 15

Cys Gly Gln Gly Arg Tyr
20

<210> SEQ ID NO 389
<211> LENGTH: 11
<212> TYPE: PRT
<213> ORGANISM: Homo sapiens

<400> SEQUENCE: 389

Leu Cys Leu Ser Pro Pro Ala Ser Asp Ser Arg
1 5 10

<210> SEQ ID NO 390
<211> LENGTH: 12
<212> TYPE: PRT
<213> ORGANISM: Homo sapiens

<400> SEQUENCE: 390

Leu Asp Leu Asp Ser Ile Ile Ala Glu Val Gly Ala
1 5 10

<210> SEQ ID NO 391
<211> LENGTH: 10
<212> TYPE: PRT
<213> ORGANISM: Homo sapiens

<400> SEQUENCE: 391

Leu Asp Asn Asn Trp Gly Lys Glu Glu Arg
1 5 10

<210> SEQ ID NO 392
<211> LENGTH: 26
<212> TYPE: PRT
<213> ORGANISM: Homo sapiens

<400> SEQUENCE: 392

Leu Asp Asn Ser Arg Asp Leu Asn Met Asp Cys Ile Ile Asp Glu Ile
1 5 10 15

Lys Ala Gln Tyr Asp Asp Ile Val Thr Arg
20 25

<210> SEQ ID NO 393
<211> LENGTH: 17
<212> TYPE: PRT
<213> ORGANISM: Homo sapiens

<400> SEQUENCE: 393

Leu Asp Asn Ser Arg Asp Leu Asn Met Asp Cys Met Val Ala Glu Ile
1 5 10 15

Lys

<210> SEQ ID NO 394
<211> LENGTH: 26
<212> TYPE: PRT
<213> ORGANISM: Homo sapiens

<400> SEQUENCE: 394

Leu Asp Asn Ser Arg Asp Leu Asn Met Asp Cys Met Val Ala Glu Ile
1 5 10 15

Lys Ala Gln Tyr Asp Asp Ile Ala Thr Arg
20 25

<210> SEQ ID NO 395
<211> LENGTH: 20
<212> TYPE: PRT
<213> ORGANISM: Homo sapiens

<400> SEQUENCE: 395

Leu Glu Ala Ala Val Ala Gln Ser Glu Gln Gln Ser Glu Ala Ala Leu
1 5 10 15

Ser Asp Ala Arg
20

<210> SEQ ID NO 396
<211> LENGTH: 22
<212> TYPE: PRT
<213> ORGANISM: Homo sapiens

<400> SEQUENCE: 396

Leu Glu Ala Ala Val Ala Gln Ser Glu Gln Gln Ser Glu Ala Ala Leu
1 5 10 15

Ser Asp Ala Arg Cys Lys
20

<210> SEQ ID NO 397
<211> LENGTH: 9
<212> TYPE: PRT
<213> ORGANISM: Homo sapiens

<400> SEQUENCE: 397

Leu Glu Gly Glu Ile Asn Met Tyr Arg
1 5

<210> SEQ ID NO 398
<211> LENGTH: 13
<212> TYPE: PRT
<213> ORGANISM: Homo sapiens

<400> SEQUENCE: 398

Leu Glu Arg Asp Asn Val Glu Leu Glu Asn Leu Ile Arg
1 5 10

<210> SEQ ID NO 399
<211> LENGTH: 9
<212> TYPE: PRT
<213> ORGANISM: Homo sapiens

<400> SEQUENCE: 399

Leu Glu Ser Glu Ile Thr Thr Tyr Arg 1 5

<210> SEQ ID NO 400
<211> LENGTH: 32
<212> TYPE: PRT
<213> ORGANISM: Homo sapiens

<400> SEQUENCE: 400

Leu Gly Cys Pro Tyr Ile Leu Asp Pro Glu Asp Tyr Gly Pro Asn Gly
1 5 10 15

Leu Asp Ile Glu Trp Met Gln Val Asn Ser Asp Pro Ala His His Arg
20 25 30

<210> SEQ ID NO 401
<211> LENGTH: 18
<212> TYPE: PRT
<213> ORGANISM: Homo sapiens

<400> SEQUENCE: 401

Leu Ile Thr Asn Val Glu Ser Gln Leu Ala Glu Ile His Ser Asp Leu
1 5 10 15

Glu Arg

<210> SEQ ID NO 402
<211> LENGTH: 9
<212> TYPE: PRT
<213> ORGANISM: Homo sapiens

<400> SEQUENCE: 402

Leu Leu Asp Asp Val Thr Leu Ala Lys
1 5

<210> SEQ ID NO 403
<211> LENGTH: 35
<212> TYPE: PRT
<213> ORGANISM: Homo sapiens

<400> SEQUENCE: 403

Leu Leu Asp Asp Val Thr Leu Ala Lys Ala Asp Leu Glu Ala Gln Gln
1 5 10 15

Glu Ser Leu Lys Glu Glu Gln Leu Ser Leu Lys Ser Asn His Glu Gln
20 25 30

Glu Val Lys
35

<210> SEQ ID NO 404
<211> LENGTH: 12
<212> TYPE: PRT
<213> ORGANISM: Homo sapiens

<400> SEQUENCE: 404

Leu Leu Glu Thr Lys Leu Pro Phe Tyr Gln Asn Arg
1 5 10

<210> SEQ ID NO 405
<211> LENGTH: 32
<212> TYPE: PRT
<213> ORGANISM: Homo sapiens

<400> SEQUENCE: 405

Leu Leu Glu Thr Lys Leu Pro Phe Tyr Gln Asn Arg Glu Cys Cys Gln
1 5 10 15

Ser Asn Leu Glu Pro Leu Phe Glu Gly Tyr Ile Glu Thr Leu Arg Arg
20 25 30

<210> SEQ ID NO 406
<211> LENGTH: 15
<212> TYPE: PRT
<213> ORGANISM: Homo sapiens

<400> SEQUENCE: 406

Leu Asn Ile Glu Val Asp Thr Ala Pro Pro Val Asp Leu Thr Arg
1 5 10 15

<210> SEQ ID NO 407
<211> LENGTH: 20
<212> TYPE: PRT
<213> ORGANISM: Homo sapiens

<400> SEQUENCE: 407

Leu Asn Met Asp Cys Ile Ile Asp Glu Ile Lys Ala Gln Tyr Asp Asp
1 5 10 15

Ile Val Thr Arg
20

<210> SEQ ID NO 408
<211> LENGTH: 15
<212> TYPE: PRT
<213> ORGANISM: Homo sapiens

<400> SEQUENCE: 408

Leu Asn Thr Thr Cys Gly Gly Gly Ser Cys Gly Gln Gly Arg Tyr
1 5 10 15

<210> SEQ ID NO 409
<211> LENGTH: 15
<212> TYPE: PRT
<213> ORGANISM: Homo sapiens

<400> SEQUENCE: 409

Leu Asn Val Glu Val Asp Ala Ala Pro Ala Val Asp Leu Asn Arg
1 5 10 15

<210> SEQ ID NO 410
<211> LENGTH: 33
<212> TYPE: PRT
<213> ORGANISM: Homo sapiens

<400> SEQUENCE: 410

Leu Asn Val Glu Val Asp Ala Ala Pro Thr Val Asp Leu Asn Arg Val
1 5 10 15

Leu Asn Glu Thr Arg Ser Gln Tyr Glu Val Leu Val Glu Thr Asn Arg
20 25 30

Arg

<210> SEQ ID NO 411
<211> LENGTH: 21
<212> TYPE: PRT
<213> ORGANISM: Homo sapiens

<400> SEQUENCE: 411

Leu Asn Val Glu Val Asp Gly Ala Pro Pro Val Asp Leu Asn Lys Ile
1 5 10 15

Leu Glu Asp Met Arg
20

<210> SEQ ID NO 412
<211> LENGTH: 7
<212> TYPE: PRT
<213> ORGANISM: Homo sapiens

<400> SEQUENCE: 412

Leu Pro Phe Tyr Gln Asn Arg
1               5

<210> SEQ ID NO 413
<211> LENGTH: 27
<212> TYPE: PRT
<213> ORGANISM: Homo sapiens

<400> SEQUENCE: 413

Leu Pro Phe Tyr Gln Asn Arg Glu Cys Cys Gln Ser Asn Leu Glu Pro
1               5                   10                  15

Leu Phe Glu Gly Tyr Ile Glu Thr Leu Arg Arg
            20                  25

<210> SEQ ID NO 414
<211> LENGTH: 55
<212> TYPE: PRT
<213> ORGANISM: Homo sapiens

<400> SEQUENCE: 414

Leu Pro Thr Thr Phe Arg Pro Ala Ser Cys Leu Ser Lys Thr Tyr Leu
1               5                   10                  15

Ser Ser Ser Cys Arg Ala Ala Ser Gly Ile Ser Gly Ser Met Gly Pro
            20                  25                  30

Gly Ser Trp Tyr Ser Glu Gly Ala Phe Asn Gly Asn Glu Lys Glu Thr
        35                  40                  45

Met Gln Phe Leu Asn Asp Arg
    50                  55

<210> SEQ ID NO 415
<211> LENGTH: 26
<212> TYPE: PRT
<213> ORGANISM: Homo sapiens

<400> SEQUENCE: 415

Leu Gln Phe Tyr Gln Asn Cys Glu Cys Cys Gln Ser Asn Leu Glu Pro
1               5                   10                  15

Leu Phe Ala Gly Tyr Ile Glu Thr Leu Arg
            20                  25

<210> SEQ ID NO 416
<211> LENGTH: 27
<212> TYPE: PRT
<213> ORGANISM: Homo sapiens

<400> SEQUENCE: 416

Leu Gln Phe Tyr Gln Asn Cys Glu Cys Cys Gln Ser Asn Leu Glu Pro
1               5                   10                  15

Leu Phe Ala Gly Tyr Ile Glu Thr Leu Arg Arg
            20                  25

<210> SEQ ID NO 417
<211> LENGTH: 13
<212> TYPE: PRT
<213> ORGANISM: Homo sapiens

<400> SEQUENCE: 417

Leu Gln Leu Glu Arg Glu Asn Leu Gln Leu Glu Thr Arg
1               5                   10

<210> SEQ ID NO 418
<211> LENGTH: 10
<212> TYPE: PRT
<213> ORGANISM: Homo sapiens

<400> SEQUENCE: 418

Leu Gln Arg Val Gln Cys Asp Leu Gln Lys
1               5                   10

<210> SEQ ID NO 419
<211> LENGTH: 29
<212> TYPE: PRT
<213> ORGANISM: Homo sapiens

<400> SEQUENCE: 419

Leu Gln Ser Tyr Gln Val Glu Ile Ile Glu Leu Arg Arg Thr Val Asn
1               5                   10                  15

Ala Leu Glu Ile Glu Leu Gln Ala Gln His Asn Leu Arg
            20                  25

<210> SEQ ID NO 420
<211> LENGTH: 13
<212> TYPE: PRT
<213> ORGANISM: Homo sapiens

<400> SEQUENCE: 420

Leu Arg Pro Val Cys Gly Gly Val Ser Cys His Thr Thr
1               5                   10

<210> SEQ ID NO 421
<211> LENGTH: 9
<212> TYPE: PRT
<213> ORGANISM: Homo sapiens

<400> SEQUENCE: 421

Leu Ser Pro Pro Ala Ser Asp Ser Arg
1               5

<210> SEQ ID NO 422
<211> LENGTH: 38
<212> TYPE: PRT
<213> ORGANISM: Homo sapiens

<400> SEQUENCE: 422

Leu Ser Ser Arg Ser Ser Leu Ser His Thr Gln Asp Val Asp Cys Ala
1               5                   10                  15

Tyr Leu Arg Lys Ser Asp Leu Glu Ala Asn Val Glu Ala Leu Val Glu
            20                  25                  30

Glu Ser Ser Phe Leu Arg
        35

<210> SEQ ID NO 423
<211> LENGTH: 34
<212> TYPE: PRT
<213> ORGANISM: Homo sapiens

<400> SEQUENCE: 423

Leu Thr Ala Glu Val Glu Asn Ala Lys Cys Gln Asn Ser Lys Leu Glu

```
1               5                   10                  15

Ala Ala Val Ala Gln Ser Glu Gln Gln Ser Glu Ala Ala Leu Ser Asp
            20                  25                  30

Ala Arg


<210> SEQ ID NO 424
<211> LENGTH: 12
<212> TYPE: PRT
<213> ORGANISM: Homo sapiens

<400> SEQUENCE: 424

Leu Thr Gly Gly Phe Gly Ser His Ser Val Cys Arg
1               5                   10


<210> SEQ ID NO 425
<211> LENGTH: 15
<212> TYPE: PRT
<213> ORGANISM: Homo sapiens

<400> SEQUENCE: 425

Leu Thr Gly Gly Phe Gly Ser His Ser Val Cys Arg Gly Phe Arg
1               5                   10                  15


<210> SEQ ID NO 426
<211> LENGTH: 26
<212> TYPE: PRT
<213> ORGANISM: Homo sapiens

<400> SEQUENCE: 426

Leu Thr Gly Gln Leu Phe Leu Gly Gly Ser Ile Val Lys Gly Gly Pro
1               5                   10                  15

Val Gln Val Leu Glu Asp Lys Glu Leu Lys
            20                  25


<210> SEQ ID NO 427
<211> LENGTH: 9
<212> TYPE: PRT
<213> ORGANISM: Homo sapiens

<400> SEQUENCE: 427

Leu Thr Val Asn Ser Ala Ile Ala Arg
1               5


<210> SEQ ID NO 428
<211> LENGTH: 15
<212> TYPE: PRT
<213> ORGANISM: Homo sapiens

<400> SEQUENCE: 428

Leu Val Pro Phe Asn His Ala Glu Ser Thr Tyr Gly Leu Tyr Arg
1               5                   10                  15


<210> SEQ ID NO 429
<211> LENGTH: 26
<212> TYPE: PRT
<213> ORGANISM: Homo sapiens

<400> SEQUENCE: 429

Leu Val Val Asn Ile Asp Asn Ala Lys Leu Ala Ser Asp Asp Phe Arg
1               5                   10                  15

Ser Lys Tyr Gln Met Glu Gln Ser Leu Arg
            20                  25
```

<210> SEQ ID NO 430
<211> LENGTH: 16
<212> TYPE: PRT
<213> ORGANISM: Homo sapiens

<400> SEQUENCE: 430

Leu Val Val Asn Ile Asp Asn Ala Lys Leu Ala Ser Asp Asn Phe Arg
1               5                   10                  15

<210> SEQ ID NO 431
<211> LENGTH: 18
<212> TYPE: PRT
<213> ORGANISM: Homo sapiens

<400> SEQUENCE: 431

Leu Val Val Asn Ile Asp Asn Ala Lys Leu Ala Ser Asp Asn Phe Arg
1               5                   10                  15

Ser Lys

<210> SEQ ID NO 432
<211> LENGTH: 26
<212> TYPE: PRT
<213> ORGANISM: Homo sapiens

<400> SEQUENCE: 432

Leu Val Val Asn Ile Asp Asn Ala Lys Leu Ala Ser Asp Asn Phe Arg
1               5                   10                  15

Ser Lys Tyr Gln Thr Glu Gln Ser Leu Arg
            20                  25

<210> SEQ ID NO 433
<211> LENGTH: 9
<212> TYPE: PRT
<213> ORGANISM: Homo sapiens

<400> SEQUENCE: 433

Leu Val Val Arg Ile Asp Asn Ala Lys
1               5

<210> SEQ ID NO 434
<211> LENGTH: 16
<212> TYPE: PRT
<213> ORGANISM: Homo sapiens

<400> SEQUENCE: 434

Leu Val Val Arg Ile Asp Asn Ala Lys Leu Ala Ser Asp Asp Phe Arg
1               5                   10                  15

<210> SEQ ID NO 435
<211> LENGTH: 18
<212> TYPE: PRT
<213> ORGANISM: Homo sapiens

<400> SEQUENCE: 435

Leu Val Val Arg Ile Asp Asn Ala Lys Leu Ala Ser Asp Asp Phe Arg
1               5                   10                  15

Thr Lys

<210> SEQ ID NO 436
<211> LENGTH: 28
<212> TYPE: PRT
<213> ORGANISM: Homo sapiens

<400> SEQUENCE: 436

Leu Val Val Ser Thr Gly Leu Cys Lys Pro Cys Gly Gln Leu Asn Thr
1 5 10 15

Thr Cys Gly Gly Gly Ser Cys Gly Gln Gly Arg Tyr
20 25

<210> SEQ ID NO 437
<211> LENGTH: 22
<212> TYPE: PRT
<213> ORGANISM: Homo sapiens

<400> SEQUENCE: 437

Met Ala Lys Pro Leu Glu Gln Ala Val Ala Ala Ile Val Cys Thr Phe
1 5 10 15

Gln Glu Tyr Ala Gly Arg
20

<210> SEQ ID NO 438
<211> LENGTH: 9
<212> TYPE: PRT
<213> ORGANISM: Homo sapiens

<400> SEQUENCE: 438

Met Asp Cys Met Val Ala Glu Ile Lys
1 5

<210> SEQ ID NO 439
<211> LENGTH: 18
<212> TYPE: PRT
<213> ORGANISM: Homo sapiens

<400> SEQUENCE: 439

Met Asp Cys Met Val Ala Glu Ile Lys Ala Gln Tyr Asp Asp Ile Ala
1 5 10 15

Thr Arg

<210> SEQ ID NO 440
<211> LENGTH: 15
<212> TYPE: PRT
<213> ORGANISM: Homo sapiens

<400> SEQUENCE: 440

Met Arg Asp Ser Gln Glu Cys Ile Leu Met Glu Thr Glu Ala Arg
1 5 10 15

<210> SEQ ID NO 441
<211> LENGTH: 15
<212> TYPE: PRT
<213> ORGANISM: Homo sapiens

<400> SEQUENCE: 441

Met Val Ala Glu Ile Lys Ala Gln Tyr Asp Asp Ile Ala Thr Arg
1 5 10 15

<210> SEQ ID NO 442
<211> LENGTH: 26
<212> TYPE: PRT
<213> ORGANISM: Homo sapiens

<400> SEQUENCE: 442

Met Val Asp Phe Ala Gly Met Lys Asp Lys Val Thr Leu Val Val Gly
1 5 10 15

Ala Ser Gln Asp Ile Ile Pro Gln Leu Lys
20 25

<210> SEQ ID NO 443
<211> LENGTH: 16
<212> TYPE: PRT
<213> ORGANISM: Homo sapiens

<400> SEQUENCE: 443

Met Val Asn Ala Leu Glu Ile Glu Leu Gln Ala Gln His Ser Met Arg
1 5 10 15

<210> SEQ ID NO 444
<211> LENGTH: 36
<212> TYPE: PRT
<213> ORGANISM: Homo sapiens

<400> SEQUENCE: 444

Met Val Ser Ser Cys Cys Gly Ser Val Cys Ser Asp Gln Gly Cys Gly
1 5 10 15

Gln Asp Leu Cys Gln Glu Thr Cys Cys His Pro Ser Cys Cys Glu Thr
20 25 30

Thr Cys Cys Arg
35

<210> SEQ ID NO 445
<211> LENGTH: 36
<212> TYPE: PRT
<213> ORGANISM: Homo sapiens

<400> SEQUENCE: 445

Met Val Ser Ser Cys Cys Gly Ser Val Cys Ser Asp Gln Gly Cys Gly
1 5 10 15

Gln Asp Leu Cys Gln Glu Thr Cys Cys Arg Pro Ser Cys Cys Gln Thr
20 25 30

Thr Cys Cys Arg
35

<210> SEQ ID NO 446
<211> LENGTH: 48
<212> TYPE: PRT
<213> ORGANISM: Homo sapiens

<400> SEQUENCE: 446

Met Val Ser Ser Cys Cys Gly Ser Val Cys Ser Asp Gln Gly Cys Ser
1 5 10 15

Gln Val Leu Cys Gln Glu Thr Cys Cys Arg Pro Ser Cys Cys Gln Thr
20 25 30

Thr Cys Cys Arg Thr Thr Cys Tyr Arg Pro Ser Cys Cys Val Ser Ser
35 40 45

<210> SEQ ID NO 447
<211> LENGTH: 32
<212> TYPE: PRT
<213> ORGANISM: Homo sapiens

<400> SEQUENCE: 447

Met Val Ser Ser Cys Cys Gly Ser Val Ser Ser Glu Gln Ser Cys Gly
1 5 10 15

Leu Glu Asn Cys Cys Cys Pro Ser Cys Cys Gln Thr Thr Cys Cys Arg
20 25 30

<210> SEQ ID NO 448
<211> LENGTH: 9
<212> TYPE: PRT
<213> ORGANISM: Homo sapiens

<400> SEQUENCE: 448

Met Val Val Asn Thr Asp Asn Ala Lys
1               5

<210> SEQ ID NO 449
<211> LENGTH: 16
<212> TYPE: PRT
<213> ORGANISM: Homo sapiens

<400> SEQUENCE: 449

Met Val Val Asn Thr Asp Asn Ala Lys Leu Ala Ala Asp Asp Phe Arg
1               5                   10                  15

<210> SEQ ID NO 450
<211> LENGTH: 14
<212> TYPE: PRT
<213> ORGANISM: Homo sapiens

<400> SEQUENCE: 450

Asn Cys Cys Cys Pro Ser Cys Cys Gln Thr Thr Cys Cys Arg
1               5                   10

<210> SEQ ID NO 451
<211> LENGTH: 21
<212> TYPE: PRT
<213> ORGANISM: Homo sapiens

<400> SEQUENCE: 451

Asn Glu Lys Glu Thr Met Gln Phe Leu Asn Asp Arg Leu Ala Asn Tyr
1               5                   10                  15

Leu Glu Lys Val Arg
            20

<210> SEQ ID NO 452
<211> LENGTH: 16
<212> TYPE: PRT
<213> ORGANISM: Homo sapiens

<400> SEQUENCE: 452

Asn His Glu Glu Glu Val Asn Leu Leu His Glu Gln Leu Gly Asp Arg
1               5                   10                  15

<210> SEQ ID NO 453
<211> LENGTH: 16
<212> TYPE: PRT
<213> ORGANISM: Homo sapiens

<400> SEQUENCE: 453

Asn His Glu Glu Glu Val Asn Ser Leu His Cys Gln Leu Gly Asp Arg
1               5                   10                  15

<210> SEQ ID NO 454
<211> LENGTH: 37
<212> TYPE: PRT
<213> ORGANISM: Homo sapiens

<400> SEQUENCE: 454

Asn His Glu Glu Glu Val Asn Ser Leu His Cys Gln Leu Gly Asp Arg
1               5                   10                  15

Leu Asn Val Glu Val Asp Ala Ala Pro Pro Val Asp Leu Asn Arg Val
20 25 30

Leu Glu Glu Met Arg
35

<210> SEQ ID NO 455
<211> LENGTH: 9
<212> TYPE: PRT
<213> ORGANISM: Homo sapiens

<400> SEQUENCE: 455

Asn Lys Tyr Glu Asp Glu Ile Asn Arg
1 5

<210> SEQ ID NO 456
<211> LENGTH: 13
<212> TYPE: PRT
<213> ORGANISM: Homo sapiens

<400> SEQUENCE: 456

Asn Leu Ser Ser Ala Asp Ala Gly His Gln Thr Met Arg
1 5 10

<210> SEQ ID NO 457
<211> LENGTH: 29
<212> TYPE: PRT
<213> ORGANISM: Homo sapiens

<400> SEQUENCE: 457

Asn Leu Val Val Ser Thr Gly Leu Cys Lys Pro Cys Gly Gln Leu Asn
1 5 10 15

Thr Thr Cys Gly Gly Gly Ser Cys Gly Gln Gly Arg Tyr
20 25

<210> SEQ ID NO 458
<211> LENGTH: 10
<212> TYPE: PRT
<213> ORGANISM: Homo sapiens

<400> SEQUENCE: 458

Asn Asn Pro Gly Cys Pro Ser Leu Met Arg
1 5 10

<210> SEQ ID NO 459
<211> LENGTH: 16
<212> TYPE: PRT
<213> ORGANISM: Homo sapiens

<400> SEQUENCE: 459

Asn Gln Val Ala Val Asn Pro Thr Asn Thr Ile Phe Asp Ala Lys Arg
1 5 10 15

<210> SEQ ID NO 460
<211> LENGTH: 9
<212> TYPE: PRT
<213> ORGANISM: Homo sapiens

<400> SEQUENCE: 460

Asn Val Glu Leu Glu Asn Leu Ile Arg
1 5

<210> SEQ ID NO 461
<211> LENGTH: 33

<212> TYPE: PRT
<213> ORGANISM: Homo sapiens

<400> SEQUENCE: 461

Asn Val Phe Val Ser Pro Ile Asp Val Gly Cys Gln Pro Val Ala Glu
1 5 10 15

Ala Ser Ala Ala Ser Met Cys Leu Leu Ala Asn Val Ala His Ala Asn
20 25 30

Arg

<210> SEQ ID NO 462
<211> LENGTH: 10
<212> TYPE: PRT
<213> ORGANISM: Homo sapiens

<400> SEQUENCE: 462

Asn Trp Asn Gly Ser Val Glu Ile Leu Lys
1 5 10

<210> SEQ ID NO 463
<211> LENGTH: 14
<212> TYPE: PRT
<213> ORGANISM: Homo sapiens

<400> SEQUENCE: 463

Asn Trp Asn Gly Ser Val Glu Ile Leu Lys Asn Trp Lys Lys
1 5 10

<210> SEQ ID NO 464
<211> LENGTH: 10
<212> TYPE: PRT
<213> ORGANISM: Homo sapiens

<400> SEQUENCE: 464

Pro Ala Cys Tyr Glu Thr Thr Cys Cys Arg
1 5 10

<210> SEQ ID NO 465
<211> LENGTH: 19
<212> TYPE: PRT
<213> ORGANISM: Homo sapiens

<400> SEQUENCE: 465

Pro Cys Gly Gln Leu Asn Thr Thr Cys Gly Gly Gly Ser Cys Gly Gln
1 5 10 15

Gly Arg Tyr

<210> SEQ ID NO 466
<211> LENGTH: 55
<212> TYPE: PRT
<213> ORGANISM: Homo sapiens

<400> SEQUENCE: 466

Pro Cys Ser Thr Thr Tyr Ser Arg Pro Leu Thr Phe Val Ser Ser Gly
1 5 10 15

Ser Gln Pro Leu Gly Gly Ile Ser Ser Val Cys Gln Pro Val Gly Gly
20 25 30

Ile Ser Thr Val Cys Gln Pro Val Gly Gly Val Ser Thr Val Cys Gln
35 40 45

Pro Ala Cys Gly Val Ser Arg
50 55

<210> SEQ ID NO 467
<211> LENGTH: 45
<212> TYPE: PRT
<213> ORGANISM: Homo sapiens

<400> SEQUENCE: 467

Pro Ile Cys Gly Ser Ser Cys Cys Gln Pro Cys Cys His Pro Thr Cys
1 5 10 15

Tyr Gln Thr Thr Cys Phe Arg Thr Thr Cys Cys Gln Pro Thr Cys Cys
20 25 30

Gln Pro Thr Cys Cys Arg Asn Thr Ser Cys Gln Pro Thr
35 40 45

<210> SEQ ID NO 468
<211> LENGTH: 11
<212> TYPE: PRT
<213> ORGANISM: Homo sapiens

<400> SEQUENCE: 468

Pro Leu Cys Cys Gln Thr Thr Cys Arg Pro Arg
1 5 10

<210> SEQ ID NO 469
<211> LENGTH: 47
<212> TYPE: PRT
<213> ORGANISM: Homo sapiens

<400> SEQUENCE: 469

Pro Leu Thr Phe Val Ser Ser Gly Ser Gln Pro Leu Gly Gly Ile Ser
1 5 10 15

Ser Val Cys Gln Pro Val Gly Gly Ile Ser Thr Val Cys Gln Pro Val
20 25 30

Gly Gly Val Ser Thr Val Cys Gln Pro Ala Cys Gly Val Ser Arg
35 40 45

<210> SEQ ID NO 470
<211> LENGTH: 17
<212> TYPE: PRT
<213> ORGANISM: Homo sapiens

<400> SEQUENCE: 470

Pro Gln Cys Cys Gln Pro Val Cys Cys Gln Pro Thr Cys Cys Arg Pro
1 5 10 15

Arg

<210> SEQ ID NO 471
<211> LENGTH: 50
<212> TYPE: PRT
<213> ORGANISM: Homo sapiens

<400> SEQUENCE: 471

Pro Gln Cys Cys Gln Ser Val Cys Tyr Gln Pro Thr Cys Cys His Pro
1 5 10 15

Ser Cys Cys Ile Ser Ser Cys Cys His Pro Tyr Cys Cys Glu Ser Ser
20 25 30

Cys Cys Arg Pro Cys Cys Cys Arg Pro Ser Cys Cys Gln Thr Thr Cys
35 40 45

Cys Arg
50

<210> SEQ ID NO 472
<211> LENGTH: 10
<212> TYPE: PRT
<213> ORGANISM: Homo sapiens

<400> SEQUENCE: 472

Pro Gln Cys Cys Gln Thr Ile Cys Cys Arg
1               5                   10

<210> SEQ ID NO 473
<211> LENGTH: 16
<212> TYPE: PRT
<213> ORGANISM: Homo sapiens

<400> SEQUENCE: 473

Pro Gln Ile Ala His Leu Leu Gln Ser Gly Asn Ser Asp Val Val Arg
1               5                   10                  15

<210> SEQ ID NO 474
<211> LENGTH: 10
<212> TYPE: PRT
<213> ORGANISM: Homo sapiens

<400> SEQUENCE: 474

Pro Ser Cys Cys Gln Thr Ser Ser Cys Arg
1               5                   10

<210> SEQ ID NO 475
<211> LENGTH: 15
<212> TYPE: PRT
<213> ORGANISM: Homo sapiens

<400> SEQUENCE: 475

Pro Ser Cys Cys Ser Pro Ser Cys Cys Gln Thr Thr Cys Cys Arg
1               5                   10                  15

<210> SEQ ID NO 476
<211> LENGTH: 40
<212> TYPE: PRT
<213> ORGANISM: Homo sapiens

<400> SEQUENCE: 476

Pro Ser Cys Cys Val Ser Ser Cys Cys Arg Pro Gln Cys Cys Gln Ser
1               5                   10                  15

Val Cys Cys Gln Pro Thr Cys Cys Arg Pro Ser Cys Cys Glu Thr Thr
            20                  25                  30

Cys Cys His Pro Arg Cys Cys Ile
        35                  40

<210> SEQ ID NO 477
<211> LENGTH: 39
<212> TYPE: PRT
<213> ORGANISM: Homo sapiens

<400> SEQUENCE: 477

Pro Ser Cys Cys Val Ser Ser Cys Cys Arg Pro Gln Cys Cys Gln Ser
1               5                   10                  15

Val Cys Cys Gln Pro Thr Cys Cys Arg Ser Ser Cys Cys Pro Ser Cys
            20                  25                  30

Cys Gln Thr Thr Cys Cys Arg
        35

<210> SEQ ID NO 478

<211> LENGTH: 57
<212> TYPE: PRT
<213> ORGANISM: Homo sapiens

<400> SEQUENCE: 478

Pro Ser Ser Cys Gln Pro Thr Cys Cys Thr Ser Ser Pro Cys Gln Gln
1               5                   10                  15

Ala Cys Cys Val Pro Val Cys Ser Lys Ser Val Cys Tyr Met Pro Val
            20                  25                  30

Cys Ser Gly Ala Ser Thr Ser Cys Cys Gln Gln Ser Ser Cys Gln Pro
        35                  40                  45

Ala Cys Cys Thr Ala Ser Cys Cys Arg
    50                  55

<210> SEQ ID NO 479
<211> LENGTH: 57
<212> TYPE: PRT
<213> ORGANISM: Homo sapiens

<400> SEQUENCE: 479

Pro Ser Ser Cys Gln Pro Thr Cys Cys Thr Ser Ser Pro Cys Gln Gln
1               5                   10                  15

Ala Cys Cys Val Pro Val Cys Ser Lys Ser Val Cys Tyr Met Pro Val
            20                  25                  30

Cys Ser Gly Ala Ser Thr Ser Cys Cys Gln Gln Ser Ser Cys Gln Pro
        35                  40                  45

Ala Cys Cys Thr Ala Ser Cys Cys Arg
    50                  55

<210> SEQ ID NO 480
<211> LENGTH: 18
<212> TYPE: PRT
<213> ORGANISM: Homo sapiens

<400> SEQUENCE: 480

Pro Thr Gly Pro Ala Thr Thr Ile Cys Ser Ser Asp Lys Ser Cys Cys
1               5                   10                  15

Cys Gly

<210> SEQ ID NO 481
<211> LENGTH: 33
<212> TYPE: PRT
<213> ORGANISM: Homo sapiens

<400> SEQUENCE: 481

Pro Val Cys Gly Gly Val Ser Cys His Thr Thr Cys Tyr Arg Pro Thr
1               5                   10                  15

Cys Val Ile Ser Ser Cys Pro Arg Pro Leu Cys Cys Ala Ser Ser Cys
            20                  25                  30

Cys

<210> SEQ ID NO 482
<211> LENGTH: 21
<212> TYPE: PRT
<213> ORGANISM: Homo sapiens

<400> SEQUENCE: 482

Pro Val Val Pro Met Cys Trp Thr Glu Gly His Met Thr Tyr Gly Asn
1               5                   10                  15

Asp Val Val Leu Lys

20

<210> SEQ ID NO 483
<211> LENGTH: 32
<212> TYPE: PRT
<213> ORGANISM: Homo sapiens

<400> SEQUENCE: 483

Gln Cys Met Ile Thr Asn Val Glu Ala Gln Leu Ala Glu Ile Gln Ala
1               5                   10                  15

Asp Leu Glu Arg Gln Asn Gln Glu Tyr Gln Val Leu Leu Asp Val Arg
            20                  25                  30

<210> SEQ ID NO 484
<211> LENGTH: 13
<212> TYPE: PRT
<213> ORGANISM: Homo sapiens

<400> SEQUENCE: 484

Gln Phe Leu Glu Gln Gln Asn Lys Leu Leu Glu Thr Lys
1               5                   10

<210> SEQ ID NO 485
<211> LENGTH: 10
<212> TYPE: PRT
<213> ORGANISM: Homo sapiens

<400> SEQUENCE: 485

Gln Leu Glu Arg Asp Asn Ala Glu Leu Lys
1               5                   10

<210> SEQ ID NO 486
<211> LENGTH: 14
<212> TYPE: PRT
<213> ORGANISM: Homo sapiens

<400> SEQUENCE: 486

Gln Leu Glu Arg Asp Asn Ala Glu Leu Lys Asn Leu Ile Arg
1               5                   10

<210> SEQ ID NO 487
<211> LENGTH: 16
<212> TYPE: PRT
<213> ORGANISM: Homo sapiens

<400> SEQUENCE: 487

Gln Leu Glu Arg Asp Asn Ala Glu Leu Lys Asn Leu Ile Arg Glu Arg
1               5                   10                  15

<210> SEQ ID NO 488
<211> LENGTH: 14
<212> TYPE: PRT
<213> ORGANISM: Homo sapiens

<400> SEQUENCE: 488

Gln Leu Glu Arg Asp Asn Val Glu Leu Glu Asn Leu Ile Arg
1               5                   10

<210> SEQ ID NO 489
<211> LENGTH: 16
<212> TYPE: PRT
<213> ORGANISM: Homo sapiens

<400> SEQUENCE: 489

Gln Leu Glu Arg Asp Asn Val Glu Leu Glu Asn Leu Ile Arg Glu Arg
1 5 10 15

<210> SEQ ID NO 490
<211> LENGTH: 12
<212> TYPE: PRT
<213> ORGANISM: Homo sapiens

<400> SEQUENCE: 490

Gln Leu Glu Arg Glu Asn Val Glu Leu Glu Ser Arg
1 5 10

<210> SEQ ID NO 491
<211> LENGTH: 14
<212> TYPE: PRT
<213> ORGANISM: Homo sapiens

<400> SEQUENCE: 491

Gln Leu Glu Arg His Asn Ala Glu Leu Glu Asn Leu Ile Arg
1 5 10

<210> SEQ ID NO 492
<211> LENGTH: 16
<212> TYPE: PRT
<213> ORGANISM: Homo sapiens

<400> SEQUENCE: 492

Gln Leu Glu Arg His Asn Ala Glu Leu Glu Asn Leu Ile Arg Glu Arg
1 5 10 15

<210> SEQ ID NO 493
<211> LENGTH: 18
<212> TYPE: PRT
<213> ORGANISM: Homo sapiens

<400> SEQUENCE: 493

Gln Leu Leu Ala Gly Leu Asp Lys Val Ala Ser Asp Leu Asp Gln Gln
1 5 10 15

Glu Lys

<210> SEQ ID NO 494
<211> LENGTH: 15
<212> TYPE: PRT
<213> ORGANISM: Homo sapiens

<400> SEQUENCE: 494

Gln Leu Leu Val Asp Phe Ser Cys Asn Lys Phe Pro Ala Ile Lys
1 5 10 15

<210> SEQ ID NO 495
<211> LENGTH: 31
<212> TYPE: PRT
<213> ORGANISM: Homo sapiens

<400> SEQUENCE: 495

Gln Leu Gln Thr Gln Val Gly Asp Thr Ser Val Val Leu Ser Met Asp
1 5 10 15

Asn Asn Cys Asn Leu Asp Leu Asp Ser Ile Ile Ala Glu Val Lys
20 25 30

<210> SEQ ID NO 496
<211> LENGTH: 24
<212> TYPE: PRT
<213> ORGANISM: Homo sapiens

<400> SEQUENCE: 496

Gln Leu Arg Glu Tyr Gln Glu Leu Met Asn Ala Lys Leu Gly Leu Asp
1 5 10 15

Ile Glu Ile Ala Thr Tyr Arg Arg
20

<210> SEQ ID NO 497
<211> LENGTH: 12
<212> TYPE: PRT
<213> ORGANISM: Homo sapiens

<400> SEQUENCE: 497

Gln Asn Gln Glu Tyr Glu Ile Leu Met Asp Val Lys
1 5 10

<210> SEQ ID NO 498
<211> LENGTH: 14
<212> TYPE: PRT
<213> ORGANISM: Homo sapiens

<400> SEQUENCE: 498

Gln Asn Gln Glu Tyr Gln Val Leu Leu Asp Val Cys Ala Arg
1 5 10

<210> SEQ ID NO 499
<211> LENGTH: 23
<212> TYPE: PRT
<213> ORGANISM: Homo sapiens

<400> SEQUENCE: 499

Gln Asn Gln Glu Tyr Gln Val Leu Leu Asp Val Cys Ala Arg Leu Glu
1 5 10 15

Cys Glu Ile Asn Thr Tyr Arg
20

<210> SEQ ID NO 500
<211> LENGTH: 23
<212> TYPE: PRT
<213> ORGANISM: Homo sapiens

<400> SEQUENCE: 500

Gln Asn Gln Glu Tyr Gln Val Leu Leu Asp Val Lys Ala Arg Leu Glu
1 5 10 15

Gly Glu Ile Asn Thr Tyr Arg
20

<210> SEQ ID NO 501
<211> LENGTH: 60
<212> TYPE: PRT
<213> ORGANISM: Homo sapiens

<400> SEQUENCE: 501

Gln Asn Thr Cys Cys Arg Thr Thr Cys Cys Gln Pro Thr Cys Val Thr
1 5 10 15

Ser Cys Cys Gln Pro Ser Cys Cys Ser Thr Pro Cys Cys Gln Pro Ile
20 25 30

Cys Cys Gly Ser Ser Cys Cys Gly Gln Thr Ser Cys Gly Ser Ser Cys
35 40 45

Gly Gln Ser Ser Ser Cys Ala Pro Val Tyr Cys Arg
50 55 60

<210> SEQ ID NO 502
<211> LENGTH: 59
<212> TYPE: PRT
<213> ORGANISM: Homo sapiens

<400> SEQUENCE: 502

Gln Pro Cys Cys His Pro Thr Cys Cys Gln Asn Thr Cys Cys Arg Thr
1 5 10 15

Thr Cys Cys Gln Pro Ile Cys Val Thr Ser Cys Cys Gln Pro Ser Cys
20 25 30

Cys Ser Thr Pro Cys Cys Gln Pro Thr Arg Cys Gly Ser Ser Cys Gly
35 40 45

Gln Ser Ser Ser Cys Ala Pro Val Tyr Cys Arg
50 55

<210> SEQ ID NO 503
<211> LENGTH: 11
<212> TYPE: PRT
<213> ORGANISM: Homo sapiens

<400> SEQUENCE: 503

Gln Pro Ser Cys Cys Gln Thr Ser Ser Cys Arg
1 5 10

<210> SEQ ID NO 504
<211> LENGTH: 31
<212> TYPE: PRT
<213> ORGANISM: Homo sapiens

<400> SEQUENCE: 504

Gln Pro Val Cys Cys Gly Ser Ser Cys Cys Gly Gln Thr Ser Cys Gly
1 5 10 15

Ser Ser Cys Gly Gln Ser Ser Ser Cys Ala Pro Val Tyr Cys Arg
20 25 30

<210> SEQ ID NO 505
<211> LENGTH: 48
<212> TYPE: PRT
<213> ORGANISM: Homo sapiens

<400> SEQUENCE: 505

Gln Pro Val Cys Cys Gln Pro Thr Cys Cys Arg Pro Arg Cys Cys Ile
1 5 10 15

Ser Ser Cys Cys Arg Pro Ser Cys Cys Val Ser Ser Cys Cys Lys Pro
20 25 30

Gln Cys Cys Gln Ser Val Cys Cys Gln Pro Asn Cys Cys Arg Pro Ser
35 40 45

<210> SEQ ID NO 506
<211> LENGTH: 38
<212> TYPE: PRT
<213> ORGANISM: Homo sapiens

<400> SEQUENCE: 506

Gln Ser His Ile Ser Asp Thr Ser Val Val Val Lys Leu Asp Asn Ser
1 5 10 15

Arg Asp Leu Asn Met Asp Cys Met Val Ala Glu Ile Lys Ala Gln Tyr
20 25 30

Asp Asp Ile Ala Thr Arg
35

<210> SEQ ID NO 507
<211> LENGTH: 11
<212> TYPE: PRT
<213> ORGANISM: Homo sapiens

<400> SEQUENCE: 507

Gln Ser Val Glu Ala Asp Leu Asn Gly Leu Arg
1               5                   10

<210> SEQ ID NO 508
<211> LENGTH: 12
<212> TYPE: PRT
<213> ORGANISM: Homo sapiens

<400> SEQUENCE: 508

Gln Ser Val Glu Ala Asp Leu Asn Gly Leu Arg Arg
1               5                   10

<210> SEQ ID NO 509
<211> LENGTH: 24
<212> TYPE: PRT
<213> ORGANISM: Homo sapiens

<400> SEQUENCE: 509

Gln Ser Val Phe Pro Phe Glu Ser Gly Lys Pro Phe Lys Ile His Val
1               5                   10                  15

Leu Val Glu Pro Asp His Phe Lys
            20

<210> SEQ ID NO 510
<211> LENGTH: 8
<212> TYPE: PRT
<213> ORGANISM: Homo sapiens

<400> SEQUENCE: 510

Gln Thr Ser Phe Cys Gly Phe Arg
1               5

<210> SEQ ID NO 511
<211> LENGTH: 18
<212> TYPE: PRT
<213> ORGANISM: Homo sapiens

<400> SEQUENCE: 511

Gln Thr Ser Tyr Val Glu Ser Arg Pro Cys Gln Thr Ser Cys Tyr Arg
1               5                   10                  15

Pro Arg

<210> SEQ ID NO 512
<211> LENGTH: 62
<212> TYPE: PRT
<213> ORGANISM: Homo sapiens

<400> SEQUENCE: 512

Gln Thr Thr Cys Ile Ser Asn Pro Cys Ser Thr Thr Tyr Ser Arg Pro
1               5                   10                  15

Leu Thr Phe Val Ser Ser Gly Ser Gln Pro Leu Gly Gly Ile Ser Ser
            20                  25                  30

Val Cys Gln Pro Val Gly Gly Ile Ser Thr Val Cys Gln Pro Val Gly
        35                  40                  45

Gly Val Ser Thr Val Cys Gln Pro Ala Cys Gly Val Ser Arg
    50                  55                  60

<210> SEQ ID NO 513
<211> LENGTH: 8
<212> TYPE: PRT
<213> ORGANISM: Homo sapiens

<400> SEQUENCE: 513

Gln Val Glu Ile Ile Glu Leu Arg
1               5

<210> SEQ ID NO 514
<211> LENGTH: 9
<212> TYPE: PRT
<213> ORGANISM: Homo sapiens

<400> SEQUENCE: 514

Gln Val Glu Ile Ile Glu Leu Arg Arg
1               5

<210> SEQ ID NO 515
<211> LENGTH: 20
<212> TYPE: PRT
<213> ORGANISM: Homo sapiens

<400> SEQUENCE: 515

Gln Val Val Ser Ser Ser Glu Gln Leu Gln Ser Cys Gln Val Glu Ile
1               5                   10                  15

Ile Glu Leu Arg
            20

<210> SEQ ID NO 516
<211> LENGTH: 21
<212> TYPE: PRT
<213> ORGANISM: Homo sapiens

<400> SEQUENCE: 516

Gln Val Val Ser Ser Ser Glu Gln Leu Gln Ser Cys Gln Val Glu Ile
1               5                   10                  15

Ile Glu Leu Arg Arg
            20

<210> SEQ ID NO 517
<211> LENGTH: 20
<212> TYPE: PRT
<213> ORGANISM: Homo sapiens

<400> SEQUENCE: 517

Gln Val Val Ser Ser Ser Glu Gln Leu Gln Ser Tyr Gln Val Glu Ile
1               5                   10                  15

Ile Glu Leu Arg
            20

<210> SEQ ID NO 518
<211> LENGTH: 21
<212> TYPE: PRT
<213> ORGANISM: Homo sapiens

<400> SEQUENCE: 518

Gln Val Val Ser Ser Ser Glu Gln Leu Gln Ser Tyr Gln Val Glu Ile
1               5                   10                  15

Ile Glu Leu Arg Arg
            20

<210> SEQ ID NO 519
<211> LENGTH: 37
<212> TYPE: PRT
<213> ORGANISM: Homo sapiens

<400> SEQUENCE: 519

Gln Val Val Ser Ser Ser Glu Gln Leu Gln Ser Tyr Gln Val Glu Ile
1 5 10 15

Ile Glu Leu Arg Arg Thr Val Asn Ala Leu Glu Ile Glu Leu Gln Ala
20 25 30

Gln His Asn Leu Arg
35

<210> SEQ ID NO 520
<211> LENGTH: 18
<212> TYPE: PRT
<213> ORGANISM: Homo sapiens

<400> SEQUENCE: 520

Arg Cys Gly Ser Ser Cys Gly Gln Ser Ser Ser Cys Ala Pro Val Tyr
1 5 10 15

Cys Arg

<210> SEQ ID NO 521
<211> LENGTH: 22
<212> TYPE: PRT
<213> ORGANISM: Homo sapiens

<400> SEQUENCE: 521

Arg Asp Leu Asn Met Asp Cys Met Val Ala Glu Ile Lys Ala Gln Tyr
1 5 10 15

Asp Asp Ile Ala Thr Arg
20

<210> SEQ ID NO 522
<211> LENGTH: 12
<212> TYPE: PRT
<213> ORGANISM: Homo sapiens

<400> SEQUENCE: 522

Arg Glu Ala Glu Cys Val Glu Ala Asn Ser Gly Arg
1 5 10

<210> SEQ ID NO 523
<211> LENGTH: 28
<212> TYPE: PRT
<213> ORGANISM: Homo sapiens

<400> SEQUENCE: 523

Arg Glu Ala Glu Cys Val Glu Ala Asn Ser Gly Arg Leu Ala Ser Glu
1 5 10 15

Leu Asn His Val Gln Glu Val Leu Glu Gly Tyr Lys
20 25

<210> SEQ ID NO 524
<211> LENGTH: 29
<212> TYPE: PRT
<213> ORGANISM: Homo sapiens

<400> SEQUENCE: 524

Arg Glu Ala Glu Cys Val Glu Ala Asn Ser Gly Arg Leu Ala Ser Glu
1 5 10 15

Leu Asn His Val Gln Glu Val Leu Glu Gly Tyr Lys Lys
20 25

<210> SEQ ID NO 525
<211> LENGTH: 37
<212> TYPE: PRT
<213> ORGANISM: Homo sapiens

<400> SEQUENCE: 525

Arg Glu Val Glu Gln Trp Phe Ala Thr Gln Thr Glu Glu Leu Asn Lys
1 5 10 15

Gln Val Val Ser Ser Ser Glu Gln Leu Gln Ser Tyr Gln Val Glu Ile
20 25 30

Ile Glu Leu Arg Arg
35

<210> SEQ ID NO 526
<211> LENGTH: 13
<212> TYPE: PRT
<213> ORGANISM: Homo sapiens

<400> SEQUENCE: 526

Arg Glu Val Glu Gln Trp Phe Ala Thr Gln Thr Glu Lys
1 5 10

<210> SEQ ID NO 527
<211> LENGTH: 16
<212> TYPE: PRT
<213> ORGANISM: Homo sapiens

<400> SEQUENCE: 527

Arg Glu Val Glu Gln Trp Phe Ala Thr Gln Thr Glu Lys Leu Asn Lys
1 5 10 15

<210> SEQ ID NO 528
<211> LENGTH: 21
<212> TYPE: PRT
<213> ORGANISM: Homo sapiens

<400> SEQUENCE: 528

Arg Glu Tyr Gln Glu Leu Met Asn Ala Lys Leu Gly Leu Asp Ile Glu
1 5 10 15

Ile Ala Thr Tyr Arg
20

<210> SEQ ID NO 529
<211> LENGTH: 14
<212> TYPE: PRT
<213> ORGANISM: Homo sapiens

<400> SEQUENCE: 529

Arg Gly Leu Thr Gly Gly Phe Gly Ser His Ser Val Cys Arg
1 5 10

<210> SEQ ID NO 530
<211> LENGTH: 18
<212> TYPE: PRT
<213> ORGANISM: Homo sapiens

<400> SEQUENCE: 530

Arg Gly Gln Ser Glu Ala Asp Ser Asp Lys Asn Ala Thr Ile Leu Glu
1 5 10 15

Leu Arg

<210> SEQ ID NO 531
<211> LENGTH: 28
<212> TYPE: PRT
<213> ORGANISM: Homo sapiens

<400> SEQUENCE: 531

Arg Ile Leu Asp Asp Leu Thr Leu Cys Lys Ala Asp Leu Glu Ala Gln
1               5                   10                  15

Val Glu Tyr Leu Lys Glu Glu Leu Met Cys Leu Lys
            20                  25

<210> SEQ ID NO 532
<211> LENGTH: 10
<212> TYPE: PRT
<213> ORGANISM: Homo sapiens

<400> SEQUENCE: 532

Arg Ile Leu Asn Glu Leu Thr Leu Cys Lys
1               5                   10

<210> SEQ ID NO 533
<211> LENGTH: 17
<212> TYPE: PRT
<213> ORGANISM: Homo sapiens

<400> SEQUENCE: 533

Arg Met Val Asn Ala Leu Glu Ile Glu Leu Gln Ala Gln His Ser Met
1               5                   10                  15

Arg

<210> SEQ ID NO 534
<211> LENGTH: 16
<212> TYPE: PRT
<213> ORGANISM: Homo sapiens

<400> SEQUENCE: 534

Arg Pro Cys Cys Cys Arg Pro Ser Cys Cys Gln Thr Thr Cys Cys Arg
1               5                   10                  15

<210> SEQ ID NO 535
<211> LENGTH: 25
<212> TYPE: PRT
<213> ORGANISM: Homo sapiens

<400> SEQUENCE: 535

Arg Pro Ser Cys Cys Ile Pro Cys Cys Cys Arg Pro Thr Cys Val Ile
1               5                   10                  15

Ser Thr Cys Pro Arg Pro Leu Cys Cys
            20                  25

<210> SEQ ID NO 536
<211> LENGTH: 15
<212> TYPE: PRT
<213> ORGANISM: Homo sapiens

<400> SEQUENCE: 536

Arg Gln Leu Glu Arg Asp Asn Val Glu Leu Glu Asn Leu Ile Arg
1               5                   10                  15

<210> SEQ ID NO 537
<211> LENGTH: 24

<212> TYPE: PRT
<213> ORGANISM: Homo sapiens

<400> SEQUENCE: 537

Arg Gln Leu Arg Glu Tyr Gln Glu Leu Met Asn Ala Lys Leu Gly Leu
1 5 10 15

Asp Ile Glu Ile Ala Thr Tyr Arg
20

<210> SEQ ID NO 538
<211> LENGTH: 63
<212> TYPE: PRT
<213> ORGANISM: Homo sapiens

<400> SEQUENCE: 538

Arg Gln Thr Thr Cys Ile Ser Asn Pro Cys Ser Thr Thr Tyr Ser Arg
1 5 10 15

Pro Leu Thr Phe Val Ser Ser Gly Ser Gln Pro Leu Gly Gly Ile Ser
20 25 30

Ser Val Cys Gln Pro Val Gly Gly Ile Ser Thr Val Cys Gln Pro Val
35 40 45

Gly Gly Val Ser Thr Val Cys Gln Pro Ala Cys Gly Val Ser Arg
50 55 60

<210> SEQ ID NO 539
<211> LENGTH: 43
<212> TYPE: PRT
<213> ORGANISM: Homo sapiens

<400> SEQUENCE: 539

Arg Ser Phe Gly Tyr His Ser Gly Gly Val Cys Gly Pro Ser Pro Pro
1 5 10 15

Cys Ile Thr Thr Val Ser Val Asn Glu Ser Leu Leu Thr Pro Leu Asn
20 25 30

Leu Glu Ile Asp Pro Asn Ala Gln Cys Val Lys
35 40

<210> SEQ ID NO 540
<211> LENGTH: 51
<212> TYPE: PRT
<213> ORGANISM: Homo sapiens

<400> SEQUENCE: 540

Arg Ser Phe Gly Tyr His Ser Gly Gly Val Cys Gly Pro Ser Pro Pro
1 5 10 15

Cys Ile Thr Thr Val Ser Val Asn Glu Ser Leu Leu Thr Pro Leu Asn
20 25 30

Leu Glu Ile Asp Pro Asn Ala Gln Cys Val Lys Gln Glu Glu Lys Glu
35 40 45

Gln Ile Lys
50

<210> SEQ ID NO 541
<211> LENGTH: 15
<212> TYPE: PRT
<213> ORGANISM: Homo sapiens

<400> SEQUENCE: 541

Arg Ser Ser Cys Cys Pro Ser Cys Cys Gln Thr Thr Cys Cys Arg
1 5 10 15

<210> SEQ ID NO 542
<211> LENGTH: 53
<212> TYPE: PRT
<213> ORGANISM: Homo sapiens

<400> SEQUENCE: 542

Arg Thr Ala Ser Ala Leu Glu Ile Glu Leu Gln Ala Gln Gln Ser Leu
1 5 10 15

Thr Glu Ser Leu Glu Cys Thr Val Ala Glu Thr Glu Ala Gln Tyr Ser
20 25 30

Ser Gln Leu Ala Gln Ile Gln Arg Leu Ile Asp Asn Leu Glu Asn Gln
35 40 45

Leu Ala Glu Ile Arg
50

<210> SEQ ID NO 543
<211> LENGTH: 29
<212> TYPE: PRT
<213> ORGANISM: Homo sapiens

<400> SEQUENCE: 543

Arg Thr Cys Tyr His Pro Thr Thr Val Cys Leu Pro Gly Cys Leu Asn
1 5 10 15

Gln Ser Cys Gly Ser Ser Cys Cys Gln Pro Cys Cys Arg
20 25

<210> SEQ ID NO 544
<211> LENGTH: 44
<212> TYPE: PRT
<213> ORGANISM: Homo sapiens

<400> SEQUENCE: 544

Arg Thr Cys Tyr His Pro Thr Thr Val Cys Leu Pro Gly Cys Leu Asn
1 5 10 15

Gln Ser Cys Gly Ser Ser Cys Cys Gln Pro Cys Cys Arg Pro Ala Cys
20 25 30

Cys Glu Thr Thr Cys Phe Gln Pro Thr Cys Val Tyr
35 40

<210> SEQ ID NO 545
<211> LENGTH: 44
<212> TYPE: PRT
<213> ORGANISM: Homo sapiens

<400> SEQUENCE: 545

Arg Thr Cys Tyr His Pro Thr Thr Val Cys Leu Pro Gly Cys Leu Asn
1 5 10 15

Gln Ser Cys Gly Ser Ser Cys Cys Gln Pro Cys Cys Arg Pro Ala Cys
20 25 30

Cys Glu Thr Thr Cys Phe Gln Pro Thr Cys Val Tyr
35 40

<210> SEQ ID NO 546
<211> LENGTH: 45
<212> TYPE: PRT
<213> ORGANISM: Homo sapiens

<400> SEQUENCE: 546

Arg Thr Cys Tyr His Pro Thr Thr Val Cys Leu Pro Gly Cys Leu Asn
1 5 10 15

```
Gln Ser Cys Gly Ser Ser Cys Cys Gln Pro Cys Cys Arg Pro Ala Cys
            20                  25                  30

Cys Glu Thr Thr Cys Phe Gln Pro Thr Cys Val Tyr Ser
        35                  40                  45


<210> SEQ ID NO 547
<211> LENGTH: 45
<212> TYPE: PRT
<213> ORGANISM: Homo sapiens

<400> SEQUENCE: 547

Arg Thr Cys Tyr His Pro Thr Thr Val Cys Leu Pro Gly Cys Leu Asn
1               5                   10                  15

Gln Ser Cys Gly Ser Ser Cys Cys Gln Pro Cys Cys Arg Pro Ala Cys
            20                  25                  30

Cys Glu Thr Thr Cys Phe Gln Pro Thr Cys Val Tyr Ser
        35                  40                  45


<210> SEQ ID NO 548
<211> LENGTH: 45
<212> TYPE: PRT
<213> ORGANISM: Homo sapiens

<400> SEQUENCE: 548

Arg Thr Cys Tyr Tyr Pro Thr Thr Val Cys Leu Pro Gly Cys Leu Asn
1               5                   10                  15

Gln Ser Cys Gly Ser Asn Cys Cys Gln Pro Cys Cys Arg Pro Ala Cys
            20                  25                  30

Cys Glu Thr Thr Cys Phe Gln Pro Thr Cys Val Tyr Ser
        35                  40                  45


<210> SEQ ID NO 549
<211> LENGTH: 52
<212> TYPE: PRT
<213> ORGANISM: Homo sapiens

<400> SEQUENCE: 549

Arg Thr Cys Tyr Tyr Pro Thr Thr Val Cys Leu Pro Gly Cys Leu Asn
1               5                   10                  15

Gln Ser Cys Gly Ser Asn Cys Cys Gln Pro Cys Cys Arg Pro Ala Cys
            20                  25                  30

Cys Glu Thr Thr Cys Phe Gln Pro Thr Cys Val Tyr Ser Cys Cys Gln
        35                  40                  45

Pro Phe Cys Cys
    50


<210> SEQ ID NO 550
<211> LENGTH: 24
<212> TYPE: PRT
<213> ORGANISM: Homo sapiens

<400> SEQUENCE: 550

Arg Thr Gly Cys Gly Ile Gly Gly Gly Ile Gly Tyr Gly Gln Glu Gly
1               5                   10                  15

Ser Ser Gly Ala Val Ser Thr Arg
            20


<210> SEQ ID NO 551
<211> LENGTH: 24
<212> TYPE: PRT
<213> ORGANISM: Homo sapiens
```

<400> SEQUENCE: 551

Arg Thr Gly Cys Gly Thr Gly Gly Gly Ile Gly Tyr Gly Gln Glu Gly
1               5                   10                  15

Ser Ser Gly Ala Val Ser Thr Arg
            20

<210> SEQ ID NO 552
<211> LENGTH: 24
<212> TYPE: PRT
<213> ORGANISM: Homo sapiens

<400> SEQUENCE: 552

Arg Thr Gly Cys Gly Thr Gly Gly Gly Ile Gly Tyr Gly Gln Glu Gly
1               5                   10                  15

Ser Ser Gly Ala Val Ser Thr Arg
            20

<210> SEQ ID NO 553
<211> LENGTH: 15
<212> TYPE: PRT
<213> ORGANISM: Homo sapiens

<400> SEQUENCE: 553

Arg Thr Lys Glu Glu Ile Asn Glu Leu Asn Cys Met Ile Gln Arg
1               5                   10                  15

<210> SEQ ID NO 554
<211> LENGTH: 17
<212> TYPE: PRT
<213> ORGANISM: Homo sapiens

<400> SEQUENCE: 554

Arg Thr Val Asn Ser Leu Glu Ile Glu Leu Gln Ala Gln His Asn Leu
1               5                   10                  15

Arg

<210> SEQ ID NO 555
<211> LENGTH: 30
<212> TYPE: PRT
<213> ORGANISM: Homo sapiens

<400> SEQUENCE: 555

Arg Thr Val Asn Ser Leu Glu Ile Glu Leu Gln Ala Gln His Asn Leu
1               5                   10                  15

Arg Asp Ser Leu Glu Asn Thr Leu Thr Glu Ser Glu Ala Arg
            20                  25                  30

<210> SEQ ID NO 556
<211> LENGTH: 30
<212> TYPE: PRT
<213> ORGANISM: Homo sapiens

<400> SEQUENCE: 556

Arg Thr Val Asn Thr Leu Glu Ile Glu Leu Gln Ala Gln His Ser Leu
1               5                   10                  15

Arg Asp Ser Leu Glu Asn Met Leu Thr Glu Ser Glu Ala Arg
            20                  25                  30

<210> SEQ ID NO 557
<211> LENGTH: 18
<212> TYPE: PRT

<213> ORGANISM: Homo sapiens

<400> SEQUENCE: 557

Arg Val Ile Val Cys Asn Thr Lys Leu Asp Asn Asn Trp Gly Lys Glu
1 5 10 15

Glu Arg

<210> SEQ ID NO 558
<211> LENGTH: 20
<212> TYPE: PRT
<213> ORGANISM: Homo sapiens

<400> SEQUENCE: 558

Arg Val Pro Val Pro Ser Cys Cys Val Pro Thr Ser Ser Cys Gln Pro
1 5 10 15

Ser Cys Ser Arg
20

<210> SEQ ID NO 559
<211> LENGTH: 21
<212> TYPE: PRT
<213> ORGANISM: Homo sapiens

<400> SEQUENCE: 559

Arg Val Pro Val Pro Ser Cys Cys Val Pro Thr Ser Ser Cys Gln Pro
1 5 10 15

Ser Cys Ser Arg Leu
20

<210> SEQ ID NO 560
<211> LENGTH: 32
<212> TYPE: PRT
<213> ORGANISM: Homo sapiens

<400> SEQUENCE: 560

Arg Val Ser Ala Met Tyr Ser Ser Ser Pro Cys Lys Leu Pro Ser Leu
1 5 10 15

Ser Pro Val Ala Arg Ser Phe Ser Ala Cys Ser Val Gly Leu Gly Arg
20 25 30

<210> SEQ ID NO 561
<211> LENGTH: 24
<212> TYPE: PRT
<213> ORGANISM: Homo sapiens

<400> SEQUENCE: 561

Arg Val Ser Ser Asp Pro Ser Asn Ser Asn Val Val Val Gly Thr Thr
1 5 10 15

Asn Ala Cys Ala Pro Ser Ala Arg
20

<210> SEQ ID NO 562
<211> LENGTH: 41
<212> TYPE: PRT
<213> ORGANISM: Homo sapiens

<400> SEQUENCE: 562

Arg Tyr Ser Ser Gln Leu Ala Gln Met Gln Cys Met Ile Thr Asn Val
1 5 10 15

Glu Ala Gln Leu Ala Glu Ile Gln Ala Asp Leu Glu Arg Gln Asn Gln
20 25 30

Glu Tyr Gln Val Leu Leu Asp Val Arg
35 40

<210> SEQ ID NO 563
<211> LENGTH: 16
<212> TYPE: PRT
<213> ORGANISM: Homo sapiens

<400> SEQUENCE: 563

Ser Ala Gly Gly Arg Pro Gly Ser Gly Pro Gln Leu Gly Ser Gly Arg
1 5 10 15

<210> SEQ ID NO 564
<211> LENGTH: 25
<212> TYPE: PRT
<213> ORGANISM: Homo sapiens

<400> SEQUENCE: 564

Ser Ala Ile Val His Leu Ile Asn Tyr Gln Asp Asp Ala Glu Leu Ala
1 5 10 15

Thr His Ala Leu Pro Glu Leu Thr Lys
20 25

<210> SEQ ID NO 565
<211> LENGTH: 37
<212> TYPE: PRT
<213> ORGANISM: Homo sapiens

<400> SEQUENCE: 565

Ser Ala Ile Val His Leu Ile Asn Tyr Gln Asp Asp Ala Glu Leu Ala
1 5 10 15

Thr His Ala Leu Pro Glu Leu Thr Lys Leu Leu Asn Asp Glu Asp Pro
20 25 30

Val Val Val Thr Lys
35

<210> SEQ ID NO 566
<211> LENGTH: 14
<212> TYPE: PRT
<213> ORGANISM: Homo sapiens

<400> SEQUENCE: 566

Ser Ala Ile Val His Leu Ile Asn Tyr Gln Asp Asp Ala Lys
1 5 10

<210> SEQ ID NO 567
<211> LENGTH: 18
<212> TYPE: PRT
<213> ORGANISM: Homo sapiens

<400> SEQUENCE: 567

Ser Ala Ile Val His Leu Ile Asn Tyr Gln Asp Asp Ala Lys Leu Ala
1 5 10 15

Thr Arg

<210> SEQ ID NO 568
<211> LENGTH: 14
<212> TYPE: PRT
<213> ORGANISM: Homo sapiens

<400> SEQUENCE: 568

Ser Ala Arg Pro Ile Cys Val Pro Cys Pro Gly Gly Arg Phe
1 5 10

<210> SEQ ID NO 569
<211> LENGTH: 21
<212> TYPE: PRT
<213> ORGANISM: Homo sapiens

<400> SEQUENCE: 569

Ser Ala Tyr Gln Glu Ala Met Asp Ile Ser Lys Lys Asp Met Pro Pro
1 5 10 15

Thr Asn Pro Ile Arg
20

<210> SEQ ID NO 570
<211> LENGTH: 33
<212> TYPE: PRT
<213> ORGANISM: Homo sapiens

<400> SEQUENCE: 570

Ser Cys Cys Gly Ser Val Cys Ser Asp Gln Gly Cys Gly Gln Val Leu
1 5 10 15

Cys Gln Glu Thr Cys Cys Arg Pro Ser Cys Cys Gln Thr Thr Cys Cys
20 25 30

Arg

<210> SEQ ID NO 571
<211> LENGTH: 20
<212> TYPE: PRT
<213> ORGANISM: Homo sapiens

<400> SEQUENCE: 571

Ser Cys Cys Ile Ser Ser Cys Cys Arg Arg Pro Thr Cys Val Ile Ser
1 5 10 15

Thr Cys Pro Arg
20

<210> SEQ ID NO 572
<211> LENGTH: 22
<212> TYPE: PRT
<213> ORGANISM: Homo sapiens

<400> SEQUENCE: 572

Ser Cys Cys Ile Ser Ser Cys Cys Arg Arg Pro Thr Cys Val Ile Ser
1 5 10 15

Thr Cys Pro Arg Pro Leu
20

<210> SEQ ID NO 573
<211> LENGTH: 37
<212> TYPE: PRT
<213> ORGANISM: Homo sapiens

<400> SEQUENCE: 573

Ser Cys Cys Gln Pro Ser Cys Cys Gln Thr Ser Ser Cys Gly Thr Gly
1 5 10 15

Cys Gly Thr Gly Gly Gly Ile Gly Tyr Gly Gln Glu Gly Ser Ser Gly
20 25 30

Ala Val Ser Thr Arg
35

<210> SEQ ID NO 574
<211> LENGTH: 11

<212> TYPE: PRT
<213> ORGANISM: Homo sapiens

<400> SEQUENCE: 574

Ser Cys Cys Gln Thr Ser Phe Cys Gly Phe Arg
1 5 10

<210> SEQ ID NO 575
<211> LENGTH: 32
<212> TYPE: PRT
<213> ORGANISM: Homo sapiens

<400> SEQUENCE: 575

Ser Cys Cys Gln Thr Ser Ser Cys Arg Thr Gly Cys Gly Ile Gly Gly
1 5 10 15

Gly Ile Gly Tyr Gly Gln Glu Gly Ser Ser Gly Ala Val Ser Thr Arg
20 25 30

<210> SEQ ID NO 576
<211> LENGTH: 49
<212> TYPE: PRT
<213> ORGANISM: Homo sapiens

<400> SEQUENCE: 576

Ser Cys Cys Gln Thr Thr Cys Cys Arg Thr Thr Cys Cys Arg Pro Ser
1 5 10 15

Cys Cys Val Ser Ser Cys Phe Arg Pro Gln Cys Cys Gln Ser Val Cys
20 25 30

Cys Gln Pro Thr Cys Cys Arg Pro Ser Cys Gly Gln Thr Thr Cys Cys
35 40 45

Arg

<210> SEQ ID NO 577
<211> LENGTH: 35
<212> TYPE: PRT
<213> ORGANISM: Homo sapiens

<400> SEQUENCE: 577

Ser Cys Cys Val Ser Ser Cys Phe Arg Pro Gln Cys Cys Gln Ser Val
1 5 10 15

Cys Cys Gln Pro Thr Cys Cys Arg Pro Ser Cys Gly Gln Thr Thr Cys
20 25 30

Cys Arg Thr
35

<210> SEQ ID NO 578
<211> LENGTH: 9
<212> TYPE: PRT
<213> ORGANISM: Homo sapiens

<400> SEQUENCE: 578

Ser Cys Gly His Ser Phe Gly Tyr Arg
1 5

<210> SEQ ID NO 579
<211> LENGTH: 54
<212> TYPE: PRT
<213> ORGANISM: Homo sapiens

<400> SEQUENCE: 579

Ser Cys Gly Arg Ser Phe Gly Tyr His Ser Gly Gly Val Cys Gly Pro
1 5 10 15

```
Ser Pro Pro Cys Ile Thr Thr Val Ser Val Asn Glu Ser Leu Leu Thr
            20                  25                  30

Pro Leu Asn Leu Glu Ile Asp Pro Asn Ala Gln Cys Val Lys Gln Glu
        35                  40                  45

Glu Lys Glu Gln Ile Lys
    50


<210> SEQ ID NO 580
<211> LENGTH: 26
<212> TYPE: PRT
<213> ORGANISM: Homo sapiens

<400> SEQUENCE: 580

Ser Cys Arg Thr Gly Cys Gly Ile Gly Gly Gly Ile Gly Tyr Gly Gln
1               5                   10                  15

Glu Gly Ser Ser Gly Ala Val Ser Thr Arg
            20                  25


<210> SEQ ID NO 581
<211> LENGTH: 6
<212> TYPE: PRT
<213> ORGANISM: Homo sapiens

<400> SEQUENCE: 581

Ser Cys Tyr Gln Pro Arg
1               5


<210> SEQ ID NO 582
<211> LENGTH: 19
<212> TYPE: PRT
<213> ORGANISM: Homo sapiens

<400> SEQUENCE: 582

Ser Asp Leu Glu Ala Asn Val Asp Ala Leu Ile Gln Glu Ile Asp Phe
1               5                   10                  15

Leu Arg Arg


<210> SEQ ID NO 583
<211> LENGTH: 26
<212> TYPE: PRT
<213> ORGANISM: Homo sapiens

<400> SEQUENCE: 583

Ser Asp Gln Gly Cys Gly Gln Asp Leu Cys Gln Glu Thr Cys Cys Arg
1               5                   10                  15

Pro Ser Cys Cys Gln Thr Thr Cys Cys Arg
            20                  25


<210> SEQ ID NO 584
<211> LENGTH: 10
<212> TYPE: PRT
<213> ORGANISM: Homo sapiens

<400> SEQUENCE: 584

Ser Glu Pro Asp Leu Tyr Tyr Asp Pro Arg
1               5                   10


<210> SEQ ID NO 585
<211> LENGTH: 42
<212> TYPE: PRT
<213> ORGANISM: Homo sapiens
```

<400> SEQUENCE: 585

Ser Phe Gly Tyr His Ser Gly Gly Val Cys Gly Pro Ser Pro Pro Cys
1               5                   10                  15

Ile Thr Thr Val Ser Val Asn Glu Ser Leu Leu Thr Pro Leu Asn Leu
            20                  25                  30

Glu Ile Asp Pro Asn Ala Gln Cys Val Lys
        35                  40

<210> SEQ ID NO 586
<211> LENGTH: 46
<212> TYPE: PRT
<213> ORGANISM: Homo sapiens

<400> SEQUENCE: 586

Ser Phe Gly Tyr His Ser Gly Gly Val Cys Gly Pro Ser Pro Pro Cys
1               5                   10                  15

Ile Thr Thr Val Ser Val Asn Glu Ser Leu Leu Thr Pro Leu Asn Leu
            20                  25                  30

Glu Ile Asp Pro Asn Ala Gln Cys Val Lys Gln Glu Glu Lys
        35                  40                  45

<210> SEQ ID NO 587
<211> LENGTH: 50
<212> TYPE: PRT
<213> ORGANISM: Homo sapiens

<400> SEQUENCE: 587

Ser Phe Gly Tyr His Ser Gly Gly Val Cys Gly Pro Ser Pro Pro Cys
1               5                   10                  15

Ile Thr Thr Val Ser Val Asn Glu Ser Leu Leu Thr Pro Leu Asn Leu
            20                  25                  30

Glu Ile Asp Pro Asn Ala Gln Cys Val Lys Gln Glu Glu Lys Glu Gln
        35                  40                  45

Ile Lys
    50

<210> SEQ ID NO 588
<211> LENGTH: 55
<212> TYPE: PRT
<213> ORGANISM: Homo sapiens

<400> SEQUENCE: 588

Ser Phe Gly Tyr His Ser Gly Gly Val Cys Gly Pro Ser Pro Pro Cys
1               5                   10                  15

Ile Thr Thr Val Ser Val Asn Glu Ser Leu Leu Thr Pro Leu Asn Leu
            20                  25                  30

Glu Ile Asp Pro Asn Ala Gln Cys Val Lys Gln Glu Glu Lys Glu Gln
        35                  40                  45

Ile Lys Ser Leu Asn Ser Arg
    50                  55

<210> SEQ ID NO 589
<211> LENGTH: 57
<212> TYPE: PRT
<213> ORGANISM: Homo sapiens

<400> SEQUENCE: 589

Ser Phe Ser Thr Ser Gly Thr Cys Ser Ser Ser Cys Cys Gln Pro Ser
1               5                   10                  15

```
Cys Cys Glu Thr Ser Cys Cys Gln Pro Ser Cys Cys Gln Thr Ser Ser
            20                  25                  30

Cys Arg Thr Gly Cys Gly Ile Gly Gly Gly Ile Gly Tyr Gly Gln Glu
        35                  40                  45

Gly Ser Ser Gly Ala Val Ser Thr Arg
    50                  55


<210> SEQ ID NO 590
<211> LENGTH: 35
<212> TYPE: PRT
<213> ORGANISM: Homo sapiens

<400> SEQUENCE: 590

Ser Gly Ala Ile Glu Ser Thr Ala Pro Ala Cys Thr Ser Ser Ser Pro
1               5                   10                  15

Cys Ser Leu Lys Glu His Cys Ser Ala Cys Gly Pro Leu Ser Gln Ile
            20                  25                  30

Leu Val Lys
        35


<210> SEQ ID NO 591
<211> LENGTH: 36
<212> TYPE: PRT
<213> ORGANISM: Homo sapiens

<400> SEQUENCE: 591

Ser Gly Ala Ile Glu Ser Thr Ala Pro Ala Cys Thr Ser Ser Ser Pro
1               5                   10                  15

Cys Ser Leu Lys Glu His Cys Ser Ala Cys Gly Pro Leu Ser Gln Ile
            20                  25                  30

Leu Val Lys Ile
        35


<210> SEQ ID NO 592
<211> LENGTH: 19
<212> TYPE: PRT
<213> ORGANISM: Homo sapiens

<400> SEQUENCE: 592

Ser Lys Cys Glu Glu Met Lys Ala Thr Val Ile Arg His Gly Glu Thr
1               5                   10                  15

Leu Cys Arg


<210> SEQ ID NO 593
<211> LENGTH: 17
<212> TYPE: PRT
<213> ORGANISM: Homo sapiens

<400> SEQUENCE: 593

Ser Lys Cys His Glu Ser Thr Val Cys Pro Asn Tyr Gln Ser Tyr Phe
1               5                   10                  15

Arg


<210> SEQ ID NO 594
<211> LENGTH: 10
<212> TYPE: PRT
<213> ORGANISM: Homo sapiens

<400> SEQUENCE: 594

Ser Lys Tyr Gln Met Glu Gln Ser Leu Arg
1               5                   10
```

<210> SEQ ID NO 595
<211> LENGTH: 19
<212> TYPE: PRT
<213> ORGANISM: Homo sapiens

<400> SEQUENCE: 595

Ser Leu Cys Asn Leu Gly Ser Cys Gly Pro Arg Ile Ala Val Gly Gly
1               5                   10                  15

Ser Arg Ala

<210> SEQ ID NO 596
<211> LENGTH: 12
<212> TYPE: PRT
<213> ORGANISM: Homo sapiens

<400> SEQUENCE: 596

Ser Leu Gly Glu Thr Asn Ala Glu Leu Glu Ser Arg
1               5                   10

<210> SEQ ID NO 597
<211> LENGTH: 27
<212> TYPE: PRT
<213> ORGANISM: Homo sapiens

<400> SEQUENCE: 597

Ser Leu Gly Tyr Gly Gly Cys Gly Phe Pro Ser Leu Gly Tyr Gly Val
1               5                   10                  15

Gly Phe Cys His Pro Thr Tyr Leu Ala Ser Arg
            20                  25

<210> SEQ ID NO 598
<211> LENGTH: 24
<212> TYPE: PRT
<213> ORGANISM: Homo sapiens

<400> SEQUENCE: 598

Ser Leu His Gln Leu Val Glu Ala Asp Lys Cys Gly Thr Gln Lys Leu
1               5                   10                  15

Leu Asp Asp Val Thr Leu Ala Lys
            20

<210> SEQ ID NO 599
<211> LENGTH: 15
<212> TYPE: PRT
<213> ORGANISM: Homo sapiens

<400> SEQUENCE: 599

Ser Leu His Gln Leu Val Glu Val Asp Lys Cys Gly Thr Gln Lys
1               5                   10                  15

<210> SEQ ID NO 600
<211> LENGTH: 18
<212> TYPE: PRT
<213> ORGANISM: Homo sapiens

<400> SEQUENCE: 600

Ser Leu Lys Glu His Cys Ser Ala Cys Gly Pro Leu Ser Gln Ile Leu
1               5                   10                  15

Val Lys

<210> SEQ ID NO 601

<211> LENGTH: 38
<212> TYPE: PRT
<213> ORGANISM: Homo sapiens

<400> SEQUENCE: 601

Ser Leu Leu Glu Ser Glu Asp Cys Lys Leu Pro Ser Asn Pro Cys Ala
1 5 10 15

Thr Thr Asn Ala Cys Asp Lys Ser Thr Gly Pro Cys Ile Ser Lys Pro
20 25 30

Cys Gly Leu Arg Ala Arg
35

<210> SEQ ID NO 602
<211> LENGTH: 14
<212> TYPE: PRT
<213> ORGANISM: Homo sapiens

<400> SEQUENCE: 602

Ser Leu Asn Asp Arg Leu Ala Asn Tyr Leu Asp Lys Val Arg
1 5 10

<210> SEQ ID NO 603
<211> LENGTH: 25
<212> TYPE: PRT
<213> ORGANISM: Homo sapiens

<400> SEQUENCE: 603

Ser Leu Ser Leu Ser Leu Ala Asp Ser Gly His Leu Pro Asp Leu His
1 5 10 15

Gly Phe Asn Ser Tyr Gly Ser His Arg
20 25

<210> SEQ ID NO 604
<211> LENGTH: 7
<212> TYPE: PRT
<213> ORGANISM: Homo sapiens

<400> SEQUENCE: 604

Ser Leu Thr Ser Leu Ile Arg
1 5

<210> SEQ ID NO 605
<211> LENGTH: 11
<212> TYPE: PRT
<213> ORGANISM: Homo sapiens

<400> SEQUENCE: 605

Ser Met Pro Val Leu Ser Thr Gly Val Leu Arg
1 5 10

<210> SEQ ID NO 606
<211> LENGTH: 13
<212> TYPE: PRT
<213> ORGANISM: Homo sapiens

<400> SEQUENCE: 606

Ser Pro Cys Lys Leu Pro Ser Leu Ser Pro Val Ala Arg
1 5 10

<210> SEQ ID NO 607
<211> LENGTH: 11
<212> TYPE: PRT
<213> ORGANISM: Homo sapiens

<400> SEQUENCE: 607

Ser Pro Cys Gln Thr Ser Cys Tyr His Pro Arg
1 5 10

<210> SEQ ID NO 608
<211> LENGTH: 10
<212> TYPE: PRT
<213> ORGANISM: Homo sapiens

<400> SEQUENCE: 608

Ser Pro Met Val Pro Leu Pro Met Pro Lys
1 5 10

<210> SEQ ID NO 609
<211> LENGTH: 38
<212> TYPE: PRT
<213> ORGANISM: Homo sapiens

<400> SEQUENCE: 609

Ser Gln Leu Ala Gln Met Gln Cys Met Ile Thr Asn Val Glu Ala Gln
1 5 10 15

Leu Ala Glu Ile Gln Ala Asp Leu Glu Arg Gln Asn Gln Glu Tyr Gln
20 25 30

Val Leu Leu Asp Val Arg
35

<210> SEQ ID NO 610
<211> LENGTH: 38
<212> TYPE: PRT
<213> ORGANISM: Homo sapiens

<400> SEQUENCE: 610

Ser Gln Leu Ala Gln Met Gln Cys Met Ile Thr Asn Val Glu Ala Gln
1 5 10 15

Leu Ala Glu Ile Arg Ala Glu Leu Glu Arg Gln Asn Gln Glu Tyr Gln
20 25 30

Val Leu Leu Asp Val Arg
35

<210> SEQ ID NO 611
<211> LENGTH: 27
<212> TYPE: PRT
<213> ORGANISM: Homo sapiens

<400> SEQUENCE: 611

Ser Gln Leu Gly Asp Cys Leu Asn Val Glu Val Asp Thr Ala Pro Thr
1 5 10 15

Val Asp Leu Asn Gln Val Leu Asn Glu Thr Arg
20 25

<210> SEQ ID NO 612
<211> LENGTH: 39
<212> TYPE: PRT
<213> ORGANISM: Homo sapiens

<400> SEQUENCE: 612

Ser Gln Leu Gly Asp Cys Leu Asn Val Glu Val Asp Thr Ala Pro Thr
1 5 10 15

Val Asp Leu Asn Gln Val Leu Asn Glu Thr Arg Ser Gln Tyr Glu Ala
20 25 30

Leu Val Glu Thr Asn Arg Arg

35

<210> SEQ ID NO 613
<211> LENGTH: 39
<212> TYPE: PRT
<213> ORGANISM: Homo sapiens

<400> SEQUENCE: 613

Ser Gln Leu Gly Asp Cys Leu Asn Val Glu Val Asp Thr Ala Pro Thr
1               5                   10                  15

Val Asp Leu Asn Gln Val Leu Asn Glu Thr Arg Ser Gln Tyr Glu Ala
            20                  25                  30

Leu Val Glu Thr Asn Arg Arg
        35

<210> SEQ ID NO 614
<211> LENGTH: 27
<212> TYPE: PRT
<213> ORGANISM: Homo sapiens

<400> SEQUENCE: 614

Ser Gln Leu Gly Asp Arg Leu Asn Leu Glu Val Asp Thr Ala Pro Thr
1               5                   10                  15

Val Asp Leu Asn Gln Val Leu Asn Glu Thr Arg
            20                  25

<210> SEQ ID NO 615
<211> LENGTH: 11
<212> TYPE: PRT
<213> ORGANISM: Homo sapiens

<400> SEQUENCE: 615

Ser Gln Tyr Glu Val Leu Val Glu Thr Asn Arg
1               5                   10

<210> SEQ ID NO 616
<211> LENGTH: 12
<212> TYPE: PRT
<213> ORGANISM: Homo sapiens

<400> SEQUENCE: 616

Ser Gln Tyr Glu Val Leu Val Glu Thr Asn Arg Arg
1               5                   10

<210> SEQ ID NO 617
<211> LENGTH: 47
<212> TYPE: PRT
<213> ORGANISM: Homo sapiens

<400> SEQUENCE: 617

Ser Gln Tyr Glu Val Leu Val Glu Thr Asn Arg Arg Glu Val Glu Gln
1               5                   10                  15

Trp Phe Thr Thr Gln Thr Glu Glu Leu Asn Lys Gln Val Val Ser Ser
            20                  25                  30

Ser Glu Gln Leu Gln Ser Tyr Gln Ala Glu Ile Ile Glu Leu Arg
        35                  40                  45

<210> SEQ ID NO 618
<211> LENGTH: 23
<212> TYPE: PRT
<213> ORGANISM: Homo sapiens

<400> SEQUENCE: 618

Ser Arg Gly Val Gly Gly Ala Val Pro Gly Ala Val Leu Glu Pro Val
1 5 10 15

Ala Pro Ala Pro Ser Val Arg
20

<210> SEQ ID NO 619
<211> LENGTH: 49
<212> TYPE: PRT
<213> ORGANISM: Homo sapiens

<400> SEQUENCE: 619

Ser Arg Pro Leu Thr Phe Val Ser Ser Gly Ser Gln Pro Leu Gly Gly
1 5 10 15

Ile Ser Ser Val Cys Gln Pro Val Gly Gly Ile Ser Thr Val Cys Gln
20 25 30

Pro Val Gly Gly Val Ser Thr Val Cys Gln Pro Ala Cys Gly Val Ser
35 40 45

Arg

<210> SEQ ID NO 620
<211> LENGTH: 64
<212> TYPE: PRT
<213> ORGANISM: Homo sapiens

<400> SEQUENCE: 620

Ser Arg Gln Thr Thr Cys Ile Ser Asn Pro Cys Ser Thr Thr Tyr Ser
1 5 10 15

Arg Pro Leu Thr Phe Val Ser Ser Gly Ser Gln Pro Leu Gly Gly Ile
20 25 30

Ser Ser Val Cys Gln Pro Val Gly Gly Ile Ser Thr Val Cys Gln Pro
35 40 45

Val Gly Gly Val Ser Thr Val Cys Gln Pro Ala Cys Gly Val Ser Arg
50 55 60

<210> SEQ ID NO 621
<211> LENGTH: 19
<212> TYPE: PRT
<213> ORGANISM: Homo sapiens

<400> SEQUENCE: 621

Ser Ser Cys Cys Pro Ser Cys Cys Gln Thr Thr Cys Cys Arg Thr Thr
1 5 10 15

Cys Cys Arg

<210> SEQ ID NO 622
<211> LENGTH: 23
<212> TYPE: PRT
<213> ORGANISM: Homo sapiens

<400> SEQUENCE: 622

Ser Ser Glu Gln Ser Cys Gly Leu Glu Asn Cys Cys Cys Pro Ser Cys
1 5 10 15

Cys Gln Thr Thr Cys Cys Arg
20

<210> SEQ ID NO 623
<211> LENGTH: 10
<212> TYPE: PRT
<213> ORGANISM: Homo sapiens

<400> SEQUENCE: 623

Ser Ser Gly Ala Val Ser Thr Cys Ile Arg
1 5 10

<210> SEQ ID NO 624
<211> LENGTH: 9
<212> TYPE: PRT
<213> ORGANISM: Homo sapiens

<400> SEQUENCE: 624

Ser Ser Gly Gly Ser Ser Ser Val Arg
1 5

<210> SEQ ID NO 625
<211> LENGTH: 12
<212> TYPE: PRT
<213> ORGANISM: Homo sapiens

<400> SEQUENCE: 625

Ser Ser Pro Cys Gln Thr Ser Cys Tyr His Pro Arg
1 5 10

<210> SEQ ID NO 626
<211> LENGTH: 47
<212> TYPE: PRT
<213> ORGANISM: Homo sapiens

<400> SEQUENCE: 626

Ser Ser Ser Glu Gln Leu Gln Ser Tyr Gln Val Glu Ile Ile Glu Leu
1 5 10 15

Arg Arg Thr Val Asn Ala Leu Glu Ile Glu Leu Gln Ala Gln His Asn
20 25 30

Leu Arg Asp Ser Leu Glu Asn Thr Leu Thr Glu Ser Glu Ala Arg
35 40 45

<210> SEQ ID NO 627
<211> LENGTH: 15
<212> TYPE: PRT
<213> ORGANISM: Homo sapiens

<400> SEQUENCE: 627

Ser Ser Ser Pro Cys Lys Leu Pro Ser Leu Ser Pro Val Ala Arg
1 5 10 15

<210> SEQ ID NO 628
<211> LENGTH: 27
<212> TYPE: PRT
<213> ORGANISM: Homo sapiens

<400> SEQUENCE: 628

Ser Ser Thr Met Gly Ala Leu Arg Asp Tyr Ala Asp Ala Asp Ile Asn
1 5 10 15

Met Ala Phe Leu Asp Ser Tyr Phe Ser Glu Lys
20 25

<210> SEQ ID NO 629
<211> LENGTH: 11
<212> TYPE: PRT
<213> ORGANISM: Homo sapiens

<400> SEQUENCE: 629

Ser Thr Cys Cys Gln Pro Ser Cys Val Ile Arg
1 5 10

<210> SEQ ID NO 630
<211> LENGTH: 11
<212> TYPE: PRT
<213> ORGANISM: Homo sapiens

<400> SEQUENCE: 630

Ser Thr Gly Pro Cys Ile Ser Lys Pro Cys Gly
1 5 10

<210> SEQ ID NO 631
<211> LENGTH: 12
<212> TYPE: PRT
<213> ORGANISM: Homo sapiens

<400> SEQUENCE: 631

Ser Thr Gly Pro Cys Ile Ser Lys Pro Cys Gly Leu
1 5 10

<210> SEQ ID NO 632
<211> LENGTH: 13
<212> TYPE: PRT
<213> ORGANISM: Homo sapiens

<400> SEQUENCE: 632

Ser Thr Gly Pro Cys Ile Ser Lys Pro Cys Gly Leu Arg
1 5 10

<210> SEQ ID NO 633
<211> LENGTH: 36
<212> TYPE: PRT
<213> ORGANISM: Homo sapiens

<400> SEQUENCE: 633

Ser Thr Pro Cys Cys Gln Pro Ile Cys Cys Gly Ser Ser Cys Cys Gly
1 5 10 15

Gln Thr Ser Cys Gly Ser Ser Cys Gly Gln Ser Ser Ser Cys Ala Pro
20 25 30

Val Tyr Cys Arg
35

<210> SEQ ID NO 634
<211> LENGTH: 12
<212> TYPE: PRT
<213> ORGANISM: Homo sapiens

<400> SEQUENCE: 634

Ser Thr Ser Cys Arg Pro Leu Ser Tyr Leu Ser Arg
1 5 10

<210> SEQ ID NO 635
<211> LENGTH: 55
<212> TYPE: PRT
<213> ORGANISM: Homo sapiens

<400> SEQUENCE: 635

Ser Thr Ser Gly Thr Cys Ser Ser Ser Cys Cys Gln Pro Ser Cys Cys
1 5 10 15

Glu Thr Ser Cys Cys Gln Pro Ser Cys Cys Gln Thr Ser Ser Cys Arg
20 25 30

Thr Gly Cys Gly Ile Gly Gly Gly Ile Gly Tyr Gly Gln Glu Gly Ser
35 40 45

Ser Gly Ala Val Ser Thr Arg
50 55

<210> SEQ ID NO 636
<211> LENGTH: 55
<212> TYPE: PRT
<213> ORGANISM: Homo sapiens

<400> SEQUENCE: 636

Ser Thr Ser Gly Thr Cys Ser Ser Ser Cys Cys Gln Pro Ser Cys Cys
1 5 10 15

Glu Thr Ser Cys Cys Gln Pro Ser Cys Cys Gln Thr Ser Ser Cys Arg
20 25 30

Thr Gly Cys Gly Thr Gly Gly Gly Ile Gly Tyr Gly Gln Glu Gly Ser
35 40 45

Ser Gly Ala Val Ser Thr Arg
50 55

<210> SEQ ID NO 637
<211> LENGTH: 55
<212> TYPE: PRT
<213> ORGANISM: Homo sapiens

<400> SEQUENCE: 637

Ser Thr Ser Gly Thr Cys Ser Ser Ser Cys Cys Gln Pro Ser Cys Cys
1 5 10 15

Glu Thr Ser Cys Cys Gln Pro Ser Cys Cys Gln Thr Ser Ser Cys Arg
20 25 30

Thr Gly Cys Gly Thr Gly Gly Gly Ile Gly Tyr Gly Gln Glu Gly Ser
35 40 45

Ser Gly Ala Val Ser Thr Arg
50 55

<210> SEQ ID NO 638
<211> LENGTH: 53
<212> TYPE: PRT
<213> ORGANISM: Homo sapiens

<400> SEQUENCE: 638

Ser Thr Thr Tyr Ser Arg Pro Leu Thr Phe Val Ser Ser Gly Ser Gln
1 5 10 15

Pro Leu Gly Gly Ile Ser Ser Val Cys Gln Pro Val Gly Gly Ile Ser
20 25 30

Thr Val Cys Gln Pro Val Gly Gly Val Ser Thr Val Cys Gln Pro Ala
35 40 45

Cys Gly Val Ser Arg
50

<210> SEQ ID NO 639
<211> LENGTH: 10
<212> TYPE: PRT
<213> ORGANISM: Homo sapiens

<400> SEQUENCE: 639

Ser Thr Val Asn Ala Leu Glu Val Glu Arg
1 5 10

<210> SEQ ID NO 640
<211> LENGTH: 26
<212> TYPE: PRT
<213> ORGANISM: Homo sapiens

<400> SEQUENCE: 640

Ser Tyr Gly Thr Gly Cys Gly Ile Gly Gly Gly Ile Gly Tyr Gly Gln
1 5 10 15

Glu Gly Ser Ser Gly Ala Val Ser Thr Arg
20 25

<210> SEQ ID NO 641
<211> LENGTH: 8
<212> TYPE: PRT
<213> ORGANISM: Homo sapiens

<400> SEQUENCE: 641

Ser Tyr Lys Pro Ile Ile Leu Arg
1 5

<210> SEQ ID NO 642
<211> LENGTH: 9
<212> TYPE: PRT
<213> ORGANISM: Homo sapiens

<400> SEQUENCE: 642

Ser Tyr Val Ser Ser Pro Cys Cys Arg
1 5

<210> SEQ ID NO 643
<211> LENGTH: 10
<212> TYPE: PRT
<213> ORGANISM: Homo sapiens

<400> SEQUENCE: 643

Thr Ala Cys Gln Pro Thr Cys Tyr Gln Arg
1 5 10

<210> SEQ ID NO 644
<211> LENGTH: 39
<212> TYPE: PRT
<213> ORGANISM: Homo sapiens

<400> SEQUENCE: 644

Thr Ala Ser Ala Leu Glu Ile Glu Leu Gln Ala Gln Gln Ser Leu Thr
1 5 10 15

Glu Ser Leu Glu Cys Thr Val Ala Glu Thr Glu Ala Gln Tyr Ser Ser
20 25 30

Gln Leu Ala Gln Ile Gln Arg
35

<210> SEQ ID NO 645
<211> LENGTH: 12
<212> TYPE: PRT
<213> ORGANISM: Homo sapiens

<400> SEQUENCE: 645

Thr Ala Thr Glu Asn Glu Phe Val Gly Leu Lys Lys
1 5 10

<210> SEQ ID NO 646
<211> LENGTH: 43
<212> TYPE: PRT
<213> ORGANISM: Homo sapiens

<400> SEQUENCE: 646

Thr Cys Tyr His Pro Thr Thr Val Cys Leu Pro Gly Cys Leu Asn Gln

```
1               5                   10                  15

Ser Cys Gly Ser Ser Cys Cys Gln Pro Cys Cys Arg Pro Ala Cys Cys
            20                  25                  30

Glu Thr Thr Cys Phe Gln Pro Thr Cys Val Tyr
        35                  40


<210> SEQ ID NO 647
<211> LENGTH: 43
<212> TYPE: PRT
<213> ORGANISM: Homo sapiens

<400> SEQUENCE: 647

Thr Cys Tyr His Pro Thr Thr Val Cys Leu Pro Gly Cys Leu Asn Gln
1               5                   10                  15

Ser Cys Gly Ser Ser Cys Cys Gln Pro Cys Cys Arg Pro Ala Cys Cys
            20                  25                  30

Glu Thr Thr Cys Phe Gln Pro Thr Cys Val Tyr
        35                  40


<210> SEQ ID NO 648
<211> LENGTH: 23
<212> TYPE: PRT
<213> ORGANISM: Homo sapiens

<400> SEQUENCE: 648

Thr Gly Cys Gly Thr Gly Gly Gly Ile Gly Tyr Gly Gln Glu Gly Ser
1               5                   10                  15

Ser Gly Ala Val Ser Thr Arg
            20


<210> SEQ ID NO 649
<211> LENGTH: 23
<212> TYPE: PRT
<213> ORGANISM: Homo sapiens

<400> SEQUENCE: 649

Thr Gly Cys Gly Thr Gly Gly Gly Ile Gly Tyr Gly Gln Glu Gly Ser
1               5                   10                  15

Ser Gly Ala Val Ser Thr Arg
            20


<210> SEQ ID NO 650
<211> LENGTH: 11
<212> TYPE: PRT
<213> ORGANISM: Homo sapiens

<400> SEQUENCE: 650

Thr Gly Gly Phe Gly Ser His Ser Val Cys Arg
1               5                   10


<210> SEQ ID NO 651
<211> LENGTH: 15
<212> TYPE: PRT
<213> ORGANISM: Homo sapiens

<400> SEQUENCE: 651

Thr Gly Gly Phe Gly Ser His Ser Val Cys Arg Gly Phe Arg Ala
1               5                   10                  15


<210> SEQ ID NO 652
<211> LENGTH: 44
<212> TYPE: PRT
```

<213> ORGANISM: Homo sapiens

<400> SEQUENCE: 652

Thr Gly Ser Cys Asn Ser Pro Cys Leu Val Gly Asn Cys Ala Trp Cys
1 5 10 15

Glu Asp Gly Val Ser Thr Ser Asn Glu Lys Glu Thr Met Gln Phe Leu
20 25 30

Asn Asp Arg Leu Ala Ser Tyr Leu Glu Lys Val Arg
35 40

<210> SEQ ID NO 653
<211> LENGTH: 40
<212> TYPE: PRT
<213> ORGANISM: Homo sapiens

<400> SEQUENCE: 653

Thr Ile Cys Ile Asp Ser Pro Ser Val Leu Ile Ser Val Asn Glu His
1 5 10 15

Ser Tyr Gly Ser Pro Phe Thr Phe Cys Val Val Asp Glu Pro Pro Gly
20 25 30

Thr Ala Asp Met Trp Asp Val Arg
35 40

<210> SEQ ID NO 654
<211> LENGTH: 14
<212> TYPE: PRT
<213> ORGANISM: Homo sapiens

<400> SEQUENCE: 654

Thr Lys Glu Glu Ile Asn Glu Leu Asn Cys Met Ile Gln Arg
1 5 10

<210> SEQ ID NO 655
<211> LENGTH: 16
<212> TYPE: PRT
<213> ORGANISM: Homo sapiens

<400> SEQUENCE: 655

Thr Asn Cys Ser Ala Arg Pro Ile Cys Val Pro Cys Pro Gly Gly Arg
1 5 10 15

<210> SEQ ID NO 656
<211> LENGTH: 17
<212> TYPE: PRT
<213> ORGANISM: Homo sapiens

<400> SEQUENCE: 656

Thr Asn Cys Ser Ala Arg Pro Ile Cys Val Pro Cys Pro Gly Gly Arg
1 5 10 15

Phe

<210> SEQ ID NO 657
<211> LENGTH: 16
<212> TYPE: PRT
<213> ORGANISM: Homo sapiens

<400> SEQUENCE: 657

Thr Asn Tyr Ser Pro Arg Pro Ile Cys Val Pro Cys Pro Gly Gly Arg
1 5 10 15

<210> SEQ ID NO 658
<211> LENGTH: 17

<212> TYPE: PRT
<213> ORGANISM: Homo sapiens

<400> SEQUENCE: 658

Thr Asn Tyr Ser Pro Arg Pro Ile Cys Val Pro Cys Pro Gly Gly Arg
1 5 10 15

Phe

<210> SEQ ID NO 659
<211> LENGTH: 7
<212> TYPE: PRT
<213> ORGANISM: Homo sapiens

<400> SEQUENCE: 659

Thr Ser Cys Tyr Gln Pro Arg
1 5

<210> SEQ ID NO 660
<211> LENGTH: 7
<212> TYPE: PRT
<213> ORGANISM: Homo sapiens

<400> SEQUENCE: 660

Thr Ser Phe Cys Gly Phe Arg
1 5

<210> SEQ ID NO 661
<211> LENGTH: 13
<212> TYPE: PRT
<213> ORGANISM: Homo sapiens

<400> SEQUENCE: 661

Thr Ser Ile Ala Val Asp Thr Ile Ile Asn Gln Lys Arg
1 5 10

<210> SEQ ID NO 662
<211> LENGTH: 32
<212> TYPE: PRT
<213> ORGANISM: Homo sapiens

<400> SEQUENCE: 662

Thr Ser Val Val Val Lys Leu Asp Asn Ser Arg Asp Leu Asn Met Asp
1 5 10 15

Cys Met Val Ala Glu Ile Lys Ala Gln Tyr Asp Asp Ile Ala Thr Arg
20 25 30

<210> SEQ ID NO 663
<211> LENGTH: 54
<212> TYPE: PRT
<213> ORGANISM: Homo sapiens

<400> SEQUENCE: 663

Thr Thr Cys Cys Gln Pro Thr Cys Val Thr Ser Cys Cys Gln Pro Ser
1 5 10 15

Cys Cys Ser Thr Pro Cys Cys Gln Pro Ile Cys Cys Gly Ser Ser Cys
20 25 30

Cys Gly Gln Thr Ser Cys Gly Ser Ser Cys Gly Gln Ser Ser Ser Cys
35 40 45

Ala Pro Val Tyr Cys Arg
50

<210> SEQ ID NO 664

<211> LENGTH: 10
<212> TYPE: PRT
<213> ORGANISM: Homo sapiens

<400> SEQUENCE: 664

Thr Thr Cys Cys Arg Pro Ser Cys Cys Gly
1               5                   10

<210> SEQ ID NO 665
<211> LENGTH: 11
<212> TYPE: PRT
<213> ORGANISM: Homo sapiens

<400> SEQUENCE: 665

Thr Thr Cys Cys Arg Pro Ser Cys Cys Gly Ser
1               5                   10

<210> SEQ ID NO 666
<211> LENGTH: 12
<212> TYPE: PRT
<213> ORGANISM: Homo sapiens

<400> SEQUENCE: 666

Thr Thr Cys Cys Arg Pro Ser Cys Cys Gly Ser Ser
1               5                   10

<210> SEQ ID NO 667
<211> LENGTH: 13
<212> TYPE: PRT
<213> ORGANISM: Homo sapiens

<400> SEQUENCE: 667

Thr Thr Cys Cys Arg Pro Ser Cys Cys Gly Ser Ser Cys
1               5                   10

<210> SEQ ID NO 668
<211> LENGTH: 12
<212> TYPE: PRT
<213> ORGANISM: Homo sapiens

<400> SEQUENCE: 668

Thr Thr Cys Cys Arg Pro Ser Cys Cys Arg Pro Arg
1               5                   10

<210> SEQ ID NO 669
<211> LENGTH: 29
<212> TYPE: PRT
<213> ORGANISM: Homo sapiens

<400> SEQUENCE: 669

Thr Thr Cys Cys Arg Pro Ser Cys Cys Val Ser Ser Cys Phe Arg Pro
1               5                   10                  15

Gln Cys Cys Gln Ser Val Cys Cys Gln Pro Thr Cys Cys
            20                  25

<210> SEQ ID NO 670
<211> LENGTH: 35
<212> TYPE: PRT
<213> ORGANISM: Homo sapiens

<400> SEQUENCE: 670

Thr Thr Cys Cys Arg Thr Thr Cys Cys Arg Pro Ser Cys Cys Val Ser
1               5                   10                  15

Ser Cys Phe Arg Pro Gln Cys Cys Gln Ser Val Cys Cys Gln Pro Thr

```
            20                  25                  30

Cys Cys Arg
        35


<210> SEQ ID NO 671
<211> LENGTH: 45
<212> TYPE: PRT
<213> ORGANISM: Homo sapiens

<400> SEQUENCE: 671

Thr Thr Cys Cys Arg Thr Thr Cys Cys Arg Pro Ser Cys Cys Val Ser
1               5                   10                  15

Ser Cys Phe Arg Pro Gln Cys Cys Gln Ser Val Cys Cys Gln Pro Thr
            20                  25                  30

Cys Cys Arg Pro Ser Cys Gly Gln Thr Thr Cys Cys Arg
        35                  40                  45


<210> SEQ ID NO 672
<211> LENGTH: 18
<212> TYPE: PRT
<213> ORGANISM: Homo sapiens

<400> SEQUENCE: 672

Thr Thr Cys Phe Gln Pro Thr Cys Val Ser Ser Ser Cys Gln Pro Ser
1               5                   10                  15

Cys Cys


<210> SEQ ID NO 673
<211> LENGTH: 18
<212> TYPE: PRT
<213> ORGANISM: Homo sapiens

<400> SEQUENCE: 673

Thr Thr Cys Phe Gln Pro Thr Cys Val Tyr Ser Cys Cys Gln Pro Phe
1               5                   10                  15

Cys Cys


<210> SEQ ID NO 674
<211> LENGTH: 13
<212> TYPE: PRT
<213> ORGANISM: Homo sapiens

<400> SEQUENCE: 674

Thr Thr Cys Gly Gly Gly Ser Cys Gly Gln Gly Arg Tyr
1               5                   10


<210> SEQ ID NO 675
<211> LENGTH: 50
<212> TYPE: PRT
<213> ORGANISM: Homo sapiens

<400> SEQUENCE: 675

Thr Thr Cys Trp Lys Pro Thr Thr Val Thr Thr Cys Ser Ser Thr Pro
1               5                   10                  15

Cys Cys Gln Pro Ser Cys Cys Val Ser Ser Cys Cys Gln Pro Cys Cys
            20                  25                  30

His Pro Thr Cys Cys Gln Asn Thr Cys Cys Arg Thr Thr Cys Cys Gln
        35                  40                  45

Pro Ile
    50
```

<210> SEQ ID NO 676
<211> LENGTH: 16
<212> TYPE: PRT
<213> ORGANISM: Homo sapiens

<400> SEQUENCE: 676

Thr Thr Cys Trp Lys Pro Thr Thr Val Thr Thr Cys Ser Ser Thr Ser
1 5 10 15

<210> SEQ ID NO 677
<211> LENGTH: 17
<212> TYPE: PRT
<213> ORGANISM: Homo sapiens

<400> SEQUENCE: 677

Thr Thr Cys Trp Lys Pro Thr Thr Val Thr Thr Cys Ser Ser Thr Ser
1 5 10 15

Cys

<210> SEQ ID NO 678
<211> LENGTH: 51
<212> TYPE: PRT
<213> ORGANISM: Homo sapiens

<400> SEQUENCE: 678

Thr Thr Cys Trp Lys Pro Thr Thr Val Thr Thr Cys Ser Ser Thr Ser
1 5 10 15

Cys Cys Gln Pro Ser Cys Cys Val Ser Ser Cys Cys Gln Pro Cys Cys
20 25 30

His Pro Thr Cys Cys Gln Asn Thr Cys Cys Arg Thr Thr Cys Cys Gln
35 40 45

Pro Thr Cys
50

<210> SEQ ID NO 679
<211> LENGTH: 11
<212> TYPE: PRT
<213> ORGANISM: Homo sapiens

<400> SEQUENCE: 679

Thr Thr Ser Cys Arg Pro Ser Cys Cys Val Ser
1 5 10

<210> SEQ ID NO 680
<211> LENGTH: 12
<212> TYPE: PRT
<213> ORGANISM: Homo sapiens

<400> SEQUENCE: 680

Thr Thr Ser Cys Arg Pro Ser Cys Cys Val Ser Ser
1 5 10

<210> SEQ ID NO 681
<211> LENGTH: 11
<212> TYPE: PRT
<213> ORGANISM: Homo sapiens

<400> SEQUENCE: 681

Thr Val Asp Leu Ile Leu Glu Leu Leu Asp Arg
1 5 10

<210> SEQ ID NO 682

<211> LENGTH: 14
<212> TYPE: PRT
<213> ORGANISM: Homo sapiens

<400> SEQUENCE: 682

Thr Val Gly Thr Pro Cys Ser Pro Cys Pro Gln Gly Arg Tyr
1 5 10

<210> SEQ ID NO 683
<211> LENGTH: 16
<212> TYPE: PRT
<213> ORGANISM: Homo sapiens

<400> SEQUENCE: 683

Thr Val Asn Ser Leu Glu Ile Glu Leu Gln Ala Gln His Asn Leu Arg
1 5 10 15

<210> SEQ ID NO 684
<211> LENGTH: 29
<212> TYPE: PRT
<213> ORGANISM: Homo sapiens

<400> SEQUENCE: 684

Thr Val Asn Ser Leu Glu Ile Glu Leu Gln Ala Gln His Asn Leu Arg
1 5 10 15

Asp Ser Leu Glu Asn Thr Leu Thr Glu Ser Glu Ala Arg
20 25

<210> SEQ ID NO 685
<211> LENGTH: 52
<212> TYPE: PRT
<213> ORGANISM: Homo sapiens

<400> SEQUENCE: 685

Thr Val Asn Ser Leu Glu Ile Glu Leu Gln Ala Gln His Asn Leu Arg
1 5 10 15

Asp Ser Leu Glu Asn Thr Leu Thr Glu Ser Glu Ala Arg Tyr Ser Ser
20 25 30

Gln Leu Ser Gln Val Gln Ser Leu Ile Thr Asn Val Glu Ser Gln Leu
35 40 45

Ala Glu Ile Arg
50

<210> SEQ ID NO 686
<211> LENGTH: 29
<212> TYPE: PRT
<213> ORGANISM: Homo sapiens

<400> SEQUENCE: 686

Thr Val Asn Thr Leu Glu Ile Glu Leu Gln Ala Gln His Ser Leu Arg
1 5 10 15

Asp Ser Leu Glu Asn Met Leu Thr Glu Ser Glu Ala Arg
20 25

<210> SEQ ID NO 687
<211> LENGTH: 8
<212> TYPE: PRT
<213> ORGANISM: Homo sapiens

<400> SEQUENCE: 687

Thr Tyr Leu Ser Ser Ser Cys Arg
1 5

<210> SEQ ID NO 688
<211> LENGTH: 19
<212> TYPE: PRT
<213> ORGANISM: Homo sapiens

<400> SEQUENCE: 688

Val Cys Cys Gln Pro Thr Cys Cys Arg Pro Ser Cys Gly Gln Thr Thr
1 5 10 15

Cys Cys Arg

<210> SEQ ID NO 689
<211> LENGTH: 28
<212> TYPE: PRT
<213> ORGANISM: Homo sapiens

<400> SEQUENCE: 689

Val Cys Ser Asp Gln Gly Cys Gly Gln Val Leu Cys Gln Glu Thr Cys
1 5 10 15

Cys Arg Pro Ser Cys Cys Gln Thr Thr Cys Cys Arg
20 25

<210> SEQ ID NO 690
<211> LENGTH: 8
<212> TYPE: PRT
<213> ORGANISM: Homo sapiens

<400> SEQUENCE: 690

Val Glu Leu Glu Asn Leu Ile Arg
1 5

<210> SEQ ID NO 691
<211> LENGTH: 14
<212> TYPE: PRT
<213> ORGANISM: Homo sapiens

<400> SEQUENCE: 691

Val His Ser Leu Glu Glu Thr Asn Ala Glu Leu Glu Ser Arg
1 5 10

<210> SEQ ID NO 692
<211> LENGTH: 17
<212> TYPE: PRT
<213> ORGANISM: Homo sapiens

<400> SEQUENCE: 692

Val Ile Val Cys Asn Thr Lys Leu Asp Asn Asn Trp Gly Lys Glu Glu
1 5 10 15

Arg

<210> SEQ ID NO 693
<211> LENGTH: 28
<212> TYPE: PRT
<213> ORGANISM: Homo sapiens

<400> SEQUENCE: 693

Val Lys Leu Asp Asn Ser Arg Asp Leu Asn Met Asp Cys Met Val Ala
1 5 10 15

Glu Ile Lys Ala Gln Tyr Asp Asp Ile Ala Thr Arg
20 25

<210> SEQ ID NO 694
<211> LENGTH: 18

<212> TYPE: PRT
<213> ORGANISM: Homo sapiens

<400> SEQUENCE: 694

Val Leu Glu Glu Met Arg Cys Gln Tyr Glu Ala Met Val Glu Ala Asn
1 5 10 15

His Arg

<210> SEQ ID NO 695
<211> LENGTH: 11
<212> TYPE: PRT
<213> ORGANISM: Homo sapiens

<400> SEQUENCE: 695

Val Leu Asn Asp Gly Thr Val Tyr Thr Ala Arg
1 5 10

<210> SEQ ID NO 696
<211> LENGTH: 17
<212> TYPE: PRT
<213> ORGANISM: Homo sapiens

<400> SEQUENCE: 696

Val Leu Asn Glu Thr Arg Ser Gln Tyr Glu Val Leu Val Glu Thr Asn
1 5 10 15

Arg

<210> SEQ ID NO 697
<211> LENGTH: 18
<212> TYPE: PRT
<213> ORGANISM: Homo sapiens

<400> SEQUENCE: 697

Val Leu Asn Glu Thr Arg Ser Gln Tyr Glu Val Leu Val Glu Thr Asn
1 5 10 15

Arg Arg

<210> SEQ ID NO 698
<211> LENGTH: 10
<212> TYPE: PRT
<213> ORGANISM: Homo sapiens

<400> SEQUENCE: 698

Val Asn Leu His His Val Asp Phe Leu Arg
1 5 10

<210> SEQ ID NO 699
<211> LENGTH: 28
<212> TYPE: PRT
<213> ORGANISM: Homo sapiens

<400> SEQUENCE: 699

Val Gln Cys Asp Leu Gln Lys Ala Asn Ser Ser Ala Thr Glu Thr Ile
1 5 10 15

Asn Lys Leu Lys Val Gln Glu Gln Glu Leu Thr Arg
20 25

<210> SEQ ID NO 700
<211> LENGTH: 10
<212> TYPE: PRT
<213> ORGANISM: Homo sapiens

<400> SEQUENCE: 700

Val Gln Glu Gln Glu Leu Thr Cys Leu Arg
1 5 10

<210> SEQ ID NO 701
<211> LENGTH: 13
<212> TYPE: PRT
<213> ORGANISM: Homo sapiens

<400> SEQUENCE: 701

Val Arg Phe Asp Ile Leu Pro Ser Gln Ser Gly Thr Lys
1 5 10

<210> SEQ ID NO 702
<211> LENGTH: 21
<212> TYPE: PRT
<213> ORGANISM: Homo sapiens

<400> SEQUENCE: 702

Val Arg Phe Leu Glu Gln Gln Asn Lys Leu Leu Glu Thr Lys Leu Pro
1 5 10 15

Phe Tyr Gln Asn Arg
20

<210> SEQ ID NO 703
<211> LENGTH: 12
<212> TYPE: PRT
<213> ORGANISM: Homo sapiens

<400> SEQUENCE: 703

Val Arg Gln Leu Glu Arg Asp Asn Ala Glu Leu Lys
1 5 10

<210> SEQ ID NO 704
<211> LENGTH: 16
<212> TYPE: PRT
<213> ORGANISM: Homo sapiens

<400> SEQUENCE: 704

Val Arg Gln Leu Glu Arg Asp Asn Ala Glu Leu Lys Asn Leu Ile Arg
1 5 10 15

<210> SEQ ID NO 705
<211> LENGTH: 16
<212> TYPE: PRT
<213> ORGANISM: Homo sapiens

<400> SEQUENCE: 705

Val Arg Gln Leu Glu Arg Asp Asn Val Glu Leu Glu Asn Leu Ile Arg
1 5 10 15

<210> SEQ ID NO 706
<211> LENGTH: 18
<212> TYPE: PRT
<213> ORGANISM: Homo sapiens

<400> SEQUENCE: 706

Val Arg Gln Leu Glu Arg Asp Asn Val Glu Leu Glu Asn Leu Ile Arg
1 5 10 15

Glu Arg

<210> SEQ ID NO 707
<211> LENGTH: 16
<212> TYPE: PRT

<213> ORGANISM: Homo sapiens

<400> SEQUENCE: 707

Val Arg Gln Leu Glu Arg His Asn Ala Glu Leu Glu Asn Leu Ile Arg
1 5 10 15

<210> SEQ ID NO 708
<211> LENGTH: 18
<212> TYPE: PRT
<213> ORGANISM: Homo sapiens

<400> SEQUENCE: 708

Val Arg Gln Leu Glu Arg His Asn Ala Glu Leu Glu Asn Leu Ile Arg
1 5 10 15

Glu Arg

<210> SEQ ID NO 709
<211> LENGTH: 9
<212> TYPE: PRT
<213> ORGANISM: Homo sapiens

<400> SEQUENCE: 709

Val Arg Trp Cys Arg Pro Asp Cys Arg
1 5

<210> SEQ ID NO 710
<211> LENGTH: 11
<212> TYPE: PRT
<213> ORGANISM: Homo sapiens

<400> SEQUENCE: 710

Val Ser Ala Met Tyr Ser Ser Ser Pro Cys Lys
1 5 10

<210> SEQ ID NO 711
<211> LENGTH: 20
<212> TYPE: PRT
<213> ORGANISM: Homo sapiens

<400> SEQUENCE: 711

Val Ser Ala Met Tyr Ser Ser Ser Pro Cys Lys Leu Pro Ser Leu Ser
1 5 10 15

Pro Val Ala Arg
20

<210> SEQ ID NO 712
<211> LENGTH: 22
<212> TYPE: PRT
<213> ORGANISM: Homo sapiens

<400> SEQUENCE: 712

Val Ser Cys His Thr Thr Cys Tyr Arg Pro Thr Cys Val Ile Ser Ser
1 5 10 15

Cys Pro Arg Pro Val Cys
20

<210> SEQ ID NO 713
<211> LENGTH: 24
<212> TYPE: PRT
<213> ORGANISM: Homo sapiens

<400> SEQUENCE: 713

Val Ser Cys His Thr Thr Cys Tyr Arg Pro Thr Cys Val Ile Ser Ser 1 5 10 15

Cys Pro Arg Pro Val Cys Cys Ala
20

<210> SEQ ID NO 714
<211> LENGTH: 14
<212> TYPE: PRT
<213> ORGANISM: Homo sapiens

<400> SEQUENCE: 714

Val Ser Gly Asn Ser Cys Gly Pro Cys Gly Thr Ser Gln Lys
1 5 10

<210> SEQ ID NO 715
<211> LENGTH: 17
<212> TYPE: PRT
<213> ORGANISM: Homo sapiens

<400> SEQUENCE: 715

Val Ser Ser Asp Pro Ser Asn Ser Asn Val Val Val Gly Thr Thr Asn
1 5 10 15

Ala

<210> SEQ ID NO 716
<211> LENGTH: 23
<212> TYPE: PRT
<213> ORGANISM: Homo sapiens

<400> SEQUENCE: 716

Val Ser Ser Asp Pro Ser Asn Ser Asn Val Val Val Gly Thr Thr Asn
1 5 10 15

Ala Cys Ala Pro Ser Ala Arg
20

<210> SEQ ID NO 717
<211> LENGTH: 43
<212> TYPE: PRT
<213> ORGANISM: Homo sapiens

<400> SEQUENCE: 717

Val Ser Ser Gly Ser Gln Pro Leu Gly Gly Ile Ser Ser Val Cys Gln
1 5 10 15

Pro Val Gly Gly Ile Ser Thr Val Cys Gln Pro Val Gly Gly Val Ser
20 25 30

Thr Val Cys Gln Pro Ala Cys Gly Val Ser Arg
35 40

<210> SEQ ID NO 718
<211> LENGTH: 18
<212> TYPE: PRT
<213> ORGANISM: Homo sapiens

<400> SEQUENCE: 718

Val Ser Ser Ser Glu Gln Leu Gln Ser Tyr Gln Val Glu Ile Ile Glu
1 5 10 15

Leu Arg

<210> SEQ ID NO 719
<211> LENGTH: 53
<212> TYPE: PRT
<213> ORGANISM: Homo sapiens

<400> SEQUENCE: 719

Val Ser Val Glu Leu Thr Asn Ser Leu Phe Lys His Asp Pro Ala Ala
1 5 10 15

Trp Glu Ala Ala Gln Ser Met Ile Pro Ile Asn Glu Pro Tyr Gly Asp
20 25 30

Asp Leu Asp Ala Thr Tyr Arg Pro Met Tyr Ser Ser Asp Val Pro Leu
35 40 45

Asp Pro Leu Glu Met
50

<210> SEQ ID NO 720
<211> LENGTH: 29
<212> TYPE: PRT
<213> ORGANISM: Homo sapiens

<400> SEQUENCE: 720

Val Val Lys Leu Asp Asn Ser Arg Asp Leu Asn Met Asp Cys Met Val
1 5 10 15

Ala Glu Ile Lys Ala Gln Tyr Asp Asp Ile Ala Thr Arg
20 25

<210> SEQ ID NO 721
<211> LENGTH: 30
<212> TYPE: PRT
<213> ORGANISM: Homo sapiens

<400> SEQUENCE: 721

Val Val Val Lys Leu Asp Asn Ser Arg Asp Leu Asn Met Asp Cys Met
1 5 10 15

Val Ala Glu Ile Lys Ala Gln Tyr Asp Asp Ile Ala Thr Arg
20 25 30

<210> SEQ ID NO 722
<211> LENGTH: 29
<212> TYPE: PRT
<213> ORGANISM: Homo sapiens

<400> SEQUENCE: 722

Trp Glu Leu Leu Gln Gln Met Asn Val Asp Thr Arg Pro Ile Asn Leu
1 5 10 15

Glu Pro Ile Phe Gln Gly Tyr Ile Asp Ser Leu Lys Arg
20 25

<210> SEQ ID NO 723
<211> LENGTH: 8
<212> TYPE: PRT
<213> ORGANISM: Homo sapiens

<400> SEQUENCE: 723

Trp Leu Tyr Glu Glu Glu Ile Arg
1 5

<210> SEQ ID NO 724
<211> LENGTH: 22
<212> TYPE: PRT
<213> ORGANISM: Homo sapiens

<400> SEQUENCE: 724

Trp Leu Tyr Glu Glu Glu Ile Arg Val Leu Gln Ser His Ile Ser Asp
1 5 10 15

Thr Ser Val Val Val Lys

20

<210> SEQ ID NO 725
<211> LENGTH: 33
<212> TYPE: PRT
<213> ORGANISM: Homo sapiens

<400> SEQUENCE: 725

Tyr Cys Gln Thr Thr Cys Cys Arg Thr Thr Ser Cys Arg Pro Ser Cys
1 5 10 15

Cys Val Ser Ser Cys Cys Arg Pro Gln Cys Cys Gln Thr Thr Cys Cys
20 25 30

Arg

<210> SEQ ID NO 726
<211> LENGTH: 20
<212> TYPE: PRT
<213> ORGANISM: Homo sapiens

<400> SEQUENCE: 726

Tyr Glu Glu Glu Val Ala Leu Gln Ala Thr Ala Glu Asn Glu Phe Val
1 5 10 15

Ala Leu Lys Lys
20

<210> SEQ ID NO 727
<211> LENGTH: 10
<212> TYPE: PRT
<213> ORGANISM: Homo sapiens

<400> SEQUENCE: 727

Tyr Glu Val Leu Val Glu Thr Asn Arg Arg
1 5 10

<210> SEQ ID NO 728
<211> LENGTH: 8
<212> TYPE: PRT
<213> ORGANISM: Homo sapiens

<400> SEQUENCE: 728

Tyr Gln Met Glu Gln Ser Leu Arg
1 5

<210> SEQ ID NO 729
<211> LENGTH: 53
<212> TYPE: PRT
<213> ORGANISM: Homo sapiens

<400> SEQUENCE: 729

Tyr Ser Leu Glu Asn Thr Leu Thr Glu Ser Glu Ala Arg Tyr Ser Ser
1 5 10 15

Gln Leu Ser Gln Val Gln Ser Leu Ile Thr Asn Val Glu Ser Gln Leu
20 25 30

Ala Glu Ile His Ser Asp Leu Glu Arg Gln Asn Gln Glu Tyr Gln Val
35 40 45

Leu Leu Asp Val Arg
50

<210> SEQ ID NO 730
<211> LENGTH: 23
<212> TYPE: PRT
<213> ORGANISM: Homo sapiens

<400> SEQUENCE: 730

Tyr Ser Ser Gln Leu Ala Gln Ile Gln Arg Leu Ile Asp Asn Leu Glu
1 5 10 15

Asn Gln Leu Ala Glu Ile Arg
20

<210> SEQ ID NO 731
<211> LENGTH: 23
<212> TYPE: PRT
<213> ORGANISM: Homo sapiens

<400> SEQUENCE: 731

Tyr Ser Ser Gln Leu Ala Gln Met Gln Cys Leu Ile Ser Thr Val Glu
1 5 10 15

Ala Gln Leu Ser Glu Ile Arg
20

<210> SEQ ID NO 732
<211> LENGTH: 28
<212> TYPE: PRT
<213> ORGANISM: Homo sapiens

<400> SEQUENCE: 732

Tyr Ser Ser Gln Leu Ala Gln Met Gln Cys Leu Ile Ser Thr Val Glu
1 5 10 15

Ala Gln Leu Ser Glu Ile Arg Cys Asp Leu Glu Arg
20 25

<210> SEQ ID NO 733
<211> LENGTH: 40
<212> TYPE: PRT
<213> ORGANISM: Homo sapiens

<400> SEQUENCE: 733

Tyr Ser Ser Gln Leu Ala Gln Met Gln Cys Leu Ile Ser Thr Val Glu
1 5 10 15

Ala Gln Leu Ser Glu Ile Arg Cys Asp Leu Glu Arg Gln Asn Gln Glu
20 25 30

Tyr Gln Val Leu Leu Asp Val Lys
35 40

<210> SEQ ID NO 734
<211> LENGTH: 28
<212> TYPE: PRT
<213> ORGANISM: Homo sapiens

<400> SEQUENCE: 734

Tyr Ser Ser Gln Leu Ala Gln Met Gln Cys Met Ile Thr Asn Val Glu
1 5 10 15

Ala Gln Leu Ala Glu Ile Gln Ala Asp Leu Glu Arg
20 25

<210> SEQ ID NO 735
<211> LENGTH: 40
<212> TYPE: PRT
<213> ORGANISM: Homo sapiens

<400> SEQUENCE: 735

Tyr Ser Ser Gln Leu Ala Gln Met Gln Cys Met Ile Thr Asn Val Glu
1 5 10 15

Ala Gln Leu Ala Glu Ile Gln Ala Asp Leu Glu Arg Gln Asn Gln Glu
20 25 30

Tyr Gln Val Leu Leu Asp Val Arg
35 40

<210> SEQ ID NO 736
<211> LENGTH: 40
<212> TYPE: PRT
<213> ORGANISM: Homo sapiens

<400> SEQUENCE: 736

Tyr Ser Ser Gln Leu Ala Gln Met Gln Cys Met Ile Thr Asn Val Glu
1 5 10 15

Ala Gln Leu Ala Glu Ile Gln Ala Glu Leu Glu Arg Gln Asn Gln Glu
20 25 30

Tyr Gln Val Leu Leu Asp Val Arg
35 40

<210> SEQ ID NO 737
<211> LENGTH: 40
<212> TYPE: PRT
<213> ORGANISM: Homo sapiens

<400> SEQUENCE: 737

Tyr Ser Ser Gln Leu Ala Gln Met Gln Cys Met Ile Thr Asn Val Glu
1 5 10 15

Ala Gln Leu Ala Glu Ile Gln Ala Glu Leu Glu Arg Gln Asn Gln Glu
20 25 30

Tyr Gln Val Leu Leu Asp Val Arg
35 40

<210> SEQ ID NO 738
<211> LENGTH: 28
<212> TYPE: PRT
<213> ORGANISM: Homo sapiens

<400> SEQUENCE: 738

Tyr Ser Ser Gln Leu Ala Gln Met Gln Cys Met Ile Thr Asn Val Glu
1 5 10 15

Ala Gln Leu Ala Glu Ile Arg Ala Glu Leu Glu Arg
20 25

<210> SEQ ID NO 739
<211> LENGTH: 40
<212> TYPE: PRT
<213> ORGANISM: Homo sapiens

<400> SEQUENCE: 739

Tyr Ser Ser Gln Leu Ala Gln Met Gln Cys Met Ile Thr Asn Val Glu
1 5 10 15

Ala Gln Leu Ala Glu Ile Arg Ala Glu Leu Glu Arg Gln Asn Gln Glu
20 25 30

Tyr Gln Val Leu Leu Asp Val Arg
35 40

<210> SEQ ID NO 740
<211> LENGTH: 23
<212> TYPE: PRT
<213> ORGANISM: Homo sapiens

<400> SEQUENCE: 740

Tyr Ser Ser Gln Leu Ser Gln Met Gln Ser Leu Ile Thr Asn Val Glu
1               5                   10                  15

Ser Gln Leu Ala Glu Ile Arg
            20

<210> SEQ ID NO 741
<211> LENGTH: 28
<212> TYPE: PRT
<213> ORGANISM: Homo sapiens

<400> SEQUENCE: 741

Tyr Ser Ser Gln Leu Ser Gln Val Gln Ser Leu Ile Thr Asn Val Glu
1               5                   10                  15

Ser Gln Leu Ala Glu Ile His Ser Asp Leu Glu Arg
            20                  25

<210> SEQ ID NO 742
<211> LENGTH: 40
<212> TYPE: PRT
<213> ORGANISM: Homo sapiens

<400> SEQUENCE: 742

Tyr Ser Ser Gln Leu Ser Gln Val Gln Ser Leu Ile Thr Asn Val Glu
1               5                   10                  15

Ser Gln Leu Ala Glu Ile His Ser Asp Leu Glu Arg Gln Asn Gln Glu
            20                  25                  30

Tyr Gln Val Leu Leu Asp Val Arg
        35                  40

<210> SEQ ID NO 743
<211> LENGTH: 40
<212> TYPE: PRT
<213> ORGANISM: Homo sapiens

<400> SEQUENCE: 743

Tyr Ser Ser Gln Leu Ser Gln Val Gln Ser Leu Ile Thr Asn Val Glu
1               5                   10                  15

Ser Gln Leu Ala Glu Ile Arg Cys Asp Leu Glu Arg Gln Asn Gln Glu
            20                  25                  30

Tyr Gln Val Leu Leu Asp Val Cys
        35                  40

<210> SEQ ID NO 744
<211> LENGTH: 40
<212> TYPE: PRT
<213> ORGANISM: Homo sapiens

<400> SEQUENCE: 744

Tyr Ser Ser Gln Leu Ser Gln Val Gln Ser Leu Ile Thr Asn Val Glu
1               5                   10                  15

Ser Gln Leu Ala Glu Ile Arg Cys Asp Leu Glu Trp Gln Asn Gln Glu
            20                  25                  30

Tyr Gln Val Leu Leu Asp Val Arg
        35                  40

<210> SEQ ID NO 745
<211> LENGTH: 16
<212> TYPE: PRT
<213> ORGANISM: Homo sapiens

<400> SEQUENCE: 745

Tyr Ser Ser Ser Pro Cys Lys Leu Pro Ser Leu Ser Pro Val Ala Arg
1 5 10 15

<210> SEQ ID NO 746
<211> LENGTH: 18
<212> TYPE: PRT
<213> ORGANISM: Homo sapiens

<400> SEQUENCE: 746

Tyr Val Ser Leu Ile Tyr Thr Asn Tyr Glu Ala Gly Lys Asp Asp Tyr
1 5 10 15

Val Lys

<210> SEQ ID NO 747
<211> LENGTH: 18
<212> TYPE: PRT
<213> ORGANISM: Homo sapiens

<400> SEQUENCE: 747

Tyr Val Ser Leu Ile Tyr Thr Asn Tyr Glu Val Gly Lys Asp Asp Tyr
1 5 10 15

Val Lys

<210> SEQ ID NO 748
<211> LENGTH: 18
<212> TYPE: PRT
<213> ORGANISM: Homo sapiens

<400> SEQUENCE: 748

Tyr Val Ser Leu Ile Tyr Thr Asn Tyr Glu Val Gly Lys Asp Asp Tyr
1 5 10 15

Val Lys

<210> SEQ ID NO 749
<211> LENGTH: 17
<212> TYPE: PRT
<213> ORGANISM: Homo sapiens

<400> SEQUENCE: 749

Ala Ala Ser Ser Gln Thr Pro Thr Met Cys Thr Thr Thr Val Thr Ile
1 5 10 15

Lys

<210> SEQ ID NO 750
<211> LENGTH: 10
<212> TYPE: PRT
<213> ORGANISM: Homo sapiens

<400> SEQUENCE: 750

Ala Glu Ala Glu Ala Leu Tyr Gln Ile Lys
1 5 10

<210> SEQ ID NO 751
<211> LENGTH: 11
<212> TYPE: PRT
<213> ORGANISM: Homo sapiens

<400> SEQUENCE: 751

Ala Gly Gly Ser Tyr Gly Phe Gly Gly Ala Arg
1 5 10

<210> SEQ ID NO 752

<211> LENGTH: 17
<212> TYPE: PRT
<213> ORGANISM: Homo sapiens

<400> SEQUENCE: 752

Ala Pro Tyr Pro Asn Tyr Asp Arg Asp Ile Leu Thr Ile Asp Ile Ser
1 5 10 15

Arg

<210> SEQ ID NO 753
<211> LENGTH: 9
<212> TYPE: PRT
<213> ORGANISM: Homo sapiens

<400> SEQUENCE: 753

Asp Ile Leu Thr Ile Asp Ile Ser Arg
1 5

<210> SEQ ID NO 754
<211> LENGTH: 17
<212> TYPE: PRT
<213> ORGANISM: Homo sapiens

<400> SEQUENCE: 754

Glu Glu Leu Gly His Leu Gln Asn Asp Leu Thr Ser Leu Glu Asn Asp
1 5 10 15

Lys

<210> SEQ ID NO 755
<211> LENGTH: 19
<212> TYPE: PRT
<213> ORGANISM: Homo sapiens

<400> SEQUENCE: 755

Glu Glu Leu Gly His Leu Gln Asn Asp Leu Thr Ser Leu Glu Asn Asp
1 5 10 15

Lys Met Arg

<210> SEQ ID NO 756
<211> LENGTH: 7
<212> TYPE: PRT
<213> ORGANISM: Homo sapiens

<400> SEQUENCE: 756

Glu Phe His Pro Val Leu Lys
1 5

<210> SEQ ID NO 757
<211> LENGTH: 20
<212> TYPE: PRT
<213> ORGANISM: Homo sapiens

<400> SEQUENCE: 757

Glu Phe His Pro Val Leu Lys Asn Pro Asp Asp Pro Asp Thr Val Asp
1 5 10 15

Val Ile Met His
20

<210> SEQ ID NO 758
<211> LENGTH: 24
<212> TYPE: PRT
<213> ORGANISM: Homo sapiens

<400> SEQUENCE: 758

Glu Phe His Pro Val Leu Lys Asn Pro Asp Asp Pro Asp Thr Val Asp
1               5                   10                  15

Val Ile Met His Met Leu Asp Arg
            20

<210> SEQ ID NO 759
<211> LENGTH: 28
<212> TYPE: PRT
<213> ORGANISM: Homo sapiens

<400> SEQUENCE: 759

Glu Gly Met Pro Ala Pro Phe Gly Asp Gln Ser His Pro Glu Pro Glu
1               5                   10                  15

Ser Trp Asn Ala Ala Gln His Cys Gln Gln Asp Arg
            20                  25

<210> SEQ ID NO 760
<211> LENGTH: 12
<212> TYPE: PRT
<213> ORGANISM: Homo sapiens

<400> SEQUENCE: 760

Glu Leu Leu Glu Lys Glu Phe His Pro Val Leu Lys
1               5                   10

<210> SEQ ID NO 761
<211> LENGTH: 23
<212> TYPE: PRT
<213> ORGANISM: Homo sapiens

<400> SEQUENCE: 761

Glu Gln Gly Thr Lys Thr Val Arg Gln Asn Met Glu Pro Leu Phe Glu
1               5                   10                  15

Gln Tyr Ile Asn Asn Leu Arg
            20

<210> SEQ ID NO 762
<211> LENGTH: 32
<212> TYPE: PRT
<213> ORGANISM: Homo sapiens

<400> SEQUENCE: 762

Phe Gly Glu Trp Ser Gly Gly Pro Gly Leu Ser Leu Cys Pro Pro Gly
1               5                   10                  15

Gly Ile Gln Glu Val Thr Ile Asn Gln Asn Pro Leu Thr Pro Leu Lys
            20                  25                  30

<210> SEQ ID NO 763
<211> LENGTH: 41
<212> TYPE: PRT
<213> ORGANISM: Homo sapiens

<400> SEQUENCE: 763

Phe Leu Glu Gln Gln Asn Gln Val Leu Gln Thr Lys Trp Glu Leu Leu
1               5                   10                  15

Gln Gln Met Asn Val Asp Thr Arg Pro Ile Asn Leu Glu Pro Ile Phe
            20                  25                  30

Gln Gly Tyr Ile Asp Ser Leu Lys Arg
        35                  40

<210> SEQ ID NO 764
<211> LENGTH: 17
<212> TYPE: PRT
<213> ORGANISM: Homo sapiens

<400> SEQUENCE: 764

Phe Ser Ser Gly Gly Ala Tyr Gly Leu Gly Gly Gly Tyr Gly Gly Gly
1               5                   10                  15

Phe

<210> SEQ ID NO 765
<211> LENGTH: 17
<212> TYPE: PRT
<213> ORGANISM: Homo sapiens

<400> SEQUENCE: 765

Phe Ser Ser Gly Gly Ala Tyr Gly Leu Gly Gly Gly Tyr Gly Gly Gly
1               5                   10                  15

Phe

<210> SEQ ID NO 766
<211> LENGTH: 60
<212> TYPE: PRT
<213> ORGANISM: Homo sapiens

<400> SEQUENCE: 766

Phe Ser Ser Gly Gly Ala Tyr Gly Leu Gly Gly Gly Tyr Gly Gly Gly
1               5                   10                  15

Phe Ser Ser Ser Ser Ser Ser Phe Gly Ser Gly Phe Gly Gly Gly Tyr
            20                  25                  30

Gly Gly Gly Leu Gly Thr Gly Leu Gly Gly Gly Phe Gly Gly Gly Phe
        35                  40                  45

Ala Gly Gly Asp Gly Leu Leu Val Gly Ser Glu Lys
    50                  55                  60

<210> SEQ ID NO 767
<211> LENGTH: 16
<212> TYPE: PRT
<213> ORGANISM: Homo sapiens

<400> SEQUENCE: 767

Gly Glu Leu Lys Glu Leu Leu Glu Lys Glu Phe His Pro Val Leu Lys
1               5                   10                  15

<210> SEQ ID NO 768
<211> LENGTH: 16
<212> TYPE: PRT
<213> ORGANISM: Homo sapiens

<400> SEQUENCE: 768

Gly Glu Thr Ile Ser Gly Gly Asn Phe His Gly Glu Tyr Pro Ala Lys
1               5                   10                  15

<210> SEQ ID NO 769
<211> LENGTH: 16
<212> TYPE: PRT
<213> ORGANISM: Homo sapiens

<400> SEQUENCE: 769

Gly Gly Gly Phe Gly Gly Gly Ser Gly Phe Gly Gly Gly Ser Gly Phe
1               5                   10                  15

<210> SEQ ID NO 770
<211> LENGTH: 21
<212> TYPE: PRT
<213> ORGANISM: Homo sapiens

<400> SEQUENCE: 770

Gly Gly Gly Phe Gly Gly Gly Ser Gly Phe Gly Gly Gly Ser Gly Phe
1 5 10 15

Ser Gly Gly Gly Phe
20

<210> SEQ ID NO 771
<211> LENGTH: 30
<212> TYPE: PRT
<213> ORGANISM: Homo sapiens

<400> SEQUENCE: 771

Gly Gly Gly Phe Gly Gly Gly Ser Gly Phe Gly Gly Gly Ser Gly Phe
1 5 10 15

Ser Gly Gly Gly Phe Gly Gly Gly Gly Phe Gly Gly Gly Arg
20 25 30

<210> SEQ ID NO 772
<211> LENGTH: 25
<212> TYPE: PRT
<213> ORGANISM: Homo sapiens

<400> SEQUENCE: 772

Gly Gly Gly Ser Phe Gly Gly Gly Phe Gly Gly Gly Phe Gly Gly Asp
1 5 10 15

Gly Gly Leu Leu Ser Gly Asn Glu Lys
20 25

<210> SEQ ID NO 773
<211> LENGTH: 23
<212> TYPE: PRT
<213> ORGANISM: Homo sapiens

<400> SEQUENCE: 773

Gly Gly Gly Ser Phe Gly Gly Gly Tyr Gly Gly Gly Ser Ser Gly Gly
1 5 10 15

Gly Ser Ser Gly Gly Gly Tyr
20

<210> SEQ ID NO 774
<211> LENGTH: 27
<212> TYPE: PRT
<213> ORGANISM: Homo sapiens

<400> SEQUENCE: 774

Gly Gly Gly Ser Phe Gly Gly Gly Tyr Gly Gly Gly Ser Ser Gly Gly
1 5 10 15

Gly Ser Ser Gly Gly Gly Tyr Gly Gly Gly His
20 25

<210> SEQ ID NO 775
<211> LENGTH: 29
<212> TYPE: PRT
<213> ORGANISM: Homo sapiens

<400> SEQUENCE: 775

Gly Gly Gly Ser Phe Gly Gly Gly Tyr Gly Gly Gly Ser Ser Gly Gly
1 5 10 15

```
Gly Ser Ser Gly Gly Gly Tyr Gly Gly Gly His Gly Gly
            20                  25


<210> SEQ ID NO 776
<211> LENGTH: 35
<212> TYPE: PRT
<213> ORGANISM: Homo sapiens

<400> SEQUENCE: 776

Gly Gly Gly Ser Phe Gly Gly Gly Tyr Gly Gly Gly Ser Ser Gly Gly
1               5                   10                  15

Gly Ser Ser Gly Gly Gly Tyr Gly Gly Gly His Gly Gly Ser Ser Gly
            20                  25                  30

Gly Gly Tyr
        35


<210> SEQ ID NO 777
<211> LENGTH: 44
<212> TYPE: PRT
<213> ORGANISM: Homo sapiens

<400> SEQUENCE: 777

Gly Gly Gly Ser Phe Gly Gly Gly Tyr Gly Gly Gly Ser Ser Gly Gly
1               5                   10                  15

Gly Ser Ser Gly Gly Gly Tyr Gly Gly Gly His Gly Gly Ser Ser Gly
            20                  25                  30

Gly Gly Tyr Gly Gly Gly Ser Ser Gly Gly Gly Tyr
        35                  40


<210> SEQ ID NO 778
<211> LENGTH: 23
<212> TYPE: PRT
<213> ORGANISM: Homo sapiens

<400> SEQUENCE: 778

Gly Gly Ser Gly Gly Gly Tyr Gly Ser Gly Cys Gly Gly Gly Gly Gly
1               5                   10                  15

Ser Tyr Gly Gly Ser Gly Arg
            20


<210> SEQ ID NO 779
<211> LENGTH: 11
<212> TYPE: PRT
<213> ORGANISM: Homo sapiens

<400> SEQUENCE: 779

Gly His Pro Ala Val Cys Gln Pro Gln Gly Arg
1               5                   10


<210> SEQ ID NO 780
<211> LENGTH: 16
<212> TYPE: PRT
<213> ORGANISM: Homo sapiens

<400> SEQUENCE: 780

Gly Ser Gly Leu Gly Ala Gly Gln Gly Thr Asn Gly Ala Ser Val Lys
1               5                   10                  15


<210> SEQ ID NO 781
<211> LENGTH: 17
<212> TYPE: PRT
<213> ORGANISM: Homo sapiens
```

<400> SEQUENCE: 781

Gly Ser Ser Ser Gly Gly Val Lys Ser Ser Gly Gly Ser Ser Ser Val
1               5                   10                  15

Arg

<210> SEQ ID NO 782
<211> LENGTH: 61
<212> TYPE: PRT
<213> ORGANISM: Homo sapiens

<400> SEQUENCE: 782

Gly Ser Tyr Gly Ser Ser Ser Phe Gly Gly Ser Tyr Gly Gly Ser Phe
1               5                   10                  15

Gly Gly Gly Ser Phe Gly Gly Gly Ser Phe Gly Gly Gly Ser Phe Gly
            20                  25                  30

Gly Gly Gly Phe Gly Gly Gly Gly Phe Gly Gly Gly Phe Gly Gly Gly
        35                  40                  45

Phe Gly Gly Asp Gly Gly Leu Leu Ser Gly Asn Glu Lys
    50                  55                  60

<210> SEQ ID NO 783
<211> LENGTH: 14
<212> TYPE: PRT
<213> ORGANISM: Homo sapiens

<400> SEQUENCE: 783

His Ala Gly Ile Gly His Gly Gln Ala Ser Ser Ala Val Arg
1               5                   10

<210> SEQ ID NO 784
<211> LENGTH: 30
<212> TYPE: PRT
<213> ORGANISM: Homo sapiens

<400> SEQUENCE: 784

His Asp Pro Ala Ala Trp Glu Ala Ala Gln Ser Met Ile Pro Ile Asn
1               5                   10                  15

Glu Pro Tyr Gly Asp Asp Leu Asp Ala Thr Tyr Arg Pro Met
            20                  25                  30

<210> SEQ ID NO 785
<211> LENGTH: 35
<212> TYPE: PRT
<213> ORGANISM: Homo sapiens

<400> SEQUENCE: 785

His Asp Pro Ala Ala Trp Glu Ala Ala Gln Ser Met Ile Pro Ile Asn
1               5                   10                  15

Glu Pro Tyr Gly Asp Asp Leu Asp Ala Thr Tyr Arg Pro Met Tyr Ser
            20                  25                  30

Ser Asp Val
        35

<210> SEQ ID NO 786
<211> LENGTH: 43
<212> TYPE: PRT
<213> ORGANISM: Homo sapiens

<400> SEQUENCE: 786

His Asp Pro Ala Ala Trp Glu Ala Ala Gln Ser Met Ile Pro Ile Asn

```
1               5                   10                  15

Glu Pro Tyr Gly Asp Asp Leu Asp Ala Thr Tyr Arg Pro Met Tyr Ser
            20                  25                  30

Ser Asp Val Pro Leu Asp Pro Leu Glu Met His
        35                  40


<210> SEQ ID NO 787
<211> LENGTH: 12
<212> TYPE: PRT
<213> ORGANISM: Homo sapiens

<400> SEQUENCE: 787

His Gly Leu Val Ala Thr His Thr Leu Thr Val Arg
1               5                   10


<210> SEQ ID NO 788
<211> LENGTH: 11
<212> TYPE: PRT
<213> ORGANISM: Homo sapiens

<400> SEQUENCE: 788

Ile Asp Lys Pro Ser Leu Leu Thr Met Met Lys
1               5                   10


<210> SEQ ID NO 789
<211> LENGTH: 19
<212> TYPE: PRT
<213> ORGANISM: Homo sapiens

<400> SEQUENCE: 789

Ile Asn Tyr Gln Asp Asp Ala Glu Leu Ala Thr His Ala Leu Pro Glu
1               5                   10                  15

Leu Thr Lys


<210> SEQ ID NO 790
<211> LENGTH: 9
<212> TYPE: PRT
<213> ORGANISM: Homo sapiens

<400> SEQUENCE: 790

Leu Glu Gln Glu Ile Thr Thr Tyr Arg
1               5


<210> SEQ ID NO 791
<211> LENGTH: 20
<212> TYPE: PRT
<213> ORGANISM: Homo sapiens

<400> SEQUENCE: 791

Leu Ile Asn Tyr Gln Asp Asp Ala Glu Leu Ala Thr His Ala Leu Pro
1               5                   10                  15

Glu Leu Thr Lys
            20


<210> SEQ ID NO 792
<211> LENGTH: 6
<212> TYPE: PRT
<213> ORGANISM: Homo sapiens

<400> SEQUENCE: 792

Leu Pro Leu His Gln Cys
1               5
```

<210> SEQ ID NO 793
<211> LENGTH: 12
<212> TYPE: PRT
<213> ORGANISM: Homo sapiens

<400> SEQUENCE: 793

Leu Arg Pro Glu Pro Ser Ile Ser Leu Glu Pro Arg
1 5 10

<210> SEQ ID NO 794
<211> LENGTH: 51
<212> TYPE: PRT
<213> ORGANISM: Homo sapiens

<400> SEQUENCE: 794

Leu Ser Gly Glu Gly Val Gly Pro Val Asn Ile Ser Val Val Thr Ser
1 5 10 15

Ser Val Ser Ser Gly Tyr Gly Ser Gly Ser Gly Tyr Gly Gly Gly Leu
20 25 30

Gly Gly Gly Leu Gly Gly Gly Leu Gly Gly Gly Leu Ala Gly Gly Gly
35 40 45

Ser Gly Ser
50

<210> SEQ ID NO 795
<211> LENGTH: 27
<212> TYPE: PRT
<213> ORGANISM: Homo sapiens

<400> SEQUENCE: 795

Leu Val Leu Ser Thr Phe Ser Asn Ile Arg Glu Glu Leu Gly His Leu
1 5 10 15

Gln Asn Asp Leu Thr Ser Leu Glu Asn Asp Lys
20 25

<210> SEQ ID NO 796
<211> LENGTH: 23
<212> TYPE: PRT
<213> ORGANISM: Homo sapiens

<400> SEQUENCE: 796

Met Asn Val Asp Thr Arg Pro Ile Asn Leu Glu Pro Ile Phe Gln Gly
1 5 10 15

Tyr Ile Asp Ser Leu Lys Arg
20

<210> SEQ ID NO 797
<211> LENGTH: 17
<212> TYPE: PRT
<213> ORGANISM: Homo sapiens

<400> SEQUENCE: 797

Asn Leu Ser Asp Val Ala Thr Lys Gln Glu Gly Leu Glu Asn Val Leu
1 5 10 15

Lys

<210> SEQ ID NO 798
<211> LENGTH: 7
<212> TYPE: PRT
<213> ORGANISM: Homo sapiens

<400> SEQUENCE: 798

Asn Thr Asn Phe Ala Gln Lys
1 5

<210> SEQ ID NO 799
<211> LENGTH: 21
<212> TYPE: PRT
<213> ORGANISM: Homo sapiens

<400> SEQUENCE: 799

Asn Val Asp Thr Arg Pro Ile Asn Leu Glu Pro Ile Phe Gln Gly Tyr
1 5 10 15

Ile Asp Ser Leu Lys
20

<210> SEQ ID NO 800
<211> LENGTH: 22
<212> TYPE: PRT
<213> ORGANISM: Homo sapiens

<400> SEQUENCE: 800

Asn Val Asp Thr Arg Pro Ile Asn Leu Glu Pro Ile Phe Gln Gly Tyr
1 5 10 15

Ile Asp Ser Leu Lys Arg
20

<210> SEQ ID NO 801
<211> LENGTH: 10
<212> TYPE: PRT
<213> ORGANISM: Homo sapiens

<400> SEQUENCE: 801

Asn Trp Asn Gly Ser Val Glu Ile Leu Lys
1 5 10

<210> SEQ ID NO 802
<211> LENGTH: 43
<212> TYPE: PRT
<213> ORGANISM: Homo sapiens

<400> SEQUENCE: 802

Pro Ile Leu Asp Pro Leu Gly Tyr Gly Asn Val Thr Val Thr Glu Ser
1 5 10 15

Phe Thr Thr Ser Asp Thr Leu Lys Pro Ser Val His Val His Asp Asn
20 25 30

Arg Pro Ala Ser Asn Val Val Val Thr Glu Arg
35 40

<210> SEQ ID NO 803
<211> LENGTH: 9
<212> TYPE: PRT
<213> ORGANISM: Homo sapiens

<400> SEQUENCE: 803

Gln Glu Gly Leu Glu Asn Val Leu Lys
1 5

<210> SEQ ID NO 804
<211> LENGTH: 15
<212> TYPE: PRT
<213> ORGANISM: Homo sapiens

<400> SEQUENCE: 804

Gln Asn Leu Glu Leu Leu Phe Glu Gln Tyr Ile Asn Asn Leu Arg
1 5 10 15

<210> SEQ ID NO 805
<211> LENGTH: 15
<212> TYPE: PRT
<213> ORGANISM: Homo sapiens

<400> SEQUENCE: 805

Gln Asn Met Glu Pro Leu Phe Glu Gln Tyr Ile Asn Asn Leu Arg
1 5 10 15

<210> SEQ ID NO 806
<211> LENGTH: 18
<212> TYPE: PRT
<213> ORGANISM: Homo sapiens

<400> SEQUENCE: 806

Arg Ala Pro Tyr Pro Asn Tyr Asp Arg Asp Ile Leu Thr Ile Asp Ile
1 5 10 15

Ser Arg

<210> SEQ ID NO 807
<211> LENGTH: 15
<212> TYPE: PRT
<213> ORGANISM: Homo sapiens

<400> SEQUENCE: 807

Arg Asp Asp Lys Ile Asp Lys Pro Ser Leu Leu Thr Met Met Lys
1 5 10 15

<210> SEQ ID NO 808
<211> LENGTH: 25
<212> TYPE: PRT
<213> ORGANISM: Homo sapiens

<400> SEQUENCE: 808

Ser Ala Ile Val His Leu Ile Asn Tyr Gln Asp Asp Ala Glu Leu Ala
1 5 10 15

Thr His Ala Leu Pro Glu Leu Thr Lys
20 25

<210> SEQ ID NO 809
<211> LENGTH: 16
<212> TYPE: PRT
<213> ORGANISM: Homo sapiens

<400> SEQUENCE: 809

Ser Ala Leu Ser Gly His Leu Glu Thr Leu Ile Leu Gly Leu Leu Lys
1 5 10 15

<210> SEQ ID NO 810
<211> LENGTH: 17
<212> TYPE: PRT
<213> ORGANISM: Homo sapiens

<400> SEQUENCE: 810

Ser Gly Gly Leu Ser Val Gly Gly Ser Gly Phe Ser Ala Ser Ser Gly
1 5 10 15

Arg

<210> SEQ ID NO 811
<211> LENGTH: 36

<212> TYPE: PRT
<213> ORGANISM: Homo sapiens

<400> SEQUENCE: 811

Ser Gly His Ser Ser Tyr Gly Gln His Gly Phe Gly Ser Ser Gln Ser
1 5 10 15

Ser Gly Tyr Gly Gln His Gly Ser Ser Ser Gly Gln Thr Ser Gly Phe
20 25 30

Gly Gln His Lys
35

<210> SEQ ID NO 812
<211> LENGTH: 7
<212> TYPE: PRT
<213> ORGANISM: Homo sapiens

<400> SEQUENCE: 812

Ser Leu Asn Ser Phe Gly Arg
1 5

<210> SEQ ID NO 813
<211> LENGTH: 9
<212> TYPE: PRT
<213> ORGANISM: Homo sapiens

<400> SEQUENCE: 813

Ser Ser Gly Gly Ser Ser Ser Val Arg
1 5

<210> SEQ ID NO 814
<211> LENGTH: 43
<212> TYPE: PRT
<213> ORGANISM: Homo sapiens

<400> SEQUENCE: 814

Ser Ser Ser Ser Ser Ser Phe Gly Ser Gly Phe Gly Gly Gly Tyr Gly
1 5 10 15

Gly Gly Leu Gly Thr Gly Leu Gly Gly Gly Phe Gly Gly Gly Phe Ala
20 25 30

Gly Gly Asp Gly Leu Leu Val Gly Ser Glu Lys
35 40

<210> SEQ ID NO 815
<211> LENGTH: 10
<212> TYPE: PRT
<213> ORGANISM: Homo sapiens

<400> SEQUENCE: 815

Ser Thr Ser Tyr Cys Tyr Leu Ala Pro Arg
1 5 10

<210> SEQ ID NO 816
<211> LENGTH: 10
<212> TYPE: PRT
<213> ORGANISM: Homo sapiens

<400> SEQUENCE: 816

Thr Arg Leu Glu Gln Glu Ile Thr Thr Tyr
1 5 10

<210> SEQ ID NO 817
<211> LENGTH: 11
<212> TYPE: PRT

<213> ORGANISM: Homo sapiens

<400> SEQUENCE: 817

Thr Arg Leu Glu Gln Glu Ile Thr Thr Tyr Arg
1 5 10

<210> SEQ ID NO 818
<211> LENGTH: 35
<212> TYPE: PRT
<213> ORGANISM: Homo sapiens

<400> SEQUENCE: 818

Thr Ser Gly Gly Gly Gly Gly Gly Gly Gly Gly Gly Gly Gly Gly Cys
1 5 10 15

Gly Phe Phe Gly Gly Gly Gly Ser Gly Gly Gly Ser Ser Gly Ser Gly
20 25 30

Cys Gly Tyr
35

<210> SEQ ID NO 819
<211> LENGTH: 7
<212> TYPE: PRT
<213> ORGANISM: Homo sapiens

<400> SEQUENCE: 819

Thr Thr Thr Val Thr Ile Lys
1 5

<210> SEQ ID NO 820
<211> LENGTH: 20
<212> TYPE: PRT
<213> ORGANISM: Homo sapiens

<400> SEQUENCE: 820

Val Asp Thr Arg Pro Ile Asn Leu Glu Pro Ile Phe Gln Gly Tyr Ile
1 5 10 15

Asp Ser Leu Lys
20

<210> SEQ ID NO 821
<211> LENGTH: 21
<212> TYPE: PRT
<213> ORGANISM: Homo sapiens

<400> SEQUENCE: 821

Val Asp Thr Arg Pro Ile Asn Leu Glu Pro Ile Phe Gln Gly Tyr Ile
1 5 10 15

Asp Ser Leu Lys Arg
20

<210> SEQ ID NO 822
<211> LENGTH: 25
<212> TYPE: PRT
<213> ORGANISM: Homo sapiens

<400> SEQUENCE: 822

Val Glu Asp Glu Asn Asp Ser His Pro Val Phe Thr Glu Ala Ile Tyr
1 5 10 15

Asn Phe Glu Val Leu Glu Ser Ser Arg
20 25

<210> SEQ ID NO 823

<211> LENGTH: 20
<212> TYPE: PRT
<213> ORGANISM: Homo sapiens

<400> SEQUENCE: 823

Val Val Ser Pro Ile Ser Gly Ala Asp Leu His Gly Met Leu Glu Met
1 5 10 15

Pro Asp Leu Arg
20

<210> SEQ ID NO 824
<211> LENGTH: 30
<212> TYPE: PRT
<213> ORGANISM: Homo sapiens

<400> SEQUENCE: 824

Val Val Ser Pro Ile Ser Gly Ala Asp Leu His Gly Met Leu Glu Met
1 5 10 15

Pro Asp Leu Arg Asp Gly Ser Asn Val Ile Val Thr Glu Arg
20 25 30

<210> SEQ ID NO 825
<211> LENGTH: 12
<212> TYPE: PRT
<213> ORGANISM: Homo sapiens

<400> SEQUENCE: 825

Trp Glu Leu Leu Gln Gln Met Asn Val Asp Thr Arg
1 5 10

<210> SEQ ID NO 826
<211> LENGTH: 23
<212> TYPE: PRT
<213> ORGANISM: Homo sapiens

<400> SEQUENCE: 826

Trp Glu Leu Leu Gln Gln Met Asn Val Asp Thr Arg Pro Ile Asn Leu
1 5 10 15

Glu Pro Ile Phe Gln Gly Tyr
20

<210> SEQ ID NO 827
<211> LENGTH: 28
<212> TYPE: PRT
<213> ORGANISM: Homo sapiens

<400> SEQUENCE: 827

Trp Glu Leu Leu Gln Gln Met Asn Val Asp Thr Arg Pro Ile Asn Leu
1 5 10 15

Glu Pro Ile Phe Gln Gly Tyr Ile Asp Ser Leu Lys
20 25

<210> SEQ ID NO 828
<211> LENGTH: 29
<212> TYPE: PRT
<213> ORGANISM: Homo sapiens

<400> SEQUENCE: 828

Trp Glu Leu Leu Gln Gln Met Asn Val Asp Thr Arg Pro Ile Asn Leu
1 5 10 15

Glu Pro Ile Phe Gln Gly Tyr Ile Asp Ser Leu Lys Arg
20 25

```
<210> SEQ ID NO 829
<211> LENGTH: 23
<212> TYPE: PRT
<213> ORGANISM: Homo sapiens

<400> SEQUENCE: 829

Tyr Ser Ser Gln Leu Ala Gln Met Gln Cys Leu Ile Ser Thr Val Glu
1               5                   10                  15

Ala Gln Leu Ser Glu Ile Arg
            20
```